US006300096B1

(12) United States Patent
Stahl et al.

(10) Patent No.: US 6,300,096 B1
(45) Date of Patent: Oct. 9, 2001

(54) POLYNUCLEOTIDES ENCODING FATTY ACID TRANSPORT PROTEINS

(75) Inventors: Andreas Stahl, Allston; David J. Hirsch; Harvey F. Lodish, both of Brookline; Ruth E. Gimeno, Wellesley; Louis A. Tartaglia, Newton, all of MA (US)

(73) Assignees: Whitehead Institute for Biomedical Research; Millennium Pharmaceuticals, Inc., both of Cambridge, MA (US)

( * ) Notice: Subject to any disclaimer, the term of this patent is extended or adjusted under 35 U.S.C. 154(b) by 0 days.

(21) Appl. No.: 09/232,197

(22) Filed: Jan. 14, 1999

Related U.S. Application Data

(60) Provisional application No. 60/071,374, filed on Jan. 15, 1998, provisional application No. 60/093,491, filed on Jul. 20, 1998, and provisional application No. 60/110,941, filed on Dec. 4, 1998.

(51) Int. Cl.[7] .............................. C12P 21/06; C07H 21/04
(52) U.S. Cl. ..................... 435/69.1; 435/70.1; 435/325; 435/320.1; 536/23.1; 536/23.5; 536/24.1
(58) Field of Search .................................. 435/69.1, 70.1, 435/325, 471, 320.1, 252.3; 536/23.1, 23.5, 24.1; 530/350

(56) References Cited

U.S. PATENT DOCUMENTS 4,935,450  6/1990  Cone, Jr. .............................. 514/728

FOREIGN PATENT DOCUMENTS

WO 00/58473  5/2000  (WO) .
WO 00/26245  11/2000  (WO) .

OTHER PUBLICATIONS

Sambrook et al. Molecular Cloning, vol. 3, (pp. 16.3–16.5, 16.17–16.18, 16.28–16.31), 1989.*
Database on GenEmbl, Kamijo, K. et al. "*Homo sapiens* mRNA for very–long–chain acyle–CoA synthetase", Accession No. D88308, Oct. 1996.*
Database on EST, Hillier et al. "melanocyte 2NbHM *Homo sapiens* cDNA", Accession No. N28667, Jan. 1996.*
Database on EST, Hillier et al, Accession No. N69873, Mar. 1996.*
Database on EST, Marra et al. "*Mus musculus* cDNA clone similar to fatty acid trasport protein precursor", Accession No. W77667, Jun. 1996.*
Database on PIR–60, Schaffer et al. Expression cloning and characterization of a novel adipocyte long chain fatty acid transport precurasor, Accession No. A55093, Jan. 1995.*
Database on EST, Hillier et al. "multiple sclerosis 2NbHMsp *Homo sapien* cDNA", Accession No. N45224, Feb. 1996.*
Rieger et al. Glossary of Gentics and Cytogentics, Springer–Verlag, Berlin Heidelberg, New York, p. 17, 1976.*
Cunningham et al, Science vol. 244, pp. 1081–1085, Jun. 1989.*
Uchiyama, A. et al., "Molecular Cloning of cDNA Encoding Rat Very–long–chain Acyl–CoA Synthetase," *J. Biol. Chem.* 271(48):30360–30365 (1996).
Stuhlsatz–Krouper, S.M. et al., "Substitution of Alanine for Serine 250 in the Murine Fatty Acid Transport Protein Inhibits Long Chain Fatty Acid Transport," *J. Biol. Chem.* 273(44):28642–28650 (1998).
Watkins, P.A. et al., "Disruption of the *Saccharomyces cerevisiae* FAT1 Gene Decreases Very Long–chain Fatty Acyl–CoA Synthetase Activity and Elevates Intracellular Very Long–chain Fatty Acid Concentrations," *J. Biol. Chem.* 273(29):18210–18219 (1998).
Hirsch, D. et al., "A family of fatty acid transporters conserved from mycobacterium to man," *Proc. Natl. Acad. Sci.* 95:8625–8629 (1998).
Berger, J. et al., "A Novel Relative of the Very–Long–Chain Acyl–CoA Synthetase and Fatty Acid Transporter Protein Genes with a Distinct Expression Pattern," *Biochem. Biophys. Res. Commun.* 247:255–260 (1998).
Hui, T.Y. et al., "Characterization of the Murine Fatty Acid Transport Protein Gene and Its Insulin Response Sequence," *J. Biol. Chem.* 274(42):27420–27429 (1998).
Færgeman, N.J. et al., "Disruption of the *Saccharomyces cerevisiae* Homologue to the Murine Fatty Acid Transport Protein Impairs Uptake and Growth on Long–chain Fatty Acids," *J. Biol. Chem.* 272(13):8531–8538 (1997).
Schaap, F.G. et al., "Molecular cloning of fatty acid–transport protein cDNA from rat," *Biochem. Biophys. Acta* 1354:29–34 (1997).
Schaffer, J.E. and Lodish, H.F., "Expression Cloning and Characterization of a Novel Adipocyte Long Chain Fatty Acid Transport Protein," *Cell* (79):427–436 (1994).
Bonaldo, M.F. et al.; Data Submission; *Rattus norvegicus* cDNA clone; *Rattus norvegicus*; GenBank Accession No. AA817672; (1996).

(List continued on next page.)

*Primary Examiner*—Jeffrey Stucker
*Assistant Examiner*—Jegatheesan Seharaseyon
(74) *Attorney, Agent, or Firm*—Hamilton, Brook, Smith & Reynolds, P.C.

(57) ABSTRACT

A family of fatty acid transport proteins (FATPs) mediate transport of long chain fatty acids (LCFAs) across cell membranes into cells. These proteins exhibit different expression patterns among the organs of mammals. Nucleic acids encoding FATPs of this family, vectors comprising these nucleic acids, as well as the production of FATP proteins in host cells are described. Also described are methods to test FATPs for fatty acid transport function, and methods to identify inhibitors or enhancers of transport function. The altering of LCFA uptake by administering to the mammal an inhibitor or enhancer of FATP transport function of a FATP in the small intestine can decrease or increase calories available as fats, and can decrease or increase circulating fatty acids. The organ specificity of FATP distribution can be exploited in methods to direct drugs, diagnostic indicators and so forth to an organ such as the heart.

66 Claims, 169 Drawing Sheets

OTHER PUBLICATIONS

Schaap, F.G. et al.; Data Submission; *Rattus norvegicus* fatty acid transport protein mRNA, complete cds.; *Rattus norvegicus;* GenBank Accession No. U89529; (1997).

Lee, N.H. et al.; Data Submission; Normalized rat heart, Bento Soares Rattus sp. cDNA clone; Rattus sp.; GenBank Accession No. AA799326; (1998).

Hui, T.Y. et al.; Data Submission; *Mus musculus* fatty acid transport protein (FATP) gene, exons 1–3; *Mus musculus;* GenBank Accession No. AF023256; (1997).

Schaffer, J.E. and Lodish, H.F.; Data Submission; *Mus musculus* fatty acid transport protein (FATP) mRNA, complete cds.; *Mus musculus;* GenBank Accession No. U15976; (1994).

Stahl, A. et al.; Data Submission; *Mus musculus* fatty acid transport protein 5 mRNA, complete cds.; *Mus musculus;* GenBank Accession No. AF072760; (1998).

Stahl, A. et al.; Data Submission; *Mus musculus* fatty acid transport protein 4 mRNA, partial cds.; *Mus musculus;* GenBank Accession No. AF072759; (1998).

Stahl, A. et al.; Data Submission; *Mus musculus* fatty acid transport protein 3 mRNA, partial cds.; *Mus musculus;* GenBank Accession No. AF072758; (1998).

Stahl, A. et al.; Data Submission; *Mus musculus* fatty acid transport protein 2 mRNA, complete cds.; *Mus musculus;* GenBank Accession No. AF072757; (1998).

Hui, T.Y. et al.; Data Submission; *Mus musculus* fatty acid transport protein (FATP) gene, exons 8–13 and complete cds.; *Mus musculus;* GenBank Accession No. AF023258; (1997).

Kamijo, K.; Data Submission; *Homo sapiens* mRNA for very–long–chain acyl–CoA synthetase, complete cds.; *Homo sapiens* (human); EMBL Accession No. D88308; (1996).

Harmon, C.M. et al.; "Labelling of an 88 kDa adipocyte membrane protein by sulpho–N–succinimidyl long–chain fatty acids: inhibition of fatty acid transport," *Biochemical Society Transactions* 20(4):811–813 (1992).

Schaffer, J.E. et al., "Cloning and Structure–Function Analysis of Human Heart Fatty Acid Transport Protein," *Circulation* 96(8):2031 (1997).

Ghosh, B. et al., "Molecular cloning and sequencing of human palmitoyl–CoA ligase and its tissue specific expression," *Mol. Cell. Biochem.* 151:77–81 (1995).

Fitscher, B.A. et al., "Tissue distribution and cDNA cloning of a human fatty acid transport protein (hsFATP4)," *Biochmica et Biophysica Acta* 1443:381–385 (1998).

Abumrad, N., et al., "Membrane Proteins Implicated in Long–Chain Fatty Acid Uptake by Mammalian Cells: CD36, FATP and FABPm," *Biochimica et Biophysica Acta* 1441: 4–13 (1999).

Berk, P.D.,and Stump D.D., "Mechanisms of Cellular Uptake of Long–Chain Free Fatty Acids," *Molecular and Cellular Biochem.* 192:17–31 (1999).

Berk, P.D., et al., "Characterization of Membrane Transport Processes: Lessons from the Study of BSP, Bilirubin, and Fatty Acid Uptake," *Seminars In Liver Disease* 16(2):107–120 (1996).

Boisclair, Y.R., et al., "Three Clustered Sp1 Sites Are Required for Efficient Transcription of the TATA–Less Promoter of the Gene for Insulin–Like Growth Factor–binding Protein–2 from the Rat," *American Society Biochem.* 268(33):24892–24901 (1993).

De Simone, V.,and Cortese, R., "Transcription Factors and Liver–Specific Genes," *Biochimica et Biophysica Acta* 1132:119–126 (1992).

Fitscher, B.A., et al., "Protein–Mediated Facilitated Uptake Processes for Fatty Acids, Bilirubin, and Other Amphiphatic Compounds (43987)," *Proc Soc Exp Biol Med* 212:15–23 (1996).

Frohnert, B.I., et al., "Identification of a Functional Peroxisome Proliferator–Response Element in the Murine Fatty Acid Transport Protein Gene," *J. of Biological Chem.* 274(7):3970–3977 (1999).

Glatz, J.F.C., et al., "Molecular Mechanism of Cellular Uptake and Intracellular Translocation of Fatty Acids," *Prostaglandins, Leukotrienes and Essential Fatty Acids* 57(1):3–9 (1997).

Göttlicher, M., et al., "Fatty Acids Activate a Chimera of the Clofibric Acid–Activated Receptor and the Glucocorticoid Receptor," *Proc. Natl. Acad. Sci.* USA 89:4653–4657 (1992).

Grimaldi, P.A., et al., "Long Chain Fatty Acids as Modulators of Gene Transcription in Preadipose Cells," *Molecular and Cellular Biochem.* 192:63–68 (1999).

Hamilton, J.A., "Fatty Acid Transport: Difficult or Easy?," *J. Lipid Res.* 39:467–481 (1998).

Hanson, R.W. "Regulation of Phosphoenolpyruvate Carboxykinase (GTP) Gene Expression" *Annu. Rev. Biochem.* 66:581–611 (1997).

Heinemeyer, T., et al., "Databases on Transcriptional Regulation: TRANSFAC, TRRD and COMPEL," *Nucleic Acids Res.* 26(1):362–367 (1998).

Heinemeyer[1], T. et al., "Expanding the TRANSFAC Database Towards an Expert System of Regulatory Molecular Mechanisms," *Nucleic Acids Res.* 27(1):318–322 (1999).

Hua[1], X., et al., "Synergistic Cooperation of TFE3 and Smad Proteins in TGF–β–Induced Transcription of the Plasminogen Activator Inhibitor–1 Gene," *Genes & Development* 12: 3084–3095 (1998).

Lai, E., "Regulation of Hepatic Gene Expression and Development," *Seminars in Liver Disease* 12(3):246–251 (1992).

Lee, Y.H., et al., "A Novel cis–Acting Element Controlling the Rat CYP2D5 Gene and Requiring Cooperativity between C/EBPβ and an SP1 Factor," *Molecular and Cellular Biology,* 14(2):1383–1394 (1994).

Martin, G., et al., "Coordinate Regulation of the Expression of the Fatty Acid Transport Protein and Acyl–CoA Synthetase Genes by PPARα and PPARγ Activators," *J. Biological Chem.* 272(45):28210–28217 (1997).

Memon, R.A., et al., "Regulation of Putative Fatty Acid Transporters and Acyl–CoA Synthetase in Liver and Adipose Tissue in ob/ob Mice," *Diabetes* 48:121–127 (1999).

Motojima, K., et al., "Expression and Putative Fatty Acid Transporter Genes Are Regulated by Peroxisome Proliferator–Activated Receptor α and γ Activators in a Tissue– and Inducer–Specific Manner," *J. Biol. Chem.* 273(27):16710–16714 (1998).

Rodenburg, R.J.T., et al., "A Functional Sp1 Binding Site Is Essential for the Activity of the Adult Liver–Specific Human Insulin–Like Growth Factor II Promoter," *Molecular Endocrinology* 11:237–250 (1997).

Rongnoparut, P., et al., "Isolation and Characterization of the Transcriptionally Regulated Mouse Liver (B–type) Phosphofructokinase Gene and Its Promoter," *J. Biological Chem.* 266(13):8086–8091 (1991).

Ryu, S., et al., "The Transcriptional Cofactor Complex CRSP is Required for Activity of the Enhancer–Binding Protein Sp1," *Nature* 397:446–450 (1999).

Schaffer, J.E., and Lodish, H.F., "Molecular Mechanism of Long–Chain Fatty Acid Uptake," *TCM* 5(6):218–224 (1995).

Schoonjans, K., et al., "The Peroxisome Proliferator Activated Receptors (PPARs) and Their Effects on Lipid Metabolism and Adipocyte Differentiation," *Biochem. Biophys. Acta* 1302:93–109 (1996).

Sorensen, P., and Wintersberger, E., "Sp1 and NF–Y Are Necessary and Sufficient for Growth–Dependent Regulation of the Hamster Thymidine Kinase Promoter*," *J. Biological Chem.* 274(43):30943–30949 (1999).

Stremmel, W., "Mechanism of Hepatic Fatty Acid Uptake," *J. Hepatology* 9:374–382 (1989).

Strausberg, R.; Data Submission; nc84e10.s1 NCI_CGAP_GC1 *Homo sapiens* cDNA clone IMAGE:797514, *Homo sapiens* (human); EMBL Accession No. Aa581592; (1997).

Hillier, L. et. al.; Data Submission; zu10c02.r1 Soares testis NHT *Homo sapiens* cDNA clone 731426 5', *Homo sapiens*(human);EMBL Accession No. AA469992; (1997).

Strausberg, R.; Data Submission; no82f09.s1 NCI_CGAP_AA1 *Homo sapiens* cDNA clone IMAGE:1113353 similar to TR:G563829 G563829 Fatty Acid Transport Protein, *Homo sapiens*(human); EMBL Accession No. Aa614135; (1997).

Hillier, L., et al.; Data Submission; zc44h06.r1 /Soares senescent fibroblasts NbHSF *Homo spiens* cDNA clone 325211 5' similar to PIR:A55093 A55093 fatty acid transport protein precursor—mouse, *Homo sapiens*(human); EMBL Accession No. W48808; (1996).

Strausberg, R.; Data Submission; nn89d05.s1 NCI_CGAP_Br2 *Homo sapiens* cDNA clone IMAGE:1098345 similar to TR:G563829 Fatty Acid Transport Protein, *Homo sapiens*(human); EMBL Accession No. AA614445; (1997).

Strausberg, R.; Data Submission; ne19b11.s1 NCI_CGAP_Co3 *Homo sapiens* cDNA clone IMAGE:881661, *Homo sapiens*(human); EMBL Accession No. AA470762; (1997).

* cited by examiner

| | | | |
|---|---|---|---|
| mmFATP1 | 473 | NKKIAH | SVFRKQDSAYLSGDYLMDELGYMYFR |
| mmFATP2 | 446 | EKKKLR | DVFKKQDIYFNSGDLLMIDRENFVLH |
| mmFATP3 | 439 | KDKLL | KDVFKKQDVFNMTGDLLVCDEQGFLHF |
| mmFATP4 | 333 | NKKIAN | DVEKKQAYLTGDVLMDELGYLYFQ |
| mmFATP5 | 488 | NRKLVA | VRRVGDLYFNTGDLLTLDQEGFFYFV |
| ceFATPa | 473 | NKKIIR | DVFAKGDSCFLTGDLLHWDRLGYLYFK |
| scFATP | 489 | KSKVVR | DYFRRQDAWYRCGDLLKADEYGLWLFL |
| mtFATP | 423 | EKKLVR | NAFRDGCWFNTGDMSPQGMGHAAEV |

FIG. 1O

| | | | | | |
|---|---|---|---|---|---|
| D | DRSGDT | FRWRGENVSTTEEVAVLSR | --- | LLGQT | DVAVYGVA |
| D | DRVGDT | FRWKGENVATTEEVADIVGL | --- | VDFFLQ | EEVNVYGVP |
| D | DRTGDT | FRWIGENVATTEEVAEVLET | --- | LDFLHM | ADVNIYGVT |
| D | DRLGDT | FRWKGENVSTTEEVEQTLSR | --- | LDFLEV | NVYGVE |
| D | DRTGDT | FRWKGENVSTTEEVECVLSS | --- | ITGLSD | ATYGVP |
| D | DRMGDT | FRWKSENVATTEEVEDQLTA | --- | NKEQYA | QLVVGIK |
| D | DRLGDT | FRWKGENVATQVEAALAS | --- | DQTVEC | TVYGVQ |

```
          VPQ VEGKAGNAALADPHSQLDPNS---MYQELQKV
mmFATP1 544 VPQ VEGKAGNAALADPHSQLDPNS---MYQELQKV
mmFATP2 517 VPQ HEGRTGMASLIKENYEFNGKK---LFQHIAEY
mmFATP3 510 VPQ HEGRAGMAALALRPQALVQ----LYSHYSEN
mmFATP4 404 VPG TEGRAGMAAVASPISNCDLES---FAQTLKKE
mmFATP5 559 VPG CEGKVGMAAVKLAPGKTDGK----LYQHVRSW
ceFATPa 544 VPQ REGRVGMASVRVVSHEEDTQFVHRVGARLASS
scFATP  562 VPKYEGRAGEAVIKLTDNSLDITKT-KLLNDSLSRL
mtFATP  494 LPRTGGRAGMAALTLRAGAEFDGQA---LARTVYGH
```

FIG. 1R

```
LASYARPIFLRLLPQVDTTGTFFKIQKTRLQREGFD
LPPYARPRFLRLRIQDTIEITGTFFKHRKVTLMEEGFN
LPLYARPIFLRFLRLQESLEITGTFFKKFQKVRMANEGFN
LPAYATPHFMRFHQDSLEITGTFFKKTELRKEGFD
LTSYAMPLFKFVRICQDVEKTGTFFKKLVKSRLVREGFD
LPSYAMPLFVVRKVDEIKMTDN--LIKFTNLQRLGIM
LPGYALPLFVVGSLAHHTTFKSRKVELRNQAYG
```

FIG. 1S

| | mmFATP1 | mmFATP2 | mmFATP3 | mmFATP4 | mmFATP5 | rnFATP1 | rnVLACS | ceFATPa | ceFATPb | scFATP | mtFATP |
|---|---|---|---|---|---|---|---|---|---|---|---|
| mmFATP1 | 100.0 | | | | | | | | | | |
| mmFATP2 | 50.1 | 100.0 | | | | | | | | | |
| mmFATP3 | 51.8 | 53.3 | 100.0 | | | | | | | | |
| mmFATP4 | 72.6 | 48.4 | 51.7 | 100.0 | | | | | | | |
| mmFATP5 | 50.2 | 54.0 | 54.4 | 50.8 | 100.0 | | | | | | |
| rnFATP1 | 97.5 | 49.7 | 51.6 | 71.4 | 50.4 | 100.0 | | | | | |
| rnVLACS | 50.7 | 95.2 | 53.0 | 50.9 | 53.6 | 50.3 | 100.0 | | | | |
| ceFATPa | 54.1 | 48.6 | 47.2 | 53.6 | 47.0 | 53.9 | 49.1 | 100.0 | | | |
| ceFATPb | 55.7 | 48.8 | 46.8 | 54.2 | 47.3 | 54.9 | 49.0 | 60.3 | 100.0 | | |
| scFATP | 45.5 | 43.2 | 42.3 | 47.0 | 42.7 | 45.5 | 43.9 | 45.3 | 43.1 | 100.0 | |
| mtFATP | 47.5 | 47.8 | 43.9 | 48.2 | 47.2 | 47.1 | 48.3 | 44.9 | 44.5 | 42.3 | 100.0 |

FIG. 7 mmFATP3 DNA sequence

```
ACGACTCACTATAGGGACAGCAGCTATCAGGTGGCATGCCAC 40
GCGTAACCTTCGGGGCTGACCATGCTCTAGAGGGGC 80
GGGACGGGCAAGCCTCTCAGGGCCGCTGCAGTCTGGCT 120
GCGGTCTGCGTAGGTGCGGGGCCAGCAGGGCACACAC 160
CTTGCTCATGCAGCGCGCCAGCGCTTTACCTAGGCGGAG 200
GCTGAGGCGAGCAAGGGATTCCTGCGGCTTTCTGC 240
GGCCAGCGCCTGCAGGGGGCGGGCAGGCTGCGCAG 280
GGGCAGCACTCAGGAAGGCGACGGGTGCGCCCTGGCT 320
GCAGATGCGCCTGCTACAGGACCAGCGCGGGCCTCTGG 360
CACGCGGGCGACGGTGCGCCTGCTGCTGGAGCGGGCC 400
```

FIG. 8A

```
GCATTTCCTTTGCATTTGGTTCGCACTGGCCAAAGCTGGC 440
CTCGGCAGGGCTTTGTGGGCACGGCTTTACGGGGAGGAC 480
CCCTGCTGCACTGCCTCGCCAGCTGCGGTGCCAGTGCCCT 520
CGTCCTGCCACAGAGTTCCTGGAGTCCCTGGAGCCGGAC 560
CTGCGGCCCTTGAGAGCCATGGGGCTCCACCTATCCCGA 600
CGGGCCCTGAAACTAATGTAGCTGGAATCAGCAATTTCCT 640
ATGGAAGCAGCAGACCAAGTGCATCACCAGTGCCGGGG 680
TACCTCTCTGCCCCCACAACATAATGGACACCTGCCTGT 720
ACATCTTCACCTCTGGCACTACTGGCCTGCCCAAGGCTGC 760
TGGAATCAGTCATCTGAAGGTTCTACAGTGCCAGGGATTC 800
TACCATCTGTGTGCCAGTCCACCAGGAGGACGTCATCTACC 840
TGGCACTGCCACTGTACCACATGTCTGGCTGCCTTCTGGG 880
CATTGTCGGCCTGCTTGGGCATTGCGGGCACCGTGGTGCTG 920
AAACCAAGTTCTCAGCTACCCAGTTCTGGACGATTGCC 960
AGAAACACAGGGTCACAGTGTTCCAGTACATTGCGGAGTT 1000
GTGCCGATACCTCGTCAACCAGCCCCGAGCAAGGCACAG 1040
TTTCACCATAAGGTGCCCTTGCCAGTGGGCAGTCCGTTGC 1080
GCCCACAGCACCTGGAGCGGTTTCCTCGCGCATTTGGACC 1120
TCTGCAGATACTGGAGACGTATGGCATCACAGAGGGCAAC 1160
GTAGCTACGTTCAATTACACAGGACGGCAGGGTGCAGTGG 1200
GGCCAGCTTCCTGGCTTTACAAGCACATCTTCGCCTTCTC 1240
CTTGATTCGATACCATGTCATGACAGGGCAGCCTATTCGG 1280
AATGCCCAGGGGCACTGCATGACCACATCTCCAGGTCAGC 1320
CAGGCCTACTGGTGGGGCCAGTGAGCCAGCAGTCCCCCTT 1360
CCTGGGCTATCCTGGGGCTCCGGAGCTGGCCAAGGACAAG 1400
CTGCTCAAGCCATGTCTTCTCGGTCTCGGGACGTTTCTTCA 1440
ATACTGGGGACCTCTTGGTCTGTGTCATCAGCAAGGCTTTCT 1480
TCACTTCCACGATCGTACTGGAGACACCATCAGGTGCAAG 1520
GGACAGAATGTGGCCACAACTGAAGTGGCTGAGGTCTTGG 1560
AGACCCTGGACTTCCTTCAGGAGGTGAACATCTATGGAGT 1600
CACGGTGCCAGGGCACGAAGGCAGGCAGCCATGCCGGCC 1640
TTGCCTCTCGCGGCCCCGCAGGCTCTGAACCTGGTGCAGC 1680
TCTACAGCCATGTTTCTGAGAACTTGCCACGGTATGCCCG 1720
ACCTCGGTTTCTCAGCCTCCAGGAATCTTTGGCCACTACT 1760
CAGAACTTCAAACAGCAGAAGGTTAGGATGGCCAATCAGG 1800
GCTTTCACCCCAGTCTACTGTCTCACCCACTCTATCTTCT 1840
GGACCAAGATATACGGGCCTACCTGCCCCTCACACCTGCC 1880
CCGTACAGTGCCCTCCTGTCTGGACACCTTCGAATCTGAA 1920
ACCTTCCACTTCAGGCACGGCCTCCAGGGTACAGGCCAC 1960
CATGGCCTGCACCAGCAGGGTTTTCGGGTATCTTTGTAT 2000
ATGGAGTCATTATTTGTAATAAACAGCTGCAGCTTAAAA 2040
AAAAAAAAAAAAAAAAAAAAAAAAAAAAAAAAAAAAAAAA 2080
AAAAAA 2087
```

FIG. 8B mmFATP3 protein sequence

```
AADPESSESGCSLAWRLAYLAREQPTHTFLIHGAQRFSYAEAERESNRIA 50
RAFLRARGWIGGRRGSGRGSTEEGARVAPPAGDAAARGTTAPPLAPGATV 100
ALLLPAGPDFLWIWFGLAKAGLRTAFVPTALRRGPLLHCLRSCGASALVL 150
ATEFLESLEPDLPALRAMGLHLWATGPEINVAGLSNLLSEAADQVDEPVP 200
GYLSAPQNIMDTCLYIFTSGTTGLPKAARISHLKVLQCQGFYHLCGVHQE 250
DVTYLALPLYHMSGSLLGTVGCLGTGATVVLKPKFSASQFWLDCQKHRVT 300
VFQYIGELCRYLVNQPPSKAEFDHKVRLAVGSGLRPDIWERFLRRFGPLQ 350
ILETYGMTEGNVATFNYTGRQGAVGRASWLYKHIFPFSLIRYDVMIGEPI 400
RNAQGHCMTTSPGEPGLLVAPVSQQSPFLGYAGAPELAKIDKLIKDVFWSG 450
DVFFNTGDLLVCDEQGFLHFHDRTGDTIRWKGENVATTEVAEVLEILDFL 500
QEVNIYGVIVPGHEGRAGMAALALRPPQAINLVQLYSHVSENLPPYARPR 550
FLRLQESLATTETFKQQKVRMANEGFDPSVLSDPLYVLDQDIGAYLPLTP 600
ARYSALLSGDLRI 613
```

FIG. 9 mmFATP4 DNA sequence

```
CCCACGCGTCCGCCACGCGTCCGGCATGGCCAAGCTGGG 40
CGTGGAGGCGGCTCTCATCAACACCAACCTTAGGCGGGAT 80
GCCCTGCGCCACTGTCTTGACACCTCAAAGGCACGAGCTC 120
TCATCTTTGGCAGTGAGATGGCCCTCAGCTATCTGTCAGAT 160
CCATGCTAGCCTGGAGCCCACACTCAGCCTCTTCTGCTCT 200
GGATCCTGGGAGCCCAGCACAGTCCCGTCAGCACAGACC 240
ATCTGGACCCTCTTCTGGAAGATGCCCGAAGCACCTGCC 280
CAGTCACCCAGACAAGGGTTTTACAGATAAGCTCTTCTAC 320
ATCTACACATGGGCACCACGGGCTACCCAAAGCTGCCA 360
TTGTGGTGCACAGCAGGTATTATCGTATGGCTTCCCTGCT 400
GTACTATGGATTCGCATGCGGCCTGATGACATTGTCTAT 440
GACTGCCTCCCCCTCTACCACTCAAGCACGAAACATCGTC 480
CGGATTGCCAGTCCTTACTCCACGGCATCACTGTGGTCAT 520
CCCGAAGAAGTTCTCAGCCTCCCGTTCTGGATCATTGT 560
ATCAAGTACAACTGCACAGTGGTACAGTACATTGCGAGC 600
TCTGCCCGCTACCTCCTGAACCAGCCACCCGTCAGGCTGA 640
GTCTCGGCACAAGGTCGCGCATGGCACTGGGCAACGGTCTC 680
CGGCAGTCCATCTGGACCGACTTCTCCAGCCGTTCCACA 720
```

FIG. 10A

```
TCCCCCAGGTGGCTGAGTTCTATCGGGCCACTGAATGGAA 760
CTGTAGCCTGGGCAACTTTGACAGCGGGTGGCCCCCTGT 800
GGCTTCAATAGCGGCATCCTGTCCTTTGTGTACCCTATCC 840
GTTTGGTAGGTGTCAATCACCATACCATGGAACTGATCCG 880
GGCACCCGATCCAGTCTGCATTCCCTGTCAACCAGGTCAG 920
CCAGGCCAGCTGGTGGGTGGCATCATCCAGCAGGACCCTC 960
TGCGCCGTTTCCAGCGGTACCTCAACCAGGGTGCCAACAA 1000
CAAGAACATTGCTAATGATGTCTTCAAGAAGGGGACCAA 1040
GCCTACCTCACTGGTCAGGTCCTGGTCATGCATGAGCTGG 1080
GTTACCTGTACTTCCGAGATGGCACTGGGACACGTTCCG 1120
CTGGAAAGGGAGAATGTATCTACCACTCAGGTGGAGGGC 1160
ACACTCAGCCGCCTGCTTCATATGGCAGATGTGGCAGTTT 1200
ATGGTGTTGAGGTGCCAGGAACTGAAGGCGAGCAGGAAT 1240
GGCTGCCGTTGCAAGTCCCATCAGCAACTGTCACCTGGAG 1280
AGCTTTGCACAGACCTTGAAAAGGAGCTGCCTCTGTATG 1320
CCCGCCCCATCTTCCTGCGCTTCTTGCCTGAGCTGCACAA 1360
GACAGGCACCTTCAAGTTCCAGAAGACACAGTTGCCGAAG 1400
GAGGGCTTTGACCCATCTGTTGTGAAAGACCCGCTGTTCT 1440
ATCTGGATGCTCGGAAGGGCTGCTACGTTGCACTGGACCA 1480
GCAGGGCTATACCGGCATCCAGCCAGGGCAGCAAGCTG 1520
TCATTTCCCCCCTACATCCCTCTGAGGGCACAAGATGCTG 1560
GATTCAGAGCCCTAGCGTCCACCCCAGAGGGTCCTGGCA 1600
ATGGCAGACCAAAGCTAGCAGGGCCCGCACCTCCGCCCT 1640
AGGTGCTGATCTCCCCTCTCCCAAACTGCCAAGTGACTCA 1680
CTGCCGCTTCCCCGACCCTCCAGAGGCTTTCTGTGAAAGT 1720
CTCATCCAAGCTGTGTCTTCTGGTCCAGGCGTGGCCCCTG 1760
GCCCCAGGGTTTCTCATAGCCTCCTTTAGCATGGTATCTT 1800
GGGTCCAGCGGGCCAGGGTGTGGCAGAGCAGTCACTAAGA 1840
TCCCTCCAATCAGAAGGGAGCTTACAAAGGAACCAAGGCA 1880
AAGCCTGTAGACTCAGGAAGCTAAGTGGCAGAGACTATA 1920
GTGCCCAGTCATCCCATGTCCACAGAGGATCTTGGTCCAG 1960
AGCTGCCAAAGTGTCACCTCTGCCTGCTGCACCTCTGGG 2000
GAAAGAGGAGCCATGTGGCCACTGGGCACCTGTCTCAA 2040
GAAGTCAGGATCACACACTCAGTCCTTGTTTCTCCAGGTT 2080
CCCTTCTTCTGTCTCGGGAGGGAGGGACCAGTGTCCTG 2120
TCTGTCCTTCCTGCCTGTCTGTCAGTCTGTGTGCCTTCTC 2160
CATCTGTCCTAGCCTGAGTGTGGGTGAACAGGCATGACG 2200
AGAGTGTGGCTCAGGGCCAATAAACTCTGCCTTGACTCC 2240
TCTTAAAAAAAAAAAAAAAAAAAAAAAAAAAAAAAAAAAA 2280
AAAAAAAAAAAAAAAAAAAAA 2301
```

FIG. 10B mmFATP4 protein sequence

```
HASAHASGMAKLGVEAALININLRRDALRHCLDTSKARAL 40
IFGSEMASAICEIHASLEPTLSLFCSGSWEPSIVPVSIEH 80
LDPLLEDAPKHLPSHPDKGFTDKLFYIVTSGTTGLPKAAI 120
VVHSRYYRMASLVYYGFRMRPDDIVYDCLPLYHSSRKHRG 160
DWQCLLHGMIVVIRKKFSASRFWDDCIKYNCIVVQYIGEL 200
CRYLLNQPPREAESRHKVRMALGNCLRQSIWIDFSSRFHI 240
PQVAEFYGATECNCSLGNFDSRVGACGENSRILSFVYPIR 280
LVRVNEDIMELIRGPDGVCIPCQPGQPGQLVGRIIQQDPL 320
RRFDGYLNQGANNKKIANDVFKKGDQAYLIGDVLVMDELG 360
YLYFRDRIGDIFRWKGENVSTIEVEGILSRLLHMADVAVY 400
GVEVPGTEGRAGMAAVASPISNCDLESFAQTIKKELPLYA 440
RPIFLRFLPELHKTGIFKFQKTELRKEGFDPSVVKDPLFY 480
LDARKGCYVALDQEAYTRIQAGEEKL 506
```

FIG. 11 mmFATP5 DNA sequence

```
CACTCATCAGAGCTAAGAGAGACTACACGCTCTCATCTAC 40
TTCAGAAAGAGCCAATGCCATGGGTATTTGCAAGAAACTA 80
ACCTTACTGCTGTTGCTGCTTCTGCTGGTTGCCCTGGGGC 120
AGCCCCCATGGCCAGCAGCTATGCCTCTGCCCCTGCGTTG 160
GTTCCTGGCGAGACCCACATGCCTTGTGCTGCTTGCCTTG 200
GCATTGCTGGGCAGACCCTGGATCAGCTCCTGGATGCCCC 240
ACTGGCTGAGCCTGGTAGCAGCAGCTCTTACCTTATTCCT 280
ATTGCCCTCTACAGCCACCCCCAGGGCTACGCTGGCTGCAT 320
AAAGATGTGGCTTTCACCTTCAAGATGCTTTTCTATGGCC 360
TAAAGTTCAGGCGACGCCTTAACAAACATCCTCCAGAGAC 400
CTTTGTGCATGCTTTAGAGCGGCAAGCACTGGCATGGCCT 440
GACCCGGTGGCCTTGGTGTGTACTGGGTCTCAGGGCTCCT 480
CAATCACAAATAGCCAGCTGGATGCCAGGTCCTGTCAGGC 520
AGCATGGGTCCTGAAAGCAAAGCTCAAGGATGCCGTAATC 560
CAGAACACAAGAGATGCTGCTGCTATCTTAGTTCTCCCGT 600
CCAAGACCATTTCTGCTTTCAGTCTCGTTTCTCGGGTTGGC 640
CAAGTTGGGCTGCCCTGTGCCCTGCATCAATCCACACAGC 680
CGACCGATGCCCTTGCTACACTCTGTACGGAGCTCTGGGG 720
CCAGTGTGCCTCATTGTGCATCCAGACCTCCAGCGAACCT 760
GGAAGAAGTCCTTCCCAAGCTGCTAGCTCAGAACATTCAC 800
```

FIG. 12A

```
TCCTTCTACCTTGGCCACAGCTCACCACCCGCCGAGTAG  840
AGGCTCTGGGAGCTTCCTCCATCCTCCACCTTCTGACCC  880
AGTACCTCCCAGCCTTCGAGCTACGATTAAGTGGAAATCT 920
CGTGCCATATTCATCTTACTTCAGGACCACTCCACTCC   960
CAAAGCCAGCCATCTTATCACATGAGGGGTCATACAAGT 1000
GAGCAAGGTCCTGTCCTTCTGTGGATGCAGAGCTGATCAT 1040
GTCGTCTATGAGGTCCTACCTCTGTACCATAGGATAGGGC 1080
TTGTCCTTGGATTCCTTGGCTGCTTACAAGTTGCAGCCAC 1120
CTCTGTCCTCGCCCGCAAGTTCTCTGCCTCCGCATTCTGG 1160
GCTCACTGCCCGCAGCATGCCGTAACACGTCATCTTGTATC 1200
TGGGTCAAATCCTGCGGTACTTGTGTAACGTCCCTGAGCA 1240
ACCAGAAGACAAGATACATACAGTCGCGCTTCGCCATGCCA 1280
ACTGGACTTCGCGCAAATGTGTCGAAAACTTCCAGCAAC 1320
GCTTTGCCTGCCATTGGATCTCGCCAATTCTACGGATCCAC 1360
AGAGGGCAATGTGGCGGTTAATCAACTATGTCGGCCACTGC 1400
GCGCCTCTGTCGGAAGGACCAGCTGCATCCTTCCAATGCTCA 1440
CTCCCTTTCAGCTTGTACAGTTCCACATACAGCAGCAGA 1480
GCCTCTCAGCCACAAACAGGGTTTTGCCATTCCTCTGCAG 1520
CCAGCAAAGCCAGGACTTCTTTGACCAAGGTTCGAAAGA 1560
ACCAACCCTTCCTCGGCTACCGTGGTTCCAGGCCCAGTC 1600
CAATCCGAAACTTCTTGCCAATGTACCACGCGTAGCACAC 1640
CTCGTACTTCAACACTGGGACGTCCTCACCTTCGACCAGG 1680
AAGCCTTCTTCTACTTTCAAGACGGCTTCGTCACACCTT   1720
CCGCTCCAAGGGCGAAAACGTATCTACTGCAGCGTCCAG 1760
TGTCTTTTGTCTAGCCTACACTTCCTACAGGAAGTCAATG 1800
TCTATCCGTGTCCCTCTGCCAGCGTGTCAGCGTAAGGTTGG 1840
CATGCCTGCCTGTCAAACTGCCTCCTGCCAACACTTTTCAT 1880
GGGCAGAAGCTATACCAGCATGTCGCCTCCTGGCTCCCTG 1920
CCTATCCCACAGCTCATTTCATCGGTATCCAGGATTCGCT 1960
CGACATCACAAACAGGTACAAGCTGGTAAAGTCACCGCTG 2000
GTCGCTCAGCCGTTTCATCTGCGCATCATTCCTCACCCCC 2040
TCTACATACTGCACAACAAGCGCAGACCTTCCGCACTCT  2080
CATGCCAGATCTGTACCAGGCTGTGTGTCAAGCAACCTGG 2120
AATCTCTGACCACCTAGCCAACTGCAAGGCAATCAAAAG   2160
TGTAGAGATTCACACTAGTCAGCTTCACAAAGTTGTCGGG 2200
GTTCCAGATGCCCATGCCCAGTAGTACTTACAGAATAAA   2240
CTTCAATGTGTATACAAAAAAAAAAAAAAAAAAAAAAA    2277
```

FIG. 12B mmFATP5 protein sequence

```
MALALRWFLGDPTCLVLLGLALLGRPWISSWMPHWLSLVG 40
AALTLFLLPLQPPPGLRWLHKDVAFTFKMLFYGLKFRRRL 80
NKHPPETFVDALERQALAWPDRVALVCIGSEGSSTINSQL 120
DARSCQAAWVLKAKLKDAVIQNIRDAAAILVLPSKTISAL 160
SVFLGLAKLGCPVAWINPHSRGMPLLHSVRSSGASVLIVD 200
PDLQENLEEVLPKLLAENIHCFYLGHSSPTPGVEALGASL 240
DAAPSDPVPASLRATIKWKSPAIFIFTSGTTGLPKPAILS 280
HERVIQVSNVLSFCGCRADDVVYDVLPLYHTIGLVLGFLG 320
CLQVGATCVLAPKFSASRFWAECRQHGVTVILYVGEILRY 360
LCNVPEQPEDKIHIVRLAMGTGLRANWWKNFQQRFGPIRI 400
WEFYGSTEGNVGLMNYVGHCGAVGRTSCILRMLTPFELVQ 440
FDIETAEPLRDKQGFCIPVEPGKPGLLLIKVRKNQPFLGY 480
RGSQAESNRKLVANVRRVGDLYFNIGDVLTLDQEGFFYFQ 520
DRLGDIFRWKGENVSTGEVECVLSSLDFLEEVNVYGVPVP 560
GCEGKVGMAAVKLAPGKTFDGQKLYQHVRSWLPAYATPHF 600
IRIQDSLETTNIYKLVKSRLVREGFDVGLIADPLYILDNK 640
AQIFRSLMPDVYQAVCEGIWNL 662
```

FIG. 13 hsFATP2 DNA sequence

```
ATGGCATTGACTCTTTCCTGGACAAAGTGGATGAAGTATC 40
AACTGAACCTATCCAGAGTCATGGAGGTCTGAAGTCACT 80
TTTTCCACTCCTGCCTTATACATTATACTTCTGGAACCA 120
CAGGTCTTCCAAAAGCAGCCATGATCACTCATCAGCGCAT 160
ATGGTATGCAACTGGCCTCACTTTTGTAAGCGGATTGAAG 200
GCAGATGATGTCATCTATATCACTCTGCCCTTTTACCACA 240
GTCCTGCACTACTGATTGGCATTCACCATGTATTGTGGC 280
TGGTGCTACTCTTGCCTTGCGGACTAAATTTTCAGCCAGC 320
CAGTTTTGGGATGACTGCAGAAAATACAAGGTCACTGTCA 360
TTCAGTATATCGGTCAACTGCTTCGGTATTTATGCAACTC 400
ACCACAGAAACCAAATGACCGTGATCATAAAGTGAGACTG 440
GCACTGCCAAATGCCTTACCAGGACATGTGTGGACAAT 480
TTGTCAAGAGATTTGGGACATATGCATCTATCAGTTCTA 520
TGCTGCCACTGAAGGCAATATTGCATTTATGAATTATGCG 560
AGAAAAGTTGGTGCTGTTGCAAGAGTAAACTACCTACAGA 600
AAAAAATCATAACTTATGACCTCATTAAATATGATGTGGA 640
GAAAGATGAACCTGTCCGGTCATCAAAATGGATATTGCGTC 680
AGAGTTCCCAAAGGTCAAGTTGCACTTCTGGTTTGCAAAA 720
TCACACAACTTACACCATTTAATGGCTATGCTGGAGCAAA 760
GGCTCAGACACAGAAGAAAAACTGAGAGATGTCTTTAAG 800
```

FIG. 14A

```
AAAGGAGACCICTATTTCAACAGTCGAGATCTCTTAATGG 840
TTGACCATGAAAATTTCATCTATTTCCACGACAGAGTTGG 880
AGATACATTCGGTTGGAAAGGCGAAAATGTGGCCACCACT 920
GAAGTTGCTGATATAGTTGGACTGGTTGATTTTTTTCCAA 960
CGAAGTAAAATGTTTATCGGAGTGCATCGGCCAAGATNAT 1000
CGAGGTTCGAATTGGCATGGCNTTCCNTTCAAAATGGAAA 1040
GAAAACCATGGAATTCATCGAAACAAATTTTTTCAGNAC 1080
ATTGCTGATAACCNACCTACTTATGCAAGGCCCGGGTTTT 1120
NTAAGAANACAGGACACCATTCAGATCACTGGAATTTTTA 1160
AACACGGCAAAATGACCTTTCGTGGAGGAGGGCTTTAACC 1200
CNGCTGTCATCAAAGATGCCTTCTATTTTCTTGGATGACA 1240
CAGCAAAAATGTATGTGCCTATGACTGACGACATNTATAA 1280
TGCCATAAGTGNTAAAACCCTGAAATTNTGAATATTCCCA 1320
GGAGGATAATTCAACATTTCCAGAAGAAACTGAATGGAC 1360
AGCCACTTGATATAATCCAACTTTAATTTGATTGAAGATT 1400
GTGAGGAAATTTTGTAGGAAATTTGCATACCCGTAAAGGG 1440
AGACTTTTTTAAATAACAGTTGAGTCTTTGCAAGTAAAAA 1480
GATTTAGACATTATTATTTTTCAGTGTGCACCTACTGTTT 1520
GTATTTGCAAACTGAGCTTGTTGGAGGGAAGGCATTATTT 1560
TTTAAAATACTTAGTAAATTAAAGAACACCAACATGTGAA 1600
AAAAAAAAAAAAAAAAAAAAAA 1622
``` hsFATP2 protein sequence

```
YIYISGTTGLPKAAMTTHQRIWYGIGLTTFVSGLKADDVTY  40
ITLPFYHSAALLTGIHGCTVAGATTALRIKFSASQFWDDC   80
RKYNVTVTQYTGELLRYLCNSPQKPNDRDHKVRLALGNGL 120
RGDVWRQFVKRFGDICTYEFYAATEGNIGFMNYARKVGAV 160
GRVNYLQKKTTTYDLIKYDVEKDEPVRDENGYCVRVPKGE 200
VGLLVCKTTQLTPFNGYAGAKAQTEKKKLRDVFKKGDLYF 240
NSGDLLMVDHENFTYFHDRVGDIFRWKGENVATTEVADIV 280
GLVDFF 286
``` hsFATP3 DNA sequence

```
CAATTGGGGACCCCCAGGGGCACTGTATGGCACATCTCC  40
AGGTCAGCCAGGGCAAGTTGCTAAAGGATGTCTCGGCC   80
TGCCATGTGTTTTCTTCAACACTGGGACCTGCTGGTCTGC 120
GATGACCAAGGTTTTCTCCGCTTCCATGATCGTACTGGAG 160
```

```
ACACCTTCAGGTGGAAAGGGAGAATGTTGCCCACAACCGA 200
GGTGGCACAGGTCTTGAGGCCCTAGATTTTCTTCAGGAG 240
GTGAACGTCTATGGAGTCACTGTGCCAGGGCATGAAGCA 280
GGGCTGGAATGGCAGCCCTAGTTCTGCGTCCCCCACGC 320
TTTCCACCTTATGCAGCTCTACACCCACGTGTCTGAGAAC 360
TGCCACCTTATGCCGGCCCGATTCCTCAGCCTCCAGG 400
AGTCTTTGGCCACCACAGAGACTTCAAACAGCAGAAAGT 440
TGGATGGCAAATGAGGGCTTGACCCAGCACCCTGTCT 480
CACCCACTGTACGTTCTGCACCAGGCTGTAGGTGCCTACC 520
TGCCCCTCACAACTGGCGGTACAGGGCCCTCCTGGCAGG 560
AAACCTTCGAATCTGAGAACTTCCACACCTGAGGCACCTG 600
AGAGAGCAACTCTGTGCGGTGGGCGGGGTTGCAGGTGTAC 640
TGGGCTGTCAGGGATCTTTCTATACCAACTGCGGTCA 680
CTATTTTGTAATAAATGTGCCTGGAGCTGATCCAGCTGTC 720
TCTGACCTACAAAAAAAAAAAAAAAAAAAAAA 753 hsFATP3 protein sequence

QFGTPRGTVWPHLQVSQGKLLKDVFRPGDVFFNIGDLLVC 40
DDQGFLRFHDRTGDTFRWKGENVATTEVAEVFEALDFLQE 80
VNVYGVIVPGHEGRAGMAALVLRPFHALDIMQLYTHVSEN 120
LPPYARPRFLRLQESLATTEIFKQQKVRMANEGFDPSTLS 160
DPLYVLDQAVGAVLPLTTARYSALLAGNLRI 191 hsFATP4 DNA sequence

TCAAGTACAACTGCACGATTGTCATANCATTGGTGAACTG 40
TGCCGNTACCTCCTGAACCAGCCACCGCGGAGGCAGAAA 80
ACCAGCACCAGGTTCGCATGGCACTAGGCAATGGCCTCCG 120
GCAGTCCATCTGGACCAACTTTTCCAGCCGCTTCCACATA 160
CCCCAGGTGCCTGAGTTYTACGGGGCACAGAGTGCAACT 200
GTAGCCTGGCCAACTTCGACAGCCAGGTGGGGCCCTGTGG 240
TTTCAATAGCGGCATCCTGTCCTTCGTGTACCCATCCGG 280
TTCGTACGTGTCAACGACGACACCATGCAGCTGATCCGGG 320
GGCCGGCAGGCGGTCTGCATTCCCTGCCAGCCAGGTGAGCC 360
GGGCCAGCTGGTCGGCCGCATCATCCAGAAGACCCCCTG 400
CGCGGCTTCGATGGCTACCTCAACCAGGCGGCAACAACA 440
AGAAGATTGCCAAGCATGTCTTCAACAACGGGACCAGGC 480
CTACCTTACTGGTCATGTGCTCGATCCATCCAGCTGGGC 520
```

```
TACCTGTACTTCCGAGACGGCACTGGGACACGTTCCGCT 560
CGAAAGGTCAGAACGTGTCCACCACCGAGGTGGAAGGCAC 600
ACTCAGCGGCTGCTGCACATGGCTCACGTGGCCGTGTAT 640
CGTGTCCAGGTGCCAGGAACCGAGGCCGGGCCGGAATGG 680
CTGCCTGTCGCAGCCCACTGGCAACTGTCACCTGCCAGC 720
GCTTTCCTCAGGTC 734
``` hsFATP4 protein sequence

```
IGELCRYLLNQPPREAENQHQVRMALGNGLRQSIWINFSS 40
RFHLPQVAEFYGATECNCSLGNFDSQVGACGENSRILSFV 80
YPIRLVRVNEDIMELIRCPDGVCIPCQPGEPGQLVGRIIQ 120
KDPLRRFDGYLNQGANNKKIAKDVFKKGDQAYLIGDVLVM 160
DELGYLYFRDRIGDIFRWKGENVSTTEVEGILSRLLIMAD 200
VAVYGVEVPGIEG 213
``` hsFATP5 DNA sequence

```
CNTGCCTCTTGTACCACGTGATGGACTTTGTCGTTGGCA 40
TCCTCGGCTGCTTACATCTGGAGCCACCTGTGTTCTCGGC 80
CCCAAGTTCTCTACTTCCTGCTTCTCGGATGACTGTCGG 120
CAGCATGGCGTCACAGTCATCCTGTATGTCGGCCAGCTCC 160
TGCGNTACTTGTCTAACATTCCCAGCAACCAGAGGACG 200
GACACATACAGTCGCCTGGCAATGGGCAATGGACTACGG 240
GCTCATGTGTCGGGAGACCTTCCAGCAGCCGTTTCGGTCCT 280
ATTTCGGATCTNGGCAAGTCTTACGGGCTYCCACAGAAGG 320
GCAACATGGGGCTTTAGTTTCAACTATTGTTGGGGCGCTG 360
CGGGGSCCTGGCRGGCAAAGATGGAGCTTGCCTCCTCGAA 400
TGCTGTCCCGCTTTCAGCTGGTGCAGTTCCACATGCAGGC 440
GGGCGAGCCTGTCAGCGACAATCAGGGCTTCTGCATCCCT 480
GTACGCCTACGGGACCGGCGGCTGCTGTTGACCAAGGTGG 520
TAAGCCAGCAACCCTTCGTCGGCTACCGCGGCCCCGAGA 560
GCTGTCCGAACGGAAGCCTGGTCGCGCAACGTCGCGCAATCG 600
GGGCACGTTTACTACAACACGGGCAGGTACTGGCCATCG 640
ACGGCGAAGCCTTCCTCTACTTCGCCACCGACTCGGGCA 680
CACCTTCCGATGCAAGGCGACGAAGGTCTCCAGCACGAG 720
GTGGACGGCGTGTTGTCGCAGGTGGACTTCTTCCAACAGG 760
TTAACGTGTATGCGGTCGTCGTCCAGGTTGTCAGCGTAA 800
GGTCGGCCATGGCTGCTGTCGGCATTAGCCCCGGCCAGACT 840
```

```
TTCGACGGGAGAAGTTGTACCAGCACGTTCGCGCTTGGC 880
TCCCTGCCTACGCTACGCCCCATTTCATCCGCATCCAGGA 920
CGCCATGGAGGTCACCAGCACGTTCAAACTGATGAAGACC 960
CGGTTCGTGCCGTCAGGGCTTCAATGTGGGCATCGTGGTTG 1000
ACCCTCTGTTTGTACTGGACAACGGGGCCAGTCCTTCCG 1040
GCCCCTGACGGCAGAAATGTACCAGGCTGTGTGTGAGGCA 1080
ACCTGGAGGCTCTGATCACCTGGCCAACCCACTGGGGTAG 1120
GCATCAAAGCCAGCCACCCCACCCCAACACACTCGGTGT 1160
CCCTTTCATCCTGGGCCTGTGTAATCCAGCCTGGCCAT 1200
ACCCTCAACCTCAGTGGGCTGGAAATGACAGTCGGCCCTG 1240
TAGCAGTGGCAGAATAAACTCAGNTGYGTTCACAGAAA 1278
``` hsFATP5 protein sequence

```
EGQHGALVQLLLGALRGPGGKDGACLLRMLSPFELVQFDM 40
EAAEPVRDNQGFCIPVGLGEPGLLLIKVVSQQPFVGYRGP 80
RELSERKLVRNVRQSGDVYYNTGDVLAMDREGFLYFRDRL 120
GDTFRWKGENVSIHEVEGVLSQVDFLQQVNVYGVCVPGCE 160
GKVGMAAVALAPGQTFDGEKLYQHVRAWLPAYATPHFIR 199
``` hsFATP6 DNA sequence

```
CGCTTGTGTGTTAAAGAAGAAATTTTCAGCAAGCCAGTTT 40
TGCAGTCACTGCAAGAAGTATGATGTCACTGTGTTTCAGT 80
ATATTGGAGAACTTTGTCGCTACCTTTGCAAACAATCTAA 120
GAGAAGGAGAAAGGATCATAAGGTGCGTTTGGCAATT 160
GGAAATGGCATACCGAGTCATGTATGGAGAGAATTTTTAG 200
ACAGATTTGGAAATATAAAGGTGTGTGAACTTTATGCAGC 240
TACCGAATCAAGCATATCTTTCATGAACTACACTGGGAGA 280
ATTGGAGCAATTGGGAGAACAAATTTGTTTTACAAACTTC 320
TTTCCACTTTTTGACTTAATAAAGTATGACTTTCAGAAGA 360
TGAACCATCAGAAATCAGCAGGTTGGGTATTCATGAGA 400
AAAAGGAGACCTGGACTTCTCATTTCTCGAGTGAATGCAA 440
AAAATCCCTTCTTTGGCTATGCTGGCCCTTATAAGCACAC 480
AAAAGACAAATTGCTTTGTCATGTTTTTAAGAAGGGAGAT 520
GTTTACCTTAATACTGGAGACTTAATAGTCCAGGATCAGG 560
ACAATTTCCTTTATTTTCGGACCGTACTGGAGACACTTT 600
CAGATGGAAAGGAGAAATGTCGCAACCACTCAGGTTGCT 640
GATGTTATTGGAATGTTCCATTTCATACACCAAGCAAACG 680
TCTATGGTGTCGCTATATCAGGTTATGAAGGAAGAGCAGG 720
```

```
AATGGCTTCTATTATTTTAAAACCAAATACATCTTTAGAT 760
TTGGAAAAGTTTATGAACAAGTTGTAACATTTCTACCAG  800
CTTATGCTTGTCCAGGATTTTAAGAATTCAGGAAAAAT   840
GGAAGCAACAGGAACATTCAAACTATTGAAGCATCAGTTG 880
GTGGAAGATGGATTTAATCCACTGAAAATTTCTGAACCAC 920
TTTACTTCATGGATAACTTGAAAAGTCTTATGTTCTACT  960
GACCAGGGAACTTTATGATCAAATAATGTTAGGGAAATA  1000
AAACTTTAAGATTTTTATATCTAGAACTTTCATATGCTTT 1040
CTTAGGAAGAGTGACAGGGGGGTATATGATTCTTTATGAA 1080
ATGGGAAAGGGAGCTAACATTAATTATGCATGTACTATA  1120
TTTCCTTAATATGAGAGATAATTTTTTAATTGCATAAGAA 1160
TTTTAATTTCTTTTAATTCATATAAACACAGTTGATTATT 1200
CTTTTTATCTATTTCCAGATTCAGTGCATAACTAAGTATT 1240
TTCCTTAATACTAAAGATTTTAAATAATAAATAGTGGCTA 1280
GCGGTTTGGACAATCACTAAAAATGTACTTTCTAATAAGT 1320
AAAATTCTAATTTTGAATAAAAGATTAAATTTTACTGAA  1360
A 1361
```

FIG. 22B hsFATP6 protein sequence

```
ACVLKKKFSASQFWSDCKKYDVIVFQYIGELCRYLCKQSKREGEKDHKVR 50
LAIGNGIRSDWWREFLDRFGNIKVCELYAATESSISFMNYTGRIGAIGRT 100
NLFYKLLSTFDLIKYDFQKDEPMRNEQGWVFMRKRRPGLLISRVNAKNPF 150
FGYAGPYKHIKDKLLCDVFKKGDVYLNIGDLIVQDQDNFLYFWDRTGDIF 200
RWKGENVATTEVADVIGMLDFIQFANVYGVAISGYEGRAGMASTILKENT 250
SLDLEKVYEQVVTFLPAYACPRFLRIQEKMEATGIFKLLKHQLVEDGFNP 300
LKTSEPLYFMDNLKKSYVLLTRELYDQIMLGEIKL 335
```

FIG. 23 mtFATP DNA sequence

```
TAGTCGATAACGTCAAGGAGGCTCTGCGGGCCTGCGCACC 40
TTCCTGAGGTTGGTGGACAACCAATTCGACATTTCGCAAA 80
CGAATCGAGGGCTTAGGTGTCCGATTACTAGGGGGCCA   120
CACACAAGGTCAGGCTGATCGACCTGCCAACTGGATGC   160
GGCGAGTGTTGGCGACAGGCGGTCATTGTCCGTGGGC    200
AATGACCGGCTGCTGGCCCGGCCGAATTCAAGCGGTCG   240
ATCGGCAGGGTGTTCCAGGACGGGCGCCTGCCTACGGTG  280
ACCGAGTCTTCCTGAAATTCGGCGATCAGCAGCTGACCTA 320
CGGCACGCTAACGCCACGGCCAACGGTACGCGGGGTG   360
```

FIG. 24A

```
TTGGCCGCCGCGGCGTCGGCCGCCGGCGACGTCGTTGGCA  400
TCATGTTGCGTAACTCACCAGCACAGTCTTGCCCATGCT  440
GGCCACGGTCAAGTCGGCGGCTATCGCGGCATGCTCAAC  480
TACCACCAGCGCGGCGAGGTGTTGCGCACAGCCTGGGTC  520
TGCTGGACGCGAAGGTACTCATCGCAGAGTCGACTTCGT  560
CAGCGCGTGCCGAATCGGCGGCCTGCCGCGGCCGGGTA  600
GCGGCGCACGTGCTGACGGTCGAGGACGTGGAGCCGATTCG  640
CCACAACGGCGCCCGCCACCAACCGGCGTCGGCGTCGGC  680
CGTGCAAGCCAAAGACACGGCGTTCTACATCTTCACCTCG  720
GCCACCACGGATTTCCCAAGGCCAGTGTCATGACCCATC  760
ATCGGTGGCTGGGGGGCTGGCCGTCTTGCCAGCCATCGG  800
GCTGCGGCTGAAGGGTTCGACAGGCTCTACAGCTCCCTG  840
CCGCTGTACCAACAACGGCGTTAACCGTCGCGCTGTCGT  880
CCGGTCATCAATTCTGCCGCCACCCTCCGCCTGGGTAAGTC  920
GTTTTGCGCGTGCGCGTTCTCGCATCAGGTGATTGCCAAC  960
CGGCCCGACGGCGTTCGTCTACATCGGCGAAATCTGCCGTT  1000
ATCTGCTCAACCAGCGCGGCAAGCGCGACCACCGTGCCCA  1040
CCAGGTCGCGGGTCATCTGCGGTAACGGCCTGCGGCCGGAG  1080
ATCTGGATCAGTTCACCACCGGCTTCGGGGTCGCGCGG  1120
TGTCCCAGTTCTACGCCGCAGCGAAGGCAACTGGCCTT  1160
TATCAACATCTTCAACGTGCCCAGGACCGCGGGGTATCG  1200
CCGATCGCGCTTGCCTTTGTCGAATACCACCTGCACACCG  1240
GCGATCGCCTGCGGCATGCGAGCGGGCAGTGCGCTCGGGT  1280
ACCCGACGGTCAACCGGCCTGTTCCTTAGCCGGGTCAAC  1320
CGGCTGCAGCGCGTTCGACGCGCTACACCGACCCGGTTGCCA  1360
GCGAAAAGAAGTTGGTGCGCCAAGGCTTTTCGAGATCGGCGA  1400
CTGTTGCGTTCAACACCGGCCACGTCATCAGCCGCAGGGC  1440
ATGGCCCATCGCGCCTTCGTCGATCGCCTGGCGCACACCT  1480
TCGGCTCGAAGGGCCAGAATGTCGCCACCACTCAGGTCGA  1520
AGGGCCACTCGCCTCCGACCACGCGTCGAGGAGTGCACG  1560
GTCTACGCGGTCCAGATTCGCGCGCACCGCGGGCGCGCCG  1600
CAATGGCCGCGATCACACTGCGCGCTGGCGCCGAATTCGA  1640
CGGCCAGGCGCTGGCCGCGAACGGTTTACGGTCACTTGCCC  1680
CGGTATGCACTTCGCGTCTTTCTTCGGGTACTGCGGGTCGC  1720
TGCGCACACCACGAGTTCAACAGTCGCAAGGTGGCAGTT  1760
GGCCAACCAGGCGTATGCGCGCACATCAGGATCGGCTG  1800
TACGTACTGGCCGCCGCGACGAAGGATATCTGCCCGTACT  1840
AGCCCGAATACCCTGACCAGCGTTTGCCTGGAAGGCGACC  1880
GCAGGGCTACGCCATTCGCGGCGCAGTCTCGATACCCGCA  1920
CTGCACGCTGCAGGTAACCAGGCACTATGCATCGGTGGCG  1960
TTCAACACCGCGGCCCTCAGCGCGGTCGTTCAACACCGGCCG  2000
GCGTTAG 2007
```

FIG. 24B mtFATP protein sequence

```
msdyyggahttvrlidlatrmprvladtpvivrgamtgll  40
arpnskasigtvfqdraarygdrvflkfgdqgltyrdana  80
tanryaavlaargvgpgdvvgimlmspstvlamlatvkc  120
gaiagmlnyhqrgevlahslglldakvliaesdlvsavae  160
cgasrgrvagdvltvedverfattapatrpasasavqakd  200
tafyiftsgttgfpkasvmthhrwlralavfggmglrlkg  240
sdtlysclplyhnnaltvavssvinsgatlalgksfsasr  280
fwdevianratafvyigeicryllngpakptdrahqvrvi  320
cgnglrpeiwdefttrfgvarvcefyaasegnsafinifn  360
vprtagvspmplafveydldtgdplrdasgrvnrvpdgep  400
glllsrvnrlqpfdgytdpvasekklvrnafrdgdcwfnt  440
gdvmspggmghaafvdrlgdtfrwkgenvattqveaalas  480
dgtveectvygvqiprtggragmaaitlragaefdgqala  520
rtvyghlpgyalplfvrvvgslahtttfksrkvelmqay  560
gadiedplyvlagpdegyvpyyaeypeevslgmrpqg  597
```

FIG. 25 hsFATP1

```
  1  tcg acc cac ggc gtc cgg gac ccc aaa gca gaa gcc cgc aca gta ggc aca gcg cac cca
                                                                               M   R
 61  aga agg gtc cag gag ctg tct gca gaa aca gaa agg tcc ccg gcc tca gcc tag tcc ctg
                                                                               L   G   L
121  cct gcc tcc ctg tgc ctg agc ctg agc ttc tgg gag act gaa ggc acg gct tgc agc ttc agg atg cgc
      P   A   P   W   S   L   C   L   S   L   S   F   W   E   T   E   G   T   A   C   S   F   R  W  R
181  gct ccg ggt gcg ggc gcc gcc gcg gcc tcg gtg gtc ctg ctg gcg ctg ttg tgg ctg ggg ctg
      A   P   G   A   G   A   A   A   A   S   V   V   L   L   A   L   L   W   L   G   L
241  ccg tgg acc agc tgg agc agc gcc gcc gca gcg gtg tac ctc ggt gtg tgg ggc agc ggc tgg cgc
      P   W   T   S   W   S   S   A   A   A   A   V   Y   L   G   V   W   G   S   G   W   R
301  ttc ctg cgc ata gtc cgc aag acc tgc aga gac cga gac ctt ggt gtc tct gtg atc
      F   L   R   I   V   R   K   T   C   R   D   R   D   L   F   G   V   L   S   V   L   I
361  cgc gtg cgc ctg gag cag cgg cac cag cgg cac ccc gag cgc ctg gcg ctg gcg acc atc ccg cgc att ttt
      R   V   R   L   E   Q   R   H   Q   R   H   P   E   R   L   A   L   A   T   I   P   R   I   F
421  cag gcg gta gtg acc ttt gcg ccg gac cag ctg gac gtg ggc gtg gat gcc aac ctc ttc gag gag
      Q   A   V   V   T   F   A   P   D   Q   L   D   V   G   V   D   A   N   L   F   E   E
481  tgc tgg acc ttt gcc cag gcg ccc gcg gac ctg gac gcc tac tcc aat gcg gta gcc ttc ctg gag ccg cgg gag ttc gtg
      C   W   T   F   A   Q   A   P   A   D   L   D   A   Y   S   N   A   V   A   F   L   E   R   P   E   F   V
541  ctg ggc ttc gcg ccg ccg ggc gac gtg gcc atc ttc gag ggc cgg ccg gag ttc gtg
      L   G   F   A   P   P   G   D   V   A   I   F   E   G   R   P   E   F   V
601  ggg ctg tgg ctg ggc ctg gcc aag gcg ggc atg gag gcg ctg ctc aac gtg aac ctg
      G   L   W   L   G   L   A   K   A   G   M   E   A   L   L   N   V   N   L
```

FIG. 26A

```
661   cgg cgc gag ccc ctg gcc ttc tgc ctg acc tcg ggc gct aag gcc ctg atc ttt gga
      R   R   E   P   L   A   F   C   L   T   S   G   A   K   A   L   I   F   G 721   gga gaa atg gtg gcg gtg gcc gaa gtg agc gcc ggg cat ctg ggg aaa gcc agt ttg atc aag
      G   E   M   V   A   V   A   E   V   S   A   G   H   L   G   K   S   L   I   K 781   ttc tgc tct gga gac ttg ggg ccc gag ggc atc ttg ccg gac acc cac ctc ctg gac ccg
      F   C   S   G   D   L   G   P   E   G   I   L   P   D   T   H   L   L   D   P 841   ctg ctg aag gag gcc tct act gcc ccc ttg gca cag atc ccc agc aag ggc atg gac gat
      L   L   K   E   A   S   T   A   P   L   A   Q   I   P   S   K   G   M   D   D 901   cgt ctt ttc tac atc tac acg tcg ggg acc ggg ctg ccc aag gct gcc att gtc gtg
      R   L   F   Y   I   Y   T   S   G   T   G   L   P   K   A   A   I   V   V 961   cac agc agg tac tac cgc atg gca gcc ttc ggc cac cac tac cgc atg cag gcg gct
      H   S   R   Y   Y   R   M   A   A   F   G   H   H   Y   R   M   Q   A   A 1021  gac gtg ctc tat gac tgc ctg ccc ctg tac cac tcg gca gga aac atc atc ggc gtg ggg
      D   V   L   Y   D   C   L   P   L   Y   H   S   A   G   N   I   I   G   V   G 1081  cag tgt ctc atc tat ggg ctg aca gtc ctc cgc aag aaa ttc tcg gcc agc cgc ttc
      Q   C   L   I   Y   G   L   T   V   L   R   K   K   F   S   A   S   R   F 1141  tgg gac gac tgc atc aag tac aac tgc acg gtg gtt cag tac atc ggg gag atc tgc cgc
      W   D   D   C   I   K   Y   N   C   T   V   V   Q   Y   I   G   E   I   C   R 1201  tac ctg ctg aag cag ccg gtg cgc gag agg cga cac cgc cgc gtg cgc ctg gcg gtg
      Y   L   L   K   Q   P   V   R   E   A   E   R   R   H   R   R   V   R   L   A   V
```

FIG. 26B

```
1261  ggg aac ggg ctg cgt cct gcc atc tgg gag gag ttc acg gag cgc ttc ggc gta cgc caa
       G   N   G   L   R   P   A   I   W   E   E   F   T   E   R   F   G   V   R   Q 1321  atc ggg gag ttc tac ggc gcc acc gag gcc aac tgc agc aac att gcc aac atg gac aag
       I   G   E   F   Y   G   A   T   E   A   N   C   S   N   I   A   N   M   D   K 1381  gtc ggc tcc tgt ggt ttc aac aca agc cgc atc ctg ccc cac gtg tac ccc atc cgg gtg
       V   G   S   C   G   F   N   T   S   R   I   L   P   H   V   Y   P   I   R   V 1441  aag gtc aat gag gac aca atg gag ctg ggt cgg gat gcc ctc tgc ggc atc ccc tgc
       K   V   N   E   D   T   M   E   L   G   R   D   A   L   C   G   I   P   C 1501  cag gcc ggg gag cct gtc agc agc gag gag ctt gtg cag caa aac atc gcc cac cgc cgc
       Q   A   G   E   P   V   S   S   E   E   L   V   Q   Q   N   I   A   H   R   R 1561  ttc gat ggc tat gtc agc gcc tac ctc tca ggt cag atc aag aag ctg atg gat gag agc
       F   D   G   Y   V   S   A   Y   L   S   G   Q   I   K   K   L   M   D   E   S 1621  aag ggc gac agc agc gcc tac ctc tca ggt gac gtg cta gtg atg ggg cga tgg cgc acc
       K   G   D   S   S   A   Y   L   S   G   D   V   L   V   M   G   R   W   R   T 1681  tac ttc cgg gac cgt gtc agc gac acc ttc cgc ctg ggc cag aca gac gtg gcc gtc tat ggg gtg
       Y   F   R   D   R   V   S   D   T   F   R   L   G   Q   T   D   V   A   V   Y   G   V 1741  gag gtg gag ggc gtg ctg agc cgc ctg ggc atg gcg gcc gtc gca gac ccc cac agc ctg
       E   V   E   G   V   L   S   R   L   G   M   A   A   V   A   D   P   H   S   L 1801  gct gtt cca gga ggt aag gca ggg gag aag gtg cag gag ctg cag gag gtg gca ccc tat gcc cgg ccc
       A   V   P   G   G   K   A   G   E   K   V   Q   E   L   Q   E   V   A   P   Y   A   R   P 1861  ctg gac ccc aac gcg ata tac cag gag ctg cag aag gtg ctg gca ccc ccc cgg ccc
       L   D   P   N   A   I   Y   Q   E   L   Q   K   V   L   A   P   Y   A   R   P
```

FIG. 26C

```
1921  atc ttc ctg cgc ctc ctg ccc cag gtg gac acc aca ggc acc ttc aag atc cag aag acg
       I   F   L   R   L   L   P   Q   V   D   T   T   G   T   F   K   I   Q   K   T
1981  agg ctg cag cga gag ggc ttt gac cca cgc cag acc cgg ctc gac ttc ctg gac
       R   L   Q   R   E   G   F   D   P   R   Q   T   R   L   D   F   L   D
2041  ctg aag cag ggc cac tac ctg ccc tta aat gag gca gtc tac act cgc atc tcg ggc
       L   K   Q   G   H   Y   L   P   L   N   E   A   V   Y   T   R   I   C   G
2101  gcc ttc gcc ctc tga agc ctc act ggc tgt tcc aaa ctc tgg gcc tgg gag agg
       A   F   A   L   *
2161  cca gct tga gcc aga cag cgc tgc cca ggg gtg gcc tag tac aca ccc acc tgg ccg
2221  agc tgt acc tgg cac ggc cca tcc tgg act gag aaa ctg gaa cct cag agg aac ccg tgc
2281  ctc tct gct gcc ttg gtg ccc ctg tgt cct gct ctc cct gct ttt ctt cag cct ctg tct
2341  cct tcc atc cct gtc cct gtc tgg cct gtc cct ctc cct ctt ctt tt cct
2401  ttc ttt ttt aag ata gag tct cac gcc cgg gct aga gtg cag tgg tgg gat
2461  ctc ggc tca ctg caa cct cct ggg gtt caa gtg atc ctc. cca cag cct cct
```

FIG. 26D

```
2521  gag tag ctg gga tta cag gca ccc gcc acc acg tcc agc taa ttt tta tat ttt tag tag
2581  aga cgg ggt ttc acc atg ttg gtc agg ctg gtc ttg aac tcc tga cct cag gtg atc cgc
2641  tgg cct cgg cct ccc aga gtg ctg aga gtg gga tta gcg tga gcc tct ggc ccg gcc ttt cct
2701  ttt tcc tct cct cct ctc ccg aga cac acg tgt cct ggg agc tgc atc ttg tgt
2761  agg gtc cag ctg ctt ttg ggg act gca gga atc gga atc tcc cct ggg ccc tgg act cgg act
2821  ggg gcc tcc cca cct cgg ctg tgc ctt acg gag ccc caa tcc agg cct cct gtg
2881  gct gtt ggg ttc cag atg ctg cag ctc ctt acg act tcc aag cag gcc ctc cgc cct ccc
2941  tgc tga atg gag gag ccg ggg gtc ccc cag gcc aac tgg aaa atc tcc cag gct agg cca
3001  att gcc ttt tgc act tcc ccg ctg ttc tca cat ttc ccc acc ccc atc ccc tcc tga
3061  tgc cct gaa agc ttc cgg aat ctg tga cca ctt gga tgt cac cac tgt cag ccc ctg
3121  cct tga tgt ccc cat tta gcc atc tcc atg gag ctc ctg ggc ctc gag ggt gaa ccc tgc
3181  act gcg tgg ctg ccc agc cag cag ctg cct gtc ctg gga ggc ctc ctg ggt gtc ctc
3241  atc tgg tgt gtc tac tgg agg gtc ctc aag cct gtt gaa tat acc cca cct
3301  cct gcc ggg ggt tgg cct ctc cga tgt ccc cac tga ttc ctc cgt gtt ggc gat gtc
3361  ggt ggg tgg ccc ctc ctc cga tgt ccc cac tga cac cgt gtt ggc gat gtc
3421  cca gac aat ccc acc agg acg gcc cag aca tcc cta ctg gct gtg gct cat ctc
3481  gaa cat cca cgc cag cct ttc tgg cca ccg cgt ctg gtc tcc tcc
3541  ctc cag cag cac ccc ctg gcc cct gga gtg ggg cca tgg caa gag aca ccg tgg cgt
3601  ctc atg tga act ttc ctg ggc act gtg gtt tta ttt cct aat tga ttt aag aaa taa acc
3661  tga aga ccg tct ggt gaa aaa aaa aaa aaa agg gcg gcc gc
```

FIG. 26E hsFATP4

```
1    cga ccc acg cgt ccg ggc ggg cgg ggc ggg gcg ggg gct ggc ggc ggg gcc ggg 61   cca tgc agg gcg cag agc cgg cta agc cct gct gag aac cgg ctc cgt agg ggc 121  ggc taa tgc ccc tca tca cgc tgt cta tgc aac atg cgc aca gca tct gga ggc 181  gcg cgg cgg agc cga cgc cgc acg atg ctg ctg gga gcc gtg tcc ctg gtg ctg
                                         M   L   L   G   A   V   S   L   V   L 241  ctg ttc tcc aag ctg gtg ctg aaa ctg ccc tgg acc cag gtg gga ttc tcc ctg ttc
     L   F   S   K   L   V   L   K   L   P   W   T   Q   V   G   F   S   L   F 301  ctc tac ttg gga tct ggc gtc ctg gtc atc cgc tgg ttc gcg ttc atc aag acc agg cgc
     L   Y   L   G   S   G   V   L   V   I   R   W   F   A   F   I   K   T   R   R 361  gat atc ttt ggc gga aca gtg ccc ctc ttt gcc aag gtg gca gtg cga cag tgc ctg cag
     D   I   F   G   G   T   V   P   L   F   A   K   V   A   V   R   Q   C   L   Q 421  gag cgg aca ttc gag atc ttc cgc aca tct gtt cgg cgc ttc cgc cac ccc gac aag acg
     E   R   T   F   E   I   F   R   T   S   V   R   R   F   R   H   P   D   K   T 481  gcc ctg atc gcc aac ttc cag gcc cgg ggc ctg gcc tgg acc ttc cgc cag ctg gat gag gtg gct gcc atc
     A   L   I   A   N   F   Q   A   R   G   L   A   W   T   F   R   Q   L   D   E   Y   A   A   I 541  agc agt gta gcc aac ttc ctg cag gcc cgg ggc ctg tcg ccc gat gtg gcc aag ctc ttg
     S   S   V   A   N   F   L   Q   A   R   G   L   S   G   D   V   A   K   L   L 601  ttc atg gag aac cgc aat gag ttc gtg ggc cta tgg ctg gtg ggc atg gcc aag ctc ggt gtg
     F   M   E   N   R   N   E   F   V   G   L   W   L   V   G   M   A   K   L   G   V
```

FIG. 27A

```
661   gag gca gcc ctc atc aac acc aac ctg cgg gat gct ctg ctc cac tgc ctc acc acc
      E   A   A   L   I   N   T   N   L   R   D   A   L   L   H   C   L   T   T 721   tcg cgc gca cgg gcc ctt gtc ttt ggc agc gaa atg gcc tca gcc atc tgt gag gtc cat
      S   R   A   R   A   L   V   F   G   S   E   M   A   S   A   I   C   E   V   H 781   gcc agc ctg gac ccc tcg ctc agc ttc tgc ctg tcc tgg gag ccc ggt gcg gtg
      A   S   L   D   P   S   L   S   F   C   L   S   W   E   P   G   A   V 841   cct cca agc aca gaa cac ctg gac cct ctg aaa gat gct ccc aag cac ctt ccc agt
      P   P   S   T   E   H   L   D   P   L   K   D   A   P   K   H   L   P   S 901   tgc cct gac aag ggc ttc aca gat aaa ctg ttc tac atc tac aca tcc acc aca ggg
      C   P   D   K   G   F   T   D   K   L   F   Y   I   Y   T   S   T   T   G 961   ctg ccc aag gcc gcc atc gtg cac agc agg tat tac cgc atg gct gcc ctc gtg tac
      L   P   K   A   A   I   V   H   S   R   Y   Y   R   M   A   A   L   V   Y 1021  tat gga ttc cgc atg cgg gga ccc aac gac atc gtc tat gac ctg tgc ctc cac tca
      Y   G   F   R   M   R   G   P   N   D   I   V   Y   D   C   L   P   L   H   S 1081  gca gga aac atc gtg gga atc ggc cag ttc ctg cat ggc atg gtg gtg att cgg
      A   G   N   I   V   G   I   G   Q   L   H   G   M   V   V   I   R 1141  aag aag ttc tca gcc tcc cgg ttt tgg gac gat tgt atc aag tac aac acg att gtg
      K   K   F   S   A   S   R   F   W   D   D   C   I   K   Y   N   T   I   V 1201  cag tac att ggt gaa ctg tgc cgc tac ctc ctg aac cag cca ccg cgg gag gca gaa aac
      Q   Y   I   G   E   L   C   R   Y   L   L   N   Q   P   P   R   E   A   E   N
```

FIG. 27B

```
1261  cag cac cag gtt cgc atg gca cta ggc aat ggc ctc cgg cag tcc atc tgg acc aac ttt
       Q   H   Q   V   R   M   A   L   G   N   G   L   R   Q   S   I   W   T   N   F
1321  tcc agc cgc ttc cac ata ccc cag gtg gct gag ttc tac ggg gcc aca gag tgc aac tgt
       S   S   R   F   H   I   P   Q   V   A   E   F   Y   G   A   T   E   C   N   C
1381  agc ctg ggc aac ttc gac agc cag gtg ggg gcc tgt ggt ttc aat agc cgc atc ctg tcc
       S   L   G   N   F   D   S   Q   V   G   A   C   G   F   N   S   R   I   L   S
1441  ttc gtg tac ccc atc cgg ttg gta cgt gtc aac gag gac atg acc atg gag ctg atc cgg ggg
       F   V   Y   P   I   R   L   V   R   V   N   E   D   T   M   E   L   I   R   G
1501  ccc gac ggc gtc atc ccc tgc cag cca ggt gag ccg cag ctg gtg ggc gcc ctg gtg cgc atc
       P   D   G   V   I   P   C   Q   P   G   E   P   Q   L   V   G   A   L   R   I
1561  atc cag gac aaa gac ccc ctg cgc cgc gat ggc tac ctc aac cag ggc gcc aac aac aag
       I   Q   D   K   D   P   L   R   R   D   G   Y   L   N   Q   G   A   N   N   K
1621  aag att gcc aag gat gtc ttc aag aag ggg gac cag tac ctt act ggt gat gtg ctg
       K   I   A   K   D   V   F   K   K   G   D   Q   Y   L   T   G   D   V   L
1681  gtg atg gac gag gag ctg ggc tac ttc cga gac cgg acg ctc agc cgc ctg gac atg
       V   M   D   E   E   L   G   Y   F   R   D   R   T   L   S   R   L   D   M
1741  aaa ggt gag aac gtg tcc acc gag gtg gaa ggc aca ctc gag gga acc ttc cgg gcc atg gct
       K   G   E   N   V   S   T   T   E   V   E   G   T   L   E   G   T   F   R   A   M   A
1801  gct gac gtg gcc gtg tat ggt gtc gag gtg cca gga ggc acc gag cgg gcc cgg gca atg gct
       A   D   V   A   V   Y   G   V   E   V   P   G   G   T   E   G   R   A   G   M   A
1861  gct gtg gcc agc ccc act ggc aac tgt gac ctg gag cgc ttt gct cag gtc ttg gag aag
       A   V   A   S   P   T   G   N   C   D   L   E   R   F   A   Q   V   L   E   K
```

FIG. 27C

```
1921  gaa ctg ccc ctg tat gcg cgc ccc atc ttc ctg cgc aag gag ctc ctg cct gag ctg cac aaa aca
       E   L   P   L   Y   A   R   P   I   F   L   R   K   E   L   L   P   E   L   H   K   T
1981  gga acc tac aag ttc cag aag aca gag acc cta cgg aag gag ggc ttt gac ccg gct att gtg
       G   T   Y   K   F   Q   K   T   E   T   L   R   K   E   G   F   D   P   A   I   V
2041  aaa gac ccg ctg ttc tat cta gat gcc cag ggc cgc tac gtc ccg ctg gac caa gag
       K   D   P   L   F   Y   L   D   A   Q   G   R   Y   V   P   L   D   Q   E
2101  gcc tac agc cgc atc cag gca ggc gag gag aag ctg tga ttc ccc cca tcc ctc tga ggg
       A   Y   S   R   I   Q   A   G   E   E   K   L   *
2161  ccg gcg gat gct gga tcc gga tcc gcc cca gag cgg tcc gcc cct cca acc agg cca
2221  gac caa agc aag cag ggc ctg gca cag ggc ctg gca cct cca gct gcc aaa act
2281  gcc aag tga ctc att gcc ttc cca acc ctt cca gag gct ttc tgt gcc agt ctc atg tcc
2341  aag ttc cgt ctt ctg ggc tgg gca ggc gta ggg cct ctg gtt ccc agg ctg acg ggt ttt
2401  ctc agg atg tct tgg gtg aga gga gtc acc gag ccc ttc cca
2461  gag agc agg gag ctt ata aat gga acc aga gca gaa gtc ccc agg aag tca aca
2521  gag tgg gca ggg aca gtg gta gca atc tgg cca ctc cag gag gta gcc cca gag
2581  ctg ccc aag ttc act ggg ctc cac ccc cat cta cag gag gtg ctg cct gac atc
2641  tgt agg tgg ccc ctg atg ccc atc ctc ctc cct ggg tgg ctg cct gat tat ccc ctg gcc tct
2701  ccc cac tcc ccc atc ctc ctc cct acc tca ggc agg gcc tct
2761  cag tcc ttg tgg gtc tgt gtc acc tca gtc ttg cct ttg gcc cta tga ctg cct gtc gcc tct
2821  gaa tgg gag agg ggg ctc agg ctc agg ggc caa taa act ctg cct tga gtc ctc cta aaa aaa aaa
2881  aaa aaa aaa aaa aaa aaa ggg cgg ccg c
```

FIG. 27D

Protein Sequence 646 a.a. MRAPGAGAASVV....VYTRICSGAFAL
646 Amino Acids MW: 71062 Dalton

|   |   | n | n% | MW | MW% |
|---|---|---|---|---|---|
| A ala | Alanine | 64 | 9.9 | 4546 | 6.4 |
| C cys | cysteine | 15 | 2.3 | 1545 | 2.2 |
| D asp | aspartic acid | 30 | 4.6 | 3450 | 4.9 |
| E glu | glutamic acid | 31 | 4.8 | 4000 | 5.6 |
| F phe | phenylalanine | 29 | 4.5 | 4264 | 6.0 |
| G gly | glycine | 63 | 9.8 | 3592 | 5.1 |
| H his | histidine | 13 | 2.0 | 1781 | 2.5 |
| I ile | isoleucine | 29 | 4.5 | 3279 | 4.6 |
| K lys | lysine | 22 | 3.4 | 2818 | 4.0 |
| L leu | leucine | 77 | 11.9 | 8707 | 12.3 |
| M met | methionine | 11 | 1.7 | 1441 | 2.0 |
| N asn | asparagine | 15 | 2.3 | 1710 | 2.4 |
| P pro | proline | 29 | 4.5 | 2814 | 4.0 |
| Q gln | glutamine | 25 | 3.9 | 3201 | 4.5 |
| R arg | arginine | 49 | 7.6 | 7648 | 10.8 |
| S ser | serine | 33 | 5.1 | 2872 | 4.0 |
| T thr | threonine | 27 | 4.2 | 2728 | 3.8 |
| V val | valine | 51 | 7.9 | 5052 | 7.1 |
| W trp | tryptophan | 9 | 1.4 | 1674 | 2.4 |
| X ukw | unknown | -- | -- |   |   |
| Y tyr | tyrosine | 24 | 3.7 | 3913 | 5.5 |
| Z --- STOP |   |   |   |   |   |

FIG. 28B hs FATP4. pep-> A.A. Usage

Protein Sequence 643 a.a. MLLGASLVGVLL...AYSRIQAGEEKL
643 Amino Acids MW: 72018 Dalton

|   |   | n | n% | MW | MW% |
|---|---|---|---|---|---|
| A ala | alanine | 46 | 7.2 | 3267 | 4.5 |
| C cys | cysteine | 16 | 2.5 | 1648 | 2.3 |
| D asp | aspartic acid | 33 | 5.1 | 3795 | 5.3 |
| E glu | glutamic acid | 33 | 5.1 | 4258 | 5.9 |
| F phe | phenylalanine | 34 | 5.3 | 5000 | 6.9 |
| G gly | glycine | 54 | 8.4 | 3079 | 4.3 |
| H his | histidine | 12 | 1.9 | 1644 | 2.3 |
| I ile | isoleucine | 30 | 4.7 | 3392 | 4.7 |
| K lys | lysine | 31 | 4.8 | 3970 | 5.5 |
| L leu | leucine | 76 | 11.8 | 8594 | 11.9 |
| M met | methionine | 12 | 1.9 | 1572 | 2.2 |
| N asn | asparagine | 21 | 3.3 | 2394 | 3.3 |
| P pro | proline | 31 | 4.8 | 3008 | 4.2 |
| Q gln | glutamine | 23 | 3.6 | 2945 | 4.1 |
| R arg | arginine | 45 | 7.0 | 7024 | 9.8 |
| S ser | serine | 35 | 5.4 | 3046 | 4.2 |
| T thr | threonine | 32 | 5.0 | 3233 | 4.5 |
| V val | valine | 46 | 7.2 | 4557 | 6.3 |
| W trp | tryptophan | 8 | 1.2 | 1488 | 2.1 |
| X ukw | unknown | -- | -- |   |   |
| Y tyr | tyrosine | 25 | 3.9 | 4076 | 5.7 |
| Z --- STOP |   |   |   |   |   |

FIG. 29B

```
  1  ATGCGGGCTCCGGGTGCGGG  hFATP1con.seq ORF
  1  ATGCGGGCTCCTGGAGCAGG  mFATP1.seq ORF (from genomic)

21  CGCGGCCTCGGTGGTCTCGC  hFATP1con.seq ORF
 21  AACAGCCTCTGTGGCCTCAC  mFATP1.seq ORF (from genomic)

41  TGGCGCTGTTGTGGCTGCTG  hFATP1con.seq ORF
 41  TGGCGCTGCTTTGGTTTCTG  mFATP1.seq ORF (from genomic)

61  GGGCTGCCGTGGACCTGGAG  hFATP1con.seq ORF
 61  GGACTTCCGTGGACCTGGAG  mFATP1.seq ORF (from genomic)

81  CGCGGCAGCGGCGCTCGGCG  hFATP1con.seq ORF
 81  CGCGGCGGCGGCGTCTGTG   mFATP1.seq ORF (from genomic)

101  TGTACGTGGGCAGCGGCGGC  hFATP1con.seq ORF
101  TGTACGTGGGTGGCGGCGGC  mFATP1.seq ORF (from genomic)

121  TGGCGCTTCCTGCGCATCGT  hFATP1con.seq ORF
121  TGGCGCTTTCTGCGTATCGT  mFATP1.seq ORF (from genomic)

141  CTGCAAGACCGCGAGGCGAG  hFATP1con.seq ORF
141  CTGCAAGACGGCGAGGCGAG  mFATP1.seq ORF (from genomic)

161  ACCTCTTCGGTCTCTCTGTG  hFATP1con.seq ORF
161  ACCTCTTTGGCCTCTCTGTT  mFATP1.seq ORF (from genomic)

181  CTGATCCGCGTGCGCCTGGA  hFATP1con.seq ORF
181  CTGATTCGTGTTCGGCTAGA  mFATP1.seq ORF (from genomic)

201  GCTGCGGCGGCACCAGCGTG  hFATP1con.seq ORF
201  GCTGCGACGACACCGGCGAG  mFATP1.seq ORF (from genomic)

221  CCGGCCACACCATCCCGCGC  hFATP1con.seq ORF
221  CAGGAGACACGATCCCGTGC  mFATP1.seq ORF (from genomic)

241  ATCTTTCAGGCGGTAGTGCA  hFATP1con.seq ORF
241  ATCTTCCAGGCTGTGGCCCG  mFATP1.seq ORF (from genomic)

261  GCGACAGCCCGAGCGCCTGG  hFATP1con.seq ORF
261  GCGACAACCAGAGCGCCTGG  mFATP1.seq ORF (from genomic)

281  CGCTGGTGGATGCCGGGACC  hFATP1con.seq ORF
281  CACTGGTGGACGCCAGTAGT  mFATP1.seq ORF (from genomic)

301  GGCGAGTGCTGGACCTTTGC  hFATP1con.seq ORF
301  GGTATATGCTGGACCTTCGC  mFATP1.seq ORF (from genomic)

321  GCAGCTGGACGCCTACTCCA  hFATP1con.seq ORF
321  ACAGCTGGACACCTACTCCA  mFATP1.seq ORF (from genomic)

341  ATGCGGTAGCCAACCTCTTC  hFATP1con.seq ORF
341  ATGCTGTAGCCAACCTGTTC  mFATP1.seq ORF (from genomic)
```

FIG. 30A

| | | |
|---|---|---|
| 361 | C G C C A G C T G G G C T T C G C G C C | hFATP1con.seq ORF |
| 361 | C G C C A G C T G G G C T T T G C A C C | mFATP1.seq ORF (from genomic) |
| 381 | G G G C G A C G T G G T G G C C A T C T | hFATP1con.seq ORF |
| 381 | A G G C G A T G T G G T G G C T G T G T | mFATP1.seq ORF (from genomic) |
| 401 | T C C T G G A G G G C C G G C C G G A G | hFATP1con.seq ORF |
| 401 | T C C T G G A G G G C C G G C C G G A G | mFATP1.seq ORF (from genomic) |
| 421 | T T C G T G G G G C T G T G G C T G G G | hFATP1con.seq ORF |
| 421 | T T C G T G G G A C T G T G G C T G G G | mFATP1.seq ORF (from genomic) |
| 441 | C C T G G C C A A G G C G G G C A T G G | hFATP1con.seq ORF |
| 441 | C C T G G C C A A G G C C G G T G T G G | mFATP1.seq ORF (from genomic) |
| 461 | A G G C C G C G C T G C T C A A C G T G | hFATP1con.seq ORF |
| 461 | T G G C T G C T C T T C T C A A T G T C | mFATP1.seq ORF (from genomic) |
| 481 | A A C C T G C G G C G C G A G C C C C T | hFATP1con.seq ORF |
| 481 | A A C C T G A G G C G G G A G C C C C T | mFATP1.seq ORF (from genomic) |
| 501 | G G C C T T C T G C C T G G G C A C C T | hFATP1con.seq ORF |
| 501 | G G C C T T C T G C C T G G G C A C A T | mFATP1.seq ORF (from genomic) |
| 521 | C G G C G C T A A G G C C C T G A T C | hFATP1con.seq ORF |
| 521 | C A G C T G C C A A G G C C C T C A T T | mFATP1.seq ORF (from genomic) |
| 541 | T T T G G A G G A G A A A T G G T G G C | hFATP1con.seq ORF |
| 541 | T A T G G C G G G G A G A T G G C A G C | mFATP1.seq ORF (from genomic) |
| 561 | G G C G G T G G C C G A A G T G A G C G | hFATP1con.seq ORF |
| 561 | G G C G G T G G C G G A G G T G A G C G | mFATP1.seq ORF (from genomic) |
| 581 | G G C A T C T G G G G A A A A G T T T G | hFATP1con.seq ORF |
| 581 | A G C A G C T G G G G A A G A G C C T C | mFATP1.seq ORF (from genomic) |
| 601 | A T C A A G T T C T G C T C T G G A G A | hFATP1con.seq ORF |
| 601 | C T C A A G T T C T G C T C T G G A G A | mFATP1.seq ORF (from genomic) |
| 621 | C T T G G G G C C C G A G G G C A T C T | hFATP1con.seq ORF |
| 621 | T C T G G G G C C T G A G A G C A T C C | mFATP1.seq ORF (from genomic) |
| 641 | T G C C G G A C A C C C A C C T C C T G | hFATP1con.seq ORF |
| 641 | T G C C T G A C A C G C A G C T C C T G | mFATP1.seq ORF (from genomic) |
| 661 | G A C C C G C T G C T G A A G G A G G C | hFATP1con.seq ORF |
| 661 | G A C C C A T G C T T G C T G A G G C | mFATP1.seq ORF (from genomic) |
| 681 | C T C T A C T G C C C C C T T G G C A C | hFATP1con.seq ORF |
| 681 | G C C C A C C A C A C C C T G G C A C | mFATP1.seq ORF (from genomic) |
| 701 | A G A T C C C C A G C A A G G G C A T G | hFATP1con.seq ORF |
| 701 | A A G C C C C A G G C A A G G G C A T G | mFATP1.seq ORF (from genomic) |

FIG. 30B

| | | |
|---|---|---|
| 721 | G A C G A T C G T C T T T C T A C A T | hFATP1con.seq ORF |
| 721 | G A T G A T C G G C T G T T T T A C A T | mFATP1.seq ORF (from genomic) |
| 741 | C T A C A C G T C G G G A C C A C C G | hFATP1con.seq ORF |
| 741 | C T A T A C T T C T G G G A C C A C C G | mFATP1.seq ORF (from genomic) |
| 761 | G G C T G C C C A A G G C T G C C A T T | hFATP1con.seq ORF |
| 761 | G G C T T C C T A A G G C T G C C A T T | mFATP1.seq ORF (from genomic) |
| 781 | G T C G T G C A C A G C A G G T A C T A | hFATP1con.seq ORF |
| 781 | G T G G T G C A C A G C A G G T A C T A | mFATP1.seq ORF (from genomic) |
| 801 | C C G C A T G G C A G C C T T C G G C C | hFATP1con.seq ORF |
| 801 | C C G C A T T G C T G C C T T T G G C C | mFATP1.seq ORF (from genomic) |
| 821 | A C C A C G C C T A C C G C A T G C A G | hFATP1con.seq ORF |
| 821 | A C C A T T C C T A C A G C A T G C G T | mFATP1.seq ORF (from genomic) |
| 841 | G C G G C T G A C G T G C T C T A T G A | hFATP1con.seq ORF |
| 841 | G C C G C C G A T G T G C T C T A T G A | mFATP1.seq ORF (from genomic) |
| 861 | C T G C C T G C C C C T G T A C C A C T | hFATP1con.seq ORF |
| 861 | C T G C C T G C C A C T C T A C C A C T | mFATP1.seq ORF (from genomic) |
| 881 | C G G C A G G A A A C A T C A T C G G C | hFATP1con.seq ORF |
| 881 | C T G C A G G G A A C A T C A T G G G T | mFATP1.seq ORF (from genomic) |
| 901 | G T G G G C A G T G T C T C A T C T A | hFATP1con.seq ORF |
| 901 | G T G G G C A G T G C G T C A T C T A | mFATP1.seq ORF (from genomic) |
| 921 | T G G G C T G A C A G T C G T C C T C C | hFATP1con.seq ORF |
| 921 | C G G G T T G A C G G T G G T A C T G C | mFATP1.seq ORF (from genomic) |
| 941 | G C A A G A A A T T C T C G G C C A G C | hFATP1con.seq ORF |
| 941 | G C A A G A A G T T C T C C G C C A G C | mFATP1.seq ORF (from genomic) |
| 961 | C G C T T C T G G G A C G A C T G C A T | hFATP1con.seq ORF |
| 961 | C G C T T C T G G G A T G A C T G T G T | mFATP1.seq ORF (from genomic) |
| 981 | C A A G T A C A A C T G C A C G G T G G | hFATP1con.seq ORF |
| 981 | C A A G T A C A A T G C A C G G T A G | mFATP1.seq ORF (from genomic) |
| 1001 | T T C A G T A C A T C G G G A G A T C | hFATP1con.seq ORF |
| 1001 | T G C A G T A C A T A G G T G A A A T C | mFATP1.seq ORF (from genomic) |
| 1021 | T G C C G C T A C C T G C T G A A G C A | hFATP1con.seq ORF |
| 1021 | T G C C G C T A C C T G C T G A G G C A | mFATP1.seq ORF (from genomic) |
| 1041 | G C C G G T G C G C G A G G C G G A G A | hFATP1con.seq ORF |
| 1041 | G C C G G T T C G C G A C G T G G A G C | mFATP1.seq ORF (from genomic) |
| 1061 | G G C G A C A C C G C G T G C G C C T G | hFATP1con.seq ORF |
| 1061 | A G C G A C A C C G C G T G C G C C T G | mFATP1.seq ORF (from genomic) |

FIG. 30C

```
1081  G C G G T G G G G A A C G G G C T G C G   hFATP1con.seq ORF
1081  G C C G T G G G T A A T G G G C T G C G   mFATP1.seq ORF (from genomic)

1101  T C C T G C C A T C T G G G A G G A G T   hFATP1con.seq ORF
1101  G C C A G C C A T C T G G G A G G A G T   mFATP1.seq ORF (from genomic)

1121  T C A C G G A G C G C T T C G G C G T A   hFATP1con.seq ORF
1121  T C A C G C A G C G C T T C G G T G T G   mFATP1.seq ORF (from genomic)

1141  C G C C A A A T C G G G G A G T T C T A   hFATP1con.seq ORF
1141  C C A C A G A T C G G C G A G T T C T A   mFATP1.seq ORF (from genomic)

1161  C G G C G C C A C C G A G T G C A A C T   hFATP1con.seq ORF
1161  C G G C G C T A C C G A G T G C A A C T   mFATP1.seq ORF (from genomic)

1181  G C A G C A T T G C C A A C A T G G A C   hFATP1con.seq ORF
1181  G C A G C A T T G C C A A C A T G G A C   mFATP1.seq ORF (from genomic)

1201  G G C A A G G T C G G C T C C T G T G G   hFATP1con.seq ORF
1201  G G C A A G G T C G G C T C C T G C G G   mFATP1.seq ORF (from genomic)

1221  T T T C A A C A G C C G C A T C C T G C   hFATP1con.seq ORF
1221  C T T C A A C A G C C G T A T C C T C A   mFATP1.seq ORF (from genomic)

1241  C C C A C G T G T A C C C C A T C C G G   hFATP1con.seq ORF
1241  C G C A T G T G T A C C C C A T C C G T   mFATP1.seq ORF (from genomic)

1261  C T G G T G A A G G T C A A T G A G G A   hFATP1con.seq ORF
1261  C T G G T C A A G G T C A A T G A G G A   mFATP1.seq ORF (from genomic)

1281  C A C A A T G G A G C T G C T G C G G G   hFATP1con.seq ORF
1281  C A C G A T G G A G C C A C T G C G G G   mFATP1.seq ORF (from genomic)

1301  A T G C C C A G G G C C T C T G C A T C   hFATP1con.seq ORF
1301  A C T C C G A G G G C C T C T G C A T C   mFATP1.seq ORF (from genomic)

1321  C C C T G C C A G G C C G G G G A G C C   hFATP1con.seq ORF
1321  C C G T G C C A G C C C G G G G A A C C   mFATP1.seq ORF (from genomic)

1341  T G G C C T C C T T G T G G G T C A G A   hFATP1con.seq ORF
1341  C G G C C T T C T C G T G G G C C A G A   mFATP1.seq ORF (from genomic)

1361  T C A A C C A A C A G G A C C C G C T G   hFATP1con.seq ORF
1361  T C A A C C A G C A G G A C C C T C T G   mFATP1.seq ORF (from genomic)

1381  C G C C G C T T C G A T G G C T A T G T   hFATP1con.seq ORF
1381  C G G C G T T T C G A T G G T T A T G T   mFATP1.seq ORF (from genomic)

1401  C A G C G A G A G C G C C A C C A G C A   hFATP1con.seq ORF
1401  T A G T G A C A G T G C C A C C A A C A   mFATP1.seq ORF (from genomic)

1421  A G A A G A T C G C C C A C A G C G T C   hFATP1con.seq ORF
1421  A G A A G A T T G C C C A C A G C G T T   mFATP1.seq ORF (from genomic)
```

FIG. 30D

```
1441  T T C A G C A A G G G C G A C A G C G C   hFATP1con.seq ORF
1441  T T C C G A A A G G G C G A T A G C G C   mFATP1.seq ORF (from genomic)

1461  C T A C C T C T C A G G T G A C G T G C   hFATP1con.seq ORF
1461  C T A C C T C T C A G G T G A C G T G C   mFATP1.seq ORF (from genomic)

1481  T A G T G A T G G A T G A G C T G G G C   hFATP1con.seq ORF
1481  T A G T G A T G G A C G A G C T G G G C   mFATP1.seq ORF (from genomic)

1501  T A C A T G T A C T T C C G G G A C C G   hFATP1con.seq ORF
1501  T A C A T G T A T T T C C G T G A C C G   mFATP1.seq ORF (from genomic)

1521  T A G C G G G G A C A C C T T C C G C T   hFATP1con.seq ORF
1521  C A G C G G G G A C A C C T T C C G C T   mFATP1.seq ORF (from genomic)

1541  G G C G A G G G G A G A A C G T C T C C   hFATP1con.seq ORF
1541  G G C G C G G G G A G A A C G T G T C C   mFATP1.seq ORF (from genomic)

1561  A C C A C C G A G G T G G A G G C G T    hFATP1con.seq ORF
1561  A C C A C G G A G G T G G A A G C C G T  mFATP1.seq ORF (from genomic)

1581  G C T G A G C C G C C T G C T G G G C C   hFATP1con.seq ORF
1581  G C T G A G C C G C C T A C T G G G C C   mFATP1.seq ORF (from genomic)

1601  A G A C A G A C G T G G C C G T C T A T   hFATP1con.seq ORF
1601  A G A C G G A C G T G G C T G T G T A T   mFATP1.seq ORF (from genomic)

1621  G G G T G G C T G T T C C A G G A G T    hFATP1con.seq ORF
1621  G G G T G G C T G T G C C A G G A G T    mFATP1.seq ORF (from genomic)

1641  G G A G G G T A A G G C A G G G A T G G   hFATP1con.seq ORF
1641  G G A G G G G A A A G C T G G C A T G G   mFATP1.seq ORF (from genomic)

1661  C G G C C G T C G C A G A C C C C C A C   hFATP1con.seq ORF
1661  C A G C C A T C G C A G A T C C C C A C   mFATP1.seq ORF (from genomic)

1681  A G C C T G C T G G A C C C C A A C G C   hFATP1con.seq ORF
1681  A G C C A G T T G G A C C C T A A C T C   mFATP1.seq ORF (from genomic)

1701  G A T A C C A G G A G C T G C A G A      hFATP1con.seq ORF
1701  A A T G T A C C A G G A A T T A C A G A  mFATP1.seq ORF (from genomic)

1721  A G G T G C T G G C A C C C T A T G C C   hFATP1con.seq ORF
1721  A G G T T C T T G C A T C C T A T G C T   mFATP1.seq ORF (from genomic)

1741  C G G C C C A T C T T C C T G C G C C T   hFATP1con.seq ORF
1741  C G G C C C A T C T T C C T G C G T C T   mFATP1.seq ORF (from genomic)

1761  C C T G C C C C A G G T G G A C A C C A   hFATP1con.seq ORF
1761  T C T G C C C C A G G T G G A T A C C A   mFATP1.seq ORF (from genomic)

1781  C A G G C A C C T T C A A G A T C C A G   hFATP1con.seq ORF
1781  C A G G C A C C T T C A A G A T C C A G   mFATP1.seq ORF (from genomic)
```

FIG. 30E

```
1801  A A G A C G A G G C T G C A G C G A G A    hFATP1con.seq ORF
1801  A A G A C C C G G C T G C A G C G T G A    mFATP1.seq ORF (from genomic)

1821  G G C T T T G A C C C A G C C A G A        hFATP1con.seq ORF
1821  A G G C T T T G A C C C C C G T C A G A    mFATP1.seq ORF (from genomic)

1841  C C T C A G A C C G G C T C T T C T T C    hFATP1con.seq ORF
1841  C C T C A G A C A G G C T C T T C T T T    mFATP1.seq ORF (from genomic)

1861  C T G G A C C T G A A G C A G G G C C A    hFATP1con.seq ORF
1861  C T A G A C C T G A A G C A G G G A C G    mFATP1.seq ORF (from genomic)

1881  C T A C C T G C C C T T A A A T G A G G    hFATP1con.seq ORF
1881  C T A T G T A C C C C T G G A T G A G A    mFATP1.seq ORF (from genomic)

1901  C A G T C T A C A C T C G C A T C T G C    hFATP1con.seq ORF
1901  G A G T C C A T G C C C G C A T T T G T    mFATP1.seq ORF (from genomic)

1921  T C G G C G C C T T C G C C T C T G        hFATP1con.seq ORF
1921  G C A G G C G A C T T C T C A C T C        mFATP1.seq ORF (from genomic)

1941  A                                          hFATP1con.seq ORF
1938                                             mFATP1.seq ORF (from genomic)
```

Decoration 'Decoration #2': Box residues that match the consensus named 'Consensus #1' exactly.

| | hsFATP4 | mmFATP4 |
|---|---|---|
| 211 | TCTACCGTTCGGCGCCACCCCGACAAGACG | |
| 211 | TCAATGGTACAGCGCCACCCGGACAAGACA | |
| 241 | GCCCTGATCTTCGAGGGCACAGATACCCAC | |
| 241 | GCCCTGATTTTCGAGGGCACAGACACTCAC | |
| 271 | TGGACCTTCCCGCCCAGCTGGATGAGTACTCA | |
| 271 | TGGACCTTCCCGCCCAGCTGGATGAGTACTCC | |
| 301 | AGCAGTGTAGCCAACTTCCTGCAGGCCCGG | |
| 301 | AGTAGTGTGGCCAACTTCCTGCAGGCCCGG | |
| 331 | GGCCTGCCCTCGGGATGTGGCTGCCATC | |
| 331 | GGCCTGGCCTCAGGCAATGTAGTTGCCCTC | |
| 361 | TTCATGGAGAACCGCAATGAGTTCGTGGGC | |
| 361 | TTTATGGAAAACCGCAATGAGTTTGTGGGT | |
| 391 | CTATGGCTGGGCATGGCCAAGCTCGGTGTG | |
| 391 | CTGTGGCTAGGCATGGCCAAGCTGGGCGTG | |

FIG. 31B

| | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|

421 GAGGCAGCCTCATCAACACCAACCTGGG hsFATP4
421 GAGGCGGCTCTCATCAACACCAACCTAGG mmFATP4

451 CGGATGCTCTGCTCCACTGCCTCACCC hsFATP4
451 CGGGATGCCCTGCCCACTGTCTTGACACC mmFATP4

481 TCGCGCACGGGCCTTGTTCTTTGGCAGC hsFATP4
481 TCAAGGCACGAGCCTCATCTTTTGGCAGT mmFATP4

511 GAATGGCCTCAGCCATCTGTGAGGTCCAT hsFATP4
511 GAGATGGCCTCAGCTATCTGTGAGATCCAT mmFATP4

541 GCAGCCTGGACCCCTCGCTCAGCCTCTTC hsFATP4
541 GCTAGCCTGGAGCCCACTCAGCCTCTTC mmFATP4

571 TGCTCTGGCTCCTGGAGCCCGGCCTGTG hsFATP4
571 TGCTCTGGATCCTGGAGCCCAGCAGTG mmFATP4

601 CCTCCAAGCACAGAACACCTGGACCCTCTG hsFATP4
601 CCCGTCAGCACAGAGCATCTGGACCCTCTT mmFATP4

```
631 C T G A A G A T G C T C C C A A G C A C C T T C C A G T  hsFATP4
631 C T G G A A G A T G T C C C A A G C A C C T G C C A G T  mmFATP4

661 T G C C C T G A C A A G G G C T T A C A G A T A A A C T G  hsFATP4
661 C A C C C A G A C A A G G G T T T A C A G A T A A G C T C  mmFATP4

691 T T C T A C A T C T A C A C A T C C G G C A C C A G G G   hsFATP4
691 T T C T A C A T C T A C A C A T C G G G C A C C A G G G   mmFATP4

721 C T G C C C A A G G C C C G C C A T C G T G G T G C A C A G C  hsFATP4
721 C T A C C C A A A G C C T G C C A T T G T G G T G C A C A G C  mmFATP4

751 A G G T A T T A C C G G C C A T G G C T G C C C T G G T G T A C  hsFATP4
751 A G G T A T T A T C G T A T G G C T T C C C C T G G T G T A C  mmFATP4

781 T A T G G A T T C C C G G C C A T G C G C G G G G C C A C G A C A T C  hsFATP4
781 T A T G G A T T C C C G G C C A T G C G C G G G G C T G A T G A C A T T  mmFATP4

811 G T C T A T G A C T G C C C C C C C T C T A C C A C T C A  hsFATP4
811 G T C T A T G A C T G C C C C C C C T C T A C C A C T C A  mmFATP4
```

| | hsFATP4 | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|
841 | - | G | C | A | G | G | A | A | A | C | A | T | C | G | T | G | G | G | A | A | T | C | G | G | C | A | G | T | G | hsFATP4
841 | A | G | C | A | G | G | A | A | A | C | A | T | C | G | T | G | T | G | G | G | A | T | T | G | G | C | - | A | G | T | G | mmFATP4

870 | C | C | T | G | C | T | G | C | A | T | G | G | C | A | T | G | A | C | G | G | T | G | G | T | G | A | T | T | C | G | hsFATP4
870 | C | C | T | T | A | C | T | C | C | A | C | G | G | C | A | T | G | A | C | T | G | T | G | G | T | G | A | T | C | C | G | mmFATP4

900 | G | A | A | G | A | A | G | T | T | C | T | C | A | G | C | C | C | T | C | C | C | G | G | T | T | C | T | G | G | G | A | hsFATP4
900 | G | A | A | A | G | A | A | G | T | T | C | T | C | A | G | C | C | C | T | C | C | C | G | G | T | T | C | T | G | G | G | A | mmFATP4

930 | C | G | A | T | T | G | T | A | T | C | A | A | G | T | A | C | A | A | C | T | G | C | A | C | G | A | T | T | G | T | hsFATP4
930 | T | G | A | T | T | G | T | A | T | C | A | A | G | T | A | C | A | A | C | T | G | C | A | C | A | G | T | G | G | T | mmFATP4

960 | G | C | A | G | T | A | C | A | T | T | G | G | T | G | A | A | C | T | G | C | C | C | G | C | T | A | C | C | T | hsFATP4
960 | A | C | A | G | T | A | C | A | T | T | G | G | C | G | A | G | C | T | G | C | C | C | G | C | T | A | C | C | T | mmFATP4

990 | C | C | T | G | A | A | C | C | A | G | C | C | A | C | C | C | G | C | G | G | A | G | G | C | A | G | A | A | A | A | hsFATP4
990 | C | C | T | G | A | A | C | C | A | G | C | C | A | G | C | C | C | C | G | T | G | A | G | G | C | T | G | A | G | T | C | mmFATP4

1020 | C | C | A | G | C | A | C | C | A | G | G | T | C | G | C | A | T | G | G | C | A | C | T | A | G | G | C | A | A | hsFATP4
1020 | T | C | G | G | C | A | C | A | A | G | G | T | G | C | G | C | A | T | G | G | C | A | C | T | G | G | G | C | A | A | mmFATP4

FIG. 31E

```
1050  TGG CCT CCG GCA GTC CAT CTG GAC CAA CTT   hsFATP4
1050  CGG TCT CCG GCA GTC CAT CTG GAC CGA CTT   mmFATP4

1080  TCC AGC CCG CTT CCA CAT ACC CCA GGT GGC   hsFATP4
1080  TCC AGC CGT TTT CCA CAT CCC CCA GGT GGC   mmFATP4

1110  TGA GTT CTA CGG GCC ACA GAG TGC AAC TG    hsFATP4
1110  TGA GTT CTA TGG GCC ACA CTG AAT GCA ACT G mmFATP4

1140  TAG CCC TGG GCA ACT TCG ACA GCC AGG TGG G hsFATP4
1140  TAG CCC TGG GCA ACT TTG ACA GCC GGG TGG G mmFATP4

1170  GGC CTG TGG TTT CAA TAG CCC CAT CCT GTC   hsFATP4
1170  GGC CTG TGG CTT CAA TAG CCC CAT CCT GTC   mmFATP4

1200  CTT CGT GTA CCC CAT CCG GTT GGT ACG TGT   hsFATP4
1200  CTT TGT GTA CCC TAT CCG TTT GGT ACG TGT   mmFATP4

1230  CAA CGA GGA CAC CAT GGA GCT GAT CCC GGG G hsFATP4
1230  CAA TGA GGA TAC CAT GGA ACT GAT CCC GGG G mmFATP4
```

FIG. 31F

| | | hsFATP4 |
|---|---|---|
| 1260 | G C C C G A C G G C G T C T G C A T T C C C T G C C A G C C | hsFATP4 |
| 1260 | A C C C G A T G G A G T C T G C A T T C C C T G T C A A C C | mmFATP4 |
| 1290 | A G G T G A G C C G G G C C A G C T G G T G G C C G C A T | hsFATP4 |
| 1290 | A G G T C A G C C A G G C C A G C T G G T G G C T C G C A T | mmFATP4 |
| 1320 | C A T C C A G A A A G A C C C C C T G C G C C C G C T T T C G A | hsFATP4 |
| 1320 | C A T C C A G C A G G A C C C T C T G C G C C C G T T T C G A | mmFATP4 |
| 1350 | T G G C T A C C T C A A C C A G G G C G C C A A C A A C A A A | hsFATP4 |
| 1350 | C G G C T A C C T C A A C C A G G G T G C C A A C A A C A A A | mmFATP4 |
| 1380 | G A A G A T T G C C A A G A T G T C T T C A A G A A G G G | hsFATP4 |
| 1380 | G A A G A T T G C T A A T G A T G T C T T C A A G A A G G G | mmFATP4 |
| 1410 | G G A C C A G G C C C T A C T T A C T G G T G A T G T G C T | hsFATP4 |
| 1410 | G G A C C A A G C C C T A C T C A C T G G T G A C G T C C T | mmFATP4 |
| 1440 | G G T G A T G G A C G A G C T G G G C T A C C T G T A C T T | hsFATP4 |
| 1440 | G G T G A T G G A T G A G C T G G G T T A C C T G T A C T T | mmFATP4 |

FIG. 31G

| | | | | | | | | | | | |
|---|---|---|---|---|---|---|---|---|---|---|---|
| 1470 | C C G A G A C | C G C A C T G G G G A C A C G T T C C G C T G | hsFATP4 |
| 1470 | C C G A G A T | C G C A C T G G G G A C A C G T T C C G C T G | mmFATP4 |
| 1500 | G A A A G G T | G A G A A C A C C A C G A G G T | hsFATP4 |
| 1500 | G A A A G G G | G A G A A T G T A T C T A C C A C T G A G G T | mmFATP4 |
| 1530 | G G A A G G | G C A C A C T C A G C C C G C C T G G A C A T | hsFATP4 |
| 1530 | G G A G G G | G C A C A C T C A G C C C G C C T T C A T A T | mmFATP4 |
| 1560 | G G C T G A C | G T G G C C C G C T A T G G T G T C G A G G T | hsFATP4 |
| 1560 | G G C A G A T | G T G G C C C G T T A T G G T G T T G A G G T | mmFATP4 |
| 1590 | G C C A G A A C | C G A G C C G G G C C G A A T G G C | hsFATP4 |
| 1590 | G C C A G A A C | T G A A G G C C G A G C A G G A A T G G C | mmFATP4 |
| 1620 | T G C T G G | C C A G C C C C A C T G G C A A C T G T G A | hsFATP4 |
| 1620 | T G C C G T | C A A G T C C C A T C A G C A A C T G T G A | mmFATP4 |
| 1650 | C C T G G A G C | G C T T T G C T C A G G T C T T G G A G A A | hsFATP4 |
| 1650 | C C T G G A G | A G C T T T G C A C A G A C A C T T G A A A A | mmFATP4 |

FIG. 31H

| | | | | | | | | | | |
|---|---|---|---|---|---|---|---|---|---|---|
| 1680 | G G A | C T G | C C C | C T G T A T G C | G C C C C A T C T T | hsFATP4 |
| 1680 | G G A | C T G | C C C | T C T G T A T G C | C C C C C A T C T T | mmFATP4 |
| 1710 | C C T | G C G | C C T | C T G C C T G A G C T G | C A C A A A A C | hsFATP4 |
| 1710 | C C T | G C G | C T T | T C T G C C T G A G C T G | C A C A A G A C | mmFATP4 |
| 1740 | A G G | A C C T A | C A A G T T C C A G A A G A | C A G A G C T | hsFATP4 |
| 1740 | A G G | A C C T T | C A A G T T C C A G A A G A | C A G A G T T | mmFATP4 |
| 1770 | A C G G A A G G A G G G C T T T G A C C C G G | C T A T T G T | hsFATP4 |
| 1770 | G C G G A A G G A G G G C T T T G A C C C C A T C T G T | mmFATP4 |
| 1800 | G A A A G A C C C C G C T G T T C T T A G A T G C C A | hsFATP4 |
| 1800 | G A A A G A C C C C G C T G T T C T T G G A T G C T C G | mmFATP4 |
| 1830 | G A A G G C C G C T A C G T C C G C T G G A C C A A G A | hsFATP4 |
| 1830 | G A A G G C T G C T A C G T T G C A C T G G A C C A G G A | mmFATP4 |
| 1860 | G G C C T A C A G C C C G C A T C C A G G C A G G C G G A G G A | hsFATP4 |
| 1860 | G G C C T A T A C C C G C C A T C C A G G C A G G C G G A G G A | mmFATP4 |
| 1890 | G A A G C T G | hsFATP4 |
| 1890 | G A A G C T G | mmFATP4 |

FIG. 31I

| | | |
|---|---|---|
| 1 | M R A P G A G A A S V V S L A L L W L L | hFATP1. |
| 1 | M R A P G A G T A S V A S L A L L W F L | mmFATP1 |
| 21 | G L P W T W S A A A A L G V Y V G S G G | hFATP1. |
| 21 | G L P W T W S A A A A F C V Y V G G G G | mmFATP1 |
| 41 | W R F L R I V C K T A R R D L F G L S V | hFATP1. |
| 41 | W R F L R I V C K T A R R D L F G L S V | mmFATP1 |
| 61 | L I R V R L E L R R H Q R A G H T I P R | hFATP1. |
| 61 | L I R V R L E L R R H R R A G D T I P C | mmFATP1 |
| 81 | I F Q A V V Q R Q P E R L A L V D A G T | hFATP1. |
| 81 | I F Q A V A R R Q P E R L A L V D A S S | mmFATP1 |
| 101 | G E C W T F A Q L D A Y S N A V A N L F | hFATP1. |
| 101 | G I C W T F A Q L D T Y S N A V A N L F | mmFATP1 |
| 121 | R Q L G F A P G D V V A I F L E G R P E | hFATP1. |
| 121 | R Q L G F A P G D V V A V F L E G R P E | mmFATP1 |
| 141 | F V G L W L G L A K A G M E A A L L N V | hFATP1. |
| 141 | F V G L W L G L A K A G V V A A L L N V | mmFATP1 |
| 161 | N L R R E P L A F C L G T S G A K A L I | hFATP1. |
| 161 | N L R R E P L A F C L G T S A A K A L I | mmFATP1 |
| 181 | F G G E M V A A V A E V S G H L G K S L | hFATP1. |
| 181 | Y G G E M A A A V A E V S E Q L G K S L | mmFATP1 |
| 201 | I K F C S G D L G P E G I L P D T H L L | hFATP1. |
| 201 | L K F C S G D L G P E S I L P D T Q L L | mmFATP1 |
| 221 | D P L L K E A S T A P L A Q I P S K G M | hFATP1. |
| 221 | D P M L A E A P T T P L A Q A P G K G M | mmFATP1 |
| 241 | D D R L F Y I Y T S G T T G L P K A A I | hFATP1. |
| 241 | D D R L F Y I Y T S G T T G L P K A A I | mmFATP1 |
| 261 | V V H S R Y Y R M A A F G H H A Y R M Q | hFATP1. |
| 261 | V V H S R Y Y R I A A F G H H S Y S M R | mmFATP1 |

FIG. 32A

```
281  A A D V L Y D C L P L Y H S A G N I I G   hFATP1.
281  A A D V L Y D C L P L Y H S A G N I M G   mmFATP1

301  V G Q C L I Y G L T V V L R K K F S A S   hFATP1.
301  V G Q C V I Y G L T V V L R K K F S A S   mmFATP1

321  R F W D D C I K Y N C T V V Q Y I G E I   hFATP1.
321  R F W D D C V K Y N C T V V Q Y I G E I   mmFATP1

341  C R Y L L K Q P V R E A E R H R V R L     hFATP1.
341  C R Y L L R Q P V R D V E Q R H R V R L   mmFATP1

361  A V G N G L R P A I W E E F T E R F G V   hFATP1.
361  A V G N G L R P A I W E E F T Q R F G V   mmFATP1

381  R Q I G E F Y G A T E C N C S I A N M D   hFATP1.
381  P Q I G E F Y G A T E C N C S I A N M D   mmFATP1

401  G K V G S C G F N S R I L P H V Y P I R   hFATP1.
401  G K V G S C G F N S R I L T H V Y P I R   mmFATP1

421  L V K V N E D T M E L L R D A Q G L C I   hFATP1.
421  L V K V N E D T M E P L R D S E G L C I   mmFATP1

441  P C Q A G E P G L L V G Q I N Q Q D P L   hFATP1.
441  P C Q P G E P G L L V G Q I N Q Q D P L   mmFATP1

461  R R F D G Y V S E S A T S K K I A H S V   hFATP1.
461  R R F D G Y V S D S A T N K K I A H S V   mmFATP1

481  F S K G D S A Y L S G D V L V M D E L G   hFATP1.
481  F R K G D S A Y L S G D V L V M D E L G   mmFATP1

501  Y M Y F R D R S G D T F R W R G E N V S   hFATP1.
501  Y M Y F R D R S G D T F R W R G E N V S   mmFATP1

521  T T E V E G V L S R L L G Q T D V A V Y   hFATP1.
521  T T E V E A V L S R L L G Q T D V A V Y   mmFATP1

541  G V A V P G V E G K A G M A A V A D P H   hFATP1.
541  G V A V P G V E G K A G M A A I A D P H   mmFATP1
```

FIG. 32B

```
561 S L L D P N A I Y Q E L Q K V L A P Y A   hFATP1.
561 S Q L D P N S M Y Q E L Q K V L A S Y A   mmFATP1

581 R P I F L R L L P Q V D T T G T F K I Q   hFATP1.
581 R P I F L R L L P Q V D T T G T F K I Q   mmFATP1

601 K T R L Q R E G F D P R Q T S D R L F F   hFATP1.
601 K T R L Q R E G F D P R Q T S D R L F F   mmFATP1

621 L D L K Q G H Y L P L N E A V Y T R I C   hFATP1.
621 L D L K Q G R Y V P L D E R V H A R I C   mmFATP1

641 S G A F A L                               hFATP1.
641 A G D F S L                               mmFATP1
```

```
L F S K L V L K L P W T Q V G F S L L                              hsFATP4pep
L G S K L V L K L P W T Q V G F S L L                              mmFATP4pep F L Y L G S G G W R F I R V F I K T I R R D I F G G L V L L        hsFATP4pep
L L Y L G S G G W R F I R V F I K T V R R D I F G G M V L L        mmFATP4pep K V K A K V R Q C L Q E R R T V P I L F A S T V R R H P D K        hsFATP4pep
K V K T K V R R Y L Q E R K T V P L L F A S M V Q R H P D K        mmFATP4pep T A L I F E G T D T H W T F R Q L D E Y S S S V A N F L Q A        hsFATP4pep
T A L I F E G T D T H W T F R Q L D E Y S S S V A N F L Q A        mmFATP4pep R G L A S G D V A A I F M E N R N E F V G L W L G M A K L G        hsFATP4pep
R G L A S G N V A L F M E N R N E F V G L W L G M A K L G         mmFATP4pep V E A A L I N T N L R R D A L L H C L T S R A R A L V F G          hsFATP4pep
V E A A L I N T N L R R D A L R H C L D T S K A R A L I F G        mmFATP4pep S E M A S A I C E V H A S L D P S L F C S G S W E P G A            hsFATP4pep
S E M A S A I C E I H A S L E P T L S L F C S G S W E P S T        mmFATP4pep
```

```
V P P S T E H L D P L L K D A P K H L P S C P D K G F T D K   hsFATP4pep
V P V S T E H L D P L L E D A P K H L P S H P D K G F T D K   mmFATP4pep L F Y I Y T S G T T G L P K A A I V V H S R Y Y R M A A L V   hsFATP4pep
L F Y I Y T S G T T G L P K A A I V V H S R Y Y R M A S L V   mmFATP4pep Y Y G F R M R P N D I V Y D C L P L Y H S A G N I V G I G Q   hsFATP4pep
Y Y G F R M R P D D I V Y D C L P L Y H S R K H R G D W Q     mmFATP4pep C L L H G M T V V I R K K F S A S R F W D D C I K Y N C T I   hsFATP4pep
C L L H G M T V V I R K K F S A S R F W D D C I K Y N C T V   mmFATP4pep V Q Y I G E L C R Y L L N Q P P R E A E N Q H Q V R M A L G   hsFATP4pep
V Q Y I G E L C R Y L L N Q P P R E A E S R H K V R M A L G   mmFATP4pep N G L R Q S I W T N F S S R F H I P Q V A E F Y G A T E C N   hsFATP4pep
N G L R Q S I W T D F S S R F H I P Q V A E F Y G A T E C N   mmFATP4pep C S L G N F D S Q V G A C G F N S R I L S F V Y P I R L V R   hsFATP4pep
C S L G N F D S R V G A C G F N S R I L S F V Y P I R L V R   mmFATP4pep
```

```
VNEDTMELIRGPDGVCIPCQPGEPGQLVGR   hsFATP4pep
VNEDTMELIRGPDGVCIPCQPGQPGQLVGR   mmFATP4pep IIQKDPLRRFDGYLNQGANNKKIAKDVFKK   hsFATP4pep
IIQDDPLRRFDGYLNQGANNKKIANDVFKK   mmFATP4pep GDQAYLTGDVLVMDELGYLYFRDRTGDTFR   hsFATP4pep
GDQAYLTGDVLVMDELGYLYFRDRTGDTFR   mmFATP4pep WKGENVSTTEVEGTLSRLLDMADVAVYGVE   hsFATP4pep
WKGENVSTTEVEGTLSRLLHMADVAVYGVE   mmFATP4pep VPGTEGRAGMAAVASPTGNCDLERFAQVLE   hsFATP4pep
VPGTEGRAGMAAVASPISNCDLESFAQTLK   mmFATP4pep KELPLYARPIFLRLLPELHKTGTYKFQKTE   hsFATP4pep
KELPLYARPIFLRFLPELHKTGTFKFQKTE   mmFATP4pep LRKEGFDPAIVKDPLFYLDAQKGRYVPLDQ   hsFATP4pep
LRKEGFDPSVVKDPLFYLDARKGCYVALDQ   mmFATP4pep EAYSRIQAGEEKL                    hsFATP4pep
EAYTRIQAGEEKL                    mmFATP4pep
``` hsFATP6

```
1    aac ggc aag taa gcg caa cgc aat taa tgt gag tag ctc act cat tag gca ccc cag gct
61   tta cac ttt atg ctt ccg ggc tcg tat gtt gtg aat acg act tgt gag cgg ata cca att tca
121  cac agg aac cag cta gaa cat gat tac gaa ttt gct act cac cgc tat agg gaa ttt ggc
181  cct cga ggc caa ttc ggc acg agg ggt ggt ccc ctg cgc ggt ttc ccg tgg tgc cga gta
241  gag act gta aat cgc tgc tct tca caa ctg ctt cca agg ctt ctg gct ctg tcc att
301  cag cct cca act caa gct cgc ggg aaa gga gga tac ctg aga gaa ctt cag ctg tcc ctg
361  gac ctt ctg agg gtg gag tcg gag gct ccc tgc gcc gcc cag tga ccc aag
421  ctt aat ctt cag cac cac ttg ggg cga cct ttt aaa cct acg att ctg ttt ctc
481  agg att cct ccc cat ccc gct tcg ccc cgg aaa agc tga caa gaa ctt cag gtg taa gcc
541  ctg agt gag gat ctg cgg tct ccg tgg aga gct gtg cct gga aga gaa ctg cgc tgg
601  tgg ggg aga ctg gag tca gag ctg tct tct ggc gtt gcc ccc atg ctt gcc tca tgg cta
661  aca gtt cta ggg gct gga atg gtc ctg gtc aaa ctc ctg aaa ctc ttc cct tac
     T   V   L   G   A   G   M   V   L   V   K   H   F   L   Q   K   L   L   F   P   Y
721  ttt tgg gat gac ttc tgg ttc gtg ttg aag gtg gtg ctc att ata att cgg ctg aag aag
     F   W   D   D   F   W   F   V   L   K   V   V   L   I   I   I   R   L   K   K
781  tat gaa aag aga ggg gag ctg gtg act gtg ctg gat aaa ttc ttg agt cat gcc aaa aga
     Y   E   K   R   G   E   L   V   T   V   L   D   K   F   L   S   H   A   K   R
```

FIG. 34A

```
841   caa cct cgg aaa cct ttc atc atc tat gag gga gac atc tac acc tat cag gat gta gac
      Q   P   R   K   P   F   I   I   Y   E   G   D   I   Y   T   Y   Q   D   V   D 901   aaa agg agc agc aga gtg gcc cat gtc ttc ctg aac cat tcc tct ctg aaa aag ggg gac
      K   R   S   S   R   V   A   H   V   F   L   N   H   S   S   L   K   K   G   D 961   acg gtg gct ctg ctg atg agc aat gag ccg gac ttc gtt cac gtg tgg ttc ggc ctc gcc
      T   V   A   L   L   M   S   N   E   P   D   F   V   H   V   W   F   G   L   A 1021  aag ctg ggc tgc gtg gtg gcc ttc ctc aac acc att cgc tcc aac tcc ctc ctg aat
      K   L   G   C   V   V   A   F   L   N   T   I   R   S   N   S   L   L   N 1081  tgc atc cgc gcc gcc tgt ggg ccc aga gcc cta gtg gtg ggc gca gat ttg ctt gga acg gta
      C   I   R   A   A   C   G   P   R   A   L   V   V   G   A   D   L   L   G   T   V 1141  gaa gaa atc ctt cca agc ctc tca gaa aat atc agt gtt tgg ggg atg aaa gat tct gtt
      E   E   I   L   P   S   L   S   E   N   I   S   V   W   G   M   K   D   S   V 1201  cca caa ggt gta att tca ctc aaa gaa ctg agc acc tca cct gat gag cct gtg cca
      P   Q   G   V   I   S   L   K   E   L   S   T   S   P   D   E   P   V   P 1261  cgc agc cac cat gtt gtc tca aaa gca gct cta aag tct act tgt ctt tac att ttt acc tct gga
      R   S   H   H   V   V   S   L   K   A   A   V   K   S   T   C   L   Y   I   F   T   S   G 1321  aca aca ggt cta cca att agt cag ctg cag gtt tta agg ggt tct gct
      T   T   G   L   P   K   A   A   V   I   S   Q   L   Q   V   L   R   G   S   A 1381  gtc ctg tgg gct ttt ggt tgt act gct cat gac att gtt tat ata acc ctt cct ctg tat
      V   L   W   A   F   G   C   T   A   H   D   I   V   Y   I   T   L   P   L   Y
```

FIG. 34B

```
1441  cat agt tca gca gct atc ctg gga att tct gga tgt gtt gag ttg ggt gcc act tgt gtg
      H   S   S   A   A   I   L   G   I   S   G   C   V   E   L   G   A   T   C   V 1501  tta aag aag aaa ttt tca gca agc cag ttt tgg agt ttt gac tgc aag tat aag gat gtg act
      L   K   K   K   F   S   A   S   Q   F   W   S   F   D   C   K   Y   K   D   V   T 1561  gtg ttt cag tat att gga gaa ctt cgt tgt cgc tac ctt tgc aaa caa tct aag aga gga
      V   F   Q   Y   I   G   E   L   R   C   R   Y   L   C   K   Q   S   K   R   E   G 1621  gaa aag gat cat aag gtg cgt ttg gca att ggc aat ggg ata cgg agt gat gta tgg aga
      E   K   D   H   K   V   R   L   A   I   G   N   G   I   R   S   D   V   W   R 1681  gaa ttt tta gac aga ttt gga aat ata aag gtg tgt gaa ctt tat gca gct acc gaa tca
      E   F   L   D   R   F   G   N   I   K   V   C   E   L   Y   A   A   T   E   S 1741  agc ata tct ttc atg aac tac act ggg aga att gga gca att ttt aga aca aat ttg ttt
      S   I   S   F   M   N   Y   T   G   R   I   G   A   I   F   R   T   N   L   F 1801  tac aaa ctt ctt tcc act ttt gac tta ata aag tat gac ttt cag gaa gat gaa ccc atg
      Y   K   L   L   S   T   F   D   L   I   K   Y   D   F   Q   K   D   E   P   M 1861  aga aat gag cag ggt tgg tgt att cat gtg aaa gga gaa cct gga cac ctc att tct
      R   N   E   Q   G   W   C   I   H   V   K   G   E   P   G   L   L   I   S 1921  cga gtg aat gca aaa ccc ttt ggc tat gct ggg cct tat aag gga cat aca aaa gac
      R   V   N   A   K   P   F   G   Y   A   G   P   Y   K   G   H   T   K   D 1981  aaa ttg ctt gat gtt ttt aag aag gga gat gtt tac ctt aat act gga gac ttc aga tgg
      K   L   L   D   V   F   K   K   G   D   V   Y   L   N   T   G   D   F   R   W 2041  gtc cag gat cag gac aat ttc tat ctt tgg gac cgt act gac act ttc aga tgg
      V   Q   D   Q   D   N   F   L   Y   F   W   D   R   T   G   D   T   F   R   W 2101  aaa gga gaa aat gtc gca acc act gag gtt gct gat gtt att gga atg ttc ata
      K   G   E   N   V   A   T   T   E   V   A   D   V   I   G   M   F   I
```

FIG. 34C

```
      K   G   E   N   V   A   T   T   E   V   A   D   V   I   G   M   L   D   F   I
2161  cag gaa gca aac gtc gct tat ggt gtg gct ata tca ggt tat gaa gga aga gca gga atg gct
      Q   E   A   N   V   A   Y   G   V   A   I   S   G   Y   E   G   R   A   G   M   A
2221  tct att att tta aaa cca aat aca tct tta gat ttg gaa aaa gtt tat gaa aaa gtt caa gtt gta
      S   I   I   L   K   P   N   T   S   L   D   L   E   K   V   Y   E   K   V   Q   V   V
2281  aca ttt cta cca gct tat gct tgt cca cga ttt tta aga att cag gaa aaa atg gaa gca
      T   F   L   P   A   Y   A   C   P   R   F   L   R   I   Q   E   K   M   E   A
2341  aca gga aca ttc aaa cta ttg aag cat cag gat gga gtg ttg gat ggt gaa ttt cca ctg aaa
      T   G   T   F   K   L   L   K   H   Q   D   G   V   L   V   E   D   G   F   N   P   L   K
2401  att tct gaa cca ctt tac ttc atg ttc atg gat aat aag aag tct taa gat ttt tat atc tag agg
      I   S   E   P   L   Y   F   M   F   M   D   N   L   K   K   S   Y   *   L   T   R
2461  gaa ctt tat gat caa ata tta ggg gaa ata ctt taa gat ttt tat atc tag aac
      E   L   Y   D   Q   I   L   G   E   I   K   L   *
2521  ttt cat atg ctt tct tag gaa gag tga gag ggt ata ttc atg aaa tgg gga
2581  aag gga gct aac att aat tta gca tgt act gca ttt cct ata ttt taa ttt ttt
2641  aat tgc ata aga att tta tct ttt aat tct aat tga tat ttt att ctt ttt
2701  atc tat ttg gag att cag tgc ttt cgg ttt act aag cat taa aga ttt taa ata
2761  ata aat agt ggc tag cgg ttt gga caa tca ctt taa atg tac ttt cta ata gt aaa att
2821  tct aat ttt gaa taa aag att aaa att tac tga aaa ttt aaa aaa aaa aaa ttg gcg
2881  gcc gc
```

FIG. 34D

Protein Sequence 619 a.a. MLLSWLTVLGAG....LYDQIMLGEIKL
619 Amino Acids MW: 70066 Dalton

|   |   | n | n% | MW | MW% |
|---|---|---|---|---|---|
| A ala | alanine | 33 | 5.3 | 2344 | 3.3 |
| C cys | cysteine | 14 | 2.3 | 1442 | 2.1 |
| D asp | aspartic acid | 34 | 5.5 | 3910 | 5.6 |
| E glu | glutamic acid | 31 | 5.0 | 4000 | 5.7 |
| F phe | phenylalanine | 34 | 5.5 | 5000 | 7.1 |
| G gly | glycine | 44 | 7.1 | 2508 | 3.6 |
| H his | histidine | 13 | 2.1 | 1781 | 2.5 |
| I ile | isoleucine | 37 | 6.0 | 4184 | 6.0 |
| K lys | lysine | 48 | 7.8 | 6148 | 8.8 |
| L leu | leucine | 75 | 12.1 | 8481 | 12.1 |
| M met | methionine | 11 | 1.8 | 1441 | 2.1 |
| N asn | asparagine | 21 | 3.4 | 2394 | 3.4 |
| P pro | proline | 21 | 3.4 | 2038 | 2.9 |
| Q gln | glutamine | 18 | 2.9 | 2305 | 3.3 |
| R arg | arginine | 27 | 4.4 | 4214 | 6.0 |
| S ser | serine | 40 | 6.5 | 3481 | 5.0 |
| T thr | threonine | 30 | 4.8 | 3031 | 4.3 |
| V val | valine | 51 | 8.2 | 5052 | 7.2 |
| W trp | tryptophan | 11 | 1.8 | 2046 | 2.9 |
| X ukw | unknown | -- | -- |   |   |
| Y tyr | tyrosine | 26 | 4.2 | 4239 | 6.1 |
| Z --- STOP |   |   |   |   |   |

FIG. 35B

|   |                                               |           |
|---|-----------------------------------------------|-----------|
| 1 | M R A P - - G A G A A S V V S L A L L W       | hsFATP1pep |
| 1 | L - - - - - - - - - - - - - - - F S K L -     | hsFATP4pep |
| 1 | M L L S W L T V L G A G M V L H F L Q         | hsFATP6pep |
| 19 | L L G L P W T S A A A A L G V Y V G S        | hsFATP1pep |
| 6 | V L K L P W T Q V G F S L L F L Y L G S       | hsFATP4pep |
| 21 | K L L F P Y F W D D F - - - - - - - -        | hsFATP6pep |
| 39 | G G W R F L R I V C K T A R R D L F G L      | hsFATP1pep |
| 26 | G G W R F I R V F I K T I R R D I F G G      | hsFATP4pep |
| 32 | - - W F V L K V - - - - - - - - - - - -      | hsFATP6pep |
| 59 | S V L I R V R L E L R R H Q R A G H T I      | hsFATP1pep |
| 46 | L V L L K V K A K V R Q C L Q E R R T V      | hsFATP4pep |
| 38 | - V L I I R L K K Y E K R G E L V T V        | hsFATP6pep |
| 79 | P R I F Q A V V Q R Q P E R L A L V D A      | hsFATP1pep |
| 66 | P I L F A S T V R R H P D K T A L I F E      | hsFATP4pep |
| 57 | L D K F L S H A K R Q P R K P F I I Y E      | hsFATP6pep |

FIG. 36A

| | | |
|---|---|---|
| 99  G T G E C W T F A Q L D A Y S N A V A N | hsFATP1pep |
| 86  G T D T H W T F R Q L D E Y S S S V A N | hsFATP4pep |
| 77  G - - D I Y T Y Q D V D K R S S R V A H | hsFATP6pep |
| | |
| 119 - L F R Q L G F A P G D V V A I F L E G | hsFATP1pep |
| 106 - F L Q A R G L A S G D V A A I F M E N | hsFATP4pep |
| 95  V F L N H S S L K K G D T V A L L M S N | hsFATP6pep |
| | |
| 138 R P E F V G L W L G L A K A G M E A A L | hsFATP1pep |
| 125 R N E F V G L W L G M A K L G V E A A L | hsFATP4pep |
| 115 E P D F V H V W F G L A K L G C V V A F | hsFATP6pep |
| | |
| 158 L N V N L R R E P L A F C L G T S G A K | hsFATP1pep |
| 145 I N T N L R R D A L L H C L T T S R A R | hsFATP4pep |
| 135 L N T N I R S N S L L N C I R A C G P R | hsFATP6pep |
| | |
| 178 A L I F G G E M V A A V A E V S G H L G | hsFATP1pep |
| 165 A L V F G S E M A S A I C E V H A S L D | hsFATP4pep |
| 155 A L V G A D L L G T V E E I L P S L S | hsFATP6pep |

FIG. 36B

```
198  K S L I K F C S G D L G P E G I L P D T   hsFATP1pep
185  P S L S L F C S G S W E P G A V P P S T   hsFATP4pep
175  E N I S V W G M K D S V P Q G V I S - -   hsFATP6pep 218  H L L D P L L K E A S T A P L A Q I P S   hsFATP1pep
205  E H L D P L L K D A P K - H L P S C P D   hsFATP4pep
193  - - L K E K L S T S P D E P V P R S H H   hsFATP6pep 238  K G - - M D D R L F Y I T S G T T G L     hsFATP1pep
224  K G - - F T D K L F Y I T S G T T G L     hsFATP4pep
211  V V S L L K S T C L Y I F T S G T T G L   hsFATP6pep 256  P K A A I V V H S R Y Y R M A A F G H H   hsFATP1pep
242  P K A A I V V H S R Y Y R M A A L V Y Y   hsFATP4pep
231  P K A A V I S Q L Q V L R G S A - V L W   hsFATP6pep 276  A Y R M Q A A D V L Y D C L P L Y H S A   hsFATP1pep
262  G F R M R P N D I V Y D C L P L Y H S A   hsFATP4pep
250  A F G C T A H D I V Y I T L P L Y H S S   hsFATP6pep
```

FIG. 36C

| | | | |
|---|---|---|---|
| 296 | G N I | I G V G Q C L I Y G L T V V L R K | hsFATP1pep |
| 282 | G N I | V G I G Q C L L H G M T V V I R K | hsFATP4pep |
| 270 | A A I | L G I S G C V E L G A T C V L K K | hsFATP6pep |
| 316 | K F S A S R F W D D C I K Y N C T V V Q | | hsFATP1pep |
| 302 | K F S A S R F W D D C I K Y N C T I V Q | | hsFATP4pep |
| 290 | K F S A S Q F W S D C K K Y D V T V F Q | | hsFATP6pep |
| 336 | Y I G E I C R Y L L K Q P V R E A E R R | | hsFATP1pep |
| 322 | Y I G E L C R Y L L N Q P P R E A E N Q | | hsFATP4pep |
| 310 | Y I G E L C R Y L C K Q S K R E G E K D | | hsFATP6pep |
| 356 | H R V R L A V G N G L R P A I W E E F T | | hsFATP1pep |
| 342 | H Q V R M A L G N G L R Q S I W T N F S | | hsFATP4pep |
| 330 | H K V R L A I G N G I R S D V W R E F L | | hsFATP6pep |
| 376 | E R F G V R Q I G E F Y G A T E C N C S | | hsFATP1pep |
| 362 | S R F H I P Q V A E F Y G A T E C N C S | | hsFATP4pep |
| 350 | D R F G N I K V C E L Y A A T E S S I S | | hsFATP6pep |

FIG. 36D

```
396  I A N M D G K V G S C G F N S R I L P H   hsFATP1pep
382  L G N F D S Q V G A C G F N S R I L S F   hsFATP4pep
370  F M N Y T G R I G A I G R T N L F Y K L   hsFATP6pep 416  V Y P I R L V K V N E D T M E L L R D A   hsFATP1pep
402  V Y P I R L V R V N E D T M E L I R G P   hsFATP4pep
390  L S T F D L I K Y D F Q K D E P M R N E   hsFATP6pep 436  Q G L C I P C Q A G E P G L L V G Q I N   hsFATP1pep
422  D G V C I P C Q P G E P G Q L V G R I I   hsFATP4pep
410  Q G W C I H V K K G E P G L L I S R V N   hsFATP6pep 456  Q D P L R R F D G Y V S E S A T S K -     hsFATP1pep
442  Q K D P L R R F D G Y L N Q G A N N K -   hsFATP4pep
430  A K N P - - - F F G Y A G P Y K H T K D   hsFATP6pep 475  K I A H S V F S K G D S A Y L - S G D V   hsFATP1pep
461  K I A K D V F K K G D Q A Y L - T G D V   hsFATP4pep
447  K L L C D V F K K G D - V Y L N T G D L   hsFATP6pep
```

FIG. 36E

| | | | | | | | | | | | | | | | | |
|---|---|---|---|---|---|---|---|---|---|---|---|---|---|---|---|---|
|494|L|V|M|D|E|L|G|Y|M|Y|F|R|D|R|S|G|D|T|F|R|hsFATP1pep|
|480|L|V|M|D|E|L|G|Y|L|Y|F|R|D|R|T|G|D|T|F|R|hsFATP4pep|
|466|I|V|Q|D|N|F|L|Y|E|W|D|R|T|G|D|T|F|R|hsFATP6pep|

|514|W|R|G|E|N|V|S|T|T|E|V|E|G|V|L|S|R|L|L|G|hsFATP1pep|
|500|W|K|G|E|N|V|S|T|T|E|V|E|G|T|L|S|R|L|L|D|hsFATP4pep|
|486|W|K|G|E|N|V|A|T|T|E|V|A|D|V|I|G|M|L|D|F|hsFATP6pep|

|534|Q|T|D|V|A|V|Y|G|V|A|V|P|G|V|E|G|K|A|G|M|hsFATP1pep|
|520|M|A|D|V|A|V|Y|G|V|E|V|P|G|T|E|G|R|A|G|M|hsFATP4pep|
|506|I|Q|E|A|N|V|Y|G|V|A|I|S|G|Y|E|G|R|A|G|M|hsFATP6pep|

|554|A|A|V|A|-|D|P|H|S|L|L|D|P|N|A|I|Y|Q|E|L|hsFATP1pep|
|540|A|A|V|A|-|S|P|T|G|N|C|D|L|E|R|F|A|Q|V|L|hsFATP4pep|
|526|A|S|I|I|L|K|P|N|T|S|L|D|E|K|V|Y|E|Q|V|hsFATP6pep|

|573|Q|K|V|L|A|P|Y|A|R|P|I|F|L|R|L|L|P|Q|V|D|hsFATP1pep|
|559|E|K|E|L|P|L|Y|A|R|P|I|F|L|R|L|L|P|E|L|H|hsFATP4pep|
|546|V|T|F|L|P|A|Y|A|C|P|R|F|L|R|I|Q|E|K|M|E|hsFATP6pep|

FIG. 36F

|     |   |   |   |   |   |   |   |   |   |   |   |   |   |   |          |
|-----|---|---|---|---|---|---|---|---|---|---|---|---|---|---|----------|
| 593 | T | T | G | T | F | K | I | Q | K | T | R | L | Q | R | E G F D P R | hsFATP1pep |
| 579 | K | T | G | T | Y | K | F | Q | K | T | E | L | R | K | E G F D P A | hsFATP4pep |
| 566 | A | T | G | T | F | K | L | L | K | H | Q | L | V | E | D G F N P L | hsFATP6pep |
|     |   |   |   |   |   |   |   |   |   |   |   |   |   |   |          |
| 613 | Q | T | S | D | R | L | F | F | L | D | L | K | Q | G | H Y L P L N | hsFATP1pep |
| 599 | I | V | K | D | P | L | F | Y | L | D | A | Q | K | G | R Y V P L D | hsFATP4pep |
| 586 | K | I | S | E | P | L | Y | F | M | D | N | L | K | K | S Y V L L T | hsFATP6pep |
|     |   |   |   |   |   |   |   |   |   |   |   |   |   |   |          |
| 633 | E | A | V | Y | T | R | I | C | S | G | A | F | A | L |          | hsFATP1pep |
| 619 | Q | E | A | Y | S | R | I | Q | A | G | E | E | K | L |          | hsFATP4pep |
| 606 | R | E | L | Y | D | Q | I | M | L | G | E | I | K | L |          | hsFATP6pep |

FIG. 36G

| | | | |
|---|---|---|---|
| hsFATP4_ | 1 | [MLL]-GASLVGVLLFSKL-[VLKLPWTQVGFSLLF] | 31 |
| mmFATP4_ | 1 | [MLL]-GASLVGVLLFSKL-[VLKLPWTQVGFSLLX] | 31 |
| hsFATP1_ | 1 | [MRAPGAGAASV][VSLALLWLLGLPWT][WSAAAALG] | 33 |
| | | | |
| hsFATP4_ | 32 | LYLGSGGWRFIRVFIKT[IRRDIFGG][LVLLKVKA] | 64 |
| mmFATP4_ | 32 | LYLGSGGWRFIRVFIKT[VRRDIFGG][MVLLKVKT] | 64 |
| hsFATP1_ | 34 | V[Y]VGSGGWRF[LR]IVCKT[ARRD][LFGLSVLI][RV][RL] | 66 |
| | | | |
| hsFATP4_ | 65 | KVRQC[L]QERR[TVPILFAST][V][RHPDKTALIFEG] | 97 |
| mmFATP4_ | 65 | KVRRYL[QERKTVPLLFASM][V][QRHPDKTALIFEG] | 97 |
| hsFATP1_ | 67 | EL[RRH]QRAGH[T][I][PRI][FQAVVQR][QPERLAL][VDAG] | 99 |
| | | | |
| hsFATP4_ | 98 | TDTHWTFRQLDEYSSSVANFLQARGLASGDV[AA] | 130 |
| mmFATP4_ | 98 | TDTHWTFRQLDEYSSSVANFLQARGLASG[N]VA | 130 |
| hsFATP1_ | 100 | [I]GECWTF[AQLD]AYSNAVANLFRQLG[FA][PGDVVA] | 132 |
| | | | |
| hsFATP4_ | 131 | IFMENRNEFVGLWLGMAKLGVEAALINTNLRRD | 163 |
| mmFATP4_ | 131 | LFMENRNEFVGLWLGMAKLGVEAALINTNLRRD | 163 |
| hsFATP1_ | 133 | I[F]L[EG][R]PEFVGLWLG[LAK][AG]MEAALL[NVNLRRE] | 165 |
| | | | |
| hsFATP4_ | 164 | ALL[HCL]TSRARAL[V]FGSEMASAICEVHASL[DP] | 196 |
| mmFATP4_ | 164 | AL[R]HCL[DT]SKARALIFGSEMASAICE[I]HASLE[P] | 196 |
| hsFATP1_ | 166 | P[LI]AFC[L]G[TSG]A[KAL]IFGG[EMVAA]VAEV[S]GHLGK | 198 |
| | | | |
| hsFATP4_ | 197 | SLSLFCSGSWEPGA[VPPSTEHLDPL][L][KDAP]-[KH] | 228 |
| mmFATP4_ | 197 | T[L]SLFCSGSWEPSTVPVSTEHLDPL[L][EDAP]-[KH] | 228 |
| hsFATP1_ | 199 | S[LI]KFCSG[DL]GPEGILP[DT][H]LLDPLLK[EA]STAP | 231 |

FIG. 39A

| | | |
|---|---|---|
| hsFATP4_ 229 | LPSCPDKGFTDKLFYIYTSGTTGLPKAAIVVHS | 261 |
| mmFATP4_ 229 | LPSHPDKGFTDKLFYIYTSGTTGLPKAAIVVHS | 261 |
| hsFATP1_ 232 | LAQIPSKGMDDRLFYIYTSGTTGLPKAAIVVHS | 264 |
| hsFATP4_ 262 | RYYRMAALVYYGFRMRPNDIVYDCLPLYHSAGN | 294 |
| mmFATP4_ 262 | RYYRMASLVYYGFRMRPDDIVYDCLPLYHSSRK | 294 |
| hsFATP1_ 265 | RYYRMAAFGHHAYRMQAADVLYDCLPLYHSAGN | 297 |
| hsFATP4_ 295 | IVGIGQCLLHGMTVVIRKKFSASRFWDDCIKYN | 327 |
| mmFATP4_ 295 | HRGDWQCLLHGMTVVIRKKFSASRFWDDCIKYN | 327 |
| hsFATP1_ 298 | IIGVGQCLIYGLTVVLRKKFSASRFWDDCIKYN | 330 |
| hsFATP4_ 328 | CTIVQYIGELCRYLLNQPPREAENQHQVRMALG | 360 |
| mmFATP4_ 328 | CTVVQYIGELCRYLLNQPPREAESRHKVRMALG | 360 |
| hsFATP1_ 331 | CTVVQYIGEICRYLLKQPVREAERRHRVRLAVG | 363 |
| hsFATP4_ 361 | NGLRQSIWTNFSSRFHIPQVAEFYGATECNCSL | 393 |
| mmFATP4_ 361 | NGLRQSIWTDFSSRFHIPQVAEFYGATECNCSL | 393 |
| hsFATP1_ 364 | NGLRPAIWEEFTERFGVRQIGEFYGATECNCSI | 396 |
| hsFATP4_ 394 | GNFDSQVGACGFNSRILSFVYPIRLVRVNEDTM | 426 |
| mmFATP4_ 394 | GNFDSRVGACGFNSRILSFVYPIRLVRVNEDTM | 426 |
| hsFATP1_ 397 | ANMDGKVGSCGFNSRILPHVYPIRLVKVNEDTM | 429 |

FIG. 39B

| | | |
|---|---|---|
| hsFATP4_ 427 | ELIRGPDGVCIPCQPGEPGGQLVGRIIQKDPLRR | 459 |
| mmFATP4_ 427 | ELIRGPDGVCIPCQPGGQPGGQLVGRIIQQDPLRR | 459 |
| hsFATP1_ 430 | ELLRDAQGLCIPCQAGEPGLLVGQINQQDPLRR | 462 |
| hsFATP4_ 460 | FDGYLNQGANNKKIAKDVFKKGDQAYLTGDVLV | 492 |
| mmFATP4_ 460 | FDGYLNQGANNKKIANDVFKKGDQAYLTGDVLV | 492 |
| hsFATP1_ 463 | FDGYVSESATSKKIAHSVFSKGDSAYLSGDVLV | 495 |
| hsFATP4_ 493 | MDELGYLYFRDRTGDTFRWKGENVSTTEVEGTL | 525 |
| mmFATP4_ 493 | MDELGYLYFRDRTGDTFRWKGENVSTTEVEGTL | 525 |
| hsFATP1_ 496 | MDELGYMYFRDRSGDTFRWRGENVSTTEVEGVL | 528 |
| hsFATP4_ 526 | SRLLDMADVAVYGVEVPGTEGRAGMAAVASPTG | 558 |
| mmFATP4_ 526 | SRLLHMADVAVYGVEVPGTEGRAGMAAVASPIS | 558 |
| hsFATP1_ 529 | SRLLGQTDVAVYGVAVPGVEGKAGMAAVADPHS | 561 |
| hsFATP4_ 559 | NCDLERFAQVLEKELPLYARPIFLRLLPELHKT | 591 |
| mmFATP4_ 559 | NCDLESFAQTLKKELPLYARPIFLRLLPELHKT | 591 |
| hsFATP1_ 562 | LLDPNAIYQELQKVLAPYARPIFLRLLPQVDTT | 594 |
| hsFATP4_ 592 | GTYKFQKTELRKEGFDPAIVKDPLFYLDAQKGR | 624 |
| mmFATP4_ 592 | GTFKFQKTELRKEGFDPSVVKDPLFYLDARKGC | 624 |
| hsFATP1_ 595 | GTFKIQKTRLQREGFDPRQTSDRLFFLDLKQGH | 627 |
| hsFATP4_ 625 | YVPLDQEAYSRIQAGEEKL | 643 |
| mmFATP4_ 625 | YVALDQEAYTRIQAGEEKL | 643 |
| hsFATP1_ 628 | YLPLNEAVYTRICSGAFAL | 646 |

FIG. 39C mmFATP4 DNA sequence

```
ATGCTGCTTGGAGCCTCTCTGGTGGGGGCGCTACTGTTCTCCAAGC
TAGTGCTGAAGCTGCCCTGGACCCAGGTGGGATTCTCCCTGTTGCT
CCTGTACTTGGGGTCTGGTGGCTGGCGTTTCATCCGGGTCTTCATC
AAGACGGTCAGGAGAGATATCTTTGGTGGCATGGTGCTCCTGAAGG
TGAAGACCAAGGTGCGACGGTACCTTCAGGAGCGGAAGACGGTGCC
CCTGCTGTTTGCTTAATGGTACAGCGCCACCCGGACAAGACAGCC
CTGATTTTCGAGGGCACAGACACTCACTGGACCTTCCGCCAGCTGG
ATGAGTACTCCAGTAGTGTGGCCAACTTCCTGCAGGCCCGGGGCCT
GGCCTCAGGCAATGTAGTTGCCCTCTTTATGGAAAACCGCAATGAG
TTTGTGGGTCTGTGGCTAGGCATGGCCAAGCTGGGCGTGGAGGCGG
CTCTCATCAACACCAACCTTAGGCGGGATGCCCTGCGCCACTGTCT
TGACACCTCAAAGGCACGAGCTCTCATCTTTGGCAGTGAGATGGCC
TCAGCTATCTGTGAGATCCATGCTAGCCTGGAGCCCACACTCAGCC
TCTTCTGCTCTGGATCCTGGGAGCCCAGCACAGTGCCCGTCAGCAC
AGAGCATCTGGACCCTCTTCTGGAAGATGCCCCGAAGCACCTGCCC
AGTCACCCAGACAAGGGTTTTACAGATAAGCTCTTCTACATCTACA
CATCGGGCACCACGGGGCTACCCAAAGCTGCCATTGTGGTGCACAG
CAGGTATTATCGTATGCTTCCCTGGTGTACTATGGATTCCGCATG
CGGCCTGATGACATTGTCTATGACTGCCTCCCCTCTACCACTCAA
GCAGGAAACATCGTGGGGATTGGCAGTGCTTACTCCACGGCATGAC
TGTGGTGATCCGGAAGAAGTTCTCAGCCTCCCGGTTCTGGGATGAT
TGTATCAAGTACAACTGCACAGTGGTACAGTACATTGGCGAGCTCT
GCCGCTACCTCCTGAACCAGCCACCCCGTGAGGCTGAGTCTCGGCA
CAAGGTGCGCATGGCACTGGGCAACGGTCTCCGGCAGTCCATCTGG
ACCGACTTCTCCAGCCGTTTCCACATCCCCCAGGTGGCTGAGTTCT
ATGGGGCCACTGAATGCAACTGTAGCCTGGGCAACTTTGACAGCCG
GGTGGGGGCCTGTGGCTTCAATAGCCGCATCCTGTCCTTTGTGTAC
CCTATCCGTTTGGTACGTGTCAATGAGGATACCATGGAACTGATCC
GGGACCCGATGGAGTCTGCATTCCCTGTCAACCAGGTCAGCCAGG
CCAGCTGGTGGGTCGCATCATCCAGCAGGACCCTCTGCGCCGTTTC
```

FIG. 43A

```
GACGGGTACCTCAACCAGGGTGCCAACAACAAGAAGATTGCTAATG
ATGTCTTCAAGAAGGGGGACCAAGCCTACCTCACTGGTGACGTCCT
GGTGATGGATGAGCTGGGTTACCTGTACTTCCGAGATCGCACTGGG
GACACGTTCGCTGGAAGGGGAGAATGTATCTACCACTGAGGTGG
AGGGCACACTCAGCCGCCTGCTTCATATGGCAGATGTGGCAGTTTA
TGGTGTTGAGGTGCCAGGAACTGAAGGCCGAGCAGGAATGGCTGCC
GTTGCAAGTCCCATCAGCAACTGTGACCTGGAGAGCTTTGCACAGA
CCTTGAAAAGGAGCTGCCTCTGTATGCCCGCCCATCTTCCTGCG
CTTCTTGCCTGAGCTGCACAAGACAGGGACCTTCAAGTTCCAGAAG
ACAGAGTTGCGGAAGGAGGGCTTTGACCCATCTGTTGTGAAAGACC
CGCTGTTCTATCTGGATGCTCGGAAGGGCTGCTACGTTGCACTGGA
CCAGGAGGCCTATACCCGCATCCAGGCAGGCGAGGAGAAGCTGTGA
TTTCCCCTACATCCCTCTGAGGGCCAGAAGATGCTGGATTCAGAG
CCCTAGCGTCCACCCAGAGGGTCCTGGGCAATGCCAGACCAAAGC
TAGCAGGGCCCGCACCTCCGCCCCTAGGTGCTGATCTCCCCTCTCC
CAAACTGCCAAGTGACTCACTGCCGCTTCCCCGACCCTCCAGAGGC
TTTCTGTGAAAGTCTCATCCAAGCTGTGTCTTCTGGTCCAGGCGTG
GCCCCTGGCCCCAGGGTTTCTGATAGGCTCCTTTAGGATGGTATCT
TGGGTCCAGCGGGCCAGGGTGTGGGAGAGGAGTCACTAAGATCCCT
CCAATCAGAAGGGAGCTTACAAAGGAACCAAGGCAAAGCCTGTAGA
CTCAGGAAGCTAAGTGGCCAGAGACTATAGTGGCCAGTCATCCCAT
GTCCACAGAGGATCTTGGTCCAGAGCTGCCAAAGTGTCACCTCTCC
CTGCCTGCACCTCTGGGGAAAAGAGGACAGCATGTGGCCACTGGGC
ACCTGTCTCAAGAAGTCAGGATCACACTCAGTCCTTGTTTCTCC
AGGTTCCCTTGTTCTTGTCTCGGGAGGGAGGGACGAGTGTCCTGT
CTGTCCTTCCTGCCTGTCTGTGAGTCTGTGTTGCTTCTCCATCTGT
CCTAGCCTGAGTGTGGGTGGAACAGGCATGAGGAGAGTGTGGCTCA
GGGGCCAATAAACTCTGCCTTGACTCCTCTTAAAAAAAAAAAAAA
AAAAAAAAAAAAAAAAAAAAAAAAAAAAAAAAAAAAAAAA
```

FIG. 43B mmFATP4 protein sequence

```
MLLGASLVGALLFSKLVLKLPWTQVGFSLLLLYLGSGGWRFIRVFI
KTVRRDIFGGMVLLKVKTKVRRYLQERKTVPLLFASMVQRHPDKTA
LIFEGTDTHWTFRQLDEYSSSVANFLQARGLASGNVVALFMENRNE
FVGLWLGMAKLGVEAALINTNLRRDALRHCLDTSKARALIFGSEMA
SAICEIHASLEPTLSLFCSGSWEPSTVPVSTEHLDPLLEDAPKHLP
SHPDKGFTDKLFYIYTSGTTGLPKAAIVVHSRYYRMASLVYYGFRM
RPDDIVYDCLPLYHSSRKHRGDWQCLLHGMTVVIRKKFSASRFWDD
CIKYNCTVVQYIGELCRYLLNQPPREAESRHKVRMALGNGLRQSIW
TDFSSRFHIPQVAEFYGATECNCSLGNFDSRVGACGFNSRILSFVY
PIRLVRVNEDTMELIRGPDGVCIPCQPGQPGQLVGRIIQQDPLRRF
DGYLNQGANNKKIANDVFKKGDQAYLTGDVLVMDELGYLYFRDRTG
DTFRWKGENVSTTEVEGTLSRLLHMADVAVYGVEVPGTEGRAGMAA
VASPISNCDLESFAQTLKKELPLYARPIFLRFLPELHKTGTFKFQK
TELRKEGFDPSVVKDPLFYLDARKGCYVALDQEAYTRIQAGEEKL
```

TCGACCCACGGCGTCCGGGACCCCAAAGCAGAAGCCCGCA  40
CAGTAGGCACAGCGCACCCAAGAAGGGTCCAGGAGTCTGC  80
AGAAACAGAAAGGTCCCCGGCCTCAGCCTCCTAGTCCCTG  120
CCTGCCTCCTGCCTGAGCTTCTGGGAGACTGAAGGCACGG  160
CTTGCAGCTTCAGGATGCGGGCTCCGGGTGCGGGCGCGGC  200

210       220       230       240
  |....|....|....|....|....|....|....|....|

CTCGGTGGTCTCGCTGGCGCTGTTGTGGCTGCTGGGGCTG  240
CCGTGGACCTGGAGCGCGGCAGCGGCGCTCGGCGTGTACG  280
TGGGCAGCGGCGGCTGGCGCTTCCTGCGCATCGTCTGCAA  320
GACCGCGAGGCGAGACCTCTTCGGTCTCTCTGTGCTGATC  360
CGCGTGCGCCTGGAGCTGCGGCGGCACCAGCGTGCCGGCC  400

410       420       430       440
  |....|....|....|....|....|....|....|....|

ACACCATCCCGCGCATCTTTCAGGCGGTAGTGCAGCGACA  440
GCCCGAGCGCCTGGCGCTGGTGGATGCCGGGACCGGCGAG  480
TGCTGGACCTTTGCGCAGCTGGACGCCTACTCCAATGCGG  520
TAGCCAACCTCTTCCGCCAGCTGGGCTTCGCGCCGGGCGA  560
CGTGGTGGCCATCTTCCTGGAGGGCCGGCCGGAGTTCGTG  600

610       620       630       640
  |....|....|....|....|....|....|....|....|

GGGCTGTGGCTGGGCCTGGCCAAGGCGGGCATGGAGGCCG  640
CGCTGCTCAACGTGAACCTGCGGCGCGAGCCCCTGGCCTT  680
CTGCCTGGGCACCTCGGGCGCTAAGGCCCTGATCTTTGGA  720
GGAGAAATGGTGGCGGCGGTGGCCGAAGTGAGCGGGCATC  760
TGGGGAAAAGTTTGATCAAGTTCTGCTCTGGAGACTTGGG  800

810       820       830       840
  |....|....|....|....|....|....|....|....|

GCCCGAGGGCATCTTGCCGGACACCCACCTCCTGGACCCG  840
CTGCTGAAGGAGGCCTCTACTGCCCCCTTGGCACAGATCC  880
CCAGCAAGGGCATGGACGATCGTCTTTTCTACATCTACAC  920
GTCGGGGACCACCGGGCTGCCCAAGGCTGCCATTGTCGTG  960
CACAGCAGGTACTACCGCATGGCAGCCTTCGGCCACCACG  1000

1010      1020      1030      1040
  |....|....|....|....|....|....|....|....|

CCTACCGCATGCAGGCGGCTGACGTGCTCTATGACTGCCT  1040
GCCCCTGTACCACTCGGCAGGAAACATCATCGGCGTGGGG  1080
CAGTGTCTCATCTATGGGCTGACAGTCGTCCTCCGCAAGA  1120
AATTCTCGGCCAGCCGCTTCTGGGACGACTGCATCAAGTA  1160
CAACTGCACGGTGGTTCAGTACATCGGGGAGATCTGCCGC  1200
```

FIG. 44A

```
          1210        1220        1230        1240
    |....|....|....|....|....|....|....|....|....|
TACCTGCTGAAGCAGCCGGTGCGCGAGGCGGAGAGGCGAC 1240
ACCGCGTGCGCCTGGCGGTGGGGAACGGGCTGCGTCCTGC 1280
CATCTGGGAGGAGTTCACGGAGCGCTTCGGCGTACGCCAA 1320
ATCGGGGAGTTCTACGGCGCCACCGAGTGCAACTGCAGCA 1360
TTGCCAACATGGACGGCAAGGTCGGCTCCTGTGGTTTCAA 1400
          1410        1420        1430        1440
    |....|....|....|....|....|....|....|....|....|
CAGCCGCATCCTGCCCCACGTGTACCCATCCGGCTGGTG 1440
AAGGTCAATGAGGACACAATGGAGCTGCTGCGGGATGCCC 1480
AGGGCCTCTGCATCCCCTGCCAGGCGGGGAGCCTGGCCT 1520
CCTTGTGGGTCAGATCAACCAACAGGACCCGCTGCGCCGC 1560
TTCGATGGCTATGTCAGCGAGAGCGCCACCAGCAAGAAGA 1600
          1610        1620        1630        1640
    |....|....|....|....|....|....|....|....|....|
TCGCCCACAGCGTCTTCAGCAAGGGCGACAGCGCCTACCT 1640
CTCAGGTGACGTGCTAGTGATGGATGAGCTGGGCTACATG 1680
TACTTCCGGGACCGTAGCGGGGACACCTTCCGCTGGCGAG 1720
GGGAGAACGTCTCCACCACCGAGGTGGAGGGCGTGCTGAG 1760
CCGCCTGCTGGGCCAGACAGACGTGGCCGTCTATGGGGTG 1800
          1810        1820        1830        1840
    |....|....|....|....|....|....|....|....|....|
GCTGTTCCAGGAGTGGAGGGTAAGGCAGGGATGGCGGCCG 1840
TCGCAGACCCCCACAGCCTGCTGGACCCCAACGCGATATA 1880
CCAGGAGCTGCAGAAGGTGCTGGCACCCTATGCCCGGCCC 1920
ATCTTCCTGCGCCTCCTGCCCCAGGTGGACACCACAGGCA 1960
CCTTCAAGATCCAGAAGACGAGGCTGCAGCGAGAGGGCTT 2000
          2010        2020        2030        2040
    |....|....|....|....|....|....|....|....|....|
TGACCCACGCCAGACCTCAGACCGGCTCTTCTTCCTGGAC 2040
CTGAAGCAGGGCCACTACCTGCCCTTAAATGAGGCAGTCT 2080
ACACTCGCATCTGCTCGGGCGCCTTCGCCCTCTGAAGCTG 2120
TTCCTCTACTGGCCACAAACTCTGGGCCTGGTGGGAGAGG 2160
CCAGCTTGAGCCAGACAGCGCTGCCCAGGGGTGGCCGCCT 2200
```

FIG. 44B

```
                2610      2620      2630      2640
         ╷┴┴┴┴╷┴┴┴┴╷┴┴┴┴╷┴┴┴┴╷┴┴┴┴╷┴┴┴┴╷┴┴┴┴╷
         GGTCAGGCTGGTCTTGAACTCCTGACCTCAGGTGATCCGC 2640
         TGGCCTCGGCCTCCCAGAGTGCTGGGATTATAGGCGTGAG 2680
         CCTCTGGCCCGGCCTTTCCTTTTCCTCTCCTCTCCTGCC 2720
         GAGAGTGGAACACACGTGTCCTGGGAGCTGCATCTTGTGT 2760
         AGGGTCCAGCTGCTTTTGGGGACTGCAGGAATCATCTCCC 2800
                2810      2820      2830      2840
         ╷┴┴┴┴╷┴┴┴┴╷┴┴┴┴╷┴┴┴┴╷┴┴┴┴╷┴┴┴┴╷┴┴┴┴╷
         CTGGGCCCTGGACTCGGACTGGGGCCTCCCCACCTCCCTC 2840
         TCGGCTGTGCCTTACGGAGCCCCAATCCAGGCCTCCTGTG 2880
         GCTGTTGGGTTCCAGATGCTGCAGCTCCATGTGACTTCCA 2920
         AGCAGGCCCTCCGCCCTCCTGCTGAATGGAGGAGCCGGG 2960
         GGTCCCCCAGGCCAACTGGAAAATCTCCCAGGCTAGGCCA 3000
                3010      3020      3030      3040
         ╷┴┴┴┴╷┴┴┴┴╷┴┴┴┴╷┴┴┴┴╷┴┴┴┴╷┴┴┴┴╷┴┴┴┴╷
         ATTGCCTTTTGCACTTCCCCGTTCCTGTCACATTTCCCCA 3040
         GCCCCACCTTCCCCTCCTGATGCCCTGAAAGCTTCCGGAA 3080
         TTGACTGTGACCACTTGGATGTCACCACTGTCAGCCCCTG 3120
         CCTTGATGTCCCCATTTAGCCATCTCCATGGAGCTCCTGC 3160
         TGGAGGGCCCTGAACCCTGCACTGCGTGGCTGCCCAGCCA 3200
                3210      3220      3230      3240
         ╷┴┴┴┴╷┴┴┴┴╷┴┴┴┴╷┴┴┴┴╷┴┴┴┴╷┴┴┴┴╷┴┴┴┴╷
         GCTGCCTCCTGTCCTGGGAGGAGGCCTCCTGGGTGTCCTC 3240
         ATCTGGTGTGTCTACTGGAGGGTCCCACAGGAGAGGCAGC 3280
         AGAGGGGTCAGGGGAGGTCTCCTGCCGGGGGTTGGCCTCT 3320
         CAAGCCTCAGGGGTTCTAGCCTGTTGAATATACCCCACCT 3360
         GGTGGGTGGCCCCTCCGATGTCCCCACTGATGGCTCTGAC 3400
                3410      3420      3430      3440
         ╷┴┴┴┴╷┴┴┴┴╷┴┴┴┴╷┴┴┴┴╷┴┴┴┴╷┴┴┴┴╷┴┴┴┴╷
         ACCGTGTTGGTGGCGATGTCCCAGACAATCCCACCAGGAC 3440
         GGCCCAGACATCCCTACTGGCTTCGCTGGTGGCTCATCTC 3480
         GAACATCCACGCCAGCCTTTCTGGGGCCGGCCACCCAGGC 3520
         CGCCTGTCCGTCTGTCCTCCCTCCAGCAGCACCCCTGGC 3560
         CCCTGGAGTGGTGGGGCCATGGCAAGAGACACCGTGGCGT 3600
                3610      3620      3630      3640
         ╷┴┴┴┴╷┴┴┴┴╷┴┴┴┴╷┴┴┴┴╷┴┴┴┴╷┴┴┴┴╷┴┴┴┴╷
         CTCATGTGAACTTTCCTGGGCACTGTGGTTTTATTTCCTA 3640
         ATTGATTTAAGAAATAAACCTGAAGACCGTCTGGTGAAAA 3680
         AAAAAAAAAAAAAA 3694
```

FIG. 44C

```
              2610       2620       2630       2640
         |....|....|....|....|....|....|....|....|
         GGTCAGGCTGGTCTTGAACTCCTGACCTCAGGTGATCCGC 2640
         TGGCCTCGGCCTCCCAGAGTGCTGGGATTATAGGCGTGAG 2680
         CCTCTGGCCCGGCCTTTCCTTTTCCTCTCCTCTCCTGCC 2720
         GAGAGTGGAACACACGTGTCCTGGGAGCTGCATCTTGTGT 2760
         AGGGTCCAGCTGCTTTTGGGGACTGCAGGAATCATCTCCC 2800
              2810       2820       2830       2840
         |....|....|....|....|....|....|....|....|
         CTGGGCCCTGGACTCGGACTGGGGCCTCCCCACCTCCCTC 2840
         TCGGCTGTGCCTTACGGAGCCCCAATCCAGGCCTCCTGTG 2880
         GCTGTTGGGTTCCAGATGCTGCAGCTCCATGTGACTTCCA 2920
         AGCAGGCCCTCCGCCCTCCCTGCTGAATGGAGGAGCCGGG 2960
         GGTCCCCAGGCCAACTGGAAAATCTCCCAGGCTAGGCCA 3000
              3010       3020       3030       3040
         |....|....|....|....|....|....|....|....|
         ATTGCCTTTTGCACTTCCCCGTTCCTGTCACATTTCCCCA 3040
         GCCCCACCTTCCCCTCCTGATGCCCTGAAAGCTTCCGGAA 3080
         TTGACTGTGACCACTTGGATGTCACCACTGTCAGCCCCTG 3120
         CCTTGATGTCCCCATTTAGCCATCTCCATGGAGCTCCTGC 3160
         TGGAGGGCCCTGAACCCTGCACTGCGTGGCTGCCCAGCCA 3200
              3210       3220       3230       3240
         |....|....|....|....|....|....|....|....|
         GCTGCCTCCTGTCCTGGGAGGAGGCCTCCTGGGTGTCCTC 3240
         ATCTGGTGTGTCTACTGGAGGGTCCCACAGGAGAGGCAGC 3280
         AGAGGGGTCAGGGGAGGTCTCCTGCCGGGGTTGGCCTCT 3320
         CAAGCCTCAGGGGTTCTAGCCTGTTGAATATACCCCACCT 3360
         GGTGGGTGGCCCCTCCGATGTCCCACTGATGGCTCTGAC 3400
              3410       3420       3430       3440
         |....|....|....|....|....|....|....|....|
         ACCGTGTTGGTGGCGATGTCCCAGACAATCCCACCAGGAC 3440
         GGCCCAGACATCCCTACTGGCTTCGCTGGTGGCTCATCTC 3480
         GAACATCCACGCCAGCCTTTCTGGGGCCGGCCACCCAGGC 3520
         CGCCTGTCCGTCTGTCCTCCCTCCAGCAGCACCCCTGGC 3560
         CCCTGGAGTGGTGGGGCCATGGCAAGAGACACCGTGGCGT 3600
              3610       3620       3630       3640
         |....|....|....|....|....|....|....|....|
         CTCATGTGAACTTTCCTGGGCACTGTGGTTTTATTTCCTA 3640
         ATTGATTTAAGAAATAAACCTGAAGACCGTCTGGTGAAAA 3680
         AAAAAAAAAAAAAA 3694
```

FIG. 44D hsFATP1 full length protein

```
         10        20        30        40
         |         |         |         |
MRAPGAGAASVVSLALLWLLGLPWTWSAAAALGVYVGSGG  40
WRFLRIVCKTARRDLFGLSVLIRVRLELRRHQRAGHTIPR  80
IFQAVVQRQPERLALVDAGTGECWTFAQLDAYSNAVANLF 120
RQLGFAPGDVVAIFLEGRPEFVGLWLGLAKAGMEAALLNV 160
NLRREPLAFCLGTSGAKALIFGGEMVAAVAEVSGHLGKSL 200
        210       220       230       240
         |         |         |         |
IKFCSGDLGPEGILPDTHLLDPLLKEASTAPLAQIPSKGM 240
DDRLFYIYTSGTTGLPKAAIVVHSRYYRMAAFGHHAYRMQ 280
AADVLYDCLPLYHSAGNIIGVGQCLIYGLTVVLRKKFSAS 320
RFWDDCIKYNCTVVQYIGEICRYLLKQPVREAERRHRVRL 360
AVGNGLRPAIWEEFTERFGVRQIGEFYGATECNCSIANMD 400
        410       420       430       440
         |         |         |         |
GKVGSCGFNSRILPHVYPIRLVKVNEDTMELLRDAQGLCI 440
PCQAGEPGLLVGQINQQDPLRRFDGYVSESATSKKIAHSV 480
FSKGDSAYLSGDVLVMDELGYMYFRDRSGDTFRWRGENVS 520
TTEVEGVLSRLLGQTDVAVYGVAVPGVEGKAGMAAVADPH 560
SLLDPNAIYQELQKVLAPYARPIFLRLLPQVDTTGTFKIQ 600
        610       620       630       640
         |         |         |         |
KTRLQREGFDPRQTSDRLFFLDLKQGHYLPLNEAVYTRIC 640
SGAFAL 646
```

FIG. 45

Hs VLACS full length DNA

```
          10         20         30         40
    ....|....|....|....|....|....|....|....|
    GGAATTCCAAAAAAAAAAAATACGACTACACCTGCTCCGG   40
    AGCCCGCGGCGGTACCTGCAGCGGAGGAGCTCTGTCTTCC   80
    CCTTCATCTCACGCGAGCCCGGCGTCCCGCCGCGTGCGCC  120
    CCGGCGCAGCCCGCCAGTCCGCCCGGAGCCCGCCCAGTCG  160
    CCGCGCTGCACGCCGGGGTGAACCCTCTGCCCTCGCTGG   200
         210        220        230        240
    ....|....|....|....|....|....|....|....|
    GACAGAGGGCCCCGCAGCCGTCATGCTTTCCGCCATCTAC  240
    ACAGTCCTGGCGGGACTGCTGTTCCTGCCGCTCCTGGTGA  280
    ACCTCTGCTGCCCATACTTCTTCCAGGACATAGGCTACTT  320
    CTTGAAGGTGGCCGCCGTGGGCCGGAGGGTGCGCAGCTAC  360
    GGGCAGCGGCGGCCGGCGCGCACCATCCTGCGGGCGTTCC  400
         410        420        430        440
    ....|....|....|....|....|....|....|....|
    TGGAGAAAGCGCGCCAGACGCCACACAAGCCTTTTCTGCT  440
    CTTCCGCGACGAGACTCTCACCTACGCGCAGGTGGACCGG  480
    CGCAGCAATCAAGTGGCCCGGGCGCTGCACGACCACCTCG  520
    GCCTGCGCCAGGGAGACTGCGTGGCGCTCCTTATGGGTAA  560
    CGAGCCGGCCTACGTGTGGCTGTGGCTGGGGCTGGTGAAG  600
         610        620        630        640
    ....|....|....|....|....|....|....|....|
    CTGGGCTGTGCCATGGCGTGCCTCAATTACAACATCCGCG  640
    CGAAGTCCCTGCTGCACTGCTTCCAGTGCTGCGGGGCGAA  680
    GGTGCTGCTGGTGTCGCCAGAACTACAAGCAGCTGTCGAA  720
    GAGATACTGCCAAGCCTTAAAAAAGATGATGTGTCCATCT  760
    ATTATGTGAGCAGAACTTCTAACACAGATGGGATTGACTC  800
         810        820        830        840
    ....|....|....|....|....|....|....|....|
    TTTCCTGGACAAAGTGGATGAAGTATCAACTGAACCTATC  840
    CCAGAGTCATGGAGGTCTGAAGTCACTTTTTCCACTCCTG  880
    CCTTATACATTTATACTTCTGGAACCACAGGTCTTCCAAA  920
    AGCAGCCATGATCACTCATCAGCGCATATGGTATGGAACT  960
    GGCCTCACTTTTGTAAGCGGATTGAAGGCAGATGATGTCA 1000
        1010       1020       1030       1040
    ....|....|....|....|....|....|....|....|
    TCTATATCACTCTGCCCTTTTACCACAGTGCTGCACTACT 1040
    GATTGGCATTCACGGATGTATTGTGGCTGGTGCTACTCTT 1080
    GCCTTGCGGACTAAATTTTCAGCCAGCCAGTTTTGGGATG 1120
    ACTGCAGAAAATACAACGTCACTGTCATTCAGTATATCGG 1160
    TGAACTGCTTCGGTATTTATGCAACTCACCACAGAAACCA 1200
```

FIG. 46A

```
                   1210      1220      1230      1240
           |....|....|....|....|....|....|....|....|
           AATGACCGTGATCATAAAGTGAGACTGGCACTGGGAAATG 1240
           GCTTACGAGGAGATGTGTGGAGACAATTTGTCAAGAGATT 1280
           TGGGGACATATGCATCTATGAGTTCTATGCTGCCACTGAA 1320
           GGCAATATTGGATTTATGAATTATGCGAGAAAGTTGGTG  1360
           CTGTTGGAAGAGTAAACTACCTACAGAAAAAATCATAAC  1400
                   1410      1420      1430      1440
           |....|....|....|....|....|....|....|....|
           TTATGACCTGATTAAATATGATGTGGAGAAAGATGAACCT 1440
           GTCCGAGATGAAAATGGATATTGCGTCAGAGTTCCCAAAG 1480
           GTGAAGTTGGACTTCTGGTTTGCAAAATCACACAACTTAC 1520
           ACCATTTAATGGCTATGCTGGAGCAAAGGCTCAGACAGAG 1560
           AAGAAAAAACTGAGAGATGTCTTTAAGAAAGGAGACCTCT 1600
                   1610      1620      1630      1640
           |....|....|....|....|....|....|....|....|
           ATTTCAACAGTGGAGATCTCTTAATGGTTGACCATGAAAA 1640
           TTTCATCTATTTCCACGACAGAGTTGGAGATACATTCCGG 1680
           TGGAAAGGGGAAAATGTGGCCACCACTGAAGTTGCTGATA 1720
           CAGTTGGACTGGTTGATTTTGTCCAAGAAGTAAATGTTTA 1760
           TGGAGTGCATGTGCCAGATCATGAGGGTCGCATTGGCATG 1800
                   1810      1820      1830      1840
           |....|....|....|....|....|....|....|....|
           GCCTCCATCAAAATGAAAGAAAACCATGAATTTGATGGAA 1840
           AGAAACTCTTTCAGCACATTGCTGATTACCTACCTAGTTA 1880
           TGCAAGGCCCCGGTTTCTAAGAATACAGGACACCATTGAG 1920
           ATCACTGGAACTTTTAAACACCGCAAAATGACCCTGGTGG 1960
           AGGAGGGCTTTAACCCTGCTGTCATCAAAGATGCCTTGTA 2000
                   2010      2020      2030      2040
           |....|....|....|....|....|....|....|....|
           TTTCTTGGATGACACAGCAAAAATGTATGTGCCTATGACT 2040
           GAGGACATCTATAATGCCATAAGTGCTAAAACCCTGAAAC 2080
           TCTGAATATTCCCAGGAGGATAACTCAACATTTCCAGAAA 2120
           GAAACTGAATGGACAGCCACTTGATATAATCCAACTTTAA 2160
           TTTGATTGAAGATTGTGAGGAAATTTGTAGGAAATTTGC  2200
                   2210      2220      2230      2240
           |....|....|....|....|....|....|....|....|
           ATACCCGTAAAGGGAGACTTTTTAAATAACAGTTGAGTC  2240
           TTTGCAAGTAAAAAGATTTAGAGATTATTATTTTCAGTG  2280
           TGCACCTACTGTTTGTATTTGCAAACTGAGCTTGTTGGAG 2320
           GGAAGGCATTATTTTTTAAAATACTTAGTAAATTAAATGA 2360
           AC                                       2362
```

FIG. 46B hs VLACS full length protein

```
          10        20        30        40
MLSAIYTVLAGLLFLPLLVNLCCPYFFQDIGYFLKVAAVG   40
RRVRSYGQRRPARTILRAFLEKARQTPHKPFLLFRDETLT   80
YAQVDRRSNQVARALHDHLGLRQGDCVALLMGNEPAYVWL  120
WLGLVKLGCAMACLNYNIRAKSLLHCFQCCGAKVLLVSPE  160
LQAAVEEILPSLKKDDVSIYYVSRTSNTDGIDSFLDKVDE  200
         210       220       230       240
VSTEPIPESWRSEVTFSTPALYIYTSGTTGLPKAAMITHQ  240
RIWYGTGLTFVSGLKADDVIYITLPFYHSAALLIGIHGCI  280
VAGATLALRTKFSASQFWDDCRKYNVTVIQYIGELLRYLC  320
NSPQKPNDRDHKVRLALGNGLRGDVWRQFVKRFGDICIYE  360
FYAATEGNIGFMNYARKVGAVGRVNYLQKKIITYDLIKYD  400
         410       420       430       440
VEKDEPVRDENGYCVRVPKGEVGLLVCKITQLTPFNGYAG  440
AKAQTEKKKLRDVFKKGDLYFNSGDLLMVDHENFIYFHDR  480
VGDTFRWKGENVATTEVADTVGLVDFVQEVNVYGVHVPDH  520
EGRIGMASIKMKENHEFDGKKLFQHIADYLPSYARPRFLR  560
IQDTIEITGTFKHRKMTLVEEGFNPAVIKDALYFLDDTAK  600
         610       620       630       640
MYVPMTEDIYNAISAKTLKL    620
```

FIG. 47

```
         10        20        30        40
  ┴┴┴┴┴┴┴┴┴┴┴┴┴┴┴┴┴┴┴┴┴┴┴┴┴┴┴┴┴┴┴┴┴┴┴┴┴┴┴┴
AAGTTCTCGGCTGGTCAGTTCTGGGAAGATTGCCAGCAGC   40
ACAGGGTGACGGTGTTCCAGTACATTGGGGAGCTGTGCCG   80
ATACCTTGTCAACCAGCCCCGAGCAAGGCAGAACGTGGC   120
CATAAGGTCCGGCTGGCAGTGGGCAGCGGGCTGCGCCCAG  160
ATACCTGGGAGCGTTTTGTGCGGCGCTTCGGGCCCCTGCA  200
        210       220       230       240
  ┴┴┴┴┴┴┴┴┴┴┴┴┴┴┴┴┴┴┴┴┴┴┴┴┴┴┴┴┴┴┴┴┴┴┴┴┴┴┴┴
GGTGCTGGAGACATATGGACTGACAGAGGGCAACGTGGCC  240
ACCATCAACTACACAGGACAGCGGGGCGCTGTGGGGCGTG  280
CTTCCTGGCTTTACAAGCATATCTTCCCCTTCTCCTTGAT  320
TCGCTATGATGTCACCACAGGAGAGCCAATTCGGGACCCC  360
CAGGGGCACTGTATGGCCACATCTCCAGGTGAGCCAGGGC  400
        410       420       430       440
  ┴┴┴┴┴┴┴┴┴┴┴┴┴┴┴┴┴┴┴┴┴┴┴┴┴┴┴┴┴┴┴┴┴┴┴┴┴┴┴┴
TGCTGGTGGCCCCGGTAAGCCAGCAGTCCCCATTCCTGGG  440
CTATGCTGGCGGGCCAGAGCTGGCCCAGGGGAAGTTGCTA  480
AAGGATGTCTTCCGGCCTGGGGATGTTTTCTTCAACACTG  520
GGGACCTGCTGGTCTGCGATGACCAAGGTTTTCTCCGCTT  560
CCATGATCGTACTGGAGACACCTTCAGGTGGAAGGGGGAG  600
        610       620       630       640
  ┴┴┴┴┴┴┴┴┴┴┴┴┴┴┴┴┴┴┴┴┴┴┴┴┴┴┴┴┴┴┴┴┴┴┴┴┴┴┴┴
AATGTGGCCACAACCGAGGTGGCAGAGGTCTTCGAGGCCC  640
TAGATTTTCTTCAGGAGGTGAACGTCTATGGAGTCACTGT  680
GCCAGGGCATGAAGGCAGGGCTGGAATGGCAGCCCTAGTT  720
CTGCGTCCCCCCACGCTTTGGACCTTATGCAGCTCTACA  760
CCCACGTGTCTGAGAACTTGCCACCTTATGCCCGGCCCG   800
        810       820       830       840
  ┴┴┴┴┴┴┴┴┴┴┴┴┴┴┴┴┴┴┴┴┴┴┴┴┴┴┴┴┴┴┴┴┴┴┴┴┴┴┴┴
ATTCCTCAGGCTCCAGGAGTCTTTGGCCACCACAGAGACC  840
TTCAAACAGCAGAAAGTTCGGATGGCAAATGAGGGCTTCG  880
ACCCCAGCACCCTGTCTGACCCACTGTACGTTCTGGACCA  920
GGCTGTAGGTGCCTACCTGCCCCTCACAACTGCCCGGTAC  960
AGCGCCCTCCTGGCAGGAAACCTTCGAATCTGAGAACTTC  1000
       1010      1020      1030      1040
  ┴┴┴┴┴┴┴┴┴┴┴┴┴┴┴┴┴┴┴┴┴┴┴┴┴┴┴┴┴┴┴┴┴┴┴┴┴┴┴┴
CACACCTGAGGCACCTGAGAGAGGAACTCTGTGGGGTGGG  1040
GGCCGTTGCAGGTGTACTGGGCTGTCAGGGATCTTTTCTA  1080
TACCAGAACTGCGGTCACTATTTTGTAATAAATGTGGCTG  1120
GAGCTGATCCAGCTGTCTCTGACAAAAAAAAAAAAAAAA   1160
AAAGGGCGGCCGC                              1173
```

FIG. 48 hsFATP3 partial protein

```
         10        20        30        40
KFSAGQFWEDCQQHRVTVFQYIGELCRYLVNQPPSKAERG  40
HKVRLAVGSGLRPDTWERFVRRFGPLQVLETYGLTEGNVA  80
TINYTGQRGAVGRASWLYKHIFPFSLIRYDVTTGEPIRDP 120
QGHCMATSPGEPGLLVAPVSQQSPFLGYAGGPELAQGKLL 160
KDVFRPGDVFFNTGDLLVCDDQGFLRFHDRTGDTFRWKGE 200
         210       220       230       240
NVATTEVAEVFEALDFLQEVNVYGVTVPGHEGRAGMAALV 240
LRPPHALDLMQLYTHVSENLPPYARPRFLRLQESLATTET 280
FKQQKVRMANEGFDPSTLSDPLYVLDQAVGAYLPLTTARY 320
SALLAGNLRI    330
```

FIG. 49 hsFATP full length

```
           10         20         30         40
    |....|....|....|....|....|....|....|....|
    CGACCCACGCGTCCGGGCGGGCGGGGCCGGGCGGCGGGCG  40
    GGGCTGGCGGGGCGGCCGGGCCATGCAGGGCGCAGAGCCG  80
    GCTAAACCCTGCTGAGACCCGGCTCCGTGCGTCCAGGGGC  120
    GGCTAATGCCCCTCACGCTGTCTACGCTGCTGCAACCGGG  160
    CCGCATCTGGACGGGGCGCCGCGCGGCGGAGCCGACGCCG  200
           210        220        230        240
    |....|....|....|....|....|....|....|....|
    GGCCACAATGCTGCTTGGAGCCTCTCTGGTGGGGGTGCTG  240
    CTGTTCTCCAAGCTGGTGCTGAAACTGCCCTGGACCCAGG  280
    TGGGATTCTCCCTGTTGTTCCTCTACTTGGGATCTGGCGG  320
    CTGGCGCTTCATCCGGGTCTTCATCAAGACCATCAGGCGC  360
    GATATCTTTGGCGGCCTGGTCCTCCTGAAGGTGAAGGCAA  400
           410        420        430        440
    |....|....|....|....|....|....|....|....|
    AGGTGCGACAGTGCCTGCAGGAGCGGCGGACAGTGCCCAT  440
    TTTGTTTGCCTCTACCGTTCGGCGCCACCCCGACAAGACG  480
    GCCCTGATCTTCGAGGGCACAGATACCCACTGGACCTTCC  520
    GCCAGCTGGATGAGTACTCAAGCAGTGTAGCCAACTTCCT  560
    GCAGGCCCGGGGCCTGGCCTCGGGCGATGTGGCTGCCATC  600
           610        620        630        640
    |....|....|....|....|....|....|....|....|
    TTCATGGAGAACCGCAATGAGTTCGTGGGCCTATGGCTGG  640
    GCATGGCCAAGCTCGGTGTGGAGGCAGCCCTCATCAACAC  680
    CAACCTGCGGCGGGATGCTCTGCTCCACTGCCTCACCACC  720
    TCGCGCGCACGGGCCCTTGTCTTTGGCAGCGAAATGGCCT  760
    CAGCCATCTGTGAGGTCCATGCCAGCCTGGACCCCTCGCT  800
           810        820        830        840
    |....|....|....|....|....|....|....|....|
    CAGCCTCTTCTGCTCTGGCTCCTGGGAGCCCGGTGCGGTG  840
    CCTCCAAGCACAGAACACCTGGACCCTCTGCTGAAAGATG  880
    CTCCCAAGCACCTTCCCAGTTGCCCTGACAAGGGCTTCAC  920
    AGATAAACTGTTCTACATCTACACATCCGGCACCACAGGG  960
    CTGCCCAAGGCCGCCATCGTGGTGCACAGCAGGTATTACC  1000
           1010       1020       1030       1040
    |....|....|....|....|....|....|....|....|
    GCATGGCTGCCCTGGTGTACTATGGATTCCGCATGCGGCC  1040
    CAACGACATCGTCTATGACTGCCTCCCCCTCTACCACTCA  1080
    GCAGGAAACATCGTGGGAATCGGCCAGTGCCTGCTGCATG  1120
    GCATGACGGTGGTGATTCGGAAGAAGTTCTCAGCCTCCCG  1160
    GTTCTGGGACGATTGTATCAAGTACAACTGCACGATTGTG  1200
```

FIG. 50A

```
         1210      1220      1230      1240
    |||||||||||||||||||||||||||||||||||||
CAGTACATTGGTGAACTGTGCCGCTACCTCCTGAACCAGC 1240
CACCGCGGGAGGCAGAAAACCAGCACCAGGTTCGCATGGC 1280
ACTAGGCAATGGCCTCCGGCAGTCCATCTGGACCAACTTT 1320
TCCAGCCGCTTCCACATACCCCAGGTGGCTGAGTTCTACG 1360
GGGCCACAGAGTGCAACTGTAGCCTGGGCAACTTCGACAG 1400
         1410      1420      1430      1440
    |||||||||||||||||||||||||||||||||||||
CCAGGTGGGGGCCTGTGGTTTCAATAGCCGCATCCTGTCC 1440
TTCGTGTACCCCATCCGGTTGGTACGTGTCAACGAGGACA 1480
CCATGGAGCTGATCCGGGGGCCCGACGGCGTCTGCATTCC 1520
CTGCCAGCCAGGTGAGCCGGGCCAGCTGGTGGGCCGCATC 1560
ATCCAGAAAGACCCCCTGCGCCGCTTCGATGGCTACCTCA 1600
         1610      1620      1630      1640
    |||||||||||||||||||||||||||||||||||||
ACCAGGGCGCCAACAACAAGAAGATTGCCAAGGATGTCTT 1640
CAAGAAGGGGGACCAGGCCTACCTTACTGGTGATGTGCTG 1680
GTGATGGACGAGCTGGGCTACCTGTACTTCCGAGACCGCA 1720
CTGGGGACACGTTCCGCTGGAAGGTGAGAACGTGTCCAC 1760
CACCGAGGTGGAAGGCACACTCAGCCGCCTGCTGGACATG 1800
         1810      1820      1830      1840
    |||||||||||||||||||||||||||||||||||||
GCTGACGTGGCCGTGTATGGTGTCGAGGTGCCAGGAACCG 1840
AGGGCCGGGCCGGAATGGCTGCTGTGGCCAGCCCCACTGG 1880
CAACTGTGACCTGGAGCGCTTTGCTCAGGTCTTGGAGAAG 1920
GAACTGCCCCTGTATGCGCGCCCCATCTTCCTGCGCCTCC 1960
TGCCTGAGCTGCACAAAACAGGAACCTACAAGTTCCAGAA 2000
         2010      2020      2030      2040
    |||||||||||||||||||||||||||||||||||||
GACAGAGCTACGGAAGGAGGGCTTTGACCCGGCTATTGTG 2040
AAAGACCCGCTGTTCTATCTAGATGCCCAGAAGGGCCGCT 2080
ACGTCCCGCTGGACCAAGAGGCCTACAGCCGCATCCAGGC 2120
AGGCGAGGAGAAGCTGTGATTCCCCCATCCCTCTGAGGG 2160
CCGGCGGATGCTGGATCCGGAGCCCCAGGTTCCGCCCCAG 2200
```

FIG. 50B

```
                2210        2220        2230        2240
        ┌┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴
        AGCGGTCCTGGACAAGGCCAGACCAAAGCAAGCAGGGCCT 2240
        GGCACCTCCATCCTGAGGTGCTGCCCCTCCATCCAAAACT 2280
        GCCAAGTGACTCATTGCCTTCCCAACCCTTCCAGAGGCTT 2320
        TCTGTGAAAGTCTCATGTCCAAGTTCCGTCTTCTGGGCTG 2360
        GGCAGGCCCTCTGGTTCCCAGGCTGAGACTGACGGGTTTT 2400
                 2410        2420        2430        2440
        ┌┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴
        CTCAGGATGATGTCTTGGGTGAGGGTAGGGAGAGGACAAG 2440
        GGGTCACCGAGCCCTTCCCAGAGAGCAGGGAGCTTATAAA 2480
        TGGAACCAGAGCAGAAGTCCCCAGACTCAGGAAGTCAACA 2520
        GAGTGGGCAGGGACAGTGGTAGCATCCATCTGGTGGCCAA 2560
        AGAGAATCGTAGCCCCAGAGCTGCCCAAGTTCACTGGGCT 2600
                       2610        2620        2630        2640
        ┌┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴
        CCACCCCCACCTCCAGGAGGGGAGGAGAGGACCTGACATC 2640
        TGTAGGTGGCCCCTGATGCCCCATCTACAGCAGGAGGTCA 2680
        GGACCACGCCCCTGGCCTCTCCCCACTCCCCATCCTCCT 2720
        CCCTGGGTGGCTGCCTGATTATCCCTCAGGCAGGGCCTCT 2760
        CAGTCCTTGTGGGTCTGTGTCACCTCCATCTCAGTCTTGG 2800
                 2810        2820        2830        2840
        ┌┴┴┴┴┴┴┴┴┴┴┴┴┴┴┴┴┴┴┴┴┴┴┴┴┴┴┴┴┴┴┴┴┴┴┴┴┴┴┴┴┴┴┴┴┴
        CCTGGCTATGAGGGGAGGAGGAATGGGAGAGGGGGCTCAG 2840
        GGGCCAATAAACTCTGCCTTGAGTCCTCCTAAAAAAAAAA 2880
        AAAAAAAAAAAAAAAAAAAAAAAAAAA 2907
```

FIG. 50C hsFATP4 full length protein

```
         10        20        30        40
         |         |         |         |
MLLGASLVGVLLFSKLVLKLPWTQVGFSLLFLYLGSGGWR   40
FIRVFIKTIRRDIFGGLVLLKVKAKVRQCLQERRTVPILF   80
ASTVRRHPDKTALIFEGTDTHWTFRQLDEYSSSVANFLQA  120
RGLASGDVAAIFMENRNEFVGLWLGMAKLGVEAALINTNL  160
RRDALLHCLTTSRARALVFGSEMASAICEVHASLDPSLSL  200
        210       220       230       240
         |         |         |         |
FCSGSWEPGAVPPSTEHLDPLLKDAPKHLPSCPDKGFTDK  240
LFYIYTSGTTGLPKAAIVVHSRYYRMAALVYYGFRMRPND  280
IVYDCLPLYHSAGNIVGIGQCLLHGMTVVIRKKFSASRFW  320
DDCIKYNCTIVQYIGELCRYLLNQPPREAENQHQVRMALG  360
NGLRQSIWTNFSSRFHIPQVAEFYGATECNCSLGNFDSQV  400
        410       420       430       440
         |         |         |         |
GACGFNSRILSFVYPIRLVRVNEDTMELIRGPDGVCIPCQ  440
PGEPGQLVGRIIQKDPLRRFDGYLNQGANNKKIAKDVFKK  480
GDQAYLTGDVLVMDELGYLYFRDRTGDTFRWKGENVSTTE  520
VEGTLSRLLDMADVAVYGVEVPGTEGRAGMAAVASPTGNC  560
DLERFAQVLEKELPLYARPIFLRLLPELHKTGTYKFQKTE  600
        610       620       630       640
         |         |         |         |
LRKEGFDPAIVKDPLFYLDAQKGRYVPLDQEAYSRIQAGE  640
EKL                                       643
```

FIG. 51 hsFATP5(partial)

```
GTCGTTGGGATCCTCGGCTGCTTAGATCTCGGAGCCACCTGTGTTCT
GGCCCCCAAGTTCTCTACTTCCTGCTTCTGGGATGACTGTCGGCAGC
ATGGCGTGACAGTGATCCTGTATGTGGGCGAGCTCCTGCGATACTTG
TGTAACATTCCCCAGCAACCAGAGGACCGGACACATACAGTCCGCC
TGGCAATGGGCAATGGACTACGGGCTGATGTGTGGGGAGACCTTCC
AGCAGCGTTTCGGTCCTATTTCGGATCTNGGGAAGTCTTACGGGCTT
CCACAGAAGGGCAACATGGGGCTTTAGTTCAAATATTGTTGGGGGC
GCTGCGGGGCCCTGGGGGCAAAGATGGAGCTTGCCTCCTCCGAATG
CTGTCCCCTTTGAGCTGGTGCAGTTCGACATGGAGGCGGCGGAGC
CTGTGAGGGACAATCAGGGCTTCTGCATCCCTGTAGGGCTAGGGGA
GCCGGGGCTGCTGTTGACCAAGGTGGTAAGCCAGCAACCCTTCGTG
GGCTACCGCGGCCCCGAGAGCTGTCGGAACGGAAGCTGGTGCGCA
ACGTGCGGCAATCGGGCGACGTTACTACAACACCGGGGACGTACT
GGCCATGGACCGCGAAGGCTTCCTCTACTTCCGCGACCGACTCGGG
GACACCTTCCGATGGAAGGGCGAGAACGTGTCCACGCACGAGGTGG
AGGGCGTGTTGTCGCAGGTGGACTTCTTGCAACAGGTTAACGTGTAT
GGCGTGTGCGTGCCAGGTTGTGAGGGTAAGGTGGGCATGGCTGCTG
TGGCATTAGCCCCCGGCCAGACTTCGACGGGGAGAAGTTGTACCA
GCACGTTCGCGCTTGGCTCCCTGCCTACGCTACCCCCATTTCATCC
GCATCCAGGACGCCATGGAGGTCACCAGCACGTTCAAACTGATGAA
GACCCGGTTGGTGCGTGAGGGCTTCAATGTGGGGATCGTGGTTGAC
CCTCTGTTTGTACTGGACAACCGGGCCCAGTCCTTCCGGCCCCTGAC
GGCAGAAATGTACCAGGCTGTGTGTGAGGGAACCTGGAGGCTCTGA
TCACCTGGCCAACCCACTGGGGTAGGGATCAAAGCCAGCCACCCCC
ACCCCAACACACTCGGTGTCCCTTTCATCCTGGGCCTGTGTGAATCC
CAGCCTGGCCATACCCTCAACCTCAGTGGGCTGGAAATGACAGTGG
GCCCTGTAGCAGTGGCAGAATAAACTCAGMTGYGTTCACAGAAA
```

FIG. 52 hsFATP partial protein

```
              10        20        30        40
     |....|....|....|....|....|....|....|....|
     VVGILGCLDLGATCVLAPKFSTSCFWDDCRQHGVTVILYV   40
     GELLRYLCNIPQQPEDRTHTVRLAMGNGLRADVWGDLPAA   80
     FRSYFGSXEVLRASTEGQHGALVQILLGALRGPGGKDGAC  120
     LLRMLSPFELVQFDMEAAEPVRDNQGFCIPVGLGEPGLLL  160
     TKVVSQQPFVGYRGPRELSERKLVRNVRQSGDVYYNTGDV  200
             210       220       230       240
     |....|....|....|....|....|....|....|....|
     LAMDREGFLYFRDRLGDTFRWKGENVSTHEVEGVLSQVDF  240
     LQQVNVYGVCVPGCEGKVGMAAVALAPGQTFDGEKLYQHV  280
     RAWLPAYATPHFIRIQDAMEVTSTFKLMKTRLVREGFNVG  320
     IVVDPLFVLDNRAQSFRPLTAEMYQAVCEGTWRL        354
```

FIG. 53 hsFATP6 full length DNA

```
          10        20        30        40
AACGGCAAGTAAGCGCAACGCAATTAATGTGAGTAGCTCA  40
CTCATTAGGCACCCCAGGCTTTACACTTTATGCTTCCGGG  80
CTCGTATGTTGTGTGGAATTGTGAGCGGATACCAATTTCA  120
CACAGGAACCAGCTATGACATGATTACGAATTTAATACGA  160
CTCACTATAGGGAATTTGGCCCTCGAGGCCAAGAATTCGG  200

210       220       230       240
CACGAGGGGTGCTGAGCCCCTGCGCGGTTTCTGGTGCGTA  240
GAGACTGTAAATCGCTGCGCTTCTCAGTCATCATCATCCC  280
AGCTTTTCCCGGCTCGAATTCAGCCTCCAACTCAAGCTCG  320
CGGGAAAGACTACCTGAGAGGAGAAAAGCTTCTGTCCCTG  360
GACCTTCTTCTGAGGGTGGAGTCGGAGGCTCCCTGCTTTC  400

410       420       430       440
CAGCCGCCCAGTGACCCAAGCTTAATCTTCAGCACCACTT  440
GGGGCGACCTTTTCGGTGCAAACCTACGATTCTGTTTCTC  480
AGGATTCCTCCCCATCCCGCTTCGCCCCGGAAAAGCTGAC  520
AAGAACTTCAGGTGTAAGCCCTGAGTAGTGAGGATCTGCG  560
GTCTCCGTGGAGAGCTGTGCCTGGAAGAGAAGGACGCTGG  600

610       620       630       640
TGGGGGCTGAGATCAGAGCTGTCTTCTGGCCCAGTTGCCC  640
CCATGCTTCTGTCATGGCTAACAGTTCTAGGGGCTGGAAT  680
GGTCGTCCTGCACTTCTTGCAGAAACTCCTGTTCCCTTAC  720
TTTTGGGATGACTTCTGGTTCGTGTTGAAGGTGGTGCTCA  760
TTATAATTCGGCTGAAGAAGTATGAAAAGAGAGGGGAGCT  800

810       820       830       840
GGTGACTGTGCTGGATAAATTCTTGAGTCATGCCAAAAGA  840
CAACCTCGGAAACCTTTCATCATCTATGAGGGAGACATCT  880
ACACCTATCAGGATGTAGACAAAAGGAGCAGCAGAGTGGC  920
CCATGTCTTCCTGAACCATTCCTCTCTGAAAAAGGGGGAC  960
ACGGTGGCTCTGCTGATGAGCAATGAGCCGGACTTCGTTC  1000

1010      1020      1030      1040
ACGTGTGGTTCGGCCTCGCCAAGCTGGGCTGCGTGGTGGC  1040
CTTTCTCAACACCAACATTCGCTCCAACTCCCTCCTGAAT  1080
TGCATCCGCGCCTGTGGGCCCAGAGCCCTAGTGGTGGGCG  1120
CAGATTTGCTTGGAACGGTAGAAGAAATCCTTCCAAGCCT  1160
CTCAGAAAATATCAGTGTTTGGGGGATGAAAGATTCTGTT  1200
```

FIG. 54A

```
                 1210       1220       1230       1240
         ....|....|....|....|....|....|....|....|....|
         CCACAAGGTGTAATTTCACTCAAAGAAAAACTGAGCACCT 1240
         CACCTGATGAGCCCGTGCCACGCAGCCACCATGTTGTCTC 1280
         ACTCCTCAAGTCTACTTGTCTTTACATTTTTACCTCTGGA 1320
         ACAACAGGTCTACCAAAAGCAGCTGTGATTAGTCAGCTGC 1360
         AGGTTTTAAGGGGTTCTGCTGTCCTGTGGGCTTTTGGTTG 1400
                 1410       1420       1430       1440
         ....|....|....|....|....|....|....|....|....|
         TACTGCTCATGACATTGTTTATATAACCCTTCCTCTGTAT 1440
         CATAGTTCAGCAGCTATCCTGGGAATTTCTGGATGTGTTG 1480
         AGTTGGGTGCCACTTGTGTGTTAAAGAAGAAATTTTCAGC 1520
         AAGCCAGTTTTGGAGTGACTGCAAGAAGTATGATGTGACT 1560
         GTGTTTCAGTATATTGGAGAACTTTGTCGCTACCTTTGCA 1600
                 1610       1620       1630       1640
         ....|....|....|....|....|....|....|....|....|
         AACAATCTAAGAGAGAAGGAGAAAAGGATCATAAGGTGCG 1640
         TTTGGCAATTGGAAATGGCATACGGAGTGATGTATGGAGA 1680
         GAATTTTAGACAGATTTGGAAATATAAAGGTGTGTGAAC  1720
         TTTATGCAGCTACCGAATCAAGCATATCTTTCATGAACTA 1760
         CACTGGGAGAATTGGAGCAATTGGGAGAACAAATTTGTTT 1800
                 1810       1820       1830       1840
         ....|....|....|....|....|....|....|....|....|
         TACAAACTTCTTTCCACTTTTGACTTAATAAAGTATGACT 1840
         TTCAGAAAGATGAACCCATGAGAAATGAGCAGGGTTGGTG 1880
         TATTCATGTGAAAAAGGAGAACCTGGACTTCTCATTTCT  1920
         CGAGTGAATGCAAAAAATCCCTTCTTTGGCTATGCTGGGC 1960
         CTTATAAGCACACAAAGACAAATTGCTTTGTGATGTTTT  2000
                 2010       2020       2030       2040
         ....|....|....|....|....|....|....|....|....|
         TAAGAAGGGAGATGTTTACCTTAATACTGGAGACTTAATA 2040
         GTCCAGGATCAGGACAATTTCCTTTATTTTGGGACCGTA  2080
         CTGGAGACACTTTCAGATGGAAGGAGAAAATGTCGCAAC  2120
         CACTGAGGTTGCTGATGTTATTGGAATGTTGGATTTCATA 2160
         CAGGAAGCAAACGTCTATGGTGTGGCTATATCAGGTTATG 2200
```

FIG. 54B

```
         2210      2220      2230      2240
   ╷┬┬┬┬╵┬┬┬┬╷┬┬┬┬╵┬┬┬┬╷┬┬┬┬╵┬┬┬┬╷┬┬┬┬╵┬┬┬┬╷
   AAGGAAGAGCAGGAATGGCTTCTATTATTTTAAAACCAAA 2240
   TACATCTTTAGATTTGGAAAAGTTTATGAACAAGTTGTA  2280
   ACATTTCTACCAGCTTATGCTTGTCCACGATTTTTAAGAA 2320
   TTCAGGAAAAAATGGAAGCAACAGGAACATTCAAACTATT 2360
   GAAGCATCAGTTGGTGGAAGATGGATTTAATCCACTGAAA 2400
         2410      2420      2430      2440
   ╷┬┬┬┬╵┬┬┬┬╷┬┬┬┬╵┬┬┬┬╷┬┬┬┬╵┬┬┬┬╷┬┬┬┬╵┬┬┬┬╷
   ATTTCTGAACCACTTTACTTCATGGATAACTTGAAAAAGT 2440
   CTTATGTTCTACTGACCAGGGAACTTTATGATCAAATAAT 2480
   GTTAGGGGAAATAAAACTTTAAGATTTTATATCTAGAAC  2520
   TTTCATATGCTTTCTTAGGAAGAGTGAGAGGGGGGTATAT 2560
   GATTCTTTATGAAATGGGGAAGGGAGCTAACATTAATTA  2600
         2610      2620      2630      2640
   ╷┬┬┬┬╵┬┬┬┬╷┬┬┬┬╵┬┬┬┬╷┬┬┬┬╵┬┬┬┬╷┬┬┬┬╵┬┬┬┬╷
   TGCATGTACTATATTTCCTTAATATGAGAGATAATTTTTT 2640
   AATTGCATAAGAATTTTAATTTCTTTTAATTGATATAAAC 2680
   ATTAGTTGATTATTCTTTTATCTATTTGGAGATTCAGTG  2720
   CATAACTAAGTATTTTCCTTAATACTAAAGATTTTAAATA 2760
   ATAAATAGTGGCTAGCGGTTTGGACAATCACTAAAAATGT 2800
         2810      2820      2830      2840
   ╷┬┬┬┬╵┬┬┬┬╷┬┬┬┬╵┬┬┬┬╷┬┬┬┬╵┬┬┬┬╷┬┬┬┬╵┬┬┬┬╷
   ACTTTCTAATAAGTAAAATTCTAATTTTGAATAAAAGAT  2840
   TAAATTTTACTGAAAAAAAAAAAAAAAAAAAATTGGCG   2880
   GCCGC 2885
```

FIG. 54C hsFATP6 full length protein

```
          10        20        30        40
MLLSWLTVLGAGMVVLHFLQKLLFPYFWDDFWFVLKVVLI  40
IIRLKKYEKRGELVTVLDKFLSHAKRQPRKPFIIYEGDIY  80
TYQDVDKRSSRVAHVFLNHSSLKKGDTVALLMSNEPDFVH  120
VWFGLAKLGCVVAFLNTNIRSNSLLNCIRACGPRALVVGA  160
DLLGTVEEILPSLSENISVWGMKDSVPQGVISLKEKLSTS  200
         210       220       230       240
PDEPVPRSHHVVSLLKSTCLYIFTSGTTGLPKAAVISQLQ  240
VLRGSAVLWAFGCTAHDIVYITLPLYHSSAAILGISGCVE  280
LGATCVLKKKFSASQFWSDCKKYDVTVFQYIGELCRYLCK  320
QSKREGEKDHKVRLAIGNGIRSDVWREFLDRFGNIKVCEL  360
YAATESSISFMNYTGRIGAIGRTNLFYKLLSTFDLIKYDF  400
         410       420       430       440
QKDEPMRNEQGWCIHVKKGEPGLLISRVNAKNPFFGYAGP  440
YKHTKDKLLCDVFKKGDVYLNTGDLIVQDQDNFLYFWDRT  480
GDTFRWKGENVATTEVADVIGMLDFIQEANVYGVAISGYE  520
GRAGMASIILKPNTSLDLEKVYEQVVTFLPAYACPRFLRI  560
QEKMEATGTFKLLKHQLVEDGFNPLKISEPLYFMDNLKKS  600
         610       620       630       640
YVLLTRELYDQIMLGEIKL 619
```

FIG. 55

```
         10        20        30        40
    |....|....|....|....|....|....|....|....|
AAGTTCCCACTCCAGACTTCTGCGAGAACCCGTGAGGAAG  40
CAGCGAGAACCGGGGGTTTGCAAGCCAGAGAAGGATGCGG  80
ACTCCGGGAGCAGGAACAGCCTCTGTGGCCTCATTGGGGC 120
TGCTTTGGCTTCTGGGACTTCCGTGGACCTGGAGCGCGGC 160
GGCGGCGTTCGGTGTGTACGTGGGTAGCGGTGGCTGGCGA 200
         210       220       230       240
    |....|....|....|....|....|....|....|....|
TTTCTGCGTATCGTCTGCAAGACGGCGAGGCGAGACCTCT 240
TTGGCCTCTCTGTTCTGATCCGCGTGCGGCTAGAGCTACG 280
ACGACACCGGCGAGCAGGAGACACGATCCCACGCATCTTC 320
CAGGCCGTGGCCCAGCGACAGCCGGAGCGCCTGGCGCTGG 360
TAGATGCGAGTAGCGGTATCTGCTGGACCTTCGCACAGCT 400
         410       420       430       440
    |....|....|....|....|....|....|....|....|
AGACACCTACTCCAATGCTGTGGCCAATCTGTTCCTCCAG 440
CTGGGCTTTGCGCCAGGCGATGTGGTGGCTGTGTTCCTGG 480
AAGGCCGGCCCGAGTTCGTGGGACTGTGGCTGGGCCTGGC 520
CAAGGCCGGTGTAGTGGCTGCGCTTCTCAATGTCAACCTG 560
AGGCGGGAGCCCCTTGCCTTCTGCTTGGGCACATCAGCTG 600
         610       620       630       640
    |....|....|....|....|....|....|....|....|
CCAAGGCCCTCATTTATGGCGGGGAGATGGCAGCGGCGGT 640
GGCGGAGGTGAGTGAGCAGCTGGGGAAGAGCCTGCTCAAG 680
TTCTGCTCTGGAGATCTGGGGCCTGAGAGCGTCCTGCCTG 720
ACACGCAGCTTCTGGACCCCATGCTTGCTGAGGCGCCCAC 760
CACACCCCTGGCACAGGCCCCAGGCAAGGGCATGGATGAT 800
         810       820       830       840
    |....|....|....|....|....|....|....|....|
CGGCTATTTTACATCTATACTTCTGGGACCACCGGACTTC 840
CTAAGGCGGCCATTGTGGTGCACAGCAGGTACTACCGCAT 880
CGCAGCCTTCGGCCACCATTCCTACAGCATGCGGGCCAAC 920
GATGTGCTCTATGACTGCCTACCTCTCTACCACTCAGCAG 960
GGAACATCATGGGCGTGGGACAGTGTATCATCTACGGGTT 1000
         1010      1020      1030      1040
    |....|....|....|....|....|....|....|....|
AACGGTGGTACTGCGCAAGAAGTTCTCCGCCAGCCGCTTC 1040
TGGGACGACTGTGTCAAATATAATTGCACGGTAGTGCAGT 1080
ACATCGGTGAAATATGCCGCTACCTGCTAAGGCAGCCGGT 1120
TCGCGATGTAGAGCGGCGGCACCGCGTGCGCCTGGCCGTG 1160
GGTAACGGACTGCGGCCAGCCATCTGGGAGGAGTTCACGC 1200
```

FIG. 56A

```
                1210      1220      1230      1240
            |||||||||||||||||||||||||||||||||||||||
AGGGTTTCGGTGTGCGACAGATTGGCGAGTTCTACGGCGC 1240
CACCGAATGCAACTGCAGCATTGCCAACATGGACGGCAAG 1280
GTCGGCTCCTGCGGCTTCAACAGCCGTATCCTCACGCATG 1320
TGTACCCCATCCGTCTGGTCAAGGTCAACGAGGACACGAT 1360
GGAGCCACTGAGGGACTCCCAAGGCCTCTGCATCCCGTGC 1400
                1410      1420      1430      1440
            |||||||||||||||||||||||||||||||||||||||
CAGCCCGGGGAACCTGGGCTTCTCGTGGGCCAGATCAACC 1440
AGCAAGACCCTCTGCGGCGCTTCGATGGCTATGTTAGTGA 1480
CAGCGCCACCAACAAGAAGATTGCCCACAGCGTGTTCCGA 1520
AAGGGGGACAGCGCCTACCTTTCAGGTGACGTGCTAGTGA 1560
TGGACGAGCTGGGGTACATGTACTTCGTGACCGCAGCGG 1600
                1610      1620      1630      1640
            |||||||||||||||||||||||||||||||||||||||
GGATACCTTCCGATGGCGCGGCGAGAACGTATCCACCACG 1640
GAGGTGGAAGCCGTGCTGAGCCGCCTGTTGGGCCAGACGG 1680
ACGTGGCTGTGTATGGAGTGGCTGTGCCAGGAGTGGAGGG 1720
GAAAAGCGGCATGGCGGCCATTGCAGACCCCCACAACCAG 1760
CTGGACCCTAACTCAATGTACCAGGAATTGCAGAAGGTTC 1800
                1810      1820      1830      1840
            |||||||||||||||||||||||||||||||||||||||
TTGCATCCTATGCCCAGCCCATCTTCCTGCGTCTTCTGCC 1840
CCAAGTGGATACAACAGGCACCTTCAAGATCCAGAAGACC 1880
CGACTACAGCGTGAAGGCTTTGACCCCCGCCAGACCTCAG 1920
ACCGGCTCTTCTTTCTAGACCTGAAACAGGGACGCTACCT 1960
ACCCCTGGATGAGAGAGTCCATGCCCGCATCTGCGCAGGC 2000
                2010      2020      2030      2040
            |||||||||||||||||||||||||||||||||||||||
GACTTCTCACTCTGAGCCTGGTGAGTGGGATGGCCCTGGA 2040
CTTGTGAGACCAGGGAGCCGGACACCCTGTTCAGGTGTT 2080
TCTCCTGCCTGGCCACGTGGCCAGCAGCACCTGTGGGTGC 2120
AGGAAACTGGAACCTGAGTGGCCGGGTGTCCCTTTCCTAC 2160
AACCCACCATGCACACATCTAGCCTCTGCCTTGGTCTTTT 2200
```

FIG. 56B

```
                  2210         2220         2230         2240
         ┷┷┷┷┷┷┷┷┷┷┷┷┷┷┷┷┷┷┷┷┷┷┷┷┷┷┷┷┷┷┷┷┷┷┷┷┷┷┷┷
         TCTCCATCTCTTTCCTCCGTGCCCAGCAGGAGCCCCACAG 2240
         ACACATTGGCTGCTGTGTCCTGCAGTGGGACCGGTGTCTA 2280
         GGGGTCCATGCTGCAGGCTGTGACCCGCACTGGTGCCCAC 2320
         CTCCCTTCCCCATTGTGCCTTAGGTTCCTCCACTGTGCGC 2360
         CGGTGAAGCAAGTGGGGACCCACATAGCTGTTGTCCTGC  2400
                  2410         2420         2430         2440
         ┷┷┷┷┷┷┷┷┷┷┷┷┷┷┷┷┷┷┷┷┷┷┷┷┷┷┷┷┷┷┷┷┷┷┷┷┷┷┷┷
         TGAGGGTTGGTAGCAAATGCACCCTCATGTCAGCTGGGAG 2440
         ACACATGCAGTCTCCCACTGACCCCAATCAACTGAAGAT  2480
         ACTGTTTTGTATTATTGTTTGAGATAGGGTCTCACTGTG  2520
         GAGGCCAAGCTGGCCTCAGGCTCACCACTCTACTGCCTCC 2560
         GGGCACCAGCCTGCAGTTTGATGACATGTATGCACTATTG 2600
                  2610         2620         2630         2640
         ┷┷┷┷┷┷┷┷┷┷┷┷┷┷┷┷┷┷┷┷┷┷┷┷┷┷┷┷┷┷┷┷┷┷┷┷┷┷┷┷
         TTCTAAGGGTCTTCTGAGTCCCTGCTTTCCCCTCATGTCC 2640
         TAAAACCTTCCAGAACTGACTCTGATCACTTGGATGTAGC 2680
         TAGTGTTGGCCCTGCCCACGTGTGTCAATTCAGGGGTCCC 2720
         CAGGCATCATCTCTGGAGGCCCTAACCTTGGCAAAGCTTG 2760
         GATGTCCTCACATCACAGCAGGAGACCCAGGAAGGTTGCT 2800
                  2810         2820         2830         2840
         ┷┷┷┷┷┷┷┷┷┷┷┷┷┷┷┷┷┷┷┷┷┷┷┷┷┷┷┷┷┷┷┷┷┷┷┷┷┷┷┷
         GTGGTGTCTCTTGGGCACCCCTGGCGGCAGCCGTGGACAT 2840
         GCTTCCCTGCTGTGATAGCCCAAACTGTTGCCTATGACAT 2880
         TTGAGGTCTACCCTTCTGGCTGCCATGGTCCCCATTGAGA 2920
         TCTTTGGTGACTCACCTCAGCCACCAAGCCAGGCCTCTGC 2960
         CTTCCTTCAGCTCTAAGGGCATGAAGGGTGTGGACAGAGC 3000
                  3010         3020         3030         3040
         ┷┷┷┷┷┷┷┷┷┷┷┷┷┷┷┷┷┷┷┷┷┷┷┷┷┷┷┷┷┷┷┷┷┷┷┷┷┷┷┷
         AGCCACAGGCTGCCCACAGTCACCCACATGCAAGTGTTAT 3040
         TTCCTTGTTTGTTTAAAAAAATAAACATGCTGAGCCTTG  3080
         AAAAAAAAAAAAAAAAAA 3098
```

FIG. 56C mFATP1 full length protein

```
          10        20        30        40
   ....|....|....|....|....|....|....|....|
   MRTPGAGTASVASLGLLWLLGLPWTWSAAAAFGVYVGSGG  40
   WRFLRIVCKTARRDLFGLSVLIRVRLELRRHRRAGDTIPR  80
   IFQAVAQRQPERLALVDASSGICWTFAQLDTYSNAVANLF  120
   LQLGFAPGDVVAVFLEGRPEFVGLWLGLAKAGVVAALLNV  160
   NLRREPLAFCLGTSAAKALIYGGEMAAAVAEVSEQLGKSL  200
          210       220       230       240
   ....|....|....|....|....|....|....|....|
   LKFCSGDLGPESVLPDTQLLDPMLAEAPTTPLAQAPGKGM  240
   DDRLFYIYTSGTTGLPKAAIVVHSRYYRIAAFGHHSYSMR  280
   ANDVLYDCLPLYHSAGNIMGVGQCIIYGLTVVLRKKFSAS  320
   RFWDDCVKYNCTVVQYIGEICRYLLRQPVRDVERRHRVRL  360
   AVGNGLRPAIWEEFTQGFGVRQIGEFYGATECNCSIANMD  400
          410       420       430       440
   ....|....|....|....|....|....|....|....|
   GKVGSCGFNSRILTHVYPIRLVKVNEDTMEPLRDSQGLCI  440
   PCQPGEPGLLVGQINQQDPLRRFDGYVSDSATNKKIAHSV  480
   FRKGDSAYLSGDVLVMDELGYMYFRDRSGDTFRWRGENVS  520
   TTEVEAVLSRLLGQTDVAVYGVAPGVEGKSGMAAIADPH   560
   NQLDPNSMYQELQKVLASYAQPIFLRLLPQVDTTGTFKIQ  600
          610       620       630       640
   ....|....|....|....|....|....|....|....|
   KTRLQREGFDPRQTSDRLFFLDLKQGRYLPLDERVHARIC  640
   AGDFSL    646
```

FIG. 57 mVLACS (FATP2) full length DNA

```
         10        20        30        40
GACACAGTACTGCCGATGTTGGACAGAGGATCGCTTAACA  40
GAACGAAATCTCAAAACAAATTAACAGGACCCGGTTGCTT  80
GATTTCCCAAATCAGAAAAGGCTCGAAATGTCTAGAGGGG  120
CTGACTGATGCAGCGGTGACCCGGACTGGAGACAGTTGGA  160
CGCGATCATCTCTGGTGCTTTTGTTCAACCTTGAAACCTT  200
        210       220       230       240
CGCCACAGGAGACTTGCCTGAGCAGAGAAGCAAACGTGGA  240
GAAACAAAGAGAGATCTAGCGAAAAGCCTCTGGGACCAAG  280
GAGGGGAGGTGGGACTCTGGGTTGGCGGTGGCACCTGCTG  320
CCGGCTATTAATAATAGGGTCGCGATGCGTTTATAAGGTG  360
TTTGATTAAACAAAGACTCTATGAGAGAAGAATAACTAGC  400
        410       420       430       440
AACAGCCCCACGTCTGAGTCGTCGCCTCCGACCTTTTTCA  440
ACGTGGGTTCTTTGGGCCGAGCGTCGTTTGCCGAGAACTA  480
GATCTCACCTGACCCCAGACGCTGAAAACAAGCGCTGTGG  520
CATCCTGGGCCACCCAAGCTGACAAGGGCGCGCCCCCTGA  560
GCACACGAGGTGCCCCACGAGGGGGAGGGACCCACAGCCG  600
        610       620       630       640
TCCCGCCCGCACCGCGGTGTCCGCTGCGGGCACCTGCAGC  640
CGAGCCGCCACCCGCAGTCGCAGCGCGTCCGGCGGCCGAA  680
CCCGGTCGTCAGCTCGTCAGCACCTGCTCTGCTTCTCTCC  720
CGCCCGCCGCCGCGCTGCACGCCTCGAGCGCTCCCTCGGC  760
CCCGGCGGGGACCGGGGACCCCGCAGCCACCGCCATGCTG  800
        810       820       830       840
CCTGTGCTCTACACCGGCCTGGCGGGGCTGCTGCTGCTGC  840
CTCTGCTGCTCACCTGCTGCTGCCCCTACCTCCTCCAGGA  880
CGTGCGGTTCTTCCTGCAACTGGCCAACATGGCCCGGCAG  920
GTGCGCAGCTACCGGCAGCGGCGACCCGTGCGCACCATCC  960
TGCATGTCTTCTTGGAGCAAGCGCGCAAGACCCCGCACAA  1000
        1010      1020      1030      1040
GCCCTTCCTGCTGTTTCGCGACGAGACGCTTACCTACGCC  1040
CAGGTAGACCGGCGCAGCAACCAAGTAGCGCGAGCGCTGC  1080
ATGATCACCTGGGCCTGCGGCAGGGGGATTGCGTGGCCCT  1120
CTTCATGGGCAATGAGCCGGCCTACGTGTGGCTCTGGCTG  1160
GGACTGCTCAAACTGGGCTGTCCCATGGCGTGCCTCAACT  1200
```

FIG. 58A

```
     1210      1220      1230      1240
ACAACATCCGTGCCAAGTCTCTGCTACACTGCTTTCAGTG 1240
CTGCGGGGCGAAGGTGCTGCTGGCCTCCCCAGAGCTACAC 1280
GAAGCTGTCGAGGAGGTTCTTCCAACCCTGAAAAGGAGG 1320
GCGTGTCGTCTTCTACGTAAGCAGAACTTCTAACACTAA 1360
TGGCGTGGACACAGTACTGGACAAAGTAGACGGGGTGTCG 1400
     1410      1420      1430      1440
GCGGACCCCATCCCGGAGTCGTGGAGGTCTGAAGTCACGT 1440
TCACCACACCCGCAGTCTACATATACTTCGGGCACCAC 1480
AGGTCTTCCAAAGGCTGCAACCATTAATCACCATCGCCTC 1520
TGGTATGGGACCAGCCTTGCCCTGAGGTCCGGAATTAAGG 1560
CTCATGACGTCATCTACACCACCATGCCCTGTACCACAG 1600
     1610      1620      1630      1640
CGCGGCGCTCATGATTGGCCTCCACGGATGCATTGTGGTT 1640
GGGGCTACATTTGCTTTGCGGAGCAAATTTTCAGCCAGCC 1680
AGTTTTGGGACGACTGCAGGAAATACAACGCCACTGTCAT 1720
TCAGTACATCGGTGAACTGCTTCGGTACCTCTGCAACACG 1760
CCCCAGAAACCAAATGACCGGGACCACAAAGTGAAAATAG 1800
     1810      1820      1830      1840
CACTAGGAAATGGCTTACGAGGAGATGTGTGGAGAGAGTT 1840
CATCAAGAGATTTGGGGACATTCACATTTATGAGTTCTAC 1880
GCTTCCACTGAAGGCAACATTGGATTTATGAACTATCCAA 1920
GAAAAATCGGAGCTGTTGGAAGAGAAAATTACCTACAAAA 1960
AAAAGTTGTAAGGCACGAGCTGATCAAGTATGACGTGGAG 2000
     2010      2020      2030      2040
AAGGATGAGCCTGTCCGTGATGCAAATGGATATTGCATCA 2040
AGTCCCCAAAGGAGAGGTTGGACTCTTGATTTGCAAAAT 2080
CACAGAGCTCACACCATTTTTTGGCTATGCTGGAGGAAAG 2120
ACCCAGACAGAGAAGAAAAAGCTCAGAGATGTTTTTAAGA 2160
AAGGAGACGTCTACTTCAACAGTGGCGATCTCCTGATGAT 2200
```

FIG. 58B

```
          2210        2220        2230        2240
   ╷┬┬┬╷┬┬┬╷┬┬┬╷┬┬┬╷┬┬┬╷┬┬┬╷┬┬┬╷┬┬┬╷
CGACCGTGAAAATTTCATCTATTTTCACGACAGAGTTGGA 2240
GACACCTTCCGGTGGAAAGGAGAGAATGTAGCTACCACGG 2280
AAGTCGCTGACATTGTGGACTGGTAGATTTTGTTGAAGA 2320
AGTGAATGTTTACGGTGTGCCCGTGCCAGGTCATGAAGGT 2360
CGCATCGGGATGGCCTCGATCAAGATGAAAGAAAACTACG 2400
          2410        2420        2430        2440
   ╷┬┬┬╷┬┬┬╷┬┬┬╷┬┬┬╷┬┬┬╷┬┬┬╷┬┬┬╷┬┬┬╷
AGTTCAATGGAAAGAAACTCTTTCAGCACATCTCGGAGTA 2440
CCTGCCCAGTTACTCGAGGCCTCGGTTCCTGAGAATACAA 2480
GATACCATTGAGATCACCGGGACTTTTAAACACCGCAAAG 2520
TGACCCTGATGGAAGAGGGCTTTAACCCCTCAGTCATCAA 2560
AGATACCTTGTATTCATGGATGACACAGAAAAACATAC 2600
          2610        2620        2630        2640
   ╷┬┬┬╷┬┬┬╷┬┬┬╷┬┬┬╷┬┬┬╷┬┬┬╷┬┬┬╷┬┬┬╷
GTGCCCATGACTGAGGACATTTATAATGCCATAATTGATA 2640
AGACTCTGAAGCTCTGAATGTTGCCTGGCTCCTAACACTT 2680
CCAGAAAGAAACACAATAGGCCTAGCATAGCCCCTTCACA 2720
TGTGTAATCCAACTTTAACTTGATTAAAGGTTATAGGTGT 2760
GATTTTCCTAGGAAATTATTCATTTAAAGGACAATTGTT 2800
          2810        2820        2830        2840
   ╷┬┬┬╷┬┬┬╷┬┬┬╷┬┬┬╷┬┬┬╷┬┬┬╷┬┬┬╷┬┬┬╷
TGTTTGTTTGTTTGTTTTTATTAATTACACCAGAACGTT 2840
TGCAAGTAAAAGATTTAAAGTCACTTATTTTCAATGTG 2880
CACCTGCCATTTGTCCTTGCAAACTTAGCTTCTTGGAGAG 2920
AGGGCCTTATTTTTTAAAGACATAATAAACTATGTAAAC 2960
ACT 2963
```

FIG. 58C mVLACS (FATP2) full length protein

```
          10        20        30        40
 ┬┬┬┬┴┬┬┬┬┴┬┬┬┬┴┬┬┬┬┴┬┬┬┬┴┬┬┬┬┴┬┬┬┬┴┬┬┬┬┴
MLPVLYTGLAGLLLLPLLLTCCCPYLLQDVRFFLQLANMA   40
RQVRSYRQRRPVRTILHVFLEQARKTPHKPFLLFRDETLT   80
YAQVDRRSNQVARALHDHLGLRQGDCVALFMGNEPAYVWL  120
WLGLLKLGCPMACLNYNIRAKSLLHCFQCCGAKVLLASPE  160
LHEAVEEVLPTLKKEGVSVFYVSRTSNTNGVDTVLDKVDG  200
         210       220       230       240
 ┬┬┬┬┴┬┬┬┬┴┬┬┬┬┴┬┬┬┬┴┬┬┬┬┴┬┬┬┬┴┬┬┬┬┴┬┬┬┬┴
VSADPIPESWRSEVTFTTPAVYIYTSGTTGLPKAATINHH  240
RLWYGTSLALRSGIKAHDVIYTTMPLYHSAALMIGLHGCI  280
VVGATFALRSKFSASQFWDDCRKYNATVIQYIGELLRYLC  320
NTPQKPNDRDHKVKIALGNGLRGDVWREFIKRFGDIHIYE  360
FYASTEGNIGFMNYPRKIGAVGRENYLQKKVVRHELIKYD  400
         410       420       430       440
 ┬┬┬┬┴┬┬┬┬┴┬┬┬┬┴┬┬┬┬┴┬┬┬┬┴┬┬┬┬┴┬┬┬┬┴┬┬┬┬┴
VEKDEPVRDANGYCIKVPKGEVGLLICKITELTPFFGYAG  440
GKTQTEKKKLRDVFKKGDVYFNSGDLLMIDRENFIYFHDR  480
VGDTFRWKGENVATTEVADIVGLVDFVEEVNVYGVPVPGH  520
EGRIGMASIKMKENYEFNGKKLFQHISEYLPSYSRPRFLR  560
IQDTIEITGTFKHRKVTLMEEGFNPSVIKDTLYFMDDTEK  600
         610       620       630       640
 ┬┬┬┬┴┬┬┬┬┴┬┬┬┬┴┬┬┬┬┴┬┬┬┬┴┬┬┬┬┴┬┬┬┬┴┬┬┬┬┴
TYVPMTEDIYNAIIDKTLKL   620
```

FIG. 59 mFATP4 partial DNA

```
         10        20        30        40
GATCAGCTCTTCTATATCTACACGTCGGGCACCACGGGGC  40
TACCCAAAGCTGCCATTGTGGTGCACAGCAGGTATTACCG  80
AATGGCTGCCCTGGTGTACTATGGATTCCGCATGCGGCCT 120
GATGACATTGTCTATGACTGCCTCCCCCTCTACCACTCAG 160
CAGGAAACATTGTGGGGATTGGCCAGTGCGTACTCCACGG 200
        210       220       230       240
CATGACTGTGGTGATCCGGAAGAAGTTTTCAGCCTCCCGG 240
TTCTGGGATGACTGTATCAAGTACAACTGCACAATTGTAC 280
AGTACATTGGTGAGCTTTGCCGCTACCTCCTGAACCAGCC 320
ACCCCGTGAGGCTGAGTCTCGGCACAAGGTGCGCATGGCA 360
CTGGGCAACGGTCTCCGGCAGTCCATCTGGACCGACTTCT 400
        410       420       430       440
CCAGCCGTTTCCACATTCCCAAGGTGGCCGAGTTCTACGG 440
GGCCACCGAGTGCAACTGTAGCTTGGGCAACTTTGACAGC 480
CAGGTGGGGGCCTGTGGCTTCAATAGCCGCATCCTGTCCT 520
TTGTGTACCCCATCCGCTTGGTACGAGTCAATGAGGATAC 560
CATGGAACTGATCCGGGGACCCGATGGCGTCTGCATTCCC 600
        610       620       630       640
TGTCAACCAGGCCAGCCAGGCCAGCTGGTGGGTCGCATCA 640
TCCAGCAGGACCCCCTACGCCGTTTTGATGGCTACCTCAA 680
CCAGGGTGCCAACAACAAGAAGATTGCTAGTGATGTCTTC 720
AAGAAAGGGGACCAAGCCTACCTCACTGGTGACGTGCTGG 760
TGATGGATGAGCTGGGCTACCTGTACTTCCGAGACCGCAC 800
        810       820       830       840
AGGGGACACGTTCCGCTGGAAAGGGGAGAATGTGTCTACC 840
ACTGAAGTGGAGGGCACACTCAGCCGCCTGCTTCAGATGG 880
CAGATGTGGCTGTTTATGGTGTTGAGGTGCCAGGAGCTGA 920
GGGCCGAGCAGGAATGGCTGCTGTGGCAAGCCCCACTAGC 960
AACTGTGACCTGGAGAGCTTTGCACAGACCTTGAAAAAGG 1000
       1010      1020      1030      1040
AGCTGCCCCTGTACGCCCGCCCCATCTTCCTCCGCTTCTT 1040
GCCTGAGCTGCACAAAACAGGAACCTTCAAGTTCCAGAAG 1080
ACAGAGTTGCGGAAGGAGGGCTTTGACCCGTCTGTTGTGA 1120
AAGACCCACTCTTCTATTTGGATGCCCGGACAGGCTGCTA 1160
TGTTGCACTGGACCAAGAGGCCTATACCCGCATCCAGGCA 1200
```

FIG. 60A

```
                1210      1220      1230      1240
          |....|....|....|....|....|....|....|....|
          GGCGAGGAGAAGCTGTGATTTCCCCCACATCCCTCTGAGG  1240
          GCCAGAGGATGCTGGATTCAGAGCCCCAGCTTCCACTCCA  1280
          GAAGGGGTCTGGGCAAGGCCAGACCAAAGCTAGCAGGGCC  1320
          CGCACCTTCACCCTAGGTGCTGATCCCCCT            1350
```

FIG. 60B mFATP4 partial DNA

```
                 10        20        30        40
          |....|....|....|....|....|....|....|....|
          DQLFYIYTSGTTGLPKAAIVVHSRYYRMAALVYYGFRMRP   40
          DDIVYDCLPLYHSAGNIVGIGQCVLHGMTVVIRKKFSASR   80
          FWDDCIKYNCTIVQYIGELCRYLLNQPPREAESRHKVRMA  120
          LGNGLRQSIWTDFSSRFHIPKVAEFYGATECNCSLGNFDS  160
          QVGACGFNSRILSFVYPIRLVRVNEDTMELIRGPDGVCIP  200
                210       220       230       240
          |....|....|....|....|....|....|....|....|
          CQPGQPGQLVGRIIQQDPLRRFDGYLNQGANNKKIASDVF  240
          KKGDQAYLTGDVLVMDELGYLYFRDRTGDTFRWKGENVST  280
          TEVEGTLSRLLQMADVAVYGVEVPGAEGRAGMAAVASPTS  320
          NCDLESFAQTLKKELPLYARPIFLRFLPELHKTGTFKFQK  360
          TELRKEGFDPSVVKDPLFYLDARTGCYVALDQEAYTRIQA  400
                410       420       430       440
          |....|....|....|....|....|....|....|....|
          GEEKL                                     405
```

FIG. 61 mmFATP1 full length DNA

```
              10        20        30        40
        |....|....|....|....|....|....|....|....|
        ATGCGGGCTCCTGGAGCAGGAACAGCCTCTGTGGCCTCAC  40
        TGGCGCTGCTTTGGTTTCTGGGACTTCCGTGGACCTGGAG   80
        CGCGGCGGCGGCGTTCTGTGTGTACGTGGGTGGCGGCGGC  120
        TGGCGCTTTCTGCGTATCGTCTGCAAGACGGCGAGGCGAG  160
        ACCTCTTTGGCCTCTCTGTTCTGATTCGTGTTCGGCTAGA  200
             210       220       230       240
        |....|....|....|....|....|....|....|....|
        GCTGCGACGACACCGGCGAGCAGGAGACACGATCCCGTGC  240
        ATCTTCCAGGCTGTGGCCCGGCGACAACCAGAGCGCCTGG  280
        CACTGGTGGACGCCAGTAGTGGTATATGCTGGACCTTCGC  320
        ACAGCTGGACACCTACTCCAATGCTGTAGCCAACCTGTTC  360
        CGCCAGCTGGGCTTTGCACCAGGCGATGTGGTGGCTGTGT  400
             410       420       430       440
        |....|....|....|....|....|....|....|....|
        TCCTGGAGGGCCGGCCGGAGTTCGTGGGACTGTGGCTGGG  440
        CCTGGCCAAGGCCGGTGTGGTGGCTGCTCTTCTCAATGTC  480
        AACCTGAGGCGGGAGCCCCTGGCCTTCTGCCTGGGCACAT  520
        CAGCTGCCAAGGCCCTCATTTATGGCGGGGAGATGGCAGC  560
        GGCGGTGGCGGAGGTGAGCGAGCAGCTGGGGAAGAGCCTC  600
             610       620       630       640
        |....|....|....|....|....|....|....|....|
        CTCAAGTTCTGCTCTGGAGATCTGGGGCCTGAGAGCATCC  640
        TGCCTGACACGCAGCTCCTGGACCCCATGCTTGCTGAGGC  680
        GCCCACCACACCCCTGGCACAAGCCCCAGGCAAGGGCATG  720
        GATGATCGGCTGTTTTACATCTATACTTCTGGGACCACCG  760
        GGCTTCCTAAGGCTGCCATTGTGGTGCACAGCAGGTACTA  800
             810       820       830       840
        |....|....|....|....|....|....|....|....|
        CCGCATTGCTGCCTTTGGCCACCATTCCTACAGCATGCGT  840
        GCCGCCGATGTGCTCTATGACTGCCTGCCACTCTACCACT  880
        CTGCAGGGAACATCATGGGTGTGGGGCAGTGCGTCATCTA  920
        CGGGTTGACGGTGGTACTGCGCAAGAAGTTCTCCGCCAGC  960
        CGCTTCTGGGATGACTGTGTCAAGTACAATTGCACGGTAG 1000
            1010      1020      1030      1040
        |....|....|....|....|....|....|....|....|
        TGGATGACATAGGTGAAATCTGCCGCTACCTGCTGAGGCA 1040
        GCCGGTTCGCGACGTGGAGCAGCGACACCGCGTGCGCCTG 1080
        GCCGTGGGTAATGGGCTGCGGCCAGCCATCTGGGAGGAGT 1120
        TCACGCAGCGCTTCGGTGTGCCACAGATCGGCGAGTTCTA 1160
        CGGCGCTACCGAGTGCAACTGCAGCATTGCCAACATGGAC 1200
```

FIG. 62A

```
            1210      1220      1230      1240
         |....|....|....|....|....|....|....|
         GGCAAGGTCGGCTCCTGCGGCTTCAACAGCCGTATCCTCA 1240
         CGCATGTGTACCCCATCCGTCTGGTCAAGGTCAATGAGGA 1280
         CACGATGGAGCCACTGCGGGACTCCGAGGGCCTCTGCATC 1320
         CCGTGCCAGCCCGGGGAACCCGGCCTTCTCGTGGGCCAGA 1360
         TCAACCAGCAGGACCCTCTGCGGCGTTTCGATGGTTATGT 1400
            1410      1420      1430      1440
         |....|....|....|....|....|....|....|
         TAGTGACAGTGCCACCAACAAGAAGATTGCCCACAGCGTT 1440
         TTCCGAAAGGGCGATAGCGCCTACCTCTCAGGTGACGTGC 1480
         TAGTGATGGACGAGCTGGGCTACATGTATTTCCGTGACCG 1520
         CAGCGGGGACACCTTCCGCTGGCGCGGGGAGAACGTGTCC 1560
         ACCACGGAGGTGGAAGCCGTGCTGAGCCGCCTACTGGGCC 1600
            1610      1620      1630      1640
         |....|....|....|....|....|....|....|
         AGACGGACGTGGCTGTGTATGGGGTGGCTGTGCCAGGAGT 1640
         GGAGGGGAAAGCTGGCATGGCAGCCATCGCAGATCCCCAC 1680
         AGCCAGTTGGACCCTAACTCAATGTACCAGGAATTACAGA 1720
         AGGTTCTTGCATCCTATGCTCGGCCCATCTTCCTGCGTCT 1760
         TCTGCCCCAGGTGGATACCACAGGCACCTTCAAGATCCAG 1800
            1810      1820      1830      1840
         |....|....|....|....|....|....|....|
         AAGACCCGGCTGCAGCGTGAAGGCTTTGACCCCCGTCAGA 1840
         CCTCAGACAGGCTCTTCTTTCTAGACCTGAAGTCCGGCAC 1880
         GAGGTATCTACCCCTGGATGAGAGTCCATGCCCGCATT 1920
         TGCGCAGGCGACTTCTCACTCTGAGCCTGGAGAGTGGGCT 1960
         GGGCCTGGACTCCTGAGACCTGGGAGCCTGACACCCTCT 2000
            2010      2020      2030      2040
         |....|....|....|....|....|....|....|
         TCGGGTGCTTCTCCTGCCTGGCCACATGGACAGCAGCACC 2040
         TGTGAGAGTAGGAAAATGGAACCTGAGTGGCTGGGACCCC 2080
         TCTCCTACTTCCCACTATGCATCCATTTGCCTCTGCCTT 2120
         GATCTTTTCTCCATCTCTTTTCTCCCTACCCAGCAGGAG 2160
         CCCCACAAACACATGTTGGCTGCTGTGTCCTGCAGTTGGA 2200
```

FIG. 62B

```
                2210         2220         2230         2240
         ┴┴┴┴┴┴┴┴┴┴┴┴┴┴┴┴┴┴┴┴┴┴┴┴┴┴┴┴┴┴┴┴┴┴┴┴┴┴┴┴┴┴
         CCAGTGTCCAGGGGTACAGGCTTCAGGCTGTGACCCACAC 2240
         TGGTACCCACCTCCCTTTCCTATTTTGCCTTAGGTTCATC 2280
         CACGGTTCCCCTGTGGAGCAAGTGGGGGCCCACATAGCTG 2320
         CTGTCCCTGCTGAGGGTTGGTAGCAATCACACCCTCATGT 2360
         CAGCTGGGAGACACGCGCAGTCTCCCACTGACCCCCAATC 2400

2410         2420         2430         2440
         ┴┴┴┴┴┴┴┴┴┴┴┴┴┴┴┴┴┴┴┴┴┴┴┴┴┴┴┴┴┴┴┴┴┴┴┴┴┴┴┴┴┴
         AACTGAAAATATTGTTTTGACTACTTTTGTTTTTTTGTT 2440
         TTTTTGTTTTTTTTTTTTCGAGACAGAGTTTCTCTGTA 2480
         TAGCCCTGGCTGTCCTGGAACTCACTTTGTAGACCAGGCT 2520
         GGCCTCGAACTCAAAAATCCTCCTGACTCTGCCTCTGCTT 2560
         CCCAAGTGCTGGGATTAAAGACGTGCGCCACCACCGCCTG 2600

2610         2620         2630         2640
         ┴┴┴┴┴┴┴┴┴┴┴┴┴┴┴┴┴┴┴┴┴┴┴┴┴┴┴┴┴┴┴┴┴┴┴┴┴┴┴┴┴┴
         GCTGTTTTGTATTTTTGTTTTGTTTTGACGATAGGGTCTC 2640
         ACTGTGGAGGCCAAGCTGGCCTCAGACTCCCCACCCCATT 2680
         GCCTCTGGGCACCATTCTATATTCTCAGACTGATGACAAT 2720
         GCACTAGTGTCCCTAGGAGTCTTGAGTCTGCACTTCCCC 2760
         TCATAGCCTCAAGCTTCCAGAACTGACTCTGATCACTTGG 2800

2810         2820         2830         2840
         ┴┴┴┴┴┴┴┴┴┴┴┴┴┴┴┴┴┴┴┴┴┴┴┴┴┴┴┴┴┴┴┴┴┴┴┴┴┴┴┴┴┴
         ATGTGGCTAGTGTTGGCTCTACCCACATGTGTCAATTCAG 2840
         GGGTCCCCAGGCATAGTCTCTGGAAGCCCTCACCCGGAAA 2880
         AAGCTTGGAGAGACCCAGGAAGGTTGTTGTGTTCTCTTGG 2920
         GCACCCCTGGTGGCAGTCCTGGGCATGCTTCCGCACTGT 2960
         ACTGGTGCATATAGCCCAGACCTATGACATTTGAGGTCTA 3000

3010         3020         3030         3040
         ┴┴┴┴┴┴┴┴┴┴┴┴┴┴┴┴┴┴┴┴┴┴┴┴┴┴┴┴┴┴┴┴┴┴┴┴┴┴┴┴┴┴
         CCCTTCTGGCTCCTGTGGTCCCCATTGAGATCCTTGGTGA 3040
         CTCACCTCAGTCACCAAGCAGAGCCTCTGCCTGCCTTCAT 3080
         CTTCAAGGTCATGAAGGATGTGGACAGAGCAGCTACAGGC 3120
         TGCCAGCAGTCAACCACATGAGAGTGTTACTTCCTTGTTG 3160
         GTTTTTAAAAAATAAATGTGCTGAGCCTCGAAAAAAAAAA 3200

3210         3220         3230         3240
         ┴┴┴┴┴┴┴┴┴┴┴┴┴┴┴┴┴┴┴┴┴┴┴┴┴┴┴┴┴┴┴┴┴┴┴┴┴┴┴┴┴┴
         AAAAAAAAAAAAAAAAA 3217
```

FIG. 62C mmFATP1 full length protein

```
          10         20         30         40
  ....|....|....|....|....|....|....|....|
MRAPGAGTASVASLALLWFLGLPWTWSAAAAFCVYVGGGG    40
WRFLRIVCKTARRDLFGLSVLIRVRLELRRHRRAGDTIPC    80
IFQAVARRQPERLALVDASSGICWTFAQLDTYSNAVANLF   120
RQLGFAPGDVVAVFLEGRPEFVGLWLGLAKAGVVAALLNV   160
NLRREPLAFCLGTSAAKALIYGGEMAAAVAEVSEQLGKSL   200
         210        220        230        240
  ....|....|....|....|....|....|....|....|
LKFCSGDLGPESILPDTQLLDPMLAEAPTTPLAQAPGKGM   240
DDRLFYIYTSGTTGLPKAAIVVHSRYYRIAAFGHHSYSMR   280
AADVLYDCLPLYHSAGNIMGVGQCVIYGLTVVLRKKFSAS   320
RFWDDCVKYNCTVVDDIGEICRYLLRQPVRDVEQRHRVRL   360
AVGNLRPAIWEEFTQRFGVPQIGEFYGATECNCSIANMD   400
         410        420        430        440
  ....|....|....|....|....|....|....|....|
GKVGSCGFNSRILTHVYPIRLVKVNEDTMEPLRDSEGLCI   440
PCQPGEPGLLVGQINQQDPLRRFDGYVSDSATNKKIAHSV   480
FRKGDSAYLSGDVLVMDELGYMYFRDRSGDTFRWRGENVS   520
TTEVEAVLSRLLGQTDVAVYGVAVPGVEGKAGMAAIADPH   560
SQLDPNSMYQELQKVLASYARPIFLRLLPQVDTTGTFKIQ   600
         610        620        630        640
  ....|....|....|....|....|....|....|....|
KTRLQREGFDPRQTSDRLFFLDLKSGTRYLPLDERVHARI   640
CAGDFSL                                    647
```

FIG. 63 mmFATP2 full length DNA

```
         10        20        30        40
    ....|....|....|....|....|....|....|....|
    GGGCGGAGGCCGAGCCCAGTCGCCAGCTCCTGCTCTGCTC   40
    CTCTCCCGCCTGCCGCCGCGCTGCACGCCTCGAGCACTCC   80
    CTCGGCCCCGGCGGGGACCGGGGACCCCGCAGCTACCGCC  120
    ATGCTGCCAGTGCTCTACACCGGCCTGGCGGGGCTGCTGC  160
    TGCTGCCTCTGCTGCTCACCTGCTGCTGCCCCTACCTCCT  200
        210       220       230       240
    ....|....|....|....|....|....|....|....|
    CCAAGATGTGCGGTACTTCCTGCGGCTGGCCAACATGGCC  240
    CGGCGGGTGCGCAGCTACCGGCAGCGGCGACCCGTGCGTA  280
    CCATCCTGCGGGCCTTCCTGGAACAAGCGCGCAAGACCCC  320
    ACACAAGCCCTTCCTGCTGTTCCGAGACGAGACGCTCACC  360
    TACGCCCAGGTGGACCGGCGCAGCAACCAAGTGGCGCGGG  400
        410       420       430       440
    ....|....|....|....|....|....|....|....|
    CGCTGCACGATCAACTGGGCCTACGACAGGGGGATTGCGT  440
    AGCCCTCTTCATGGGCAATGAGCCGGCCTACGTGTGGATC  480
    TGGCTGGGACTGCTCAAACTGGGCTGTCCCATGGCGTGCC  520
    TCAACTACAACATTCGTGCCAAGTCTCTGCTGCACTGCTT  560
    TCAATGCTGCGGGGCGAAGGTGCTGCTGGCCTCCCCAGAT  600
        610       620       630       640
    ....|....|....|....|....|....|....|....|
    CTACAAGAAGCTGTGGAGGAGGTTCTTCCAACCCTGAAAA  640
    AGGATGCCGTGTCCGTCTTTTACGTAAGCAGAACTTCTAA  680
    CACAAATGGTGTGGACACAATACTGGACAAAGTAGACGGA  720
    GTGTCGGCGGAACCCACCCCGGAGTCGTGGAGGTCTGAAG  760
    TCACTTTTACCACGCCAGCAGTATACATTTATACTTCGGG  800
        810       820       830       840
    ....|....|....|....|....|....|....|....|
    AACCACAGGTCTTCCAAAAAGCGGAACCATCAATCATCAT  840
    CGCCTAAGGTATGGGACAAGCCTTGCTATGTCGAGTGGGA  880
    ATCACGGCCAAGGATGTCATCTATACCAACAATGCCCTG  920
    TTCCAACAGTGCAACGCTCAAGATCGGCCTTCACGGATGC  960
    ATCCTGGGTTGGGGCTACTTTAACCTTGGCGGGGCAAATT 1000
        1010      1020      1030      1040
    ....|....|....|....|....|....|....|....|
    CTCAAGCAAGCCAATTTTGGGAACGACTGGCAGGAAATAC 1040
    AACGTCAACGGTCATTCAGTACATTGGTGAACTGCTTCGG 1080
    TACCTGTGCAACACACCGCAGAAACCAAATGACCGGGACC 1120
    ACAAAGTGAAAAAGCCCTGGGAAATGGCTTACGAGGAGA  1160
    TGTGTGGAGAGAGTTCATCAAGAGATTTGGGGACATCCAC 1200
```

FIG. 64A

```
          1210      1220      1230      1240
    ....|....|....|....|....|....|....|....|
GTGTATGAGTTCTACGCATCCACTGAAGGCAACATTGGAT 1240
TTGTGAACTATCCAAGGAAAATCGGTGCTGTCGGGAGAGC 1280
AAACTACCTACAAAGAAAAGTTGCAAGGTATGAGCTGATC 1320
AAGTATGACGTGGAGAAGGACGAGCCGGTCCGTGACGCAA 1360
ATGGATATTGCATCAAAGTCCCCAAAGGTGAGGTTGGACT 1400
          1410      1420      1430      1440
    ....|....|....|....|....|....|....|....|
CTTGGTTTGCAAAATCACACAGCTCACACCATTTATTGGC 1440
TATGCTGGAGGAAAGACCCAGACAGAGAAGAAAAAACTCA 1480
GAGATGTCTTTAAGAAGGCGACATCTACTTCAACAGCGG 1520
AGACCTCCTGATGATCGACCGTGAGAACTTCGTCTACTTT 1560
CACGACAGGGTTGGAGATACTTTCCGGTGGAAAGGAGAGA 1600
          1610      1620      1630      1640
    ....|....|....|....|....|....|....|....|
ACGTAGCTACCACAGAAGTCGCTGACATCGTGGGACTGGT 1640
AGATTTTGTTGAAGAAGTGAATGTGTATGGCGTGCCTGTG 1680
CCAGGTCATGAGGGTCGAATTGGGATGGCCTCCCTCAAGA 1720
TCAAAGAAAACTACGAGTTCAATGGAAAGAAACTCTTTCA 1760
ACACATCGCGGAGTACCTGCCCAGTTACGCGAGGCCTCGG 1800
          1810      1820      1830      1840
    ....|....|....|....|....|....|....|....|
TTCCTGAGGATACAAGATACCATTGAGATCACTGGGACTT 1840
TTAAACACCGCAAAGTGACCCTGATGGAAGAGGGCTTCAA 1880
TCCCACAGTCATCAAAGATACCTTGTATTTCATGGATGAT 1920
GCAGAGAAAACATTTGTGCCCATGACTGAGAACATTTATA 1960
ATGCCATAATTGATAAAACTCTGAAGCTCTGAATATTCCC 2000
          2010      2020      2030      2040
    ....|....|....|....|....|....|....|....|
TGGTGGTTTAGCTCATGACATTTCCAGAAAGAAACTCGAT 2040
AGACCTCGCAGAGCCACTTCATACGTAGAATCCAACTTTA 2080
ACTTGATTGAAGACTATAAGGTGCGATTTTATTTTTAGGA 2120
AATTATTCATTAAAAGGATAGTTTTTTTTTTTTTTTTAA 2160
TTACACCTGAACCTTTGCAAGTAAAAAGATTTAGAGACAA 2200
          2210      2220      2230      2240
    ....|....|....|....|....|....|....|....|
TTATTTTTCAATGTGCACCTGCCATTTGTCCTTGCAAACT 2240
AAGCTTCTTGGAGAGAGGGCCTTATTTTTTAAAGACATA 2280
ATAAACTATATTAACACTAAAAAAAAAAAAAAAAAAAAAA 2320
AAAAAAAAAAAAAAAAAA 2338
```

FIG. 64B mmFATP2 full length protein

```
          10        20        30        40
   ..|....|....|....|....|....|....|....|
MLPVLYTGLAGLLLLPLLLTCCCPYLLQDVRYFLRLANMA  40
RRVRSYRQRRPVRTILRAFLEQARKTPHKPFLLFRDETLT  80
YAQVDRRSNQVARALHDQLGLRQGDCVALFMGNEPAYVWI 120
WLGLLKLGCPMACLNYNIRAKSLLHCFQCCGAKVLLASPD 160
LQEAVEEVLPTLKKDAVSVFYVSRTSNTNGVDTILDKVDG 200
         210       220       230       240
   ..|....|....|....|....|....|....|....|
VSAEPTPESWRSEVTFTTPAVYIYTSGTTGLPKSGTINHH 240
RLRYGTSLAMSSGNHGQGCHLYQQCPCSNSATLKIGLHGC 280
ILGWGYFNLGGANSQASQFWERLAGNTTSTVIQYIGELLR 320
YLCNTPQKPNDRDHKVKKALGNGLRGDVWREFIKRFGDIH 360
VYEFYASTEGNIGFVNYPRKIGAVGRANYLQRKVARYELI 400
         410       420       430       440
   ..|....|....|....|....|....|....|....|
KYDVEKDEPVRDANGYCIKVPKGEVGLLVCKITQLTPFIG 440
YAGGKTQTEKKKLRDVFKKGDIYFNSGDLLMIDRENFVYF 480
HDRVGDTFRWKGENVATTEVADIVGLVDFVEEVNVYGVPV 520
PGHEGRIGMASLKIKENYEFNGKKLFQHIAEYLPSYARPR 560
FLRIQDTIEITGTFKHRKVTLMEEGFNPTVIKDTLYFMDD 600
         610       620       630       640
   ..|....|....|....|....|....|....|....|
AEKTFVPMTENIYNAIIDKTLKL  623
```

FIG. 65 mmFATP3 partial DNA

```
         10        20        30        40
GAAAGCTCTGAGAGCGGGTGCAGTCTGGCCTGGCGTCTCG  40
CGTACCTGGCCCGGGAGCAGCCGACACACACCTTCCTCAT  80
CCACGGCGCGCAGCGCTTTAGCTACGCGGAGGCTGAGCGC  120
GAGAGCAACCGGATTGCTCGCGCCTTTCTGCGCGCACGGG  160
GCTGGACCGGGGGCCGCCGAGGCTCGGGCAGGGGCAGCAC  200
        210       220       230       240
TGAGGAAGGCGCACGCGTGGCGCCTCCGGCTGGAGATGCG  240
GCTGCTAGAGGGACGACCGCGCCCCTCTGGCACCCGGGG   280
CGACCGTGGCGCTGCTCCTCCCAGCGGGCCCGGATTTCCT  320
TTGGATTTGGTTCGGACTGGCCAAAGCTGGCCTGCGCACG  360
GCCTTTGTGCCCACCGCTTTACGCCGAGGACCCCTGCTGC  400
        410       420       430       440
ACTGCCTCCGCAGCTGCGGTGCGAGTGCGCTCGTGCTGGC  440
CACAGAGTTCCTGGAGTCCCTGGAGCCGGACCTGCCGGCC  480
TTGAGAGCCATGGGGCTCCACCTATGGGCGACGGGCCCTG  520
AAACTAATGTAGCTGGAATCAGCAATTTGCTATCGGAAGC  560
AGCAGACCAAGTGGATGAGCCAGTGCCGGGGTACCTCTCT  600
        610       620       630       640
GCCCCCCAGAACATAATGGACACCTGCCTGTACATCTTCA  640
CCTCTGGCACTACTGGCCTGCCCAAGGCTGCTCGAATCAG  680
TCATCTGAAGGTTCTACAGTGCCAGGGATTCTACCATCTG  720
TGTGGAGTCCACCAGGAGGACGTGATCTACCTCGCACTCC  760
CACTGTACCACATGTCTGGCTCCCTTCTGGGCATTGTGGG  800
        810       820       830       840
CTGCTTGGGCATTGGGGCCACCGTGGTGCTGAAACCCAAG  840
TTCTCAGCTAGCCAGTTCTGGGACGATTGCCAGAAACACA  880
GGGTGACAGTGTTCCAGTACATTGGGGAGTTGTGCCGATA  920
CCTCGTCAACCAGCCCCGAGCAAGGCAGAGTTTGACCAT   960
AAGGTGCGCTTGGCAGTGGGCAGTGGGTTGCGCCCAGACA  1000
       1010      1020      1030      1040
CCTGGGAGCGTTTCCTGCGGCGATTTGGACCTCTGCAGAT  1040
ACTGGAGACGTATGGCATGACAGAGGGCAACGTAGCTACG  1080
TTCAATTACACAGGACGGCAGGGTGCAGTGGGGCGAGCTT  1120
CCTGGCTTTACAAGCACATCTTCCCCTTCTCCTTGATTCG  1160
ATACGATGTCATGACAGGGGAGCCTATTCGGAATGCCCAG  1200
```

FIG. 66A

```
          1210       1220       1230       1240
GGGCACTGCATGACCACATCTCCAGGTGAGCCAGGCCTAC 1240
TGGTGGCCCCAGTGAGCCAGCAGTCCCCTTCCTGGGCTA 1280
TGCTGGGGCTCCGGAGCTGGCCAAGGACAAGCTGCTGAAG 1320
GATGTCTTCTGGTCTGGGGACGTTTTCTTCAATACTGGGG 1360
ACCTCTTGGTCTGTGATGAGCAAGGCTTTCTTCACTTCCA 1400
          1410       1420       1430       1440
CGATCGTACTGGAGACACCATCAGGTGGAAGGGAGAGAAT 1440
GTGGCCACAACTGAAGTGGCTGAGGTCTTGGAGACCCTGG 1480
ACTTCCTTCAGGAGGTGAACATCTATGGAGTCACGGTGCC 1520
AGGGCACGAAGGCAGGGCAGGCATGGCGGCCTTGGCTCTG 1560
CGGCCCCGCAGGCTCTGAACCTGGTGCAGCTCTACAGCC 1600
          1610       1620       1630       1640
ATGTTTCTGAGAACTTGCCACCGTATGCCCGACCTCGGTT 1640
TCTCAGGCTCCAGGAATCTTTGGCCACTACTGAGACCTTC 1680
AAACAGCAGAAGGTTAGGATGGCCAATGAGGGCTTTGACC 1720
CCAGTGTACTGTCTGACCCACTCTATGTTCTGGACCAAGA 1760
TATAGGGGCCTACCTGCCCCTCACACCTGCCCGGTACAGT 1800
          1810       1820       1830       1840
GCCCTCCTGTCTGGAGACCTTCGAATCTGAAACCTTCCAC 1840
TTGAGGGAGGGGCTCGGAGGGTACAGGCCACCATGGCTGC 1880
ACCAGGGAGGGTTTTCGGGTATCTTTGTATATGGAGTCA 1920
TTATTTTGTAATAAACAGCTGGAGCTTAAAAAAAAAAAA 1960
AAAAAAAAAAAAAAAAAAAAAAAAAAAAAAAAAAAA 1998
```

FIG. 66B mmFATP3 partial protein

```
        10          20          30          40
|....|....|....|....|....|....|....|....|....|
ESSESGCSLAWRLAYLAREQPTHTFLIHGAQRFSYAEAER    40
ESNRIARAFLRARGWTGGRRGSGRGSTEEGARVAPPAGDA    80
AARGTTAPPLAPGATVALLLPAGPDFLWIWFGLAKAGLRT   120
AFVPTALRRGPLLHCLRSCGASALVLATEFLESLEPDLPA   160
LRAMGLHLWATGPETNVAGISNLLSEAADQVDEPVPGYLS   200
        210         220         230         240
|....|....|....|....|....|....|....|....|....|
APQNIMDTCLYIFTSGTTGLPKAARISHLKVLQCQGFYHL   240
CGVHQEDVIYLALPLYHMSGSLLGIVGCLGIGATVVLKPK   280
FSASQFWDDCQKHRVTVFQYIGELCRYLVNQPPSKAEFDH   320
KVRLAVGSGLRPDTWERFLRRFGPLQILETYGMTEGNVAT   360
FNYTGRQGAVGRASWLYKHIFPFSLIRYDVMTGEPIRNAQ   400
        410         420         430         440
|....|....|....|....|....|....|....|....|....|
GHCMTTSPGEPGLLVAPVSQQSPFLGYAGAPELAKDKLLK   440
DVFWSGDVFFNTGDLLVCDEQGFLHFHDRTGDTIRWKGEN   480
VATTEVAEVLETLDFLQEVNIYGVTVPGHEGRAGMAALAL   520
RPPQALNLVQLYSHVSENLPPYARPRFLRLQESLATTETF   560
KQQKVRMANEGFDPSVLSDPLYVLDQDIGAYLPLTPARYS   600
        610         620         630         640
|....|....|....|....|....|....|....|....|....|
ALLSGDLRI    609
```

FIG. 67 mmFATP4 full length DNA

```
         10        20        30        40
ATGCTGCTTGGAGCCTCTCTGGTGGGGGCGCTACTGTTCT  40
CCAAGCTAGTGCTGAAGCTGCCCTGGACCCAGGTGGGATT  80
CTCCCTGTTGCTCCTGTACTTGGGGTCTGGTGGCTGGCGT 120
TTCATCCGGGTCTTCATCAAGACGGTCAGGAGAGATATCT 160
TTGGTGGCATGGTGCTCCTGAAGGTGAAGACCAAGGTGCG 200
        210       220       230       240
ACGGTACCTTCAGGAGCGGAAGACGGTGCCCCTGCTGTTT 240
GCTTCAATGGTACAGCGCCACCCGGACAAGACAGCCCTGA 280
TTTTCGAGGGCACAGACACTCACTGGACCTTCCGCCAGCT 320
GGATGAGTACTCCAGTAGTGTGGCCAACTTCCTGCAGGCC 360
CGGGGCCTGGCCTCAGGCAATGTAGTTGCCCTCTTTATGG 400
        410       420       430       440
AAAACCGCAATGAGTTTGTGGGTCTGTGGCTAGGCATGGC 440
CAAGCTGGGCGTGGAGGCGGCTCTCATCAACACCAACCTT 480
AGGCGGGATGCCCTGCGCCACTGTCTTGACACCTCAAAGG 520
CACGAGCTCTCATCTTTGGCAGTGAGATGGCCTCAGCTAT 560
CTGTGAGATCCATGCTAGCCTGGAGCCCACACTCAGCCTC 600
        610       620       630       640
TTCTGCTCTGGATCCTGGGAGCCCAGCACAGTGCCCGTCA 640
GCACAGAGCATCTGGACCCTCTTCTGGAAGATGCCCCGAA 680
GCACCTGCCCAGTCACCCAGACAAGGGTTTTACAGATAAG 720
CTCTTCTACATCTACACATCGGGCACCACGGGGCTACCCA 760
AAGCTGCCATTGTGGTGCACAGCAGGTATTATCGTATGGC 800
        810       820       830       840
TTCCCTGGTGTACTATGGATTCCGCATGCGGCCTGATGAC 840
ATTGTCTATGACTGCCTCCCCCTCTACCACTCAAGCAGGA 880
AACATCGTGGGGATTGGCAGTGCTTACTCCACGGCATGAC 920
TGTGGTGATCCGGAAGAAGTTCTCAGCCTCCCGGTTCTGG 960
GATGATTGTATCAAGTACAACTGCACAGTGGTACAGTACA 1000
       1010      1020      1030      1040
TTGGCGAGCTCTGCCGCTACCTCCTGAACCAGCCACCCCG 1040
TGAGGCTGAGTCTCGGCACAAGGTGCGCATGGCACTGGGC 1080
AACGGTCTCCGGCAGTCCATCTGGACCGACTTCTCCAGCC 1120
GTTTCCACATCCCCCAGGTGGCTGAGTTCTATGGGGCCAC 1160
TGAATGCAACTGTAGCCTGGGCAACTTTGACAGCCGGGTG 1200
```

FIG. 68A

```
          1210        1220        1230        1240
     |    |    |    |    |    |    |    |    |    |
GGGGCCTGTGGCTTCAATAGCCGCATCCTGTCCTTTGTGT  1240
ACCCTATCCGTTTGGTACGTGTCAATGAGGATACCATGGA  1280
ACTGATCCGGGGACCCGATGGAGTCTGCATTCCCTGTCAA  1320
CCAGGTCAGCCAGGCCAGCTGGTGGGTCGCATCATCCAGC  1360
AGGACCCTCTGCGCCGTTTCGACGGGTACCTCAACCAGGG  1400
          1410        1420        1430        1440
     |    |    |    |    |    |    |    |    |    |
TGCCAACAACAAGAAGATTGCTAATGATGTCTTCAAGAAG  1440
GGGGACCAAGCCTACCTCACTGGTGACGTCCTGGTGATGG  1480
ATGAGCTGGGTTACCTGTACTTCCGAGATCGCACTGGGGA  1520
CACGTTCCGCTGGAAGGGGAGAATGTATCTACCACTGAG  1560
GTGGAGGGCACACTCAGCCGCCTGCTTCATATGGCAGATG  1600
          1610        1620        1630        1640
     |    |    |    |    |    |    |    |    |    |
TGGCAGTTTATGGTGTTGAGGTGCCAGGAACTGAAGGCCG  1640
AGCAGGAATGGCTGCCGTTGCAAGTCCCATCAGCAACTGT  1680
GACCTGGAGAGCTTTGCACAGACCTTGAAAAAGGAGCTGC  1720
CTCTGTATGCCCGCCCCATCTTCCTGCGCTTCTTGCCTGA  1760
GCTGCACAAGACAGGGACCTTCAAGTTCCAGAAGACAGAG  1800
          1810        1820        1830        1840
     |    |    |    |    |    |    |    |    |    |
TTGCGGAAGGAGGGCTTTGACCCATCTGTTGTGAAAGACC  1840
CGCTGTTCTATCTGGATGCTCGGAAGGGCTGCTACGTTGC  1880
ACTGGACCAGGAGGCCTATACCGCATCCAGGCAGGCGAG  1920
GAGAAGCTGTGATTTCCCCCTACATCCCTCTGAGGGCCAG  1960
AAGATGCTGGATTCAGAGCCCTAGCGTCCACCCCAGAGGG  2000
```

FIG. 68B

```
              2010        2020        2030        2040
       |....|....|....|....|....|....|....|....|
       TCCTGGGCAATGCCAGACCAAAGCTAGCAGGGCCCGCACC  2040
       TCCGCCCCTAGGTGCTGATCTCCCTCTCCCAAACTGCCA   2080
       AGTGACTCACTGCCGCTTCCCCGACCCTCCAGAGGCTTTC  2120
       TGTGAAAGTCTCATCCAAGCTGTGTCTTCTGGTCCAGGCG  2160
       TGGCCCCTGGCCCCAGGGTTTCTGATAGGCTCCTTTAGGA  2200
              2210        2220        2230        2240
       |....|....|....|....|....|....|....|....|
       TGGTATCTTGGGTCCAGCGGGCCAGGGTGTGGGAGAGGAG  2240
       TCACTAAGATCCCTCCAATCAGAAGGGAGCTTACAAAGGA  2280
       ACCAAGGCAAAGCCTGTAGACTCAGGAAGCTAAGTGGCCA  2320
       GAGACTATAGTGGCCAGTCATCCCATGTCCACAGAGGATC  2360
       TTGGTCCAGAGCTGCCAAAGTGTCACCTCTCCCTGCCTGC   2400
              2410        2420        2430        2440
       |....|....|....|....|....|....|....|....|
       ACCTCTGGGGAAAAGAGGACAGCATGTGGCCACTGGGCAC  2440
       CTGTCTCAAGAAGTCAGGATCACACACTCAGTCCTTGTTT  2480
       CTCCAGGTTCCCTTGTTCTTGTCTCGGGGAGGGAGGGACG  2520
       AGTGTCCTGTCTGTCCTTCCTGCCTGTCTGTGAGTCTGTG  2560
       TTGCTTCTCCATCTGTCCTAGCCTGAGTGTGGGTGGAACA  2600
              2610        2620        2630        2640
       |....|....|....|....|....|....|....|....|
       GGCATGAGGAGAGTGTGGCTCAGGGGCCAATAAACTCTGC  2640
       CTTGACTCCTCTTAAAAAAAAAAAAAAAAAAAAAAAAAAA  2680
       AAAAAAAAAAAAAAAAAAAAAAAAAAAAAA           2710
```

FIG. 68C

```
         10        20        30        40
 ⌊⌊⌊⌊⌊|⌊⌊⌊⌊⌊|⌊⌊⌊⌊⌊|⌊⌊⌊⌊⌊|⌊⌊⌊⌊⌊|⌊⌊⌊⌊⌊|⌊⌊⌊⌊⌊|⌊⌊⌊⌊⌊|
MLLGASLVGALLFSKLVLKLPWTQVGFSLLLLYLGSGGWR  40
FIRVFIKTVRRDIFGGMVLLKVKTKVRRYLQERKTVPLLF  80
ASMVQRHPDKTALIFEGTDTHWTFRQLDEYSSSVANFLQA 120
RGLASGNVVALFMENRNEFVGLWLGMAKLGVEAALINTNL 160
RRDALRHCLDTSKARALIFGSEMASAICEIHASLEPTLSL 200
        210       220       230       240
FCSGSWEPSTVPVSTEHLDPLLEDAPKHLPSHPDKGFTDK 240
LFYIYTSGTTGLPKAAIVVHSRYYRMASLVYYGFRMRPDD 280
IVYDCLPLYHSSRKHRGDWQCLLHGMTVVIRKKFSASRFW 320
DDCIKYNCTVVQYIGELCRYLLNQPPREAESRHKVRMALG 360
NGLRQSIWTDFSSRFHIPQVAEFYGATECNCSLGNFDSRV 400
        410       420       430       440
GACGFNSRILSFVYPIRLVRVNEDTMELIRGPDGVCIPCQ 440
PGQPGQLVGRIIQQDPLRRFDGYLNQGANNKKIANDVFKK 480
GDQAYLTGDVLVMDELGYLYFRDRTGDTFRWKGENVSTTE 520
VEGTLSRLLHMADVAVYGVEVPGTEGRAGMAAVASPISNC 560
DLESFAQTLKKELPLYARPIFLRFLPELHKTGTFKFQKTE 600
        610       620       630       640
LRKEGFDPSVVKDPLFYLDARKGCYVALDQEAYTRIQAGE 640
EKL 643
```

FIG. 69 mmFATP5 full length DNA

```
                10        20        30        40
      ....|....|....|....|....|....|....|....|
CACTCATCAGAGCTAAGAGAGACTACACGCTCTCATCTAC  40
TTCAGAAAGAGCCAATGCCATGGGTATTTGGAAGAAACTA  80
ACCTTACTGCTGTTGCTGCTTCTGCTGGTTGGCCTGGGGC  120
AGCCCCCATGGCCAGCAGCTATGGCTCTGGCCCTGCGTTG  160
GTTCCTGGGAGACCCCACATGCCTTGTGCTGCTTGGCTTG  200
               210       220       230       240
      ....|....|....|....|....|....|....|....|
GCATTGCTGGGCAGACCCTGGATCAGCTCCTGGATGCCCC  240
ACTGGCTGAGCCTGGTAGGAGCAGCTCTTACCTTATTCCT  280
ATTGCCTCTACAGCCACCCCCAGGGCTACGCTGGCTGCAT  320
AAAGATGTGGCTTTCACCTTCAAGATGCTTTTCTATGGCC  360
TAAAGTTCAGGCGACGCCTTAACAAACATCCTCCAGAGAC  400
               410       420       430       440
      ....|....|....|....|....|....|....|....|
CTTTGTGGATGCTTTAGAGCGGCAAGCACTGGCATGGCCT  440
GACCGGGTGGCCTTGGTGTGTACTGGGTCTGAGGGCTCCT  480
CAATCACAAATAGCCAGCTGGATGCCAGGTCCTGTCAGGC  520
AGCATGGGTCCTGAAAGCAAAGCTGAAGGATGCCGTAATC  560
CAGAACACAAGAGATGCTGCTGCTATCTTAGTTCTCCCGT  600
               610       620       630       640
      ....|....|....|....|....|....|....|....|
CCAAGACCATTTCTGCTTTGAGTGTGTTTCTGGGGTTGGC  640
CAAGTTGGGCTGCCCTGTGGCCTGGATCAATCCACACAGC  680
CGAGGGATGCCCTTGCTACACTCTGTACGGAGCTCTGGGG  720
CCAGTGTGCTGATTGTGGATCCAGACCTCCAGGAGAACCT  760
GGAAGAAGTCCTTCCCAAGCTGCTAGCTGAGAACATTCAC  800
               810       820       830       840
      ....|....|....|....|....|....|....|....|
TGCTTCTACCTTGGCCACAGCTCACCCACCCCGGGAGTAG  840
AGGCTCTGGGAGCTTCCCTGGATGCTGCACCTTCTGACCC  880
AGTACCTGCCAGCCTTCGAGCTACGATTAAGTGGAAATCT  920
CCTGCCATATTCATCTTTACTTCAGGGACCACTGGACTCC  960
CAAAGCCAGCCATCTTATCACATGAGCGGGTCATACAAGT  1000
              1010      1020      1030      1040
      ....|....|....|....|....|....|....|....|
GAGCAACGTGCTGTCCTTCTGTGGATGCAGAGCTGATGAT  1040
GTGGTCTATGACGTCCTACCTCTGTACCATACGATAGGGC  1080
TTGTCCTTGGATTCCTTGGCTGCTTACAAGTTGGAGCCAC  1120
CTGTGTCCTGGCCCCCAAGTTCTCTGCCTCCCGATTCTGG  1160
GCTGAGTGCCGGCAGCATGGCGTAACAGTGATCTTGTATG  1200
```

FIG. 70A

```
              1210       1220       1230       1240
         |    |    |    |    |    |    |    |    |    |
TGGGTGAAATCCTGCGGTACTTGTGTAACGTCCCTGAGCA  1240
ACCAGAAGACAAGATACATACAGTGCGCTTGGCCATGGGA  1280
ACTGGACTTCGGGCAAATGTGTGGAAAAACTTCCAGCAAC  1320
GCTTTGGTCCCATTCGGATCTGGGAATTCTACGGATCCAC  1360
AGAGGGCAATGTGGGCTTAATGAACTATGTGGCCACTGC   1400
              1410       1420       1430       1440
         |    |    |    |    |    |    |    |    |    |
GGGGCTGTGGGAAGGACCAGCTGCATCCTTCGAATGCTGA  1440
CTCCCTTTGAGCTTGTACAGTTCGACATAGAGACAGCAGA  1480
GCCTCTGAGGGACAAACAGGGTTTTTGCATTCCTGTGGAG  1520
CCAGGAAAGCCAGGACTTCTTTTGACCAAGGTTCGAAAGA  1560
ACCAACCCTTCCTGGGCTACCGTGGTTCCCAGGCCGAGTC  1600
              1610       1620       1630       1640
         |    |    |    |    |    |    |    |    |    |
CAATCGGAAACTTGTTGCGAATGTACGACGCGTAGGAGAC  1640
CTGTACTTCAACACTGGGGACGTGCTGACCTTGGACCAGG  1680
AAGGCTTCTTCTACTTTCAAGACCGCCTTGGTGACACCTT  1720
CCGGTGGAAGGGCGAAAACGTATCTACTGGAGAGGTGGAG  1760
TGTGTTTTGTCTAGCCTAGACTTCCTAGAGGAAGTCAATG  1800
              1810       1820       1830       1840
         |    |    |    |    |    |    |    |    |    |
TCTATGGTGTGCCTGTGCCAGGGTGTGAGGGTAAGGTTGG  1840
CATGGCTGCTGTGAAACTGGCTCCTGGGAAGACTTTTGAT  1880
GGGCAGAAGCTATACCAGCATGTCCGCTCCTGGCTCCCTG  1920
CCTATGCCACACCTCATTTCATCCGTATCCAGGATTCCCT  1960
GGAGATCACAAACACCTACAAGCTGGTAAAGTCACGGCTG  2000
              2010       2020       2030       2040
         |    |    |    |    |    |    |    |    |    |
GTGCGTGAGGGTTTTGATGTGGGGATCATTGCTGACCCCC  2040
TCTACATACTGGACAACAAGGCCCAGACCTTCCGGAGTCT  2080
GATGCCAGATGTGTACCAGGCTGTGTGTGAAGGAACCTGG  2120
AATCTCTGACCACCTAGCCAACTGGAAGGCAATCCAAAAG  2160
TGTAGAGATTGACACTAGTCAGCTTCACAAAGTTGTCCGG  2200
              2210       2220       2230       2240
         |    |    |    |    |    |    |    |    |    |
GTTCCAGATGCCCATGGCCCAGTAGTACTTAGAGAATAAA  2240
CTTGAATGTGTATACAAAAAAAAAAAAAAAAAAAAAAAA   2277
```

FIG. 70B mmFATP5 full length protein

```
          10        20        30        40
 ┬┬┬┬┬┬┬┬┬┼┬┬┬┬┬┬┬┬┬┼┬┬┬┬┬┬┬┬┬┼┬┬┬┬┬┬┬┬┬┼
MGIWKKLTLLLLLLLLVGLGQPPWPAAMALALRWFLGDPT   40
CLVLLGLALLGRPWISSWMPHWLSLVGAALTLFLLPLQPP   80
PGLRWLHKDVAFTFKMLFYGLKFRRRLNKHPPETFVDALE  120
RQALAWPDRVALVCTGSEGSSITNSQLDARSCQAAWVLKA  160
KLKDAVIQNTRDAAAILVLPSKTISALSVFLGLAKLGCPV  200
          210       220       230       240
AWINPHSRGMPLLHSVRSSGASVLIVDPDLQENLEEVLPK  240
LLAENIHCFYLGHSSPTPGVEALGASLDAAPSDPVPASLR  280
ATIKWKSPAIFIFTSGTTGLPKPAILSHERVIQVSNVLSF  320
CGCRADDVVYDVLPLYHTIGLVLGFLGCLQVGATCVLAPK  360
FSASRFWAECRQHGVTVILYVGEILRYLCNVPEQPEDKIH  400
          410       420       430       440
TVRLAMGTGLRANVWKNFQQRFGPIRIWEFYGSTEGNVGL  440
MNYVGHCGAVGRTSCILRMLTPFELVQFDIETAEPLRDKQ  480
GFCIPVEPGKPGLLLTKVRKNQPFLGYRGSQAESNRKLVA  520
NVRRVGDLYFNTGDVLTLDQEGFFYFQDRLGDTFRWKGEN  560
VSTGEVECVLSSLDFLEEVNVYGVPVPGCEGKVGMAAVKL  600
          610       620       630       640
APGKTFDGQKLYQHVRSWLPAYATPHFIRIQDSLEITNTY  640
KLVKSRLVREGFDVGIIADPLYILDNKAQTFRSLMPDVYQ  680
AVCEGTWNL   689
```

FIG. 71 dmFATP partial DNA

```
         10        20        30        40
GCTCTCTGGGCCTATATCAAGCTGCTGAGGTACACGAAGC  40
GCCATGAGCGGCTCAACTACACGGTGGCGGACGTCTTCGA  80
ACGAAATGTTCAGGCCCATCCGGACAAGGTGGCTGTGGTC 120
AGTGAGACGCAACGCTGGACCTTCGTCAGGTGAACGAGC  160
ATGCGAACAAGGTGGCCAATGTGCTGCAGGCTCAGGGCTA 200
         210       220       230       240
CAAAAAGGGCGATGTGGTGGCCCTGTTGCTGGAGAACCGC 240
GCCGAGTACGTGGCCACCTGGCTGGGTCTCTCCAAGATCG 280
GTGTGATCACACCGCTGATCAACACGAATCTGCGCGGTCC 320
CTCCCTGCTGCACAGCATCACGGTGGCCCATTGCTCGGCT 360
CTCATTTACGGCGAGGACTTCCTGGAAGCTGTCACCGACG 400
         410       420       430       440
TGGCCAAGGATCTGCCAGCGAACCTCACACTCTTCCAGTT 440
CAACAACGAGAACAACAACAGCGAGACGGAAAAGAACATA 480
CCGCAGGCCAAGAATCTGAACGCGCTGCTGACCACGGCCA 520
GCTATGAGAAGCCTAACAAGACGCAGGTTAACCACCACGA 560
CAAGCTGGTCTACATCTACACCTCCGGCACCACAGGATTG 600
         610       620       630       640
CCAAAGGCTGCGGTTATCTCTCACTCCCGTTATCTGTTTA 640
TCGCTGCTGGCATCCACTACACCATGGGTTTCCAGGAGGA 680
GGACATCTTCTACACGCCCTTGCCTTTGTACCACACCGCT 720
GGTGGCATTATGTGCATGGGTCAGTCGGTGCTCTTTGGCT 760
CCACGGTCTCCATTCGCAAGAAGTTCTCGGCATCCAACTA 800
         810       820       830       840
TTTCGCCGACTGCGCCAAGTATAATGCAACTATTGGTCAG 840
TATATCGGTGAGATGGCTCGCTACATTCTAGCTACGAAAC 880
CCTCGGAATACGACCAGAAACACCGAGTGCGTCTGGTCTT 920
TGGAAACGGACTGCGACCGCAGATTTGGCCACAGTTTGTG 960
CAGCGCTTCAACATTGCCAAGGTTGGCGAGTTCTACGGCG 1000
         1010      1020      1030      1040
CCACCGAGGGTAATGCGAACATCATGAATCATGACAACAC 1040
GGTGGGCGCCATCGGCTTTGTGTCGCGCATCCTGCCCAAG 1080
ATCTACCCAATCTCGATCATTCGCGCCGATCCGGACACCG 1120
GAGAGCCCATTAGAGATAGGAATGGCCTATGCCAACTGTG 1160
CGCTCCCAACGAGCCAGGCGTATTCATCGGCAAGATCGTC 1200
```

FIG. 72A

```
         1210      1220      1230      1240
   ↳↳↳↳↳↳↳↳↳↳↳↳↳↳↳↳↳↳↳↳↳↳↳↳↳↳↳↳↳↳↳↳↳↳↳↳↳
AAAGGAAATCCTTCTCGCGAATTCCTCGGATACGTCGATG 1240
AAAAGGCCTCCGCGAAGAAGATTGTTAAGGATGTGTTCAA 1280
GCATGGCGATATGGCTTTCATCTCCGGAGATCTGCTGGTT 1320
GCCGACGAGAAGGGTTATCTGTACTTCAAGGATCGCACCG 1360
GTGACACCTTCCGCTGGAAGGGCGAGAATGTTTCCACCAG 1400
         1410      1420      1430      1440
   ↳↳↳↳↳↳↳↳↳↳↳↳↳↳↳↳↳↳↳↳↳↳↳↳↳↳↳↳↳↳↳↳↳↳↳↳↳
CGAGGTGGAGGCGCAAGTCAGCAATGTGGCCGGTTACAAG 1440
GATACCGTCGTTTACGGCGTAACCATTCCGCACACCGAGG 1480
GAAGGGCCGGCATGGCCGCCATCTATGATCCGGAGCGAGA 1520
ATTGGACCTCGACGTCTTCGCCGCTAGCTTGGCCAAGGTG 1560
CTGCCCGCGTACGCTCGTCCCCAGATCATTCGATTGCTCA 1600
         1610      1620      1630      1640
   ↳↳↳↳↳↳↳↳↳↳↳↳↳↳↳↳↳↳↳↳↳↳↳↳↳↳↳↳↳↳↳↳↳↳↳↳↳
CCAAGGTGGACCTGACTGGAACCTTTAAGCTGCGCAAGGT 1640
AGACCTGCAGAAGGAGGGCTACGATCCGAACGCGATCAAG 1680
GACGCGCTGTACTACCAGACTTCCAAGGGTCGGTACGAGC 1720
TGCTCACGCCCCAGGTTTACGACCAGGTGCAGCGCAACGA 1760
AATCCGCTTCTAAGAGCTGCAATAGAGTTGTGTCTGAACC 1800
         1810      1820      1830      1840
   ↳↳↳↳↳↳↳↳↳↳↳↳↳↳↳↳↳↳↳↳↳↳↳↳↳↳↳↳↳↳↳↳↳↳↳↳↳
TTGCCTTTTGCCCAATATGCTGTTAATTAGTTTGTAAGGC 1840
TAAGTGTAGTAGAGGAAAATCGGGGGAAATCGGCAGCAAA 1880
GATCATTCAGCCTAGGAGAGATGCATCCGAAGCACATTTC 1920
CATGTCAACAATGCACTTTTGTATATCGTAAGCATATATA 1960
TATCGTATATCGTAAACGTAGTTGTATCTGCATTTGTGTA 2000
         2010      2020      2030      2040
   ↳↳↳↳↳↳↳↳↳↳↳↳↳↳↳↳↳↳↳↳↳↳↳↳↳↳↳↳↳↳↳↳↳↳↳↳↳
GATGATAGCCTCCTATACGCATTTCAATTGTTTTTAGCGT 2040
GCTAAAGAACCTTGTTAAATGCAATTTCAGCTATTGTTTA 2080
GTCAGTTTTAGTGGCATTTACACTTCCATTCTCGTTGCGT 2120
TTCGTTTTTGCCTGTACATATGAGAAGCTCTGATGTTTTT 2160
GTATCAAATAAAGTTTTTCCTTCACCACGGACCACGTGA 2200
         2210      2220      2230      2240
   ↳↳↳↳↳↳↳↳↳↳↳↳↳↳↳↳↳↳↳↳↳↳↳↳↳↳↳↳↳↳↳↳↳↳↳↳↳
AAAAAAAAAAAAAAAAAAAAA 2221
```

FIG. 72B dmFATP partial protein

```
         10         20         30         40
         |          |          |          |
ALWAYIKLLRYTKRHERLNYTVADVFERNVQAHPDKVAVV   40
SETQRWTFRQVNEHANKVANVLQAQGYKKGDVVALLLENR   80
AEYVATWLGLSKIGVITPLINTNLRGPSLLHSITVAHCSA  120
LIYGEDFLEAVTDVAKDLPANLTLFQFNNENNNSETEKNI  160
PQAKNLNALLTTASYEKPNKTQVNHHDKLVYIYTSGTTGL  200
        210        220        230        240
         |          |          |          |
PKAAVISHSRYLFIAAGIHYTMGFQEEDIFYTPLPLYHTA  240
GGIMCMGQSVLFGSTVSIRKKFSASNYFADCAKYNATIGQ  280
YIGEMARYILATKPSEYDQKHRVRLVFGNGLRPQIWPQFV  320
QRFNIAKVGEFYGATEGNANIMNHDNTVGAIGFVSRILPK  360
IYPISIIRADPDTGEPIRDRNGLCQLCAPNEPGVFIGKIV  400
        410        420        430        440
         |          |          |          |
KGNPSREFLGYVDEKASAKKIVKDVFKHGDMAFISGDLLV  440
ADEKGYLYFKDRTGDTFRWKGENVSTSEVEAQVSNVAGYK  480
DTVVYGVTIPHTEGRAGMAAIYDPERELDLDVFAASLAKV  520
LPAYARPQIIRLLTKVDLTGTFKLRKVDLQKEGYDPNAIK  560
DALYYQTSKGRYELLTPQVYDQVQRNEIRF            590
```

FIG. 73 drFATP partial DNA

```
           10        20        30        40
 ....|....|....|....|....|....|....|....|....
AGTGTAGATACCACAGGAACGTTTAAAATCCAGAAGACCA  40
GACTGCAAAGGGAAGGATACGATCCACGGCTCACAACTGA  80
CCAGATCTACTTCCTAAACTCCAGAGCAGGGCGTTACGAG 120
CTTGTCAACGAGGAGCTGTACAATGCATTTGAACAAGGGC 160
AGGATTTCCCTTT 173
```

FIG. 74 drFATP partial protein

```
           10        20        30        40
 ....|....|....|....|....|....|....|....|....
SVDTTGTFKIQKTRLQREGYDPRLTTDQIYFLNSRAGRYE 40
LVNEELYNAFEQGQDFP 57
```

FIG. 75 ceFATPa coding only DNA

```
         10        20        30        40
ATGAAGCTGGAGGAGCTTGTGACAGTTATGCTTCTCACAG  40
TGGCTGTCATTGCTCAGAATCTTCCGATTGGAGTAATATT  80
GGCTGGAGTTCTTATTTTATACATCACAGTGGTTCATGGA  120
GATTTCATTTATAGAAGTTATCTTACGTTGAATAGGGATT  160
TAACAGGATTGGCTCTAATTATTGAAGTCAAAATCGACCT  200
        210       220       230       240
ATGGTGGAGGTTGCATCAGAATAAAGGAATCCATGAACTG  240
TTTTGGATATTGTGAAAAGAATCCAAATAAGCCGGCGA    280
TGATTGACATCGAGACGAATACAACAGAAACATACGCAGA  320
GTTCAATGCACATTGTAATAGATATGCCAATTATTTCCAG  360
GGTCTTGGCTATCGATCCGGAGACGTTGTCGCCTTGTACA  400
        410       420       430       440
TGGAGAACTCGGTCGAGTTTGTGGCCGCGTGGATGGGACT  440
CGCAAAAATCGGAGTTGTAACGGCTTGGATCAACTCGAAT  480
TTGAAAAGAGAGCAACTTGTTCATTGTATCACTGCGAGCA  520
AGACAAAGGCGATTATCACAAGTGTAACACTTCAGAATAT  560
TATGCTTGATGCTATCGATCAGAAGCTGTTTGATGTTGAG  600
        610       620       630       640
GGAATTGAGGTTTACTCTGTCGGAGAGCCCAAGAAGAATT  640
CTGGATTCAAGAATCTCAAGAAGAAGTTGGATGCTCAAAT  680
TACTACGGAACCAAAGACCCTTGACATAGTAGATTTTAAA  720
AGTATTCTTTGCTTCATCTATACAAGTGGTACTACTGGAA  760
TGCCAAAAGCCGCTGTCATGAAGCACTTCAGATATTACTC  800
        810       820       830       840
GATTGCCGTTGGAGCCGCAAAATCATTCGGAATCCGCCCT  840
TCTGATCGTATGTACGTCTCGATGCCAATTTATCACACTG  880
CAGCTGGAATTCTTGGAGTTGGGCAAGCTCTGTTGGGTGG  920
ATCATCGTGTGTCATTAGAAAAAAATTCTCGGCTAGCAAC  960
TTTTGGAGGGATTGTGTAAAGTATGATTGTACAGTTTCAC  1000
       1010      1020      1030      1040
AATACATTGGAGAGATTTGTCGGTACTTGTTGGCTCAGCC  1040
AGTTGTGGAAGAGGAATCCAGGCATAGAATGAGATTGTTG  1080
GTTGGAAACGGACTCCGTGCTGAAATCTGGCAACCATTTG  1120
TAGATCGATTCCGTGTCAGAATTGGAGAACTTTATGGTTC  1160
AACTGAAGGAACTTCATCTCTCGTGAACATTGACGGACAT  1200
```

FIG. 76A

```
           1210       1220       1230       1240
GTCGGAGCTTGCGGATTCTTGCCAATATCCCCATTAACAA 1240
AGAAAATGCATCCGGTTCGATTAATTAAGGTTGATGATGT 1280
CACTGGAGAAGCAATCCGAACTTCCGATGGACTTTGCATT 1320
GCATGTAATCCAGGAGAGTCTGGAGCAATGGTGTCGACGA 1360
TCAGAAAAATAATCCATTATTGCAATTCGAGGGATATCT 1400
           1410       1420       1430       1440
GAATAAGAAGGAAACGAATAAAAGATTATCAGAGATGTC 1440
TTCGCAAAGGGAGATAGTTGCTTTTGACTGGAGATCTTC 1480
TTCATTGGGATCGTCTTGGTTATGTATATTTCAAGGATCG 1520
TACTGGAGATACTTTCCGTTGGAAGGGAGAGAATGTGTCG 1560
ACTACTGAAGTCGAGGCAATTCTTCATCCAATTACTGGAT 1600
           1610       1620       1630       1640
TGTCTGATGCAACTGTTTATGGTGTAGAGGTTCCTCAAAG 1640
AGAGGGAAGAGTTGGAATGGCGTCAGTTGTTCGAGTTGTA 1680
TCGCATGAGGAAGATGAAACTCAATTTGTTCATAGAGTTG 1720
GAGCAAGACTTGCCTCTTCGCTTACCAGCTACGCGATTCC 1760
TCAGTTTATGCAATTTGTCAGGATGTTGAGAAACAGGT 1800
           1810       1820       1830       1840
ACATTCAAACTTGTGAAGACGAATCTACAACGATTAGGTA 1840
TCATGGATGCTCCTTCAGATTCAATTTACATCTACAATTC 1880
TGAAAATCGCAATTTTGTGCCGTTCGACAATGATTTGAGG 1920
TGCAAGGTCTCACTGGGAAGTTATCCATTTTAA 1953
```

FIG. 76B ceFATPa coding only protein

```
          10          20          30          40
    |....|....|....|....|....|....|....|....|
MKLEELVTVMLLTVAVIAQNLPIGVILAGVLILYITVVHG  40
DFIYRSYLTLNRDLTGLALIIEVKIDLWWRLHQNKGIHEL  80
FLDIVKKNPNKPAMIDIETNTTETYAEFNAHCNRYANYFQ 120
GLGYRSGDVVALYMENSVEFVAAWMGLAKIGVVTAWINSN 160
LKREQLVHCITASKTKAIITSVTLQNIMLDAIDQKLFDVE 200

210         220         230         240
    |....|....|....|....|....|....|....|....|
GIEVYSVGEPKKNSGFKNLKKKLDAQITTEPKTLDIVDFK 240
SILCFIYTSGTTGMPKAAVMKHFRYYSIAVGAAKSFGIRP 280
SDRMYVSMPIYHTAAGILGVGQALLGGSSCVIRKKFSASN 320
FWRDCVKYDCTVSQYIGEICRYLLAQPVVEEESRHRMRLL 360
VGNGLRAEIWQPFVDRFRVRIGELYGSTEGTSSLVNIDGH 400

410         420         430         440
    |....|....|....|....|....|....|....|....|
VGACGFLPISPLTKKMHPVRLIKVDDVTGEAIRTSDGLCI 440
ACNPGESGAMVSTIRKNNPLLQFEGYLNKKETNKKIIRDV 480
FAKGDSCFLTGDLLHWDRLGYVYFKDRTGDTFRWKGENVS 520
TTEVEAILHPITGLSDATVYGVEVPQREGRVGMASVVRVV 560
SHEEDETQFVHRVGARLASSLTSYAIPQFMRICQDVEKTG 600

610         620         630         640
    |....|....|....|....|....|....|....|....|
TFKLVKTNLQRLGIMDAPSDSIYIYNSENRNFVPFDNDLR 640
CKVSLGSYPF    650
```

FIG. 77 ceFATPb coding only DNA

```
         10        20        30        40
ATGAGGGAAATGCCGGACAGTCCCAAGTTTGCGTTAGTCA  40
CGTTTGTTGTGTATGCAGTGGTTTTGTACAATGTCAACAG  80
CGTTTTCTGGAAATTTGTATTCATCGGATATGTTGTATTT  120
AGGCTGCTTCGCACTGATTTTGGAAGAAGAGCACTTGCCA  160
CGTTACCTAGAGATTTTGCGGGACTGAAGCTCTTAATATC  200
        210       220       230       240
GGTTAAGTCGACAATTCGTGGCTTGTTCAAGAAAGATCGC  240
CCAATTCATGAAATCTTTTTGAATCAGGTGAAACAGCATC  280
CAAACAAAGTGGCGATTATTGAAATTGAAAGTGGTAGGCA  320
GTTGACGTATCAAGAATTGAATGCGTTAGCTAATCAGTAT  360
GCTAACCTTTACGTGAGTGAAGGTTACAAAATGGGCGACG  400
        410       420       430       440
TTGTCGCTTTGTTTATGGAAAATAGCATCGACTTCTTTGC  440
AATTTGGCTGGGACTTTCCAAGATTGGAGTCGTGTCGGCG  480
TTCATCAACTCAAACTTGAAGTTGGAGCCATTGGCACATT  520
CGATTAATGTTTCGAAGTGCAAATCATGCATTACCAATAT  560
CAATCTGTTGCCGATGTTCAAAGCCGCTCGTGAAAAGAAT  600
        610       620       630       640
CTGATCAGTGACGAGATCCACGTGTTTCTGGCTGGAACTC  640
AGGTTGATGGACGTCATAGAAGTCTTCAGCAAGATCTCCA  680
TCTTTTCTCTGAGGATGAACCTCCAGTTATAGACGGACTC  720
AATTTTAGAAGCGTTCTGTGTTATATTTACACTTCCGGTA  760
CTACCGGAAATCCAAAGCCAGCCGTCATTAAACACTTCCG  800
        810       820       830       840
TTACTTCTGGATTGCGATGGGAGCAGGAAAAGCATTTGGA  840
ATTAATAAGTCAGACGTTGTGTACATTACGATGCCAATGT  880
ATCACTCTGCCGCCGGTATCATGGGTATTGGATCATTAAT  920
TGCATTCGGGTCGACCGCTGTTATTAGGAAAAAGTTTTCG  960
GCAAGCAACTTCTGGAAAGATTGCGTCAAGTACAACGTCA  1000
        1010      1020      1030      1040
CAGCGACACAGTACATTGGAGAAATCTGCAGGTATCTTCT  1040
GGCAGCGAATCCATGTCCTGAAGAGAAACAACACAACGTG  1080
CGATTGATGTGGGGAAATGGTTTGAGAGGACAAATTTGGA  1120
AAGAGTTTGTAGGAAGATTTGGAATTAAGAAAATTGGAGA  1160
GTTGTACGGCTCAACAGAAGGAAACTCCAATATTGTTAAC  1200
```

FIG. 78A

```
                    1210      1220      1230      1240
                     |         |         |         |
GTGGATAACCATGTTGGAGCTTGTGGATTCATGCCAATTT 1240
ATCCCCATATTGGATCCCTCTACCCAGTTCGACTTATTAA 1280
GGTTGATAGAGCCACTGGAGAGCTTGAACGTGATAAGAAC 1320
GGACTCTGTGTGCCGTGTGTGCCTGGTGAAACTGGGGAAA 1360
TGGTTGGCGTTATCAAGGAGAAAGATATTCTTCTAAAGTT 1400
                    1410      1420      1430      1440
                     |         |         |         |
CGAAGGATATGTCAGCGAAGGGGATACTGCAAAGAAAATC 1440
TACAGAGATGTGTTCAAGCATGGAGATAAGGTGTTTGCAA 1480
GTGGAGATATTCTTCATTGGGATGATCTTGGATACTTGTA 1520
CTTTGTGGACCGTTGTGGAGACACTTTCCGTTGGAAAGGG 1560
GAGAACGTGTCAACTACTGAAGTTGAGGGAATTCTTCAGC 1600
                    1610      1620      1630      1640
                     |         |         |         |
CTGTGATGGATGTGGAAGATGCAACTGTTTATGGAGTCAC 1640
TGTCGGTAAAATGGAGGGGCGTGCCGGAATGGCTGGTATT 1680
GTCGTCAAGGATGGAACGGATGTTGAGAAATTCATCGCCG 1720
ATATTACTTCTCGACTGACCGAAAATCTGGCGTCTTACGC 1760
AATCCCTGTTTTCATTCGGCTGTGCAAGGAAGTTGATCGA 1800
                    1810      1820      1830      1840
                     |         |         |         |
ACCGGAACCTTCAAACTCAAGAAGACTGATCTTCAAAAAC 1840
AAGGTTACGACCTGGTTGCTTGTAAAGGAGACCCAATTTA 1880
CTACTGGTCAGCTGCAGAAAAATCCTACAAACCACTGACT 1920
GACAAAATGCAACAGGATATTGACACTGGTGTTTATGATC 1960
GCATTTAA 1968
```

FIG. 78B ceFATPb coding only protein

```
          10        20        30        40
     |    |    |    |    |    |    |    |
MREMPDSPKFALVTFVVYAVVLYNVNSVFWKFVFIGYVVF   40
RLLRTDFGRRALATLPRDFAGLKLLISVKSTIRGLFKKDR   80
PIHEIFLNQVKQHPNKVAIIEIESGRQLTYQELNALANQY  120
ANLYVSEGYKMGDVVALFMENSIDFFAIWLGLSKIGVVSA  160
FINSNLKLEPLAHSINVSKCKSCITNINLLPMFKAAREKN  200
         210       220       230       240
     |    |    |    |    |    |    |    |
LISDEIHVFLAGTQVDGRHRSLQQDLHLFSEDEPPVIDGL  240
NFRSVLCYIYTSGTTGNPKPAVIKHFRYFWIAMGAGKAFG  280
INKSDVVYITMPMYHSAAGIMGIGSLIAFGSTAVIRKKFS  320
ASNFWKDCVKYNVTATQYIGEICRYLLAANPCPEEKQHNV  360
RLMWGNGLRGQIWKEFVGRFGIKKIGELYGSTEGNSNIVN  400
         410       420       430       440
     |    |    |    |    |    |    |    |
VDNHVGACGFMPIYPHIGSLYPVRLIKVDRATGELERDKN  440
GLCVPCVPGETGEMVGVIKEKDILLKFEGYVSEGDTAKKI  480
YRDVFKHGDKVFASGDILHWDDLGYLYFVDRCGDTFRWKG  520
ENVSTTEVEGILQPVMDVEDATVYGVTVGKMEGRAGMAGI  560
VVKDGTDVEKFIADITSRLTENLASYAIPVFIRLCKEVDR  600
         610       620       630       640
     |    |    |    |    |    |    |    |
TGTFKLKKTDLQKQGYDLVACKGDPIYYWSAAEKSYKPLT  640
DKMQQDIDTGVYDRI  655
```

FIG. 79 chFATP coding only DNA

```
         10        20        30        40
ATGGCGTGTATGCATCAGGCTCAGCTATACAATGATCTAG  40
AGGAATTGCTAACTGGTCCATCAGTACCCATCGTTGCTGG  80
AGCTGCTGGAGCTGCAGCTCTCACTGCCTACATTAACGCC 120
AAATACCACATAGCCCATGATCTCAAGACCCTCGGTGGTG 160
GATTGACACAATCGTCCGAAGCGATTGATTTCATAAACCG 200
        210       220       230       240
CCGCGTCGCACAAAAGCGCGTCCTCACGCACCACATCTTC 240
CAGGAGCAGGTCCAAAAACAATCAAATCATCCCTTTCTTA 280
TCTTTGAGGGCAAGACATGGTCTTACAAGGAGTTCTCTGA 320
GGCATACACGAGGGTCGCGAACTGGCTGATTGATGAGCTG 360
GACGTACAAGTAGGGGAGATGGTCGCAATTGATGGCGGAA 400
        410       420       430       440
ATAGTGCAGAGCACCTGATGCTTTGGCTTGCACTTGATGC 440
AATCGGTGCGGCTACGAGTTTTTTGAACTGGAACCTGACA 480
GGGGCAGGGTTAATTCATTGCATAAAGCTATGCGAATGTC 520
GATTCGTTATCGCAGACATCGATATTAAAGCGAACATTGA 560
ACCGTGCCGTGGCGAACTGGAGGAGACGGGCATCAACATT 600
        610       620       630       640
CACTACTATGACCCATCCTTCATCTCATCGCTACCGAATA 640
ACACGCCAATTCCCGACAGCCGCACTGAGAACATTGAATT 680
AGATTCAGTACGAGGACTGATATACACATCTGGAACCACT 720
GGTCTACCTAAAGGCGTGTTTATAAGCACTGGCCGCGAGC 760
TTAGGACTGACTGGTCGATTTCAAAGTATCTAAATCTCAA 800
        810       820       830       840
GCCCACGGATCGAATGTATACATGTATGCCGCTCTACCAT 840
GCCGCTGCACACAGCCTCTGTACAGCATCAGTTATTCATG 880
GTGGAGGTACCGTGGTATTGAGCAGGAAATTCTCACACAA 920
GAAGTTCTGGCCTGAAGTTGTGGCTTCGGAAGCAAATATC 960
ATTCAGTACGTTGGTGAATTAGGTCGATATCTCCTGAATG 1000
       1010      1020      1030      1040
GTCCAAAGAGTCCTTACGACAGGGCCCATAAAGTCCAGAT 1040
GGCGTGGGGCAATGGCATGCGTCCAGACGTGTGGGAAGCG 1080
TTTCGTGAACGCTTCAACATACCAATTATTCATGAGCTCT 1120
ATGCCGCAACCGATGGGCTCGGGTCAATGACCAATCGTAA 1160
CGCGGGCCCTTTTACAGCAAACTGTATTGCGCTGCGAGGG 1200
```

FIG. 80A

```
          1210      1220      1230      1240
CTGATCTGGCACTGGAAATTTCGAAATCAGGAAGTGCTGG 1240
TCAAGATGGATCTCGATACTGATGAGATCATGAGAGATCG 1280
CAATGGGTTTGCGATACGATGCGCTGTCAATGAACCTGGA 1320
CAGATGCTTTTTCGGCTGACACCCGAAACTCTGGCTGGTG 1360
CACCAAGCTACTACAACAACGAAACGGCCACACAGAGCAG 1400
          1410      1420      1430      1440
GCGGATTACAGATGTGTTTCAAAAGGGTGACCTGTGGTTC 1440
AAGTCCGGTGACATGCTACGGCAAGACGCCGAAGGCCGCG 1480
TCTACTTTGTCGATCGACTAGGCGATACGTTCCGCTGGAA 1520
ATCCGAAAACGTTCTACCAATGAAGTCGCGGACGTGATG 1560
GGCACATTTCCTCAGATTGCTGAAACGAATGTATACGGTG 1600
          1610      1620      1630      1640
TCCTTGTGCCGGGTAACGATGGTCGAGTGCGCAGCCTCAA 1640
TTGTCATGGCAGACGGCGTGACAGAGTCGACATTCGCTTC 1680
GCTGCCCTTGCAAAGCACGCCGAGATCGGTTACCGGGTT 1720
ATGCTGTACCACTGTTTCTGAGGGTAACTCCAGCACTTGA 1760
ATATACGGGCACATTAAAGATTCAGAAGGACGCCTCAAG 1800
          1810      1820      1830      1840
CAGGAAGGTATAGACCCAGATAAGATTTCCGGCGAAGATA 1840
AGTTATACTGGCTGCCGCCTGGTAGCGATATATATTTACC 1880
ATTTGGAAAGATGGAGTGGCAGGGAATTGTAGATAAGCGT 1920
ATACGGCTGTGA 1932
```

FIG. 80B chFATP coding only protein

```
          10        20        30        40
 |....|....|....|....|....|....|....|....|
MACMHQAQLYNDLEELLTGPSVPIVAGAAGAAALTAYINA   40
KYHIAHDLKTLGGGLTQSSEAIDFINRRVAQKRVLTHHIF   80
QEQVQKQSNHPFLIFEGKTWSYKEFSEAYTRVANWLIDEL  120
DVQVGEMVAIDGGNSAEHLMLWLALDAIGAATSFLNWNLT  160
GAGLIHCIKLCECRFVIADIDIKANIEPCRGELEETGINI  200
         210       220       230       240
 |....|....|....|....|....|....|....|....|
HYYDPSFISSLPNNTPIPDSRTENIELDSVRGLIYTSGTT  240
GLPKGVFISTGRELRTDWSISKYLNLKPTDRMYTCMPLYH  280
AAAHSLCTASVIHGGGTVVLSRKFSHKKFWPEVVASEANI  320
IQYVGELGRYLLNGPKSPYDRAHKVQMAWGNGMRPDVWEA  360
FRERFNIPIIHELYAATDGLGSMTNRNAGPFTANCIALRG  400
         410       420       430       440
 |....|....|....|....|....|....|....|....|
LIWHWKFRNQEVLVKMDLDTDEIMRDRNGFAIRCAVNEPG  440
QMLFRLTPETLAGAPSYYNNETATQSRRITDVFQKGDLWF  480
KSGDMLRQDAEGRVYFVDRLGDTFRWKSENVSTNEVADVM  520
GTFPQIAETNVYGVLVPGNDGRVRSLNCHGRRRDRVDIRF  560
AALAKHARDRLPGYAVPLFLRVTPALEYTGTLKIQKGRLK  600
         610       620       630       640
 |....|....|....|....|....|....|....|....|
QEGIDPDKISGEDKLYWLPPGSDIYLPFGKMEWQGIVDKR  640
IRL                                      643
```

FIG. 81 aspergillus partial DNA

```
         10        20        30        40
CTTTACCATTCATCAGCTTCATTCTGCATTTTTAGCTTGA  40
CGGCAGCCGGGTCTACGCTGATCATCGGCCGCAAGTTCTC  80
CGCGAGAAACTTCATAAAGGAAGCGCGCGAGAACGACGCC 120
ACGGTCATCCAGTACGTGGGTGAGACCTTGCGATATCTGC 160
TCGCCACCCCCGGTGAAACCGATCCAGTTACTGGCGAAGA 200
        210       220       230       240
CCTGGACAAAAAGCACAATATTCGAGCAGTATACGGCAAC 240
GGGCTACGGCCGGATATCTGGAACCGCTTCAAGGAGCGCT 280
TCAACGTGCCGACGGTTGCCGAATTTTATGCTGCAACCGA 320
GAGCCCAGGCGGAACATGGAACTATTCAACAAATGACTTC 360
ACTGCCGGAGCCATTGGGCACACTGGCGTGCTTAGTGGAT 400
        410       420       430       440
GGCTTCTTGGACGCGGCCTTACTATTGTCGAGGTGGACCA 440
GGAATCACAGGAACCATGGCGCGATCCCCAAACCGGGTTC 480
TGCAAGCCGGTCCCGCGAGGCGAAGCAGGCGAGCTCCTGT 520
ATGCCATTGATCCGGCCGACCCGGGCGAGACCTTCCAGGG 560
CTACTACCGCAACTCCTTTAGAGCACACTGGCGGCCG    597
```

FIG 82 aspergillus partial protein

```
         10        20        30        40
LYHSSASFCIFSLTAAGSTLIIGRKFSARNFIKEARENDA  40
TVIQYVGETLRYLLATPGETDPVTGEDLDKKHNIRAVYGN  80
GLRPDIWNRFKERFNVPTVAEFYAATESPGGTWNYSTNDF 120
TAGAIGHTGVLSGWLLGRGLTIVEVDQESQEPWRDPQTGF 160
CKPVPRGEAGELLYAIDPADPGETFQGYYRNSFRAHWRP  199
```

FIG. 83 mgFATP partial DNA

```
         10        20        30        40
 ┬┬┬┬┬┬┬┬┬┬┬┬┬┬┬┬┬┬┬┬┬┬┬┬┬┬┬┬┬┬┬┬┬┬┬┬┬┬┬┬
GCAAAGGCCGACGCGTGGCTGCGGACGGGTAACGTGATCA   40
GGGCGGACAACGAAGGGCGACTCTTCTTCCACGACCGGAT   80
CGGAGACACGTTCCGATGGAAGGGAGAGACNGTCAGCACA  120
CAAGAGGTCAGTTTGGTGCTCGGACGACACGACTCAATCA  160
AGGAGGCCAACGTGTACGGCGTGACGGTGCCGAACCACGA  200
        210       220       230       240
 ┬┬┬┬┬┬┬┬┬┬┬┬┬┬┬┬┬┬┬┬┬┬┬┬┬┬┬┬┬┬┬┬┬┬┬┬┬┬┬┬
CGGGCGGGCCGGCTGCGCTGCGCTCACGCTATCAGACGCT  240
CTGGCGACTGAAAAGAAGCTGGGCGATGAGCTGCTAAAGG  280
GATTGGCTACTCACTCGTCGACTTCGCTTCCCAAGTTTGC  320
GGTGCCGCAGTTCCTACGGGTGGTGCGCGGCGAGATGCAG  360
TCAACGGGCACCAACAAGCAACAGAAGCACGACCTGAGGG  400
        410       420       430       440
 ┬┬┬┬┬┬┬┬┬┬┬┬┬┬┬┬┬┬┬┬┬┬┬┬┬┬┬┬┬┬┬┬┬┬┬┬┬┬┬┬
TGCAGGGTGTAGAGCCGGGCAAGGTGGGCGTAGACGAGGT  440
GTACTGGTTGCGGGGAGGGACATATGTACCATTCGGAACA  480
GAGGATTGGGATGGGTTGAAGAAGGGTCTTGTGAAGTTGT  520
GA                                        522
```

FIG. 84 mgFATP partial protein

```
         10        20        30        40
 ┬┬┬┬┬┬┬┬┬┬┬┬┬┬┬┬┬┬┬┬┬┬┬┬┬┬┬┬┬┬┬┬┬┬┬┬┬┬┬┬
AKADAWLRTGNVIRADNEGRLFFHDRIGDTFRWKGETVST   40
QEVSLVLGRHDSIKEANVYGVTVPNHDGRAGCAALTLSDA   80
LATEKKLGDELLKGLATHSSTSLPKFAVPQFLRVVRGEMQ  120
STGTNKQQKHDLRVQGVEPGKVGVDEVYWLRGGTYVPFGT  160
EDWDGLKKGLVKL                             173
```

FIG. 85 scFATP coding only DNA

```
         10        20        30        40
  ｜｜｜｜｜｜｜｜｜｜｜｜｜｜｜｜｜｜｜｜｜｜｜｜｜｜｜｜｜｜｜｜｜｜｜｜｜｜｜｜
ATGTCTCCCATACAGGTTGTTGTCTTTGCCTTGTCAAGGA   40
TTTTCCTGCTATTATTCAGACTTATCAAGCTAATTATAAC   80
CCCTATCCAGAAATCACTGGGTTATCTATTTGGTAATTAT  120
TTTGATGAATTAGACCGTAAATATAGATACAAGGAGGATT  160
GGTATATTATTCCTTACTTTTGAAAAGCGTGTTTTGTTA   200
        210       220       230       240
  ｜｜｜｜｜｜｜｜｜｜｜｜｜｜｜｜｜｜｜｜｜｜｜｜｜｜｜｜｜｜｜｜｜｜｜｜｜｜｜｜
TATCATTGATGTGAGAAGACATAGGTTTCAAAACTGGTAC  240
TTATTTATTAAACAGGTCCAACAAAATGGTGACCATTTAG  280
CGATTAGTTACACCCGTCCCATGGCCGAAAAGGGAGAATT  320
TCAACTCGAAACCTTTACGTATATTGAAACTTATAACATA  360
GTGTTGAGATTGTCTCATATTTTGCATTTTGATTATAACG  400
        410       420       430       440
  ｜｜｜｜｜｜｜｜｜｜｜｜｜｜｜｜｜｜｜｜｜｜｜｜｜｜｜｜｜｜｜｜｜｜｜｜｜｜｜｜
TTCAGGCCGGTGACTACGTGGCAATCGATTGTACTAATAA  440
ACCTCTTTTCGTATTTTTATGGCTTTCTTTGTGGAACATT  480
GGGGCTATTCCAGCTTTTTTAAACTATAATACTAAAGGCA  520
CTCCGCTGGTTCACTCCCTAAAGATTTCCAATATTACGCA  560
GGTATTTATTGACCCTGATGCCAGTAATCCGATCAGAGAA  600
        610       620       630       640
  ｜｜｜｜｜｜｜｜｜｜｜｜｜｜｜｜｜｜｜｜｜｜｜｜｜｜｜｜｜｜｜｜｜｜｜｜｜｜｜｜
TCGGAAGAAGAAATCAAAAACGCACTTCCTGATGTTAAAT  640
TAAACTATCTTGAAGAACAAGACTTAATGCATGAACTTTT  680
AAATTCGCAATCACCGGAATTCTTACAACAAGACAACGTT  720
AGGACACCACTAGGCTTGACCGATTTTAAACCCTCTATGT  760
TAATTTATACATCTGGAACCACTGGTTTGCCTAAATCCGC  800
        810       820       830       840
  ｜｜｜｜｜｜｜｜｜｜｜｜｜｜｜｜｜｜｜｜｜｜｜｜｜｜｜｜｜｜｜｜｜｜｜｜｜｜｜｜
TATTATGTCTTGGAGAAAATCCTCCGTAGGTTGTCAAGTT  840
TTTGGTCATGTTTTACATATGACTAATGAAAGCACTGTGT  880
TCACAGCCATGCCATTGTTCCATTCAACTGCTGCCTTATT  920
AGGTGCGTGCGCCATTCTATCTCACGGTGGTTGCCTTGCG  960
TTATCGCATAAATTTCTGCCAGTACATTTTGGAAGCAAG  1000
        1010      1020      1030      1040
  ｜｜｜｜｜｜｜｜｜｜｜｜｜｜｜｜｜｜｜｜｜｜｜｜｜｜｜｜｜｜｜｜｜｜｜｜｜｜｜｜
TTTATTTAACAGGAGCCACGCACATCCAATATGTCGGAGA  1040
AGTCTGTAGATACCTGTTACATACGCCAATTTCTAAGTAT  1080
GAAAGATGCATAAGGTGAAGGTTGCTTATGGTAACGGGC   1120
TGAGACCTGACATCTGGCAGGACTTCAGGAAGAGGTTCAA  1160
CATAGAAGTTATTGGTGAATTCTATGCCGCAACTGAAGCT  1200
```

FIG. 86A

```
         1210      1220      1230      1240
    ╷┈┈╷┈┈┈╷┈┈┈╷┈┈┈╷┈┈┈╷┈┈┈╷┈┈┈╷┈┈┈╷┈┈┈╷┈┈┈╷
CCTTTTGCTACAACTACCTTCCAGAAAGGTGACTTTGGAA  1240
TTGGCGCATGTAGGAACTATGGTACTATAATTCAATGGTT  1280
TTTGTCATTCCAACAAACATTGGTAAGGATGGACCCAAAT  1320
GACGATTCCGTTATATATAGAAATTCCAAGGGTTTCTGCG  1360
AAGTGGCCCCTGTTGGCGAACCAGGAGAAATGTTAATGAG  1400
         1410      1420      1430      1440
    ╷┈┈╷┈┈┈╷┈┈┈╷┈┈┈╷┈┈┈╷┈┈┈╷┈┈┈╷┈┈┈╷┈┈┈╷┈┈┈╷
AATCTTTTTCCCTAAAAAACCAGAAACATCTTTTCAAGGT  1440
TATCTTGGTAATGCCAAGGAAACAAAGTCCAAAGTTGTGA  1480
GGGATGTCTTCAGACGTGGCGATGCTTGGTATAGATGTGG  1520
AGATTTATTAAAAGCGGACGAATATGGATTATGGTATTTC  1560
CTTGATAGAATGGGTGATACTTTCAGATGGAAATCTGAAA  1600
         1610      1620      1630      1640
    ╷┈┈╷┈┈┈╷┈┈┈╷┈┈┈╷┈┈┈╷┈┈┈╷┈┈┈╷┈┈┈╷┈┈┈╷┈┈┈╷
ATGTTTCCACTACTGAAGTAGAAGATCAGTTGACGGCCAG  1640
TAACAAGAACAATATGCACAAGTTCTAGTTGTTGGTATT  1680
AAAGTACCTAAATATGAAGGTAGAGCTGGTTTTGCAGTTA  1720
TTAAACTAACTGACAACTCTCTTGACATCACTGCAAAGAC  1760
CAAATTATTAAATGATTCCTTGAGCCGGTTAAATCTACCG  1800
         1810      1820      1830      1840
    ╷┈┈╷┈┈┈╷┈┈┈╷┈┈┈╷┈┈┈╷┈┈┈╷┈┈┈╷┈┈┈╷┈┈┈╷┈┈┈╷
TCTTATGCTATGCCCCTATTTGTTAAATTTGTTGATGAAA  1840
TTAAAATGACAGATAACCTCATAAAATTTTGA  1872
```

FIG. 86B scFATP coding only protein

```
           10        20        30        40
     ․․․․․|․․․․․|․․․․․|․․․․․|․․․․․|․․․․․|․․․․․|․․․․․|
     MSPIQVVVFALSRIFLLLFRLIKLIITPIQKSLGYLFGNY  40
     FDELDRKYRYKEDWYIIPYFLKSVFCYIIDVRRHRFQNWY  80
     LFIKQVQQNGDHLAISYTRPMAEKGEFQLETFTYIETYNI  120
     VLRLSHILHFDYNVQAGDYVAIDCTNKPLFVFLWLSLWNI  160
     GAIPAFLNYNTKGTPLVHSLKISNITQVFIDPDASNPIRE  200
           210       220       230       240
     ․․․․․|․․․․․|․․․․․|․․․․․|․․․․․|․․․․․|․․․․․|․․․․․|
     SEEEIKNALPDVKLNYLEEQDLMHELLNSQSPEFLQQDNV  240
     RTPLGLTDFKPSMLIYTSGTTGLPKSAIMSWRKSSVGCQV  280
     FGHVLHMTNESTVFTAMPLFHSTAALLGACAILSHGGCLA  320
     LSHKFSASTFWKQVYLTGATHIQYVGEVCRYLLHTPISKY  360
     EKMHKVKVAYGNGLRPDIWQDFRKRFNIEVIGEFYAATEA  400
           410       420       430       440
     ․․․․․|․․․․․|․․․․․|․․․․․|․․․․․|․․․․․|․․․․․|․․․․․|
     PFATTTFQKGDFGIGACRNYGTIIQWFLSFQQTLVRMDPN  440
     DDSVIYRNSKGFCEVAPVGEPGEMLMRIFFPKKPETSFQG  480
     YLGNAKETKSKVVRDVFRRGDAWYRCGDLLKADEYGLWYF  520
     LDRMGDTFRWKSENVSTTEVEDQLTASNKEQYAQVLVVGI  560
     KVPKYEGRAGFAVIKLTDNSLDITAKTKLLNDSLSRLNLP  600
           610       620       630       640
     ․․․․․|․․․․․|․․․․․|․․․․․|․․․․․|․․․․․|․․․․․|․․․․․|
     SYAMPLFVKFVDEIKMTDNLIKF  623
```

FIG. 87 mtFATP coding only DNA

```
         10        20        30        40
GTGTCCGATTACTACGGCGGCGCACACAACGGTCAGGC  40
TGATCGACCTGGCAACTCGGATGCCGCGAGTGTTGGCGGA 80
CACGCCGGTGATTGTGCGTGGGGCAATGACCGGGCTGCTG 120
GCCCGGCCGAATTCCAAGGCGTCGATCGGCACGGTGTTCC 160
AGGACCGGGCCGCTCGCTACGGTGACCGAGTCTTCCTGAA 200
         210       220       230       240
ATTCGGCGATCAGCAGCTGACCTACCGCGACGCTAACGCC 240
ACCGCCAACCGGTACGCCGCGGTGTTGGCCGCCCGCGGCG 280
TCGGCCCCGGCGACGTCGTTGGCATCATGTTGCGTAACTC 320
ACCCAGCACAGTCTTGGCGATGCTGGCCACGGTCAAGTGC 360
GGCGCTATCGCCGGCATGCTCAACTACCACCAGCGCGGCG 400
         410       420       430       440
AGGTGTTGGCGCACAGCCTGGGTCTGCTGGACGCGAAGGT 440
ACTGATCGCAGAGTCCGACTTGGTCAGCGCCGTCGCCGAA 480
TGCGGCGCCTCGCGCGGCCGGGTAGCGGGCGACGTGCTGA 520
CCGTCGAGGACGTGGAGCGATTCGCCACAACGGCGCCCGC 560
CACCAACCCGGCGTCGGCGTCGGCGGTGCAAGCCAAAGAC 600
         610       620       630       640
ACCGCGTTCTACATCTTCACCTCGGGCACCACCGGATTTC 640
CCAAGGCCAGTGTCATGACGCATCATCGGTGGCTGCGGGC 680
GCTGGCCGTCTTCGGAGGGATGGGGCTGCGGCTGAAGGGT 720
TCCGACACGCTCTACAGCTGCCTGCCGCTGTACCACAACA 760
ACGCGTTAACGGTCGCGGTGTCGTCGGTGATCAATTCTGG 800
         810       820       830       840
GGCGACCCTGGCGCTGGGTAAGTCGTTTTCGGCGTCGCGG 840
TTCTGGGATGAGGTGATTGCCAACCGGGCGACGGCGTTCG 880
TCTACATCGGCGAAATCTGCCGTTATCTGCTCAACCAGCC 920
GGCCAAGCCGACCGACCGTGCCCACCAGGTGCGGGTGATC 960
TGCGGTAACGGGCTGCGGCCGGAGATCTGGGATGAGTTCA 1000
         1010      1020      1030      1040
CCACCCGCTTCGGGGTCGCGCGGGTGTGCGAGTTCTACGC 1040
CGCCAGCGAAGGCAACTCGGCCTTTATCAACATCTTCAAC 1080
GTGCCCAGGACCGCCGGGGTATCGCCGATGCCGCTTGCCT 1120
TTGTGGAATACGACCTGGACACCGGCGATCCGCTGCGGGA 1160
TGCGAGCGGGCGAGTGCGTCGGGTACCCGACGGTGAACCC 1200
```

FIG. 88A

```
       1210       1220       1230       1240
    ╷┄┄┄┄┼┄┄┄┄┄┼┄┄┄┄┄┼┄┄┄┄┄┼┄┄┄┄┄┼┄┄┄┄┄┼
    GGCCTGTTGCTTAGCCGGGTCAACCGGCTGCAGCCGTTCG  1240
    ACGGCTACACCGACCCGGTTGCCAGCGAAAAGAAGTTGGT  1280
    GCGCAACGCTTTTCGAGATGGCGACTGTTGGTTCAACACC  1320
    GGTGACGTGATGAGCCCGCAGGGCATGGGCCATGCCGCCT  1360
    TCGTCGATCGGCTGGGCGACACCTTCCGCTGGAAGGGCGA  1400
       1410       1420       1430       1440
    ╷┄┄┄┄┼┄┄┄┄┄┼┄┄┄┄┄┼┄┄┄┄┄┼┄┄┄┄┄┼┄┄┄┄┄┼
    GAATGTCGCCACCACTCAGGTCGAAGCGGCACTGGCCTCC  1440
    GACCAGACCGTCGAGGAGTGCACGGTCTACGGCGTCCAGA  1480
    TTCCGCGCACCGGCGGGCGCGCCGGAATGGCCGCGATCAC  1520
    ACTGCGCGCTGGCGCCGAATTCGACGGCCAGGCGCTGGCC  1560
    CGAACGGTTTACGGTCACTTGCCCGGCTATGCACTTCCGC  1600
       1610       1620       1630       1640
    ╷┄┄┄┄┼┄┄┄┄┄┼┄┄┄┄┄┼┄┄┄┄┄┼┄┄┄┄┄┼┄┄┄┄┄┼
    TCTTTGTTCGGGTAGTGGGGTCGCTGGCGCACACCACGAC  1640
    GTTCAAGAGTCGCAAGGTGGAGTTGCGCAACCAGGCCTAT  1680
    GGCGCCGACATCGAGGATCCGCTGTACGTACTGGCCGGCC  1720
    CGGACGAAGGATATGTGCCGTACTACGCCGAATACCCTGA  1760
    GGAGGTTTCGCTCGGAAGGCGACCGCAGGGCTAG        1794
```

FIG. 88B mtFATP coding only protein

```
       10         20         30         40
    ╷┄┄┄┄┼┄┄┄┄┄┼┄┄┄┄┄┼┄┄┄┄┄┼┄┄┄┄┄┼┄┄┄┄┄┼
    MSDYYGGAHTTVRLIDLATRMPRVLADTPVIVRGAMTGLL   40
    ARPNSKASIGTVFQDRAARYGDRVFLKFGDQQLTYRDANA   80
    TANRYAAVLAARGVGPGDVVGIMLRNSPSTVLAMLATVKC  120
    GAIAGMLNYHQRGEVLAHSLGLLDAKVLIAESDLVSAVAE  160
    CGASRGRVAGDVLTVEDVERFATTAPATNPASASAVQAKD  200
       210        220        230        240
    ╷┄┄┄┄┼┄┄┄┄┄┼┄┄┄┄┄┼┄┄┄┄┄┼┄┄┄┄┄┼┄┄┄┄┄┼
    TAFYIFTSGTTGFPKASVMTHHRWLRALAVFGGMGLRLKG  240
    SDTLYSCLPLYHNNALTVAVSSVINSGATLALGKSFSASR  280
    FWDEVIANRATAFVYIGEICRYLLNQPAKPTDRAHQVRVI  320
    CGNGLRPEIWDEFTTRFGVARVCEFYAASEGNSAFINIFN  360
    VPRTAGVSPMPLAFVEYDLDTGDPLRDASGRVRRVPDGEP  400
       410        420        430        440
    ╷┄┄┄┄┼┄┄┄┄┄┼┄┄┄┄┄┼┄┄┄┄┄┼┄┄┄┄┄┼┄┄┄┄┄┼
    GLLLSRVNRLQPFDGYTDPVASEKKLVRNAFRDGCWFNT  440
    GDVMSPQGMGHAAFVDRLGDTFRWKGENVATTQVEAALAS  480
    DQTVEECTVYGVQIPRTGGRAGMAAITLRAGAEFDGQALA  520
    RTVYGHLPGYALPLFVRVVGSLAHTTTFKSRKVELRNQAY  560
    GADIEDPLYVLAGPDEGYVPYYAEYPEEVSLGRRPQG    597
```

FIG. 89

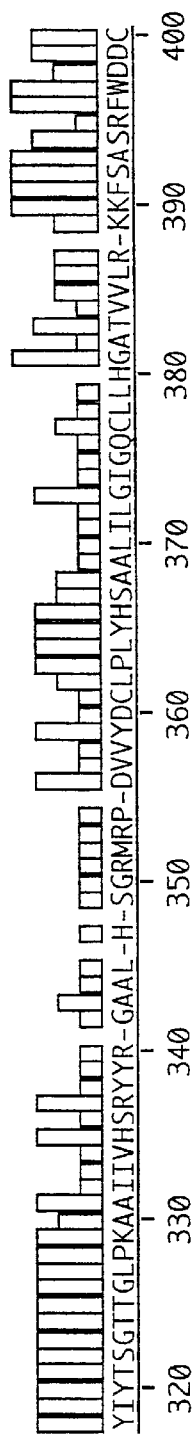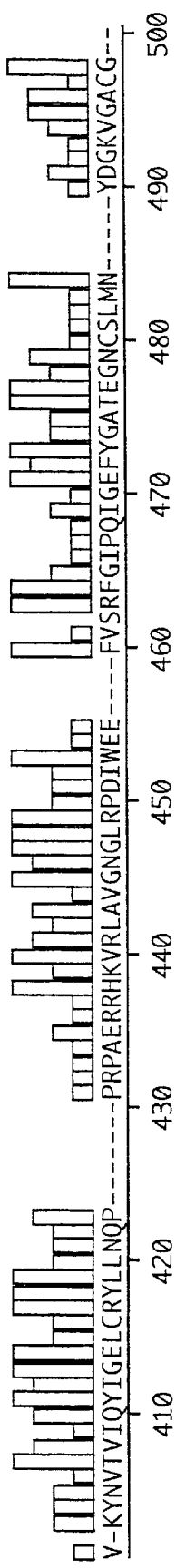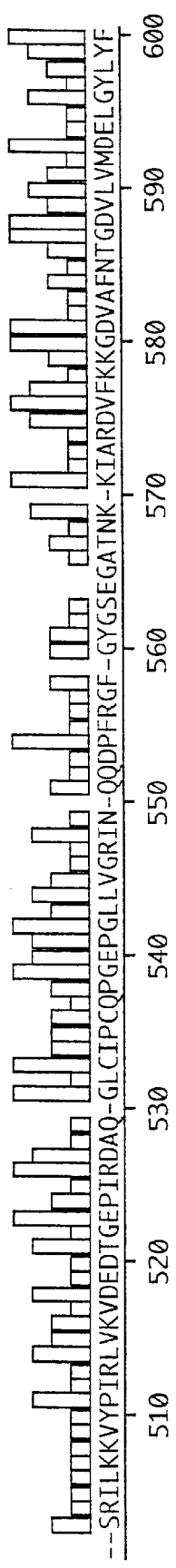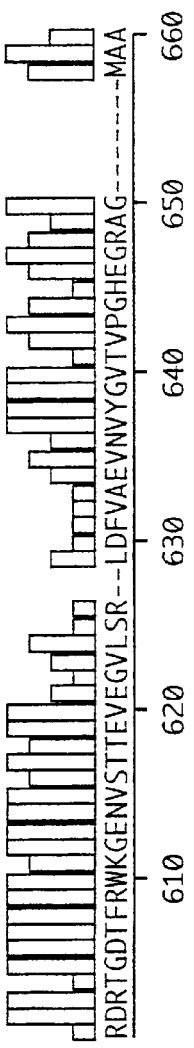
FIG. 90 hsFATP3

```
1     cga ccc acg cgt ccg ggg atg ttt gcg agc
1                                 M   F   A   S 31    ggc tgg aac cag acg gtg ccg ata gag gaa
5      G   W   N   Q   T   V   P   I   E   E 61    gcg ggc tcc atg gct gcc ctc ctg ctg ctg
15     A   G   S   M   A   A   L   L   L   L 91    ccc ctg ctg ctg ttg cta ccg ctg ctg ctg
25     P   L   L   L   L   L   P   L   L   L 121   ctg ctg aag cta cac ctc tgg ccg cag ttg
35     L   L   K   L   H   L   W   P   Q   L 151   cgc tgg ctt ccg gcg gac ttg gcc ttt gcg
45     R   W   L   P   A   D   L   A   F   A 181   gtg cga gct ctg tgc tgc aaa agg gct ctt
55     V   R   A   L   C   C   K   R   A   L 211   cga gct cgc gcc ctg gcc gcg gct gcc gcc
65     R   A   R   A   L   A   A   A   A   A 241   gac ccg gaa ggt ccc gag ggg ggc tgc agc
75     D   P   E   G   P   E   G   G   C   S
```

FIG. 94A

```
271   ctg gcc tgg cgc ctc gcg gaa ctg gcc cag
85     L   A   W   R   L   A   E   L   A   Q 301   cag cgc gcc gcg cac acc ttt ctc att cac
95     Q   R   A   A   H   T   F   L   I   H 331   ggc tcg cgg cgc ttt agc tac tca gag gcg
105    G   S   R   R   F   S   Y   S   E   A 361   gag cgc gag agt aac agg gct gca cgc gcc
115    E   R   E   S   N   R   A   A   R   A 391   ttc cta cgt gcg cta ggc tgg gac tgg gga
125    F   L   R   A   L   G   W   D   W   G
```

FIG. 94B

```
421   ccc gac ggc ggc gac agc ggc gag ggg agc
135    P   D   G   G   D   S   G   E   G   S 451   gct gga gaa ggc gag cgg gca gcg ccg gga
145    A   G   E   G   E   R   A   A   P   G 481   gcc gga gat gca gcg gcc gga agc ggc gcg
155    A   G   D   A   A   A   G   S   G   A 521   gag ttt gcc gga ggg gac ggt gcc gcc aga
165    E   F   A   G   G   D   G   A   A   R 541   ggt gga gga gag ccc gcc gcc cct ctg tca
175    G   G   G   E   P   A   A   P   L   S 571   cct gga gca act gtg gcg ctg ctc ctc ccc
185    P   G   A   T   V   A   L   L   L   P 601   gct ggc cca gag ttt ctg tgg ctc tgg ttc
195    A   G   P   E   F   L   W   L   W   F
```

FIG. 94C

```
631     ggg ctg gcc aag gcc ggc ctg cgc act gcc
205      G   L   A   K   A   G   L   R   T   A 661     ttt gtg ccc acc gcc ctg cgc cgg ggc ccc
215      F   V   P   T   A   L   R   R   G   P 691     ctg ctg cac tgc ctc cgc agc tgc ggc gcg
225      L   L   H   C   L   R   S   C   G   A 721     cgc gcg ctg gtg ctg gcg cca gag ttt ctg
235      R   A   L   V   L   A   P   E   F   L 751     gag tcc ctg gag ccg gac ctg ccc gcc ctg
245      E   S   L   E   P   D   L   P   A   L 781     aga gcc atg ggg ctc cac ctg tgg gct gca
255      R   A   M   G   L   H   L   W   A   A 811     ggc cca gga acc cac cct gct gga att agc
265      G   P   G   T   H   P   A   G   I   S 841     gat ttg ctg gct gaa gtg tcc gct gaa gtg
275      D   L   L   A   E   V   S   A   E   V
```

FIG. 94D

| | | | | | | | | | | |
|---|---|---|---|---|---|---|---|---|---|---|
| 871 | | gat | ggg | cca | gtg | cca | gga | tac | ctc | tct | tcc |
| 285 | | D | G | P | V | P | G | Y | L | S | S |
| 901 | | ccc | cag | agc | ata | aca | gac | acg | tgc | ctg | tac |
| 295 | | P | Q | S | I | T | D | T | C | L | Y |
| 931 | | atc | ttc | acc | tct | ggc | acc | acg | ggc | ctc | ccc |
| 305 | | I | F | T | S | G | T | T | G | L | P |
| 961 | | aag | gct | gct | cgg | atc | agt | cat | ctg | aag | atc |
| 315 | | K | A | A | R | I | S | H | L | K | I |
| 991 | | ctg | caa | tgc | cag | ggc | ttc | tat | cag | ctg | tgt |
| 325 | | L | Q | C | Q | G | F | Y | Q | L | C |
| 1021 | | ggt | gtc | cac | cag | gaa | gat | gtg | atc | tac | ctc |
| 335 | | G | V | H | Q | E | D | V | I | Y | L |

FIG. 94E

```
1051    gcc  ctc  cca  ctc  tac  cac  atg  tcc  ggt  tcc
345      A    L    P    L    Y    H    M    S    G    S 1081    ctg  ctg  ggc  atc  gtg  ggc  tgc  atg  ggc  att
355      L    L    G    I    V    G    C    M    G    I 1111    ggg  gcc  aca  gtg  gtg  ctg  aaa  tcc  aag  ttc
365      G    A    T    V    V    L    K    S    K    F 1141    tcg  gct  ggt  cag  ttc  tgg  gaa  gat  tgc  cag
375      S    A    G    Q    F    W    E    D    C    Q 1171    cag  cac  agg  gtg  acg  gtg  ttc  cag  tac  att
385      Q    H    R    V    T    V    F    Q    Y    I 1201    ggg  gag  ctg  tgc  cga  tac  ctt  gtc  aac  cag
395      G    E    L    C    R    Y    L    V    N    Q 1231    ccc  ccg  agc  aag  gca  gaa  cgt  ggc  cat  aag
405      P    P    S    K    A    E    R    G    H    K 1261    gtc  cgg  ctg  gca  gtg  ggc  agc  ggg  ctg  cgc
415      V    R    L    A    V    G    S    G    L    R
```

FIG. 94F

```
1291    cca gat acc tgg gag cgt ttt gtg cgg cgc
425      P   D   T   W   E   R   F   V   R   R 1321    ttc ggg ccc ctg cag gtg ctg gag aca tat
435      F   G   P   L   Q   V   L   E   T   Y 1351    gga ctg aca gag ggc aac gtg gcc acc atc
445      G   L   T   E   G   N   V   A   T   I 1381    aac tac aca gga cag cgg ggc gct gtg ggg
455      N   Y   T   G   Q   R   G   A   V   G 1411    cgt gct tcc tgg ctt tac aag cat atc ttc
465      R   A   S   W   L   Y   K   H   I   F 1441    ccc ttc tcc ttg att cgc tat gat gtc acc
475      P   F   S   L   I   R   Y   D   V   T 1471    aca gga gag cca att cgg gac ccc cag ggg
485      T   G   E   P   I   R   D   P   Q   G 1501    cac tgt atg gcc aca tct cca ggt gag cca
495      H   C   M   A   T   S   P   G   E   P 1531    ggg ctg ctg gtg gcc ccg gta agc cag cag
505      G   L   L   V   A   P   V   S   Q   Q
```

FIG. 94G

```
1561    tcc cca ttc ctg ggc tat gct ggc ggg cca
515      S   P   F   L   G   Y   A   G   G   P 1591    gag ctg gcc cag ggg aag ttg cta aag gat
525      E   L   A   Q   G   K   L   L   K   D 1621    gtc ttc cgg cct ggg gat gtt ttc ttc aac
535      V   F   R   P   G   D   V   F   F   N 1651    act ggg gac ctg ctg gtc tgc gat gac caa
545      T   G   D   L   L   V   C   D   D   Q 1681    ggt ttt ctc cgc ttc cat gat cgt act gga
555      G   F   L   R   F   H   D   R   T   G 1711    gac acc ttc agg tgg aag ggg gag aat gtg
565      D   T   F   R   W   K   G   E   N   V 1741    gcc aca acc gag gtg gca gag gtc ttc gag
575      A   T   T   E   V   A   E   V   F   E
```

FIG. 94H

| | | | | | | | | | |
|---|---|---|---|---|---|---|---|---|---|
| 1741 | gcc | aca | acc | gag | gtg | gca | gag | gtc | ttc | gag |
| 575 | A | T | T | E | V | A | E | V | F | E |
| 1771 | gcc | cta | gat | ttt | ctt | cag | gag | gtg | aac | gtc |
| 585 | A | L | D | F | L | Q | E | V | N | V |
| 1801 | tat | gga | gtc | act | gtg | cca | ggg | cat | gaa | ggc |
| 595 | Y | G | V | T | V | P | G | H | E | G |
| 1831 | agg | gct | gga | atg | gca | gcc | cta | gtt | ctg | cgt |
| 605 | R | A | G | M | A | A | L | V | L | R |
| 1861 | ccc | ccc | cac | gct | ttg | gac | ctt | atg | cag | ctc |
| 615 | P | P | H | A | L | D | L | M | Q | L |
| 1891 | tac | acc | cac | gtg | tct | gag | aac | ttg | cca | cct |
| 625 | Y | T | H | V | S | E | N | L | P | P |
| 1921 | tat | gcc | cgg | ccc | cga | ttc | ctc | agg | ctc | cag |
| 635 | Y | A | R | P | R | F | L | R | L | Q |

FIG. 94I

```
1951    gag  tct  ttg  gcc  acc  aca  gag  acc  ttc  aaa
645      E    S    L    A    T    T    E    T    F    K 1981    cag  cag  aaa  gtt  cgg  atg  gca  aat  gag  ggc
655      Q    Q    K    V    R    M    A    N    E    G 2011    ttc  gac  ccc  agc  acc  ctg  tct  gac  cca  ctg
665      F    D    P    S    T    L    S    D    P    L 2041    tac  gtt  ctg  gac  cag  gct  gta  ggt  gcc  tac
675      Y    V    L    D    Q    A    V    G    A    Y 2071    ctg  ccc  ctc  aca  act  gcc  cgg  tac  agc  gcc
685      L    P    L    T    T    A    R    Y    S    A 2101    ctc  ctg  gca  gga  aac  ctt  cga  atc  tga  gaa
695      L    L    A    G    N    L    R    I    *

2131    ctt  cca  cac  ctg  agg  cac  ctg  aga  gag  gaa
2161    ctc  tgt
```

FIG. 94J

POLYNUCLEOTIDES ENCODING FATTY ACID TRANSPORT PROTEINS

RELATED APPLICATIONS

This application claims the benefit of U.S. Provisional Application Number 60/071,374 entitled "Identification of a Family of Fatty Acid Transporters Conserved From Mycobacterium to Man," by Andreas Stahl, David Hirsch and Harvey F. Lodish, filed on Jan. 15, 1998; U.S. Provisional Application Number 60/093,491 entitled "Fatty Acid Transport Proteins," by Andreas Stahl, David J. Hirsch, Harvey F. Lodish, Ruth E. Gimeno and Louis A. Tartaglia, filed on Jul. 20, 1998; and U.S. Provisional Application Number 60/110,941 entitled "Fatty Acid Transport Proteins," by Andreas Stahl, David J. Hirsch, Harvey F. Lodish, Ruth E. Gimeno and Louis A. Tartaglia, filed on Dec. 4, 1998. The teachings of each of these referenced applications are incorporated herein by reference in their entirety.

GOVERNMENT SUPPORT

The invention was supported, in whole or in part, by National Institutes of Health Grant DK 47618 and National Institutes of Health Grant 5 T32 CA 09541. The United States Government has certain rights in the invention.

BACKGROUND OF THE INVENTION

Long chain fatty acids (LCFAs) are an important source of energy for most organisms. They also function as blood hormones, regulating key metabolic functions such as hepatic glucose production. Although LCFAs can diffuse through the hydrophobic core of the plasma membrane into cells, this nonspecific transport cannot account for the high affinity and specific transport of LCFAs exhibited by cells such as cardiac muscle, hepatocytes, enterocytes, and adipocytes. The molecular mechanisms of LCFA transport remains largely unknown. Identifying these mechanisms can lead to pharmaceuticals that modulate fatty acid uptake by the intestine and by other organs, thereby alleviating certain medical conditions (e.g. obesity).

SUMMARY OF THE INVENTION

Described herein is a diverse family of fatty acid transport proteins (FATPs) which are evolutionarily conserved; these FATPs are plasma membrane proteins which mediate transport of LCFAs across the membranes and into cells. Members of the FATP family described herein are present in a wide variety of organisms, from mycobacteria to humans, and exhibit very different expression patterns in tissues among the organisms. FATP family members are expressed in prokaryotic and eukaryotic organisms and comprise characteristic amino acid domains or sequences which are highly conserved across family members. In addition, the function of the FATP gene family is conserved throughout evolution, as shown by the fact that the *Caenorhabditis* (*C.*) *elegans* and mycobacterial FATPs described herein facilitate LCFA uptake when they are overexpressed in COS cells or *Escherichia* (*E.*) *coli*, respectively. FATPs are expressed in a wide variety of tissues, including all tissues which are important to fatty acid metabolism (uptake and processing).

In specific embodiments, FATPs of the present invention are from such diverse organisms as humans (*Homo* (*H.*) *sapiens*), mice, (*Mus* (*M.*) *musculus*), *F. rubripes, C. elegans, Drosophila* (*D.*) *melanogaster, Saccharomyces* (*S.*) *cerevisiae, Aspergillus nidulans, Cochliobolu heterostrophus, Magnaporthe grisea* and Mycobacterium (*M.*), such as *M. tuberculosis*. As described herein, four novel mouse FATPs, referred to as mmFATP2, mmFATP3, mmFATP4 and mmFATP5, and six human FATPs, referred to as hsFATP1, hsFATP2, hsFATP3, hsFATP4, hsFATP5 and hsFATP6, have been identified. All four novel murine FATPs (mmFATP2–5) and a previously identified murine FATP (renamed herein FATP1) have orthologs in humans (hsFATP1–5); the sixth human FATP (hsFATP6) does not as yet have a mouse ortholog. The expression patterns of these FATPs vary, as described in detail below.

The present invention relates to FATP family members from prokaryotes and eukaryotes, nucleic acids (DNA, RNA) encoding FATPs, and nucleic acids which are useful as probes or primers (e.g., for use in hybridization methods, amplification methods) for example, in methods of detecting FATP-encoding genes, producing FATPs, and purifying or isolating FATP-encoding DNA or RNA. Also the subject of this invention are antibodies (polyclonal or monoclonal) which bind an FATP or FATPs; methods of identifying additional FATP family members (for example, orthologs of those FATPs described herein by amino acid sequence) and variant alleles of known FATP genes; methods of identifying compounds which bind to an FATP, or modulate or alter (enhance or inhibit) FATP function; compounds which modulate or alter FATP function; methods of modulating or altering (enhancing or inhibiting) FATP function and, thus, LCFA uptake into tissues of a mammal (e.g. human) by administering a compound or molecule (a drug or agent) which increases or reduces FATP activity; and methods of targeting compounds to tissues by administering a complex of the compound to be targeted to tissues and a component which is bound by an FATP present on cells of the tissues to which the compound is to be targeted. For example, a complex of a drug to be delivered to the liver and a component which is bound by an FATP present on liver cells (e.g., FATP5) can be administered.

In one embodiment, the present invention relates to modulating or altering (enhancing or inhibiting/reducing) LCFA uptake in the small intestine and, thus, increasing or reducing the number of calories in the form of fats available to an individual. In another embodiment, the present invention relates to inhibiting or reducing LCFA uptake in the small intestine in order to reduce circulating fatty acid levels; that is, LCFA uptake in the small intestine is reduced and, therefore, circulating (blood) levels are not as high as they otherwise would be. FATP4 has been shown to be expressed in epithelial cells of the small intestine and particularly in the brush border layer of the small intestine. FATP2 has also been shown to be expressed at low levels in epithelial cells of the small intestine, particularly in the duodenum. In contrast, FATP1, FATP3, FATP5 and FATP6 were not detected in any of the intestinal tissues. Thus, also described herein are FATPs which are present in the epithelial cell layer of the small intestine where they mediate LCFA uptake. These FATPs, particularly FATP4 and also FATP2, are targets for methods and drugs which block their function or activity and are useful in treating obesity, diabetes and heart disease. The ability of these FATPs to mediate fat uptake can be modulated or altered (enhanced or inhibited), thus modulating fat uptake in the small intestine. This can be done, for example, by administering to an individual, such as a human or other animal, a drug which blocks interaction of LCFAs with FATP4 and/or FATP2 in the small intestine, thus inhibiting LCFA passage into the cells of the small intestine. As a result, fat absorption is reduced and, although the individual has consumed a certain quantity of fat, the LCFAs are not absorbed to the same extent they would have been in the absence of the compound administered.

Thus, one embodiment of this invention is a method of reducing LCFA uptake (absorption) in the small intestine and, as a result, reducing caloric uptake in the form of fat. A further embodiment is a compound (drug) useful in inhibiting or reducing fat absorption in the small intestine. In another embodiment, the invention is a method of reducing circulating fatty acid levels by administering to an individual a compound which blocks interactions of LCFAs with FATP4 and/or FATP2 in the small intestine, thus inhibiting LCFA passage into cells of the small intestine. As a result, fatty acids pass into the circulatory system at a diminished level and/or rate, and circulating fatty acid levels are lower than they would be in the absence of the compound administered. This method is particularly useful for therapy in individuals who are at risk for or have hyperlipidemia. That is, it can be used to prevent the occurrence of elevated levels of lipids in the blood or to treat an individual in whom blood lipid levels are elevated. Also the subject of this invention is a method of identifying compounds which alter FATP function (and thus, in the case of FATP2 and/or FATP4, alter LCFA uptake in the small intestine).

In another embodiment, the present invention relates to a method of modulating or altering (enhancing or inhibiting) the function of FATP6, which is expressed at high levels in the heart. A method of inhibiting FATP6 function is useful, for example, in individuals with heart disease, such as ischemia, since reducing LCFA uptake into heart muscle in an individual who has ischemic heart disease, which may be manifested by, for example, angina or heart attack, can reduce symptoms or reduce the extent of damage caused by the ischemia. In this embodiment, a drug which inhibits FATP6 function is administered to an individual who has had or is having a heart attack, to reduce LCFA uptake by the individual's heart and, as a result, reduce the damage caused by ischemia. In a further embodiment, this invention is a method of targeting a compound, such as a therapeutic drug or an imaging reagent, to heart tissue by administering to an individual (e.g., a human) a complex of the compound and a component (e.g., a LCFA or LCFA-like compound) which is bound by an FATP (e.g., FATP6) present in cells of heart tissue.

In a further embodiment, LCFA uptake by the liver is modulated or altered (enhanced or reduced), in an individual. For example, a drug which inhibits the function of an FATP present in liver (e.g., FATP5) is administered to an individual who is diabetic, in order to reduce LCFA uptake by liver cells and, thus reduce insulin resistance.

The present invention, thus, provides methods which are useful to alter, particularly reduce, LCFA uptake in individuals and, as a result, to alter (particularly reduce), availability of the LCFAs for further metabolism. In a specific embodiment, the present invention provides methods useful to reduce LCFA uptake and, thus, fatty acid metabolism in individuals, with the result that caloric availability from fats is reduced, and circulating fatty acid levels are lower than they otherwise would be. These methods are useful, for example, as a means of weight control in individuals, (e.g., humans) and as a means of preventing elevated serum lipid levels or reducing serum lipid levels in humans. FATPs expressed in the small intestine, such as FATP4, are useful targets to be blocked in treating obesity (e.g., chronic obesity) or to be enhanced in treating conditions in which enhanced LCFA uptake is desired (e.g., malabsorption syndrome or other wasting conditions).

The identification of this evolutionarily conserved fatty acid transporter family will allow a better understanding of the mechanisms whereby LCFAs traverse the lipid bilayer as well as yield insight into the control of energy homeostasis and its dysregulation in diseases such as diabetes and obesity.

BRIEF DESCRIPTION OF THE DRAWINGS

FIGS. 1A–1S shows the amino acid sequence alignment of FATPs: mmFATP1 (SEQ ID NO:92), mmFATP2 (SEQ ID NO:93), mmFATP3 (SEQ ID NO:94), mmFATP4 (SEQ ID NO:95), mmFATP5 (SEQ ID NO:96), ceFATPa (SEQ ID NO:97), scFATP (SEQ ID NO:98) and mtFATP (SEQ ID NO:99). The underlining (amino acid residues 204–212 of mtFATP) indicates an AMP binding motif which is found in many classes of proteins; the underlining at amino acid residues 204–507 of the mtFATP sequence indicates the FATP 360 amino acid signature sequence.

FIGS. 2A–2D: COS cells were cotransfected using the DEAE-dextran method with the mammalian expression vectors pCDNA-CD2 either alone (control; FIG. 2A) or in combination with one of the FATP-containing expression vectors (pCDNA-mmFATP1, FIG. 2B; pCDNA-mmFATP2, FIG. 2C; or pCMV-SPORT2-mmFATP5, FIG. 2D) as described in Materials and Methods for Example 2. COS cells were gated on forward scatter (FSC) and side scatter (SS), and the results shown represent >10,000 cells. Cells exhibiting >300 CD2 fluorescence units (vertical line) representing 15% of all cells were deemed CD2 positive.

FIG. 7 shows the sequence identity among the FATP family members and VLACs, based on the 360 amino acid signature sequence of FATP from FIG. 1.

FIGS. 8A and 8B are the mmFATP3 DNA sequence (SEQ ID NO:6).

FIG. 9 is the mmFATP3 protein sequence (SEQ ID NO:7).

FIGS. 10A and 10B are the mm FATP4 DNA sequence (SEQ ID NO:8).

FIG. 11 is the mmFATP4 protein sequence (SEQ ID NO:9).

FIGS. 12A and 12B are the mmFATP5 DNA sequence (SEQ ID NO:10).

FIG. 13 is the mmFATP5 protein sequence (SEQ ID NO:11).

FIGS. 14A and 14B are the hsFATP2 DNA sequence (SEQ ID NO:12).

FIG. 15 is the hsFATP2 protein sequence (SEQ ID NO:13).

FIGS. 16A and 16B are the hsFATP3 DNA sequence (SEQ ID NO:14).

FIG. 17 is the hsFATP3 protein sequence (SEQ ID NO:15).

FIGS. 18A and 18B are the hsFATP4 DNA sequence (SEQ ID NO:16).

FIG. 19 is the hsFATP4 protein sequence (SEQ ID NO:17).

FIGS. 20A and 20B are the hsFATP5 DNA sequence (SEQ ID NO:18).

FIG. 21 is the hsFATP5 protein sequence (SEQ ID NO:19).

FIGS. 22A and 22B are the hsFATP6 DNA sequence (SEQ ID NO:20).

FIG. 23 is the hsFATP6 protein sequence (SEQ ID NO:21).

FIGS. 24A and 24B are the mtFATP DNA sequence (SEQ ID NO:22).

FIG. 25 is the mtFATP protein sequence (SEQ ID NO:23).

FIGS. 26A–26E shows the DNA sequence (SEQ ID NO:24) and predicted amino acid sequence (SEQ ID NO:25) of human FATP1.

FIGS. 27A–27D shows the DNA sequence (SEQ ID NO:26) and predicted amino acid sequence (SEQ ID NO:27) of human FATP4.

FIG. 28B is the amino acid composition of hsFATP1.

FIG. 29B is a listing of the amino acid composition of hsFATP4.

FIGS. 30A–30F show a comparison of the nucleotide sequence of human FATP1 (SEQ ID NO:28) and the nucleotide sequence of mouse FATP1 (SEQ ID NO:29).

FIGS. 31A–31I show a comparison of the nucleotide sequence of human FATP4 (SEQ ID NO:30) and the nucleotide sequence of mouse FATP4 (SEQ ID NO:31).

FIGS. 32A–32C shows a comparison of the amino acid sequence of human FATP1 (SEQ ID NO:32) and the amino acid sequence of mouse FATP1 (SEQ ID NO:33). Shaded amino acid residues match the consensus sequence exactly FIG. 33 shows a comparison at the amino acid level of human FATP (SEQ ID NO:34) and mouse FATP (SEQ ID NO:35). Shaded amino acid residues match the concensus sequence exactly.

FIGS. 34A–34D shows the nucleotide sequence (SEQ ID NO:36) and predicted amino acid sequence (SEQ ID NO:37) of hsFATP6.

FIG. 35B is a listing of the amino acid composition of hsFATP6.

FIGS. 36A–36G shows an alignment of the amino acid sequences of hsFATP1 (SEQ ID NO:38), hsFATP4 (SEQ ID NO:39) and hsFATP6 (SEQ ID NO:40). Shaded amino acid residues match the consensus sequence exactly.

FIGS. 39A–39C are an illustration of the amino acid sequences of human FATP4 (SEQ ID NO:41) and mouse FATP4 (SEQ ID NO:42) compared to human FATP1 (SEQ ID NO:43). Shown by underlining are the FATP consensus sequence (236–556 of hsFATP1) and the AMP-binding motif (246–254 of hsFATP1). The human FATPs were cloned by screening libraries with sequences from ESTs (expressed sequence tags). Mouse FATP4 was cloned by PCR using degenerate primers.

FIGS. 43A–43B show the nucleotide sequence of the gene encoding mouse FATP4 (SEQ ID NO:44).

FIG. 43C shows the amino acid sequence of mouse FATP4 protein (SEQ ID NO:45).

FIGS. 44A–44D show the hsFATP1 DNA sequence (SEQ ID NO:46). Coding region: 175–2115 (1941 nt).

FIG. 45 is the hsFATP1 protein sequence (SEQ ID NO:47).

FIGS. 46A and 46B are the hsFATP2 DNA sequence (SEQ ID NO:48). Coding region: 223–2085 (1863 nt).

FIG. 47 is the hsFATP2 protein sequence (SEQ ID NO:49).

FIG. 48 is the partial DNA sequence of hsFATP3 (SEQ ID NO:50). Coding region: 1–993.

FIG. 49 is the partial protein sequence of hsFATP3 (SEQ ID NO:51).

FIGS. 50A, 50B, and 50C are the hsFATP4 DNA sequence (SEQ ID NO:52). Coding region: 208–2139 (1932 nt).

FIG. 51 is the hsFATP4 protein sequence (SEQ ID NO:53).

FIG. 52 is the hsFATP5 partial DNA sequence (SEQ ID NO:54). Coding region: 1–1062.

FIG. 53 is the hsFATP5 partial protein sequence (SEQ ID NO:55).

FIGS. 54A, 54B, and 54C are the hsFATP6 DNA sequence (SEQ ID NO:56). Coding region: 643–2502 (1860 nt).

FIG. 55 is the hsFATP6 protein sequence (SEQ ID NO:57).

FIGS. 56A, 56B, and 56C are the rnFATP1 DNA sequence (rn=*Rattus norvegicus;* (SEQ ID NO:58). Coding region: 75–2015 (1941 nt).

FIG. 57 is the rnFATP1 protein sequence (SEQ ID NO:59).

FIGS. 58A, 58B, and 58C are the rnFATP2 DNA sequence (SEQ ID NO:60). Coding region: 795–2657 (1863 nt).

FIG. 59 is the rnFATP2 protein sequence (SEQ ID NO:61).

FIGS. 60A and 60B are the rnFATP4 partial DNA sequence (SEQ ID NO:62). Coding region: 1–1218.

FIG. 61 is the rnFATP4 partial DNA sequence (SEQ ID NO:63).

FIGS. 62A, 62B, and 62C are the mmFATP1 DNA sequence (SEQ ID NO:64). Coding region: 1–1944.

FIG. 63 is the mmFATP1 protein sequence (SEQ ID NO:65).

FIGS. 64A and 64B are the mmFATP2 DNA sequence (SEQ ID NO:66). Coding region: 121–1992 (1872 nt).

FIG. 65 is the mmFATP2 protein sequence (SEQ ID NO:67).

FIGS. 66A and 66B are the mmFATP3 partial DNA sequence (SEQ ID NO:68). Coding region: 1–1830.

FIG. 67 is the mmFATP3 partial protein sequence (SEQ ID NO:69).

FIGS. 68A, 68B, and 68C are the mmFATP4 DNA sequence (SEQ ID NO:70). Coding region: 1–1932.

FIGS. 69 is the mmFATP4 protein sequence (SEQ ID NO:71).

FIGS. 70A and 70B are the mmFATP5 DNA sequence (SEQ ID NO:72). Coding region: 60–2129.

FIG. 71 is the mmFATP5 protein sequence (SEQ ID NO:73).

FIGS. 72A and 72B are the dmFATP partial DNA sequence (dm=*Drosophila melanogaster;* SEQ ID NO:74). Coding region: 1–1773.

FIGS. 73 is the dmFATP partial protein sequence (SEQ ID NO:75).

FIG. 74 is the drFATP partial DNA sequence (dr=*Danio rerio,* zebrafish; SEQ ID NO:76) Coding region: 1–173.

FIG. 75 is the drFATP partial protein sequence (SEQ ID NO:77).

FIG. 76A and 76B are the ceFATPa DNA sequence (SEQ ID NO:78). Coding region: 1–1953.

FIG. 77 is the ceFATPa protein sequence (SEQ ID NO:79).

FIGS. 78A and 78B are the ceFATPb DNA sequence (SEQ ID NO:80). Coding region: 1–1968.

FIG. 79 is the ceFATPb protein sequence (SEQ ID NO:81).

FIGS. 80A and 80B are the chFATP DNA sequence (SEQ ID NO:82; ch=*Cochliobolu heterostrophus*). Coding region: 1–1932.

FIG. 81 is the chFATP protein sequence (SEQ ID NO:83).

FIG. 82 is the anFATP partial protein sequence (an=*Aspergillus nidulans;* SEQ ID NO:84). Coding region: 1–597.

FIG. 83 is the anFATP partial protein sequence (SEQ ID NO:85).

FIG. 84 is the mgFATP partial DNA sequence (mg=*Magnaporthe grisea,* rice blast; SEQ ID NO:86). Coding region: 1–522.

FIG. 85 is the mgFATP partial protein sequence (SEQ ID NO:87).

FIGS. 86A and 86B are the scFATP DNA sequence (SEQ ID NO:88). Coding region: 1–1872.

FIG. 87 is the scFATP protein sequence (SEQ ID NO:89).

FIGS. 88A and 88B are the mtFATP DNA sequence (SEQ ID NO:90).

FIG. 89 is the mtFATP protein sequence (SEQ ID NO:91). Coding region: 1–1794.

FIG. 90 is a concensus sequence of the FATP signature sequence (SEQ ID NO: 100), based on 23 independent sequences aligned in ClustalX. The height of the bar at each amino acid residue position indicates the degree of conservation at that position. Gaps have been inserted to maintain the strength of the alignment.

FIGS. 94A–94J are a representation of the DNA sequence (SEQ ID NO:101) of the 3 gene, and the amino acid sequence (SEQ ID NO:102) of the 3 protein.

DETAILED DESCRIPTION OF THE INVENTION

Figure 2A:
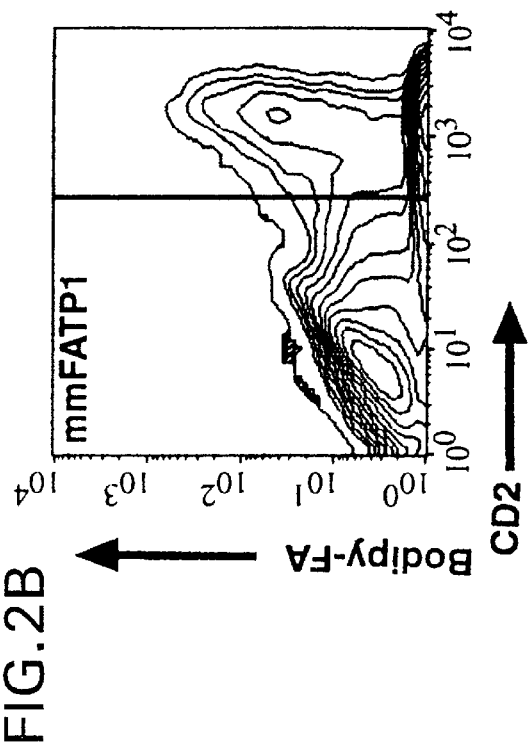
FIGS. 2A–2D show results of LCFA uptake assays.
Figure 2C:
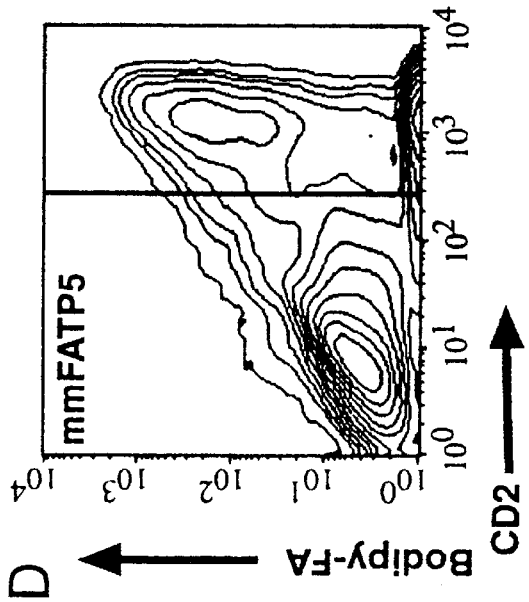
Figure 2B:
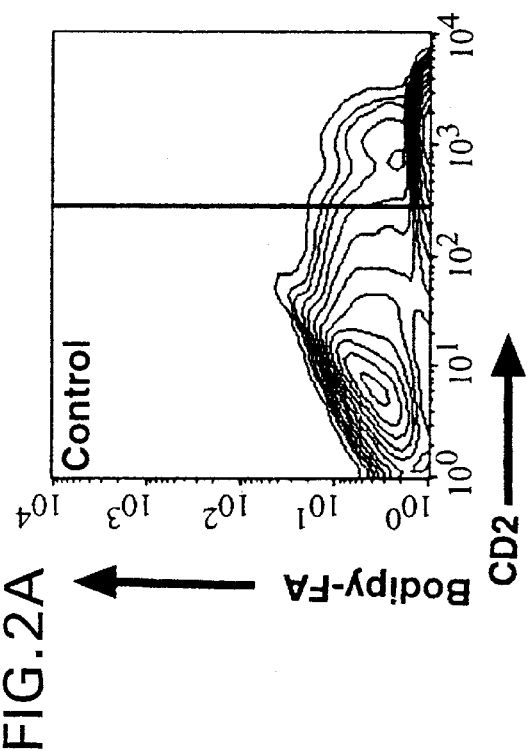
Figure 2D:
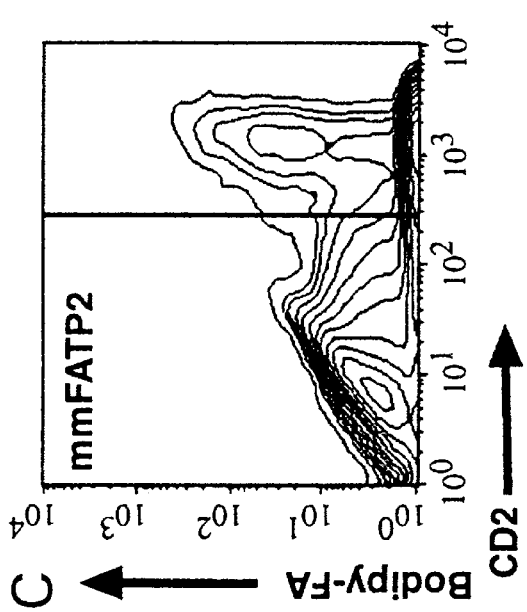

As described herein, FATPs are a large evolutionarily conserved family of proteins that mediate the transport of LCFAs into cells. The family includes proteins which are conserved from mycobacteria to humans and exhibit very different expression patterns in tissues. Specific embodiments described include FATPs from mice, humans, nematodes, fungi and mycobacteria which have been shown to be functional LCFA transporters. The term "fatty acid transport proteins" ("FATPs") as used herein, refers to the proteins described herein as FATP1, FATP2, FATP3, FATP4, FATP5 and FATP6, which have been described in one or more species of mammals, as well as mtFATP, ceFATP, scFATP, anFATP, mgFATP, and chFATP, and other proteins sharing at least about 50% amino acid sequence similarity, preferably at least about 60% sequence similarity, more preferably at least about 70% sequence similarity, and still more preferably, at least about 80% sequence similarity, and most preferably, at least about 90% sequence similarity in the approximately 360 amino acid signature sequence. The approximately 360 amino acid FATP signature sequence is shown in FIG. 1. The concensus sequence of the signature sequence is shown in FIG. 90. The nomenclature used herein to refer to FATPs includes a species-specific prefix (e.g., mm, *Mus musculus;* hs or h, *Homo sapiens* or human; mt *M. tuberculosis;* dm. *D. melanogaster;* ce, *C. elegans;* sc, *Saccharomyces cerevisiae*) and a number such that mammalian homologues in different species share the same number. For example, six human and five mouse FATP genes which are expressed in a variety of tissues are described herein and are referred to, respectively, as hsFATP1-hsFATP6 and mmFATP1-mmFATP5; for example, hsFATP4 and mmFATP4 are the human and mouse orthologs.

Expression patterns of human and mouse FATPs have been assessed and are described below. Briefly, results of these assessments show that FATP5 is a liver-specific gene. FATP2 is highly expressed in liver and kidney. Both of these proteins, as well as FATP4 and FATPs from nematodes and mycobacteria, have been shown to be functional LCFA transporters. Results have also shown that FATP4 mRNA is present at high levels in epithelial cells of two regions of the small intestine (the jejunum and ileum) and at lower, but significant, levels in a third region (the duodenum). They further showed that FATP2 mRNA is present in epithelial cells of the duodenum at a level similar to that of FATP4 mRNA levels, but is present at lower levels in the jejunum and ileum. FATP4 mRNA was absent from other cell types of the small intestine and no FATP4 mRNA could be detected in any cells of the colon. No signals above background could be detected for FATP1, FATP3 and FATP5 in any of the intestinal tissues. Thus, FATP4 is the major FATP in the mouse small intestine, which supports a major role for FATP4 (along with FATP2 to a lesser extent) in absorption of free fatty acids. hsFATP4 was clearly expressed in the jejunum and ileum; expression was absent in the stomach. This, too, is consistent with a major role for FATP4 in absorption of fatty acids in the human gut. Analysis of FATP expression in human tissues, also described in detail below, showed that hsFATP6, which has no mouse ortholog as yet, is expressed at high levels in the heart and at low levels in the placenta, but is undetectable in the other tissues assessed (Example 9). This is consistent with a major role for FATP6 in absorption of fatty acids in the heart.

Long chain fatty acids (LCFAs) are an important energy source for pro- and eukaryotes and are involved in diverse cellular processes, such as membrane synthesis, intracellular signaling, protein modification, and transcriptional regulation. In developed Western countries, human dietary lipids are mainly di- and triglycerides and account for approximately 40% of caloric intake (Weisburger, J. H. (1997) *J. Am. Diet. Assoc.* 97:S16–S23). These lipids are broken down into fatty acids and glycerol by pancreatic lipases in the small intestine (Chapus, C., Rovery, M., Sarda, L & Verger, R. (1988) *Biochimie* 70:1223–34); LCFAs are then transported into brush border cells, where the majority is re-esterified and secreted into the lymphatic system as chylomicrons (Green, P. H. & Riley, J. W. (1981) *Aust. N.Z.J. Med.* 11:84–90). Fatty acids are liberated from lipoproteins by the enzyme lipoprotein lipase, which is bound to the luminal side of endothelial cells (Scow, R. O. & Blachette-Mackie, E. J. (1992) *Mol. Cell. Biochem* 116:181–191). "Free" fatty acids in the circulation are bound to serum albumin (Spector, A. A. (1984) *Clin. Physiol. Biochem* 2:123–134) and are rapidly incorporated by adipocytes, hepatocytes, and cardiac muscle cells. The latter derive 60–90% of their energy through the oxidation of LCFAs (Neely, J. F. Rovetto, M. J. & Oram, J. F. (1972) *Prog. Cardiovasc. Dis:* 15:289–329). Although saturable and specific uptake of LCFAs has been demonstrated for intestinal cells, hepatocytes, cardiac myocytes, and adipocytes, the molecular mechanisms of LCFA transport across the plasma membrane have remained controversial (Hui, T. Y. & Bernlohr, D. A. (1997) *Front. Biosci.* 15:d222–31-d231; Schaffer, J. E. & Lodish, H. F, (1995) *Trends Cardiovasc. Med.* 5:218–224). Described herein is a large family of highly homologous mammalian LCFA transporters which show wide expression, including in all tissues relevant to fatty acid metabolism. Further described are novel members of this family in other species, including mycobacterial and nematode FATPs which, like their mammalian counterparts, are functional fatty acid transporters.

The discovery of a diverse but highly homologous family of FATPs is reminiscent of the glucose transporter family. In a manner similar to the FATPs, the glucose transporters have very divergent patterns of tissue expression (McGowan, K. M., Long, S. D. & Pekala, P. H. (1995) *Pharmacol. Ther.* 66:465–505). The FATPs, like glucose transporters, may also differ in their substrate specificities, uptake kinetics, and hormonal regulation (Thorens, B. (1996) *Am. J. Physiol.* 270:G541–G553). Indeed, the levels of fatty acids in the blood, like those of glucose, can be regulated by insulin and are dysregulated in diseases such as noninsulin-dependent diabetes and obesity (Boden, G. (1997) *Diabetes* 46:3–10). The underlying mechanisms for the regulation of free fatty acid concentrations in the blood are not understood, but could be explained by hormonal modulation of FATPs.

Insulin-resistance is thought to be the major defect in non insulin-dependent diabetes mellitus (NIDDM) and is one of the earliest manifestations of NIDDM (McGarry (1992) *Science* 258:766–770). Free fatty acids (FFAs) may provide an explanation for why obesity is a risk factor for NIDDM. Plasma levels of FFAs are elevated in diabetic patients (Reaven et al. (1988) *Diabetes* 37:1020). Elevated plasma free fatty acids (FFAs) have been demonstrated to induce insulin-resistance in whole animals and humans (Boden (1998) *Front. Biosci.* 3:D169–D175). This insulin-resistance is likely mediated by effects of FFAs on a variety of issues. FFAs added to adipocytes in vitro induce insulin resistance in this cell type as evidenced by inhibition of insulin-induced glucose transport (Van Epps-Fung et al. (1997) *Endocrinology* 138:4338–4345). Rats fed a high fat diet developed skeletal muscle insulin resistance as evidenced by a decrease in insulin-induced glucose uptake by skeletal muscle (Han et al., (1997) *Diabetes* 46:1761–1767). In addition, elevated plasma FFAs increase insulin-suppressed endogenous glucose production in the liver (Boden (1998) *Front. Biosci.* 3:D169–D175), thus increasing hepatic glucose output. It has been postulated that the adverse effects of plasma free fatty acids are due to the FFAs being taken up into the cell, leading to an increase in intracellular long chain fatty acyl CoA; intracellular long chain acyl CoAs are thought to mediate the effects of FFAs inside the cell. Thus, fatty acid induced insulin-resistance may be prevented by blocking uptake of FFAs into select tissues, in particular liver (by blocking FATP2 and/or FATP5), adipocyte (by blocking FATP1), and skeletal muscle (by blocking FATP1). Blocking intestinal fat absorption (by blocking FATP4) is also expected to reduce plasma FFA levels and thus improve insulin resistance.

During the pathogenesis of NIDDM insulin-resistance can initially be counteracted by increasing insulin output by the pancreatic beta cell. Ultimately, this compensation fails, beta cell function decreases and overt diabetes results (McGarry (1992) *Science* 258: 766–770). Manipulating beta cell function is a second point where fatty acid transporter blockers may be beneficial for diabetes. While no FATP homolog has been identified so far that is expressed in the beta cell of the pancreas, the data described below suggest the existence of such a transporter and the sequence information included herein provides the means to identify such a transporter by degenerate PCR, using primers to regions conserved in all FATP family members or by low stringency hybridization. It has been demonstrated that exposure of pancreatic beta-cells to FFAs increases the basal rate of insulin secretion; this in turn leads to a decrease in the intracellular stores of insulin, resulting in decreased capacity for insulin secretion after chronic exposure (Bollheimer et al., (1998) *J. Clin. Invest.* 101:1094–1101). The effects of FFAs are again likely to be mediated by intracellular long chain fatty acyl CoA molecules (Liu et al., (1998) *J. Clin. Invest.* 101:1870–1875). FFAs have also been demonstrated to increase beta cell apoptosis (Shimabukuro et al., (1998) *Proc. Nat. Acad. Sci. USA* 95:2498–2502), possibly contributing to the decrease in beta cell numbers in late stage NIDDM.

Another finding with potentially broad implications is the identification of a FATP homologue in *M. tuberculosis.* Tuberculosis causes more deaths worldwide than any other infectious agent and drug-resistant tuberculosis is re-emerging as a problem in industrialized nations (Bloom, B. R. & Small, P. M. (1998) *N. Engl. J. Med.* 338:677–678). *Mycobacterium tuberculosis* has about 250 enzymes involved in fatty acid metabolism, compared with only about 50 in *E. coli.* It has been suggested that, living as a pathogen, the mycobacteria are largely lipolytic, rather than lipogenic, relying on the lipds within mammalian cells and the tubercle (Cole, S. T. et al., *Nature* 393:537–544 (1998)). The de novo synthesis of fatty acids in *Mycobacterium leprae* is insufficient to maintain growth (Wheeler, P. R., Bulmer, K & Ratledge, C. (1990) *J. Gene. Microbiol.* 136:211–217). Thus, it is reasonable to expect that inhibitors of mtFATP will serve as therapeutics for tuberculosis. FATPs expressed in mycobacteria can be targeted to reduce or prevent replication of mycobacteria (e.g., to reduce or prevent replication of *M. tuberculosis*) and, thus, reduce or prevent their adverse effects. For example, a FATP or FATPs expressed by *M. tuberculosis* can be targeted and inhibited, thus reducing or preventing growth of this pathogen (and tuberculosis in humans and other mammals). An inhibitor of an *M. tuberculosis* FATP can be identified, using methods described herein (e.g., expressing the FATP in an appropriate host cell, such as *E. coli* or COS cells; contacting the cells with an agent or drug to be assessed for its ability to inhibit the FATP and, as a result, mycobacterial growth, and assessing its effects on growth). A drug or agent identified in this manner can be further tested for its ability to inhibit a *M. tuberculosis* FATP and *M. tuberculosis* infection in an appropriate animal model or in humans. A method of inhibiting mycobacterial growth, particularly growth of *M. tuberculosis*, and compounds useful as drugs for doing so are also the subject of this invention.

An isolated polynucleotide encoding mtFATP, like other polynucleotides encoding FATPs of the FATP family, can be incorporated into vectors, nucleic acids of viruses, and other nucleic acid constructs that can be used in various types of host cells to produce mtFATP. This mtFATP can be used, as it appears on the surface of cells, or in various artificial membrane systems, to assess fatty acid transport function, to identify ligands and molecules that are modulators of fatty acid transport activity. Molecules found to be inhibitors of mtFATP function can be incorporated into pharmaceutical compositions to administer to a human for the treatment of tuberculosis.

Particular embodiments of the invention are polynucleotides encoding a FATP of *Cochliobolus* (Helminthosporium) *heterostrophus* or portions or variants thereof, the isolated or recombinantly produced FATP, methods for assessing whether an agent binds to the chFATP, and further methods for assessing the effect of an agent being tested for its ability to modulate fatty acid transport activity. *Cochiobolus heterostrophus* is an ascomycete that is the cause of southern corn leaf blight, an economically important threat to the corn crop in the United States. The related species *C. sativus* causes crown rot and common root rot in wheat and barley. One or more FATPs of *C. heterostrophus* can be targeted for the identification of an inhibitor of chFATP function, which can be then be used as an agent effective against infection of plants by *C. heterostrophus* and related organisms. Methods described herein that were applied in studying the expression of a FATP gene and the function of the FATP in its natural site of expression or in a host cell, can be used in the study of the chFATP gene and protein.

*Magnaporthe grisea* (rice blast) is an economically important fungal pathogen of rice. Further embodiments of the invention are nucleic acid molecules encoding a FATP of *Magnaporthe grisea,* portions thereof, or variants thereof, isolated mgFATP, nucleic acid constructs, and engineered cells expressing mgFATP. Other aspects of the invention are assays to identify an agent which binds to mgFATP and assays to identify an agent which modulates the function of mgFATP in cells in which mgFATP is expressed or in artificial membrane systems. Agents identified as inhibiting mgFATP activity can be developed into anti-fungal agents to be used to treat rice infected with rice blast.

*Caenorhabditis elegans* is a nematode related to plant pathogens and human parasites. An isolated polynucleotide which encodes ceFATP, like other polynucleotides encoding FATPs of the FATP family described herein, can be incorporated into nucleic acid vectors and other constructs that can be used in various types of cells to produce ceFATP. ceFATP as it occurs in cells or as it can be isolated or incorporated into various artificial or reconstructed membrane systems, can be used to assess fatty acid transport, and to identify ligands and agents that modulate fatty acid transport activity. Agents found by such assays to be inhibitors of ceFATP activity can be incorporated into compositions for the treatment of diseases caused by genetically related organisms with a FATP of similar sensitivity to the agents.

*Aspergillus nidulans* is one of a family of fungal species that can infect humans. Further embodiments of the invention of the family of polynucleotides encoding FATPs are polynucleotides encoding a FATP of *Aspergillus nidulans,* and vectors and host cells that can be constructed to comprise such polynucleotides. Further embodiments are a polypeptide encoded by such polynucleotides, portions thereof having one or more functions characteristic of a FATP, and various methods. The methods include those for identifying agents that bind to anFATP and those for assessing the effect of an agent being tested for its ability to modulate fatty acid transport activity. Those agents found to inhibit fatty acid transport function can be used in compositions as anti-fungal pharmaceuticals, or can be modified for greater effectiveness as a pharmaceutical.

One aspect of the invention relates to isolated nucleic acids that encode a FATP as described herein, such as those FATPs having an amino acid sequence in FIG. 45 (SEQ ID NO:47), FIG. 47 (SEQ ID NO:49), FIG. 49 (SEQ ID NO:51), FIG. 51 (SEQ ID NO:53), FIGS. 94A–94J (SEQ ID NO:102), and FIG. 55 (SEQ ID NO:57) and nucleic acids closely related thereto as described herein.

Using the information provided herein, such as a nucleic acid sequence set forth in FIGS. 44A–44D (SEQ ID NO:46), FIGS. 46A–46B (SEQ ID NO:38), FIG. 48 (SEQ ID NO:50), FIGS. 50A–50C (SEQ ID NO:52), FIGS. 94A–94J (SEQ ID NO:101), and FIGS. 54A–54C (SEQ ID NO:56), a nucleic acid of the invention encoding a FATP polypeptide may be obtained using standard cloning and screening methods, such as those for cloning and sequencing cDNA library fragments, followed by obtaining a full length clone. For example, to obtain a nucleic acid of the invention, a library of clones of cDNA of human or other mammalian DNA can be probed with a labeled oligonucleotide, such as radiolabeled oligonucleotide, preferably about 17 nucleotides or longer, derived from a partial sequence. Clones carrying DNA identical to that of the probe can then be distinguished using stringent (also, "high stringency") hybridization conditions. By sequencing the individual clones thus identified with sequencing primers designed from the original sequence it is then possible to extend the sequence in both directions to determine the full length sequence. Suitable techniques are described, for example, in *Current Protocols in Molecular Biology* (F.M. Ausubel et al, eds), containing supplements through Supplement 42, 1998, Wiley and Sons, Inc., especially chapters 5, 6 and 7.

Embodiments of the invention include isolated nucleic acid molecules comprising any of the following nucleotide sequences: 1.) a nucleotide sequence which encodes a protein comprising the amino acid sequence of hsFATP1 (SEQ ID NO;47), the amino acid sequence of hsFATP2 (SEQ ID NO:49), the amino acid sequence of hsFATP3 (SEQ ID NO:102), the amino acid sequence of hsFATP4 (SEQ ID NO: 53), the amino acid sequence of hsFATP5 (SEQ ID NO: 55) or the amino acid sequence of hsFATP6 (SEQ ID NO:57); 2.) nucleotide sequences of hsFATP1, hsFATP2, hsFATP3, hsFATP4, hsFATP5, or hsFATP6 (SEQ ID NO:46, 48, 101, 52, 54, or 56, respectively); 3.) a nucleotide sequence which is complementary to the nucleotide sequence of hsFATP1 (SEQ ID NO:46), hsFATP2 (SEQ ID NO:48), hsFATP3 (SEQ ID NO:101), hsFATP4 (SEQ ID NO:52), hsFATP5 (SEQ ID NO:54) or hsFATP6 (SEQ ID NO:56); 4.) a nucleotide sequence which consists of the coding region of hsFATP1 (SEQ ID NO:46), the coding region of hsFATP2 (SEQ ID NO:48), the coding region of hsFATP3 (SEQ ID NO:101), the coding region of hsFATP4 (SEQ ID NO:52), the coding region of hsFATP5 (SEQ ID NO:54), or the coding region of hsFATP6 (SEQ ID NO:56).

The invention further relates to nucleic acids (nucleic acid molecules or polynucleotides) having nucleotide sequences identical over their entire length to those shown in the figures, for instance FIGS. 44A–44D (SEQ ID NO:46), FIGS. 46A–46B (SEQ ID NO:48), FIG. 48 (SEQ ID NO:50), FIGS. 50A–50C (SEQ ID NO:52), FIGS. 94A–94J (SEQ ID NO:101), and FIGS. 54A–54C (SEQ ID NO:56). It further relates to DNA, which due to the degeneracy of the genetic code, encodes a FATP encoded by one of the FATP-encoding DNAs, whose amino acid sequence is provided herein. Also provided by the invention are nucleic acids having the coding sequences for the mature polypeptides or fragments in reading frame with other coding sequences, such as those encoding a leader or secretory sequence, a pre-, or pro- or prepro-protein sequence. The nucleic acids of the invention encompass nucleic acids that include a single continuous region or discontinuous regions encoding the polypeptide, together with additional regions, that may also contain coding or non-coding sequences. The nucleic acids may also contain non-coding sequences, including, for example, but not limited to, non-coding 5' and 3' sequences, such as the transcribed, non-translated sequences, termination signals, ribosome binding sites, sequences that stabilize mRNA, introns, polyadenylation signals, and additional coding sequences which encode additional amino acids. For example, a marker sequence that facilitates purification of the fused polypeptide can be encoded. In certain embodiments of the invention, the marker sequence can be a hexa-histidine peptide, as provided in the pQE vector (Qiagen, Inc.) and described in Gentz et al., *Proc. Natl. Acad. Sci. USA* 86: 821–824 (1989), or an HA tag (Wilson et al., *Cell* 37: 767 (1984)), or a sequence encoding glutathione S-transferase of *Schistosoma japonicum* (vectors available from Phannacia; see Smith, D. B. and Johnson K. S., *Gene* 67:31 (1988) and Kaelin, W. G. et al., *Cell* 70:351 (1992)). Nucleic acids of the invention also include, but are not limited to, nucleic acids comprising a structural gene and its naturally associated sequences that control gene expression.

The invention further relates to variants, including naturally-occurring allelic variants, of those nucleic acids described specifically herein by DNA sequence, that encode variants of such polypeptides as those having the amino acid sequences shown in FIG. 45 (SEQ ID NO:47), FIG. 47 (SEQ ID NO:49), FIG. 49 (SEQ ID NO:51), FIG. 51 (SEQ ID NO:53), FIGS. 94A–94J (SEQ ID NO:102), or FIG. 55 (SEQ ID NO:57). Such variants include nucleic acids encoding variants of the above-listed amino acid sequences, wherein those variants have several, such as 5 to 10, 1 to 5, or 3, 2 or 1 amino acids substituted, deleted, or added, in any combination. Variants include polynucleotides encoding polypeptides with at least 95% but less than 100% amino acid sequence identity to the polypeptides described herein by amino acid sequence. Variant polynucleotides hybridize, under low to high stringency conditions, to the alleles described herein by DNA sequence. In one embodiment, variants have silent substitutions, additions and deletions that do not alter the properties and activities of the FATP. Allelic variants of the polynucleotides encoding hsFATP1 (FIG. 45; SEQ ID NO:47), hsFATP2 (FIG. 47; SEQ ID NO:49), hsFATP3 (FIG. 49; SEQ ID NO:51), hsFATP4 (FIG. 51; SEQ ID NO:53), hsFATP5 (FIGS. 94A–94J; SEQ ID NO:102) and hsFATP6 (FIG. 55; SEQ ID NO:57) will be identified as mapping to chromosomal locations listed for the corresponding wild type genes in Table 2 in Example 1.

Orthologous genes are gene loci in different species that are sufficiently similar to each other in their nucleotide sequences to suggest that they originated from a common ancestral gene. Orthologous genes arise when a lineage splits into two species, rather than when a gene is duplicated within a genome. Proteins that are orthologs are encoded by genes of two different species, wherein the genes are said to be orthologous.

The invention further relates to polynucleotides encoding polypeptides which are orthologous to those polypeptides having a specific amino acid sequence described herein, such as the amino acid sequences shown in FIG. 45 (SEQ ID NO:47), FIG. 47 (SEQ ID NO:49), FIG. 49 (SEQ ID NO:51), FIG. 51 (SEQ ID NO:53), FIGS. 94A–94J (SEQ ID NO:102), or FIG. 55 (SEQ ID NO:57). These polynucleotides, which can be called ortholog polynucleotides, encode orthologous polypeptides that can range in amino acid sequence identity to a reference amino acid sequence described herein, from about 65% to less than 100%, but preferably 70% to 80%, more preferably 80% to 90%, and still more preferably 90% to less than 100%.

Orthologous polypeptides can also be those polypeptides that range in amino acid sequence similarity to a reference amino acid sequence described herein from about 75% to 100%, within the signature sequence. The amino acid sequence similarity between the signature sequences of orthologous polypeptides is preferably 80%, more preferably 90%, and still more preferably, 95%. The ortholog polynucleotides encode polypeptides that have similar functional characteristics (e.g., fatty acid transport activity) and similar tissue distribution, as appropriate to the organism from which the ortholog polynucleotides can be isolated.

Ortholog polynucleotides can be isolated from (e.g., by cloning or nucleic acid amplification methods) a great number of species, as shown by the sample of FATPs from evolutionarily divergent species described herein (see, e.g., FIGS. 44A–D through FIG. 89). Ortholog polynucleotides corresponding to those in FIG. 45 (SEQ ID NO:47), FIG. 47 (SEQ ID NO:49), FIG. 49 (SEQ ID NO:51), FIG. 51 (SEQ ID NO:53), FIGS. 94A–94J (SEQ ID NO: 102) and FIG. 55 (SEQ ID NO:57) are those which can be isolated from mammals such as rat, dog, chimpanzee, monkey, baboon, pig, rabbit and guinea pig, for example.

Further variants that are fragments of the nucleic acids of the invention may be used to synthesize full-length nucleic acids of the invention, such as by use as primers in a polymerase chain reaction. As used herein, the term primer refers to a single-stranded oligonucleotide which acts as a point of initiation of template-directed DNA synthesis under appropriate conditions (e.g., in the presence of four different nucleoside triphosphates and an agent for polymerization, such as DNA or RNA polymerase or reverse transcriptase) in an appropriate buffer and at a suitable temperature. The appropriate length of a primer depends on the intended use of the primer, but typically ranges from 15 to 30 nucleotides. Short primer molecules generally require cooler temperatures to form sufficiently stable hybrid complexes with the template. A primer need not reflect the exact sequence of the template, but must be sufficiently complementary to hybridize with a template. The term primer site refers to the area of the target DNA to which a primer hybridizes. The term primer pair refers to a set of primers including a 5' (upstream) primer that hybridizes with the 5' end of the DNA sequence to be amplified and a 3' (downstream) primer that hybridizes with the complement of the 3' end of the sequence to be amplified.

Further embodiments of the invention are nucleic acids that are at least 80% identical over their entire length to a nucleic acid described herein, for example a nucleic acid having the nucleotide sequence in FIGS. 44A–44D (SEQ ID NO:46), FIGS. 46A–46B (SEQ ID NO:48), FIG. 48 (SEQ ID NO:50), FIGS. 50A–50C (SEQ ID NO:52), FIGS. 94A–94J (SEQ ID NO:101), and FIGS. 54A–54C (SEQ ID NO:56). Additional embodiments are nucleic acids, and the complements of such nucleic acids, having at least 90% nucleotide sequence identity to the above-described sequences, and nucleic acids having at least 95% nucleotide sequence identity. In preferred embodiments, DNA of the present invention has 97% nucleotide sequence identity, 98% nucleotide sequence identity, or at least 99% nucleotide sequence identity with the DNA whose sequences are presented herein.

Other embodiments of the invention are nucleic acids that are at least 80% identical in nucleotide sequence to a nucleic acid encoding a polypeptide having an amino acid sequence as set forth in FIG. 45 (SEQ ID NO:47), FIG. 47 (SEQ ID NO:49), FIG. 49 (SEQ ID NO:51), FIG. 51 (SEQ ID NO:53), FIGS. 94A–94J (SEQ ID NO:102) or FIG. 55 (SEQ ID NO:57), or as such amino acid sequences are set forth elsewhere herein, and nucleic acids that are complementary to such nucleic acids. Specific embodiments are nucleic acids having at least 90% nucleotide sequence identity to a nucleic acid encoding a polypeptide having an amino acid sequence as described in the list above, nucleic acids having at least 95% sequence identity, and nucleic acids having at least 97% sequence identity.

The terms "complementary" or "complementarity" as used herein, refer to the natural binding of polynucleotides under permissive salt and temperature conditions by base-pairing. Complementarity between two single-stranded molecules may be "partial" in which only some of the nucleic acids bind, or it may be complete when total complementarity exists between the single-stranded molecules (that is, when A-T and G-C base pairing is 100% complete). The degree of complementarity between nucleic acid strands has significant effects on the efficiency and strength of hybridization between nucleic acid strands. This is of particular importance in amplification reactions, which depend on binding between nucleic acid strands.

The invention further includes nucleic acids that hybridize to the above-described nucleic acids, especially those nucleic acids that hybridize under stringent hybridization conditions. "Stringent hybridization conditions" or "high stringency conditions" generally occur within a range from about $T_m$ minus 5° C. (5° C. below the strand dissociation temperature or melting temperature ($T_m$) of the probe nucleic acid molecule) to about 20° C. to 25° C. below $T_m$. As will be understood by those of skill in the art, the stringency of hybridization may be altered in order to identify or detect molecules having identical or related polynucleotide sequences. An example of high stringency hybridization follows. Hybridization solution is (6×SSC/10 mM EDTA/0.5% SDS/5×Denhardt's solution/100 µg/ml sheared and denatured salmon sperm DNA). Hybridization is at 64–65° C. for 16 hours. The hybridized blot is washed two times with 2×SSC/0.5% SDS solution at room temperature for 15 minutes each, and two times with 0.2×SSC/0.5% SDS at 65° C., for one hour each. Further examples of high stringency conditions can be found on pages 2.10.1–2.10.16 (see particularly 2.10.8–11) and pages 6.3.1–6 in *Current Protocols in Molecular Biology* (Ausubel, F. M. et al., eds., containing supplements up through Supplement 42, 1998). Examples of high, medium, and low stringency conditions can be found on pages 36 and 37 of WO 98/40404, which are incorporated herein by reference.

The invention further relates to nucleic acids obtainable by screening an appropriate library with a probe having a nucleotide sequence such as that set forth in FIGS. 44A–44D (SEQ ID NO:46), FIGS. 46A–46B (SEQ ID NO:48), FIG. 48 (SEQ ID NO:50), FIGS. 50A–50C (SEQ ID NO:52), FIGS. 94A–94J (SEQ ID NO:101) or FIGS. 54A–54C (SEQ ID NO:56), or a probe which is a sufficiently long fragment of any of the above; and isolating the nucleic acid. Such probes generally can comprise at least 15 nucleotides. Nucleic acids obtainable by such screenings may include RNAs, cDNAs and genomic DNA, for example, encoding FATPs of the FATP family described herein.

Further uses for the nucleic acid molecules of the invention, whether encoding a full-length FATP or whether comprising a contiguous portion of a nucleic acid molecule such as one given in SEQ ID NO:46, 48, 50, 52, 101, or 56, include use as markers for tissues in which the corresponding protein is preferentially expressed (to identify constitutively expressed proteins or proteins produced at a particular stage of tissue differentiation or stage of development of a disease state); as molecular weight markers on southern gels; as chromosome markers or tags (when labeled, for example with biotin, a radioactive label or a fluorescent label) to identify chromosomes or to map related gene positions; to compare with endogenous DNA sequences in a mammal to identify potential genetic disorders; as probes to hybridize and thus identify, related DNA sequences; as a source of information to derive PCR primers for genetic fingerprinting; as a probe to "subtract-out" known sequences in the process of discovering other novel nucleic acid molecules; for selecting and making oligomers for attachment to a "gene chip" or other support, to be used, for example, for examination of expression patterns; to raise anti-protein antibodies using DNA immunization techniques; and as an antigen to raise anti-DNA antibodies or to elicit another immune response.

Further methods to obtain nucleic acids encoding FATPs of the FATP family include PCR and variations thereof (e.g., "RACE" PCR and semi-specific PCR methods). Portions of the nucleic acids having a nucleotide sequence set forth in FIGS. 44A–44D (SEQ ID NO:46), FIGS. 46A–46B (SEQ ID NO:48), FIG. 48 (SEQ ID NO:50), FIGS. 50A–50C (SEQ ID NO:52), FIGS. 94A–94J (SEQ ID NO:101) or FIGS. 54A–54C (SEQ ID NO:56), (especially "flanking sequences" on either side of a coding region) can be used as primers in methods using the polymerase chain reaction, to produce DNA from an appropriate template nucleic acid.

Once a fragment of the FATP gene is generated by PCR, it can be sequenced, and the sequence of the product can be compared to other DNA sequences, for example, by using the BLAST Network Service at the National Center for Biotechnology Information. The boundaries of the open reading frame can then be identified using semi-specific PCR or other suitable methods such as library screening. Once the 5' initiator methionine codon and the 3' stop codon have been identified, a PCR product encoding the full-length gene can be generated using genomic DNA as a template, with primers complementary to the extreme 5' and 3' ends of the gene or to their flanking sequences. The full-length genes can then be cloned into expression vectors for the production of functional proteins.

The invention also relates to isolated proteins or polypeptides such as those encoded by nucleic acids of the present invention. Isolated proteins can be purified from a natural source or can be made recombinantly. Proteins or polypeptides referred to herein as "isolated" are proteins or polypeptides that exist in a state different from the state in which they exist in cells in which they are normally expressed in an organism, and include proteins or polypeptides obtained by methods described herein, similar methods or other suitable methods, and also include essentially pure proteins or polypeptides, proteins or polypeptides produced by chemical synthesis or by combinations of biological and chemical methods, and recombinant proteins or polypeptides which are isolated. Thus, the term "isolated" as used herein, indicates that the polypeptide in question exists in a physical milieu distinct from that in which it occurs in nature. Thus, "isolated" includes existing in membrane fragments and vesicles membrane fractions, liposomes, lipid bilayers and other artificial membrane systems. An isolated FATP may be substantially isolated with respect to the complex cellular milieu in which it naturally occurs, and may even be purified essentially to homogeneity, for example as determined by PAGE or column chromatography (for example, HPLC), but may also have further cofactors or molecular stabilizers, such as detergents, added to the purified protein to enhance activity. In one embodiment, proteins or polypeptides are isolated to a state at least about 75% pure; more preferably at least about 85% pure, and still more preferably at least about 95% pure, as determined by Coomassie blue staining of proteins on SDS-polyacrylamide gels. Proteins or polypeptides referred to herein as "recombinant" are proteins or polypeptides produced by the expression of recombinant nucleic acids.

In a preferred embodiment, an isolated polypeptide comprising a FATP, a functional portion thereof, or a functional equivalent of the FATP, has at least one function characteristic of a FATP, for example, transport activity, binding function (e.g., a domain which binds to AMP), or antigenic function (e.g., binding of antibodies that also bind to a naturally-occurring FATP, as that function is found in an antigenic determinant). Functional equivalents can have activities that are quantitatively similar to, greater than, or less than, the reference protein. These proteins include, for example, naturally occurring FATPs that can be purified from tissues in which they are produced (including polymorphic or allelic variants), variants (e.g., mutants) of those proteins and/or portions thereof. Such variants include mutants differing by the addition, deletion or substitution of one or more amino acid residues, or modified polypeptides in which one or more residues are modified, and mutants comprising one or more modified residues. Portions or fragments of a FATP can range in size from four amino acid residues to the entire amino acid sequence minus one amino acid.

The isolated proteins of the invention preferably include mammalian fatty acid transport proteins of the FATP family of homologous proteins. In one embodiment, the extent of amino acid sequence similarity between a polypeptide having one of the amino acid sequences shown in FIG. 45 (SEQ ID NO:47), FIG. 47 (SEQ ID NO:49), FIG. 49 (SEQ ID NO:51), FIG. 51 (SEQ ID NO:53), FIGS. 94A 94J (SEQ ID NO:102), or FIG. 55 (SEQ ID NO:57), and the respective functional equivalents of these polypeptides is at least about 88%. In other embodiments, the degree of amino acid sequence similarity between a FATP and its respective functional equivalent is at least about 91%, at least about 94%, or at least about 97%.

The polypeptides of the invention also include those FATPs encoded by polynucleotides which are orthologous to those polynucleotides, the sequences of which are described herein in whole or in part. FATPs which are orthologs to those described herein by amino acid sequence, in whole or in part, are, for example fatty acid transport proteins 1–6 of dog, rat chimpanzee, monkey, rabbit, guinea pig, baboon and pig, and are also embodiments of the invention.

To determine the percent identity or similarity of two amino acid sequences or of two nucleic acid sequences, the sequences are aligned for optimal comparison purposes (e.g., gaps can be introduced in one or both of a first and a second amino acid or nucleic acid sequence for optimal alignment, and non-homologous (dissimilar) sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein, amino acid or nucleic acid "identity" is equivalent to amino acid or nucleic acid "similarity"). The percent identity between the two sequences is a function of the number of identical positions shared by the sequences, taking into account the number of gaps, and the length of each gap, which need to be introduced for optimal alignment of the two sequences.

The invention also encompasses polypeptides having a lower degree of identity but having sufficient similarity so as to perform one or more of the same functions performed by the polypeptides described herein by amino acid sequence. Similarity for a polypeptide is determined by conserved amino acid substitution. Such substitutions are those that substitute a given amino acid in a polypeptide by another amino acid of like characteristics. Conservative substitutions are likely to be phenotypically silent. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr. Guidance concerning which amino acid changes are likely to be phenotypically silent is found in Bowie et al, *Science* 247:1306–1310 (1990).

TABLE 1

Conservative Amino Acid Substitutions

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing, Informatics and Genome Projects*, Smith, D. W., ed., Academic Press, New York, 1993; *Computer Analysis of Sequence Data*, Part 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereaux, J., eds., M. Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg.com), using a NWS-gapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (*CABIOS*, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, word length=12 to obtain nucleotide sequences homologous to (with calculatably significant similarity to) the nucleic acid molecules of the invention. BLAST protein searches can be performed with the XBLAST program, score=50, word length=3 to obtain amino acid sequences homologous to the proteins of the invention. To obtain gapped alignments for comparison purposes, Gapped BLAST can be utilized as described in Altschul et al., (*Nucleic Acids Res.* 25(17) :3389–3402 (1997)). When utilizing BLAST and gapped BLAST programs, the default parameters of the respective programs (e.g., XBLAST and NBLAST) can be used. See http://www.ncbi.nlm.nih.gov.

Similarity for nucleotide and amino acid sequences can be defined in terms of the parameters set by the Advanced Blast search available from NCBI (the National Center for Biotechnology Information; see, for Advanced BLAST page, www.ncbi.nlm.nih.gov/cgi-bin/BLAST/nph-newblast?Jform=1). These default parameters, recommended for a query molecule of length greater than 85 amino acid residues or nucleotides have been set as follows: gap existence cost, 11, per residue gap cost, 1; lambda ratio, 0.85. Further explanation of version 2.0 of BLAST can be found on related website pages and in Altschul, S. F. et al., *Nucleic Acids Res.* 25:3389–3402 (1997).

The invention further relates to fusion proteins, comprising a FATP or functional portion thereof (as described above) as a first moiety, linked to second moiety not occurring in the FATP as found in nature. Thus, the second moiety can be an amino acid, peptide or polypeptide. The first moiety can be in an N-terminal location, C-terminal location or internal to the fusion protein. In one embodiment, the fusion protein comprises a FATP as the first moiety, and a second moiety comprising a linker sequence and an affinity ligand. Fusion proteins can be produced by a variety of methods. For example, a fusion protein can be produced by the insertion of a FATP gene or portion thereof into a suitable expression vector, such as Bluescript SK +/− (Stratagene), pGEX-4T-2 (Pharmacia), pET-24(+) (Novagen), or vectors of similar construction. The resulting construct can be introduced into a suitable host cell for expression. Upon expression, fusion protein can be purified from cells by means of a suitable affinity matrix (See e.g., *Current Protocols in Molecular Biology*, Ausubel, F. M. et al., eds., Vol. 2, pp. 16.4.1–16.7.8, containing supplements up through Supplement 42, 1998).

The invention also relates to enzymatically produced, synthetically produced, or recombinantly produced portions of a fatty acid transport protein. Portions of a FATP can be made which have full or partial function on their own, or which when mixed together (though fully, partially, or nonfunctional alone), spontaneously assemble with one or more other polypeptides to reconstitute a functional protein having at least one function characteristic of a FATP.

Fragments of a FATP can be produced by direct peptide synthesis, for example those using solid-phase techniques (Roberge, J. Y. et al., *Science* 269:202–204 (1995); Merrifield, J., *J. Am. Chem. Soc.* 85:2149–2154 (1963)). Protein synthesis can be performed using manual techniques or by automation. Automated synthesis can be carried out using, for instance, an Applied Biosystems 431A Peptide Synthesizer (Perkin Elmer). Various fragments of a FATP can be synthesized separately and combined using chemical methods.

One aspect of the invention is a peptide or polypeptide having the amino acid sequence of a portion of a fatty acid transport protein which is hydrophilic rather than hydrophobic, and ordinarily can be detected as facing the outside of the cell membrane. Such a peptide or polypeptide can be thought of as being an extracellular domain of the FATP, or a mimetic of said extracellular domain. It is known, for example, that a portion of human FATP4 that includes a highly conserved motif is involved in AMP-CoA binding function (Stuhlsatz-Krouper, S. M. et al., *J. Biol. Chem.* 44:28642–28650 (1998)).

The term "mimetic" as used herein, refers to a molecule, the structure of which is developed from knowledge of the structure of the FATP of interest, or one or more portions thereof, and, as such, is able to effect some or all of the functions of a FATP.

Portions of an FATP can be prepared by enzymatic cleavage of the isolated protein, or can be made by chemical synthesis methods. Portions of a FATP can also be made by recombinant DNA methods in which restriction fragments, or fragments that may have undergone further enzymatic processing, or synthetically made DNAs are joined together to construct an altered FATP gene. The gene can be made such that it encodes one or more desired portions of a FATP. These portions of FATP can be entirely homologous to a known FATP, or can be altered in amino acid sequence relative to naturally occurring FATPs to enhance or introduce desired properties such as solubility, stability, or affinity to a ligand. A further feature of the gene can be a sequence encoding an N-terminal signal peptide directed to the plasma membrane.

Figure 28A:
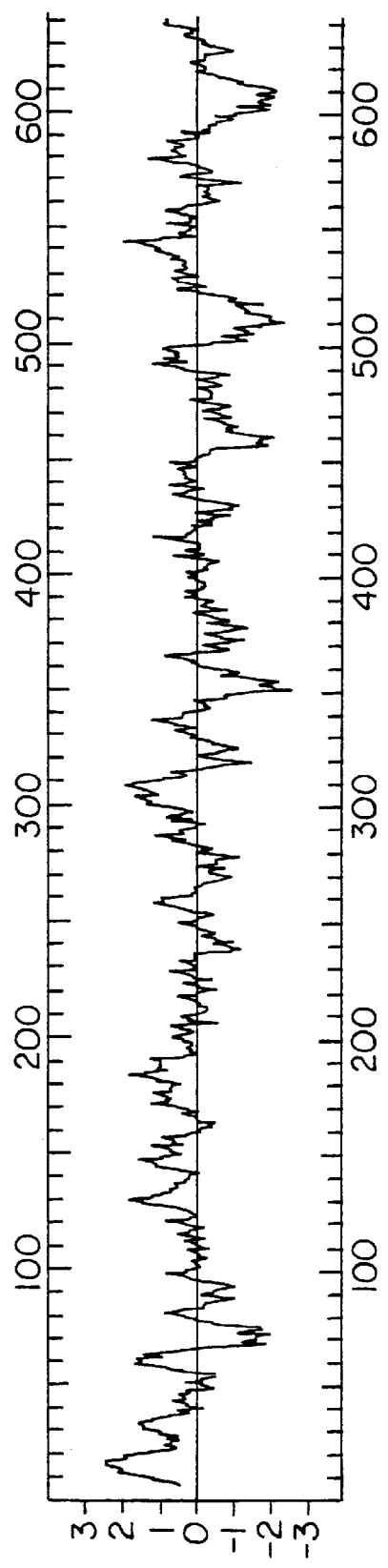
FIG. 28A is a hydrophobicity plot for hsFATP1, showing that it has multiple membrane-spanning domains.
Figure 28C:
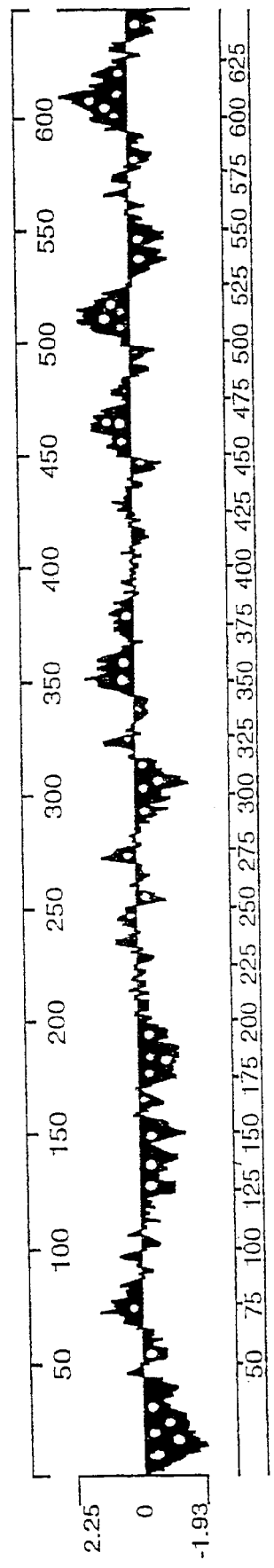
FIG. 28C is a hydrophilicity plot for hsFATP1, made using the Kyte-Doolittle method, averaging hydrophilicity values for 18 amino acid residues at a time.
Figure 29A:
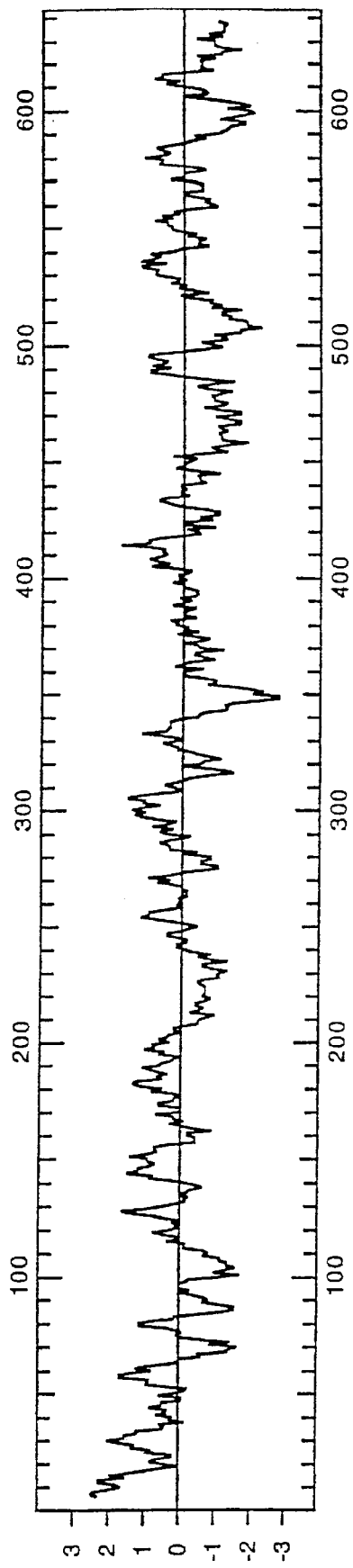
FIG. 29A is a hydrophobicity plot for hsFATP4, showing that it has multiple membrane-spanning domains.
Figure 29C:
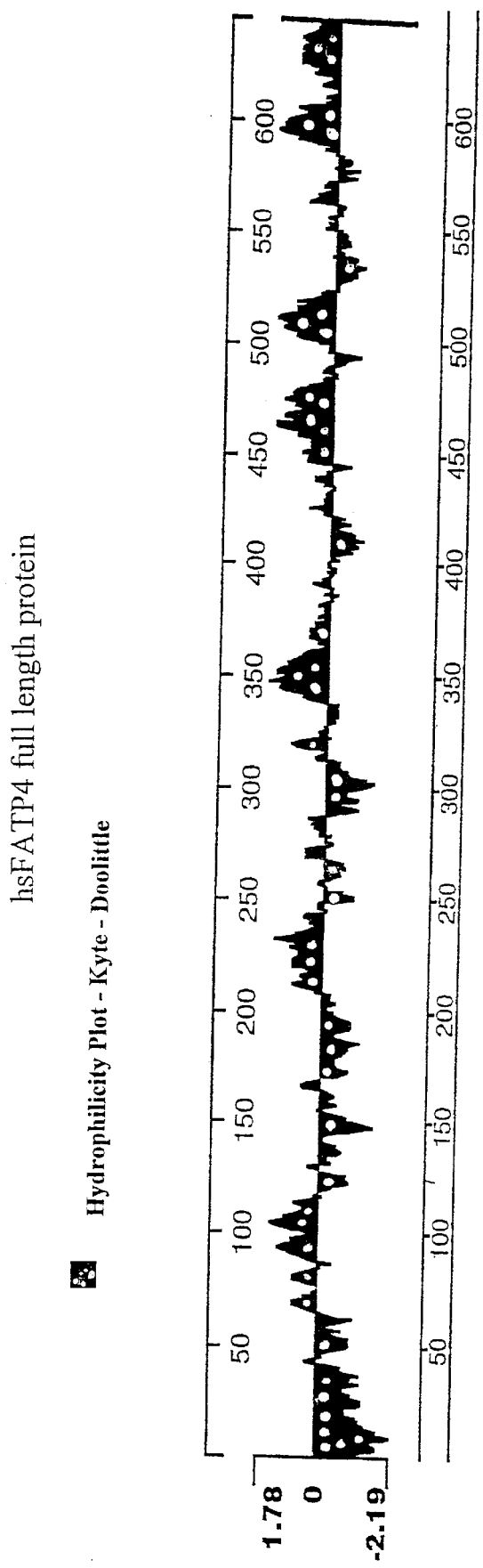
FIG. 29C is a hydrophilicity plot for hsFATP4, made using the Kyte-Doolittle method, averaging hydrophilicity values for 18 amino acid residues at a time.
Figure 35A:
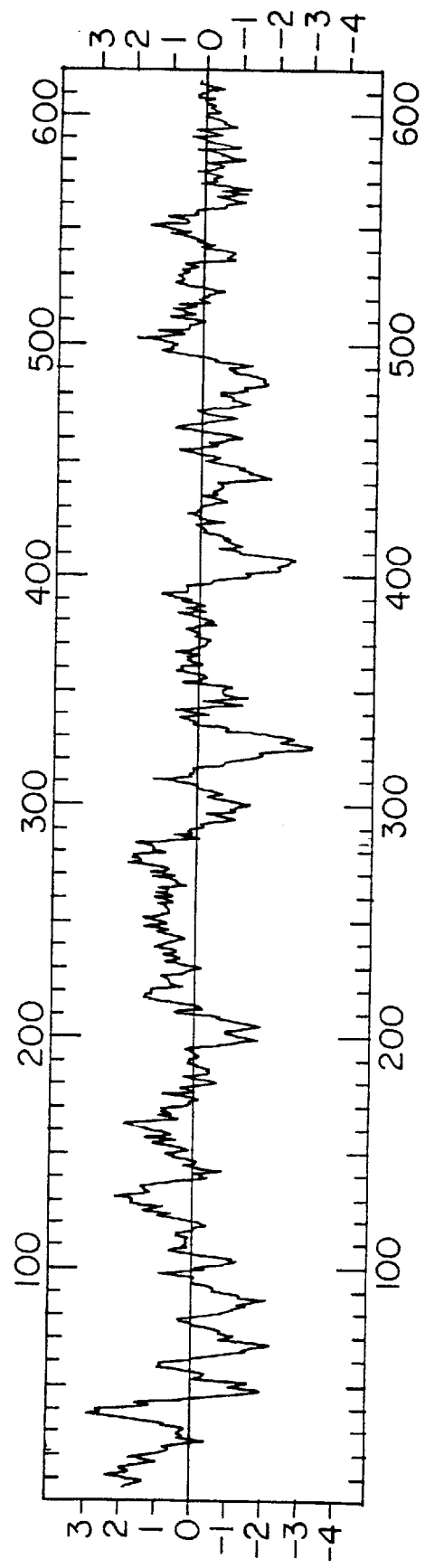
FIG. 35A is a hydrophobicity plot for hsFATP6, showing that it has multiple membrane-spanning domains.
Figure 35C:
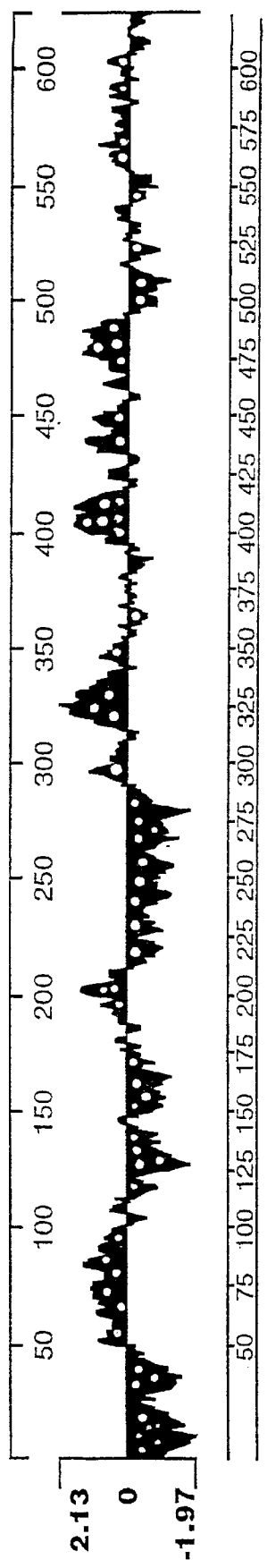
FIG. 35C is a hydrophilicity plot for hsFATP6, made using the Kyte-Doolittle method, averaging hydrophilicity values for 18 amino acid residues at a time.

An extracellular domain can be determined by a hydrophobicity plot, such as those shown in FIGS. 28A, 29A, and 35A, or by a hydrophilicity plot such as those shown in FIGS. 28C, 29C, 35C, 91, 92 and 93. A polypeptide or peptide comprising all or a portion of a FATP extracellular domain can be used in a pharmaceutical composition. When administered to a mammal by an appropriate route, the polypeptide or peptide can bind to fatty acids and compete with the native FATPs in the membrane of cells, thereby making fewer fatty acid molecules available as substrates for transport into cells, and reducing the amount of fatty acids taken up by, for example, the heart, in the case of FATP6.

Another aspect of the invention relates to a method of producing a fatty acid transport protein, variants or portions thereof, and to expression systems and host cells containing a vector appropriate for expression of a fatty acid transport protein.

Cells that express a FATP, a variant or a portion thereof, or an ortholog of a FATP described herein by amino acid sequence, can be made and maintained in culture, under conditions suitable for expression, to produce protein in the cells for cell-based assays, or to produce protein for isolation. These cells can be procaryotic or eucaryotic. Examples of procaryotic cells that can be used for expression include *Escherichia coli, Bacillus subtilis* and other bacteria. Examples of eucaryotic cells that can be used for expression include yeasts such as *Saccharomyces cerevisiae, Schizosaccharomyces pombe, Pichia pastoris* and other lower eucaryotic cells, and cells of higher eucaryotes such as those from insects and mammals, such as primary cells and cell lines such as CHO, HeLa, 3T3 and BHK cells, preferably COS cells and human kidney 293 cells, and more preferably Jurkat cells. (See, e.g., Ausubel, F. M. et al, eds. *Current Protocols in Molecular Biology,* Greene Publishing Associates and John Wiley & Sons, Inc., containing Supplements up through Supplement 42, 1998)).

In one embodiment, host cells that produce a recombinant FATP, or a portion thereof, a variant, or an ortholog of a FATP described herein by amino acid sequence, can be made as follows. A gene encoding a FATP, variant or a portion thereof can be inserted into a nucleic acid vector, e.g., a DNA vector, such as a plasmid, phage, cosmid, phagemid, virus, virus-derived vector (e.g., SV40, vaccinia, adenovirus, fowl pox virus, pseudorabies viruses, retroviruses) or other suitable replicon, which can be present in a single copy or multiple copies, or the gene can be integrated in a host cell chromosome. A suitable replicon or integrated gene can contain all or part of the coding sequence for a FATP or variant, operably linked to one or more expression control regions whereby the coding sequence is under the control of transcription signals and linked to appropriate translation signals to permit translation. The vector can be introduced into cells by a method appropriate to the type of host cells (e.g., transfection, electroporation, infection). For expression from the FATP gene, the host cells can be maintained tinder appropriate conditions (e.g., in the presence of inducer, normal growth conditions, etc.). Proteins or polypeptides thus produced can be recovered (e.g., from the cells, as in a membrane fraction, from the periplasmic space of bacteria, from culture medium) using suitable techniques. Appropriate membrane targeting signals may be incorporated into the expressed polypeptide. These signals may be endogenous to the polypeptide or they may be heterologous signals.

Polypeptides of the invention can be recovered and purified from cell cultures (or from their primary cell source) by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and high performance liquid chromatography. Known methods for refolding protein can be used to regenerate active conformation if the polypeptide is denatured during isolation or purification.

In a further aspect of the invention are methods for assessing the transport function of any of the fatty acid transport proteins or polypeptides described herein, including orthologs, and in variations of these, methods for identifying an inhibitor (or an enhancer) of such function and methods for assessing the transport function in the presence of a candidate inhibitor or a known inhibitor.

A variety of systems comprising living cells can be used for these methods. Cells to be used in fatty acid transport assays, and further in methods for identifying an inhibitor or enhancer of this function, express one or more FATPs. See Examples 3, 6, 9, 12 and 14 for data on tissue distribution of expression of FATPs, and Examples 10 and 11 describing recombinant cells expressing FATP. Cells for use in cell-based assays described herein can be drawn from a variety of sources, such as isolated primary cells of various organs and tissues wherein one or more FATPs are naturally expressed. In some cases, the cells can be from adult organs, and in some cases, from embryonic or fetal organs, such as heart, lung, liver, intestine, skeletal muscle, kidney and the like. Cells for this purpose can also include cells cultured as fragments of organs or in conditions simulating the cell type and/or tissue organization of organs, in which artificial materials may be used as substrates for cell growth. Other types of cells suitable for this purpose include cells of a cell strain or cell line (ordinarily comprising cells considered to be "transformed") transfected to express one or more FATPs.

A further embodiment of the invention is a method for detecting, in a sample of cells, a fatty acid transport protein, a portion or fragment thereof, a fusion protein comprising a FATP or a portion thereof, or an ortholog as described herein, wherein the cells can be, for instance, cells of a tissue, primary culture cells, or cells of a cell line, including cells into which nucleic acid has been introduced. The method comprises adding to the sample an agent that specifically binds to the protein, and detecting the agent specifically bound to the protein. Appropriate washing steps can be added to reduce nonspecific binding to the agent. The agent can be, for example, an antibody, a ligand or a substrate mimic. The agent can have incorporated into it, or have bound to it, covalently or by high affinity non-covalent interactions, for instance, a label that facilitates detection of the agent to which it is bound, wherein the label can be, but is not limited to, a phosphorescent label, a fluorescent label, a biotin or avidin label, or a radioactive label. The means of detection of a fatty acid transport protein can vary, as appropriate to the agent and label used. For example, for an antibody that binds to the fatty acid transport protein, the means of detection may call for binding a second antibody, which has been conjugated to an enzyme, to the antibody which binds the fatty acid transport protein, and detecting the presence of the second antibody by means of the enzymatic activity of the conjugated enzyme.

Similar principles can also be applied to a cell lysate or a more purified preparation of proteins from cells that may comprise a fatty acid transport protein of interest, for example in the methods of immunoprecipitation, immunoblotting, immunoaffinity methods, that in addition to detection of the particular FATP, can also be used in purification steps, and qualitative and quantitative immunoassays. See, for instance, chapters 11 through 14 in *Antibodies. A Laboratory Manual,* E. Harlow and D. Lane, eds., Cold Spring Harbor Laboratory, 1988.

Isolated fatty acid transport protein or, an antigenically similar portion thereof, especially a portion that is soluble, can be used in a method to select and identify molecules which bind specifically to the FATP. Fusion proteins comprising all of, or a portion of, the fatty acid transport protein linked to a second moiety not occurring in the FATP as found in nature, can be prepared for use in another embodiment of the method. Suitable fusion proteins for this purpose include those in which the second moiety comprises an affinity ligand (e.g., an enzyme, antigen, epitope). FATP fusion proteins can be produced by the insertion of a gene encoding the FATP or a variant thereof, or a suitable portion of such gene into a suitable expression vector, which encodes an affinity ligand (e.g., pGEX-4T-2 and pET-15b, encoding glutathione S-transferase and His-Tag affinity ligands, respectively). The expression vector can be introduced into a suitable host cell for expression. Host cells are lysed and the lysate, containing fusion protein, can be bound to a suitable affinity matrix by contacting the lysate with an affinity matrix.

In one embodiment, the fusion protein can be immobilized on a suitable affinity matrix under conditions sufficient to bind the affinity ligand portion of the fusion protein to the matrix, and is contacted with one or more candidate binding agents (e.g., a mixture of peptides) to be tested, under conditions suitable for binding of the binding agents to the FATP portion of the bound fusion protein. Next, the affinity matrix with bound fusion protein can be washed with a suitable wash buffer to remove unbound candidate binding agents and non-specifically bound candidate binding agents. Those agents which remain bound can be released by contacting the affinity matrix with fusion protein bound thereto with a suitable elution buffer. Wash buffer can be formulated to permit binding of the fusion protein to the affinity matrix, without significantly disrupting binding of specifically bound binding agents. In this aspect, elution buffer can be formulated to permit retention of the fusion protein by the affinity matrix, but can be formulated to interfere with binding of the candidate binding agents to the target portion of the fusion protein. For example, a change in the ionic strength or pH of the elution buffer can lead to release of specifically bound agent, or the elution buffer can comprise a release component or components designed to disrupt binding of specifically bound agent to the target portion of the fusion protein.

Immobilization can be performed prior to, simultaneous with, or after, contacting the fusion protein with candidate binding agent, as appropriate. Various permutations of the method are possible, depending upon factors such as the candidate molecules tested, the affinity matrix-ligand pair selected, and elution buffer formulation. For example, after the wash step, fusion protein with binding agent molecules bound thereto can be eluted from the affinity matrix with a suitable elution buffer (a matrix elution buffer, such as glutathione for a GST fusion). Where the fusion protein comprises a cleavable linker, such as a thrombin cleavage site, cleavage from the affinity ligand can release a portion of the fusion with the candidate agent bound thereto. Bound agent molecules can then be released from the fusion protein or its cleavage product by an appropriate method, such as extraction.

One or more candidate binding agents can be tested simultaneously. Where a mixture of candidate binding agents is tested, those found to bind by the foregoing processes can be separated (as appropriate) and identified by suitable methods (e.g., PCR, sequencing, chromatography). Large libraries of candidate binding agents (e.g., peptides, RNA oligonucleotides) produced by combinatorial chemical synthesis or by other methods can be tested (see e.g., Ohlmeyer, M. H. J. et al., *Proc. Natl. Acad. Sci. USA* 90:10922–10926 (1993) and DeWitt, S. H. et al., *Proc. Natl. Acad. Sci. USA* 90:6909–6913 (1993), relating to tagged compounds; see also Rutter, W. J. et al. U.S. Pat. No. 5,010,175; Huebner, V. D. et al., U.S. Pat. No. 5,182,366; and Geysen, H. M., U.S. Pat. No. 4,833,092). Random sequence RNA libraries (see Ellington, A. D. et al., *Nature* 346:818–822 (1990); Bock, L. C. et al., *Nature* 355:584–566 (1992); and Szostak, J. W., *Trends in Biochem. Sci.* 17:89–93 (March, 1992)) can also be screened according to the present method to select RNA molecules which bind to a target FATP or FATP fusion protein. Where binding agents selected from a combinatorial library by the present method carry unique tags, identification of individual biomolecules by chromatographic methods is possible. Where binding agents do not carry tags, chromatographic separation, followed by mass spectrometry to ascertain structure, can be used to identify binding agents selected by the method, for example.

The invention also comprises a method for identifying an agent which inhibits interaction between a fatty acid transport protein (e.g., one comprising the amino acid sequence in SEQ ID NO:47, SEQ ID NO:49, SEQ ID NO:51, SEQ ID NO:53, SEQ ID NO:102, or SEQ ID NO:57), and a ligand of said protein. The FATP can be one described by amino acid sequence herein, a portion or fragment thereof, a variant thereof, or an ortholog thereof, or a FATP fusion protein. Here, a ligand can be, for instance, a substrate, or a substrate mimic, an antibody, or a compound, such as a peptide, that binds with specificity to a site on the protein. The method comprises combining, not limited to a particular order, the fatty acid protein, the ligand of the protein, and a candidate agent to be assessed for its ability to inhibit interaction between the protein and the ligand, under conditions appropriate for interaction between the protein and the ligand (e.g., pH, salt, temperature conditions conducive to appropriate conformation and molecular interactions); determining the extent to which the protein and ligand interact; and comparing (1) the extent of protein-ligand interaction in the presence of candidate agent with (2) the extent of protein-ligand interaction in the absence of candidate agent, wherein if (1) is less than (2), then the candidate agent is one which inhibits interaction between the protein and the ligand.

The method can be facilitated, for example, by using an experimental system which employs a solid support (column chromatography matrix, wall of a plate, microtiter wells, column pore glass, pins to be submerged in a solution, beads, etc.) to which the protein can be attached. Accordingly, in one embodiment, the protein can be fixed to a solid phase directly or indirectly, by a linker. The candidate agent to be tested is added under conditions conducive for interaction and binding to the protein. The ligand is added to the solid phase system under conditions appropriate for binding. Excess ligand is removed, as by a series of washes done under conditions that do not disrupt protein-ligand interactions. Detection of bound ligand can be facilitated by using a ligand that carries a label (e.g., fluorescent, chemiluminescent, radioactive). In a control experiment, protein and ligand are allowed to interact in the absence of any candidate agent, under conditions otherwise identical to those used for the "test" conditions where candidate inhibiting agent is present, and any washes used in the test conditions are also used in the control. The extent to which ligand binds to the protein in the presence of candidate agent is compared to the extent to which ligand binds to the protein in the absence of the candidate agent. If the extent to which interaction of the protein and the ligand occurs is less in the presence of the candidate agent than in the absence of the candidate agent, the candidate agent is an agent which inhibits interaction between the protein and the ligand of the protein.

In a further embodiment, an inhibitor (or an enhancer) of a fatty acid transport protein can be identified. The method comprises steps which are, or are variations of the following: contacting the cells with fatty acid, wherein the fatty acid can be labeled for convenience of detection; contacting a first aliquot of the cells with an agent being tested as an inhibitor (or enhancer) of fatty acid uptake while maintaining a second aliquot of cells under the same conditions but without contact with the agent; and measuring (e.g., quantitating) fatty acid in the first and second aliquots of cells; wherein a lesser quantity of fatty acid in the first aliquot compared to that in the second aliquot is indicative that the agent is an inhibitor of fatty acid uptake by a fatty acid transport protein. A greater quantity of fatty acid in the first aliquot compared to that in the second aliquot is indicative that the agent is an enhancer of fatty acid uptake by a fatty acid transport protein.

A particular embodiment of identifying an inhibitor or enhancer of fatty acid transport function employs the above steps, but also employs additional steps preceding those given above: introducing into cells of a cell strain or cell line ("host cells" for the intended introduction of, or after the introduction of, a vector) a vector comprising a fatty acid transport protein gene, wherein expression of the gene can be regulatable or constitutive, and providing conditions to the host cells under which expression of the gene can occur.

The terms "contacting" and "combining" as used herein in the context of bringing molecules into close proximity to each other, can be accomplished by conventional means. For example, when referring to molecules that are soluble, contacting is achieved by adding the molecules together in a solution. "Contacting" can also be adding an agent to a test system, such as a vessel containing cells in tissue culture.

The term "inhibitor" or "antagonist", as used herein, refers to an agent which blocks, diminishes, inhibits, hinders, limits, decreases, reduces, restricts or interferes with fatty acid transport into the cytoplasm of a cell, or alternatively and additionally, prevents or impedes the cellular effects associated with fatty acid transport. The term "enhancer" or "agonist", as used herein, refers to an agent which augments, enhances, or increases fatty acid transport into the cytoplasm of a cell. An antagonist will decrease fatty acid concentration, fatty acid metabolism and byproduct levels in the cell, leading to phenotypic and molecular changes.

In order to produce a "host cell" type suitable for fatty acid uptake assays and for assays derived therefrom for identifying inhibitors or enhancers thereof, a nucleic acid vector can be constructed to comprise a gene encoding a fatty acid transport protein, for example, human FATP1, FATP2, FATP3, FATP4, FATP5, FATP6, a mutant or variant thereof, an ortholog of the human proteins, such as mouse orthologs or orthologs found in other mammals, or a FATP family protein of origin in an organism other than a mammal. The gene of the vector can be regulatable, such as by the placement of the gene under the control of an inducible or repressible promoter in the vector (e.g., inducible or repressible by a change in growth conditions of the host cell harboring the vector, such as addition of inducer, binding or functional removal of repressor from the cell millieu, or change in temperature) such that expression of the FATP gene can be turned on or initiated by causing a change in growth conditions, thereby causing the protein encoded by the gene to be produced, in host cells comprising the vector, as a plasma membrane protein. Alternatively, the FATP gene can be constitutively expressed.

A vector comprising an FATP gene, such as a vector described herein, can be introduced into host cells by a means appropriate to the vector and to the host cell type. For example, commonly used methods such as electroporation, transfection, for instance, transfection using $CaCl_2$, and transduction (as for a virus or bacteriophage) can be used. Host cells can be, for example, mammalian cells such as primary culture cells or cells of cell lines such as COS cells, 293 cells or Jurkat cells. Host cells can also be, in some cases, cells derived from insects, cells of insect cell lines, bacterial cells, such as *E. coli,* or yeast cells, such as *S. cerevisiae.* It is preferred that the fatty acid transport protein whose function is to be assessed, with or without a candidate inhibitor or enhancer, be produced in host cells whose ancestor cells originated in a species related to the species of origin of the FATP gene encoding the fatty acid transport protein. For example, it is preferable that tests of function or of inhibition or enhancement of a mammalian FATP be carried out in host mammalian cells producing the FATP, rather than bacterial cells or yeast cells.

Host cells comprising a vector comprising a regulatable FATP gene can be treated so as to allow expression of the FATP gene and production of the encoded protein (e.g., by contacting the cells with an inducer compound that effects transcription from an inducible promoter operably linked to the FATP gene).

The test agent (e.g., an agonist or antagonist) is added to the cells to be used in a fatty acid transport assay, in the presence or absence of test agent, under conditions suitable for production and/or maintenance of the expressed FATP in a conformation appropriate for association of the FATP with test agent and substrate. For example, conditions under which an agent is assessed, such as media and temperature requirements, can, initially, be similar to those necessary for transport of typical fatty acid substrates across the plasma membrane. One of ordinary skill in the art will know how to vary experimental conditions depending upon the biochemical nature of the test agent. The test agent can be added to the cells in the presence of fatty acid, or in the absence of fatty acid substrate, with the fatty acid substrate being added following the addition of the test agent. The concentration at which the test agent can be evaluated can be varied, as appropriate, to test for an increased effect with increasing concentrations.

Test agents to be assessed for their effects on fatty acid transport can be any chemical (element, molecule, compound), made synthetically, made by recombinant techniques or isolated from a natural source. For example, test agents can be peptides, polypeptides, peptoids, sugars, hormones, or nucleic acid molecules, such as antisense nucleic acid molecules. In addition, test agents can be small molecules or molecules of greater complexity made by combinatorial chemistry, for example, and compiled into libraries. These libraries can comprise, for example, alcohols, alkyl halides, amines, amides, esters, aldehydes, ethers and other classes of organic compounds. Test agents can also be natural or genetically engineered products isolated from lysates of cells, bacterial, animal or plant, or can be the cell lysates themselves. Presentation of test compounds to the test system can be in either an isolated form or as mixtures of compounds, especially in initial screening steps.

Thus, the invention relates to a method for identifying agents which alter fatty acid transport, the method comprising providing the test agent to the cell (wherein "cell" includes the plural, and can include cells of a cell strain, cell line or culture of primary cells or organ culture, for example), under conditions suitable for binding to its target, whether to the FATP itself or to another target on or in the cell, wherein the transformed cell comprises a FATP.

In greater detail, to test one or more agents or compounds (e.g., a mixture of compounds can conveniently be screened initially) for inhibition of the transport function of a fatty acid transport protein, the agent(s) can be contacted with the cells. The cells can be contacted with a labeled fatty acid. The fatty acid can be, for example, a known substrate of the fatty acid transport protein such as oleate or palmitate. The fatty acid can itself be labeled with a radioactive isotope, (e.g., $^3$H or $^{14}$C) or can have a radioactively labeled adduct attached. In other variations, the fatty acid can have chemically attached to it a fluorescent label, or a substrate for an enzyme occurring within the cells, wherein the substrate yields a detectable product, such as a highly colored or fluorescent product. Addition of candidate inhibitors and labeled substrate to the cells comprising fatty acid transport protein can be in either order or can be simultaneous.

A second aliquot of cells, which can be called "control" cells (a "first" aliquot of cells can be called "test" cells), is treated, if necessary (as in the case of transformed "host" cells), so as to allow expression of the FATP gene, and is contacted with the labeled substrate of the fatty acid transport protein. The second aliquot of cells is not contacted with one or more agents to be tested for inhibition of the transport function of the protein produced in the cells, but is otherwise kept under the same culture conditions as the first aliquot of cells.

In a further step of a method to identify inhibitors of a fatty acid transport protein, the labeled fatty acid is measured in the first and second aliquots of cells. A preliminary step of this measurement process can be to separate the external medium from the cells so as to be able to distinguish the labeled fatty acid external to the cells from that which has been transported inside the cells. This can be accomplished, for instance, by removing the cells from their growth container, centrifuging the cell suspension, removing the supernatant and performing one or more wash steps to extensively dilute the remaining medium which may contain labeled fatty acid. Detection of the labeled fatty acid can be by a means appropriate to the label used. For example, for a radioactive label, detection can be by scintillation counting of appropriately prepared samples of cells (e.g., lysates or protein extracts); for a fluorescent label, by measuring fluorescence in the cells by appropriate instrumentation.

If a compound tested as a candidate inhibitor of transport function causes the test cells to have less labeled fatty acid detected in the cells than that detected in the control cells, then the compound is an inhibitor of the fatty acid transport protein. Procedures analogous to those above can be devised for identifying enhancers (agonists of FATPs) of fatty acid transport function wherein if the test cells contain more labeled fatty acid than that detected in the control cells, or if the fatty acid is taken up at a higher rate, then the compound being tested can be concluded to be an enhancer of the fatty acid transport protein.

Example 13 describes use of an assay of this type to identify an inhibitor of a FATP. In Example 13, an antisense oligonucleotide which specifically inhibits biosynthesis of mmFATP4 was demonstrated to inhibit fatty acid uptake into mouse enterocytes. Similarly, antisense oligonucleotides directed towards specifically inhibiting the biosynthesis of FATP6 in heart cells, FATP5 in liver cells, FATP3 in lung cells, and FATP2 in colon cells, can be demonstrated as examples of "test agents" that inhibit fatty acid transport.

Another assay to determine whether an agent is an inhibitor (or enhancer) of fatty acid transport employs animals, one or more of which are administered the agent, and one or more of which are maintained under similar conditions, but are not administered the agent. Both groups of animals are given fatty acids (e.g., orally, intravenously, by tube inserted into stomach or intestine), and the fatty acids taken up into a bodily fluid (e.g., serum) or into an organ or tissue of interest are measured from comparable samples taken from each group of animals. The fatty acids may carry a label (e.g., radioactive) to facilitate detection and quantitation of fatty acids taken up into the fluid or tissue being sampled.

This type of assay can be used alone or can be used in addition to in vitro assays of a candidate inhibitor or enhancer.

An agent determined to be an inhibitor (or enhancer) of FATP function, such as fatty acid binding and/or fatty acid uptake, can be administered to cells in culture, or in vivo, to a mammal (e.g. human) to inhibit (or enhance) FATP function. Such an agent may be one that acts directly on the FATP (for example, by binding) or can act on an intermediate in a biosynthetic pathway to produce FATP, such as transcription of the FATP gene, processing of the mRNA, or translation of the mRNA. An example of such an agent is antisense oligonucleotide.

Antisense methods similar to those illustrated in Example 13 can be used to determine the target FATP of a compound or agent that has an inhibitory or enhancing effect on fatty acid uptake. For example, antisense oligonucleotide directed to the inhibition of FATP4 biosynthesis can be added to lung cells or cell lines derived from lung cells. In addition, antisense oligonucleotides directed to the inhibition of other FATPs, except for FATP3, can also be added to the lung cells. The administration of antisense oligonucleotides in this manner ensures that the predominant FATP activity remaining in the cells comes from FATP3. After a period of incubation of the cells with the antisense oligonucleotides sufficient to deplete the plasma membrane of the FATPs whose biosynthesis has been inhibited, a test agent, preferably one that has been shown by some preliminary test to have an inhibitory or enhancing activity on fatty acid transport, can be added to the lung cells. If the test agent is now demonstrated, after treatment of the cells with antisense oligonucleotides, to have an inhibitory or enhancing activity on fatty acid transport in the lung cells, it can be concluded that the target of the test agent is FATP3, or a molecule involved in the biosynthesis or activity of FATP3.

In another type of cell-based assay for uptake of fatty acids, a change of intracellular pH resulting from the uptake of fatty acids can be followed by an indicator fluorophore. The fluorophore can be taken up by the cells in a preincubation step. Fatty acids can be added to the cell medium, and after some period of incubation to allow FATP-mediated uptake of fatty acids, the change in $\lambda_{max}$ of fluorescence can be measured, as an indicator of a change in intracellular pH, as the $\lambda_{max}$ of fluorescence of the fluorophore changes with the pH of its environment, thereby indicating uptake of fatty acids. One such fluorophore is BCECF (2', 7'-bis(2-carboxyethyl)-5(6)-carboxyfluorescein; Rink, T. J. et al., *J. Cell. Biol.* 95: 189 (1982)).

In assays similar to those described above, a candidate inhibitor or enhancer of fatty acid transport function can be added (or mock-added, for control cultures) to cultures of cells engineered to express a desired FATP to which fatty acid substrate is also added. Inhibition of fatty acid uptake is indicated by a lack of the drop in pH, indicating fatty acid uptake, that is seen in control cells. Enhancement of fatty acid uptake is indicated by a decrease in intracellular pH, as compared to control cells not receiving the candidate enhancer of fatty acid transport function.

Yeast cells can be used in a similar cell-based assay for the uptake of fatty acids mediated by a FATP, and such an assay can be adapted to a screening assay for the identification of agents that inhibit or enhance fatty acid uptake by an FATP. Yeast cells lacking an endogenous FATP activity (mutated, disrupted or deleted for *FAT*1; Faergeman, N. J. et al., *J. Biol. Chem.* 272(13):8531–8538 (1997); Watkins, P. A. et al., *J. Biol. Chem.* 273(29):18210–18219 (1998)) can be engineered to harbor a related gene of the family of FATP-encoding genes, such as a mammalian FATP (e.g., human FATP4).

Examples of expression vectors include pEG (Mitchell, D. A., et al., *Yeast* 9:715–723 (1993)) and pDAD1 and pDAD2, which contain a *GAL*1 promoter (Davis, L. I. and Fink, G. R., *Cell* 61:965–978 (1990)). A variety of promoters are suitable for expression. Available yeast vectors offer a choice of promoters. In one embodiment, the inducible *GAL*1 promoter is used. In another embodiment, the constitutive *ADH*1 promoter (alcohol dehyrodrogenase; Bennetzen, J. L. and Hall, B. D., *J. Biol. Chem.* 257:3026–3031 (1982)) can be used to express an inserted gene on glucose-containing media. An example of a vector suitable for expression of a heterologous FATP gene in yeast is pQB169.

With the introduced FATP gene providing the only fatty acid transport protein function for the yeast cells, it is possible to study effect of the heterologous FATP on fatty acid transport into the yeast cells in isolation. Assays for the uptake of fatty acids into the yeast cells can be devised that are similar to those described above and/or those assays that have been illustrated in the Examples. Tests for candidate inhibitors or enhancers of the heterologous FATP can be done in cultures of yeast cells, wherein the yeast cells are incubated with fatty acid substrate and an agent to be tested as an S inhibitor or enhancer of FATP function. FATP uptake after a period of time can be measured by analyzing the contents of the yeast cells for fatty acid substrate, as compared with control yeast cells incubated with the fatty acid, but not with the test agent. Yeast cells have the additional advantage, over mammalian cells in culture, for example, that yeast cells can be forced to rely upon fatty acids as their only source of carbon, if the growth medium supplied to the yeast cells is formulated to contain no other source of carbon. Thus, the effect of the heterologous FATP on fatty acid uptake and metabolism in the engineered yeast cells can be amplified. An agent that efficiently blocks transport function of the heterologous FATP could result in death of the yeast cells. Thus, in this case, inhibition of function of the heterologous FATP can result in loss of viability. A simple measure of viability is turbidity of the yeast suspension culture, which can be adapted to a high throughput screening assay for effects of various agents to be tested, using microtiter plates or similar devices for small-volume cultures of the engineered yeast cells.

Cell-free assays can also be used to measure the transport of fatty acids across a membrane, and therefor also to assess a test treatment or test agent for its effect on the rate or extent of fatty acid transport. An isolated FATP, for example in the presence of a detergent that preserves the native 3-dimensional structure of the FATP, or partially purified FATP, can be used in an artificial membrane system typically used to preserve the native conformation and activity of membrane proteins. Such systems include liposomes, artificial bilayers of phospholipids, isolated plasma membrane such as cell membrane fragments, cell membrane fractions, or cell membrane vesicles, and other systems in which the FATP can be properly oriented within the membrane to have transport activity. Assays for transport activity can be performed using methods analogous to those that can be used in cells engineered to predominantly express one FATP whose function is to be measured. A labeled (e.g., radioactively labeled) fatty acid substrate can be incubated with one side of a bilayer or in a suspension of liposomes constructed to integrate a properly oriented FATP. The accumulation of fatty acids with time can be measured, using appropriate means to detect the label (e.g., scintillation counting of medium on each side of the bilayer, or of the contents of liposomes isolated from the surrounding medium). Assays such as these can be adapted to use for the testing of agents which might interact with the FATP to produce an inhibitory or an enhancing effect on the rate or extent of fatty acid transport. That is, the above-described assay can be done in the presence or absence of the agent to be tested, and the results compared.

For examples of isolation of membrane proteins (ADP/ATP carrier and uncoupling protein), reconstitution into phospholipid vesicles, and assays of transport, see Klingenberg, M. et al., *Methods Enzymol.* 260:369–389 (1995). For an example of a membrane protein (phosphate carrier of *Saccharomyces cerevisiae*) that was purified and solubilized from *E. coli* inclusion bodies, see Schroer, A. et al., *J. Biol. Chem.* 273: 14269–14276 (1998). The Glut1 glucose transporter of rat has been expressed in yeast. A crude membrane fraction of the yeast was prepared and reconstituted with soybean phospholipids into liposomes. Glucose transport activity could be measured in the liposomes (Kasahara, T. and Kasahara, M., *J. Biol. Chem.* 273: 29113–29117 (1998)). Similar methods can be applied to the proteins and polypeptides of the invention.

Another embodiment of the invention is a method for inhibiting fatty acid uptake in a mammal (e.g., a human), comprising administering to the mammal a therapeutically effective amount of an inhibitor of the transport function of one or more of the fatty acid transport proteins, thereby decreasing fatty acid uptake by cells comprising the fatty acid protein(s). Where it is desirable to reduce the uptake of fatty acids, for example, in the treatment of chronic obesity or as a part of a program of weight control or hyperlipidemia control in a human, one or more inhibitors of one or more of the fatty acid transport proteins can be administered in an effective dose, and by an effective route, for example, orally, or by an indwelling device that can deliver doses to the small intestine. The inhibitor can be one identified by methods described herein, or can be one that is, for instance, structurally related to an inhibitor identified by methods described herein (e.g., having chemical adducts to better stabilize or solubilize the inhibitor). The invention further relates to compositions comprising inhibitors of fatty acid uptake in a mammal, which may further comprise pharmaceutical carriers suitable for administration to a subject mammal, such as sterile solubilizing or emulsifying agents.

A further embodiment of the present invention is a method of enhancing or increasing fatty acid uptake, such as enhancing or increasing LCFA uptake in the small intestine (e.g., to treat or prevent a malabsorption syndrome or other wasting condition) or in the liver (e.g., by an enhancer of FATP5 transport activity to treat acute liver failure) or in the kidney (e.g., by an enhancer of FATP2 transport activity to treat kidney failure). In this embodiment, a therapeutically effective amount of an enhancer of the transport function of one or more of the fatty acid transport proteins can be administered to a mammalian subject, with the result that fatty acid uptake in the small intestine is enhanced. In this embodiment, one or more enhancers of one or more of fatty acid transport proteins is administered in an effective dose and by a route (e.g., orally or by a device, such as an indwelling catheter or other device) which can deliver doses to the gut. The enhancer of FATP function (e.g., an enhancer of FATP4 function) can be identified by methods described herein or can be one that is structurally similar to an enhancer identified by methods described herein.

Aerobic reperfusion of ischemic myocardium is a common clinical event which can occur during such treatments as cardiac surgery, angioplasty, and thrombolytic therapy after a myocardial infarction. During reperfusion, a rapid recovery of myocardial energy production is essential for the complete recovery of contractile function. Not only the extent of recovery of myocardial energy metabolism but also the type of energy substrate used by the heart during reperfusion are important determinants of functional recovery. Circulating fatty acid levels increase following acute myocardial infarction or during cardiac surgery, such that during and following ischemia the heart muscle can be exposed to very high concentrations of fatty acids (Lopaschuk, G. D. and W. C. Stanley, *Science and Medicine* (November/December 1997)). High plasma fatty acid concentrations increase the severity of ischemic damage in a number of experimental models of cardiac ischemia and have been linked to depression of mechanical function during aerobic reperfusion of previously ischemic hearts. Further data show that modifying fatty acid utilization can be beneficial for heart function in ischemia and can be a useful approach for the treatment of angina. See, e.g., Desideri and Celegon, *Am. J. Cardiol.* 82(5A):50K–53K; Lopaschuk, *Am. J Cardiol.* 82(5A): 14K–17K. Plasma fatty acid concentrations can be reduced by administering to a human subject or other mammal an effective amount of an inhibitor of a FATP such as FATP2 or FATP4, thereby providing a way of reducing fatty acid utilization by the heart.

In a further embodiment of the invention, a therapeutically effective amount of an inhibitor of hsFATP6 can be administered to a human patient by a suitable route, to reduce the uptake of fatty acids by cardiac muscle. This treatment is desirable in patients who are diagnosed as having, or who are at risk of, abnormal accumulations of fatty acids in the heart or a detrimentally high rate of uptake of fatty acids into the heart, because of ischemic heart disease, or following ischemia or trauma to the heart.

The invention further relates to antibodies that bind to an isolated or recombinant fatty acid transport protein of the FATP family, including portions of antibodies, which can specifically recognize and bind to one or more FATPs. The antibodies and portions thereof of the invention include those which bind to one or more FATPs of mouse or other mammalian species. In a preferred embodiment, the antibodies specifically bind to a naturally occurring FATP of humans. The antibodies can be used in methods to detect or to purify a protein of the present invention or a portion thereof by various methods of immunoaffinity chromatography, to inhibit the function of a protein in a method of therapy, or to selectively inactivate an active site, or to study other aspects of the structure of these proteins, for example.

The antibodies of the present invention can be polyclonal or monoclonal. The term antibody is intended to encompass both polyclonal and monoclonal antibodies. Antibodies of the present invention can be raised against an appropriate immunogen, including proteins or polypeptides of the present invention, such as an isolated or recombinant FATP1, FATP2, FATP3, FATP4, FATP5, FATP6, mtFATP, ceFATPa, ceFATPb, scFATP or portions thereof, or synthetic molecules, such as synthetic peptides (e.g., conjugated to a suitable carrier). Preferred embodiments are antibodies that bind to any of the following: hsFATP1, hsFATP2, hsFATP3, hsFATP4, hsFATP5 or hsFATP6. The immunogen can be a polypeptide comprising a portion of a FATP and having at least one function of a fatty acid transport protein, as described herein.

The term antibody is also intended to encompass single chain antibodies, chimeric, humanized or primatized (CDR-grafted) antibodies and the like, as well as chimeric or CDR-grafted single chain antibodies, comprising portions from more than one species. For example, the chimeric antibodies can comprise portions of proteins derived from two different species, joined together chemically by conventional techniques or prepared as a single contiguous protein using genetic engineering techniques (e.g., DNA encoding the protein portions of the chimeric antibody can be expressed to produce a contiguous protein chain. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., U.S. Pat. No. 5,585,089; and Queen et al., European Patent No. EP 0 451 216 B1. See also, Newman, R. et al., BioTechnology, 10:1455–1460 (1992), regarding primatized antibody, and Ladner et al., U.S. Pat. No. 4,946, 778 and Bird, R. E. et al., Science, 242:423–426 (1988) regarding single chain antibodies.)

Whole antibodies and biologically functional fragments thereof are also encompassed by the term antibody. Biologically functional antibody fragments which can be used include those fragments sufficient for binding of the antibody fragment to a FATP to occur, such as Fv, Fab, Fab' and F(ab')$_2$ fragments. Such fragments can be produced by enzymatic cleavage or by recombinant techniques. For instance, papain or pepsin cleavage can generate Fab or F(ab')$_2$ fragments, respectively. Antibodies can also be produced in a variety of truncated forms using antibody genes in which one or more stop codons have been introduced upstream of the natural stop site. For example, a chimeric gene encoding a F(ab')$_2$ heavy chain portion can be designed to include DNA sequences encoding the CH$_1$ domain and hinge region of the heavy chain.

Preparation of immunizing antigen (whole cells comprising FATP on the cell surface or purified FATP), and polyclonal and monoclonal antibody production can be performed using any suitable technique. A variety of methods have been described (See e.g., Kohler et al., Nature, 256: 495–497 (1975) and Eur. J. Immunol. 6: 511–519 (1976); Milstein et al.; Nature 266: 550–552 (1977), Koprowski et al., U.S. Pat. No. 4,172,124; Harlow, E. and D. Lane, 1988, Antibodies: A Laboratory Manual, (Cold Spring Harbor Laboratory: Cold Spring Harbor, N.Y.); Chapter 11 In Current Protocols In Molecular Biology, Vol. 2 (containing supplements up through Supplement 42, 1998), Ausubel, F. M. et al., eds., (John Wiley & Sons: New York, N.Y.)). Generally, a hybridoma can be produced by fusing a suitable immortal cell line (e.g., a myeloma cell line such as SP2/0) with antibody producing cells. The antibody producing cells, preferably those obtained from the spleen or lymph nodes, can be obtained from animals immunized with the antigen of interest. Immunization of animals can be by introduction of whole cells comprising fatty acid transport protein on the cell surface. The fused cells (hybridomas) can be isolated using selective culture conditions, and cloned by limiting dilution. Cells which produce antibodies with the desired specificity can be selected by a suitable assay (e.g., ELISA).

Other suitable methods of producing or isolating antibodies (including human antibodies) of the requisite specificity can used, including, for example, methods which select recombinant antibody from a library (e.g., Hoogenboom et al., WO 93/06213; Hoogenboom et al., U.S. Pat. No. 5,565, 332; WO 94/13804, published Jun. 23, 1994; and Dower, W. J. et al., U.S. Pat. No. 5,427,908), or which rely upon immunization of transgenic animals (e.g., mice) capable of producing a full repertoire of human antibodies (see e.g., Jakobovits et al., Proc. Natl. Acad. Sci. USA, 90: 2551–2555 (1993); Jakobovits et al., Nature, 362:255–258 (1993); Lonberg et al., U.S. Pat. No. 5,569,825; Lonberg et al., U.S. Pat. No. 5,545,806; Surani et al., U.S. Pat. No. 5,545,807; and Kucherlapati, R. et al., European Patent No. EP 0 463 151 B1).

Another aspect of the invention is a method for directing an agent to cardiac muscle. The differential expression of FATP6 in cardiac muscle but not in other tissue types allows for the specific targeting of drugs, diagnostic agents, tagging labels, histological stains or other substances specifically to cardiac muscle. A targeting vehicle can be used for the delivery of such a substance. Targeting vehicles which bind specifically to FATP6- can be linked to a substance to be delivered to the cells of cardiac muscle. The linkage can be, for instance, via one or more covalent bonds, or by high affinity non-covalent bonds. A targeting vehicle can be an antibody, for instance, or other compound (e.g., a fatty acid or fatty acid analog) which binds to FATP6 with high specificity.

Targeting vehicles specific to the heart-specific protein FATP6 have in vivo (e.g., therapeutic and diagnostic) applications. For example, an antibody which specifically binds to FATP6 can be conjugated to a drug to be targeted to the heart (e.g., a cardiac glycoside to treat congestive heart failure, or β-adrenergic agents, sodium channel blockers or calcium channel blockers to treat arrhythmias). A substance (e.g., a radioactive substance) which can be detected (e.g., a label) in vivo can also be linked to a targeting vehicle which specifically binds to a heart-specific protein such as FATP6, and the conjugate can be used as a labeling agent to identify cardiac muscle cells.

Targeting vehicles specific to FATP6 find further applications in vitro. For example, an FATP6-specific targeting vehicle, such as an antibody (a polyclonal preparation or monoclonal) which specifically binds to FATP6, can be linked to a substance which can be used as a stain for a tissue sample (e.g., horseradish peroxidase) to provide a method for the identification of cardiac muscle in a sample, as can be used in embryology studies, for example.

In a similar manner, an agent can be directed to the liver of a mammal, as FATP5 is expressed in liver but not in other tissue types. A targeting vehicle which specifically binds to FATP5 can be conjugated to a drug for delivery of the drug to the liver, such as a drug to treat hepatitis, Wilson's disease, lipid storage diseases and liver cancer. As with targeting vehicles specific to FATP6, targeting vehicles specific to FATP5 can be used in studying tissue samples in vitro.

The invention also relates to compositions comprising a modulator of FATP function. The term "modulate" as used herein refers to the ability of a molecule to alter the function of another molecule. Thus, modulate could mean, for example, inhibit, antagonize, agonize, upregulate, downregulate, induce, or suppress. A modulator has the capability of altering function of its target. Such alteration can be accomplished at any stage of the transcription, translation, expression or function of the protein, so that, for example, modulation of a target gene can be accomplished by modulation of the DNA or RNA encoding the protein, and the protein itself.

Antagonists or agonists (inhibitors or enhancers) of the FATPs of the invention, antibodies that bind a FATP, or mimetics of a FATP can be employed in combination with a non-sterile or sterile carrier or carriers for use with cells, tissues or organisms, such as a pharmaceutical carrier suitable for administration to a mammalian subject. Such compositions comprise, for instance, a media additive or a therapeutically effective amount of an inhibitor or enhancer compound to be identified by an assay of the invention and a pharmaceutically acceptable carrier or excipient. Such carriers may include, but are not limited to, saline, buffered saline, dextrose, water, ethanol, surfactants, such as glycerol, excipients such as lactose and combinations thereof. The formulation can be chosen by one of ordinary skill in the art to suit the mode of administration. The chosen route of administration will be influenced by the predominant tissue or organ location of the FATP whose function is to be inhibited or enhanced. For example, for affecting the function of FATP4, a preferred administration can be oral or through a tube inserted into the stomach (e.g., direct stomach tube or nasopharyngeal tube), or through other means to accomplish delivery to the small intestine. The invention further relates to diagnostic and pharmaceutical packs and kits comprising one or more containers filled with one or more of the ingredients of the aforementioned compositions of the invention.

Compounds of the invention which are FATPs, FATP fusion proteins, FATP mimetics, FATP gene-specific antisense poly- or oligonucleotides, inhibitors or enhancers of a FATP may be employed alone or in conjunction with other compounds, such as therapeutic compounds. The pharmaceutical compositions may be administered in any effective, convenient manner, including administration by topical, oral, anal, vaginal, intravenous, intraperitoneal, intramuscular, subcutaneous, intranasal, transdermal or intradermal routes, among others. In therapy or as a prophylactic, the active agent may be administered to an individual as an injectable composition, for example as a sterile aqueous dispersion, preferably isotonic.

Alternatively, the composition may be formulated for topical application, for example, in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions.

In addition, the amount of the compound will vary depending on the size, age, body weight, general health, sex, and diet of the host, and the time of administration, the biological half-life of the compound, and the particular characteristics and symptoms of the disorder to be treated. Adjustment and manipulation of established dose ranges are well within the ability of those of skill in the art.

A further aspect of the invention is a method to identify a polymorphism, or the presence of an alternative or variant allele of a gene in the genome of an organism (of interest here, genes encoding FATPs). As used herein, polymorphism refers to the occurrence of two or more genetically determined alternative sequences or alleles in a population. A polymorphic locus may be as small as a base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified alleleic form, or the most frequently occurring form can be arbitrarily designated as the reference (usually, "wildtype") form, and other allelic forms are designated as alternative (sometimes, "mutant" or "variant"). Dipolid organisms may be homozygous or heterozygous for allelic forms.

An "allele" or "allelic sequence" is an alternative form of a gene which may result from at least one mutation in the nucleotide sequence. Alleles may result in altered mRNAs or polypeptides whose structure or function may or may not be altered. Any given gene may have none, one, or many allelic forms (polymorphism). Common mutational changes which give rise to alleles are generally ascribed to natural deletions, additions, or substitutions of nucleotides. Each of these types of changes may occur alone, or in combination with the others, one or more times in a given sequence.

Several different types of polymorphisms have been reported. A restriction fragment length polymorphism (RFLP) is a variation in DNA sequence that alters the length of a restriction fragment (Botstein et al., *Am. J. Hum. Genet.* 32:314–331 (1980)). The restriction fragment length polymorphism may create or delete a restriction site, thus changing the length of the restriction fragment. RFLPs have been widely used in human and animal genetic analyses (see WO 90/13668; WO 90/11369; Donis-Keller, *Cell* 51:319–337 (1987); Lander et al., *Genetics* 121:85–99 (1989)). When a heritable trait can be linked to a particular RFLP, the presence of the RFLP in an individual can be used to predict the likelihood that the individual will also exhibit the trait.

Other polymorphisms take the form of short tandem repeats (STRs) that include tandem di-, tri- and tetranucleotide repeated motifs. These tandem repeats are also referred to as variable number tandem repeat (VNTR) polymorphisms. VNTRs have been used in identity and paternity analysis (U.S. Pat. No. 5,075,217; Armour et al., *FEBS Lett.* 307:113–115 (1992); Horn et al., WO 91/14003; Jeffreys, EP 370,719), and in a large number of genetic mapping studies.

Other polymorphisms take the form of single nucleotide variations between individuals of the same species. Such polymorphisms are far more frequent than RFLPs, STRs (short tandem repeats) and VNTRs (variable number tandem repeats). Some single nucleotide polymorphisms occur in protein-coding sequences, in which case, one of the polymorphic forms may give rise to the expression of a defective or other variant protein and, potentially, a genetic disease. Other single nucleotide polymorphisms occur in noncoding regions. Some of these polymorphisms may also result in defective protein expression (e.g., as a result of defective splicing). Other single nucleotide polymorphisms have no phenotypic effects.

Many of the methods described below require amplification of DNA from target samples and purification of the amplified products. This can be accomplished by PCR, for instance. See generally, *PCR Technology, Principles and Applications for DNA Amplification* (ed. H. A. Erlich), Freeman Press, New York, N.Y., 1992; *PCR Protocols: A Guide to Methods and Applications* (eds. Innis, et al.), Academic Press, San Diego, Calif., 1990; Mattila et al., *Nucleic Acids Res.* 19:4967 (1991); Eckert et al., *PCR Methods and Applications* 1:17 (1991); PCR (eds. McPherson et al., IRS Press, Oxford); and U.S. Pat. No. 4,683,202.

Other suitable amplification methods include the ligase chain reaction (LCR) (see Wu and Wallace, *Genomics* 4:560 (1989); Landegren et al., *Science* 241:1077 (1988)), transcription amplification (Kwoh et al., *Proc. Natl. Acad. Sci. USA* 86:1173 (1989), self-sustained sequence replication (Guatelli et al., *Proc. Natl. Acad. Sci. USA* 87:1874 (1990), and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

Another aspect of the invention is a method for detecting a variant allele of a human FATP gene, comprising preparing amplified, purified FATP DNA from a reference human and amplified, purified, FATP DNA from a "test" human to be compared to the reference as having a variant allele, using the same or comparable amplification procedures, and determining whether the reference DNA and test DNA differ in DNA sequence in the FATP gene, whether in a coding or a noncoding region, wherein, if the test DNA differs in sequence from the reference DNA, the test DNA comprises a variant allele of a human FATP gene. The following is a discussion of some of the methods by which it can be determined whether the reference FATP DNA and test FATP DNA differ in sequence.

Direct Sequencing. The direct analysis of the sequence of variant alleles of the present invention can be accomplished using either the dideoxy chain termination method or the Maxam and Gilbert method (see Sambrook et al., *Molecular Cloning: A Laboratory Manual,* 2nd ed., Cold Spring Harbor Press, New York 1989; Zyskind et al, *Recombinant DNA Laboratory Manual,* Acad. Press, 1988)).

Denaturing Gradient Gel Electrophoresis. Amplification products generated using the polymerase chain reaction can be analyzed by the use of denaturing gradient gel eletrophoresis. Different alleles can be identified based on the different sequence-dependent strand dissociation properties and electrophoretic migration of DNA in solution (chapter 7 in Erlich, ed. *PCR Technology, Principles and Applications for DNA Amplification,* W. H. Freeman and Co., New York, 1992).

Single-strand Conformation Polymorphism Analysis. Alleles of target sequences can be differentiated using single-strand conformation polymorphism analysis, which identifies base differences by alteration in electrophoretic migration of single stranded PCR products, as described in Orita et al., *Proc. Natl. Acad. Sci. USA* 86:2766–2770 (1989). Amplified PCR products can be generated as described above, and heated or otherwise denatured, to form single-stranded amplification products. Single-stranded nucleic acids may refold or form secondary structures which are partially dependent on the base sequence. The different electrophoretic mobilities of single-stranded amplification products can be related to base-sequence differences between alleles of target sequences.

Detection of Binding by Protein That Binds to Mismatches. Amplified DNA comprising the FATP gene or portion of the gene of interest from genomic DNA, for example, of a normal individual is prepared, using primers designed on the basis of the DNA sequences provided herein. Amplified DNA is also prepared, in a similar manner, from genomic DNA of an individual to be tested for bearing a distinguishable allele. The primers used in PCR carry different labels, for example, primer 1 with biotin, and primer 2 with $^{32}$P. Unused primers are separated form the PCR products, and the products are quantitated. The heteroduplexes are used in a mismatch detection assay using immobilized mismatch binding protein (MutS) bound to nitrocellulose. The presence of biotin-labeled DNA wherein mismatched regions are bound to the nitrocellulose via MutS protein, is detected by visualizing the binding of streptavidin to biotin. See WO 95/12689. MutS protein has also been used in the detection of point mutations in a gel-mobility-shift assay (Lishanski, A. et al., *Proc. Natl. Acad. Sci. USA* 91:2674–2678 (1994)).

Other methods, such as those described below, can be used to distinguish a FATP allele from a reference allele, once a particular allele has been characterized as to DNA sequence.

Allele-specific probes. The design and use of allele-specific probes for analyzing polymorphims is described by e.g., Saiki et al, *Nature* 324:163–1 66 (1986); Dattagupta, EP 235,726, Saiki, WO 89/11548. Allele-specific probes can be designed so that they hybridize to a segment of a target DNA from one individual but do not hybridize to the corresponding segment from another individual due to the presence of different polymorphic forms in the respective segments from the two individuals. Hybridization conditions should be sufficiently stringent that there is a significant difference in hybridization intensity between alleles, and preferably an essentially binary response, whereby a probe hybridizes to only one of the alleles. Some probes are designed to hybridize to a segment of target DNA such that the polymorphic site aligns with a central position (e.g., in a 15-mer at the 7 position; in a 16-mer, at either the 8 or 9 position) of the probe. This design of probe achieves good discrimination in hybridization between different allelic forms.

Allele-specific probes are often used in pairs, one member of a pair showing a perfect match to a reference form of a target sequence and the other member showing a perfect match to a variant form. Several pairs of probes can then be immobilized on the same support for simultaneous analysis of multiple polymorphisms within the same target sequence.

Allele-specific Primers. An allele-specific primer hybridizes to a site on target DNA overlapping a polymorphism, and only primes amplification of an allelic form to which the primer exhibits perfect complementarity. See Gibbs, *Nucleic Acid Res.* 17:2427–2448 (1989). This primer is used in conjunction with a second primer which hybridizes at a distal site. Amplification proceeds from the two primers, resulting in a detectable product which indicates the particular allelic form is present. A control is usually performed with a second pair of primers, one of which shows a single base mismatch at the polymorphic site and the other of which exhibits perfect complementarity to a distal site. The single-base mismatch prevents amplification and no detectable product is formed. The method works best when the mismatch is included in the 3'-most position of the oligonucleotide aligned with the polymorphism because this position is most destabilizing to elongation from the primer (see, e.g., WO 93/22456).

Gene Chips. Allelic variants can also be identified by hybridization to nucleic acids immobilized on solid supports (gene chips), as described, for example, in WO 95/11995 and U.S. Pat. No. 5,143,854, both of which are incorporated herein by reference. WO 95/11995 describes subarrays that are optimized for detection of a characterized variant allele. Such a subarray contains probes designed to be complementary to a second reference sequence, which is an allelic variant of the first reference sequence.

The present method is illustrated by the following examples, which are not intended to be limiting in any way.

EXAMPLES

Materials and Methods

The following Materials and Methods were used in the work described in Examples 1–5.

Sequence Alignment of FATP Clones. The DNA sequence for mouse FATP1 was obtained from the National Center for Biotechnology Information nonredundant database. cDNAs for mmFATP2, 3, 4, and 5 were obtained by screening mouse expression libraries (purchased from GIBCO/BRL) with probes derived from the cloned expressed sequence tags (ESTs) (Research Genetics, Huntsville, Ala.). Full-length clones were obtained for mmFATP2 and 5 and partial sequences for mmFATP3 and 4. The sequences described herein have been deposited in the GenBank database (Accession Nos. FATP2, AF072760; FATP3, AF072759; FATP4, AF072758; FATP5, AF072757).

Neither FATP2 nor FATP5 contains an in-frame stop codon upstream of the putative initiator methionine; initiator methionines were assigned by homology with that in mmFATP 1 and by the presence of a signal sequence immediately after it. The *Mycobacterium tuberculosis, Caenorhabditis elegans,* and *Saccharomyces cerevisiae* sequences were present in the dbEST database as part of the sequencing projects for these organisms. Sequences were aligned utilizing a ClustalX algorithm and the resulting alignment exported to SeqVu. Homologous amino acid substitutions are boxed in FIG. 1 and were determined using the Dayhoff 250 method with a 50% homology cutoff.

Cell Transfection and LCFA Uptake. COS cells were cotransfected using the DEAE-dextran method with the mammalian expression vector pCDNA 3.1 (Invitrogen) expressing the gene for CD2 (pCDNA-CD2) in combination with either a pCDNA 3.1 or pCMVSPORT2 (GIBCO/BRL) expression vector containing one of the murine or nematode FATP genes (pCDNA-mmFATP1 , pCDNA-FATP2, p CMVSPORT-FATP5, pCDNA-ceFATPb). Two days after transfection, cells were assayed for CD2 expression with a phycoerythrin-coupled anti-CD2(PE-CD2) monoclonal antibody (PharMingen), and fatty acid uptake was assayed with a BODIPY-labeled fatty acid analogue (Molecular Probes). Briefly, cells were washed twice with PBS (phosphate buffered saline) and stained with PE-CD2 at 4° C. for 30 min in PBS containing 10% fetal calf serum. They were then washed three times with PBS/fetal calf serum for 5 min followed by an incubation for 2 min at 37° C. in fatty acid uptake solution, which contained 0.1 $\mu$M BODIPY-FA and 0.1% fatty acid-free BSA (bovine serum albumin) in PBS (Schaffer, J. E. & Lodish, H. F. (1994) *Cell* 79:427–436). After 2 min, the cells were washed four times with ice-cold PBS/0.1% BSA. The cells were then removed from the plates with PBS containing 5 mM EDTA and resuspended in PBS containing 10% fetal calf serum and 10 mM EDTA. PE-CD2 and BODIPY-FA fluorescence were measured using a FACScan (Becton Dickinson). COS cells were gated on forward scatter (FSC) and side scatter (SS). Cells exhibiting more than 300 CD2 fluorescence units (dsim) representing 15% of all cells were deemed CD2 positive and their BODIPY-FA fluorescence was quantitated.

*E. coli*-Based LCFA Uptake Assay. The full-length coding region of mtFATP and a control protein, the mammalian transcription factor TFE3, were subcloned into the inducible, prokaryotic expression vector pET (Novagen). Expression was induced with 1 mM isopropyl β-D-thiogalactoside (IPTG) for 1 hour, or cells were left uninduced. Cells were washed in PBS/0.1% BSA and resuspended in 1 ml PBS/0.1% BSA containing 0.1 $\mu$M [$^3$H] palmitate (NEN) at 37° C. . Uptake was stopped after the indicated incubation time by transferring the cells onto filter paper using a cell harvester (Brandel, Bethesda, Md.). Filters were washed extensively with ice-cold PBS/0.1% BSA, and [$^3$H]palmitate was quantitated by scintillation counting.

Northern Blots. Northern blot analysis of murine FATP expression was done using poly(A) mRNA blots (Clontech). Probes of each of the FATPs were derived from the 3' untranslated regions of each gene and were <60% identical in sequence. Probes were labeled by random priming (Boehringer Mannheim) and hybridized at 65 ° C. Blots were extensively washed in 0.2% SSC/0.1% SDS at 65° C.

Figure 5:
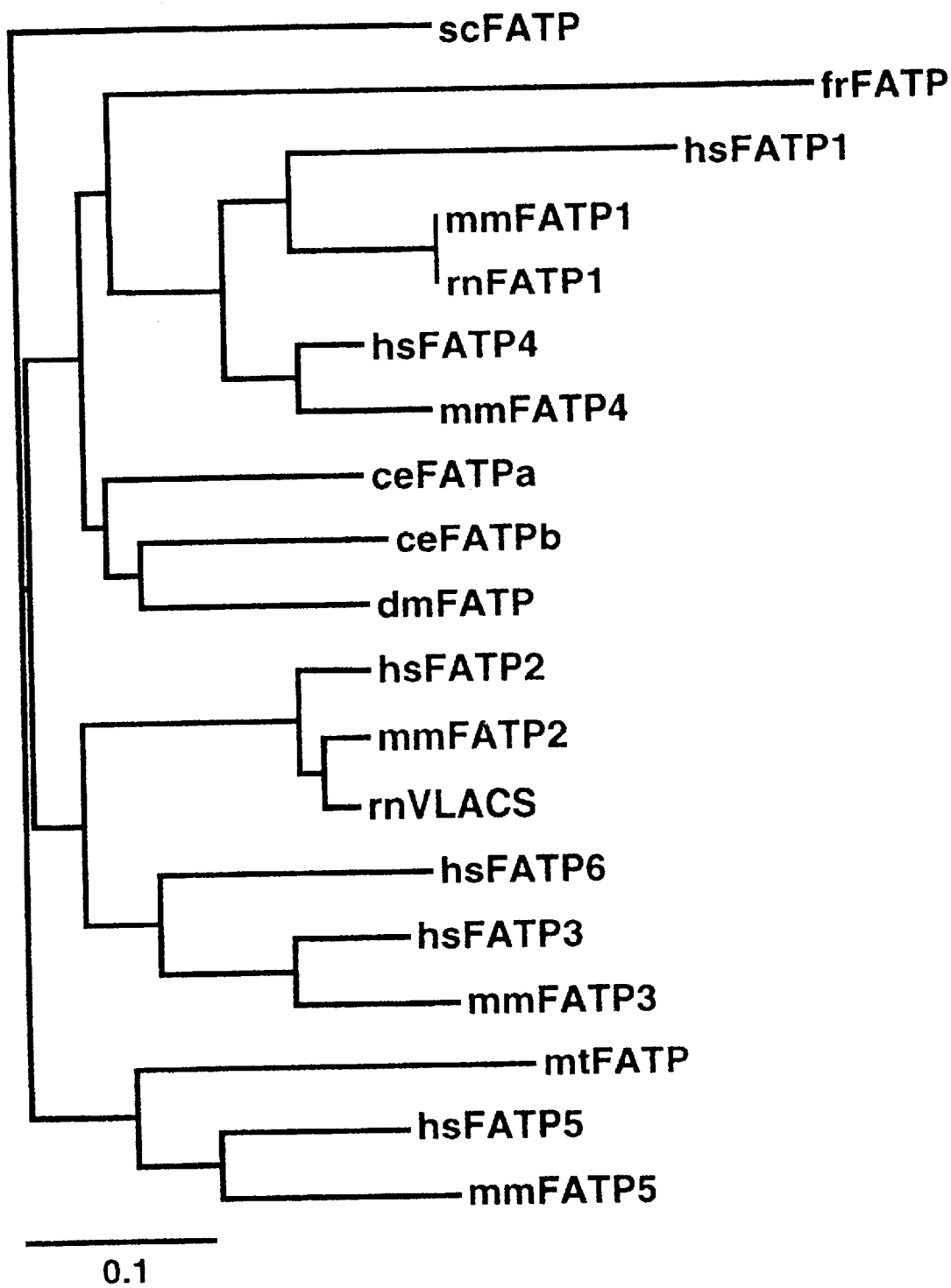
FIG. 5 is a phylogenetic tree produced by aligning complete and partial sequences for FATP genes from human, rat, mouse, puffer fish, D. melanogaster, C. elegans, S. cerevisiae, and M. tuberculosis using ClustalX and using these data to produce a phylogenetic tree using TreeView-PPC. The bar indicates the number of substitutions per residue, i.e., 0.1 corresponds to a distance of 10 substitutions per 100 residues.
Figure 6:
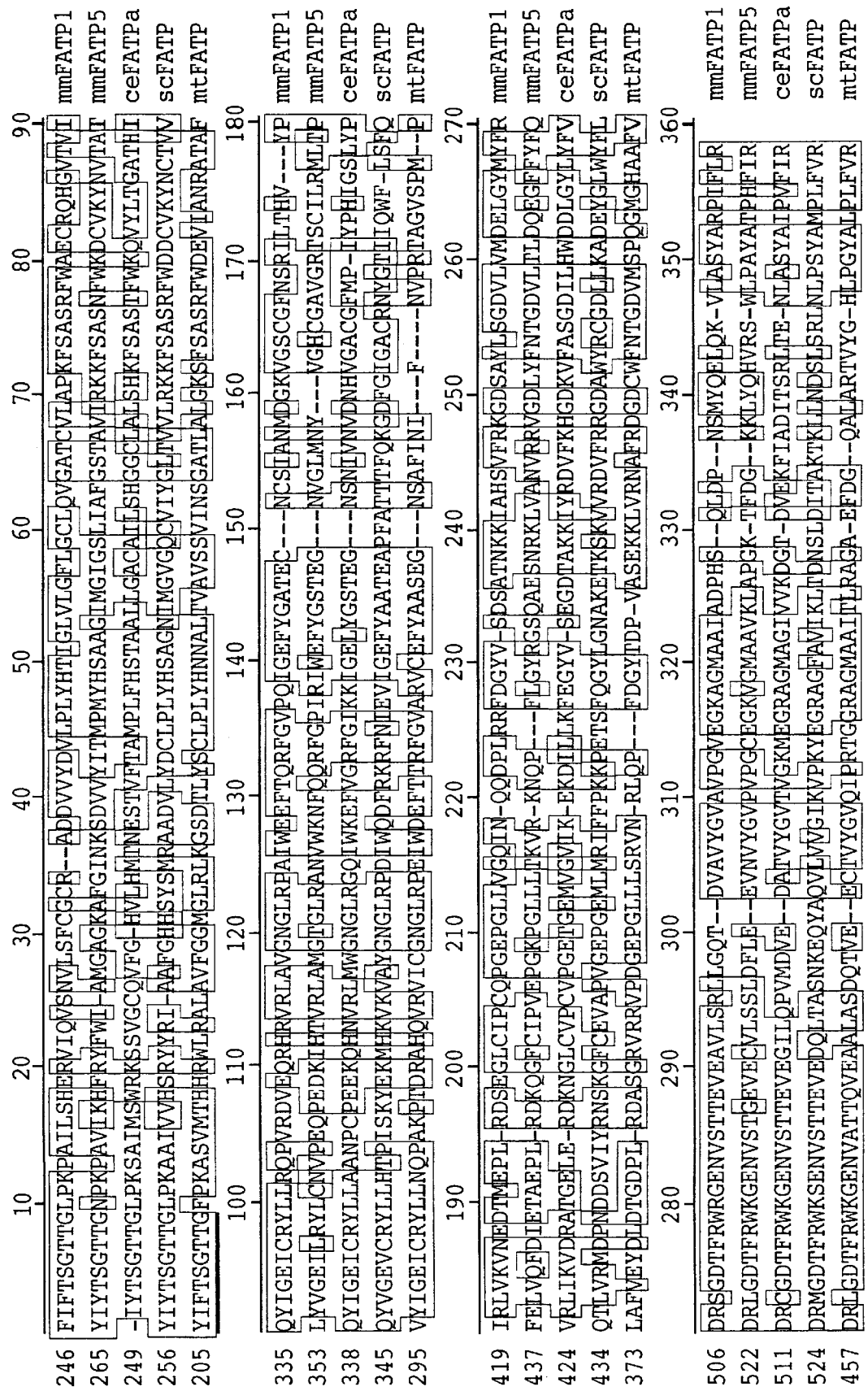
FIG. 6 shows a comparison of the FATP signature sequences of mmFATP 1 (SEQ ID NO:1), mmFATP5, (SEQ ID NO:2), ceFATPa (SEQ ID NO:3), scFATP (SEQ ID NO:4) and mtFATP (SEQ ID NO:5).

Generation of Phylogenetic Trees. Complete and partial sequences for FATP genes from human, rat, mouse, puffer fish, *Drosophila melanogaster, C. elegans, S. cerevisiae,* and *M. tuberculosis* were aligned using ClustalX. A homologous region of 48 amino acids (residues 472–519 in mmFATP1) from all of the genes was used to determine phylogenetic relationship within ClustalX. Based on these data a phylogenetic tree was generated using Tree View PPC (FIG. 5).

Nomenclature. It is proposed that the FATP genes be given a species specific prefix (mm, *Mus musculus;* hs, *Homo sapiens;* mt, *M. tuberculosis;* dm, *D. melanogaster;* ce, *C. elegans,* sc, *S. cerevisiae*) and numbered such that mammalian homologues in different species share the same number but differ in their prefix. Since the two *C. elegans* genes cannot be paired with a specific human or mouse FATP, they have been designated ceFATPa and ceFATPb.

Example 1: Identification of Novel Mammalian FATPs

The National Center for Biotechnology Information EST database was screened, using the mouse FATP protein sequence (mmFATP 1), to identify novel FATPs. This strategy led to the identification of more than 50 murine EST sequences which could be assembled into five distinct contiguous DNA sequences (contigs). One contig was identical to the previously cloned FATP, which has been renamed FATP1. Another, which has been renamed FATP2, is the murine homologue of a rat gene previously identified by others as a very long chain acyl-CoA synthase (Uchiyama, A., Aoyama, T., Kamijo, K., Uchida, Y., Kondo, N., Orii, T. & Hashimoto, T. (1996) *J. Biol. Chem.* 271:30360–30365). The other three contigs represented novel genes (FATP3, 4, and 5). Full-length clones for FATP2 and FATP5 and nearly complete sequences for FATP3 and 4 (FIG. 1) were obtained by screening cDNA libraries made from mouse day 10.5 embryos and adult liver. Also identified were human homologues for each of the murine genes in the EST database. A sixth human gene was also identified; whether this gene is also present in the mouse will require additional studies. Map positions are given in Tables 2 and 3.

The genetic loci for all of the human genes, with the exception of FATP5 which was already mapped as an unknown EST, were determined using the radiation hybrid panels. The map positions given below show the distance (in centiRays) from the closest framework marker. As a guideline, there are approximately 300 kb/cR.

TABLE 2

Mapping Data for Human Genes

| | |
|---|---|
| hsFATP1 | Chromosome Chr19 |
| | places 13.35 cR from WI-6344 (lod > 3.0) |
| hsFATP2 | Chromosome Chr15 |
| | places 4.92 cR from D15S126 (lod > 3.0) |
| hsFATP3 | Chromosome Chr1 |
| | places 13.24 cR from WI-2862 (lod > 3.0) |
| hsFATP4 | Chromosome Chr9 |
| | places 7.80 cR from WI-9685 (lod > 3.0) |
| hsFATP5 | unknown EST previously mapped to near D19S418 |
| hsFATP6 | Chromosome Chr5 |
| | places 1.41 cR from WI-4907 (lod > 3.0) |

The mouse map is an internal backcross panel consisting of 188 mouse backcross DNA's plus 4 controls (B6, Spretus, F1, Water). The backcross was constructed by crossing B6 by Spretus animals and then crossing those F1's back to B6. Mapping is accomplished by taking advantage of recombinational events during meiosis, and the use of PCR primers to detect the differences (by size or re-annealing events) at any given locus between the B6 and Spretus allele.

For the purposes of mapping, a novel set of primers (gene of interest) is used to amplify from all 188 DNA's and then typed as being a B6 ("B") or a Spretus ("S"). This string of B's and S's is entered into the Map Manager program, which does a best fit calculation by comparing the string of 188 typings from the gene of interest to all loci already extant in the panel, for all 20 chromosomes. The gene of interest is then assigned to a particular area on a particular chromosome according to a number of parameters, including the minimalization of double cross-overs, and the highest LOD scores. Indicated in Table 3 are distances to the closest markers on either side of the FATP locus.

TABLE 3

Mapping Data for Mouse Genes

| | |
|---|---|
| mmFATP1 | Chromosome 8 |
| | places 2.82 cM from D8Mit132 (lod 43.4) and 1.81 cM from D8Mit74 (lod 43.5) |
| mmFATP2 | Chromosome 2 |
| | places 1.29 cM from D2Mit258 (lod 47.9) and 1.75 cM from D2NDS3 (lod 44.9) |
| mmFATP3 | Chromosome 3 |
| | places 2.54 cM from D3Mit22 (lod 29.5) and 19.62 cM from D3Mit42 (lod 13.6) |
| mmFATP4 | Chromosome 2 |
| | places 13.78 cM from D2Mit1 (lod 22.9) and 3.85 cM from D2Mit65 (lod 41.9) |
| mmFATP5 | Chromosome 7 |
| | places 7.28 cM proximal of D7Mit21 (lod 28.3) |

Example 2: Assessment of Function

The ability of the newly identified mouse genes to function as fatty acid transporters was assessed using a fluorescence-activated cell sorting-based assay. COS cells were transiently cotransfected with expression vectors encoding the cell surface protein CD2 and either FATP1, mmFATP2, or mmFATP5, respectively. Two days after transfection, COS cells were stained with an antibody to CD2 and then incubated with a BODIPY-labeled fatty acid [BODIPY-FA, (Schaffer, J. E. & Lodish, H. F. (1994) Cell 79.427–436)]. The cells were then washed extensively, lifted off the dish, and analyzed by fluorescence-activated cell sorting. As judged by the number of CD2-positive cells, the transfection efficiency was approximately 20–30%. Fatty acid uptake was quantitated in the transiently transfected COS cells by measuring the BODIPY-FA fluorescence of the CD2-positive cells. Expression of CD2 had no effect on fatty acid uptake as shown by the finding that COS cells expressing only the transfected CD2 cDNA (CD2-positive) had the same low level of BODIPY-FA uptake as did untransfected (CD2-negative) control cells (FIG. 2A, control). In COS cells cotransfected with CD2 and mmFATP1, mmFATP2, or mmFATP5, uptake of BODIPY-FA by the transfected (CD2-positive) cells was increased between 15- to 90-fold over control (CD2 cDNA only) cells (FIGS. 2A–2D).

Example 3: Expression Patterns of Murine FATPs

Expression patterns of members of the murine FATP gene family were characterized by Northern blot analysis; to avoid cross-hybridization, the probes used were from the 3' untranslated region of these genes, which are less than 60% identical in sequence. The expression pattern of FATP1 agrees with that previously found (Schaffer, J. E. & Lodish, H. F. (1994) Cell 79:427–436). Here, expression was seen primarily in heart and kidney. FATP2 is expressed almost exclusively in liver and kidney, which corresponds to the reported tissue distribution of the rat homologue [very long chain acyl-CoA (VLACS)] as assessed by Western blotting (Uchiyama, A., Aoyama, T., Kamijo, K., Uchida, Y., Kondo, N., Orii, T. & Hashimoto, T. (1996) J. Biol. Chem. 271:30360–30365). FATP3 is present in lung, liver, and testis. FATP5 is expressed only in liver and cannot be detected in other tissues even when the blot is overexposed. The human homologue of FATP5 is also liver specific and is not expressed in a wide array of other tissues tested, including fetal liver.

Example 4: FATPs Are Evolutionarily Conserved

Figure 3:
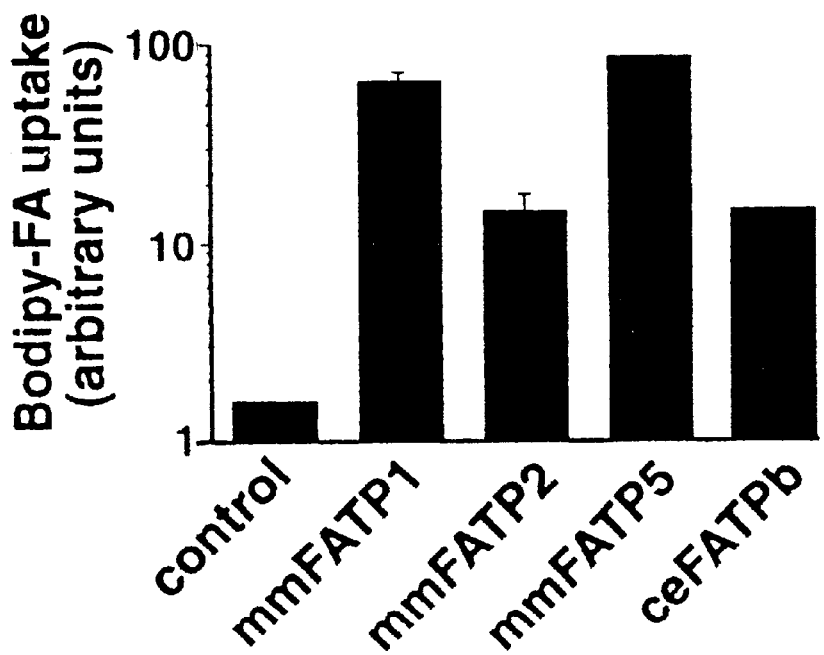
FIG. 3 is a graph of fluorescence of cells expressing a FATP gene. As in FIGS. 2A–2D, COS cells were cotransfected with pCDNA-CD2 either alone (control) or in combination with one of the FATP-containing expression vectors (pCDNA-mmFATP1, pCDNA-mmFATP2, pCMV-SPORT2-mmFATP5, or pCDNA-ceFATPb). The mean BODIPY-FA fluorescence of the CD2-positive cells is plotted; results shown represent the average of three experiments, each consisting of greater than 50,000 COS cells. Note that a logarithmic scale is used on the ordinate.
Figure 4:
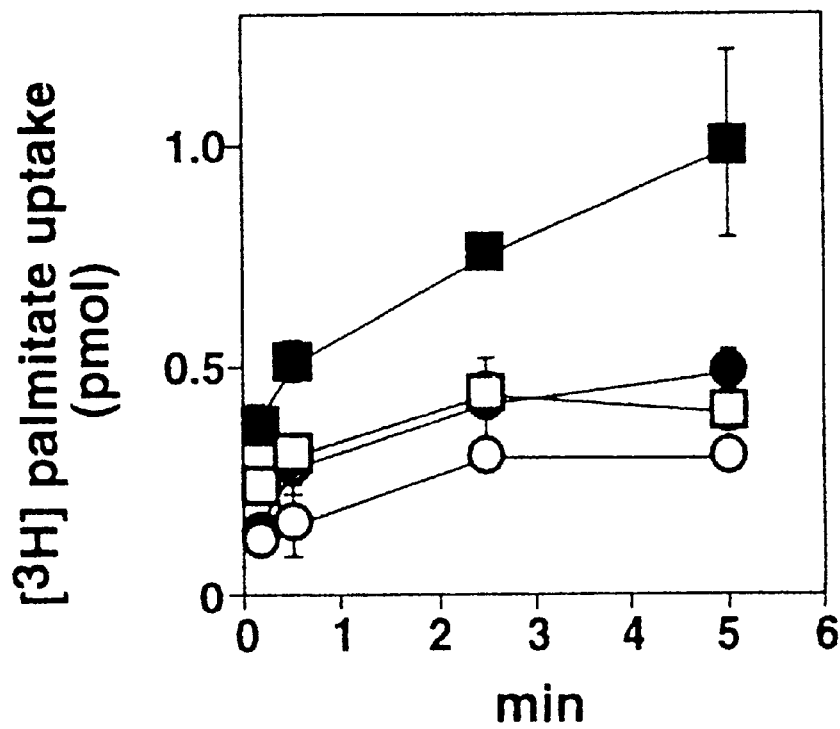
FIG. 4 is a graph of the uptake of palmitate with time. The full-length coding region of mtFATP (squares) or a control protein (TFE3; circles) was subcloned into the inducible, prokaryotic expression vector pET (Novagen). Expression from the resulting plasmid was induced (solid symbols) in transformed E. coli cells with 1 mM isopropyl-β-D-thiogalactoside (IPTG) for 1 hour, or cells were left uninduced (open symbols). Data points were done in triplicate and counts were normalized to the number of bacteria as determined by $OD_{600}$.

The EST database was searched, using sequences conserved among the five murine FATP genes, for FATP genes in other organisms. Two homologues were found in C. elegans and one in M. tuberculosis. One of the C. elegans genes was cloned from a cDNA library and expressed in COS cells, as described for the murine FATPs. Overexpression of the nematode FATP resulted in a 15-fold increase of BODIPY-FA uptake compared with control cells (FIG. 3). The mycobacterial FATP gene was isolated from a phage library and assessed for its ability to facilitate fatty acid uptake. E. coli transformed with a prokaryotic, isopropyl β-D-thiogalactoside-inducible expression vector containing the mycobacterial FATP gene demonstrated a significant increase in the rate of [$^3$H]palmitate uptake after induction, compared with uninduced bacteria or E. coli transformed with a control protein (FIG. 4). Novel FATP genes were also identified in F. rubripes (puffer fish) and D. melanogaster.

Example 5: Phylogenetic Tree of FATPs

Faergeman et al. (Faergeman, N. J., DiRusso. C. C., Elberger, A., Knudsen, J. & Black, P. N. (1997) J. Biol. Chem. 272:8531–8538) identified three regions of very strong conservation between the scFATP and mmFATP1 genes. The sequences of the FATPS were compared over a 311-amino acid FATP "signature sequence" which includes these conserved regions corresponding to amino acids 246–557 in mmFATP1 (underlined in FIG. 1). When compared with the National Center for Biotechnology Information nonredundant database, only one region of the "FATP signature sequence" shows significant homology to other proteins. This small stretch of amino acids (underlined in FIG. 1) is an AMP-binding motif found in a multitude of other proteins, such as acyl-CoA synthase, several CoA lipases, and gramicidin S synthetase component II (Schaffer, J. E. & Lodish, H. F. (1994) Cell 79:427–436). The relevance of this motif to fatty acid transport is unclear. Other highly conserved regions among the FATPs, including long stretches of amino acids >90% identical from mycobacteria to humans, are not found in any other class of proteins. A 48-amino acid segment of the FATP signature sequence was used to construct a phylogenetic tree (FIG. 5). Each of the human and mouse genes form their own branch; hsFATP6, which as yet has no murine homologue, is most closely related to hsFATP3 and mmFATP3. As expected, rnVLACS is closer in sequence to mmFATP2 than to hsFATP2. The FATP genes of invertebrates i.e., *C. elegans* and *D. melanogaster*, are most closely related to each other. Surprisingly, the mycobacteral gene is more closely related to the human and mouse FATP5 genes than to the FATPs of any of the lower organisms. Whether this reflects coevolution of the mycobacterial and human genes awaits further study.

Materials and Methods

The following materials and methods were used in the work described in Examples 6–10.

Isolation of Full-length Human FATP 1 and 4

Full-length clones encoding human FATP1 and human FATP4 were identified by searching databases for sequences similar to murine FATP1–5 coding regions using the BlastX algorithm (Altschul et al., *J. Mol. Biol.* 215: 403–410, 1990).

A concatamer of nucleotide sequences comprising the coding sequences of mmFATP1 (Genbank Accession U15976), mmFATP2, mmFATP3 (SEQ ID NO:6), mmFATP4 (SEQ ID NO:8) and mmFATP5 (SEQ ID NO:10) was used to search the Millennium database using the BLASTX algorithm. Sequences with a score >150 were evaluated for whether they represented known FATP coding sequences.

Human clones with similarity to the 5' end of murine FATP sequences were sequenced completely. Clones encoding full-length human FATP1 were obtained from a heart cDNA library constructed in the mammalian expression vector pMET7 (Tartaglia et al., *Cell*, 83: 1263–1271, 1995). Clones encoding full-length human FATP4 were obtained from a spleen cDNA library constructed in the mammalian expression vector pMET7.

Isolation of Full-length Human FATP6

Several clones encoding human FATP6 were identified by searching public databases as described above. Five clones were analyzed further by restriction digestion and DNA sequencing. One of these clones (Genbank Accession #AA412064) appeared to be full-length and its entire insert was sequenced.

DNA Sequence Analysis

Sequences were aligned with the DNAStar program using the Clustal method. Hydrophobicity plots were generated with DNA Strider using the Kyte Doolittle method.

In situ Hybridization

Tissues were collected from 8 week old C57/B16 mice. Tissues were fresh frozen, cut on a cryostat at 10 μm thickness and mounted on Superfrost Plus slides (VWR). Sections were air dried for 20 minutes and then incubated with ice cold 4% paraformaldehyde (PFA)/phosphate buffered saline (PBS) for 10 minutes. Slides were washed 2 times 5 minutes with PBS, incubated with 0.25% acetic anhydride/1 M triethanolamine for 10 minutes, washed with PBS for 5 minutes and dehydrated with 70%, 80%, 95% and 100% ethanol for 1 minute each. Sections were incubated with chloroform for 5 minutes. Hybridizations were performed with $^{35}$S-radiolabeled ($5\times10^7$ cpm/ml) cRNA probes generated from the 3' untranslated regions of mouse FATPs by PCR followed by in vitro transcription in the presence of 50% formamide, 10% dextran sulfate, 1×Denhardt's solution, 600 mM NaCl, 10 mM DTT, 0.25% SDS and 10 μg/ml tRNA for 18 hours at 55 °C. After hybridization, slides were washed with 10 mM Tris-HCl pH 7.6, 500 mM NaCl, 1 mM EDTA (TNE) for 10 minutes, incubated in 40 μg/ml RNase A in TNE at 37° C. for 30 minutes, washed in TNE for 10 minutes, incubated once in 2×SSC at 60° C. for 1 hour, once in 0.2×SSC at 60° C. for 1 hour, once in 0.2×SSC at 65° C. for 1 hour and dehydrated with 50%, 70%, 80%, 90% and 100% ethanol. Localization of mRNA transcripts was detected by dipping slides in Kodak NBT-2 photoemulsion and exposing for 7 days at 4° C., followed by development with Kodak Dektol developer. Slides were counter stained with haematoxylon and eosin and photographed. Controls for the in situ hybridization experiments include the use of a sense probe which showed no signal above background in all cases.

Northern Blotting

Human mRNA blots were obtained from Invitrogen or Clontech. PCR fragments from the 3' untranslated regions of human FATPs were used as probes. Blots were probed with $^{32}$P-labeled DNA probes using the Rapid-Hyb buffer (Amersham) according to the manufacturer's instructions.

Cell transfection and LCFA uptake. COS cells were cotransfected, using lipofectamine (GIBCO BRL) according to the manufacturer's instructions, with the mammalian expression vector pCDNA3.1 (Invitrogen) expressing the gene for CD2 in combination with a pMET7 expression vector (Tartaglia et al., *Cell,* 83:1263–1271, 1995) containing hsFATP1 (pMET7-hsFATP1) or hsFATP4 (pMET7-hsFATP4) or pMET7 alone. Two days after transfection, cells were assayed for CD2 expression with a phycoerythrin-coupled anti-CD2 (PE-CD2) monoclonal antibody (PharMingen), and fatty acid uptake was assayed with a BODIPY-labeled fatty acid analog (Molecular Probes) as described above.

Example 6: Determination of Expression of mmFATPs mmFATP4, and to lesser extent mmFATP2, are expressed at high levels in the brush border layer of the small intestine.

Cell transfection and LCFA uptake. COS cells were cotransfected, using lipofectamine (GIBCO BRL) according to the manufacturer's instructions, with the mammalian expression vector pCDNA3.1 (Invitrogen) expressing the gene for CD2 in combination with a pMET7 expression vector (Tartaglia et al., *Cell,* 83:1263–1271, 1995) containing hsFATP1 (pMET7-hsFATP1) or hsFATP4 (pMET7-hsFATP4) or pMET7 alone. Two days after transfection, cells were assayed for CD2 expression with a phycoerythrin-coupled anti-CD2 (PE-CD2) monoclonal antibody (PharMingen), and fatty acid uptake was assayed with a BODIPY-labeled fatty acid analog (Molecular Probes) as described above.

Absorption of dietary fat requires transport of free fatty acids across the apical membrane of epithelial cells in the small intestine. Previous studies suggested that this transport is protein-mediated; however, the transport protein had not yet been identified. In situ hybridization was performed on each of the three regions of the small intestine—duodenum, jejunum and ileum—as well as the colon, using probes from the 3' untranslated regions of mmFATP1, mmFATP2, mmFATP3, mmFATP4 and mmFATP5, to determine whether any of the mouse FATPs are expressed in the small intestine. It was expected that a protein involved in fatty acid absorption would be expressed in the epithelial cells of the small intestine, but absent from the colon.

Expression of mmFATPs in the jejunum was identical to that in the ileum in all cases. High levels of mmFATP4 mRNA were present in the epithelial cells of the jejunum and ileum, and lower, but significant, amounts were detected in the epithelial cells of the duodenum. Significantly, FATP4 mRNA was absent from other cell types of the small intestine and no FATP4 mRNA could be detected in any of the cells of the colon. FATP2 mRNA was present in the epithelial cells of the duodenum at a level similar to that of FATP4, but was present at lower levels in the jejunum and ileum. No signals above background were detected for mmFATP1, mmFATP3 and mmFATP5 in any of the intestinal tissues. mmFATP3 and FATP5 were clearly detectable by in situ hybridization in adult liver and mmFATP1 could be detected in a variety of tissues on a whole embryo in situ, indicating that the FATP 1, 3, and 5 probes were working.

mmFATP4 expression is predominant in the small intestine compared to the other organs of the mouse embryo. In the small intestine, FATP4 expression is limited to differentiated enterocytes, while no signal is detected in the connective tissue or the undifferentiated epithelial cells in the crypts. Differentiated enterocytes are known to be the cells that mediate the uptake of fatty acids. FATP4 is specifically and strongly expressed in the epithelial cells of adult murine duodenum and ileum but not colon. Other FATPs, such as FATP5, are not expressed in the small intestine. Thus, FATP4 is the major FATP in the mouse small intestine. Given its high level of expression, it is likely that FATP4, and to a lesser extent FATP2, play an important role in the absorption of fatty acids.

mmFATP2, and mmFATP5 are Expressed in Hepatocytes

Northern analysis of mmFATP2, mmFATP3, mmFATP4 and mmFATP5 showed expression in the liver. To determine whether these proteins are present in hepatocytes or other cells types present in liver homogenates, in situ hybridizations were performed. mmFATP2, and mmFATP5 mRNA was clearly present in hepatocytes, and was not concentrated in other cell types such as endothelial cells or macrophages. No signal above background was detected for mmFATP1 in any of the cell types in the liver, consistent with the results of the Northern blotting.

Example 7: Isolation and Sequence Analysis of Full-length Human FATP1 and Full-length Human FATP4

To identify human cDNA clones encoding FATP family members, Millennium databases were searched for sequences similar to murine FATP1–5 coding regions. Two clones were analyzed in detail; inspection of the entire DNA sequence of these two clones showed that they encode the human orthologs of mmFATP 1 and mm FATP4, respectively. These two clones were designated hsFATP 1 and hsFATP4, and their DNA and predicted protein sequences are shown in FIGS. 44A–44D and 45, and 50A–50C and 51.

hsFATP 1 is predicted to encode a 646 amino acid, 71 kD protein with multiple membrane-spanning domains (FIG. 28A). HsFATP4 is predicted to encode a 643 amino acid, 72 kD protein with multiple membrane spanning domains (See FIG. 29A). A comparison of the DNA sequences of mouse and human FATP1and mouse and human FATP4 (FIGS. 30A–30F and 31A–31I) shows that the mouse and human orthologs are 85% (FATP1) and 87% (FATP4) identical to each other within the coding sequences given in these figures. At the amino acid level, hsFATP1 and hsFATP4 are ~90% identical to their respective mouse orthologs within the coding region shown in these figures (FIGS. 32A–32C and 33A–33C). The sequence identities between mouse and human FATP1 and FATP4 are considerably higher than the ones observed between different FATP family members within one species (~40%–60%) and are present in the N-terminal part of the protein, a region that is poorly conserved between different FATP family members. This high degree of sequence conservation clearly demonstrates that the newly identified human FATPs are orthologs of mouse FATP1and FATP4 rather than novel FATP family members.

Table 4 is an identity/similarity matrix comparing the amino acid sequences of FATP1and 4 from human and mouse. This shows that the gene whose sequence is shown in FIG. 43A is indeed human FATP4, since it is 91% identical with the murine FATP4 but only 62% identical with the closest related human FATP, which is FATP1.

TABLE 4

Identity/Similarity Matrix

| | hsFATP4 | mmFATP4 | hsFATP1 | mmFATP1 |
|---|---|---|---|---|
| hsFATP4 | — | 93.2 | 72.3 | 72.0 |
| mmFATP4 | 91.0 | — | 71.2 | 71.1 |
| hsFATP1 | 61.9 | 61.0 | — | 92.4 |
| mmFATP1 | 60.7 | 59.6 | 89.5 | — |

Example 8: Isolation and Sequence Analysis of Full-length Human FATP6

A search of EST databases identified a set of overlapping human sequences that were similar to FATPs, but did not have a clear mouse ortholog. One of these EST clones was found to encode a full-length cDNA. The entire insert of this clone was sequenced and designated hsFATP6. The DNA and predicted protein sequences of hsFATP6 are shown in FIGS. 54A–54C and 55. HsFATP6 is predicted to encode a 619 amino acid, 70 kD protein with multiple membrane-spanning domains (FIG. 35A). A comparison of the amino acid sequences of hsFATP6 with other human FATPs shows about 37% identity to either hsFATP1 or hsFATP4 (FIGS. 36A–36G). This degree of sequence identity is similar to what is observed between different mouse FATPs. The phylogenetic analysis described above clearly demonstrates that hsFATP6 is a member of the FATP family, but not an ortholog of any of the mouse FATPs. Comparisons were done with "ALIGN" (E. Myers and W. Miller, "Optimal Alignments in Linear Space," CABIOS 4:11–17 (1988) using standard settings.

Example 9: Tissue Distribution of Human FATPs

The tissue distribution of human FATPs was assessed by Northern blotting. Human FATP3 was expressed in a large variety of tissues. In contrast, human FATP5 was present at high levels in the liver, but was undetectable in all other tissues examined. Thus, both hsFATP3 and hsFATP5 recapitulate the expression pattern of their mouse orthologs (see above). HsFATP6 is a novel FATP with no mouse ortholog as yet. Northern blotting shows that hsFATP6 is expressed at high levels in the heart, but is undetectable in other tissues, including skeletal and smooth muscle. This tissue distribution suggests that human FATP6 performs an important role in energy metabolism in the heart; blocking FATP6-mediated fatty acid transport may therefore be beneficial for a number of heart diseases, e.g., ischemic heart disease.

To identify the major FATP expressed in the human small intestine, Northern blotting was performed on a blot containing mRNA from human stomach, jejunum, ileum, colon, rectum and lung. hsFATP5 and hsFATP6 were undetectable in any of these tissues. FATP5 is only expressed in liver and FATP6 only in heart. hsFATP2 was weakly expressed in the colon, and an even weaker signal was detectable in jejunum, ileum and lung lanes. hsFATP3 was expressed well in the lung, but was only weakly expressed in the other tissues tested. Importantly, no difference was seen in the expression of hsFATP3 between small intestine and stomach or colon, suggesting that the expression observed is not related to fatty acid absorption in the small intestine. hsFATP4 was clearly expressed in both jejunum and ileum; expression was significantly lower in the colon and was absent in the stomach. This expression pattern is consistent with a major role for FATP4 in absorption of fatty acids in the human gut.

Example 10: Expression of hsFATP1 and hsFATP4 Promotes Transport of Fatty Acids

Figure 37:
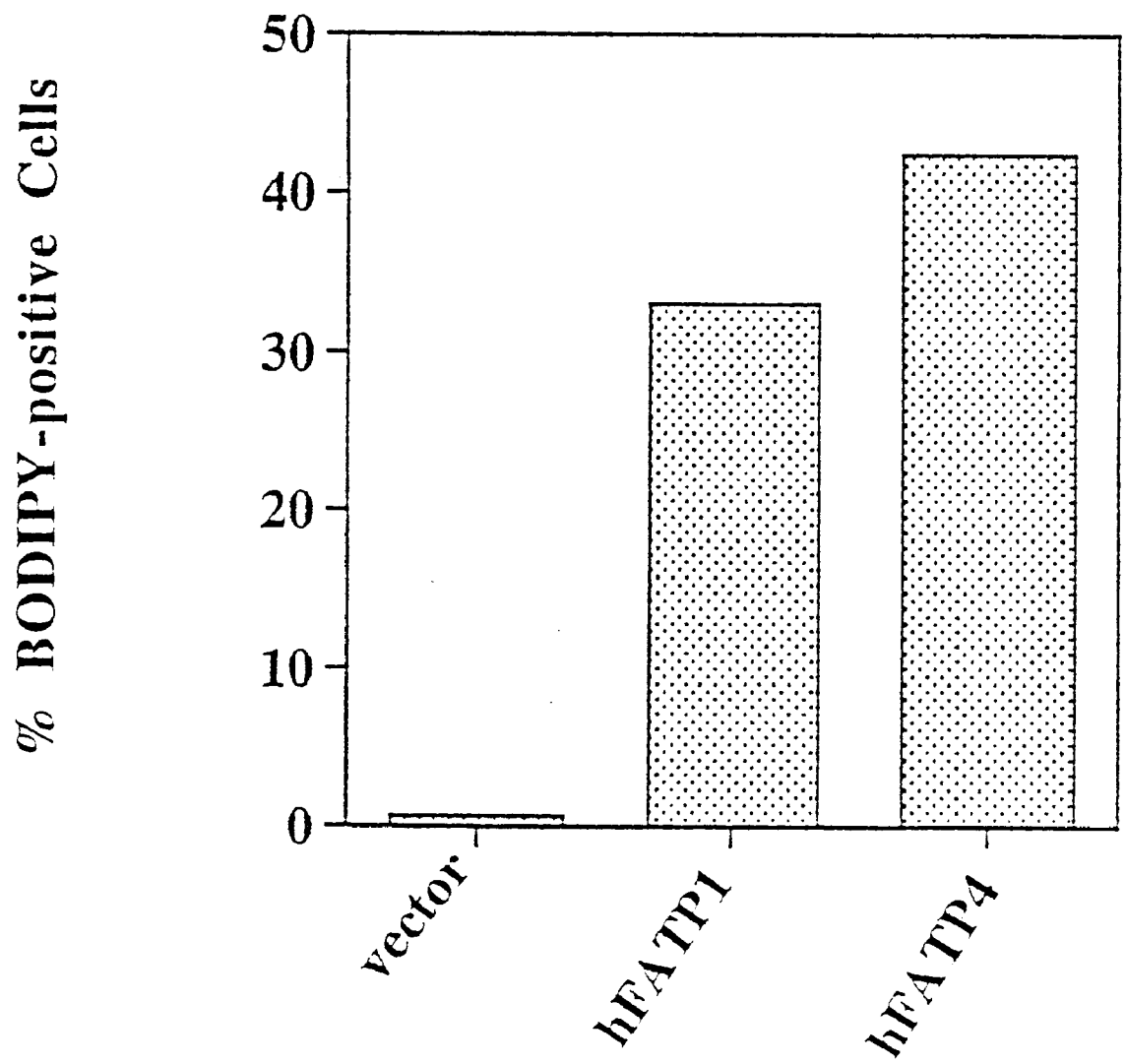
FIG. 37 shows results of assessment of fatty acid uptake by human FATP 1 and human FATP4. The percent of CD2-positive cells exhibiting a BODIPY-fluorescence of more than 300 arbitrary units is plotted for the three different conditions tested.

COS cells were cotransfected using lipofectamine with the mammalian expression vector pCDNA-CD2 in combination with one of the FATP-containing expression vectors (pMET7-hsFATP1 or pMET7-hsFATP4) or an insertless expression vector (pMET7, control) as described in Materials and Methods for Examples 6–10. COS cells were gated on forward scatter and side scatter. Cells exhibiting more than 400 CD2 fluorescence units representing ~30% of all cells were deemed CD2-positive. The percent of CD2-positive cells exhibiting a BODIPY-fluorescence of >300 is plotted for the three different vectors tested (FIG. 37).

Example 11: Stable Expression of Human FATP4 in 293 Cells

Stable cell lines were generated as follows. A DNA fragment containing the entire hsFATP4 coding sequence as well as 100 nucleotides of 5' and 50 nucleotides of 3' untranslated region was inserted into the vector pIRES-neo (Clontech) using standard cloning techniques. The resulting construct or a vector control (pIRES-neo) was transfected into 293 cells using the lipofectamine method (Gibco BRL) according to the manufacturer's directions. Cells that had taken up the DNA were selected with 1 mg/ml G418 (Gibco BRL). Single colonies were picked 1 to 2 weeks after transfection and grown in medium containing 0.8 mg/ml G418. Colonies were screened for the ability to take up fatty acids by measuring uptake of a fluorescently labeled fatty acid (BODIPY-FA).

About 40 colonies transfected with the pIRES-neo containing FATP4 and ~20 colonies transfected with pIRES-neo control were analyzed. All 20 of the vector control clones showed amounts of BODIFY-FA uptake similar to each other and to untransfected 293 cells. In contrast, among the 40 FATP4 transfected clones, 3 had a 5- to 10-fold increased BODIPY-FA uptake compared to any of the vector controls, and a large number (~20) showed an approximately two-fold increase in BODIPY-FA levels. This distribution is consistent with FATP4 conferring increased fatty acid uptake in these cells. One of the cell lines with the highest amount of BODIPY-FA uptake was selected to be used for measuring uptake of tritiated fatty acid.

Figure 38:
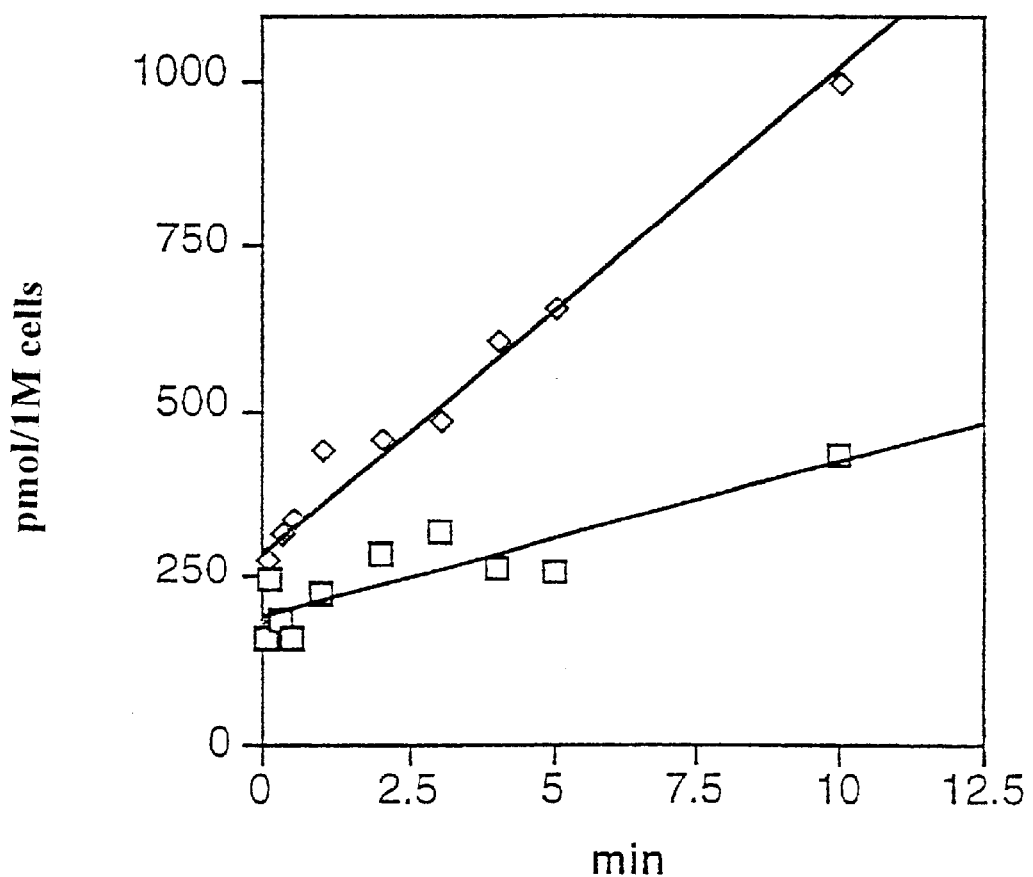
FIG. 38 is a graph showing uptake of tritiated oleate, with time, by 293 cells transfected with either (diamonds) a plasmid for expression of human FATP4 or (squares) a control plasmid.

The uptake of tritiated oleate over time by either FATP4 expressing or control cells was assayed over time. Expression of FATP4 increases the rate of fatty acid uptake by over 3-fold, demonstrating that FATP4 is, like the other FATPs, a functional fatty acid transporter (FIG. 38).

Example 12: Immuno-staining with FATP4-Specific Antiserum

A polyclonal antiserum against the C-terminus of mmFATP4 was raised using a GST-fusion protein having mmFATP4-specific amino acid sequence 552–643 (AVASP . . . GEEKL). In western blot experiments, the purified antibody reacted strongly with a synthetic peptide matching the C-terminus of mmFATP4, but not with a corresponding region of mmFATP2, mmFATP3, or mmFATP5. The mmFATP4 specific polyclonal antiserum detects, in western blot experiments with enterocyte lysates from 3 different mice, a ~70 kDa protein, which is in accordance with mmFATP4's predicted molecular weight of 72 kDa. The binding is specific for mmFATP4, since it can be completely abolished by preincubation of the antiserum with the GST-fusion peptide used to raise the antibody.

Immunofluorescence experiments were performed using the anti-mmFATP4 antiserum on fresh frozen sections of murine small intestine. The antibody binding demonstrates strong expression of mmFATP4 in enterocytes, confirming the results of the in situ hybridization experiments. At higher magnifications it is apparent that mmFATP4 is expressed at the apical side of the enterocyte, indicating that the transporter is present in the brush border membrane, which is known to mediate the uptake of fatty acids from the intestinal lumen.

Immuno-electron microscopy studies were performed on fresh frozen murine intestinal cells. The gold particles used, appearing as black specks on the electron micrographs, indicate the subcellular localization of mmFATP4 to be on the microvilli of the enterocyte. It can be seen from the electron micrographs that mmFATP4 is localized exclusively in membranes, preferentially the apical plasma membrane, confirming that it is indeed a membrane protein.

Example 13: Inhibition of Fatty Acid Uptake Specific to FATP4 Demonstrated in Isolated Mouse Enterocytes Phosphorothioate derivatives of the following oligonucleotides were synthesized:

```
FATP4-AS2    CCCCCACCAGAGAGGCTCC  (SEQ ID NO:103)

FATP4-       CCACCCCCGGAAAGCCTGC  (SEQ ID NO:104)
AS2MM

FATP4-S2     GGAGCCTCTCTGGTGGGGG  (SEQ ID NO:105)
```

FATP4 AS2 is the antisense oligo; it is designed to be complementary to the sequence extending from nucleotide 10 to nucleotide 28 of the mouse FATP4 coding sequence. FATP4-AS2MM is a control oligo; in the oligo every third nucleotide was changed creating mismatches; the overall nucleotide composition is identical to FATP4-AS2 (same number of G, A, T, C). FATP4-S2 is the sense control.

Figure 40:
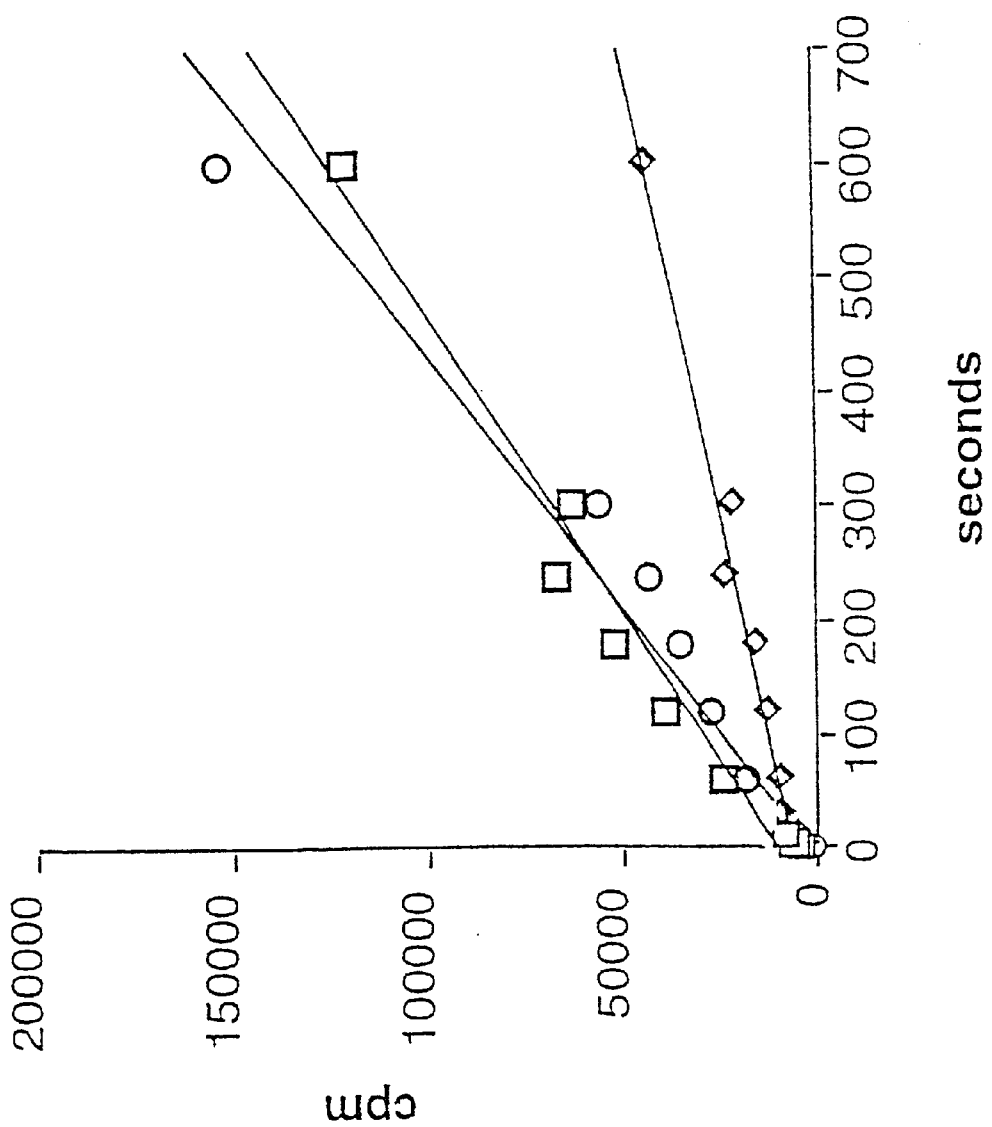
FIG. 40 is a graph showing the uptake, with time, of tritiated oleate by mouse enterocytes in the presence of no oligonucleotide (squares), sense oligonucleotide (circles) or antisense oligonucleotide (diamonds).

Enterocytes were isolated from the small intestine of mice and incubated for 48 h in tissue culture (FIG. 40) either without oligonucleotides (squares) or with 100 μM FATP4 specific sense (circles) or antisense (diamonds) oligonucleotides. The uptake over time of 25 μM oleate was then measured. While the FATP4 sense oligonucleotide did not significantly influence the uptake, the antisense oligonucleotide inhibited fatty acid uptake by ~50%.

Figure 41:
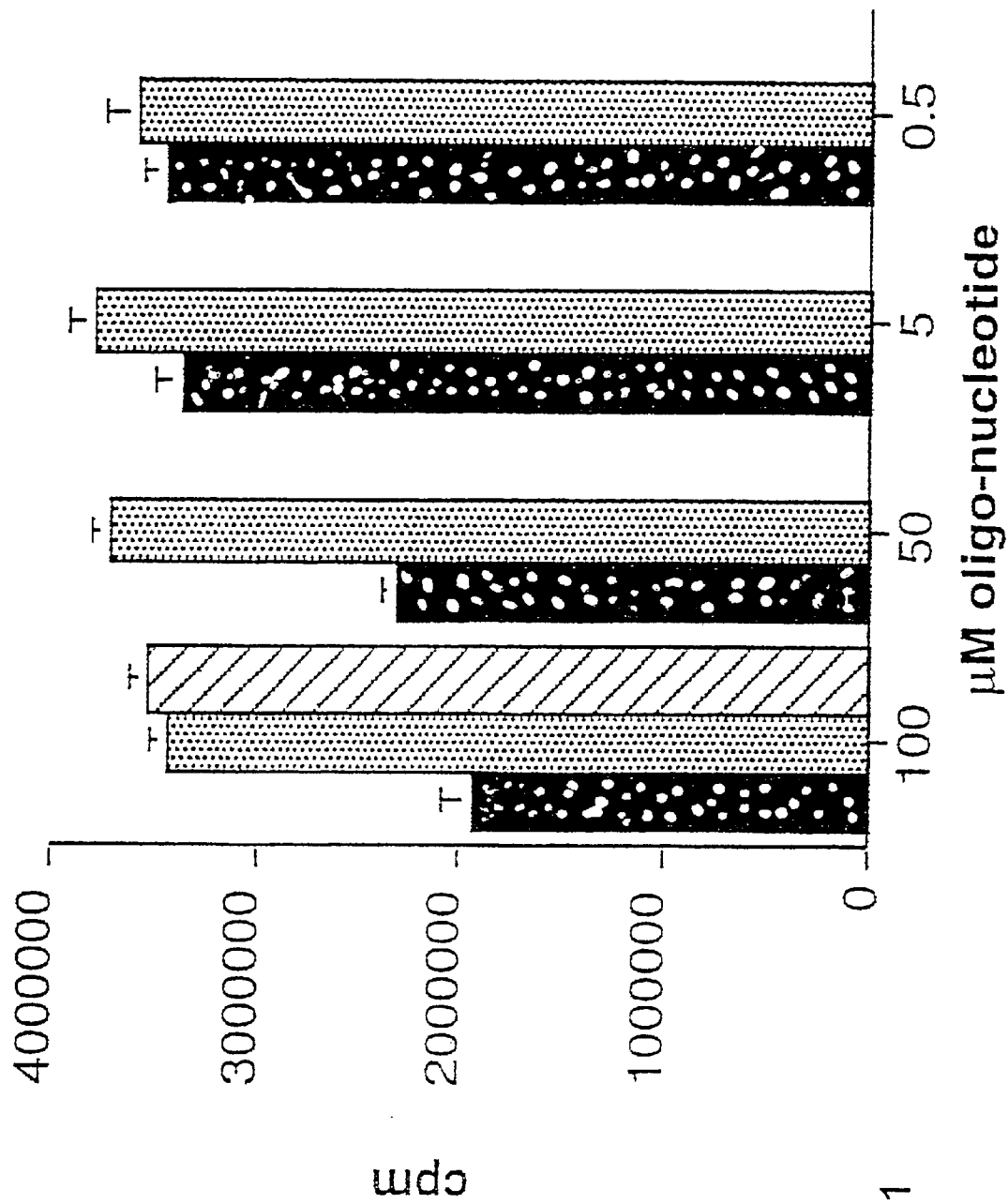
FIG. 41 is a bar graph showing uptake of tritiated oleate, by mouse enterocytes in the presence of various concentrations of antisense (solid bars), mismatch (stippled bars) or sense (lined bars) oligonucleotides.

The effect of either FATP4 sense, antisense or mismatch sequence oligonucleotides on the uptake of fatty acids was measured in enterocytes. Isolated enterocytes were incubated with increasing concentrations of FATP4 antisense oligonucleotides (solid bars in FIG. 41), or a mismatch control oligonucleotide with identical nucleotide composition (stippled bars), or with 100 μM of the FATP4 sense-oligonucleotide (lined bar). The medium for this incubation was Dulbecco's modified Eagle's medium with 4.5 g/L glucose, 1 mM sodium pyruvate, 0.01 mg/ml human transferrin and 10% fetal bovine serum. After 48 hours of incubation the uptake of oleate by enterocytes was measured over a 5 minute time interval. Measurements were done in quadruplicate. The uptake assay was done in Hank's buffered salt solution with 10 mM taurocholate. Only the enterocytes given FATP4 antisense oligonucleotide showed a concentration dependent decrease of fatty acid uptake, inhibiting it at a 100 μM concentration by ~50%. This effect was FATP4 specific, since only the antisense oligonucleotide which can bind to the FATP4 mRNA and block its translation inhibited uptake, but not a control oligonucleotide differing only in the sequence but not the nucleotide content, ruling out a toxic or otherwise nonspecific inhibitory effect of this oligonucleotide due to its chemical composition.

Figure 42:
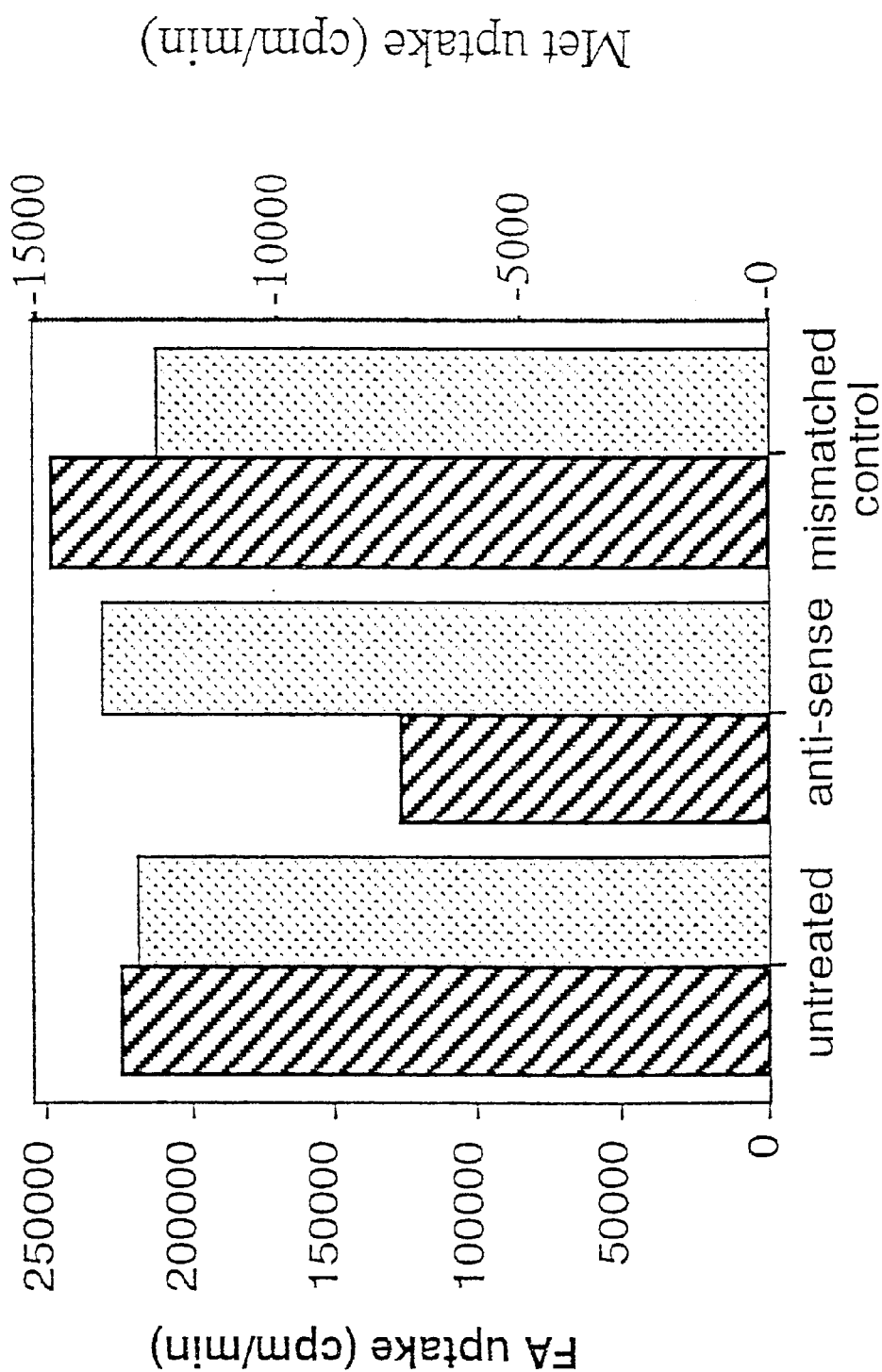
FIG. 42 is a bar graph showing uptake of tritiated oleate and uptake of $^{35}$S-labeled methionine by mouse enterocytes to which were added no oligonucleotide, the antisense oligonucleotide, or the mismatch oligonucleotide.
Figure 91:
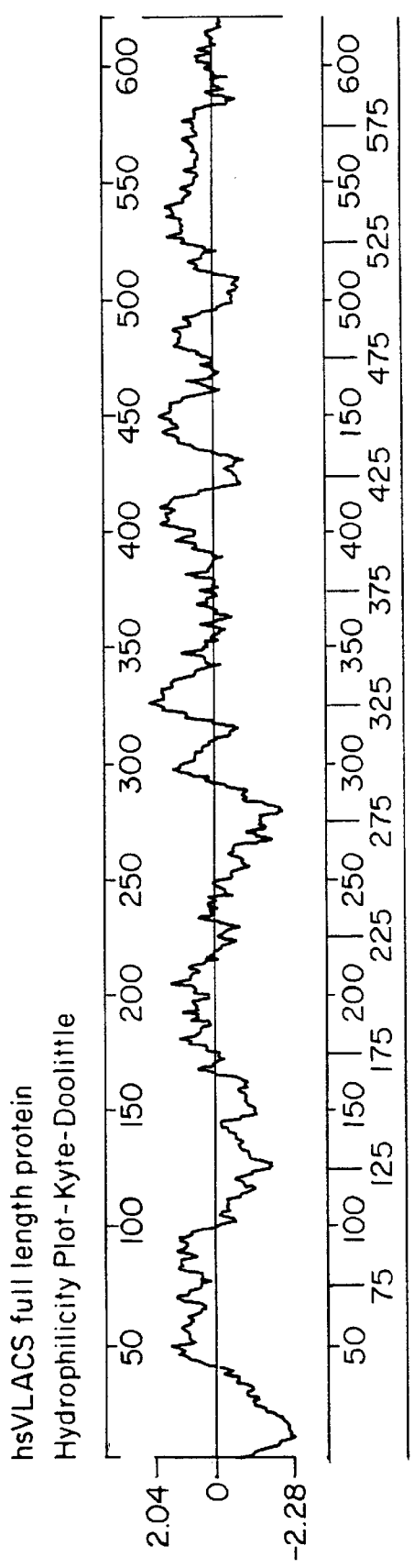
FIG. 91 is a hydrophilicity plot for hsFATP2, made using the Kyte-Doolittle method, averaging hydrophilicity values for 18 amino acid residues at a time.
Figure 92:
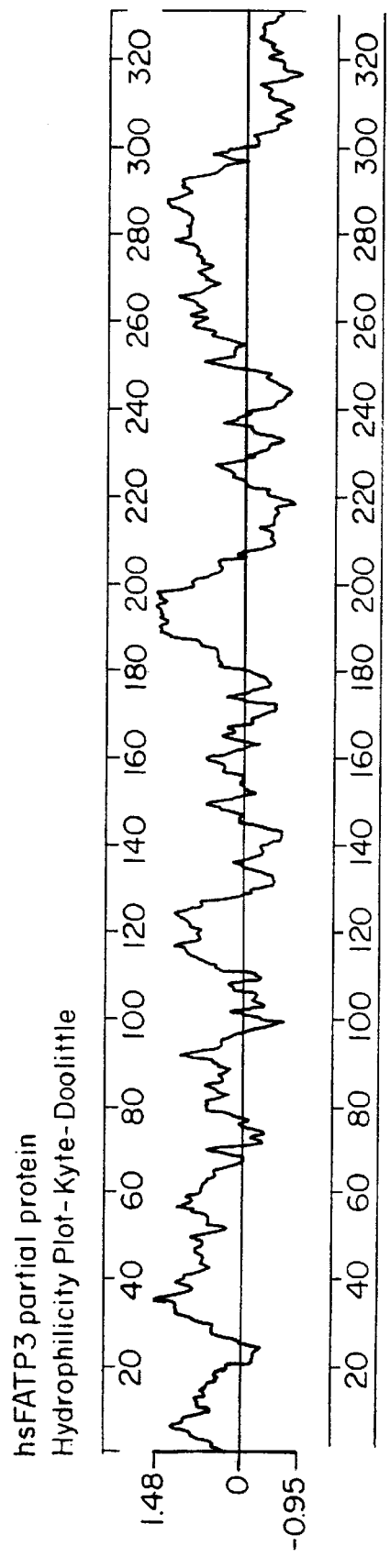
FIG. 92 is a hydrophilicity plot for the hsFATP3 partial protein, made using the Kyte-Doolittle method, averaging hydrophilicity values for 18 amino acid residues at a time.
Figure 93:
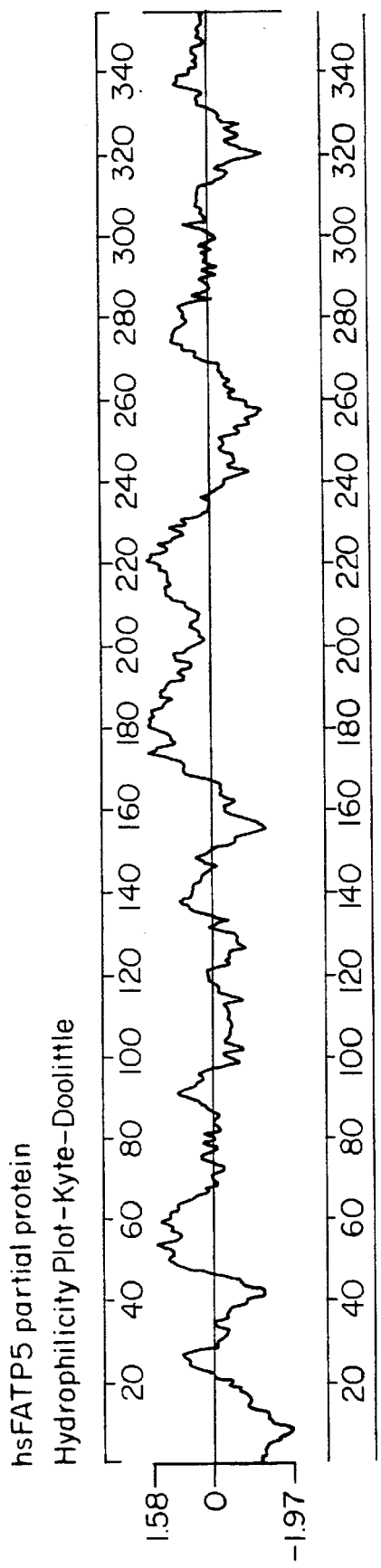
FIG. 93 is a hydrophilicity plot for the hsFATP5 partial protein, made using the Kyte-Doolittle method, averaging hydrophilicity values for 18 amino acid residues at a time.

As a further control experiment, the uptake of oleate was measured along with the uptake of methionine in the same cultured enterocytes. Antisense oligonucleotide, mismatch sequence oligonucleotide, or no oligonucleotide was added to a concentration of 100 μM to cultures of enterocytes. After incubation for 48 hours, the uptake of both $^3$H-labeled oleate and $^{35}$S-labeled methionine was assayed. Results are shown in FIG. 42. Fatty acid uptake is at the left side of the paired bars; methionine uptake is on the right side of the paired bars. The fact that amino acid uptake was not influenced by the antisense oligonucleotide treatment further supports the conclusion that the antisense oligonucleotide causes a specific reduction in translation of FATP4-specific mRNA.

Example 14: mmFATP2 Is Expressed in Proximal Renal Tubule Epithelium

Northern analysis showed that mmFATP 1, mmFATP2, and mmFATP4 are present in the kidney. In situ hybridization (methods as for Example 6) was performed to determine which cell type(s) of the kidney these mRNAs are expressed in. mmFATP1 mRNA was present in virtually all cells throughout the kidney with no obvious preference for a particular cell type. In contrast, mmFATP2 was expressed only in the renal cortex. Within the cortex, expression of mmFATP2 was restricted to the epithelial cells of the proximal renal tubules. The primary function of proximal renal tubule cells is the reabsorption of filtered salts and nutrients (e.g., glucose), a process that requires mitochondrial oxidation and that can utilize fatty acids as energy substrates. Based on the localization of mmFATP2, it is possible that mmFATP2 is important for reabsorption in the kidney by allowing uptake of an energy source (fatty acids) from the blood into renal epithelial cells. Alternatively, if fatty acids need to be reabsorbed in the kidney, similarly to glucose, FATP2 could be involved in the reabsorption of fatty acids. Determination of the subcellular localization of FATP2 will distinguish between these two possibilities.

Table 5 summarizes data on expression of the mouse FATPs in various organs.

TABLE 5

Mouse FATP mRNA Expression

| Mouse Probes | mFATP1 | mFATP2 | mFATP3 | mFATP4 | mFATP5 |
|---|---|---|---|---|---|
| E18.5 embryo expression | everywhere, brain = thymus > heart > brown fat, others | liver (hepatocytes) | — | Brain, small intestine, superior cervical ganglion (SCG), dorsal root ganglion (DRG), other regions have lower expression | Mouse Probes |
| Duodenum | — | villi (surface epithelium) | — | villi (surface epithelium) | — |
| Jejunum | — | villi (surface epithelium) | — | villi (surface epithelium) | — |
| Ileum | — | villi (surface (epithelium) | — | villi (surface (epithelium) | — |
| Colon | low expression in the crypt | very low level in the crypt | — | — | — |
| Kidney | cortex and medulla | proximal tubules | — | — | — |
| Liver | — | hepatocytes | hepatocytes | — | hepatocytes |
| Pancreas | exocrine secretory units or acinar cells; endocrine pancreas (islet) are negative | exocrine secretory units or acinar cells; endocrine pancreas (islet) are negative | — | — | — |
| Brain | Neuronal expression | — | — | Neuronal expression | — |

TABLE 5-continued

Mouse FATP mRNA Expression

| Mouse Probes | mFATP1 | mFATP2 | mFATP3 | mFATP4 | mFATP5 |
|---|---|---|---|---|---|
|  | throughout the brain including hypothalamus |  |  | throughout the brain including hypothalamus |  |
| Heart | myocytes | — | — |  |  |
| Testis | seminiferous tubules | — | seminiferous tubules |  |  |
| Lung | bronchiole | — |  |  |  |
| Adipose | adipocyte | adipocyte | — |  |  |

Example 15: Isolation of full-length human FATP3

Full-length clones encoding human FATP3 were identified by searching databases for sequences similar to the murine FATP1–5 coding regions using the BlastX algorithm (Altschul et al., *J. Mol. Biol.* 215: 403–410, 1990). Human clones with similarity to the 5' end of murine FATP sequences were sequenced completely. A clone encoding full-length human FATP3 was obtained from a human bone library constructed in the mammalian expression vector pMET7 (Tartaglia, L. A. et al., *Cell* 83: 1263–1271, 1995). To identify human cDNA clones encoding FATP family members, databases were searched for sequences similar to murine FATP1–5 coding regions. One clone was found to encode the human ortholog of mmFATP3 and was designated hsFATP3. The DNA and predicted protein sequences of hsFATP3 are shown in FIGS. 94A–94J. hsFATP5 is predicted to encode a 703 amino acid 75.6 kD protein with multiple membrane-spanning domains. A comparison of the DNA sequences of mouse and human FATP3 shows that the mouse and human orthologs are 81 % identical to each other within the coding region. At the amino acid level, hsFATP3 is ~86% identical to mm FATP3 within the coding region. The sequence identities between mouse and human FATP3 are considerably higher than those observed between part of the protein, a region that is poorly conserved between different FATP family members.

All references cited herein are incorporated by reference in their entirety.

While this invention has been particularly shown and described with references to preferred embodiments thereof, it will be understood by those skilled in the art that various changes in form and details may be made therein without departing from the spirit and scope of the invention as defined by the appended claims.

SEQUENCE LISTING

<160> NUMBER OF SEQ ID NOS: 105

<210> SEQ ID NO 1
<211> LENGTH: 340
<212> TYPE: PRT
<213> ORGANISM: Mus musculus

<400> SEQUENCE: 1

```
Phe Ile Phe Thr Ser Gly Thr Thr Gly Leu Pro Lys Pro Ala Ile Leu
 1               5                  10                  15

Ser His Glu Arg Val Ile Gln Val Ser Asn Val Leu Ser Phe Cys Gly
            20                  25                  30

Cys Arg Ala Asp Asp Val Val Tyr Asp Val Leu Pro Leu Tyr His Thr
        35                  40                  45

Ile Gly Leu Val Leu Gly Phe Leu Gly Cys Leu Gln Val Gly Ala Thr
    50                  55                  60

Cys Val Leu Ala Pro Lys Phe Ser Ala Ser Arg Phe Trp Ala Glu Cys
65                  70                  75                  80

Arg Gln His Gly Val Thr Val Ile Gln Tyr Ile Gly Glu Ile Cys Arg
                85                  90                  95

Tyr Leu Leu Arg Gln Pro Val Arg Asp Val Glu Gln Arg His Arg Val
            100                 105                 110

Arg Leu Ala Val Gly Asn Gly Leu Arg Pro Ala Ile Trp Glu Glu Phe
        115                 120                 125

Thr Gln Arg Phe Gly Val Pro Gln Ile Gly Glu Phe Tyr Gly Ala Thr
    130                 135                 140
```

```
Glu Cys Asn Cys Ser Ile Ala Asn Met Asp Gly Lys Val Gly Ser Cys
145                 150                 155                 160

Gly Phe Asn Ser Arg Ile Leu Thr His Val Tyr Pro Ile Arg Leu Val
            165                 170                 175

Lys Val Asn Glu Asp Thr Met Glu Pro Leu Arg Asp Ser Glu Gly Leu
            180                 185                 190

Cys Ile Pro Cys Gln Pro Gly Glu Pro Gly Leu Leu Val Gly Gln Ile
            195                 200                 205

Asn Gln Gln Asp Pro Leu Arg Arg Phe Asp Gly Tyr Val Ser Asp Ser
    210                 215                 220

Ala Thr Asn Lys Lys Ile Ala His Ser Val Phe Arg Lys Gly Asp Ser
225                 230                 235                 240

Ala Tyr Leu Ser Gly Asp Val Leu Val Met Asp Glu Leu Gly Tyr Met
            245                 250                 255

Tyr Phe Arg Asp Arg Ser Gly Asp Thr Phe Arg Trp Arg Gly Glu Asn
            260                 265                 270

Val Ser Thr Thr Glu Val Glu Ala Val Leu Ser Arg Leu Leu Gly Gln
            275                 280                 285

Thr Asp Val Ala Val Tyr Gly Val Ala Val Pro Gly Val Glu Gly Lys
    290                 295                 300

Ala Gly Met Ala Ala Ile Ala Asp Pro His Ser Gln Leu Asp Pro Asn
305                 310                 315                 320

Ser Met Tyr Gln Glu Leu Gln Lys Val Leu Ala Ser Tyr Ala Arg Pro
            325                 330                 335

Ile Phe Leu Arg
            340

<210> SEQ ID NO 2
<211> LENGTH: 339
<212> TYPE: PRT
<213> ORGANISM: Mus musculus

<400> SEQUENCE: 2

Tyr Ile Tyr Thr Ser Gly Thr Thr Gly Asn Pro Lys Pro Ala Val Ile
1               5                   10                  15

Lys His Phe Arg Tyr Phe Trp Ile Ala Met Gly Ala Gly Lys Ala Phe
            20                  25                  30

Gly Ile Asn Lys Ser Asp Val Val Tyr Ile Thr Met Pro Met Tyr His
            35                  40                  45

Ser Ala Ala Gly Ile Met Gly Ile Gly Ser Leu Ile Ala Phe Gly Ser
    50                  55                  60

Thr Ala Val Ile Arg Lys Lys Phe Ser Ala Ser Asn Phe Trp Lys Asp
65                  70                  75                  80

Cys Val Lys Tyr Asn Val Thr Ala Thr Leu Tyr Val Gly Glu Ile Leu
            85                  90                  95

Arg Tyr Leu Cys Asn Val Pro Glu Gln Pro Glu Asp Lys Ile His Thr
            100                 105                 110

Val Arg Leu Ala Met Gly Thr Gly Leu Arg Ala Asn Val Trp Lys Asn
            115                 120                 125

Phe Gln Gln Arg Phe Gly Pro Ile Arg Ile Trp Glu Phe Tyr Gly Ser
    130                 135                 140

Thr Glu Gly Asn Val Gly Leu Met Asn Tyr Val Gly His Cys Gly Ala
145                 150                 155                 160

Val Gly Arg Thr Ser Cys Ile Leu Arg Met Leu Thr Pro Phe Glu Leu
```

```
                165                 170                 175
Val Gln Phe Asp Ile Glu Thr Ala Glu Pro Leu Arg Asp Lys Gln Gly
            180                 185                 190

Phe Cys Ile Pro Val Glu Pro Gly Lys Pro Gly Leu Leu Leu Thr Lys
        195                 200                 205

Val Arg Lys Asn Gln Pro Phe Leu Gly Tyr Arg Gly Ser Gln Ala Glu
    210                 215                 220

Ser Asn Arg Lys Leu Val Ala Asn Val Arg Arg Val Gly Asp Leu Tyr
225                 230                 235                 240

Phe Asn Thr Gly Asp Val Leu Thr Leu Asp Gln Glu Gly Phe Phe Tyr
                245                 250                 255

Phe Gln Asp Arg Leu Gly Asp Thr Phe Arg Trp Lys Gly Glu Asn Val
            260                 265                 270

Ser Thr Gly Glu Val Glu Cys Val Leu Ser Ser Leu Asp Phe Leu Glu
        275                 280                 285

Glu Val Asn Val Tyr Gly Val Pro Val Pro Gly Cys Glu Gly Lys Val
    290                 295                 300

Gly Met Ala Ala Val Lys Leu Ala Pro Gly Lys Thr Phe Asp Gly Lys
305                 310                 315                 320

Lys Tyr Gln His Val Arg Ser Trp Leu Pro Ala Tyr Ala Thr Pro His
                325                 330                 335

Phe Ile Arg

<210> SEQ ID NO 3
<211> LENGTH: 345
<212> TYPE: PRT
<213> ORGANISM: Caenorhabditis elegans

<400> SEQUENCE: 3

Ile Tyr Thr Ser Gly Thr Thr Gly Leu Pro Lys Ser Ala Ile Met Ser
1               5                   10                  15

Trp Arg Lys Ser Ser Val Gly Cys Gln Val Phe Gly His Val Leu His
            20                  25                  30

Met Thr Asn Glu Ser Thr Val Phe Thr Ala Met Pro Leu Phe His Ser
        35                  40                  45

Thr Ala Leu Leu Gly Ala Cys Ala Ile Leu Ser His Gly Gly Cys
    50                  55                  60

Leu Ala Leu Ser His Lys Phe Ser Ala Ser Thr Phe Trp Lys Gln Val
65                  70                  75                  80

Tyr Leu Thr Gly Ala Thr His Ile Gln Tyr Ile Gly Glu Ile Cys Arg
                85                  90                  95

Tyr Leu Leu Ala Ala Asn Pro Cys Pro Glu Glu Lys Gln His Asn Val
            100                 105                 110

Arg Leu Met Trp Gly Asn Gly Leu Arg Gly Gln Ile Trp Lys Glu Phe
        115                 120                 125

Val Gly Arg Phe Gly Ile Lys Lys Ile Gly Glu Leu Tyr Gly Ser Thr
    130                 135                 140

Glu Gly Asn Ser Asn Ile Val Asn Val Asp Asn His Val Gly Ala Cys
145                 150                 155                 160

Gly Phe Met Pro Ile Tyr Pro His Ile Gly Ser Leu Tyr Pro Val Arg
                165                 170                 175

Leu Ile Lys Val Asp Arg Ala Thr Gly Glu Leu Glu Arg Asp Lys Asn
            180                 185                 190

Gly Leu Cys Val Pro Cys Val Pro Gly Glu Thr Gly Glu Met Val Gly
```

```
          195                 200                 205
Val Ile Lys Glu Lys Asp Ile Leu Lys Phe Glu Gly Tyr Val Ser
    210                 215                 220
Glu Gly Asp Thr Ala Lys Lys Ile Tyr Arg Asp Val Phe Lys His Gly
225                 230                 235                 240
Asp Lys Val Phe Ala Ser Gly Asp Ile Leu His Trp Asp Asp Leu Gly
                245                 250                 255
Tyr Leu Tyr Phe Val Asp Arg Cys Gly Asp Thr Phe Arg Trp Lys Gly
                260                 265                 270
Glu Asn Val Ser Thr Thr Glu Val Glu Gly Ile Leu Gln Pro Val Met
            275                 280                 285
Asp Val Glu Asp Ala Thr Val Tyr Gly Val Thr Val Gly Lys Met Glu
290                 295                 300
Gly Arg Ala Gly Met Ala Gly Ile Val Val Lys Asp Gly Thr Asp Val
305                 310                 315                 320
Glu Lys Phe Ile Ala Asp Ile Thr Ser Arg Leu Thr Glu Asn Leu Ala
                325                 330                 335
Ser Tyr Ala Ile Pro Val Phe Ile Arg
                340                 345

<210> SEQ ID NO 4
<211> LENGTH: 356
<212> TYPE: PRT
<213> ORGANISM: Saccharomyces cerevisiae

<400> SEQUENCE: 4

Tyr Ile Tyr Thr Ser Gly Thr Thr Gly Leu Pro Lys Ala Ala Ile Val
1               5                   10                  15
Val His Ser Arg Tyr Tyr Arg Ile Ala Ala Phe Gly His His Ser Tyr
                20                  25                  30
Ser Met Arg Ala Ala Asp Val Leu Tyr Asp Cys Leu Pro Leu Tyr His
            35                  40                  45
Ser Ala Gly Asn Ile Met Gly Val Gly Gln Cys Val Ile Tyr Gly Leu
        50                  55                  60
Thr Val Val Leu Arg Lys Lys Phe Ser Ala Ser Arg Phe Trp Asp Asp
65                  70                  75                  80
Cys Val Lys Tyr Asn Cys Thr Val Val Gln Tyr Val Gly Glu Val Cys
                85                  90                  95
Arg Tyr Leu Leu His Thr Pro Ile Ser Lys Tyr Glu Lys Met His Lys
                100                 105                 110
Val Lys Val Ala Tyr Gly Asn Gly Leu Arg Pro Asp Ile Trp Gln Asp
            115                 120                 125
Phe Arg Lys Arg Phe Asn Ile Glu Val Ile Gly Glu Phe Tyr Ala Ala
        130                 135                 140
Thr Glu Ala Pro Phe Ala Thr Thr Phe Gln Lys Gly Asp Phe Gly
145                 150                 155                 160
Ile Gly Ala Cys Arg Asn Tyr Gly Thr Ile Ile Gln Trp Phe Leu Ser
                165                 170                 175
Phe Gln Gln Thr Leu Val Arg Met Asp Pro Asn Asp Ser Val Ile
                180                 185                 190
Tyr Arg Asn Ser Lys Gly Phe Cys Glu Val Ala Pro Val Gly Glu Pro
            195                 200                 205
Gly Glu Met Leu Met Arg Ile Phe Phe Pro Lys Lys Pro Glu Thr Ser
        210                 215                 220
```

```
Phe Gln Gly Tyr Leu Gly Asn Ala Lys Glu Thr Lys Ser Lys Val Val
225                 230                 235                 240

Arg Asp Val Phe Arg Arg Gly Asp Ala Trp Tyr Arg Cys Gly Asp Leu
                245                 250                 255

Leu Lys Ala Asp Glu Tyr Gly Leu Trp Tyr Phe Leu Asp Arg Met Gly
                260                 265                 270

Asp Thr Phe Arg Trp Lys Ser Glu Asn Val Ser Thr Thr Glu Val Glu
            275                 280                 285

Asp Gln Leu Thr Ala Ser Asn Lys Glu Gln Tyr Ala Gln Val Leu Val
            290                 295                 300

Val Gly Ile Lys Val Pro Lys Tyr Glu Gly Arg Ala Gly Phe Ala Val
305                 310                 315                 320

Ile Lys Leu Thr Asp Asn Ser Leu Asp Ile Thr Ala Lys Thr Lys Leu
                325                 330                 335

Leu Asn Asp Ser Leu Ser Arg Leu Asn Leu Pro Ser Tyr Ala Met Pro
                340                 345                 350

Leu Phe Val Lys
            355

<210> SEQ ID NO 5
<211> LENGTH: 334
<212> TYPE: PRT
<213> ORGANISM: Mycobacterium tuberculosis

<400> SEQUENCE: 5

Tyr Ile Phe Thr Ser Gly Thr Thr Gly Phe Pro Lys Ala Ser Val Met
1               5                   10                  15

Thr His His Arg Trp Leu Arg Ala Leu Ala Val Phe Gly Gly Met Gly
                20                  25                  30

Leu Arg Leu Lys Gly Ser Asp Thr Leu Tyr Ser Cys Leu Pro Leu Tyr
            35                  40                  45

His Asn Asn Ala Leu Thr Val Ala Val Ser Ser Val Ile Asn Ser Gly
        50                  55                  60

Ala Thr Leu Ala Leu Gly Lys Ser Phe Ser Ala Ser Arg Phe Trp Asp
65                  70                  75                  80

Glu Val Ile Ala Asn Arg Ala Thr Ala Phe Val Tyr Ile Gly Glu Ile
                85                  90                  95

Cys Arg Tyr Leu Leu Asn Gln Pro Ala Lys Pro Thr Asp Arg Ala His
                100                 105                 110

Gln Val Arg Val Ile Cys Gly Asn Gly Leu Arg Pro Glu Ile Trp Asp
            115                 120                 125

Glu Phe Thr Thr Arg Phe Gly Val Ala Arg Val Cys Glu Phe Tyr Ala
        130                 135                 140

Ala Ser Glu Gly Asn Ser Ala Phe Ile Asn Ile Phe Asn Val Pro Arg
145                 150                 155                 160

Thr Ala Gly Val Ser Pro Met Pro Leu Ala Phe Val Glu Tyr Asp Leu
                165                 170                 175

Asp Thr Gly Asp Pro Leu Arg Asp Ala Ser Gly Arg Val Arg Arg Val
            180                 185                 190

Pro Asp Gly Glu Pro Gly Leu Leu Leu Ser Arg Val Asn Arg Leu Gln
        195                 200                 205

Pro Phe Asp Gly Tyr Thr Asp Pro Val Ala Ser Glu Lys Lys Leu Val
    210                 215                 220

Arg Asn Ala Phe Arg Asp Gly Asp Cys Trp Phe Asn Thr Gly Asp Val
225                 230                 235                 240
```

-continued

```
Met Ser Pro Gln Gly Met Gly His Ala Ala Phe Val Asp Arg Leu Gly
                245                 250                 255

Asp Thr Phe Arg Trp Lys Gly Glu Asn Val Ala Thr Thr Gln Val Glu
            260                 265                 270

Ala Ala Leu Ala Ser Asp Gln Thr Val Glu Glu Cys Thr Val Tyr Gly
        275                 280                 285

Val Gln Ile Pro Arg Thr Gly Arg Ala Gly Met Ala Ala Ile Thr
    290                 295                 300

Leu Arg Ala Gly Ala Glu Phe Asp Gly Gln Ala Leu Ala Arg Thr Val
305                 310                 315                 320

Tyr Gly His Leu Pro Gly Tyr Ala Leu Pro Leu Phe Val Arg
                325                 330
```

<210> SEQ ID NO 6
<211> LENGTH: 2087
<212> TYPE: DNA
<213> ORGANISM: Mus musculus

<400> SEQUENCE: 6

```
acgactcact ataggagag agctatgacg tcgcatgcac gcgtaagctt gggcccctcg      60
agggatcctc tagagcggcc gccgaccccg aaagctctga gagcgggtgc agtctggcct    120
ggcgtctcgc gtacctggcc cgggagcagc cgacacacac cttcctcatc acggcgcgc    180
agcgctttag ctacgcggag gctgagcgcg agagcaaccg gattgctcgc gcctttctgc    240
gcgcacgggg ctggaccggg ggccgccgag gctcgggcag gggcagcact gaggaaggcg    300
cacgcgtggc gcctccggct ggagatgcgg ctgctagagg acgaccgcg ccccctctgg    360
cacccggggc gaccgtggcg ctgctcctcc cagcgggccc ggatttcctt tggatttggt    420
tcggactggc caaagctggc ctgcgcacgg cctttgtgcc caccgcttta cgccgaggac    480
ccctgctgca ctgcctccgc agctgcggtg cgagtgcgct cgtgctggcc acagagttcc    540
tggagtccct ggagccggac ctgccggcct tgagagccat ggggctccac ctatgggcga    600
cgggccctga aactaatgta gctggaatca gcaatttgct atcggaagca gcagaccaag    660
tggatgagcc agtgccgggg tacctctctg cccccagaa cataatggac acctgcctgt    720
acatcttcac ctctggcact actggcctgc ccaaggctgc tcgaatcagt catctgaagg    780
ttctacagtg ccagggattc taccatctgt gtggagtcca ccaggaggac gtgatctacc    840
tcgcactccc actgtaccac atgtctggct cccttctggg cattgtgggc tgcttgggca    900
ttggggccac cgtggtgctg aaacccaagt tctcagctag ccagttctgg gacgattgcc    960
agaaacacag ggtgacagtg ttccagtaca ttggggagtt gtgccgatac ctcgtcaacc   1020
agcccccgag caaggcagag tttgaccata aggtgcgctt ggcagtgggc agtgggttgc   1080
gcccagacac ctgggagcgt ttcctgcggc gatttggacc tctgcagata ctggagacgt   1140
atggcatgac agagggcaac gtagctacgt tcaattacac aggacggcag ggtgcagtgg   1200
ggcgagcttc ctggctttac aagcacatct tccccttctc cttgattcga tacgatgtca   1260
tgacagggga gcctattcgg aatgcccagg gcactgcat gaccacatct ccaggtgagc   1320
caggcctact ggtggcccca gtgagccagc agtcccccttt cctgggctat gctgggctc   1380
cggagctggc caaggacaag ctgctgaagg atgtcttctg gtctggggac gttttcttca   1440
atactgggga cctcttggtc tgtgatgagc aaggctttct tcacttccac gatcgtactg   1500
gagacaccat caggtggaag ggagagaatg tggccacaac tgaagtggct gaggtcttgg   1560
```

```
agaccctgga cttccttcag gaggtgaaca tctatggagt cacgtgcca gggcacgaag    1620 gcagggcagg catggcggcc ttggctctgc ggcccccgca ggctctgaac ctggtgcagc    1680
tctacagcca tgtttctgag aacttgccac cgtatgcccg acctcggttt ctcaggctcc    1740
aggaatcttt ggccactact gagaccttca acagcagaa ggttaggatg ccaatgagg     1800 gctttgaccc cagtgtactg tctgacccac tctatgttct ggaccaagat atagggggcct  1860 acctgcccct cacacctgcc cggtacagtg ccctcctgtc tggagacctt cgaatctgaa    1920
accttccact tgagggaggg gctcggaggg tacaggccac catggctgca ccagggaggg    1980
ttttcgggta tcttttgtat atggagtcat tattttgtaa taaacagctg gagcttaaaa    2040
aaaaaaaaaa aaaaaaaaaa aaaaaaaaaa aaaaaaaaaa aaaaaaa               2087

<210> SEQ ID NO 7
<211> LENGTH: 613
<212> TYPE: PRT
<213> ORGANISM: Mus musculus

<400> SEQUENCE: 7

Ala Ala Asp Pro Glu Ser Ser Glu Ser Gly Cys Ser Leu Ala Trp Arg
  1               5                  10                  15

Leu Ala Tyr Leu Ala Arg Glu Gln Pro Thr His Thr Phe Leu Ile His
                 20                  25                  30

Gly Ala Gln Arg Phe Ser Tyr Ala Glu Ala Glu Arg Glu Ser Asn Arg
             35                  40                  45

Ile Ala Arg Ala Phe Leu Arg Ala Arg Gly Trp Thr Gly Gly Arg Arg
         50                  55                  60

Gly Ser Gly Arg Gly Ser Thr Glu Glu Gly Ala Arg Val Ala Pro Pro
 65                  70                  75                  80

Ala Gly Asp Ala Ala Ala Arg Gly Thr Thr Ala Pro Pro Leu Ala Pro
                 85                  90                  95

Gly Ala Thr Val Ala Leu Leu Leu Pro Ala Gly Pro Asp Phe Leu Trp
            100                 105                 110

Ile Trp Phe Gly Leu Ala Lys Ala Gly Leu Arg Thr Ala Phe Val Pro
        115                 120                 125

Thr Ala Leu Arg Arg Gly Pro Leu Leu His Cys Leu Arg Ser Cys Gly
    130                 135                 140

Ala Ser Ala Leu Val Leu Ala Thr Glu Phe Leu Glu Ser Leu Glu Pro
145                 150                 155                 160

Asp Leu Pro Ala Leu Arg Ala Met Gly Leu His Leu Trp Ala Thr Gly
                165                 170                 175

Pro Glu Thr Asn Val Ala Gly Ile Ser Asn Leu Leu Ser Glu Ala Ala
            180                 185                 190

Asp Gln Val Asp Glu Pro Val Pro Gly Tyr Leu Ser Ala Pro Gln Asn
        195                 200                 205

Ile Met Asp Thr Cys Leu Tyr Ile Phe Thr Ser Gly Thr Thr Gly Leu
    210                 215                 220

Pro Lys Ala Ala Arg Ile Ser His Leu Lys Val Leu Gln Cys Gln Gly
225                 230                 235                 240

Phe Tyr His Leu Cys Gly Val His Gln Glu Asp Val Ile Tyr Leu Ala
                245                 250                 255

Leu Pro Leu Tyr His Met Ser Gly Ser Leu Leu Gly Ile Val Gly Cys
            260                 265                 270

Leu Gly Ile Gly Ala Thr Val Val Leu Lys Pro Lys Phe Ser Ala Ser
        275                 280                 285
```

```
Gln Phe Trp Asp Asp Cys Gln Lys His Arg Val Thr Val Phe Gln Tyr
    290                 295                 300
Ile Gly Glu Leu Cys Arg Tyr Leu Val Asn Gln Pro Pro Ser Lys Ala
305                 310                 315                 320
Glu Phe Asp His Lys Val Arg Leu Ala Val Gly Ser Gly Leu Arg Pro
                325                 330                 335
Asp Thr Trp Glu Arg Phe Leu Arg Arg Phe Gly Pro Leu Gln Ile Leu
            340                 345                 350
Glu Thr Tyr Gly Met Thr Glu Gly Asn Val Ala Thr Phe Asn Tyr Thr
        355                 360                 365
Gly Arg Gln Gly Ala Val Gly Arg Ala Ser Trp Leu Tyr Lys His Ile
    370                 375                 380
Phe Pro Phe Ser Leu Ile Arg Tyr Asp Val Met Thr Gly Glu Pro Ile
385                 390                 395                 400
Arg Asn Ala Gln Gly His Cys Met Thr Thr Ser Pro Gly Glu Pro Gly
                405                 410                 415
Leu Leu Val Ala Pro Val Ser Gln Gln Ser Pro Phe Leu Gly Tyr Ala
            420                 425                 430
Gly Ala Pro Glu Leu Ala Lys Asp Lys Leu Leu Lys Asp Val Phe Trp
        435                 440                 445
Ser Gly Asp Val Phe Asn Thr Gly Asp Leu Leu Val Cys Asp Glu
    450                 455                 460
Gln Gly Phe Leu His Phe His Asp Arg Thr Gly Asp Thr Ile Arg Trp
465                 470                 475                 480
Lys Gly Glu Asn Val Ala Thr Thr Glu Val Ala Glu Val Leu Glu Thr
                485                 490                 495
Leu Asp Phe Leu Gln Glu Val Asn Ile Tyr Gly Val Thr Val Pro Gly
            500                 505                 510
His Glu Gly Arg Ala Gly Met Ala Ala Leu Ala Leu Arg Pro Pro Gln
        515                 520                 525
Ala Leu Asn Leu Val Gln Leu Tyr Ser His Val Ser Glu Asn Leu Pro
    530                 535                 540
Pro Tyr Ala Arg Pro Arg Phe Leu Arg Leu Gln Glu Ser Leu Ala Thr
545                 550                 555                 560
Thr Glu Thr Phe Lys Gln Gln Lys Val Arg Met Ala Asn Glu Gly Phe
                565                 570                 575
Asp Pro Ser Val Leu Ser Asp Pro Leu Tyr Val Leu Asp Gln Asp Ile
            580                 585                 590
Gly Ala Tyr Leu Pro Leu Thr Pro Ala Arg Tyr Ser Ala Leu Leu Ser
        595                 600                 605
Gly Asp Leu Arg Ile
    610
```

<210> SEQ ID NO 8
<211> LENGTH: 2301
<212> TYPE: DNA
<213> ORGANISM: Mus musculus

<400> SEQUENCE: 8

```
cccacgcgtc cgcccacgcg tccggcatgg ccaagctggg cgtggaggcg gctctcatca      60
acaccaacct taggcgggat gccctgcgcc actgtcttga cacctcaaag gcacgagctc     120
tcatctttgg cagtgagatg gcctcagcta tctgtgagat ccatgctagc ctggagccca     180
cactcagcct cttctgctct ggatcctggg agcccagcac agtgcccgtc agcacagagc     240
```

-continued

| | |
|---|---|
| atctggaccc tcttctggaa gatgccccga agcacctgcc cagtcaccca gacaagggtt | 300 |
| ttacagataa gctcttctac atctacacat cgggcaccac gggctaccc aaagctgcca | 360 |
| tgtggtgca cagcaggtat tatcgtatgg cttccctggt gtactatgga ttccgcatgc | 420 |
| ggcctgatga cattgtctat gactgcctcc cctctacca ctcaagcagg aaacatcgtg | 480 |
| gggattggca gtgcttactc cacggcatga ctgtggtgat ccggaagaag ttctcagcct | 540 |
| cccggttctg ggatgattgt atcaagtaca actgcacagt ggtacagtac attggcgagc | 600 |
| tctgccgcta cctcctgaac cagccacccc gtgaggctga gtctcggcac aaggtgcgca | 660 |
| tggcactggg caacggtctc cggcagtcca tctggaccga cttctccagc cgtttccaca | 720 |
| tcccccaggt ggctgagttc tatggggcca ctgaatgcaa ctgtagcctg ggcaactttg | 780 |
| acagccgggt gggggcctgt ggcttcaata gccgcatcct gtcctttgtg taccctatcc | 840 |
| gtttggtacg tgtcaatgag gataccatgg aactgatccg gggacccgat ggagtctgca | 900 |
| ttccctgtca accaggtcag ccaggccagc tggtgggtcg catcatccag caggaccctc | 960 |
| tgcgccgttt cgacgggtac ctcaaccagg gtgccaacaa caagaagatt gctaatgatg | 1020 |
| tcttcaagaa gggggaccaa gcctacctca ctggtgacgt cctggtgatg gatgagctgg | 1080 |
| gttacctgta cttccgagat cgcactgggg acacgttccg ctggaaaggg gagaatgtat | 1140 |
| ctaccactga ggtggagggc acactcagcc gcctgcttca tatggcagat gtggcagttt | 1200 |
| atggtgttga ggtccagga actgaaggcc gagcaggaat ggctgccgtt gcaagtccca | 1260 |
| tcagcaactg tgacctggag agctttgcac agaccttgaa aaaggagctg cctctgtatg | 1320 |
| cccgccccat cttcctgcgc ttcttgcctg agctgcacaa gacagggacc ttcaagttcc | 1380 |
| agaagacaga gttgcggaag gagggctttg acccatctgt tgtgaaagac ccgctgttct | 1440 |
| atctggatgc tcggaagggc tgctacgttg cactggacca ggaggcctat acccgcatcc | 1500 |
| aggcaggcga ggagaagctg tgatttcccc ctacatccct ctgagggcca aagatgctg | 1560 |
| gattcagagc cctagcgtcc accccagagg gtcctgggca atgccagacc aaagctagca | 1620 |
| gggcccgcac ctccgccct aggtgctgat ctcccctctc ccaaactgcc aagtgactca | 1680 |
| ctgccgcttc cccgacccct cagaggcttt ctgtgaaagt ctcatccaag ctgtgtcttc | 1740 |
| tggtccaggc gtggcccctg gccccaggt ttctgatagg ctcctttagg atggtatctt | 1800 |
| gggtccagcg ggccagggtg tgggagagga gtcactaaga tccctccaat cagaagggag | 1860 |
| cttacaaagg aaccaaggca aagcctgtag actcaggaag ctaagtggcc agagactata | 1920 |
| gtggccagtc atcccatgtc cacagaggat cttggtccag agctgccaaa gtgtcacctc | 1980 |
| tccctgcctg cacctctggg gaaaagagga cagcatgtgg ccactgggca cctgtctcaa | 2040 |
| gaagtcagga tcacacactc agtccttgtt tctccaggtt cccttgttct tgtctcgggg | 2100 |
| agggagggac gagtgtcctg tctgtccttc ctgcctgtct gtgagtctgt gttgcttctc | 2160 |
| catctgtcct agcctgagtg tgggtggaac aggcatgagg agagtgtggc tcagggcca | 2220 |
| ataaactctg ccttgactcc tcttaaaaaa aaaaaaaaa aaaaaaaaa aaaaaaaaa | 2280 |
| aaaaaaaaa aaaaaaaaa a | 2301 |

<210> SEQ ID NO 9
<211> LENGTH: 506
<212> TYPE: PRT
<213> ORGANISM: Mus musculus

<400> SEQUENCE: 9

-continued

```
His Ala Ser Ala His Ala Ser Gly Met Ala Lys Leu Gly Val Glu Ala
 1               5                  10                  15

Ala Leu Ile Asn Thr Asn Leu Arg Arg Asp Ala Leu Arg His Cys Leu
            20                  25                  30

Asp Thr Ser Lys Ala Arg Ala Leu Ile Phe Gly Ser Glu Met Ala Ser
        35                  40                  45

Ala Ile Cys Glu Ile His Ala Ser Leu Glu Pro Thr Leu Ser Leu Phe
50                  55                  60

Cys Ser Gly Ser Trp Glu Pro Ser Thr Val Pro Val Ser Thr Glu His
65                  70                  75                  80

Leu Asp Pro Leu Leu Glu Asp Ala Pro Lys His Leu Pro Ser His Pro
                85                  90                  95

Asp Lys Gly Phe Thr Asp Lys Leu Phe Tyr Ile Tyr Thr Ser Gly Thr
                100                 105                 110

Thr Gly Leu Pro Lys Ala Ala Ile Val Val His Ser Arg Tyr Tyr Arg
            115                 120                 125

Met Ala Ser Leu Val Tyr Tyr Gly Phe Arg Met Arg Pro Asp Asp Ile
130                 135                 140

Val Tyr Asp Cys Leu Pro Leu Tyr His Ser Ser Arg Lys His Arg Gly
145                 150                 155                 160

Asp Trp Gln Cys Leu Leu His Gly Met Thr Val Val Ile Arg Lys Lys
                165                 170                 175

Phe Ser Ala Ser Arg Phe Trp Asp Asp Cys Ile Lys Tyr Asn Cys Thr
            180                 185                 190

Val Val Gln Tyr Ile Gly Glu Leu Cys Arg Tyr Leu Leu Asn Gln Pro
        195                 200                 205

Pro Arg Glu Ala Glu Ser Arg His Lys Val Arg Met Ala Leu Gly Asn
210                 215                 220

Gly Leu Arg Gln Ser Ile Trp Thr Asp Phe Ser Ser Arg Phe His Ile
225                 230                 235                 240

Pro Gln Val Ala Glu Phe Tyr Gly Ala Thr Glu Cys Asn Cys Ser Leu
                245                 250                 255

Gly Asn Phe Asp Ser Arg Val Gly Ala Cys Gly Phe Asn Ser Arg Ile
            260                 265                 270

Leu Ser Phe Val Tyr Pro Ile Arg Leu Val Arg Val Asn Glu Asp Thr
        275                 280                 285

Met Glu Leu Ile Arg Gly Pro Asp Gly Val Cys Ile Pro Cys Gln Pro
290                 295                 300

Gly Gln Pro Gly Gln Leu Val Gly Arg Ile Ile Gln Gln Asp Pro Leu
305                 310                 315                 320

Arg Arg Phe Asp Gly Tyr Leu Asn Gln Gly Ala Asn Lys Lys Ile
                325                 330                 335

Ala Asn Asp Val Phe Lys Lys Gly Asp Gln Ala Tyr Leu Thr Gly Asp
            340                 345                 350

Val Leu Val Met Asp Glu Leu Gly Tyr Leu Tyr Phe Arg Asp Arg Thr
        355                 360                 365

Gly Asp Thr Phe Arg Trp Lys Gly Glu Asn Val Ser Thr Thr Glu Val
370                 375                 380

Glu Gly Thr Leu Ser Arg Leu Leu His Met Ala Asp Val Ala Val Tyr
385                 390                 395                 400

Gly Val Glu Val Pro Gly Thr Glu Gly Arg Ala Gly Met Ala Ala Val
            405                 410                 415

Ala Ser Pro Ile Ser Asn Cys Asp Leu Glu Ser Phe Ala Gln Thr Leu
```

```
          420              425              430
Lys Lys Glu Leu Pro Leu Tyr Ala Arg Pro Ile Phe Leu Arg Phe Leu
            435              440              445

Pro Glu Leu His Lys Thr Gly Thr Phe Lys Phe Gln Lys Thr Glu Leu
        450              455              460

Arg Lys Glu Gly Phe Asp Pro Ser Val Val Lys Asp Pro Leu Phe Tyr
465              470              475              480

Leu Asp Ala Arg Lys Gly Cys Tyr Val Ala Leu Asp Gln Ala Tyr
            485              490              495

Thr Arg Ile Gln Ala Gly Glu Glu Lys Leu
        500              505
```

<210> SEQ ID NO 10
<211> LENGTH: 2277
<212> TYPE: DNA
<213> ORGANISM: Mus musculus

<400> SEQUENCE: 10

| | | | | | |
|---|---|---|---|---|---|
| cactcatcag | agctaagaga | gactacacgc | tctcatctac | ttcagaaaga | gccaatgcca | 60 |
| tgggtatttg | gaagaaacta | accttactgc | tgttgctgct | tctgctggtt | ggcctggggc | 120 |
| agcccccatg | ccagcagct | atggctctgg | ccctgcgttg | gttcctggga | gaccccacat | 180 |
| gccttgtgct | gcttggcttg | gcattgctgg | gcagaccctg | gatcagctcc | tggatgcccc | 240 |
| actggctgag | cctggtagga | gcagctctta | ccttattcct | attgcctcta | cagccacccc | 300 |
| cagggctacg | ctggctgcat | aaagatgtgg | ctttcacctt | caagatgctt | ttctatggcc | 360 |
| taaagttcag | gcgacgcctt | aacaaacatc | tccagagac | ctttgtggat | gctttagagc | 420 |
| ggcaagcact | ggcatggcct | gaccgggtgg | ccttggtgtg | tactgggtct | gagggctcct | 480 |
| caatcacaaa | tagccagctg | gatgccaggt | cctgtcaggc | agcatgggtc | ctgaaagcaa | 540 |
| agctgaagga | tgccgtaatc | agaacacaa | gagatgctgc | tgctatctta | gttctcccgt | 600 |
| ccaagaccat | ttctgctttg | agtgtgtttc | tggggttggc | caagttgggc | tgccctgtgg | 660 |
| cctggatcaa | tccacacagc | cgagggatgc | ccttgctaca | ctctgtacgg | agctctgggg | 720 |
| ccagtgtgct | gattgtggat | ccagacctcc | aggagaacct | ggaagaagtc | cttcccaagc | 780 |
| tgctagctga | gaacattcac | tgcttctacc | ttggccacag | ctcacccacc | ccgggagtag | 840 |
| aggctctggg | agcttccctg | gatgctgcac | cttctgaccc | agtacctgcc | agccttcgag | 900 |
| ctacgattaa | gtggaaatct | cctgccatat | tcatctttac | ttcagggacc | actggactcc | 960 |
| caaagccagc | catcttatca | catgagcggg | tcatacaagt | gagcaacgtg | ctgtccttct | 1020 |
| gtggatgcag | agctgatgat | gtggtctatg | acgtcctacc | tctgtaccat | cgatagggc | 1080 |
| ttgtccttgg | attccttggc | tgcttacaag | ttggagccac | ctgtgtcctg | gcccccaagt | 1140 |
| tctctgcctc | ccgattctgg | gctgagtgcc | ggcagcatgg | cgtaacagtg | atcttgtatg | 1200 |
| tgggtgaaat | cctgcggtac | ttgtgtaacg | tccctgagca | accagaagac | aagatacata | 1260 |
| cagtgcgctt | ggccatggga | actggacttc | gggcaaatgt | gtggaaaaac | ttccagcaac | 1320 |
| gctttggtcc | cattcggatc | tgggaattct | acggatccac | agagggcaat | gtgggcttaa | 1380 |
| tgaactatgt | gggccactgc | ggggctgtgg | gaaggaccac | ctgcatcctt | cgaatgctga | 1440 |
| ctccctttga | gcttgtacag | ttcgacatag | agacagcaga | gcctctgagg | gacaaacagg | 1500 |
| gttttttgcat | tcctgtggag | ccaggaaagc | caggacttct | tttgaccaag | gttcgaaaga | 1560 |
| accaacccctt | cctgggctac | cgtggttccc | aggccgagtc | caatcggaaa | cttgttgcga | 1620 |

-continued

```
atgtacgacg cgtaggagac ctgtacttca acactgggga cgtgctgacc ttggaccagg    1680
aaggcttctt ctactttcaa gaccgccttg gtgacacctt ccggtggaag ggcgaaaacg    1740
tatctactgg agaggtggag tgtgttttgt ctagcctaga cttcctagag gaagtcaatg    1800
tctatggtgt gcctgtgcca gggtgtgagg gtaaggttgg catggctgct gtgaaactgg    1860
ctcctgggaa gacttttgat gggcagaagc tataccagca tgtccgctcc tggctccctg    1920
cctatgccac acctcatttc atccgtatcc aggattccct ggagatcaca aacacctaca    1980
agctggtaaa gtcacggctg gtgcgtgagg gttttgatgt ggggatcatt gctgaccccc    2040
tctacatact ggacaacaag gcccagacct tccggagtct gatgccagat gtgtaccagg    2100
ctgtgtgtga aggaacctgg aatctctgac cacctagcca actggaaggc aatccaaaag    2160
tgtagagatt gacactagtc agcttcacaa agttgtccgg gttccagatg cccatggccc    2220
agtagtactt agagaataaa cttgaatgtg tatacaaaaa aaaaaaaaaa aaaaaaa      2277
```

<210> SEQ ID NO 11
<211> LENGTH: 662
<212> TYPE: PRT
<213> ORGANISM: Mus musculus

<400> SEQUENCE: 11

```
Met Ala Leu Ala Leu Arg Trp Phe Leu Gly Asp Pro Thr Cys Leu Val
 1               5                  10                  15

Leu Leu Gly Leu Ala Leu Leu Gly Arg Pro Trp Ile Ser Ser Trp Met
            20                  25                  30

Pro His Trp Leu Ser Leu Val Gly Ala Ala Leu Thr Leu Phe Leu Leu
        35                  40                  45

Pro Leu Gln Pro Pro Gly Leu Arg Trp Leu His Lys Asp Val Ala
    50                  55                  60

Phe Thr Phe Lys Met Leu Phe Tyr Gly Leu Lys Phe Arg Arg Arg Leu
65                  70                  75                  80

Asn Lys His Pro Pro Glu Thr Phe Val Asp Ala Leu Glu Arg Gln Ala
                85                  90                  95

Leu Ala Trp Pro Asp Arg Val Ala Leu Val Cys Thr Gly Ser Glu Gly
            100                 105                 110

Ser Ser Ile Thr Asn Ser Gln Leu Asp Ala Arg Ser Cys Gln Ala Ala
        115                 120                 125

Trp Val Leu Lys Ala Lys Leu Lys Asp Ala Val Ile Gln Asn Thr Arg
    130                 135                 140

Asp Ala Ala Ile Leu Val Leu Pro Ser Lys Thr Ile Ser Ala Leu
145                 150                 155                 160

Ser Val Phe Leu Gly Leu Ala Lys Leu Gly Cys Pro Val Ala Trp Ile
                165                 170                 175

Asn Pro His Ser Arg Gly Met Pro Leu Leu His Ser Val Arg Ser Ser
            180                 185                 190

Gly Ala Ser Val Leu Ile Val Asp Pro Asp Leu Gln Glu Asn Leu Glu
        195                 200                 205

Glu Val Leu Pro Lys Leu Leu Ala Glu Asn Ile His Cys Phe Tyr Leu
    210                 215                 220

Gly His Ser Ser Pro Thr Pro Gly Val Glu Ala Leu Gly Ala Ser Leu
225                 230                 235                 240

Asp Ala Ala Pro Ser Asp Pro Val Pro Ala Ser Leu Arg Ala Thr Ile
                245                 250                 255

Lys Trp Lys Ser Pro Ala Ile Phe Ile Phe Thr Ser Gly Thr Thr Gly
```

-continued

```
                260                 265                 270
Leu Pro Lys Pro Ala Ile Leu Ser His Glu Arg Val Ile Gln Val Ser
            275                 280                 285
Asn Val Leu Ser Phe Cys Gly Cys Arg Ala Asp Asp Val Val Tyr Asp
        290                 295                 300
Val Leu Pro Leu Tyr His Thr Ile Gly Leu Val Leu Gly Phe Leu Gly
305                 310                 315                 320
Cys Leu Gln Val Gly Ala Thr Cys Val Leu Ala Pro Lys Phe Ser Ala
                325                 330                 335
Ser Arg Phe Trp Ala Glu Cys Arg Gln His Gly Val Thr Val Ile Leu
            340                 345                 350
Tyr Val Gly Glu Ile Leu Arg Tyr Leu Cys Asn Val Pro Glu Gln Pro
        355                 360                 365
Glu Asp Lys Ile His Thr Val Arg Leu Ala Met Gly Thr Gly Leu Arg
    370                 375                 380
Ala Asn Val Trp Lys Asn Phe Gln Gln Arg Phe Gly Pro Ile Arg Ile
385                 390                 395                 400
Trp Glu Phe Tyr Gly Ser Thr Glu Gly Asn Val Gly Leu Met Asn Tyr
                405                 410                 415
Val Gly His Cys Gly Ala Val Gly Arg Thr Ser Cys Ile Leu Arg Met
            420                 425                 430
Leu Thr Pro Phe Glu Leu Val Gln Phe Asp Ile Glu Thr Ala Glu Pro
        435                 440                 445
Leu Arg Asp Lys Gln Gly Phe Cys Ile Pro Val Glu Pro Gly Lys Pro
    450                 455                 460
Gly Leu Leu Leu Thr Lys Val Arg Lys Asn Gln Pro Phe Leu Gly Tyr
465                 470                 475                 480
Arg Gly Ser Gln Ala Glu Ser Asn Arg Lys Leu Val Ala Asn Val Arg
                485                 490                 495
Arg Val Gly Asp Leu Tyr Phe Asn Thr Gly Asp Val Leu Thr Leu Asp
            500                 505                 510
Gln Glu Gly Phe Phe Tyr Phe Gln Asp Arg Leu Gly Asp Thr Phe Arg
        515                 520                 525
Trp Lys Gly Glu Asn Val Ser Thr Gly Glu Val Glu Cys Val Leu Ser
    530                 535                 540
Ser Leu Asp Phe Leu Glu Glu Val Asn Val Tyr Gly Val Pro Val Pro
545                 550                 555                 560
Gly Cys Glu Gly Lys Val Gly Met Ala Ala Val Lys Leu Ala Pro Gly
                565                 570                 575
Lys Thr Phe Asp Gly Gln Lys Leu Tyr Gln His Val Arg Ser Trp Leu
            580                 585                 590
Pro Ala Tyr Ala Thr Pro His Phe Ile Arg Ile Gln Asp Ser Leu Glu
        595                 600                 605
Ile Thr Asn Thr Tyr Lys Leu Val Lys Ser Arg Leu Val Arg Glu Gly
    610                 615                 620
Phe Asp Val Gly Ile Ile Ala Asp Pro Leu Tyr Ile Leu Asp Asn Lys
625                 630                 635                 640
Ala Gln Thr Phe Arg Ser Leu Met Pro Asp Val Tyr Gln Ala Val Cys
                645                 650                 655
Glu Gly Thr Trp Asn Leu
            660
```

<210> SEQ ID NO 12

<211> LENGTH: 1622
<212> TYPE: DNA
<213> ORGANISM: Homo sapiens
<220> FEATURE:
<221> NAME/KEY: misc_feature
<222> LOCATION: (1)...(1622)
<223> OTHER INFORMATION: n = A,T,C or G

<400> SEQUENCE: 12

```
atgggattga ctctttcctg gacaaagtgg atgaagtatc aactgaacct atcccagagt      60
catggaggtc tgaagtcact ttttccactc ctgccttata catttatact ctggaaccaa     120
caggtcttcc aaaagcagcc atgatcactc atcagcgcat atggtatgga actggcctca     180
cttttgtaag cggattgaag gcagatgatg tcatctatat cactctgccc ttttaccaca     240
gtgctgcact actgattggc attacggat gtattgtggc tggtgctact cttgccttgc     300
ggactaaatt ttcagccagc cagttttggg atgactgcag aaaatacaac gtcactgtca     360
ttcagtatat cggtgaactg cttcggtatt tatgcaactc accacagaaa ccaaatgacc     420
gtgatcataa agtgagactg gcactgggaa atggcttacg aggagatgtg tggagacaat     480
ttgtcaagag atttggggac atatgcatct atgagttcta tgctgccact gaaggcaata     540
ttggatttat gaattatgcg agaaaagttg gtgctgttgg aagagtaaac tacctacaga     600
aaaaaatcat aacttatgac ctgattaaat atgatgtgga gaaagatgaa cctgtccgtg     660
atgaaaatgg atattgcgtc agagttccca aaggtgaagt tggacttctg gtttgcaaaa     720
tcacacaact tacaccattt aatggctatg ctggagcaaa ggctcagaca gagaagaaaa     780
aactgagaga tgtctttaag aaaggagacc tctatttcaa cagtggagat ctcttaatgg     840
ttgaccatga aaatttcatc tatttccacg acagagttgg agatacattc cggtggaaag     900
gggaaaatgt ggccaccact gaagttgctg atatagttgg actggttgat tttttttccaa     960
ggaagtaaaa tgtttatggg agtgcatggg ccaagatnat ggaggttcga attggcatgg    1020
cnttccnttc aaaatggaaa gaaaaccatg gaatttgatg gaaagaaatt ttttcagnac    1080
attgctgata accacctag ttatgcaagg ccccggtttt ntaagaanac aggacaccat    1140
tgagatcact ggaattttta acaccgcaa atgacctttt ggtggaggag ggctttaacc    1200
cngctgtcat caaagatgcc ttgtattttc ttggatgaca cagcaaaaat gtatgtgcct    1260
atgactgagg acatntataa tgccataagt gntaaaaccc tgaaattntg aatattccca    1320
ggaggataat tcaacatttc cagaaagaaa ctgaatggac agccacttga tataatccaa    1380
ctttaatttg attgaagatt gtgaggaaat tttgtaggaa atttgcatac ccgtaaaggg    1440
agacttttttt aaataacagt tgagtctttg caagtaaaaa gatttagaga ttattattttt    1500
tcagtgtgca cctactgttt gtatttgcaa actgagcttg ttggagggaa ggcattattt    1560
tttaaaatac ttagtaaatt aaagaacacc aacatgtgaa aaaaaaaaa aaaaaaaaa    1620
aa                                                                    1622
```

<210> SEQ ID NO 13
<211> LENGTH: 286
<212> TYPE: PRT
<213> ORGANISM: Homo sapiens

<400> SEQUENCE: 13

```
Tyr Ile Tyr Thr Ser Gly Thr Thr Gly Leu Pro Lys Ala Ala Met Ile
 1               5                  10                  15

Thr His Gln Arg Ile Trp Tyr Gly Thr Gly Leu Thr Phe Val Ser Gly
            20                  25                  30
```

```
Leu Lys Ala Asp Asp Val Ile Tyr Ile Thr Leu Pro Phe Tyr His Ser
        35                  40                  45

Ala Ala Leu Leu Ile Gly Ile His Gly Cys Ile Val Ala Gly Ala Thr
 50                      55                  60

Leu Ala Leu Arg Thr Lys Phe Ser Ala Ser Gln Phe Trp Asp Asp Cys
65                  70                  75                  80

Arg Lys Tyr Asn Val Thr Val Ile Gln Tyr Ile Gly Glu Leu Leu Arg
                 85                  90                  95

Tyr Leu Cys Asn Ser Pro Gln Lys Pro Asn Asp Arg Asp His Lys Val
            100                 105                 110

Arg Leu Ala Leu Gly Asn Gly Leu Arg Gly Asp Val Trp Arg Gln Phe
        115                 120                 125

Val Lys Arg Phe Gly Asp Ile Cys Ile Tyr Glu Phe Tyr Ala Ala Thr
130                 135                 140

Glu Gly Asn Ile Gly Phe Met Asn Tyr Ala Arg Lys Val Gly Ala Val
145                 150                 155                 160

Gly Arg Val Asn Tyr Leu Gln Lys Lys Ile Ile Thr Tyr Asp Leu Ile
                165                 170                 175

Lys Tyr Asp Val Glu Lys Asp Glu Pro Val Arg Asp Glu Asn Gly Tyr
            180                 185                 190

Cys Val Arg Val Pro Lys Gly Glu Val Gly Leu Leu Val Cys Lys Ile
        195                 200                 205

Thr Gln Leu Thr Pro Phe Asn Gly Tyr Ala Gly Ala Lys Ala Gln Thr
210                 215                 220

Glu Lys Lys Lys Leu Arg Asp Val Phe Lys Lys Gly Asp Leu Tyr Phe
225                 230                 235                 240

Asn Ser Gly Asp Leu Leu Met Val Asp His Glu Asn Phe Ile Tyr Phe
                245                 250                 255

His Asp Arg Val Gly Asp Thr Phe Arg Trp Lys Gly Glu Asn Val Ala
            260                 265                 270

Thr Thr Glu Val Ala Asp Ile Val Gly Leu Val Asp Phe Phe
        275                 280                 285

<210> SEQ ID NO 14
<211> LENGTH: 753
<212> TYPE: DNA
<213> ORGANISM: Homo sapiens

<400> SEQUENCE: 14
caattcggga ccccccagggg cactgtatgg ccacatctcc aggtgagcca ggggaagttg    60
ctaaaggatg tcttccggcc tggggatgtt ttcttcaaca ctggggacct gctggtctgc   120
gatgaccaag gttttctccg cttccatgat cgtactggag acaccttcag gtggaaaggg   180
gagaatgtgg ccacaaccga ggtggcagag gtcttcgagg ccctagattt tcttcaggag   240
gtgaacgtct atggagtcac tgtgccaggg catgaaggca gggctggaat ggcagcccta   300
gttctgcgtc ccccccacgc tttggacctt atgcagctct acacccacgt gtctgagaac   360
ttgccacctt atgcccggcc ccgattcctc aggctccagg agtctttggc caccacagag   420
accttcaaac agcagaaagt tcggatggca aatgagggct cgacccccag caccctgtct   480
gacccactgt acgttctgga ccaggctgta ggtgcctacc tgccctcac aactgcccgg   540 tacagcgccc tcctggcagg aaaccttcga atctgagaac ttccacacct gaggcacctg   600
agagaggaac tctgtggggt gggggccgtt gcaggtgtac tgggctgtca gggatctttt   660
```

```
ctataccaga actgcggtca ctattttgta ataaatgtgg ctggagctga tccagctgtc      720
tctgacctac aaaaaaaaaa aaaaaaaaaa aaa                                   753
```

<210> SEQ ID NO 15
<211> LENGTH: 191
<212> TYPE: PRT
<213> ORGANISM: Homo sapiens

<400> SEQUENCE: 15

```
Gln Phe Gly Thr Pro Arg Gly Thr Val Trp Pro His Leu Gln Val Ser
  1               5                  10                  15

Gln Gly Lys Leu Leu Lys Asp Val Phe Arg Pro Gly Asp Val Phe Phe
             20                  25                  30

Asn Thr Gly Asp Leu Leu Val Cys Asp Asp Gln Gly Phe Leu Arg Phe
         35                  40                  45

His Asp Arg Thr Gly Asp Thr Phe Arg Trp Lys Gly Glu Asn Val Ala
     50                  55                  60

Thr Thr Glu Val Ala Glu Val Phe Glu Ala Leu Asp Phe Leu Gln Glu
 65                  70                  75                  80

Val Asn Val Tyr Gly Val Thr Val Pro Gly His Glu Gly Arg Ala Gly
                 85                  90                  95

Met Ala Ala Leu Val Leu Arg Pro Pro His Ala Leu Asp Leu Met Gln
            100                 105                 110

Leu Tyr Thr His Val Ser Glu Asn Leu Pro Pro Tyr Ala Arg Pro Arg
        115                 120                 125

Phe Leu Arg Leu Gln Glu Ser Leu Ala Thr Thr Glu Thr Phe Lys Gln
    130                 135                 140

Gln Lys Val Arg Met Ala Asn Glu Gly Phe Asp Pro Ser Thr Leu Ser
145                 150                 155                 160

Asp Pro Leu Tyr Val Leu Asp Gln Ala Val Gly Ala Tyr Leu Pro Leu
                165                 170                 175

Thr Thr Ala Arg Tyr Ser Ala Leu Leu Ala Gly Asn Leu Arg Ile
            180                 185                 190
```

<210> SEQ ID NO 16
<211> LENGTH: 734
<212> TYPE: DNA
<213> ORGANISM: Homo sapiens
<220> FEATURE:
<221> NAME/KEY: misc_feature
<222> LOCATION: (1)...(734)
<223> OTHER INFORMATION: n = A,T,C or G

<400> SEQUENCE: 16

```
tcaagtacaa ctgcacgatt gtcatancat tggtgaactg tgccgntacc tcctgaacca      60
gccaccgcgg gaggcagaaa accagcacca ggttcgcatg cactaggca atggcctccg      120 gcagtccatc tggaccaact tttccagccg cttccacata ccccaggtgg ctgagtttyta    180 cggggccaca gagtgcaact gtagcctggg caacttcgac agccaggtgg gggcctgtgg     240
tttcaatagc cgcatcctgt ccttcgtgta ccccatccgg ttggtacgtg tcaacgagga     300
caccatggag ctgatccggg ggcccgacgg cgtctgcatt ccctgccagc caggtgagcc     360
gggccagctg gtgggccgca tcatccagaa agacccctg cgccgcttcg atggctacct      420
caaccagggc gccaacaaca agaagattgc caaggatgtc ttcaagaagg ggaccaggc      480 ctaccttact ggtgatgtgc tggtgatgga cgagctgggc tacctgtact ccgagaccg      540 cactggggac acgttccgct ggaaaggtga gaacgtgtcc accaccgagg tggaaggcac     600
```
actcagccgc ctgctggaca tgctgacgt ggccgtgtat ggtgtcgagg tgccaggaac    660
cgagggccgg gccggaatgg ctgctgtggc cagccccact ggcaactgtg acctgggagc    720
gctttgctca ggtc    734

<210> SEQ ID NO 17
<211> LENGTH: 213
<212> TYPE: PRT
<213> ORGANISM: Homo sapiens

<400> SEQUENCE: 17

Ile Gly Glu Leu Cys Arg Tyr Leu Leu Asn Gln Pro Pro Arg Glu Ala
 1               5                  10                  15

Glu Asn Gln His Gln Val Arg Met Ala Leu Gly Asn Gly Leu Arg Gln
                20                  25                  30

Ser Ile Trp Thr Asn Phe Ser Ser Arg Phe His Ile Pro Gln Val Ala
            35                  40                  45

Glu Phe Tyr Gly Ala Thr Glu Cys Asn Cys Ser Leu Gly Asn Phe Asp
        50                  55                  60

Ser Gln Val Gly Ala Cys Gly Phe Asn Ser Arg Ile Leu Ser Phe Val
65                  70                  75                  80

Tyr Pro Ile Arg Leu Val Arg Val Asn Glu Asp Thr Met Glu Leu Ile
                85                  90                  95

Arg Gly Pro Asp Gly Val Cys Ile Pro Cys Gln Pro Gly Glu Pro Gly
            100                 105                 110

Gln Leu Val Gly Arg Ile Ile Gln Lys Asp Pro Leu Arg Arg Phe Asp
        115                 120                 125

Gly Tyr Leu Asn Gln Gly Ala Asn Asn Lys Lys Ile Ala Lys Asp Val
    130                 135                 140

Phe Lys Lys Gly Asp Gln Ala Tyr Leu Thr Gly Asp Val Leu Val Met
145                 150                 155                 160

Asp Glu Leu Gly Tyr Leu Tyr Phe Arg Asp Arg Thr Gly Asp Thr Phe
                165                 170                 175

Arg Trp Lys Gly Glu Asn Val Ser Thr Thr Glu Val Glu Gly Thr Leu
            180                 185                 190

Ser Arg Leu Leu Asp Met Ala Asp Val Ala Val Tyr Gly Val Glu Val
        195                 200                 205

Pro Gly Thr Glu Gly
    210

<210> SEQ ID NO 18
<211> LENGTH: 1278
<212> TYPE: DNA
<213> ORGANISM: Homo sapiens
<220> FEATURE:
<221> NAME/KEY: misc_feature
<222> LOCATION: (1)...(1278)
<223> OTHER INFORMATION: n = A,T,C or G

<400> SEQUENCE: 18
cntgcctctt gtaccacgtg atgggacttt gtcgttggga tcctcggctg cttagatctc     60
ggagccacct gtgttctggc ccccaagttc tctacttcct gcttctggga tgactgtcgg    120
cagcatggcg tgacagtgat cctgtatgtg ggcgagctcc tgcgntactt gtgtaacatt    180
ccccagcaac cagaggaccg gacacataca gtccgcctgg caatgggcaa tggactacgg    240
gctgatgtgt ggggagacct tccagcagcg tttcggtcct atttcggatc tngggaagtc    300

-continued

```
ttacgggcty ccacagaagg gcaacatggg gctttagttc aactattgtt ggggcgctg    360 cggggscctg grggcaaaga tggagcttgc ctcctccgaa tgctgtcccc ctttgagctg    420
gtgcagttcg acatggaggc ggcggagcct gtgagggaca atcagggctt ctgcatccct    480
gtagggctag gggagccggg gctgctgttg accaaggtgg taagccagca accttcgtg    540 ggctaccgcg gccccgaga gctgtcggaa cggaagctgg tgcgcaacgt gcggcaatcg    600
ggcgacgttt actacaacac cggggacgta ctggccatgg accgcgaagg cttcctctac    660
ttccgcgacc gactcgggga caccttccga tggaagggcg agaacgtgtc cacgcacgag    720
gtggagggcg tgttgtcgca ggtggacttc ttgcaacagg ttaacgtgta tggcgtgtgc    780
gtgccaggtt gtgagggtaa ggtgggcatg gctgctgtgg cattagcccc cggccagact    840
ttcgacgggg agaagttgta ccagcacgtt cgcgcttggc tccctgccta cgctaccccc    900
catttcatcc gcatccagga cgccatggag gtcaccagca cgttcaaact gatgaagacc    960
cggttggtgc gtgagggctt caatgtgggg atcgtggttg accctctgtt tgtactggac   1020
aaccgggccc agtccttccg gccctgacg gcagaaatgt accaggctgt gtgtgaggga   1080
acctggaggc tctgatcacc tggccaaccc actggggtag ggatcaaagc cagccacccc   1140
caccccaaca cactcggtgt cccttcatc ctgggcctgt gtgaatccca gcctggccat   1200
accctcaacc tcagtgggct ggaaatgaca gtgggccctg tagcagtggc agaataaact   1260
cagmtgygtt cacagaaa                                                  1278
```

<210> SEQ ID NO 19
<211> LENGTH: 199
<212> TYPE: PRT
<213> ORGANISM: Homo sapiens

<400> SEQUENCE: 19

```
Glu Gly Gln His Gly Ala Leu Val Gln Leu Leu Gly Ala Leu Arg
  1               5                  10                  15

Gly Pro Gly Gly Lys Asp Gly Ala Cys Leu Leu Arg Met Leu Ser Pro
                 20                  25                  30

Phe Glu Leu Val Gln Phe Asp Met Glu Ala Ala Glu Pro Val Arg Asp
         35                  40                  45

Asn Gln Gly Phe Cys Ile Pro Val Gly Leu Gly Glu Pro Gly Leu Leu
 50                  55                  60

Leu Thr Lys Val Val Ser Gln Gln Pro Phe Val Gly Tyr Arg Gly Pro
 65                  70                  75                  80

Arg Glu Leu Ser Glu Arg Lys Leu Val Arg Asn Val Arg Gln Ser Gly
                 85                  90                  95

Asp Val Tyr Tyr Asn Thr Gly Asp Val Leu Ala Met Asp Arg Glu Gly
                100                 105                 110

Phe Leu Tyr Phe Arg Asp Arg Leu Gly Asp Thr Phe Arg Trp Lys Gly
         115                 120                 125

Glu Asn Val Ser Thr His Glu Val Gly Val Leu Ser Gln Val Asp
 130                 135                 140

Phe Leu Gln Gln Val Asn Val Tyr Gly Val Cys Val Pro Gly Cys Glu
145                 150                 155                 160

Gly Lys Val Gly Met Ala Ala Val Ala Leu Ala Pro Gly Gln Thr Phe
                165                 170                 175

Asp Gly Glu Lys Leu Tyr Gln His Val Arg Ala Trp Leu Pro Ala Tyr
                180                 185                 190

Ala Thr Pro His Phe Ile Arg
```

<210> SEQ ID NO 20
<211> LENGTH: 1361
<212> TYPE: DNA
<213> ORGANISM: Homo sapiens

<400> SEQUENCE: 20

```
cgcttgtgtg ttaaagaaga aattttcagc aagccagttt tggagtgact gcaagaagta      60
tgatgtgact gtgtttcagt atattggaga actttgtcgc taccttttgca aacaatctaa    120
gagagaagga gaaaaggatc ataaggtgcg tttggcaatt ggaaatggca tacggagtga    180
tgtatggaga gaattttttag acagatttgg aaatataaag gtgtgtgaac tttatgcagc    240
taccgaatca agcatatctt tcatgaacta cactgggaga attggagcaa ttgggagaac    300
aaatttgttt tacaaacttc tttccacttt tgacttaata aagtatgact ttcagaaaga    360
tgaacccatg agaaatgagc agggttgggt attcatgaga aaaggagac ctggacttct     420
catttctcga gtgaatgcaa aaaatccctt ctttggctat gctgggcctt ataagcacac    480
aaaagacaaa ttgctttgtg atgttttttaa gaagggagag tgttaccttta aatactggaga   540
cttaatagtc caggatcagg acaatttcct ttattttttgg gaccgtactg gagacacttt    600
cagatggaaa ggagaaaatg tcgcaaccac tgaggttgct gatgttattg aatgttgga     660
tttcatacag gaagcaaacg tctatggtgt ggctatatca ggttatgaag gaagagcagg    720
aatggcttct attattttaa aaccaaatac atctttagat ttggaaaaag tttatgaaca    780
agttgtaaca tttctaccag cttatgcttg tccacgattt ttaagaattc aggaaaaaat    840
ggaagcaaca ggaacattca aactattgaa gcatcagttg gtggaagatg gatttaatcc    900
actgaaaatt tctgaaccac tttacttcat ggataacttg aaaaagtctt atgttctact    960
gaccagggaa ctttatgatc aaataatgtt aggggaaata aaactttaag atttttatat   1020
ctagaacttt catatgcttt cttaggaaga gtgagagggg ggtatatgat tctttatgaa   1080
atggggaaag ggagctaaca ttaattatgc atgtactata tttccttaat atgagagata   1140
attttttaat tgcataagaa ttttaatttc ttttaattga tataaacaga gttgattatt   1200
cttttttatct atttggagat tcagtgcata actaagtatt ttccttaata ctaaagattt   1260
taaataataa atagtggcta gcggtttgga caatcactaa aaatgtactt tctaataagt   1320
aaaatttcta attttgaata aaagattaaa ttttactgaa a                       1361
```

<210> SEQ ID NO 21
<211> LENGTH: 335
<212> TYPE: PRT
<213> ORGANISM: Homo sapiens

<400> SEQUENCE: 21

```
Ala Cys Val Leu Lys Lys Phe Ser Ala Ser Gln Phe Trp Ser Asp
 1               5                  10                  15
Cys Lys Lys Tyr Asp Val Thr Val Phe Gln Tyr Ile Gly Glu Leu Cys
                20                  25                  30
Arg Tyr Leu Cys Lys Gln Ser Lys Arg Glu Gly Lys Asp His Lys
            35                  40                  45
Val Arg Leu Ala Ile Gly Asn Gly Ile Arg Ser Asp Val Trp Arg Glu
        50                  55                  60
Phe Leu Asp Arg Phe Gly Asn Ile Lys Val Cys Glu Leu Tyr Ala Ala
 65                  70                  75                  80
```

-continued

```
Thr Glu Ser Ser Ile Ser Phe Met Asn Tyr Thr Gly Arg Ile Gly Ala
                85                  90                  95

Ile Gly Arg Thr Asn Leu Phe Tyr Lys Leu Leu Ser Thr Phe Asp Leu
            100                 105                 110

Ile Lys Tyr Asp Phe Gln Lys Asp Glu Pro Met Arg Asn Glu Gln Gly
        115                 120                 125

Trp Val Phe Met Arg Lys Arg Arg Pro Gly Leu Leu Ile Ser Arg Val
    130                 135                 140

Asn Ala Lys Asn Pro Phe Phe Gly Tyr Ala Gly Pro Tyr Lys His Thr
145                 150                 155                 160

Lys Asp Lys Leu Leu Cys Asp Val Phe Lys Lys Gly Asp Val Tyr Leu
                165                 170                 175

Asn Thr Gly Asp Leu Ile Val Gln Asp Gln Asp Asn Phe Leu Tyr Phe
            180                 185                 190

Trp Asp Arg Thr Gly Asp Thr Phe Arg Trp Lys Gly Glu Asn Val Ala
        195                 200                 205

Thr Thr Glu Val Ala Asp Val Ile Gly Met Leu Asp Phe Ile Gln Glu
    210                 215                 220

Ala Asn Val Tyr Gly Val Ala Ile Ser Gly Tyr Glu Gly Arg Ala Gly
225                 230                 235                 240

Met Ala Ser Ile Ile Leu Lys Pro Asn Thr Ser Leu Asp Leu Glu Lys
                245                 250                 255

Val Tyr Glu Gln Val Val Thr Phe Leu Pro Ala Tyr Ala Cys Pro Arg
            260                 265                 270

Phe Leu Arg Ile Gln Glu Lys Met Glu Ala Thr Gly Thr Phe Lys Leu
        275                 280                 285

Leu Lys His Gln Leu Val Glu Asp Gly Phe Asn Pro Leu Lys Ile Ser
    290                 295                 300

Glu Pro Leu Tyr Phe Met Asp Asn Leu Lys Lys Ser Tyr Val Leu Leu
305                 310                 315                 320

Thr Arg Glu Leu Tyr Asp Gln Ile Met Leu Gly Glu Ile Lys Leu
                325                 330                 335
```

<210> SEQ ID NO 22
<211> LENGTH: 2007
<212> TYPE: DNA
<213> ORGANISM: Mycobacterium tuberculosis

<400> SEQUENCE: 22

```
tagtcgataa cgtcaaggac gctctgcggg cctgcgcacc ttcctgaggt tggtcgacaa      60
ccaattcgac atttcgcaaa cgaatcgagg gcttacgtgt ccgattacta cggcggcgca     120
cacacaacgg tcaggctgat cgacctggca actcggatgc cgcgagtgtt ggcggacacg     180
ccggtgattg tgcgtggggc aatgaccggg ctgctggccc ggccgaattc caaggcgtcg     240
atcggcacgg tgttccagga ccgggccgct cgctacggtg accgagtctt cctgaaattc     300
ggcgatcagc agctgaccta ccgcgacgct aacgccaccg ccaaccggta cgccgcggtg     360
ttggccgccc gcggcgtcgg ccccggcgac gtcgttggca tcatgttgcg taactcaccc     420
agcacagtct tggcgatgct ggccacggtc aagtgcggcg ctatcgccgg catgctcaac     480
taccaccagc gcggcgaggt gttggcgcac agcctgggtc tgctggacgc gaaggtactg     540
atcgcagagt ccgacttggt cagcgccgtc gccgaatgcg gcgcctcgcg cggccgggta     600
gcgggcgacg tgctgaccgt cgaggacgtg gagcgattcg ccacaacggc gcccgccacc     660
aacccggcgt cggcgtcggc ggtgcaagcc aaagacaccg cgttctacat cttcacctcg     720
```

-continued

```
ggcaccaccg gatttcccaa ggccagtgtc atgacgcatc atcggtggct gcgggcgctg    780
gccgtcttcg gagggatggg gctgcggctg aagggttccg acacgctcta cagctgcctg    840
ccgctgtacc acaacaacgc gttaacggtc gcggtgtcgt cggtgatcaa ttctggggcg    900
accctggcgc tgggtaagtc gttttcggcg tcgcggttct gggatgaggt gattgccaac    960
cgggcgacgg cgttcgtcta catcggcgaa atctgccgtt atctgctcaa ccagccggcc   1020
aagccgaccg accgtgccca ccaggtgcgg gtgatctgcg gtaacgggct gcggccggag   1080
atctgggatg agttcaccac ccgcttcggg gtcgcgcggg tgtgcgagtt ctacgccgcc   1140
agcgaaggca actcggcctt tatcaacatc ttcaacgtgc ccaggaccgc cggggtatcg   1200
ccgatgccgc ttgcctttgt ggaatacgac ctggacaccg gcgatccgct gcgggatgcg   1260
agcgggcgag tgcgtcgggt acccgacggt gaacccggcc tgttgcttag ccgggtcaac   1320
cggctgcagc cgttcgacgg ctacaccgac ccggttgcca gcgaaaagaa gttggtgcgc   1380
aacgcttttc gagatggcga ctgttggttc aacaccggtg acgtgatgag cccgcagggc   1440
atgggccatg ccgccttcgt cgatcggctg ggcgacacct tccgctggaa gggcgagaat   1500
gtcgccacca ctcaggtcga agcggcactg gcctccgacc agaccgtcga ggagtgcacg   1560
gtctacggcg tccagattcc gcgcaccggc gggcgcgccg gaatggccgc gatcacactg   1620
cgcgctggcg ccgaattcga cggccaggcg ctggcccgaa cggtttacgg tcacttgccc   1680
ggctatgcac ttccgctctt tgttcgggta gtggggtcgc tggcgcacac cacgacgttc   1740
aagagtcgca aggtggagtt gcgcaaccag gcctatggcg ccgacatcga ggatccgctg   1800
tacgtactgg ccggcccgga cgaaggatat gtgccgtact acgccgaata ccctgaggag   1860
gtttcgctcg gaaggcgacc gcagggctag cggattccgg gcgcagtctc gatacccgca   1920
ctggacgctc gacggtaacc aggcactatg gatgcgtgcg ttcaacaccg ccggcctcag   1980
ccggtcgttc aacaccgccg gcgttag                                       2007
```

<210> SEQ ID NO 23
<211> LENGTH: 597
<212> TYPE: PRT
<213> ORGANISM: Mycobacterium tuberculosis

<400> SEQUENCE: 23

```
Met Ser Asp Tyr Tyr Gly Gly Ala His Thr Thr Val Arg Leu Ile Asp
 1               5                  10                  15

Leu Ala Thr Arg Met Pro Arg Val Leu Ala Asp Thr Pro Val Ile Val
            20                  25                  30

Arg Gly Ala Met Thr Gly Leu Leu Ala Arg Pro Asn Ser Lys Ala Ser
        35                  40                  45

Ile Gly Thr Val Phe Gln Asp Arg Ala Ala Arg Tyr Gly Asp Arg Val
    50                  55                  60

Phe Leu Lys Phe Gly Asp Gln Gln Leu Thr Tyr Arg Asp Ala Asn Ala
65                  70                  75                  80

Thr Ala Asn Arg Tyr Ala Ala Val Leu Ala Ala Arg Gly Val Gly Pro
                85                  90                  95

Gly Asp Val Val Gly Ile Met Leu Arg Asn Ser Pro Ser Thr Val Leu
            100                 105                 110

Ala Met Leu Ala Thr Val Lys Cys Gly Ala Ile Ala Gly Met Leu Asn
        115                 120                 125

Tyr His Gln Arg Gly Glu Val Leu Ala His Ser Leu Gly Leu Leu Asp
    130                 135                 140
```

-continued

```
Ala Lys Val Leu Ile Ala Glu Ser Asp Leu Val Ser Ala Val Ala Glu
145                 150                 155                 160

Cys Gly Ala Ser Arg Gly Arg Val Ala Gly Asp Val Leu Thr Val Glu
            165                 170                 175

Asp Val Glu Arg Phe Ala Thr Thr Ala Pro Ala Thr Asn Pro Ala Ser
        180                 185                 190

Ala Ser Ala Val Gln Ala Lys Asp Thr Ala Phe Tyr Ile Phe Thr Ser
    195                 200                 205

Gly Thr Thr Gly Phe Pro Lys Ala Ser Val Met Thr His His Arg Trp
210                 215                 220

Leu Arg Ala Leu Ala Val Phe Gly Gly Met Gly Leu Arg Leu Lys Gly
225                 230                 235                 240

Ser Asp Thr Leu Tyr Ser Cys Leu Pro Leu Tyr His Asn Asn Ala Leu
                245                 250                 255

Thr Val Ala Val Ser Ser Val Ile Asn Ser Gly Ala Thr Leu Ala Leu
            260                 265                 270

Gly Lys Ser Phe Ser Ala Ser Arg Phe Trp Asp Glu Val Ile Ala Asn
        275                 280                 285

Arg Ala Thr Ala Phe Val Tyr Ile Gly Glu Ile Cys Arg Tyr Leu Leu
    290                 295                 300

Asn Gln Pro Ala Lys Pro Thr Asp Arg Ala His Gln Val Arg Val Ile
305                 310                 315                 320

Cys Gly Asn Gly Leu Arg Pro Glu Ile Trp Asp Glu Phe Thr Thr Arg
                325                 330                 335

Phe Gly Val Ala Arg Val Cys Glu Phe Tyr Ala Ala Ser Glu Gly Asn
            340                 345                 350

Ser Ala Phe Ile Asn Ile Phe Asn Val Pro Arg Thr Ala Gly Val Ser
        355                 360                 365

Pro Met Pro Leu Ala Phe Val Glu Tyr Asp Leu Asp Thr Gly Asp Pro
    370                 375                 380

Leu Arg Asp Ala Ser Gly Arg Val Arg Val Pro Asp Gly Glu Pro
385                 390                 395                 400

Gly Leu Leu Leu Ser Arg Val Asn Arg Leu Gln Pro Phe Asp Gly Tyr
                405                 410                 415

Thr Asp Pro Val Ala Ser Glu Lys Lys Leu Val Arg Asn Ala Phe Arg
            420                 425                 430

Asp Gly Asp Cys Trp Phe Asn Thr Gly Asp Val Met Ser Pro Gln Gly
        435                 440                 445

Met Gly His Ala Ala Phe Val Asp Arg Leu Gly Asp Thr Phe Arg Trp
    450                 455                 460

Lys Gly Glu Asn Val Ala Thr Thr Gln Val Glu Ala Ala Leu Ala Ser
465                 470                 475                 480

Asp Gln Thr Val Glu Glu Cys Thr Val Tyr Gly Val Gln Ile Pro Arg
                485                 490                 495

Thr Gly Gly Arg Ala Gly Met Ala Ala Ile Thr Leu Arg Ala Gly Ala
            500                 505                 510

Glu Phe Asp Gly Gln Ala Leu Ala Arg Thr Val Tyr Gly His Leu Pro
        515                 520                 525

Gly Tyr Ala Leu Pro Leu Phe Val Arg Val Val Gly Ser Leu Ala His
    530                 535                 540

Thr Thr Thr Phe Lys Ser Arg Lys Val Glu Leu Arg Asn Gln Ala Tyr
545                 550                 555                 560
```

```
Gly Ala Asp Ile Glu Asp Pro Leu Tyr Val Leu Ala Gly Pro Asp Glu
                565                 570                 575
Gly Tyr Val Pro Tyr Tyr Ala Glu Tyr Pro Glu Glu Val Ser Leu Gly
            580                 585                 590
Arg Arg Pro Gln Gly
        595

<210> SEQ ID NO 24
<211> LENGTH: 3704
<212> TYPE: DNA
<213> ORGANISM: Homo sapiens
<220> FEATURE:
<221> NAME/KEY: CDS
<222> LOCATION: (175)...(2112)

<400> SEQUENCE: 24
tcgacccacg gcgtccggga ccccaaagca gaagcccgca cagtaggcac agcgcaccca        60
agaagggtcc aggagtctgc agaaacagaa aggtccccgg cctcagcctc ctagtccctg       120
cctgcctcct gcctgagctt ctgggagact gaaggcacgg cttgcagctt cagg atg        177
                                                              Met
                                                                1 cgg gct ccg ggt gcg ggc gcg gcc tcg gtg gtc tcg ctg gcg ctg ttg        225
Arg Ala Pro Gly Ala Gly Ala Ala Ser Val Val Ser Leu Ala Leu Leu
        5                  10                  15 tgg ctg ctg ggg ctg ccg tgg acc tgg agc gcg gca gcg gcg ctc ggc        273
Trp Leu Leu Gly Leu Pro Trp Thr Trp Ser Ala Ala Ala Ala Leu Gly
         20                  25                  30 gtg tac gtg ggc agc ggc ggc tgg cgc ttc ctg cgc atc gtc tgc aag        321
Val Tyr Val Gly Ser Gly Gly Trp Arg Phe Leu Arg Ile Val Cys Lys
     35                  40                  45 acc gcg agg cga gac ctc ttc ggt ctc tct gtg ctg atc cgc gtg cgc        369
Thr Ala Arg Arg Asp Leu Phe Gly Leu Ser Val Leu Ile Arg Val Arg
 50                  55                  60                  65 ctg gag ctg cgg cgg cac cag cgt gcc ggc cac acc atc ccg cgc atc        417
Leu Glu Leu Arg Arg His Gln Arg Ala Gly His Thr Ile Pro Arg Ile
                 70                  75                  80 ttt cag gcg gta gtg cag cga cag ccc gag cgc ctg gcg ctg gtg gat        465
Phe Gln Ala Val Val Gln Arg Gln Pro Glu Arg Leu Ala Leu Val Asp
             85                  90                  95 gcc ggg acc ggc gag tgc tgg acc ttt gcg cag ctg gac gcc tac tcc        513
Ala Gly Thr Gly Glu Cys Trp Thr Phe Ala Gln Leu Asp Ala Tyr Ser
        100                 105                 110 aat gcg gta gcc aac ctc ttc cgc cag ctg ggc ttc gcg ccg ggc gac        561
Asn Ala Val Ala Asn Leu Phe Arg Gln Leu Gly Phe Ala Pro Gly Asp
    115                 120                 125 gtg gtg gcc atc ttc ctg gag ggc cgg ccg gag ttc gtg ggg ctg tgg        609
Val Val Ala Ile Phe Leu Glu Gly Arg Pro Glu Phe Val Gly Leu Trp
130                 135                 140                 145 ctg ggc ctg gcc aag gcg ggc atg gag gcc gcg ctc aac gtg aac        657
Leu Gly Leu Ala Lys Ala Gly Met Glu Ala Ala Leu Leu Asn Val Asn
                150                 155                 160 ctg cgg cgc gag ccc ctg gcc ttc tgc ctg ggc acc tcg ggc gct aag        705
Leu Arg Arg Glu Pro Leu Ala Phe Cys Leu Gly Thr Ser Gly Ala Lys
            165                 170                 175 gcc ctg atc ttt gga gga gaa atg gtg gcg gcg gtg gcc gaa gtg agc        753
Ala Leu Ile Phe Gly Gly Glu Met Val Ala Ala Val Ala Glu Val Ser
        180                 185                 190 ggg cat ctg ggg aaa agt ttg atc aag ttc tgc tct gga gac ttg ggg        801
Gly His Leu Gly Lys Ser Leu Ile Lys Phe Cys Ser Gly Asp Leu Gly
    195                 200                 205
```

-continued

```
ccc gag ggc atc ttg ccg gac acc cac ctc ctg gac ccg ctg ctg aag      849
Pro Glu Gly Ile Leu Pro Asp Thr His Leu Leu Asp Pro Leu Leu Lys
210             215                 220                 225 gag gcc tct act gcc ccc ttg gca cag atc ccc agc aag ggc atg gac      897
Glu Ala Ser Thr Ala Pro Leu Ala Gln Ile Pro Ser Lys Gly Met Asp
                230                 235                 240 gat cgt ctt ttc tac atc tac acg tcg ggg acc acc ggg ctg ccc aag      945
Asp Arg Leu Phe Tyr Ile Tyr Thr Ser Gly Thr Thr Gly Leu Pro Lys
            245                 250                 255 gct gcc att gtc gtg cac agc agg tac tac cgc atg gca gcc ttc ggc      993
Ala Ala Ile Val Val His Ser Arg Tyr Tyr Arg Met Ala Ala Phe Gly
        260                 265                 270 cac cac gcc tac cgc atg cag gcg gct gac gtg ctc tat gac tgc ctg     1041
His His Ala Tyr Arg Met Gln Ala Ala Asp Val Leu Tyr Asp Cys Leu
    275                 280                 285 ccc ctg tac cac tcg gca gga aac atc atc ggc gtg ggg cag tgt ctc     1089
Pro Leu Tyr His Ser Ala Gly Asn Ile Ile Gly Val Gly Gln Cys Leu
290                 295                 300                 305 atc tat ggg ctg aca gtc gtc ctc cgc aag aaa ttc tcg gcc agc cgc     1137
Ile Tyr Gly Leu Thr Val Val Leu Arg Lys Lys Phe Ser Ala Ser Arg
            310                 315                 320 ttc tgg gac gac tgc atc aag tac aac tgc acg gtg gtt cag tac atc     1185
Phe Trp Asp Asp Cys Ile Lys Tyr Asn Cys Thr Val Val Gln Tyr Ile
        325                 330                 335 ggg gag atc tgc cgc tac ctg ctg aag cag ccg gtg cgc gag gcg gag     1233
Gly Glu Ile Cys Arg Tyr Leu Leu Lys Gln Pro Val Arg Glu Ala Glu
    340                 345                 350 agg cga cac cgc gtg cgc ctg gcg gtg ggg aac ggg ctg cgt cct gcc     1281
Arg Arg His Arg Val Arg Leu Ala Val Gly Asn Gly Leu Arg Pro Ala
355                 360                 365 atc tgg gag gag ttc acg gag cgc ttc ggc gta cgc caa atc ggg gag     1329
Ile Trp Glu Glu Phe Thr Glu Arg Phe Gly Val Arg Gln Ile Gly Glu
370                 375                 380                 385 ttc tac ggc gcc acc gag tgc aac tgc agc att gcc aac atg gac ggc     1377
Phe Tyr Gly Ala Thr Glu Cys Asn Cys Ser Ile Ala Asn Met Asp Gly
            390                 395                 400 aag gtc ggc tcc tgt ggt ttc aac agc cgc atc ctg ccc cac gtg tac     1425
Lys Val Gly Ser Cys Gly Phe Asn Ser Arg Ile Leu Pro His Val Tyr
        405                 410                 415 ccc atc cgg ctg gtg aag gtc aat gag gac aca atg gag ctg ctg cgg     1473
Pro Ile Arg Leu Val Lys Val Asn Glu Asp Thr Met Glu Leu Leu Arg
    420                 425                 430 gat gcc cag ggc ctc tgc atc ccc tgc cag gcc ggg gag cct ggc ctc     1521
Asp Ala Gln Gly Leu Cys Ile Pro Cys Gln Ala Gly Glu Pro Gly Leu
435                 440                 445 ctt gtg ggt cag atc aac caa cag gac ccg ctg cgc cgc ttc gat ggc     1569
Leu Val Gly Gln Ile Asn Gln Gln Asp Pro Leu Arg Arg Phe Asp Gly
450                 455                 460                 465 tat gtc agc gag agc gcc acc agc aag aag atc gcc cac agc gtc ttc     1617
Tyr Val Ser Glu Ser Ala Thr Ser Lys Lys Ile Ala His Ser Val Phe
            470                 475                 480 agc aag ggc gac agc gcc tac ctc tca ggt gac gtg cta gtg atg gat     1665
Ser Lys Gly Asp Ser Ala Tyr Leu Ser Gly Asp Val Leu Val Met Asp
        485                 490                 495 gag ctg ggc tac atg tac ttc cgg gac cgt agc ggg gac acc ttc cgc     1713
Glu Leu Gly Tyr Met Tyr Phe Arg Asp Arg Ser Gly Asp Thr Phe Arg
    500                 505                 510 tgg cga ggg gag aac gtc tcc acc acc gag gtg gag ggc gtg ctg agc     1761
Trp Arg Gly Glu Asn Val Ser Thr Thr Glu Val Glu Gly Val Leu Ser
```

```
                515                 520                 525
cgc ctg ctg ggc cag aca gac gtg gcc gtc tat ggg gtg gct gtt cca    1809
Arg Leu Leu Gly Gln Thr Asp Val Ala Val Tyr Gly Val Ala Val Pro
530                 535                 540                 545 gga gtg gag ggt aag gca ggg atg gcg gcc gtc gca gac ccc cac agc    1857
Gly Val Glu Gly Lys Ala Gly Met Ala Ala Val Ala Asp Pro His Ser
                550                 555                 560 ctg ctg gac ccc aac gcg ata tac cag gag ctg cag aag gtg ctg gca    1905
Leu Leu Asp Pro Asn Ala Ile Tyr Gln Glu Leu Gln Lys Val Leu Ala
            565                 570                 575 ccc tat gcc cgg ccc atc ttc ctg cgc ctc ctg ccc cag gtg gac acc    1953
Pro Tyr Ala Arg Pro Ile Phe Leu Arg Leu Leu Pro Gln Val Asp Thr
        580                 585                 590 aca ggc acc ttc aag atc cag aag acg agg ctg cag cga gag ggc ttt    2001
Thr Gly Thr Phe Lys Ile Gln Lys Thr Arg Leu Gln Arg Glu Gly Phe
595                 600                 605 gac cca cgc cag acc tca gac cgg ctc ttc ttc ctg gac ctg aag cag    2049
Asp Pro Arg Gln Thr Ser Asp Arg Leu Phe Phe Leu Asp Leu Lys Gln
610                 615                 620                 625 ggc cac tac ctg ccc tta aat gag gca gtc tac act cgc atc tgc tcg    2097
Gly His Tyr Leu Pro Leu Asn Glu Ala Val Tyr Thr Arg Ile Cys Ser
                630                 635                 640 ggc gcc ttc gcc ctc tgaagctgtt cctctactgg ccacaaactc tgggcctggt    2152
Gly Ala Phe Ala Leu
            645 gggagaggcc agcttgagcc agacagcgct gcccagggt ggccgcctag tacacaccca     2212 cctggccgag ctgtacctgg cacggcccat cctggactga gaaactggaa cctcagagga    2272 acccgtgcct ctctgctgcc ttggtgcccc tgtgtctgcc tcctctccct gcttttcagc    2332 ctctgtctcc ttccatccct gtccctgtct ggccttaact cttccctctc tttctttttct  2392 ttctttcttt ctttttttt aagatagagt ctcactctgc tgcccgggct agagtgcagt    2452 ggtgggatct cggctcactg caacctctgc ctcctgggt tcaagtgatc ctcccacctc    2512 agcctcctga gtagctggga ttacaggcac ccgccaccac gtccagctaa tttttatatt    2572 tttagtagag acggggtttc accatgttgg tcaggctggt cttgaactcc tgacctcagg    2632 tgatccgctg gcctcggcct cccagagtgc tgggattata gcgtgagcc tctggcccgg    2692 cctttccttt ttcctctcct ctcctgccga gagtggaaca cacgtgtcct gggagctgca    2752 tcttgtgtag gtccagctg cttttgggga ctgcaggaat catctcccct gggccctgga    2812 ctcggactgg ggcctcccca cctccctctc ggctgtgcct tacggagccc caatccaggc    2872 ctcctgtggc tgttgggttc cagatgctgc agctccatgt gacttccaag caggccctcc    2932 gccctccctg ctgaatggag gagccggggg tcccccaggc caactggaaa atctcccagg    2992 ctaggccaat tgccttttgc acttccccgt tcctgtcaca tttccccagc ccaccttcc    3052 cctcctgatg ccctgaaagc ttccggaatt gactgtgacc acttggatgt caccactgtc    3112 agccctgcc ttgatgtccc catttagcca tctccatgga gctcctgctg gagggccctg    3172 aaccctgcac tgcgtggctg cccagccagc tgcctcctgt cctgggagga ggcctcctgg    3232 gtgtcctcat ctggtgtgtc tactggaggg tcccacagga gaggcagcag aggggtcagg    3292 ggaggtctcc tgccgggggt tggcctctca agcctcaggg gttctagcct gttgaatata    3352 ccccacctgg tgggtggccc ctccgatgtc cccactgatg gctctgacac cgtgttggtg    3412 gcgatgtccc agacaatccc accaggacgg cccagacatc cctactggct tcgctggtgg    3472 ctcatctcga acatccacgc cagcctttct ggggccggcc acccaggccg cctgtccgtc    3532
```

```
tgtcctccct ccagcagcac ccctggccc ctggagtggt ggggccatgg caagagacac    3592
cgtggcgtct catgtgaact ttcctgggca ctgtggtttt atttcctaat tgatttaaga    3652
aataaacctg aagaccgtct ggtgaaaaaa aaaaaaaaaa aagggcggcc gc            3704
```

<210> SEQ ID NO 25
<211> LENGTH: 646
<212> TYPE: PRT
<213> ORGANISM: Homo sapiens

<400> SEQUENCE: 25

```
Met Arg Ala Pro Gly Ala Gly Ala Ser Val Val Ser Leu Ala Leu
 1               5                  10                  15

Leu Trp Leu Leu Gly Leu Pro Trp Thr Trp Ser Ala Ala Ala Leu
             20                  25                  30

Gly Val Tyr Val Gly Ser Gly Gly Trp Arg Phe Leu Arg Ile Val Cys
         35                  40                  45

Lys Thr Ala Arg Arg Asp Leu Phe Gly Leu Ser Val Leu Ile Arg Val
     50                  55                  60

Arg Leu Glu Leu Arg Arg His Gln Arg Ala Gly His Thr Ile Pro Arg
 65                  70                  75                  80

Ile Phe Gln Ala Val Val Gln Arg Gln Pro Glu Arg Leu Ala Leu Val
                 85                  90                  95

Asp Ala Gly Thr Gly Glu Cys Trp Thr Phe Ala Gln Leu Asp Ala Tyr
            100                 105                 110

Ser Asn Ala Val Ala Asn Leu Phe Arg Gln Leu Gly Phe Ala Pro Gly
        115                 120                 125

Asp Val Val Ala Ile Phe Leu Glu Gly Arg Pro Glu Phe Val Gly Leu
    130                 135                 140

Trp Leu Gly Leu Ala Lys Ala Gly Met Glu Ala Ala Leu Leu Asn Val
145                 150                 155                 160

Asn Leu Arg Arg Glu Pro Leu Ala Phe Cys Leu Gly Thr Ser Gly Ala
                165                 170                 175

Lys Ala Leu Ile Phe Gly Gly Glu Met Val Ala Ala Val Ala Glu Val
            180                 185                 190

Ser Gly His Leu Gly Lys Ser Leu Ile Lys Phe Cys Ser Gly Asp Leu
        195                 200                 205

Gly Pro Glu Gly Ile Leu Pro Asp Thr His Leu Leu Asp Pro Leu Leu
    210                 215                 220

Lys Glu Ala Ser Thr Ala Pro Leu Ala Gln Ile Pro Ser Lys Gly Met
225                 230                 235                 240

Asp Asp Arg Leu Phe Tyr Ile Tyr Thr Ser Gly Thr Thr Gly Leu Pro
                245                 250                 255

Lys Ala Ala Ile Val Val His Ser Arg Tyr Tyr Arg Met Ala Ala Phe
            260                 265                 270

Gly His His Ala Tyr Arg Met Gln Ala Ala Asp Val Leu Tyr Asp Cys
        275                 280                 285

Leu Pro Leu Tyr His Ser Ala Gly Asn Ile Ile Gly Val Gly Gln Cys
    290                 295                 300

Leu Ile Tyr Gly Leu Thr Val Val Leu Arg Lys Lys Phe Ser Ala Ser
305                 310                 315                 320

Arg Phe Trp Asp Asp Cys Ile Lys Tyr Asn Cys Thr Val Val Gln Tyr
                325                 330                 335

Ile Gly Glu Ile Cys Arg Tyr Leu Leu Lys Gln Pro Val Arg Glu Ala
```

```
                    340              345              350
        Glu Arg Arg His Arg Val Arg Leu Ala Val Gly Asn Gly Leu Arg Pro
                        355              360              365
        Ala Ile Trp Glu Glu Phe Thr Glu Arg Phe Gly Val Arg Gln Ile Gly
                370              375              380
        Glu Phe Tyr Gly Ala Thr Glu Cys Asn Cys Ser Ile Ala Asn Met Asp
        385              390              395              400
        Gly Lys Val Gly Ser Cys Gly Phe Asn Ser Arg Ile Leu Pro His Val
                            405              410              415
        Tyr Pro Ile Arg Leu Val Lys Val Asn Glu Asp Thr Met Glu Leu Leu
                        420              425              430
        Arg Asp Ala Gln Gly Leu Cys Ile Pro Cys Gln Ala Gly Glu Pro Gly
                    435              440              445
        Leu Leu Val Gly Gln Ile Asn Gln Gln Asp Pro Leu Arg Arg Phe Asp
                450              455              460
        Gly Tyr Val Ser Glu Ser Ala Thr Ser Lys Lys Ile Ala His Ser Val
        465              470              475              480
        Phe Ser Lys Gly Asp Ser Ala Tyr Leu Ser Gly Asp Val Leu Val Met
                            485              490              495
        Asp Glu Leu Gly Tyr Met Tyr Phe Arg Asp Arg Ser Gly Asp Thr Phe
                        500              505              510
        Arg Trp Arg Gly Glu Asn Val Ser Thr Thr Glu Val Glu Gly Val Leu
                    515              520              525
        Ser Arg Leu Leu Gly Gln Thr Asp Val Ala Val Tyr Gly Val Ala Val
                530              535              540
        Pro Gly Val Glu Gly Lys Ala Gly Met Ala Ala Val Ala Asp Pro His
        545              550              555              560
        Ser Leu Leu Asp Pro Asn Ala Ile Tyr Gln Glu Leu Gln Lys Val Leu
                            565              570              575
        Ala Pro Tyr Ala Arg Pro Ile Phe Leu Arg Leu Leu Pro Gln Val Asp
                        580              585              590
        Thr Thr Gly Thr Phe Lys Ile Gln Lys Thr Arg Leu Gln Arg Glu Gly
                    595              600              605
        Phe Asp Pro Arg Gln Thr Ser Asp Arg Leu Phe Phe Leu Asp Leu Lys
                610              615              620
        Gln Gly His Tyr Leu Pro Leu Asn Glu Ala Val Tyr Thr Arg Ile Cys
        625              630              635              640
        Ser Gly Ala Phe Ala Leu
                        645

<210> SEQ ID NO 26
<211> LENGTH: 2917
<212> TYPE: DNA
<213> ORGANISM: Homo sapiens
<220> FEATURE:
<221> NAME/KEY: CDS
<222> LOCATION: (208)...(2136)

<400> SEQUENCE: 26
cgacccacgc gtccgggcgg gcggggccgg gcggcgggcg gggctggcgg ggcggccggg      60
ccatgcaggg cgcagagccg gctaaaccct gctgagaccc ggctccgtgc gtccagggGc     120
ggctaatgcc cctcacgctg tctacgctgc tgcaaccggg ccgcatctgg acggggcgcc    180
gcgcggcgga gccgacgccg ggccaca atg ctg ctt gga gcc tct ctg gtg ggg    234
                                Met Leu Leu Gly Ala Ser Leu Val Gly
                                 1               5
```

```
gtg ctg ctg ttc tcc aag ctg gtg ctg aaa ctg ccc tgg acc cag gtg      282
Val Leu Leu Phe Ser Lys Leu Val Leu Lys Leu Pro Trp Thr Gln Val
 10              15                  20                  25 gga ttc tcc ctg ttg ttc ctc tac ttg gga tct ggc ggc tgg cgc ttc      330
Gly Phe Ser Leu Leu Phe Leu Tyr Leu Gly Ser Gly Gly Trp Arg Phe
             30                  35                  40 atc cgg gtc ttc atc aag acc atc agg cgc gat atc ttt ggc ggc ctg      378
Ile Arg Val Phe Ile Lys Thr Ile Arg Arg Asp Ile Phe Gly Gly Leu
                 45                  50                  55 gtc ctc ctg aag gtg aag gca aag gtg cga cag tgc ctg cag gag cgg      426
Val Leu Leu Lys Val Lys Ala Lys Val Arg Gln Cys Leu Gln Glu Arg
             60                  65                  70 cgg aca gtg ccc att ttg ttt gcc tct acc gtt cgg cgc cac ccc gac      474
Arg Thr Val Pro Ile Leu Phe Ala Ser Thr Val Arg Arg His Pro Asp
 75                  80                  85 aag acg gcc ctg atc ttc gag ggc aca gat acc cac tgg acc ttc cgc      522
Lys Thr Ala Leu Ile Phe Glu Gly Thr Asp Thr His Trp Thr Phe Arg
 90                  95                 100                 105 cag ctg gat gag tac tca agc agt gta gcc aac ttc ctg cag gcc cgg      570
Gln Leu Asp Glu Tyr Ser Ser Ser Val Ala Asn Phe Leu Gln Ala Arg
             110                 115                 120 ggc ctg gcc tcg ggc gat gtg gct gcc atc ttc atg gag aac cgc aat      618
Gly Leu Ala Ser Gly Asp Val Ala Ala Ile Phe Met Glu Asn Arg Asn
             125                 130                 135 gag ttc gtg ggc cta tgg ctg ggc atg gcc aag ctc ggt gtg gag gca      666
Glu Phe Val Gly Leu Trp Leu Gly Met Ala Lys Leu Gly Val Glu Ala
             140                 145                 150 gcc ctc atc aac acc aac ctg cgg cgg gat gct ctg ctc cac tgc ctc      714
Ala Leu Ile Asn Thr Asn Leu Arg Arg Asp Ala Leu Leu His Cys Leu
 155                 160                 165 acc acc tcg cgc gca cgg gcc ctt gtc ttt ggc agc gaa atg gcc tca      762
Thr Thr Ser Arg Ala Arg Ala Leu Val Phe Gly Ser Glu Met Ala Ser
170                 175                 180                 185 gcc atc tgt gag gtc cat gcc agc ctg gac ccc tcg ctc agc ctc ttc      810
Ala Ile Cys Glu Val His Ala Ser Leu Asp Pro Ser Leu Ser Leu Phe
             190                 195                 200 tgc tct ggc tcc tgg gag ccc ggt gcg gtg cct cca agc aca gaa cac      858
Cys Ser Gly Ser Trp Glu Pro Gly Ala Val Pro Pro Ser Thr Glu His
             205                 210                 215 ctg gac cct ctg ctg aaa gat gct ccc aag cac ctt ccc agt tgc cct      906
Leu Asp Pro Leu Leu Lys Asp Ala Pro Lys His Leu Pro Ser Cys Pro
             220                 225                 230 gac aag ggc ttc aca gat aaa ctg ttc tac atc tac aca tcc ggc acc      954
Asp Lys Gly Phe Thr Asp Lys Leu Phe Tyr Ile Tyr Thr Ser Gly Thr
             235                 240                 245 aca ggg ctg ccc aag gcc gcc atc gtg gtg cac agc agg tat tac cgc     1002
Thr Gly Leu Pro Lys Ala Ala Ile Val Val His Ser Arg Tyr Tyr Arg
250                 255                 260                 265 atg gct gcc ctg gtg tac tat gga ttc cgc atg cgg ccc aac gac atc     1050
Met Ala Ala Leu Val Tyr Tyr Gly Phe Arg Met Arg Pro Asn Asp Ile
                 270                 275                 280 gtc tat gac tgc ctc ccc ctc tac cac tca gca gga aac atc gtg gga     1098
Val Tyr Asp Cys Leu Pro Leu Tyr His Ser Ala Gly Asn Ile Val Gly
             285                 290                 295 atc ggc cag tgc ctg ctg cat ggc atg acg gtg gtg att cgg aag aag     1146
Ile Gly Gln Cys Leu Leu His Gly Met Thr Val Val Ile Arg Lys Lys
             300                 305                 310 ttc tca gcc tcc cgg ttc tgg gac gat tgt atc aag tac aac tgc acg     1194
Phe Ser Ala Ser Arg Phe Trp Asp Asp Cys Ile Lys Tyr Asn Cys Thr
```

-continued

```
            315                 320                 325
att gtg cag tac att ggt gaa ctg tgc cgc tac ctc ctg aac cag cca      1242
Ile Val Gln Tyr Ile Gly Glu Leu Cys Arg Tyr Leu Leu Asn Gln Pro
330                 335                 340                 345 ccg cgg gag gca gaa aac cag cac cag gtt cgc atg gca cta ggc aat      1290
Pro Arg Glu Ala Glu Asn Gln His Gln Val Arg Met Ala Leu Gly Asn
            350                 355                 360 ggc ctc cgg cag tcc atc tgg acc aac ttt tcc agc cgc ttc cac ata      1338
Gly Leu Arg Gln Ser Ile Trp Thr Asn Phe Ser Ser Arg Phe His Ile
        365                 370                 375 ccc cag gtg gct gag ttc tac ggg gcc aca gag tgc aac tgt agc ctg      1386
Pro Gln Val Ala Glu Phe Tyr Gly Ala Thr Glu Cys Asn Cys Ser Leu
    380                 385                 390 ggc aac ttc gac agc cag gtg ggg gcc tgt ggt ttc aat agc cgc atc      1434
Gly Asn Phe Asp Ser Gln Val Gly Ala Cys Gly Phe Asn Ser Arg Ile
395                 400                 405 ctg tcc ttc gtg tac ccc atc cgg ttg gta cgt gtc aac gag gac acc      1482
Leu Ser Phe Val Tyr Pro Ile Arg Leu Val Arg Val Asn Glu Asp Thr
410                 415                 420                 425 atg gag ctg atc cgg ggg ccc gac ggc gtc tgc att ccc tgc cag cca      1530
Met Glu Leu Ile Arg Gly Pro Asp Gly Val Cys Ile Pro Cys Gln Pro
                430                 435                 440 ggt gag ccg ggc cag ctg gtg ggc cgc atc atc cag aaa gac ccc ctg      1578
Gly Glu Pro Gly Gln Leu Val Gly Arg Ile Ile Gln Lys Asp Pro Leu
            445                 450                 455 cgc cgc ttc gat ggc tac ctc aac cag ggc gcc aac aac aag aag att      1626
Arg Arg Phe Asp Gly Tyr Leu Asn Gln Gly Ala Asn Asn Lys Lys Ile
        460                 465                 470 gcc aag gat gtc ttc aag aag ggg gac cag gcc tac ctt act ggt gat      1674
Ala Lys Asp Val Phe Lys Lys Gly Asp Gln Ala Tyr Leu Thr Gly Asp
    475                 480                 485 gtg ctg gtg atg gac gag ctg ggc tac ctg tac ttc cga gac cgc act      1722
Val Leu Val Met Asp Glu Leu Gly Tyr Leu Tyr Phe Arg Asp Arg Thr
490                 495                 500                 505 ggg gac acg ttc cgc tgg aaa ggt gag aac gtg tcc acc acc gag gtg      1770
Gly Asp Thr Phe Arg Trp Lys Gly Glu Asn Val Ser Thr Thr Glu Val
                510                 515                 520 gaa ggc aca ctc agc cgc ctg ctg gac atg gct gac gtg gcc gtg tat      1818
Glu Gly Thr Leu Ser Arg Leu Leu Asp Met Ala Asp Val Ala Val Tyr
            525                 530                 535 ggt gtc gag gtg cca gga acc gag ggc cgg gcc gga atg gct gct gtg      1866
Gly Val Glu Val Pro Gly Thr Glu Gly Arg Ala Gly Met Ala Ala Val
        540                 545                 550 gcc agc ccc act ggc aac tgt gac ctg gag cgc ttt gct cag gtc ttg      1914
Ala Ser Pro Thr Gly Asn Cys Asp Leu Glu Arg Phe Ala Gln Val Leu
    555                 560                 565 gag aag gaa ctg ccc ctg tat gcg cgc ccc atc ttc ctg cgc ctc ctg      1962
Glu Lys Glu Leu Pro Leu Tyr Ala Arg Pro Ile Phe Leu Arg Leu Leu
570                 575                 580                 585 cct gag ctg cac aaa aca gga acc tac aag ttc cag aag aca gag cta      2010
Pro Glu Leu His Lys Thr Gly Thr Tyr Lys Phe Gln Lys Thr Glu Leu
                590                 595                 600 cgg aag gag ggc ttt gac ccg gct att gtg aaa gac ccg ctg ttc tat      2058
Arg Lys Glu Gly Phe Asp Pro Ala Ile Val Lys Asp Pro Leu Phe Tyr
            605                 610                 615 cta gat gcc cag aag ggc cgc tac gtc ccg ctg gac caa gag gcc tac      2106
Leu Asp Ala Gln Lys Gly Arg Tyr Val Pro Leu Asp Gln Glu Ala Tyr
        620                 625                 630 agc cgc atc cag gca ggc gag gag aag ctg tgattccccc catccctctg         2156
Ser Arg Ile Gln Ala Gly Glu Glu Lys Leu
```

-continued

```
Ser Arg Ile Gln Ala Gly Glu Glu Lys Leu
    635                 640
```

| | |
|---|---|
| agggccggcg gatgctggat ccggagcccc aggttccgcc ccagagcggt cctggacaag | 2216 |
| gccagaccaa agcaagcagg gcctggcacc tccatcctga ggtgctgccc ctccatccaa | 2276 |
| aactgccaag tgactcattg ccttcccaac ccttccagag gctttctgtg aaagtctcat | 2336 |
| gtccaagttc cgtcttctgg gctgggcagg ccctctggtt cccaggctga gactgacggg | 2396 |
| ttttctcagg atgatgtctt gggtgagggt agggagagga caagggtca ccgagccctt | 2456 |
| cccagagagc agggagctta taatggaac agagcagaa gtccccagac tcaggaagtc | 2516 |
| aacagagtgg gcagggacag tggtagcatc catctggtgg ccaaagagaa tcgtagcccc | 2576 |
| agagctgccc aagttcactg ggctccaccc ccacctccag gaggggagga gaggacctga | 2636 |
| catctgtagg tggcccctga tgccccatct acagcaggag gtcaggacca cgcccctggc | 2696 |
| ctctccccac tcccccatcc tcctccctgg gtggctgcct gattatccct caggcagggc | 2756 |
| ctctcagtcc ttgtgggtct gtgtcacctc catctcagtc ttggcctggc tatgagggga | 2816 |
| ggaggaatgg gagaggggc tcaggggcca ataaactctg ccttgagtcc tcctaaaaaa | 2876 |
| aaaaaaaaaa aaaaaaaaaa aaaaaaaaaa agggcggccg c | 2917 |

```
<210> SEQ ID NO 27
<211> LENGTH: 643
<212> TYPE: PRT
<213> ORGANISM: Homo sapiens

<400> SEQUENCE: 27

Met Leu Leu Gly Ala Ser Leu Val Gly Val Leu Phe Ser Lys Leu
  1               5                  10                  15

Val Leu Lys Leu Pro Trp Thr Gln Val Gly Phe Ser Leu Leu Phe Leu
                 20                  25                  30

Tyr Leu Gly Ser Gly Gly Trp Arg Phe Ile Arg Val Phe Ile Lys Thr
             35                  40                  45

Ile Arg Arg Asp Ile Phe Gly Gly Leu Val Leu Leu Lys Val Lys Ala
         50                  55                  60

Lys Val Arg Gln Cys Leu Gln Glu Arg Arg Thr Val Pro Ile Leu Phe
 65                  70                  75                  80

Ala Ser Thr Val Arg Arg His Pro Asp Lys Thr Ala Leu Ile Phe Glu
                 85                  90                  95

Gly Thr Asp Thr His Trp Thr Phe Arg Gln Leu Asp Glu Tyr Ser Ser
            100                 105                 110

Ser Val Ala Asn Phe Leu Gln Ala Arg Gly Leu Ala Ser Gly Asp Val
        115                 120                 125

Ala Ala Ile Phe Met Glu Asn Arg Asn Glu Phe Val Gly Leu Trp Leu
    130                 135                 140

Gly Met Ala Lys Leu Gly Val Glu Ala Ala Leu Ile Asn Thr Asn Leu
145                 150                 155                 160

Arg Arg Asp Ala Leu Leu His Cys Leu Thr Thr Ser Arg Ala Arg Ala
                165                 170                 175

Leu Val Phe Gly Ser Glu Met Ala Ser Ala Ile Cys Glu Val His Ala
            180                 185                 190

Ser Leu Asp Pro Ser Leu Ser Leu Phe Cys Ser Gly Ser Trp Glu Pro
        195                 200                 205

Gly Ala Val Pro Pro Ser Thr Glu His Leu Asp Pro Leu Leu Lys Asp
    210                 215                 220
```

-continued

```
Ala Pro Lys His Leu Pro Ser Cys Pro Asp Lys Gly Phe Thr Asp Lys
225                 230                 235                 240

Leu Phe Tyr Ile Tyr Thr Ser Gly Thr Thr Gly Leu Pro Lys Ala Ala
            245                 250                 255

Ile Val Val His Ser Arg Tyr Tyr Arg Met Ala Ala Leu Val Tyr Tyr
                260                 265                 270

Gly Phe Arg Met Arg Pro Asn Asp Ile Val Tyr Asp Cys Leu Pro Leu
            275                 280                 285

Tyr His Ser Ala Gly Asn Ile Val Gly Ile Gly Gln Cys Leu Leu His
        290                 295                 300

Gly Met Thr Val Val Ile Arg Lys Lys Phe Ser Ala Ser Arg Phe Trp
305                 310                 315                 320

Asp Asp Cys Ile Lys Tyr Asn Cys Thr Ile Val Gln Tyr Ile Gly Glu
                325                 330                 335

Leu Cys Arg Tyr Leu Leu Asn Gln Pro Pro Arg Glu Ala Glu Asn Gln
            340                 345                 350

His Gln Val Arg Met Ala Leu Gly Asn Gly Leu Arg Gln Ser Ile Trp
        355                 360                 365

Thr Asn Phe Ser Ser Arg Phe His Ile Pro Gln Val Ala Glu Phe Tyr
370                 375                 380

Gly Ala Thr Glu Cys Asn Cys Ser Leu Gly Asn Phe Asp Ser Gln Val
385                 390                 395                 400

Gly Ala Cys Gly Phe Asn Ser Arg Ile Leu Ser Phe Val Tyr Pro Ile
            405                 410                 415

Arg Leu Val Arg Val Asn Glu Asp Thr Met Glu Leu Ile Arg Gly Pro
        420                 425                 430

Asp Gly Val Cys Ile Pro Cys Gln Pro Gly Glu Pro Gly Gln Leu Val
            435                 440                 445

Gly Arg Ile Ile Gln Lys Asp Pro Leu Arg Arg Phe Asp Gly Tyr Leu
    450                 455                 460

Asn Gln Gly Ala Asn Asn Lys Lys Ile Ala Lys Asp Val Phe Lys Lys
465                 470                 475                 480

Gly Asp Gln Ala Tyr Leu Thr Gly Asp Val Leu Val Met Asp Glu Leu
            485                 490                 495

Gly Tyr Leu Tyr Phe Arg Asp Arg Thr Gly Asp Thr Phe Arg Trp Lys
        500                 505                 510

Gly Glu Asn Val Ser Thr Thr Glu Val Glu Gly Thr Leu Ser Arg Leu
    515                 520                 525

Leu Asp Met Ala Asp Val Ala Val Tyr Gly Val Glu Val Pro Gly Thr
530                 535                 540

Glu Gly Arg Ala Gly Met Ala Ala Val Ala Ser Pro Thr Gly Asn Cys
545                 550                 555                 560

Asp Leu Glu Arg Phe Ala Gln Val Leu Glu Lys Glu Leu Pro Leu Tyr
            565                 570                 575

Ala Arg Pro Ile Phe Leu Arg Leu Leu Pro Glu Leu His Lys Thr Gly
            580                 585                 590

Thr Tyr Lys Phe Gln Lys Thr Glu Leu Arg Lys Glu Gly Phe Asp Pro
        595                 600                 605

Ala Ile Val Lys Asp Pro Leu Phe Tyr Leu Asp Ala Gln Lys Gly Arg
        610                 615                 620

Tyr Val Pro Leu Asp Gln Glu Ala Tyr Ser Arg Ile Gln Ala Gly Glu
625                 630                 635                 640

Glu Lys Leu
```

<210> SEQ ID NO 28
<211> LENGTH: 1941
<212> TYPE: DNA
<213> ORGANISM: Homo sapiens

<400> SEQUENCE: 28

| | | | | | | |
|---|---|---|---|---|---|---|
| atgcgggctc | cgggtgcggg | cgcggcctcg | gtggtctcgc | tggcgctgtt | gtggctgctg | 60 |
| gggctgccgt | ggacctggag | cgcggcagcg | gcgctcggcg | tgtacgtggg | cagcggcggc | 120 |
| tggcgcttcc | tgcgcatcgt | ctgcaagacc | gcgaggcgag | acctcttcgg | tctctctgtg | 180 |
| ctgatccgcg | tgcgcctgga | gctgcggcgg | caccagcgtg | ccggccacac | catcccgcgc | 240 |
| atctttcagg | cggtagtgca | gcgacagccc | gagcgcctgg | cgctggtgga | tgccgggacc | 300 |
| ggcgagtgct | ggacctttgc | gcagctggac | gcctactcca | atgcggtagc | caacctcttc | 360 |
| cgccagctgg | gcttcgcgcc | gggcgacgtg | gtggccatct | tcctggaggg | ccggccggag | 420 |
| ttcgtggggc | tgtggctggg | cctggccaag | gcgggcatgg | aggccgcgct | gctcaacgtg | 480 |
| aacctgcggc | gcgagcccct | ggccttctgc | ctgggcacct | cggcgctaa | ggccctgatc | 540 |
| tttggaggag | aaatggtggc | ggcggtggcc | gaagtgagcg | ggcatctggg | gaaaagtttg | 600 |
| atcaagttct | gctctggaga | cttggggccc | gagggcatct | tgccggacac | ccacctcctg | 660 |
| gacccgctgc | tgaaggaggc | ctctactgcc | cccttggcac | agatccccag | caagggcatg | 720 |
| gacgatcgtc | ttttctacat | ctacacgtcg | ggaccaccg | gctgcccaa | ggctgccatt | 780 |
| gtcgtgcaca | gcaggtacta | ccgcatggca | gccttcggcc | accacgccta | ccgcatgcag | 840 |
| gcggctgacg | tgctctatga | ctgcctgccc | ctgtaccact | cggcaggaaa | catcatcggc | 900 |
| gtggggcagt | gtctcatcta | tgggctgaca | gtcgtcctcc | gcaagaaatt | ctcggccagc | 960 |
| cgcttctggg | acgactgcat | caagtacaac | tgcacggtgg | ttcagtacat | cggggagatc | 1020 |
| tgccgctacc | tgctgaagca | gccggtgcgc | gaggcggaga | ggcgacaccg | cgtgcgcctg | 1080 |
| gcggtgggga | acgggctgcg | tcctgccatc | tgggaggagt | tcacggagcg | cttcggcgta | 1140 |
| cgccaaatcg | gggagttcta | cggcgccacc | gagtgcaact | gcagcattgc | caacatggac | 1200 |
| ggcaaggtcg | gctcctgtgg | tttcaacagc | cgcatcctgc | cccacgtgta | ccccatccgg | 1260 |
| ctggtgaagg | tcaatgagga | cacaatggag | ctgctgcggg | atgcccaggg | cctctgcatc | 1320 |
| ccctgccagg | ccggggagcc | tggcctcctt | gtgggtcaga | tcaaccaaca | ggacccgctg | 1380 |
| cgccgcttcg | atggctatgt | cagcgagagc | gccaccagca | agaagatcgc | ccacagcgtc | 1440 |
| ttcagcaagg | gcgacagcgc | ctacctctca | ggtgacgtgc | tagtgatgga | tgagctgggc | 1500 |
| tacatgtact | tccgggaccg | tagcggggac | accttccgct | ggcgagggga | gaacgtctcc | 1560 |
| accaccgagg | tggagggcgt | gctgagccgc | ctgctgggcc | agacagacgt | ggccgtctat | 1620 |
| ggggtggctg | ttccaggagt | ggagggtaag | gcagggatgg | cggccgtcgc | agaccccac | 1680 |
| agcctgctgg | accccaacgc | gatataccag | gagctgcaga | aggtgctggc | accctatgcc | 1740 |
| cggcccatct | tcctgcgcct | cctgcccag | gtggacacca | caggcacctt | caagatccag | 1800 |
| aagacgaggc | tgcagcgaga | gggctttgac | ccacgccaga | cctcagaccg | gctcttcttc | 1860 |
| ctggacctga | agcagggcca | ctacctgccc | ttaaatgagg | cagtctacac | tcgcatctgc | 1920 |
| tcgggcgcct | tcgccctctg | a | | | | 1941 |

<210> SEQ ID NO 29
<211> LENGTH: 1938
<212> TYPE: DNA

<213> ORGANISM: Mus musculus

<400> SEQUENCE: 29

| | | | | | |
|---|---|---|---|---|---|
| atgcgggctc | ctggagcagg | aacagcctct | gtggcctcac | tggcgctgct | ttggtttctg | 60 |
| ggacttccgt | ggacctggag | cgcggcggcg | gcgttctgtg | tgtacgtggg | tggcggcggc | 120 |
| tggcgctttc | tgcgtatcgt | ctgcaagacg | gcgaggcgag | acctctttgg | cctctctgtt | 180 |
| ctgattcgtg | ttcggctaga | gctgcgacga | caccggcgag | caggagacac | gatcccgtgc | 240 |
| atcttccagg | ctgtggcccg | cgacaaccca | gagcgcctgg | cactggtgga | cgccagtagt | 300 |
| ggtatatgct | ggaccttcgc | acagctggac | acctactcca | atgctgtagc | caacctgttc | 360 |
| cgccagctgg | gctttgcacc | aggcgatgtg | gtggctgtgt | tcctggaggg | ccggccggag | 420 |
| ttcgtgggac | tgtggctggg | cctggccaag | gccggtgtgg | tggctgctct | tctcaatgtc | 480 |
| aacctgaggc | gggagcccct | ggccttctgc | ctgggcacat | cagctgccaa | ggccctcatt | 540 |
| tatggcgggg | agatggcagc | ggcggtggcg | gaggtgagcg | agcagctggg | gaagagcctc | 600 |
| ctcaagttct | gctctggaga | tctgggggcct | gagagcatcc | tgcctgacac | gcagctcctg | 660 |
| gaccccatgc | ttgctgaggc | gcccaccaca | cccctggcac | aagcccagg | caagggcatg | 720 |
| gatgatcggc | tgttttacat | ctatacttct | gggaccaccg | ggcttcctaa | ggctgccatt | 780 |
| gtggtgcaca | gcaggtacta | ccgcattgct | gcctttggcc | accattccta | cagcatgcgt | 840 |
| gccgccgatg | tgctctatga | ctgcctgcca | ctctaccact | ctgcaggaa | catcatgggt | 900 |
| gtggggcagt | gcgtcatcta | cggttgacg | gtggtactgc | gcaagaagtt | ctccgccagc | 960 |
| cgcttctggg | atgactgtgt | caagtacaat | tgcacggtag | tgcagtacat | aggtgaaatc | 1020 |
| tgccgctacc | tgctgaggca | gccggttcgc | gacgtggagc | agcgacaccg | cgtgcgcctg | 1080 |
| gccgtgggta | atgggctgcg | gccagccatc | tgggaggagt | tcacgcagcg | cttcggtgtg | 1140 |
| ccacagatcg | gcgagttcta | cggcgctacc | gagtgcaact | gcagcattgc | caacatggac | 1200 |
| ggcaaggtcg | gctcctgcgg | cttcaacagc | cgtatcctca | cgcatgtgta | ccccatccgt | 1260 |
| ctggtcaagg | tcaatgagga | cacgatggag | ccactgcggg | actccgaggg | cctctgcatc | 1320 |
| ccgtgccagc | ccggggaacc | cggccttctc | gtgggccaga | tcaaccagca | ggaccctctg | 1380 |
| cggcgtttcg | atggttatgt | tagtgacagt | gccaccaaca | agaagattgc | ccacagcgtt | 1440 |
| ttccgaaagg | gcgatagcgc | ctacctctca | ggtgacgtgc | tagtgatgga | cgagctgggc | 1500 |
| tacatgtatt | tccgtgaccg | cagcggggac | accttccgct | ggcgcgggga | gaacgtgtcc | 1560 |
| accacggagg | tggaagccgt | gctgagccgc | ctactgggcc | agacggacgt | ggctgtgtat | 1620 |
| ggggtggctg | tgccaggagt | ggaggggaaa | gctggcatgg | cagccatcgc | agatccccac | 1680 |
| agccagttgg | accctaactc | aatgtaccag | gaattacaga | aggttcttgc | atcctatgct | 1740 |
| cggcccatct | tcctgcgtct | tctgccccag | gtggatacca | caggcacctt | caagatccag | 1800 |
| aagacccggc | tgcagcgtga | aggctttgac | ccccgtcaga | cctcagacag | gctcttcttt | 1860 |
| ctagacctga | agcagggacg | ctatgtaccc | ctggatgaga | gagtccatgc | ccgcatttgt | 1920 |
| gcaggcgact | tctcactc | | | | | 1938 |

<210> SEQ ID NO 30
<211> LENGTH: 1896
<212> TYPE: DNA
<213> ORGANISM: Homo sapiens

<400> SEQUENCE: 30

| | | | | | |
|---|---|---|---|---|---|
| ctgttctcca | agctggtgct | gaaactgccc | tggacccagg | tggattctc | cctgttgttc | 60 |

```
ctctacttgg gatctggcgg ctggcgcttc atccgggtct tcatcaagac catcaggcgc    120
gatatctttg gcggcctggt cctcctgaag gtgaaggcaa aggtgcgaca gtgcctgcag    180
gagcggcgga cagtgcccat tttgtttgcc tctaccgttc ggcgccaccc cgacaagacg    240
gccctgatct tcgagggcac agatacccac tggaccttcc gccagctgga tgagtactca    300
agcagtgtag ccaacttcct gcaggcccgg ggcctggcct cgggcgatgt ggctgccatc    360
ttcatggaga accgcaatga gttcgtgggc ctatggctgg gcatggccaa gctcggtgtg    420
gaggcagccc tcatcaacac caacctgcgg cgggatgctc tgctccactg cctcaccacc    480
tcgcgcgcac gggcccttgt ctttggcagc gaaatggcct cagccatctg tgaggtccat    540
gccagcctgg acccctcgct cagcctcttc tgctctggct cctgggagcc cggtgcggtg    600
cctccaagca cagaacacct ggaccctctg ctgaaagatg ctcccaagca ccttccagt     660 tgccctgaca agggcttcac agataaactg ttctacatct acacatccgg caccacaggg    720
ctgcccaagg ccgccatcgt ggtgcacagc aggtattacc gcatggctgc cctggtgtac    780
tatggattcc gcatgcggcc caacgacatc gtctatgact gcctccccct ctaccactca    840
gcaggaaaca tcgtgggaat cggccagtgc ctgctgcatg gcatgacggt ggtgattcgg    900
aagaagttct cagcctcccg gttctgggac gattgtatca agtacaactg cacgattgtg    960
cagtacattg gtgaactgtg ccgctacctc ctgaaccagc caccgcggga ggcagaaaac   1020
cagcaccagg ttcgcatggc actaggcaat ggcctccggc agtccatctg gaccaacttt   1080
tccagccgct tccacatacc ccaggtggct gagttctacg gggccacaga gtgcaactgt   1140
agcctgggca acttcgacag ccaggtgggg gcctgtggtt tcaatagccg catcctgtcc   1200
ttcgtgtacc ccatccggtt ggtacgtgtc aacgaggaca ccatggagct gatccggggg   1260
cccgacggcg tctgcattcc ctgccagcca ggtgagccgg ccagctggt gggccgcatc    1320 atccagaaag accccctgcg ccgcttcgat ggctacctca accagggcgc caacaacaag   1380
aagattgcca aggatgtctt caagaagggg gaccaggcct accttactgg tgatgtgctg   1440
gtgatggacg agctgggcta cctgtacttc cgagaccgca ctgggacac gttccgctgg    1500 aaaggtgaga acgtgtccac caccgaggtg aaggcacac tcagccgcct gctggacatg    1560
gctgacgtgg ccgtgtatgg tgtcgaggtg ccaggaaccg agggccgggc cggaatggct   1620
gctgtggcca gccccactgg caactgtgac ctggagcgct tgctcaggt cttggagaag    1680 gaactgcccc tgtatgcgcg ccccatcttc ctgcgcctcc tgcctgagct gcacaaaaca   1740
ggaacctaca agttccagaa gacagagcta cggaaggagg gctttgaccc ggctattgtg   1800
aaagacccgc tgttctatct agatgcccag aagggccgca cgtcccgct ggaccaagag    1860 gcctacagcc gcatccaggc aggcgaggag aagctg                              1896
```

<210> SEQ ID NO 31
<211> LENGTH: 1896
<212> TYPE: DNA
<213> ORGANISM: Mus musculus

<400> SEQUENCE: 31

```
cttgggtcca agctagtgct gaagctgccc tggacccagg tgggattctc cctgttgctc     60
ctgtacttgg ggtctggtgg ctggcgtttc atccgggtct tcatcaagac ggtcaggaga    120
gatatctttg gtggcatggt gctcctgaag gtgaagacca aggtgcgacg gtaccttcag    180
gagcggaaga cggtgcccct gctgtttgct tcaatggtac agcgccaccc ggacaagaca    240
```

-continued

```
gccctgattt tcgagggcac agacactcac tggaccttcc gccagctgga tgagtactcc    300
agtagtgtgg ccaacttcct gcaggcccgg ggcctggcct caggcaatgt agttgccctc    360
tttatggaaa accgcaatga gtttgtgggt ctgtggctag catggccaa gctgggcgtg     420 gaggcggctc tcatcaacac caaccttagg cgggatgccc tgcgccactg tcttgacacc    480
tcaaaggcac gagctctcat ctttggcagt gagatggcct cagctatctg tgagatccat    540
gctagcctgg agcccacact cagcctcttc tgctctggat cctgggagcc cagcacagtg    600
cccgtcagca cagagcatct ggaccctctt ctggaagatg ccccgaagca cctgcccagt    660
cacccagaca agggttttac agataagctc ttctacatct acacatcggg caccacgggg    720
ctacccaaag ctgccattgt ggtgcacagc aggtattatc gtatggcttc cctggtgtac    780
tatggattcc gcatgcggcc tgatgacatt gtctatgact gcctcccct ctaccactca     840 agcaggaaac atcgtgggga ttggcagtgc ttactccacg gcatgactgt ggtgatccgg    900
aagaagttct cagcctcccg gttctgggat gattgtatca agtacaactg cacagtggta   960
cagtacattg gcgagctctg ccgctacctc ctgaaccagc caccccgtga ggctgagtct   1020
cggcacaagg tgcgcatggc actgggcaac ggtctccggc agtccatctg gaccgacttc   1080
tccagccgtt tccacatccc ccaggtggct gagttctatg gggccactga atgcaactgt   1140
agcctgggca actttgacag ccgggtgggg gcctgtggct tcaatagccg catcctgtcc   1200
tttgtgtacc ctatccgttt ggtacgtgtc aatgaggata ccatggaact gatccgggga   1260
cccgatggag tctgcattcc ctgtcaacca gtcagccag gccagctggt gggtcgcatc    1320
atccagcagg accctctgcg ccgtttcgac gggtacctca accagggtgc caacaacaag   1380
aagattgcta atgatgtctt caagaagggg gaccaagcct acctcactgg tgacgtcctg   1440
gtgatggatg agctgggtta cctgtacttc cgagatcgca ctggggacac gttccgctgg   1500 aaagggggaga atgtatctac cactgaggtg gagggcacac tcagccgcct gcttcatatg   1560
gcagatgtgg cagtttatgg tgttgaggtg ccaggaactg aaggccgagc aggaatggct   1620
gccgttgcaa gtcccatcag caactgtgac ctggagagct tgcacagac cttgaaaaag    1680 gagctgcctc tgtatgcccg ccccatcttc ctgcgcttct gcctgagct gcacaagaca    1740 gggaccttca gttccagaa acagagttg cggaaggagg gctttgaccc atctgttgtg     1800
aaagacccgc tgttctatct ggatgctcgg aagggctgct acgttgcact ggaccaggag   1860
gcctataccc gcatccaggc aggcgaggag aagctg                              1896
```

<210> SEQ ID NO 32
<211> LENGTH: 646
<212> TYPE: PRT
<213> ORGANISM: Homo sapiens

<400> SEQUENCE: 32

```
Met Arg Ala Pro Gly Ala Gly Ala Ala Ser Val Val Ser Leu Ala Leu
 1               5                  10                  15

Leu Trp Leu Leu Gly Leu Pro Trp Thr Trp Ser Ala Ala Ala Ala Leu
            20                  25                  30

Gly Val Tyr Val Gly Ser Gly Gly Trp Arg Phe Leu Arg Ile Val Cys
        35                  40                  45

Lys Thr Ala Arg Arg Asp Leu Phe Gly Leu Ser Val Leu Ile Arg Val
    50                  55                  60

Arg Leu Glu Leu Arg Arg His Gln Arg Ala Gly His Thr Ile Pro Arg
65                  70                  75                  80
```

```
Ile Phe Gln Ala Val Val Gln Arg Gln Pro Glu Arg Leu Ala Leu Val
                85                  90                  95
Asp Ala Gly Thr Gly Glu Cys Trp Thr Phe Ala Gln Leu Asp Ala Tyr
               100                 105                 110
Ser Asn Ala Val Ala Asn Leu Phe Arg Gln Leu Gly Phe Ala Pro Gly
               115                 120                 125
Asp Val Val Ala Ile Phe Leu Glu Gly Arg Pro Glu Phe Val Gly Leu
           130                 135                 140
Trp Leu Gly Leu Ala Lys Ala Gly Met Glu Ala Ala Leu Leu Asn Val
145                 150                 155                 160
Asn Leu Arg Arg Glu Pro Leu Ala Phe Cys Leu Gly Thr Ser Gly Ala
                165                 170                 175
Lys Ala Leu Ile Phe Gly Gly Glu Met Val Ala Ala Val Ala Glu Val
               180                 185                 190
Ser Gly His Leu Gly Lys Ser Leu Ile Lys Phe Cys Ser Gly Asp Leu
           195                 200                 205
Gly Pro Glu Gly Ile Leu Pro Asp Thr His Leu Leu Asp Pro Leu Leu
           210                 215                 220
Lys Glu Ala Ser Thr Ala Pro Leu Ala Gln Ile Pro Ser Lys Gly Met
225                 230                 235                 240
Asp Asp Arg Leu Phe Tyr Ile Tyr Thr Ser Gly Thr Thr Gly Leu Pro
                245                 250                 255
Lys Ala Ala Ile Val Val His Ser Arg Tyr Tyr Arg Met Ala Ala Phe
               260                 265                 270
Gly His His Ala Tyr Arg Met Gln Ala Ala Asp Val Leu Tyr Asp Cys
           275                 280                 285
Leu Pro Leu Tyr His Ser Ala Gly Asn Ile Ile Gly Val Gly Gln Cys
           290                 295                 300
Leu Ile Tyr Gly Leu Thr Val Leu Arg Lys Lys Phe Ser Ala Ser
305                 310                 315                 320
Arg Phe Trp Asp Asp Cys Ile Lys Tyr Asn Cys Thr Val Val Gln Tyr
                325                 330                 335
Ile Gly Glu Ile Cys Arg Tyr Leu Leu Lys Gln Pro Val Arg Glu Ala
               340                 345                 350
Glu Arg Arg His Arg Val Arg Leu Ala Val Gly Asn Gly Leu Arg Pro
           355                 360                 365
Ala Ile Trp Glu Glu Phe Thr Glu Arg Phe Gly Val Arg Gln Ile Gly
           370                 375                 380
Glu Phe Tyr Gly Ala Thr Glu Cys Asn Cys Ser Ile Ala Asn Met Asp
385                 390                 395                 400
Gly Lys Val Gly Ser Cys Gly Phe Asn Ser Arg Ile Leu Pro His Val
                405                 410                 415
Tyr Pro Ile Arg Leu Val Lys Val Asn Glu Asp Thr Met Glu Leu Leu
               420                 425                 430
Arg Asp Ala Gln Gly Leu Cys Ile Pro Cys Gln Ala Gly Glu Pro Gly
           435                 440                 445
Leu Leu Val Gly Gln Ile Asn Gln Gln Asp Pro Leu Arg Arg Phe Asp
           450                 455                 460
Gly Tyr Val Ser Glu Ser Ala Thr Ser Lys Lys Ile Ala His Ser Val
465                 470                 475                 480
Phe Ser Lys Gly Asp Ser Ala Tyr Leu Ser Gly Asp Val Leu Val Met
                485                 490                 495
Asp Glu Leu Gly Tyr Met Tyr Phe Arg Asp Arg Ser Gly Asp Thr Phe
```

```
                    500                 505                 510
Arg Trp Arg Gly Glu Asn Val Ser Thr Thr Glu Val Glu Gly Val Leu
                515                 520                 525

Ser Arg Leu Leu Gly Gln Thr Asp Val Ala Val Tyr Gly Val Ala Val
        530                 535                 540

Pro Gly Val Glu Gly Lys Ala Gly Met Ala Ala Val Ala Asp Pro His
545                 550                 555                 560

Ser Leu Leu Asp Pro Asn Ala Ile Tyr Gln Glu Leu Gln Lys Val Leu
                565                 570                 575

Ala Pro Tyr Ala Arg Pro Ile Phe Leu Arg Leu Leu Pro Gln Val Asp
                580                 585                 590

Thr Thr Gly Thr Phe Lys Ile Gln Lys Thr Arg Leu Gln Arg Glu Gly
        595                 600                 605

Phe Asp Pro Arg Gln Thr Ser Asp Arg Leu Phe Phe Leu Asp Leu Lys
        610                 615                 620

Gln Gly His Tyr Leu Pro Leu Asn Glu Ala Val Tyr Thr Arg Ile Cys
625                 630                 635                 640

Ser Gly Ala Phe Ala Leu
                645

<210> SEQ ID NO 33
<211> LENGTH: 646
<212> TYPE: PRT
<213> ORGANISM: Mus musculus

<400> SEQUENCE: 33

Met Arg Ala Pro Gly Ala Gly Thr Ala Ser Val Ala Ser Leu Ala Leu
1               5                   10                  15

Leu Trp Phe Leu Gly Leu Pro Trp Thr Trp Ser Ala Ala Ala Ala Phe
                20                  25                  30

Cys Val Tyr Val Gly Gly Gly Trp Arg Phe Leu Arg Ile Val Cys
            35                  40                  45

Lys Thr Ala Arg Arg Asp Leu Phe Gly Leu Ser Val Leu Ile Arg Val
        50                  55                  60

Arg Leu Glu Leu Arg Arg His Arg Arg Ala Gly Asp Thr Ile Pro Cys
65                  70                  75                  80

Ile Phe Gln Ala Val Ala Arg Arg Gln Pro Glu Arg Leu Ala Leu Val
                85                  90                  95

Asp Ala Ser Ser Gly Ile Cys Trp Thr Phe Ala Gln Leu Asp Thr Tyr
            100                 105                 110

Ser Asn Ala Val Ala Asn Leu Phe Arg Gln Leu Gly Phe Ala Pro Gly
        115                 120                 125

Asp Val Val Ala Val Phe Leu Glu Gly Arg Pro Glu Phe Val Gly Leu
    130                 135                 140

Trp Leu Gly Leu Ala Lys Ala Gly Val Val Ala Ala Leu Leu Asn Val
145                 150                 155                 160

Asn Leu Arg Arg Glu Pro Leu Ala Phe Cys Leu Gly Thr Ser Ala Ala
                165                 170                 175

Lys Ala Leu Ile Tyr Gly Gly Glu Met Ala Ala Ala Val Ala Glu Val
            180                 185                 190

Ser Glu Gln Leu Gly Lys Ser Leu Leu Lys Phe Cys Ser Gly Asp Leu
        195                 200                 205

Gly Pro Glu Ser Ile Leu Pro Asp Thr Gln Leu Leu Asp Pro Met Leu
    210                 215                 220
```

```
Ala Glu Ala Pro Thr Thr Pro Leu Ala Gln Ala Pro Gly Lys Gly Met
225                 230                 235                 240

Asp Asp Arg Leu Phe Tyr Ile Tyr Thr Ser Gly Thr Thr Gly Leu Pro
            245                 250                 255

Lys Ala Ala Ile Val Val His Ser Arg Tyr Tyr Arg Ile Ala Ala Phe
            260                 265                 270

Gly His His Ser Tyr Ser Met Arg Ala Ala Asp Val Leu Tyr Asp Cys
            275                 280                 285

Leu Pro Leu Tyr His Ser Ala Gly Asn Ile Met Gly Val Gly Gln Cys
        290                 295                 300

Val Ile Tyr Gly Leu Thr Val Leu Arg Lys Lys Phe Ser Ala Ser
305                 310                 315                 320

Arg Phe Trp Asp Asp Cys Val Lys Tyr Asn Cys Thr Val Val Gln Tyr
                325                 330                 335

Ile Gly Glu Ile Cys Arg Tyr Leu Leu Arg Gln Pro Val Arg Asp Val
            340                 345                 350

Glu Gln Arg His Arg Val Arg Leu Ala Val Gly Asn Gly Leu Arg Pro
            355                 360                 365

Ala Ile Trp Glu Glu Phe Thr Gln Arg Phe Gly Val Pro Gln Ile Gly
370                 375                 380

Glu Phe Tyr Gly Ala Thr Glu Cys Asn Cys Ser Ile Ala Asn Met Asp
385                 390                 395                 400

Gly Lys Val Gly Ser Cys Gly Phe Asn Ser Arg Ile Leu Thr His Val
                405                 410                 415

Tyr Pro Ile Arg Leu Val Lys Val Asn Glu Asp Thr Met Glu Pro Leu
            420                 425                 430

Arg Asp Ser Glu Gly Leu Cys Ile Pro Cys Gln Pro Gly Glu Pro Gly
            435                 440                 445

Leu Leu Val Gly Gln Ile Asn Gln Gln Asp Pro Leu Arg Arg Phe Asp
        450                 455                 460

Gly Tyr Val Ser Asp Ser Ala Thr Asn Lys Lys Ile Ala His Ser Val
465                 470                 475                 480

Phe Arg Lys Gly Asp Ser Ala Tyr Leu Ser Gly Asp Val Leu Val Met
                485                 490                 495

Asp Glu Leu Gly Tyr Met Tyr Phe Arg Asp Arg Ser Gly Asp Thr Phe
            500                 505                 510

Arg Trp Arg Gly Glu Asn Val Ser Thr Thr Glu Val Glu Ala Val Leu
            515                 520                 525

Ser Arg Leu Leu Gly Gln Thr Asp Val Ala Val Tyr Gly Val Ala Val
        530                 535                 540

Pro Gly Val Glu Gly Lys Ala Gly Met Ala Ala Ile Ala Asp Pro His
545                 550                 555                 560

Ser Gln Leu Asp Pro Asn Ser Met Tyr Gln Glu Leu Gln Lys Val Leu
                565                 570                 575

Ala Ser Tyr Ala Arg Pro Ile Phe Leu Arg Leu Leu Pro Gln Val Asp
            580                 585                 590

Thr Thr Gly Thr Phe Lys Ile Gln Lys Thr Arg Leu Gln Arg Glu Gly
            595                 600                 605

Phe Asp Pro Arg Gln Thr Ser Arg Leu Phe Leu Asp Leu Lys
        610                 615                 620

Gln Gly Arg Tyr Val Pro Leu Asp Glu Arg Val His Ala Arg Ile Cys
625                 630                 635                 640

Ala Gly Asp Phe Ser Leu
```

-continued

645

<210> SEQ ID NO 34
<211> LENGTH: 632
<212> TYPE: PRT
<213> ORGANISM: Homo sapiens

<400> SEQUENCE: 34

Leu Phe Ser Lys Leu Val Leu Lys Leu Pro Trp Thr Gln Val Gly Phe
1               5                   10                  15

Ser Leu Leu Phe Leu Tyr Leu Gly Ser Gly Trp Arg Phe Ile Arg
            20                  25                  30

Val Phe Ile Lys Thr Ile Arg Arg Asp Ile Phe Gly Gly Leu Val Leu
        35                  40                  45

Leu Lys Val Lys Ala Lys Val Arg Gln Cys Leu Gln Glu Arg Arg Thr
    50                  55                  60

Val Pro Ile Leu Phe Ala Ser Thr Val Arg Arg His Pro Asp Lys Thr
65                  70                  75                  80

Ala Leu Ile Phe Glu Gly Thr Asp Thr His Trp Thr Phe Arg Gln Leu
                85                  90                  95

Asp Glu Tyr Ser Ser Val Ala Asn Phe Leu Gln Ala Arg Gly Leu
            100                 105                 110

Ala Ser Gly Asp Val Ala Ala Ile Phe Met Glu Asn Arg Asn Glu Phe
        115                 120                 125

Val Gly Leu Trp Leu Gly Met Ala Lys Leu Gly Val Glu Ala Ala Leu
    130                 135                 140

Ile Asn Thr Asn Leu Arg Arg Asp Ala Leu Leu His Cys Leu Thr Thr
145                 150                 155                 160

Ser Arg Ala Arg Ala Leu Val Phe Gly Ser Glu Met Ala Ser Ala Ile
                165                 170                 175

Cys Glu Val His Ala Ser Leu Asp Pro Ser Leu Ser Leu Phe Cys Ser
            180                 185                 190

Gly Ser Trp Glu Pro Gly Ala Val Pro Pro Ser Thr Glu His Leu Asp
        195                 200                 205

Pro Leu Leu Lys Asp Ala Pro Lys His Leu Pro Ser Cys Pro Asp Lys
    210                 215                 220

Gly Phe Thr Asp Lys Leu Phe Tyr Ile Tyr Thr Ser Gly Thr Thr Gly
225                 230                 235                 240

Leu Pro Lys Ala Ala Ile Val Val His Ser Arg Tyr Tyr Arg Met Ala
                245                 250                 255

Ala Leu Val Tyr Tyr Gly Phe Arg Met Arg Pro Asn Asp Ile Val Tyr
            260                 265                 270

Asp Cys Leu Pro Leu Tyr His Ser Ala Gly Asn Ile Val Gly Ile Gly
        275                 280                 285

Gln Cys Leu Leu His Gly Met Thr Val Val Ile Arg Lys Lys Phe Ser
    290                 295                 300

Ala Ser Arg Phe Trp Asp Asp Cys Ile Lys Tyr Asn Cys Thr Ile Val
305                 310                 315                 320

Gln Tyr Ile Gly Glu Leu Cys Arg Tyr Leu Leu Asn Gln Pro Pro Arg
                325                 330                 335

Glu Ala Glu Asn Gln His Gln Val Arg Met Ala Leu Gly Asn Gly Leu
            340                 345                 350

Arg Gln Ser Ile Trp Thr Asn Phe Ser Ser Arg Phe His Ile Pro Gln
        355                 360                 365

-continued

```
Val Ala Glu Phe Tyr Gly Ala Thr Glu Cys Asn Cys Ser Leu Gly Asn
            370                 375                 380

Phe Asp Ser Gln Val Gly Ala Cys Gly Phe Asn Ser Arg Ile Leu Ser
385                 390                 395                 400

Phe Val Tyr Pro Ile Arg Leu Val Arg Val Asn Glu Asp Thr Met Glu
                405                 410                 415

Leu Ile Arg Gly Pro Asp Gly Val Cys Ile Pro Cys Gln Pro Gly Glu
            420                 425                 430

Pro Gly Gln Leu Val Gly Arg Ile Ile Gln Lys Asp Pro Leu Arg Arg
            435                 440                 445

Phe Asp Gly Tyr Leu Asn Gln Gly Ala Asn Asn Lys Lys Ile Ala Lys
        450                 455                 460

Asp Val Phe Lys Lys Gly Asp Gln Ala Tyr Leu Thr Gly Asp Val Leu
465                 470                 475                 480

Val Met Asp Glu Leu Gly Tyr Leu Tyr Phe Arg Asp Arg Thr Gly Asp
                485                 490                 495

Thr Phe Arg Trp Lys Gly Glu Asn Val Ser Thr Thr Glu Val Glu Gly
            500                 505                 510

Thr Leu Ser Arg Leu Leu Asp Met Ala Asp Val Ala Val Tyr Gly Val
            515                 520                 525

Glu Val Pro Gly Thr Glu Gly Arg Ala Gly Met Ala Ala Val Ala Ser
    530                 535                 540

Pro Thr Gly Asn Cys Asp Leu Glu Arg Phe Ala Gln Val Leu Glu Lys
545                 550                 555                 560

Glu Leu Pro Leu Tyr Ala Arg Pro Ile Phe Leu Arg Leu Leu Pro Glu
                565                 570                 575

Leu His Lys Thr Gly Thr Tyr Lys Phe Gln Lys Thr Glu Leu Arg Lys
            580                 585                 590

Glu Gly Phe Asp Pro Ala Ile Val Lys Asp Pro Leu Phe Tyr Leu Asp
            595                 600                 605

Ala Gln Lys Gly Arg Tyr Val Pro Leu Asp Gln Glu Ala Tyr Ser Arg
        610                 615                 620

Ile Gln Ala Gly Glu Glu Lys Leu
625                 630
```

<210> SEQ ID NO 35
<211> LENGTH: 632
<212> TYPE: PRT
<213> ORGANISM: Mus musculus

<400> SEQUENCE: 35

```
Leu Gly Ser Lys Leu Val Leu Lys Leu Pro Trp Thr Gln Val Gly Phe
  1               5                  10                  15

Ser Leu Leu Leu Tyr Leu Gly Ser Gly Gly Trp Arg Phe Ile Arg
            20                  25                  30

Val Phe Ile Lys Thr Val Arg Arg Asp Ile Phe Gly Gly Met Val Leu
            35                  40                  45

Leu Lys Val Lys Thr Lys Val Arg Arg Tyr Leu Gln Glu Arg Lys Thr
    50                  55                  60

Val Pro Leu Leu Phe Ala Ser Met Val Gln Arg His Pro Asp Lys Thr
65                  70                  75                  80

Ala Leu Ile Phe Glu Gly Thr Asp Thr His Trp Thr Phe Arg Gln Leu
                85                  90                  95

Asp Glu Tyr Ser Ser Val Ala Asn Phe Leu Gln Ala Arg Gly Leu
            100                 105                 110
```

-continued

```
Ala Ser Gly Asn Val Val Ala Leu Phe Met Glu Asn Arg Asn Glu Phe
        115                 120                 125
Val Gly Leu Trp Leu Gly Met Ala Lys Leu Gly Val Glu Ala Ala Leu
    130                 135                 140
Ile Asn Thr Asn Leu Arg Arg Asp Ala Leu Arg His Cys Leu Asp Thr
145                 150                 155                 160
Ser Lys Ala Arg Ala Leu Ile Phe Gly Ser Glu Met Ala Ser Ala Ile
                165                 170                 175
Cys Glu Ile His Ala Ser Leu Glu Pro Thr Leu Ser Leu Phe Cys Ser
            180                 185                 190
Gly Ser Trp Glu Pro Ser Thr Val Pro Val Ser Thr Glu His Leu Asp
        195                 200                 205
Pro Leu Leu Glu Asp Ala Pro Lys His Leu Pro Ser His Pro Asp Lys
    210                 215                 220
Gly Phe Thr Asp Lys Leu Phe Tyr Ile Tyr Thr Ser Gly Thr Thr Gly
225                 230                 235                 240
Leu Pro Lys Ala Ala Ile Val Val His Ser Arg Tyr Tyr Arg Met Ala
                245                 250                 255
Ser Leu Val Tyr Tyr Gly Phe Arg Met Arg Pro Asp Asp Ile Val Tyr
            260                 265                 270
Asp Cys Leu Pro Leu Tyr His Ser Ser Arg Lys His Arg Gly Asp Trp
        275                 280                 285
Gln Cys Leu Leu His Gly Met Thr Val Val Ile Arg Lys Lys Phe Ser
    290                 295                 300
Ala Ser Arg Phe Trp Asp Asp Cys Ile Lys Tyr Asn Cys Thr Val Val
305                 310                 315                 320
Gln Tyr Ile Gly Glu Leu Cys Arg Tyr Leu Leu Asn Gln Pro Pro Arg
                325                 330                 335
Glu Ala Glu Ser Arg His Lys Val Arg Met Ala Leu Gly Asn Gly Leu
            340                 345                 350
Arg Gln Ser Ile Trp Thr Asp Phe Ser Ser Arg Phe His Ile Pro Gln
        355                 360                 365
Val Ala Glu Phe Tyr Gly Ala Thr Glu Cys Asn Cys Ser Leu Gly Asn
    370                 375                 380
Phe Asp Ser Arg Val Gly Ala Cys Gly Phe Asn Ser Arg Ile Leu Ser
385                 390                 395                 400
Phe Val Tyr Pro Ile Arg Leu Val Arg Val Asn Glu Asp Thr Met Glu
                405                 410                 415
Leu Ile Arg Gly Pro Asp Gly Val Cys Ile Pro Cys Gln Pro Gly Gln
            420                 425                 430
Pro Gly Gln Leu Val Gly Arg Ile Ile Gln Gln Asp Pro Leu Arg Arg
        435                 440                 445
Phe Asp Gly Tyr Leu Asn Gln Gly Ala Asn Asn Lys Lys Ile Ala Asn
    450                 455                 460
Asp Val Phe Lys Lys Gly Asp Gln Ala Tyr Leu Thr Gly Asp Val Leu
465                 470                 475                 480
Val Met Asp Glu Leu Gly Tyr Leu Tyr Phe Arg Asp Arg Thr Gly Asp
                485                 490                 495
Thr Phe Arg Trp Lys Gly Glu Asn Val Ser Thr Thr Glu Val Glu Gly
            500                 505                 510
Thr Leu Ser Arg Leu Leu His Met Ala Asp Val Ala Val Tyr Gly Val
        515                 520                 525
```

```
Glu Val Pro Gly Thr Glu Gly Arg Ala Gly Met Ala Ala Val Ala Ser
    530                 535                 540
Pro Ile Ser Asn Cys Asp Leu Glu Ser Phe Ala Gln Thr Leu Lys Lys
545                 550                 555                 560
Glu Leu Pro Leu Tyr Ala Arg Pro Ile Phe Leu Arg Phe Leu Pro Glu
                565                 570                 575
Leu His Lys Thr Gly Thr Phe Lys Phe Gln Lys Thr Glu Leu Arg Lys
            580                 585                 590
Glu Gly Phe Asp Pro Ser Val Val Lys Asp Pro Leu Phe Tyr Leu Asp
        595                 600                 605
Ala Arg Lys Gly Cys Tyr Val Ala Leu Asp Gln Glu Ala Tyr Thr Arg
    610                 615                 620
Ile Gln Ala Gly Glu Glu Lys Leu
625                 630
```

<210> SEQ ID NO 36
<211> LENGTH: 2885
<212> TYPE: DNA
<213> ORGANISM: Homo sapiens

<400> SEQUENCE: 36

```
aacggcaagt aagcgcaacg caattaatgt gagtagctca ctcattaggc accccaggct    60
ttacacttta tgcttccggg ctcgtatgtt gtgtggaatt gtgagcggat accaatttca   120
cacaggaacc agctatgaca tgattacgaa tttaatacga ctcactatag ggaatttggc   180
cctcgaggcc aagaattcgg cacgagggt gctgagcccc tgcgcggttt ctggtgcgta    240
gagactgtaa atcgctgcgc ttctcagtca tcatcatccc agcttttccc ggctcgaatt   300
cagcctccaa ctcaagctcg cgggaaagac tacctgagag gagaaaagct tctgtccctg   360
gaccttcttc tgagggtgga gtcggaggct ccctgctttc cagccgccca gtgacccaag   420
cttaatcttc agcaccactt ggggcgacct tttcggtgca aacctacgat tctgtttctc   480
aggattcctc cccatcccgc ttcgccccgg aaaagctgac aagaacttca ggtgtaagcc   540
ctgagtagtg aggatctgcg gtctccgtgg agagctgtgc ctggaagaga aggacgctgg   600
tgggggctga gatcagagct gtcttctggc ccagttgccc ccatgcttct gtcatggcta   660
acagttctag gggctggaat ggtcgtcctg cacttcttgc agaaactcct gttcccttac   720
ttttgggatg acttctggtt cgtgttgaag gtggtgctca ttataattcg gctgaagaag   780
tatgaaaaga gaggggagct ggtgactgtg ctggataaat tcttgagtca tgccaaaaga   840
caacctcgga aacctttcat catctatgag ggagacatct acacctatca ggatgtagac   900
aaaaggagca gcagagtggc ccatgtcttc ctgaaccatt cctctctgaa aaaggggac    960
acggtggctc tgctgatgag caatgagccg gacttcgttc acgtgtggtt cggcctcgcc  1020
aagctgggct gctggtggc ctttctcaac accaacattg ctccaactc cctcctgaat   1080
tgcatccgcg cctgtgggcc cagagcccta gtggtgggcg cagatttgct tggaacggta  1140
gaagaaatcc ttccaagcct ctcagaaaat atcagtgttt gggggatgaa agattctgtt  1200
ccacaaggtg taatttcact caaagaaaaa ctgagcacct cacctgatga gcccgtgcca  1260
cgcagccacc atgttgtctc actcctcaag tctacttgtc tttacatttt tacctctgga  1320
acaacaggtc taccaaaagc agctgtgatt agtcagctgc aggttttaag gggttctgct  1380
gtcctgtggg cttttggttg tactgctcat gacattgttt atataaccct tcctctgtat  1440
catagttcag cagctatcct gggaatttct ggatgtgttg agttgggtgc cacttgtgtg  1500
```

-continued

```
ttaaagaaga aattttcagc aagccagttt tggagtgact gcaagaagta tgatgtgact      1560
gtgtttcagt atattggaga actttgtcgc tacctttgca acaatctaa gagagaagga       1620 gaaaaggatc ataaggtgcg tttggcaatt ggaaatggca tacggagtga tgtatggaga     1680 gaattttag acagatttgg aaatataaag gtgtgtgaac tttatgcagc taccgaatca      1740
agcatatctt tcatgaacta cactgggaga attggagcaa ttgggagaac aaatttgttt    1800
tacaaacttc tttccacttt tgacttaata aagtatgact tcagaaaga tgaacccatg     1860 agaaatgagc agggttggtg tattcatgtg aaaaaggag aacctggact tctcatttct     1920
cgagtgaatg caaaaaatcc cttctttggc tatgctgggc cttataagca cacaaaagac    1980
aaattgcttt gtgatgtttt taagaaggga gatgtttacc ttaatactgg agacttaata   2040
gtccaggatc aggacaattt cctttatttt tgggaccgta ctggagacac tttcagatgg    2100
aaaggagaaa atgtcgcaac cactgaggtt gctgatgtta ttggaatgtt ggatttcata   2160
caggaagcaa acgtctatgg tgtggctata tcaggttatg aaggaagagc aggaatggct    2220
tctattattt taaaccaaa tacatcttta gatttggaaa aagtttatga acaagttgta    2280
acatttctac cagcttatgc ttgtccacga ttttaagaa ttcaggaaaa aatggaagca    2340
acaggaacat tcaaactatt gaagcatcag ttggtggaag atggatttaa tccactgaaa   2400
atttctgaac cactttactt catggataac ttgaaaaagt cttatgttct actgaccagg    2460 gaacttatg atcaaataat gttaggggaa ataaaactt aagatttta tatctagaac      2520 tttcatatgc tttcttagga agagtgagag gggggtatat gattctttat gaaatgggga   2580
aagggagcta acattaatta tgcatgtact atatttcctt aatatgagag ataatttttt    2640
aattgcataa gaatttaat ttcttttaat tgatataaac attagttgat tattcttttt    2700
atctatttgg agattcagtg cataactaag tattttcctt aatactaaag attttaaata   2760
ataaatagtg gctagcggtt tggacaatca ctaaaaatgt actttctaat aagtaaaatt   2820
tctaattttg aataaaagat taaattttac tgaaaaaaaa aaaaaaaaaa aaaattggcg   2880
gccgc                                                                2885
```

<210> SEQ ID NO 37
<211> LENGTH: 619
<212> TYPE: PRT
<213> ORGANISM: Homo sapiens

<400> SEQUENCE: 37

```
Met Leu Leu Ser Trp Leu Thr Val Leu Gly Ala Gly Met Val Val Leu
 1               5                  10                  15

His Phe Leu Gln Lys Leu Leu Phe Pro Tyr Phe Trp Asp Asp Phe Trp
            20                  25                  30

Phe Val Leu Lys Val Val Leu Ile Ile Ile Arg Leu Lys Lys Tyr Glu
        35                  40                  45

Lys Arg Gly Glu Leu Val Thr Val Leu Asp Lys Phe Leu Ser His Ala
    50                  55                  60

Lys Arg Gln Pro Arg Lys Pro Phe Ile Ile Tyr Glu Gly Asp Ile Tyr
65                  70                  75                  80

Thr Tyr Gln Asp Val Asp Lys Arg Ser Ser Arg Val Ala His Val Phe
                85                  90                  95

Leu Asn His Ser Ser Leu Lys Lys Gly Asp Thr Val Ala Leu Leu Met
            100                 105                 110

Ser Asn Glu Pro Asp Phe Val His Val Trp Phe Gly Leu Ala Lys Leu
        115                 120                 125
```

-continued

```
Gly Cys Val Ala Phe Leu Asn Thr Asn Ile Arg Ser Asn Ser Leu
    130                 135                 140
Leu Asn Cys Ile Arg Ala Cys Gly Pro Arg Ala Leu Val Val Gly Ala
145                 150                 155                 160
Asp Leu Leu Gly Thr Val Glu Glu Ile Leu Pro Ser Leu Ser Glu Asn
                165                 170                 175
Ile Ser Val Trp Gly Met Lys Asp Ser Val Pro Gln Gly Val Ile Ser
                180                 185                 190
Leu Lys Glu Lys Leu Ser Thr Ser Pro Asp Glu Pro Val Pro Arg Ser
            195                 200                 205
His His Val Val Ser Leu Leu Lys Ser Thr Cys Leu Tyr Ile Phe Thr
    210                 215                 220
Ser Gly Thr Thr Gly Leu Pro Lys Ala Ala Val Ile Ser Gln Leu Gln
225                 230                 235                 240
Val Leu Arg Gly Ser Ala Val Leu Trp Ala Phe Gly Cys Thr Ala His
                245                 250                 255
Asp Ile Val Tyr Ile Thr Leu Pro Leu Tyr His Ser Ser Ala Ala Ile
                260                 265                 270
Leu Gly Ile Ser Gly Cys Val Glu Leu Gly Ala Thr Cys Val Leu Lys
            275                 280                 285
Lys Lys Phe Ser Ala Ser Gln Phe Trp Ser Asp Cys Lys Lys Tyr Asp
    290                 295                 300
Val Thr Val Phe Gln Tyr Ile Gly Glu Leu Cys Arg Tyr Leu Cys Lys
305                 310                 315                 320
Gln Ser Lys Arg Glu Gly Glu Lys Asp His Lys Val Arg Leu Ala Ile
                325                 330                 335
Gly Asn Gly Ile Arg Ser Asp Val Trp Arg Glu Phe Leu Asp Arg Phe
                340                 345                 350
Gly Asn Ile Lys Val Cys Glu Leu Tyr Ala Ala Thr Glu Ser Ser Ile
            355                 360                 365
Ser Phe Met Asn Tyr Thr Gly Arg Ile Gly Ala Ile Gly Arg Thr Asn
    370                 375                 380
Leu Phe Tyr Lys Leu Leu Ser Thr Phe Asp Leu Ile Lys Tyr Asp Phe
385                 390                 395                 400
Gln Lys Asp Glu Pro Met Arg Asn Glu Gln Gly Trp Cys Ile His Val
                405                 410                 415
Lys Lys Gly Glu Pro Gly Leu Leu Ile Ser Arg Val Asn Ala Lys Asn
                420                 425                 430
Pro Phe Phe Gly Tyr Ala Gly Pro Tyr Lys His Thr Lys Asp Lys Leu
            435                 440                 445
Leu Cys Asp Val Phe Lys Lys Gly Asp Val Tyr Leu Asn Thr Gly Asp
    450                 455                 460
Leu Ile Val Gln Asp Gln Asp Asn Phe Leu Tyr Phe Trp Asp Arg Thr
465                 470                 475                 480
Gly Asp Thr Phe Arg Trp Lys Gly Glu Asn Val Ala Thr Thr Glu Val
                485                 490                 495
Ala Asp Val Ile Gly Met Leu Asp Phe Ile Gln Glu Ala Asn Val Tyr
                500                 505                 510
Gly Val Ala Ile Ser Gly Tyr Glu Gly Arg Ala Gly Met Ala Ser Ile
            515                 520                 525
Ile Leu Lys Pro Asn Thr Ser Leu Asp Leu Glu Lys Val Tyr Glu Gln
    530                 535                 540
```

```
Val Val Thr Phe Leu Pro Ala Tyr Ala Cys Pro Arg Phe Leu Arg Ile
545                 550                 555                 560

Gln Glu Lys Met Glu Ala Thr Gly Thr Phe Lys Leu Leu Lys His Gln
                565                 570                 575

Leu Val Glu Asp Gly Phe Asn Pro Leu Lys Ile Ser Glu Pro Leu Tyr
                580                 585                 590

Phe Met Asp Asn Leu Lys Lys Ser Tyr Val Leu Leu Thr Arg Glu Leu
        595                 600                 605

Tyr Asp Gln Ile Met Leu Gly Glu Ile Lys Leu
        610                 615
```

<210> SEQ ID NO 38
<211> LENGTH: 646
<212> TYPE: PRT
<213> ORGANISM: Homo sapiens

<400> SEQUENCE: 38

```
Met Arg Ala Pro Gly Ala Gly Ala Ala Ser Val Val Ser Leu Ala Leu
1               5                   10                  15

Leu Trp Leu Leu Gly Leu Pro Trp Thr Trp Ser Ala Ala Ala Ala Leu
                20                  25                  30

Gly Val Tyr Val Gly Ser Gly Gly Trp Arg Phe Leu Arg Ile Val Cys
                35                  40                  45

Lys Thr Ala Arg Arg Asp Leu Phe Gly Leu Ser Val Leu Ile Arg Val
50                  55                  60

Arg Leu Glu Leu Arg Arg His Gln Arg Ala Gly His Thr Ile Pro Arg
65                  70                  75                  80

Ile Phe Gln Ala Val Val Gln Arg Gln Pro Glu Arg Leu Ala Leu Val
                85                  90                  95

Asp Ala Gly Thr Gly Glu Cys Trp Thr Phe Ala Gln Leu Asp Ala Tyr
                100                 105                 110

Ser Asn Ala Val Ala Asn Leu Phe Arg Gln Leu Gly Phe Ala Pro Gly
                115                 120                 125

Asp Val Val Ala Ile Phe Leu Glu Gly Arg Pro Glu Phe Val Gly Leu
                130                 135                 140

Trp Leu Gly Leu Ala Lys Ala Gly Met Glu Ala Ala Leu Leu Asn Val
145                 150                 155                 160

Asn Leu Arg Arg Glu Pro Leu Ala Phe Cys Leu Gly Thr Ser Gly Ala
                165                 170                 175

Lys Ala Leu Ile Phe Gly Gly Glu Met Val Ala Val Ala Glu Val
                180                 185                 190

Ser Gly His Leu Gly Lys Ser Leu Ile Lys Phe Cys Ser Gly Asp Leu
                195                 200                 205

Gly Pro Glu Gly Ile Leu Pro Asp Thr His Leu Leu Asp Pro Leu Leu
                210                 215                 220

Lys Glu Ala Ser Thr Ala Pro Leu Ala Gln Ile Pro Ser Lys Gly Met
225                 230                 235                 240

Asp Asp Arg Leu Phe Tyr Ile Tyr Thr Ser Gly Thr Thr Gly Leu Pro
                245                 250                 255

Lys Ala Ala Ile Val Val His Ser Arg Tyr Tyr Arg Met Ala Ala Phe
                260                 265                 270

Gly His His Ala Tyr Arg Met Gln Ala Ala Asp Val Leu Tyr Asp Cys
                275                 280                 285

Leu Pro Leu Tyr His Ser Ala Gly Asn Ile Ile Gly Val Gly Gln Cys
                290                 295                 300
```

-continued

```
Leu Ile Tyr Gly Leu Thr Val Val Leu Arg Lys Lys Phe Ser Ala Ser
305                 310                 315                 320

Arg Phe Trp Asp Asp Cys Ile Lys Tyr Asn Cys Thr Val Val Gln Tyr
                325                 330                 335

Ile Gly Glu Ile Cys Arg Tyr Leu Leu Lys Gln Pro Val Arg Glu Ala
            340                 345                 350

Glu Arg Arg His Arg Val Arg Leu Ala Val Gly Asn Gly Leu Arg Pro
        355                 360                 365

Ala Ile Trp Glu Glu Phe Thr Glu Arg Phe Gly Val Arg Gln Ile Gly
370                 375                 380

Glu Phe Tyr Gly Ala Thr Glu Cys Asn Cys Ser Ile Ala Asn Met Asp
385                 390                 395                 400

Gly Lys Val Gly Ser Cys Gly Phe Asn Ser Arg Ile Leu Pro His Val
                405                 410                 415

Tyr Pro Ile Arg Leu Val Lys Val Asn Glu Asp Thr Met Glu Leu Leu
            420                 425                 430

Arg Asp Ala Gln Gly Leu Cys Ile Pro Cys Gln Ala Gly Glu Pro Gly
        435                 440                 445

Leu Leu Val Gly Gln Ile Asn Gln Gln Asp Pro Leu Arg Arg Phe Asp
450                 455                 460

Gly Tyr Val Ser Glu Ser Ala Thr Ser Lys Lys Ile Ala His Ser Val
465                 470                 475                 480

Phe Ser Lys Gly Asp Ser Ala Tyr Leu Ser Gly Asp Val Leu Val Met
                485                 490                 495

Asp Glu Leu Gly Tyr Met Tyr Phe Arg Asp Arg Ser Gly Asp Thr Phe
            500                 505                 510

Arg Trp Arg Gly Glu Asn Val Ser Thr Thr Glu Val Glu Gly Val Leu
        515                 520                 525

Ser Arg Leu Leu Gly Gln Thr Asp Val Ala Val Tyr Gly Val Ala Val
530                 535                 540

Pro Gly Val Glu Gly Lys Ala Gly Met Ala Ala Val Ala Asp Pro His
545                 550                 555                 560

Ser Leu Leu Asp Pro Asn Ala Ile Tyr Gln Glu Leu Gln Lys Val Leu
                565                 570                 575

Ala Pro Tyr Ala Arg Pro Ile Phe Leu Arg Leu Leu Pro Gln Val Asp
            580                 585                 590

Thr Thr Gly Thr Phe Lys Ile Gln Lys Thr Arg Leu Gln Arg Glu Gly
        595                 600                 605

Phe Asp Pro Arg Gln Thr Ser Asp Arg Leu Phe Phe Leu Asp Leu Lys
610                 615                 620

Gln Gly His Tyr Leu Pro Leu Asn Glu Ala Val Tyr Thr Arg Ile Cys
625                 630                 635                 640

Ser Gly Ala Phe Ala Leu
                645

<210> SEQ ID NO 39
<211> LENGTH: 632
<212> TYPE: PRT
<213> ORGANISM: Homo sapiens

<400> SEQUENCE: 39

Leu Phe Ser Lys Leu Val Leu Lys Leu Pro Trp Thr Gln Val Gly Phe
  1               5                  10                  15

Ser Leu Leu Phe Leu Tyr Leu Gly Ser Gly Gly Trp Arg Phe Ile Arg
```

```
                    20                  25                  30
Val Phe Ile Lys Thr Ile Arg Arg Asp Ile Phe Gly Gly Leu Val Leu
                35                  40                  45

Leu Lys Val Lys Ala Lys Val Arg Gln Cys Leu Gln Glu Arg Arg Thr
 50                  55                  60

Val Pro Ile Leu Phe Ala Ser Thr Val Arg Arg His Pro Asp Lys Thr
 65                  70                  75                  80

Ala Leu Ile Phe Glu Gly Thr Asp Thr His Trp Thr Phe Arg Gln Leu
                85                  90                  95

Asp Glu Tyr Ser Ser Val Ala Asn Phe Leu Gln Ala Arg Gly Leu
                100                 105                 110

Ala Ser Gly Asp Val Ala Ala Ile Phe Met Glu Asn Arg Asn Glu Phe
                115                 120                 125

Val Gly Leu Trp Leu Gly Met Ala Lys Leu Gly Val Glu Ala Ala Leu
                130                 135                 140

Ile Asn Thr Asn Leu Arg Arg Asp Ala Leu Leu His Cys Leu Thr Thr
145                 150                 155                 160

Ser Arg Ala Arg Ala Leu Val Phe Gly Ser Glu Met Ala Ser Ala Ile
                165                 170                 175

Cys Glu Val His Ala Ser Leu Asp Pro Ser Leu Ser Leu Phe Cys Ser
                180                 185                 190

Gly Ser Trp Glu Pro Gly Ala Val Pro Pro Ser Thr Glu His Leu Asp
                195                 200                 205

Pro Leu Leu Lys Asp Ala Pro Lys His Leu Pro Ser Cys Pro Asp Lys
                210                 215                 220

Gly Phe Thr Asp Lys Leu Phe Tyr Ile Tyr Thr Ser Gly Thr Thr Gly
225                 230                 235                 240

Leu Pro Lys Ala Ala Ile Val Val His Ser Arg Tyr Tyr Arg Met Ala
                245                 250                 255

Ala Leu Val Tyr Tyr Gly Phe Arg Met Arg Pro Asn Asp Ile Val Tyr
                260                 265                 270

Asp Cys Leu Pro Leu Tyr His Ser Ala Gly Asn Ile Val Gly Ile Gly
                275                 280                 285

Gln Cys Leu Leu His Gly Met Thr Val Val Ile Arg Lys Lys Phe Ser
                290                 295                 300

Ala Ser Arg Phe Trp Asp Asp Cys Ile Lys Tyr Asn Cys Thr Ile Val
305                 310                 315                 320

Gln Tyr Ile Gly Glu Leu Cys Arg Tyr Leu Leu Asn Gln Pro Pro Arg
                325                 330                 335

Glu Ala Glu Asn Gln His Gln Val Arg Met Ala Leu Gly Asn Gly Leu
                340                 345                 350

Arg Gln Ser Ile Trp Thr Asn Phe Ser Ser Arg Phe His Ile Pro Gln
                355                 360                 365

Val Ala Glu Phe Tyr Gly Ala Thr Glu Cys Asn Cys Ser Leu Gly Asn
                370                 375                 380

Phe Asp Ser Gln Val Gly Ala Cys Gly Phe Asn Ser Arg Ile Leu Ser
385                 390                 395                 400

Phe Val Tyr Pro Ile Arg Leu Val Arg Val Asn Glu Asp Thr Met Glu
                405                 410                 415

Leu Ile Arg Gly Pro Asp Gly Val Cys Ile Pro Cys Gln Pro Gly Glu
                420                 425                 430

Pro Gly Gln Leu Val Gly Arg Ile Ile Gln Lys Asp Pro Leu Arg Arg
                435                 440                 445
```

-continued

```
Phe Asp Gly Tyr Leu Asn Gln Gly Ala Asn Asn Lys Lys Ile Ala Lys
    450                 455                 460

Asp Val Phe Lys Lys Gly Asp Gln Ala Tyr Leu Thr Gly Asp Val Leu
465                 470                 475                 480

Val Met Asp Glu Leu Gly Tyr Leu Tyr Phe Arg Asp Arg Thr Gly Asp
                485                 490                 495

Thr Phe Arg Trp Lys Gly Glu Asn Val Ser Thr Thr Glu Val Glu Gly
                500                 505                 510

Thr Leu Ser Arg Leu Leu Asp Met Ala Asp Val Ala Val Tyr Gly Val
            515                 520                 525

Glu Val Pro Gly Thr Glu Gly Arg Ala Gly Met Ala Ala Val Ala Ser
530                 535                 540

Pro Thr Gly Asn Cys Asp Leu Glu Arg Phe Ala Gln Val Leu Glu Lys
545                 550                 555                 560

Glu Leu Pro Leu Tyr Ala Arg Pro Ile Phe Leu Arg Leu Leu Pro Glu
                565                 570                 575

Leu His Lys Thr Gly Thr Tyr Leu Phe Gln Lys Thr Glu Leu Arg Lys
                580                 585                 590

Glu Gly Phe Asp Pro Ala Ile Val Lys Asp Pro Leu Phe Tyr Leu Asp
            595                 600                 605

Ala Gln Lys Gly Arg Tyr Val Pro Leu Asp Gln Glu Ala Tyr Ser Arg
610                 615                 620

Ile Gln Ala Gly Glu Glu Lys Leu
625                 630

<210> SEQ ID NO 40
<211> LENGTH: 619
<212> TYPE: PRT
<213> ORGANISM: Homo sapiens

<400> SEQUENCE: 40

Met Leu Leu Ser Trp Leu Thr Val Leu Gly Ala Gly Met Val Val Leu
1               5                   10                  15

His Phe Leu Gln Lys Leu Leu Phe Pro Tyr Phe Trp Asp Asp Phe Trp
                20                  25                  30

Phe Val Leu Lys Val Val Leu Ile Ile Ile Arg Leu Lys Lys Tyr Glu
            35                  40                  45

Lys Arg Gly Glu Leu Val Thr Val Leu Asp Lys Phe Leu Ser His Ala
50                  55                  60

Lys Arg Gln Pro Arg Lys Pro Phe Ile Ile Tyr Glu Gly Asp Ile Tyr
65                  70                  75                  80

Thr Tyr Gln Asp Val Asp Lys Arg Ser Ser Arg Val Ala His Val Phe
                85                  90                  95

Leu Asn His Ser Ser Leu Lys Lys Gly Asp Thr Val Ala Leu Leu Met
                100                 105                 110

Ser Asn Glu Pro Asp Phe Val His Val Trp Phe Gly Leu Ala Lys Leu
            115                 120                 125

Gly Cys Val Val Ala Phe Leu Asn Thr Asn Ile Arg Ser Asn Ser Leu
130                 135                 140

Leu Asn Cys Ile Arg Ala Cys Gly Pro Arg Ala Leu Val Val Gly Ala
145                 150                 155                 160

Asp Leu Leu Gly Thr Val Glu Glu Ile Leu Pro Ser Leu Ser Glu Asn
                165                 170                 175

Ile Ser Val Trp Gly Met Lys Asp Ser Val Pro Gln Gly Val Ile Ser
```

-continued

```
                180                 185                 190
Leu Lys Glu Lys Leu Ser Thr Ser Pro Asp Glu Pro Val Pro Arg Ser
            195                 200                 205

His His Val Val Ser Leu Leu Lys Ser Thr Cys Leu Tyr Ile Phe Thr
210                 215                 220

Ser Gly Thr Thr Gly Leu Pro Lys Ala Ala Val Ile Ser Gln Leu Gln
225                 230                 235                 240

Val Leu Arg Gly Ser Ala Val Leu Trp Ala Phe Gly Cys Thr Ala His
            245                 250                 255

Asp Ile Val Tyr Ile Thr Leu Pro Leu Tyr His Ser Ser Ala Ala Ile
            260                 265                 270

Leu Gly Ile Ser Gly Cys Val Glu Leu Gly Ala Thr Cys Val Leu Lys
            275                 280                 285

Lys Lys Phe Ser Ala Ser Gln Phe Trp Ser Asp Cys Lys Lys Tyr Asp
            290                 295                 300

Val Thr Val Phe Gln Tyr Ile Gly Glu Leu Cys Arg Tyr Leu Cys Lys
305                 310                 315                 320

Gln Ser Lys Arg Glu Gly Glu Lys Asp His Lys Val Arg Leu Ala Ile
            325                 330                 335

Gly Asn Gly Ile Arg Ser Asp Val Trp Arg Glu Phe Leu Asp Arg Phe
            340                 345                 350

Gly Asn Ile Lys Val Cys Glu Leu Tyr Ala Ala Thr Glu Ser Ser Ile
            355                 360                 365

Ser Phe Met Asn Tyr Thr Gly Arg Ile Gly Ala Ile Gly Arg Thr Asn
            370                 375                 380

Leu Phe Tyr Lys Leu Leu Ser Thr Phe Asp Leu Ile Lys Tyr Asp Phe
385                 390                 395                 400

Gln Lys Asp Glu Pro Met Arg Asn Glu Gln Gly Trp Cys Ile His Val
            405                 410                 415

Lys Lys Gly Glu Pro Gly Leu Leu Ile Ser Arg Val Asn Ala Lys Asn
            420                 425                 430

Pro Phe Phe Gly Tyr Ala Gly Pro Tyr Lys His Thr Lys Asp Lys Leu
            435                 440                 445

Leu Cys Asp Val Phe Lys Lys Gly Asp Val Tyr Leu Asn Thr Gly Asp
450                 455                 460

Leu Ile Val Gln Asp Gln Asp Asn Phe Leu Tyr Phe Trp Asp Arg Thr
465                 470                 475                 480

Gly Asp Thr Phe Arg Trp Lys Gly Glu Asn Val Ala Thr Thr Glu Val
            485                 490                 495

Ala Asp Val Ile Gly Met Leu Asp Phe Ile Gln Glu Ala Asn Val Tyr
            500                 505                 510

Gly Val Ala Ile Ser Gly Tyr Glu Gly Arg Ala Gly Met Ala Ser Ile
            515                 520                 525

Ile Leu Lys Pro Asn Thr Ser Leu Asp Leu Glu Lys Val Tyr Glu Gln
            530                 535                 540

Val Val Thr Phe Leu Pro Ala Tyr Ala Cys Pro Arg Phe Leu Arg Ile
545                 550                 555                 560

Gln Glu Lys Met Glu Ala Thr Gly Thr Phe Lys Leu Leu Lys His Gln
            565                 570                 575

Leu Val Glu Asp Gly Phe Asn Pro Leu Lys Ile Ser Glu Pro Leu Tyr
            580                 585                 590

Phe Met Asp Asn Leu Lys Lys Ser Tyr Val Leu Leu Thr Arg Glu Leu
            595                 600                 605
```

```
Tyr Asp Gln Ile Met Leu Gly Glu Ile Lys Leu
    610                 615

<210> SEQ ID NO 41
<211> LENGTH: 643
<212> TYPE: PRT
<213> ORGANISM: Homo sapiens

<400> SEQUENCE: 41

Met Leu Leu Gly Ala Ser Leu Val Gly Val Leu Leu Phe Ser Lys Leu
 1               5                  10                  15

Val Leu Lys Leu Pro Trp Thr Gln Val Gly Phe Ser Leu Leu Phe Leu
             20                  25                  30

Tyr Leu Gly Ser Gly Gly Trp Arg Phe Ile Arg Val Phe Ile Lys Thr
         35                  40                  45

Ile Arg Arg Asp Ile Phe Gly Gly Leu Val Leu Lys Val Lys Ala
 50                  55                  60

Lys Val Arg Gln Cys Leu Gln Glu Arg Thr Val Pro Ile Leu Phe
 65                  70                  75                  80

Ala Ser Thr Val Arg Arg His Pro Asp Lys Thr Ala Leu Ile Phe Glu
                 85                  90                  95

Gly Thr Asp Thr His Trp Thr Phe Arg Gln Leu Asp Glu Tyr Ser Ser
                100                 105                 110

Ser Val Ala Asn Phe Leu Gln Ala Arg Gly Leu Ala Ser Gly Asp Val
            115                 120                 125

Ala Ala Ile Phe Met Glu Asn Arg Asn Glu Phe Val Gly Leu Trp Leu
        130                 135                 140

Gly Met Ala Lys Leu Gly Val Glu Ala Ala Leu Ile Asn Thr Asn Leu
145                 150                 155                 160

Arg Arg Asp Ala Leu Leu His Cys Leu Thr Thr Ser Arg Ala Arg Ala
                165                 170                 175

Leu Val Phe Gly Ser Glu Met Ala Ser Ala Ile Cys Glu Val His Ala
            180                 185                 190

Ser Leu Asp Pro Ser Leu Ser Leu Phe Cys Ser Gly Ser Trp Glu Pro
        195                 200                 205

Gly Ala Val Pro Pro Ser Thr Glu His Leu Asp Pro Leu Leu Lys Asp
    210                 215                 220

Ala Pro Lys His Leu Pro Ser Cys Pro Asp Lys Gly Phe Thr Asp Lys
225                 230                 235                 240

Leu Phe Tyr Ile Tyr Thr Ser Gly Thr Thr Gly Leu Pro Lys Ala Ala
                245                 250                 255

Ile Val Val His Ser Arg Tyr Tyr Arg Met Ala Ala Leu Val Tyr Tyr
            260                 265                 270

Gly Phe Arg Met Arg Pro Asn Asp Ile Val Tyr Asp Cys Leu Pro Leu
        275                 280                 285

Tyr His Ser Ala Gly Asn Ile Val Gly Ile Gly Gln Cys Leu Leu His
    290                 295                 300

Gly Met Thr Val Val Ile Arg Lys Lys Phe Ser Ala Ser Arg Phe Trp
305                 310                 315                 320

Asp Asp Cys Ile Lys Tyr Asn Cys Thr Ile Val Gln Tyr Ile Gly Glu
                325                 330                 335

Leu Cys Arg Tyr Leu Leu Asn Gln Pro Pro Arg Glu Ala Glu Asn Gln
            340                 345                 350

His Gln Val Arg Met Ala Leu Gly Asn Gly Leu Arg Gln Ser Ile Trp
```

```
              355                 360                 365

Thr Asn Phe Ser Ser Arg Phe His Ile Pro Gln Val Ala Glu Phe Tyr
        370                 375                 380

Gly Ala Thr Glu Cys Asn Cys Ser Leu Gly Asn Phe Asp Ser Gln Val
385                 390                 395                 400

Gly Ala Cys Gly Phe Asn Ser Arg Ile Leu Ser Phe Val Tyr Pro Ile
                405                 410                 415

Arg Leu Val Arg Val Asn Glu Asp Thr Met Glu Leu Ile Arg Gly Pro
            420                 425                 430

Asp Gly Val Cys Ile Pro Cys Gln Pro Gly Glu Pro Gly Gln Leu Val
        435                 440                 445

Gly Arg Ile Ile Gln Lys Asp Pro Leu Arg Arg Phe Asp Gly Tyr Leu
    450                 455                 460

Asn Gln Gly Ala Asn Asn Lys Lys Ile Ala Lys Asp Val Phe Lys Lys
465                 470                 475                 480

Gly Asp Gln Ala Tyr Leu Thr Gly Asp Val Leu Val Met Asp Glu Leu
                485                 490                 495

Gly Tyr Leu Tyr Phe Arg Asp Arg Thr Gly Asp Thr Phe Arg Trp Lys
            500                 505                 510

Gly Glu Asn Val Ser Thr Thr Glu Val Glu Gly Thr Leu Ser Arg Leu
        515                 520                 525

Leu Asp Met Ala Asp Val Ala Val Tyr Gly Val Glu Val Pro Gly Thr
    530                 535                 540

Glu Gly Arg Ala Gly Met Ala Ala Val Ala Ser Pro Thr Gly Asn Cys
545                 550                 555                 560

Asp Leu Glu Arg Phe Ala Gln Val Leu Glu Lys Glu Leu Pro Leu Tyr
                565                 570                 575

Ala Arg Pro Ile Phe Leu Arg Leu Leu Pro Glu Leu His Lys Thr Gly
            580                 585                 590

Thr Tyr Lys Phe Gln Lys Thr Glu Leu Arg Lys Glu Gly Phe Asp Pro
        595                 600                 605

Ala Ile Val Lys Asp Pro Leu Phe Tyr Leu Asp Ala Gln Lys Gly Arg
    610                 615                 620

Tyr Val Pro Leu Asp Gln Glu Ala Tyr Ser Arg Ile Gln Ala Gly Glu
625                 630                 635                 640

Glu Lys Leu

<210> SEQ ID NO 42
<211> LENGTH: 643
<212> TYPE: PRT
<213> ORGANISM: Mus musculus
<220> FEATURE:
<221> NAME/KEY: VARIANT
<222> LOCATION: (1)...(643)
<223> OTHER INFORMATION: Xaa = Any Amino Acid

<400> SEQUENCE: 42

Met Leu Leu Gly Ala Ser Leu Val Gly Val Leu Leu Phe Ser Lys Leu
  1               5                  10                  15

Val Leu Lys Leu Pro Trp Thr Gln Val Gly Phe Ser Leu Leu Xaa Leu
            20                  25                  30

Tyr Leu Gly Ser Gly Gly Trp Arg Phe Ile Arg Val Phe Ile Lys Thr
        35                  40                  45

Val Arg Arg Asp Ile Phe Gly Gly Met Val Leu Leu Lys Val Lys Thr
    50                  55                  60
```

```
Lys Val Arg Arg Tyr Leu Gln Glu Arg Lys Thr Val Pro Leu Leu Phe
 65                  70                  75                  80

Ala Ser Met Val Gln Arg His Pro Asp Lys Thr Ala Leu Ile Phe Glu
                 85                  90                  95

Gly Thr Asp Thr His Trp Thr Phe Arg Gln Leu Asp Glu Tyr Ser Ser
            100                 105                 110

Ser Val Ala Asn Phe Leu Gln Ala Arg Gly Leu Ala Ser Gly Asn Val
        115                 120                 125

Val Ala Leu Phe Met Glu Asn Arg Asn Glu Phe Val Gly Leu Trp Xaa
130                 135                 140

Gly Met Ala Lys Leu Gly Val Glu Ala Ala Leu Ile Asn Thr Asn Leu
145                 150                 155                 160

Arg Arg Asp Ala Leu Arg His Cys Leu Asp Thr Ser Lys Ala Arg Ala
                165                 170                 175

Leu Ile Phe Gly Ser Glu Met Ala Ser Ala Ile Cys Glu Ile His Ala
            180                 185                 190

Ser Leu Gly Pro Thr Leu Ser Leu Phe Cys Ser Gly Ser Trp Glu Pro
        195                 200                 205

Ser Thr Val Pro Val Ser Thr Glu His Leu Asp Pro Leu Leu Glu Asp
210                 215                 220

Ala Pro Lys His Leu Pro Ser His Pro Asp Lys Gly Phe Thr Asp Lys
225                 230                 235                 240

Leu Phe Tyr Ile Tyr Thr Ser Gly Thr Thr Gly Leu Pro Lys Ala Ala
                245                 250                 255

Ile Val Val His Ser Arg Tyr Tyr Arg Met Ala Ser Leu Val Tyr Tyr
            260                 265                 270

Gly Phe Arg Met Arg Pro Asp Asp Ile Val Tyr Asp Cys Leu Pro Leu
        275                 280                 285

Tyr His Ser Ser Arg Lys His Arg Gly Asp Trp Gln Cys Leu Leu His
290                 295                 300

Gly Met Thr Val Val Ile Arg Lys Lys Phe Ser Ala Ser Arg Phe Trp
305                 310                 315                 320

Asp Asp Cys Ile Lys Tyr Asn Cys Thr Ile Val Gln Tyr Ile Gly Glu
                325                 330                 335

Leu Cys Arg Tyr Leu Leu Asn Gln Pro Pro Arg Glu Ala Glu Ser Arg
            340                 345                 350

His Lys Val Arg Met Ala Leu Gly Asn Gly Leu Arg Gln Ser Ile Trp
        355                 360                 365

Thr Asp Phe Ser Ser Arg Phe His Ile Pro Gln Val Ala Glu Phe Tyr
370                 375                 380

Gly Ala Thr Glu Cys Asn Cys Ser Leu Gly Asn Phe Asp Ser Arg Val
385                 390                 395                 400

Gly Ala Cys Gly Phe Asn Ser Arg Ile Leu Ser Phe Val Tyr Pro Ile
                405                 410                 415

Arg Leu Val Arg Val Asn Glu Asp Thr Met Glu Leu Ile Arg Gly Pro
            420                 425                 430

Asp Gly Val Cys Ile Pro Cys Gln Pro Gly Gln Pro Gly Gln Leu Val
        435                 440                 445

Gly Arg Ile Ile Gln Lys Asp Pro Leu Arg Arg Phe Asp Gly Tyr Leu
450                 455                 460

Asn Gln Gly Ala Asn Asn Lys Lys Ile Ala Asn Asp Val Phe Lys Lys
465                 470                 475                 480

Gly Asp Gln Ala Tyr Leu Thr Gly Asp Val Leu Val Met Asp Glu Leu
```

```
                      485                 490                 495
Gly Tyr Leu Tyr Phe Arg Asp Arg Thr Gly Asp Thr Phe Arg Trp Lys
                500                 505                 510

Gly Glu Asn Val Ser Thr Thr Glu Val Glu Gly Thr Leu Ser Arg Leu
            515                 520                 525

Leu His Met Ala Asp Val Ala Val Tyr Gly Val Glu Val Pro Gly Thr
        530                 535                 540

Glu Gly Arg Ala Gly Met Ala Ala Val Ala Ser Pro Ile Ser Asn Cys
545                 550                 555                 560

Asp Leu Glu Ser Phe Ala Gln Thr Leu Lys Lys Glu Leu Pro Leu Tyr
                565                 570                 575

Ala Arg Pro Ile Phe Leu Arg Phe Leu Pro Glu Leu His Lys Thr Gly
            580                 585                 590

Thr Phe Lys Phe Gln Lys Thr Glu Leu Arg Lys Glu Gly Phe Asp Pro
        595                 600                 605

Ser Val Val Lys Asp Pro Leu Phe Tyr Leu Asp Ala Arg Lys Gly Cys
    610                 615                 620

Tyr Val Ala Leu Asp Gln Glu Ala Tyr Thr Arg Ile Gln Ala Gly Glu
625                 630                 635                 640

Glu Lys Leu

<210> SEQ ID NO 43
<211> LENGTH: 646
<212> TYPE: PRT
<213> ORGANISM: Homo sapiens

<400> SEQUENCE: 43

Met Arg Ala Pro Gly Ala Gly Ala Ala Ser Val Val Ser Leu Ala Leu
 1               5                  10                  15

Leu Trp Leu Leu Gly Leu Pro Trp Thr Trp Ser Ala Ala Ala Ala Leu
            20                  25                  30

Gly Val Tyr Val Gly Ser Gly Gly Trp Arg Phe Leu Arg Ile Val Cys
        35                  40                  45

Lys Thr Ala Arg Arg Asp Leu Phe Gly Leu Ser Val Leu Ile Arg Val
    50                  55                  60

Arg Leu Glu Leu Arg Arg His Gln Arg Ala Gly His Thr Ile Pro Arg
65                  70                  75                  80

Ile Phe Gln Ala Val Gln Arg Gln Pro Glu Arg Leu Ala Leu Val
                85                  90                  95

Asp Ala Gly Thr Gly Glu Cys Trp Thr Phe Ala Gln Leu Asp Ala Tyr
            100                 105                 110

Ser Asn Ala Val Ala Asn Leu Phe Arg Gln Leu Gly Phe Ala Pro Gly
        115                 120                 125

Asp Val Val Ala Ile Phe Leu Glu Gly Arg Pro Glu Phe Val Gly Leu
    130                 135                 140

Trp Leu Gly Leu Ala Lys Ala Gly Met Glu Ala Ala Leu Leu Asn Val
145                 150                 155                 160

Asn Leu Arg Arg Glu Pro Leu Ala Phe Cys Leu Gly Thr Ser Gly Ala
                165                 170                 175

Lys Ala Leu Ile Phe Gly Gly Glu Met Val Ala Val Ala Glu Val
            180                 185                 190

Ser Gly His Leu Gly Lys Ser Leu Ile Lys Phe Cys Ser Gly Asp Leu
        195                 200                 205

Gly Pro Glu Gly Ile Leu Pro Asp Thr His Leu Leu Asp Pro Leu Leu
```

```
            210                 215                 220
Lys Glu Ala Ser Thr Ala Pro Leu Ala Gln Ile Pro Ser Lys Gly Met
225                 230                 235                 240

Asp Asp Arg Leu Phe Tyr Ile Tyr Thr Ser Gly Thr Thr Gly Leu Pro
                245                 250                 255

Lys Ala Ala Ile Val Val His Ser Arg Tyr Tyr Arg Met Ala Ala Phe
            260                 265                 270

Gly His His Ala Tyr Arg Met Gln Ala Ala Asp Val Leu Tyr Asp Cys
                275                 280                 285

Leu Pro Leu Tyr His Ser Ala Gly Asn Ile Ile Gly Val Gly Gln Cys
            290                 295                 300

Leu Ile Tyr Gly Leu Thr Val Leu Arg Lys Lys Phe Ser Ala Ser
305                 310                 315                 320

Arg Phe Trp Asp Asp Cys Ile Lys Tyr Asn Cys Thr Val Val Gln Tyr
                325                 330                 335

Ile Gly Glu Ile Cys Arg Tyr Leu Leu Lys Gln Pro Val Arg Glu Ala
                340                 345                 350

Glu Arg Arg His Arg Val Arg Leu Ala Val Gly Asn Gly Leu Arg Pro
            355                 360                 365

Ala Ile Trp Glu Glu Phe Thr Glu Arg Phe Gly Val Arg Gln Ile Gly
370                 375                 380

Glu Phe Tyr Gly Ala Thr Glu Cys Asn Cys Ser Ile Ala Asn Met Asp
385                 390                 395                 400

Gly Lys Val Gly Ser Cys Gly Phe Asn Ser Arg Ile Leu Pro His Val
                405                 410                 415

Tyr Pro Ile Arg Leu Val Lys Val Asn Glu Asp Thr Met Glu Leu Leu
                420                 425                 430

Arg Asp Ala Gln Gly Leu Cys Ile Pro Cys Gln Ala Gly Glu Pro Gly
            435                 440                 445

Leu Leu Val Gly Gln Ile Asn Gln Gln Asp Pro Leu Arg Arg Phe Asp
450                 455                 460

Gly Tyr Val Ser Glu Ser Ala Thr Ser Lys Lys Ile Ala His Ser Val
465                 470                 475                 480

Phe Ser Lys Gly Asp Ser Ala Tyr Leu Ser Gly Asp Val Leu Val Met
                485                 490                 495

Asp Glu Leu Gly Tyr Met Tyr Phe Arg Asp Arg Ser Gly Asp Thr Phe
            500                 505                 510

Arg Trp Arg Gly Glu Asn Val Ser Thr Thr Glu Val Glu Gly Val Leu
            515                 520                 525

Ser Arg Leu Leu Gly Gln Thr Asp Val Ala Val Tyr Gly Val Ala Val
            530                 535                 540

Pro Gly Val Glu Gly Lys Ala Gly Met Ala Ala Val Ala Asp Pro His
545                 550                 555                 560

Ser Leu Leu Asp Pro Asn Ala Ile Tyr Gln Glu Leu Gln Lys Val Leu
                565                 570                 575

Ala Pro Tyr Ala Arg Pro Ile Phe Leu Arg Leu Leu Pro Gln Val Asp
                580                 585                 590

Thr Thr Gly Thr Phe Lys Ile Gln Lys Thr Arg Leu Gln Arg Glu Gly
            595                 600                 605

Phe Asp Pro Arg Gln Thr Ser Asp Arg Leu Phe Phe Leu Asp Leu Lys
            610                 615                 620

Gln Gly His Tyr Leu Pro Leu Asn Glu Ala Val Tyr Thr Arg Ile Cys
625                 630                 635                 640
```

Ser Gly Ala Phe Ala Leu
             645

<210> SEQ ID NO 44
<211> LENGTH: 2710
<212> TYPE: DNA
<213> ORGANISM: Mus musculus

<400> SEQUENCE: 44

| | | | | |
|---|---|---|---|---|
| atgctgcttg | gagcctctct | ggtggggggcg | ctacttgggt | ccaagctagt | gctgaagctg    60 |
| ccctggaccc | aggtgggatt | ctccctgttg | ctcctgtact | tggggtctgg | tggctggcgt   120 |
| ttcatccggg | tcttcatcaa | gacggtcagg | agagatatct | ttggtggcat | ggtgctcctg   180 |
| aaggtgaaga | ccaaggtgcg | acggtacctt | caggagcgga | agacggtgcc | cctgctgttt   240 |
| gcttcaatgg | tacagcgcca | cccggacaag | acagccctga | ttttcgaggg | cacagacact   300 |
| cactggacct | tccgccagct | ggatgagtac | tccagtagtg | tggccaactt | cctgcaggcc   360 |
| cggggcctgg | cctcaggcaa | tgtagttgcc | ctctttatgg | aaaaccgcaa | tgagtttgtg   420 |
| ggtctgtggc | taggcatggc | caagctgggc | gtggaggcgg | ctctcatcaa | caccaacctt   480 |
| aggcgggatg | ccctgcgcca | ctgtcttgac | acctcaaagg | cacgagctct | catctttggc   540 |
| agtgagatgg | cctcagctat | ctgtgagatc | catgctagcc | tggagcccac | actcagcctc   600 |
| ttctgctctg | gatcctggga | gcccagcaca | gtgcccgtca | gcacagagca | tctggaccct   660 |
| cttctggaag | atgccccgaa | gcacctgccc | agtcacccag | acaagggttt | tacagataag   720 |
| ctcttctaca | tctacacatc | gggcaccacg | gggctaccca | agctgccat | tgtggtgcac   780 |
| agcaggtatt | atcgtatggc | ttccctggtg | tactatggat | tccgcatgcg | gcctgatgac   840 |
| attgtctatg | actgcctccc | cctctaccac | tcaagcagga | acatcgtgg | ggattggcag   900 |
| tgcttactcc | acggcatgac | tgtggtgatc | cggaagaagt | tctcagcctc | ccggttctgg   960 |
| gatgattgta | tcaagtacaa | ctgcacagtg | gtacagtaca | ttggcgagct | ctgccgctac  1020 |
| ctcctgaacc | agccacccg | tgaggctgag | tctcggcaca | aggtgcgcat | ggcactgggc  1080 |
| aacggtctcc | ggcagtccat | ctggaccgac | ttctccagcc | gtttccacat | ccccaggtg  1140 |
| gctgagttct | atggggccac | tgaatgcaac | tgtagcctgg | caactttga | cagccgggtg  1200 |
| ggggcctgtg | gcttcaatag | ccgcatcctg | tcctttgtgt | accctatccg | tttggtacgt  1260 |
| gtcaatgagg | ataccatgga | actgatccgg | ggacccgatg | gagtctgcat | tccctgtcaa  1320 |
| ccaggtcagc | caggccagct | ggtgggtcgc | atcatccagc | aggaccctct | gcgccgtttc  1380 |
| gacgggtacc | tcaaccaggg | tgccaacaac | aagaagattg | ctaatgatgt | cttcaagaag  1440 |
| ggggaccaag | cctacctcac | tggtgacgtc | ctggtgatgg | atgagctggg | ttacctgtac  1500 |
| ttccgagatc | gcactgggga | cacgttccgc | tggaaagggg | agaatgtatc | taccactgag  1560 |
| gtggagggca | cactcagccg | cctgcttcat | atggcagatg | tggcagttta | tggtgttgag  1620 |
| gtgccaggaa | ctgaaggccg | agcaggaatg | gctgccgttg | caagtcccat | cagcaactgt  1680 |
| gacctggaga | gctttgcaca | gaccttgaaa | aaggagctgc | ctctgtatgc | ccgccccatc  1740 |
| ttcctgcgct | tcttgcctga | gctgcacaag | acagggacct | tcaagttcca | gaagacagag  1800 |
| ttgcggaagg | agggctttga | cccatctgtt | gtgaaagacc | cgctgttcta | tctggatgct  1860 |
| cggaagggct | gctacgttgc | actggaccag | gaggcctata | cccgcatcca | ggcaggcgag  1920 |
| gagaagctgt | gatttccccc | tacatccctc | tgagggccag | aagatgctgg | attcagagcc  1980 |
| ctagcgtcca | ccccagaggg | tcctgggcaa | tgccagacca | agctagcag | ggcccgcacc  2040 |

-continued

```
tccgcccta ggtgctgatc tcccctctcc caaactgcca agtgactcac tgccgcttcc    2100
ccgaccctcc agaggctttc tgtgaaagtc tcatccaagc tgtgtcttct ggtccaggcg    2160
tggcccctgg ccccagggtt tctgataggc tcctttagga tggtatcttg ggtccagcgg    2220
gccagggtgt gggagaggag tcactaagat ccctccaatc agaagggagc ttacaaagga    2280
accaaggcaa agcctgtaga ctcaggaagc taagtggcca gagactatag tggccagtca    2340
tcccatgtcc acagaggatc ttggtccaga gctgccaaag tgtcacctct ccctgcctgc    2400
acctctgggg aaaagaggac agcatgtggc cactgggcac ctgtctcaag aagtcaggat    2460
cacacactca gtccttgttt ctccaggttc ccttgttctt gtctcgggga gggagggacg    2520
agtgtcctgt ctgtccttcc tgcctgtctg tgagtctgtg ttgcttctcc atctgtccta    2580
gcctgagtgt gggtggaaca ggcatgagga gagtgtggct caggggccaa taaactctgc    2640
cttgactcct cttaaaaaaa aaaaaaaaaa aaaaaaaaaa aaaaaaaaaa aaaaaaaaaa    2700
aaaaaaaaaa                                                          2710
```

<210> SEQ ID NO 45
<211> LENGTH: 643
<212> TYPE: PRT
<213> ORGANISM: Mus musculus

<400> SEQUENCE: 45

```
Met Leu Leu Gly Ala Ser Leu Val Gly Ala Leu Leu Phe Ser Lys Leu
 1               5                  10                  15

Val Leu Lys Leu Pro Trp Thr Gln Val Gly Phe Ser Leu Leu Leu Leu
             20                  25                  30

Tyr Leu Gly Ser Gly Gly Trp Arg Phe Ile Arg Val Phe Ile Lys Thr
         35                  40                  45

Val Arg Arg Asp Ile Phe Gly Gly Met Val Leu Leu Lys Val Lys Thr
     50                  55                  60

Lys Val Arg Arg Tyr Leu Gln Glu Arg Lys Thr Val Pro Leu Leu Phe
 65                  70                  75                  80

Ala Ser Met Val Gln Arg His Pro Asp Lys Thr Ala Leu Ile Phe Glu
                 85                  90                  95

Gly Thr Asp Thr His Trp Thr Phe Arg Gln Leu Asp Glu Tyr Ser Ser
            100                 105                 110

Ser Val Ala Asn Phe Leu Gln Ala Arg Gly Leu Ala Ser Gly Asn Val
        115                 120                 125

Val Ala Leu Phe Met Glu Asn Arg Asn Glu Phe Val Gly Leu Trp Leu
    130                 135                 140

Gly Met Ala Lys Leu Gly Val Glu Ala Ala Leu Ile Asn Thr Asn Leu
145                 150                 155                 160

Arg Arg Asp Ala Leu Arg His Cys Leu Asp Thr Ser Lys Ala Arg Ala
                165                 170                 175

Leu Ile Phe Gly Ser Glu Met Ala Ser Ala Ile Cys Glu Ile His Ala
            180                 185                 190

Ser Leu Glu Pro Thr Leu Ser Leu Phe Cys Ser Gly Ser Trp Glu Pro
        195                 200                 205

Ser Thr Val Pro Val Ser Thr Glu His Leu Asp Pro Leu Leu Glu Asp
    210                 215                 220

Ala Pro Lys His Leu Pro Ser His Pro Asp Lys Gly Phe Thr Asp Lys
225                 230                 235                 240

Leu Phe Tyr Ile Tyr Thr Ser Gly Thr Thr Gly Leu Pro Lys Ala Ala
```

```
                    245                 250                 255
Ile Val Val His Ser Arg Tyr Tyr Arg Met Ala Ser Leu Val Tyr Tyr
                260                 265                 270

Gly Phe Arg Met Arg Pro Asp Asp Ile Val Tyr Asp Cys Leu Pro Leu
            275                 280                 285

Tyr His Ser Ser Arg Lys His Arg Gly Asp Trp Gln Cys Leu Leu His
        290                 295                 300

Gly Met Thr Val Val Ile Arg Lys Lys Phe Ser Ala Ser Arg Phe Trp
305                 310                 315                 320

Asp Asp Cys Ile Lys Tyr Asn Cys Thr Val Gln Tyr Ile Gly Glu
                325                 330                 335

Leu Cys Arg Tyr Leu Leu Asn Gln Pro Pro Arg Glu Ala Glu Ser Arg
                340                 345                 350

His Lys Val Arg Met Ala Leu Gly Asn Gly Leu Arg Gln Ser Ile Trp
                355                 360                 365

Thr Asp Phe Ser Ser Arg Phe His Ile Pro Gln Val Ala Glu Phe Tyr
            370                 375                 380

Gly Ala Thr Glu Cys Asn Cys Ser Leu Gly Asn Phe Asp Ser Arg Val
385                 390                 395                 400

Gly Ala Cys Gly Phe Asn Ser Arg Ile Leu Ser Phe Val Tyr Pro Ile
                405                 410                 415

Arg Leu Val Arg Val Asn Glu Asp Thr Met Glu Leu Ile Arg Gly Pro
                420                 425                 430

Asp Gly Val Cys Ile Pro Cys Gln Pro Gly Gln Pro Gly Gln Leu Val
                435                 440                 445

Gly Arg Ile Ile Gln Gln Asp Pro Leu Arg Arg Phe Asp Gly Tyr Leu
450                 455                 460

Asn Gln Gly Ala Asn Asn Lys Lys Ile Ala Asn Asp Val Phe Lys Lys
465                 470                 475                 480

Gly Asp Gln Ala Tyr Leu Thr Gly Asp Val Leu Val Met Asp Glu Leu
                485                 490                 495

Gly Tyr Leu Tyr Phe Arg Asp Arg Thr Gly Asp Thr Phe Arg Trp Lys
                500                 505                 510

Gly Glu Asn Val Ser Thr Thr Glu Val Glu Gly Thr Leu Ser Arg Leu
            515                 520                 525

Leu His Met Ala Asp Val Ala Val Tyr Gly Val Glu Val Pro Gly Thr
530                 535                 540

Glu Gly Arg Ala Gly Met Ala Ala Val Ala Ser Pro Ile Ser Asn Cys
545                 550                 555                 560

Asp Leu Glu Ser Phe Ala Gln Thr Leu Lys Lys Glu Leu Pro Leu Tyr
                565                 570                 575

Ala Arg Pro Ile Phe Leu Arg Phe Leu Pro Glu Leu His Lys Thr Gly
            580                 585                 590

Thr Phe Lys Phe Gln Lys Thr Glu Leu Arg Lys Glu Gly Phe Asp Pro
        595                 600                 605

Ser Val Val Lys Asp Pro Leu Phe Tyr Leu Asp Ala Arg Lys Gly Cys
            610                 615                 620

Tyr Val Ala Leu Asp Gln Glu Ala Tyr Thr Arg Ile Gln Ala Gly Glu
625                 630                 635                 640

Glu Lys Leu

<210> SEQ ID NO 46
<211> LENGTH: 3694
```

<212> TYPE: DNA
<213> ORGANISM: Homo sapiens

<400> SEQUENCE: 46

```
tcgacccacg gcgtccggga ccccaaagca gaagcccgca cagtaggcac agcgcaccca      60
agaaggtcc aggagtctgc agaaacagaa aggtccccgg cctcagcctc ctagtccctg     120
cctgcctcct gcctgagctt ctgggagact gaaggcacgg cttgcagctt caggatgcgg     180
gctccgggtg cgggcgcggc ctcggtggtc tcgctggcgc tgttgtggct gctggggctg     240
ccgtggacct ggagcgcggc agcggcgctc ggcgtgtacg tgggcagcgg cggctggcgc     300
ttcctgcgca tcgtctgcaa gaccgcgagg cgagacctct tcggtctctc tgtgctgatc     360
cgcgtgcgcc tggagctgcg gcggcaccag cgtgccggcc acaccatccc gcgcatcttt     420
caggcggtag tgcagcgaca gcccgagcgc ctggcgctgg tggatgccgg gaccggcgag     480
tgctggacct ttgcgcagct ggacgcctac tccaatgcgg tagccaacct cttccgccag     540
ctgggcttcg cgccgggcga cgtggtggcc atcttcctgg agggccggcc ggagttcgtg     600
gggctgtggc tgggcctggc caaggcgggc atggaggcc cgctgctcaa cgtgaacctg     660
cggcgcgagc ccctggcctt ctgcctgggc acctcgggcg ctaaggccct gatctttgga     720
ggagaaatgg tggcggcgt ggccgaagtg agcgggcatc tggggaaaag tttgatcaag     780
ttctgctctg gagacttggg gcccgagggc atcttgccgg acacccacct cctggacccg     840
ctgctgaagg aggcctctac tgcccccttg gcacagatcc ccagcaaggg catggacgat     900
cgtcttttct acatctacac gtcggggacc accgggctgc ccaaggctgc cattgtcgtg     960
cacagcaggt actaccgcat ggcagccttc ggccaccacg cctaccgcat gcaggcggct    1020
gacgtgctct atgactgcct gcccctgtac cactcggcag gaaacatcat cggcgtgggg    1080
cagtgtctca tctatgggct gacagtcgtc tccgcaaga aattctcggc cagccgcttc    1140
tgggacgact gcatcaagta caactgcacg gtggttcagt acatcgggga gatctgccgc    1200
tacctgctga gcagccggt gcgcgaggcg gagaggcgac accgcgtgcg cctggcggtg    1260
gggaacgggc tgcgtcctgc catctgggag gagttcacgg agcgcttcgg cgtacgccaa    1320
atcgggggagt tctacggcgc caccgagtgc aactgcagca ttgccaacat ggacggcaag    1380
gtcggctcct gtggttttcaa cagccgcatc ctgccccacg tgtaccccat ccggctggtg    1440
aaggtcaatg aggacacaat ggagctgctg cgggatgccc agggcctctg catcccctgc    1500
caggccgggg agcctggcct ccttgtgggt cagatcaacc aacaggaccc gctgcgccgc    1560
ttcgatggct atgtcagcga gagcgccacc agcaagaaga tcgcccacag cgtcttcagc    1620
aagggcgaca gcgcctacct ctcaggtgac gtgctagtga tggatgagct gggctacatg    1680
tacttccggg accgtagcgg ggacaccttc cgctggcgag gggagaacgt ctccaccacc    1740
gaggtggagg gcgtgctgag ccgcctgctg gccagacag acgtggccgt ctatggggtg    1800
gctgttccag gagtggaggg taaggcaggg atggcggccg tcgcagaccc ccacagcctg    1860
ctggacccca acgcgatata ccaggagctg cagaaggtgc tggcaccta tgcccggccc    1920
atcttcctgc gcctcctgcc ccaggtggac accacaggca ccttcaagat ccagaagacg    1980
aggctgcagc gagagggctt tgacccacgc cagacctcag accggctctt cttcctggac    2040
ctgaagcagg gccactacct gcccttaaat gaggcagtct acactcgcat ctgctcgggc    2100
gccttcgccc tctgaagctg ttcctctact ggccacaaac tctgggcctg gtgggagagg    2160
ccagcttgag ccagacagcg ctgcccaggg gtggccgcct agtacacacc cacctggccg    2220
```

-continued

```
agctgtacct ggcacggccc atcctggact gagaaactgg aacctcagag gaacccgtgc    2280
ctctctgctg ccttggtgcc cctgtgtctg cctcctctcc ctgcttttca gcctctgtct    2340
ccttccatcc ctgtccctgt ctggccttaa ctcttccctc tctttctttt ctttctttct    2400 ttctttttt ttaagataga gtctcactct gctgcccggg ctagagtgca gtggtgggat     2460
ctcggctcac tgcaacctct gcctcctggg gttcaagtga tcctcccacc tcagcctcct    2520
gagtagctgg gattacaggc acccgccacc acgtccagct aattttata ttttagtag      2580 agacgggtt tcaccatgtt ggtcaggctg gtcttgaact cctgacctca ggtgatccgc     2640
tggcctcggc ctcccagagt gctgggatta taggcgtgag cctctggccc ggcctttcct    2700
ttttcctctc ctctcctgcc gagagtggaa cacacgtgtc ctgggagctg catcttgtgt    2760
agggtccagc tgcttttggg gactgcagga atcatctccc ctgggccctg gactcggact    2820
ggggcctccc cacctccctc tcggctgtgc cttacggagc cccaatccag gcctcctgtg    2880
gctgttgggt tccagatgct gcagctccat gtgacttcca agcaggccct ccgccctccc    2940
tgctgaatgg aggagccggg ggtcccccag gccaactgga aaatctccca ggctaggcca    3000 attgccttt gcacttcccc gttcctgtca catttcccca gccccacctt ccctcctga     3060 tgccctgaaa gcttccggaa ttgactgtga ccacttggat gtcaccactg tcagcccctg    3120
ccttgatgtc cccatttagc catctccatg gagctcctgc tggagggccc tgaaccctgc    3180
actgcgtggc tgcccagcca gctgcctcct gtcctgggag gaggcctcct gggtgtcctc    3240
atctggtgtg tctactggag ggtcccacag gagaggcagc agaggggtca ggggaggtct    3300
cctgccgggg gttggcctct caagcctcag gggttctagc ctgttgaata tacccccacct   3360 ggtgggtggc ccctccgatg tccccactga tggctctgac accgtgttgg tggcgatgtc    3420
ccagacaatc ccaccaggac ggcccagaca tccctactgg cttcgctggt ggctcatctc    3480
gaacatccac gccagccttt ctggggccgg ccacccaggc cgcctgtccg tctgtcctcc    3540
ctccagcagc accccctggc ccctggagtg gtggggccat ggcaagagac accgtggcgt    3600
ctcatgtgaa ctttcctggg cactgtggtt ttatttccta attgatttaa gaaataaacc    3660
tgaagaccgt ctggtgaaaa aaaaaaaaa aaaa                                 3694
```

<210> SEQ ID NO 47
<211> LENGTH: 646
<212> TYPE: PRT
<213> ORGANISM: Homo sapiens

<400> SEQUENCE: 47

Met Arg Ala Pro Gly Ala Gly Ala Ala Ser Val Val Ser Leu Ala Leu
1               5                   10                  15

Leu Trp Leu Leu Gly Leu Pro Trp Thr Trp Ser Ala Ala Ala Ala Leu
            20                  25                  30

Gly Val Tyr Val Gly Ser Gly Gly Trp Arg Phe Leu Arg Ile Val Cys
        35                  40                  45

Lys Thr Ala Arg Arg Asp Leu Phe Gly Leu Ser Val Leu Ile Arg Val
    50                  55                  60

Arg Leu Glu Leu Arg Arg His Gln Arg Ala Gly His Thr Ile Pro Arg
65                  70                  75                  80

Ile Phe Gln Ala Val Val Gln Arg Gln Pro Glu Arg Leu Ala Leu Val
                85                  90                  95

Asp Ala Gly Thr Gly Glu Cys Trp Thr Phe Ala Gln Leu Asp Ala Tyr
            100                 105                 110

-continued

```
Ser Asn Ala Val Ala Asn Leu Phe Arg Gln Leu Gly Phe Ala Pro Gly
        115                 120                 125

Asp Val Val Ala Ile Phe Leu Glu Gly Arg Pro Glu Phe Val Gly Leu
    130                 135                 140

Trp Leu Gly Leu Ala Lys Ala Gly Met Glu Ala Ala Leu Leu Asn Val
145                 150                 155                 160

Asn Leu Arg Arg Glu Pro Leu Ala Phe Cys Leu Gly Thr Ser Gly Ala
                165                 170                 175

Lys Ala Leu Ile Phe Gly Gly Glu Met Val Ala Val Ala Glu Val
            180                 185                 190

Ser Gly His Leu Gly Lys Ser Leu Ile Lys Phe Cys Ser Gly Asp Leu
        195                 200                 205

Gly Pro Glu Gly Ile Leu Pro Asp Thr His Leu Leu Asp Pro Leu Leu
    210                 215                 220

Lys Glu Ala Ser Thr Ala Pro Leu Ala Gln Ile Pro Ser Lys Gly Met
225                 230                 235                 240

Asp Asp Arg Leu Phe Tyr Ile Tyr Thr Ser Gly Thr Thr Gly Leu Pro
                245                 250                 255

Lys Ala Ala Ile Val Val His Ser Arg Tyr Tyr Arg Met Ala Ala Phe
            260                 265                 270

Gly His His Ala Tyr Arg Met Gln Ala Ala Asp Val Leu Tyr Asp Cys
        275                 280                 285

Leu Pro Leu Tyr His Ser Ala Gly Asn Ile Ile Gly Val Gly Gln Cys
    290                 295                 300

Leu Ile Tyr Gly Leu Thr Val Val Leu Arg Lys Lys Phe Ser Ala Ser
305                 310                 315                 320

Arg Phe Trp Asp Asp Cys Ile Lys Tyr Asn Cys Thr Val Val Gln Tyr
                325                 330                 335

Ile Gly Glu Ile Cys Arg Tyr Leu Leu Lys Gln Pro Val Arg Glu Ala
            340                 345                 350

Glu Arg Arg His Arg Val Arg Leu Ala Val Gly Asn Gly Leu Arg Pro
        355                 360                 365

Ala Ile Trp Glu Glu Phe Thr Glu Arg Phe Gly Val Arg Gln Ile Gly
    370                 375                 380

Glu Phe Tyr Gly Ala Thr Glu Cys Asn Cys Ser Ile Ala Asn Met Asp
385                 390                 395                 400

Gly Lys Val Gly Ser Cys Gly Phe Asn Ser Arg Ile Leu Pro His Val
                405                 410                 415

Tyr Pro Ile Arg Leu Val Lys Val Asn Glu Asp Thr Met Glu Leu Leu
            420                 425                 430

Arg Asp Ala Gln Gly Leu Cys Ile Pro Cys Gln Ala Gly Glu Pro Gly
        435                 440                 445

Leu Leu Val Gly Gln Ile Asn Gln Gln Asp Pro Leu Arg Arg Phe Asp
    450                 455                 460

Gly Tyr Val Ser Glu Ser Ala Thr Ser Lys Lys Ile Ala His Ser Val
465                 470                 475                 480

Phe Ser Lys Gly Asp Ser Ala Tyr Leu Ser Gly Asp Val Leu Val Met
                485                 490                 495

Asp Glu Leu Gly Tyr Met Tyr Phe Arg Asp Arg Ser Gly Asp Thr Phe
            500                 505                 510

Arg Trp Arg Gly Glu Asn Val Ser Thr Thr Glu Val Glu Gly Val Leu
        515                 520                 525

Ser Arg Leu Leu Gly Gln Thr Asp Val Ala Val Tyr Gly Val Ala Val
```

-continued

```
                            530                 535                 540
Pro Gly Val Glu Gly Lys Ala Gly Met Ala Ala Val Ala Asp Pro His
545                 550                 555                 560

Ser Leu Leu Asp Pro Asn Ala Ile Tyr Gln Glu Leu Gln Lys Val Leu
                565                 570                 575

Ala Pro Tyr Ala Arg Pro Ile Phe Leu Arg Leu Leu Pro Gln Val Asp
                580                 585                 590

Thr Thr Gly Thr Phe Lys Ile Gln Lys Thr Arg Leu Gln Arg Glu Gly
                595                 600                 605

Phe Asp Pro Arg Gln Thr Ser Asp Arg Leu Phe Leu Asp Leu Lys
                610                 615                 620

Gln Gly His Tyr Leu Pro Leu Asn Glu Ala Val Tyr Thr Arg Ile Cys
625                 630                 635                 640

Ser Gly Ala Phe Ala Leu
                645
```

<210> SEQ ID NO 48
<211> LENGTH: 2362
<212> TYPE: DNA
<213> ORGANISM: Homo sapiens

<400> SEQUENCE: 48

```
ggaattccaa aaaaaaaaaa tacgactaca cctgctccgg agcccgcggc ggtacctgca    60
gcggaggagc tctgtcttcc ccttcatctc acgcgagccc ggcgtcccgc cgcgtgcgcc   120
ccggcgcagc ccgccagtcc gcccggagcc cgcccagtcg ccgcgctgca cgcccggggt   180
gaaccctctg ccctcgctgg gacagagggc ccgcagccg tcatgctttc cgccatctac    240
acagtcctgg cgggactgct gttcctgccg ctcctggtga acctctgctg cccatacttc   300
ttccaggaca taggctactt cttgaaggtg gccgccgtgg gccggagggt gcgcagctac   360
gggcagcggc ggccggcgcg caccatcctg cgggcgttcc tggagaaagc gcgccagacg   420
ccacacaagc ctttctgct cttccgcgac gagactctca cctacgcgca ggtggaccgg   480
cgcagcaatc aagtggcccg ggcgctgcac gaccacctcg gcctgcgcca gggagactgc   540
gtggcgctcc ttatgggtaa cgagccggcc tacgtgtggc tgtggctggg gctggtgaag   600
ctgggctgtg ccatggcgtg cctcaattac aacatccgcg cgaagtccct gctgcactgc   660
ttccagtgct gcggggcgaa ggtgctgctg gtgtcgccag aactacaagc agctgtcgaa   720
gagatactgc caagccttaa aaagatgat gtgtccatct attatgtgag cagaacttct   780
aacacagatg ggattgactc tttcctggac aaagtggatg aagtatcaac tgaacctatc   840
ccagagtcat ggaggtctga agtcactttt tccactcctg ccttatacat ttatacttct   900
ggaaccacag gtcttccaaa agcagccatg atcactcatc agcgcatatg gtatggaact   960
ggcctcactt ttgtaagcgg attgaaggca gatgatgtca tctatatcac tctgcccttt  1020
taccacagtg ctgcactact gattggcatt acggatgta ttgtggctgg tgctactctt  1080
gccttgcgga ctaaatttc agccagccag ttttgggatg actgcagaaa atacaacgtc  1140
actgtcattc agtatatcgg tgaactgctt cggtatttat gcaactcacc acagaaacca  1200
aatgaccgta tcataaagt gagactggca ctgggaaatg gcttacgagg agatgtgtgg  1260
agacaatttg tcaagagatt tgggggacata tgcatctatg agttctatgc tgccactgaa  1320
ggcaatattg gatttatgaa ttatgcgaga aaagttggtg ctgttggaag agtaaactac  1380
ctacagaaaa aaatcataac ttatgacctg attaaatatg atgtggagaa agatgaacct  1440
```

-continued

```
gtccgagatg aaaatggata ttgcgtcaga gttcccaaag gtgaagttgg acttctggtt    1500
tgcaaaatca cacaacttac accatttaat ggctatgctg agcaaaggc tcagacagag     1560 aagaaaaaac tgagagatgt ctttaagaaa ggagacctct atttcaacag tggagatctc    1620
ttaatggttg accatgaaaa tttcatctat ttccacgaca gagttggaga tacattccgg    1680
tggaaagggg aaaatgtggc caccactgaa gttgctgata cagttggact ggttgatttt    1740
gtccaagaag taaatgttta tggagtgcat gtgccagatc atgagggtcg cattggcatg    1800
gcctccatca aaatgaaaga aaccatgaa tttgatggaa agaaactctt tcagcacatt     1860
gctgattacc tacctagtta tgcaaggccc cggtttctaa gaatacagga caccattgag    1920
atcactggaa cttttaaaca ccgcaaaatg accctggtgg aggagggctt taaccctgct    1980
gtcatcaaag atgccttgta tttcttggat gacacagcaa aatgtatgt gcctatgact      2040 gaggacatct ataatgccat aagtgctaaa accctgaaac tctgaatatt cccaggagga    2100
taactcaaca tttccagaaa gaaactgaat ggacagccac ttgatataat ccaactttaa    2160
tttgattgaa gattgtgagg aaattttgta ggaaatttgc atacccgtaa agggagactt    2220
ttttaaataa cagttgagtc tttgcaagta aaaagattta gagattatta ttttttcagtg   2280 tgcacctact gtttgtattt gcaaactgag cttgttggag ggaaggcatt attttttaaa    2340
atacttagta aattaaatga ac                                              2362
```

<210> SEQ ID NO 49
<211> LENGTH: 620
<212> TYPE: PRT
<213> ORGANISM: Homo sapiens

<400> SEQUENCE: 49

```
Met Leu Ser Ala Ile Tyr Thr Val Leu Ala Gly Leu Leu Phe Leu Pro
  1               5                  10                  15

Leu Leu Val Asn Leu Cys Cys Pro Tyr Phe Phe Gln Asp Ile Gly Tyr
                 20                  25                  30

Phe Leu Lys Val Ala Ala Val Gly Arg Arg Val Arg Ser Tyr Gly Gln
             35                  40                  45

Arg Arg Pro Ala Arg Thr Ile Leu Arg Ala Phe Leu Glu Lys Ala Arg
         50                  55                  60

Gln Thr Pro His Lys Pro Phe Leu Leu Phe Arg Asp Glu Thr Leu Thr
 65                  70                  75                  80

Tyr Ala Gln Val Asp Arg Ser Asn Gln Val Ala Arg Ala Leu His
                 85                  90                  95

Asp His Leu Gly Leu Arg Gln Gly Asp Cys Val Ala Leu Leu Met Gly
                100                 105                 110

Asn Glu Pro Ala Tyr Val Trp Leu Trp Leu Gly Leu Val Lys Leu Gly
            115                 120                 125

Cys Ala Met Ala Cys Leu Asn Tyr Asn Ile Arg Ala Lys Ser Leu Leu
        130                 135                 140

His Cys Phe Gln Cys Cys Gly Ala Lys Val Leu Leu Val Ser Pro Glu
145                 150                 155                 160

Leu Gln Ala Ala Val Glu Glu Ile Leu Pro Ser Leu Lys Lys Asp Asp
                165                 170                 175

Val Ser Ile Tyr Tyr Val Ser Arg Thr Ser Asn Thr Asp Gly Ile Asp
            180                 185                 190

Ser Phe Leu Asp Lys Val Asp Glu Val Ser Thr Glu Pro Ile Pro Glu
        195                 200                 205
```

-continued

```
Ser Trp Arg Ser Glu Val Thr Phe Ser Thr Pro Ala Leu Tyr Ile Tyr
    210                 215                 220

Thr Ser Gly Thr Thr Gly Leu Pro Lys Ala Ala Met Ile Thr His Gln
225                 230                 235                 240

Arg Ile Trp Tyr Gly Thr Gly Leu Thr Phe Val Ser Gly Leu Lys Ala
                245                 250                 255

Asp Asp Val Ile Tyr Ile Thr Leu Pro Phe Tyr His Ser Ala Ala Leu
                260                 265                 270

Leu Ile Gly Ile His Gly Cys Ile Val Ala Gly Ala Thr Leu Ala Leu
            275                 280                 285

Arg Thr Lys Phe Ser Ala Ser Gln Phe Trp Asp Asp Cys Arg Lys Tyr
    290                 295                 300

Asn Val Thr Val Ile Gln Tyr Ile Gly Glu Leu Leu Arg Tyr Leu Cys
305                 310                 315                 320

Asn Ser Pro Gln Lys Pro Asn Asp Arg Asp His Lys Val Arg Leu Ala
                325                 330                 335

Leu Gly Asn Gly Leu Arg Gly Asp Val Trp Arg Gln Phe Val Lys Arg
            340                 345                 350

Phe Gly Asp Ile Cys Ile Tyr Glu Phe Tyr Ala Ala Thr Glu Gly Asn
        355                 360                 365

Ile Gly Phe Met Asn Tyr Ala Arg Lys Val Gly Ala Val Gly Arg Val
    370                 375                 380

Asn Tyr Leu Gln Lys Lys Ile Ile Thr Tyr Asp Leu Ile Lys Tyr Asp
385                 390                 395                 400

Val Glu Lys Asp Glu Pro Val Arg Asp Glu Asn Gly Tyr Cys Val Arg
                405                 410                 415

Val Pro Lys Gly Glu Val Gly Leu Leu Val Cys Lys Ile Thr Gln Leu
            420                 425                 430

Thr Pro Phe Asn Gly Tyr Ala Gly Ala Lys Ala Gln Thr Glu Lys Lys
        435                 440                 445

Lys Leu Arg Asp Val Phe Lys Lys Gly Asp Leu Tyr Phe Asn Ser Gly
    450                 455                 460

Asp Leu Leu Met Val Asp His Glu Asn Phe Ile Tyr Phe His Asp Arg
465                 470                 475                 480

Val Gly Asp Thr Phe Arg Trp Lys Gly Glu Asn Val Ala Thr Thr Glu
                485                 490                 495

Val Ala Asp Thr Val Gly Leu Val Asp Phe Val Gln Glu Val Asn Val
            500                 505                 510

Tyr Gly Val His Val Pro Asp His Glu Gly Arg Ile Gly Met Ala Ser
        515                 520                 525

Ile Lys Met Lys Glu Asn His Glu Phe Asp Gly Lys Lys Leu Phe Gln
    530                 535                 540

His Ile Ala Asp Tyr Leu Pro Ser Tyr Ala Arg Pro Arg Phe Leu Arg
545                 550                 555                 560

Ile Gln Asp Thr Ile Glu Ile Thr Gly Thr Phe Lys His Arg Lys Met
                565                 570                 575

Thr Leu Val Glu Glu Gly Phe Asn Pro Ala Val Ile Lys Asp Ala Leu
            580                 585                 590

Tyr Phe Leu Asp Asp Thr Ala Lys Met Tyr Val Pro Met Thr Glu Asp
        595                 600                 605

Ile Tyr Asn Ala Ile Ser Ala Lys Thr Leu Lys Leu
    610                 615                 620
```

<210> SEQ ID NO 50
<211> LENGTH: 1173
<212> TYPE: DNA
<213> ORGANISM: Homo sapiens

<400> SEQUENCE: 50

```
aagttctcgg ctggtcagtt ctgggaagat tgccagcagc acagggtgac ggtgttccag        60
tacattgggg agctgtgccg ataccttgtc aaccagcccc cgagcaaggc agaacgtggc       120
cataaggtcc ggctggcagt gggcagcggg ctgcgcccag atacctggga gcgttttgtg       180
cggcgcttcg ggcccctgca ggtgctggag acatatggac tgacagaggg caacgtggcc       240
accatcaact acacaggaca gcggggcgct gtggggcgtg cttcctggct ttacaagcat       300
atcttcccct tctccttgat tcgctatgat gtcaccacag agagccaat  tcgggacccc       360
caggggcact gtatggccac atctccaggt gagccagggc tgctggtggc cccggtaagc       420
cagcagtccc cattcctggg ctatgctggc gggccagagc tgcccaggg  gaagttgcta       480
aaggatgtct tccggcctgg ggatgttttc ttcaacactg ggacctgct  ggtctgcgat       540
gaccaaggtt ttctccgctt ccatgatcgt actggagaca ccttcaggtg gaaggggggag       600
aatgtggcca caaccgaggt ggcagaggtc ttcgaggccc tagattttct tcaggaggtg       660
aacgtctatg gagtcactgt gccagggcat gaaggcaggg ctggaatggc agccctagtt       720
ctgcgtcccc ccacgctttt ggaccttatg cagctctaca cccacgtgtc tgagaacttg       780
ccaccttatg cccggccccg attcctcagg ctccaggagt cttttggccac acagagacc       840
ttcaaacagc agaaagttcg gatggcaaat gagggcttcg accccagcac cctgtctgac       900
ccactgtacg ttctggacca ggctgtaggt gcctacctgc ccctcacaac tgcccggtac       960
agcgccctcc tggcaggaaa ccttcgaatc tgagaacttc cacacctgag gcacctgaga      1020
gaggaactct gtgggtggg  ggccgttgca ggtgtactgg gctgtcaggg atcttttcta      1080
taccagaact gcggtcacta ttttgtaata aatgtggctg agctgatcc  agctgtctct      1140
gacaaaaaaa aaaaaaaaa  aaagggcggc cgc                                   1173
```

<210> SEQ ID NO 51
<211> LENGTH: 330
<212> TYPE: PRT
<213> ORGANISM: Homo sapiens

<400> SEQUENCE: 51

```
Lys Phe Ser Ala Gly Gln Phe Trp Glu Asp Cys Gln Gln His Arg Val
  1               5                  10                  15

Thr Val Phe Gln Tyr Ile Gly Glu Leu Cys Arg Tyr Leu Val Asn Gln
             20                  25                  30

Pro Pro Ser Lys Ala Glu Arg Gly His Lys Val Arg Leu Ala Val Gly
         35                  40                  45

Ser Gly Leu Arg Pro Asp Thr Trp Glu Arg Phe Val Arg Arg Phe Gly
     50                  55                  60

Pro Leu Gln Val Leu Glu Thr Tyr Gly Leu Thr Glu Gly Asn Val Ala
 65                  70                  75                  80

Thr Ile Asn Tyr Thr Gly Gln Arg Gly Ala Val Gly Arg Ala Ser Trp
                 85                  90                  95

Leu Tyr Lys His Ile Phe Pro Phe Ser Leu Ile Arg Tyr Asp Val Thr
            100                 105                 110

Thr Gly Glu Pro Ile Arg Asp Pro Gln Gly His Cys Met Ala Thr Ser
            115                 120                 125
```

```
Pro Gly Glu Pro Gly Leu Leu Val Ala Pro Val Ser Gln Gln Ser Pro
    130                 135                 140

Phe Leu Gly Tyr Ala Gly Gly Pro Glu Leu Ala Gln Gly Lys Leu Leu
145                 150                 155                 160

Lys Asp Val Phe Arg Pro Gly Asp Val Phe Phe Asn Thr Gly Asp Leu
                165                 170                 175

Leu Val Cys Asp Asp Gln Gly Phe Leu Arg Phe His Asp Arg Thr Gly
            180                 185                 190

Asp Thr Phe Arg Trp Lys Gly Glu Asn Val Ala Thr Thr Glu Val Ala
        195                 200                 205

Glu Val Phe Glu Ala Leu Asp Phe Leu Gln Glu Val Asn Val Tyr Gly
    210                 215                 220

Val Thr Val Pro Gly His Glu Gly Arg Ala Gly Met Ala Ala Leu Val
225                 230                 235                 240

Leu Arg Pro Pro His Ala Leu Asp Leu Met Gln Leu Tyr Thr His Val
                245                 250                 255

Ser Glu Asn Leu Pro Pro Tyr Ala Arg Pro Arg Phe Leu Arg Leu Gln
            260                 265                 270

Glu Ser Leu Ala Thr Thr Glu Thr Phe Lys Gln Gln Lys Val Arg Met
        275                 280                 285

Ala Asn Glu Gly Phe Asp Pro Ser Thr Leu Ser Asp Pro Leu Tyr Val
    290                 295                 300

Leu Asp Gln Ala Val Gly Ala Tyr Leu Pro Leu Thr Thr Ala Arg Tyr
305                 310                 315                 320

Ser Ala Leu Leu Ala Gly Asn Leu Arg Ile
                325                 330

<210> SEQ ID NO 52
<211> LENGTH: 2907
<212> TYPE: DNA
<213> ORGANISM: Homo sapiens

<400> SEQUENCE: 52
cgacccacgc gtccgggcgg gcggggccgg gcggcgggcg gggctggcgg ggcggccggg      60
ccatgcaggg cgcagagccg gctaaaccct gctgagaccc ggctccgtgc gtccaggggc     120
ggctaatgcc cctcacgctg tctacgctgc tgcaaccggg ccgcatctgg acggggcgcc     180
gcgcggcgga gccgacgccg ggccacaatg ctgcttggag cctctctggt gggggtgctg     240
ctgttctcca agctggtgct gaaactgccc tggacccagg tgggattctc cctgttgttc     300
ctctacttgg gatctggcgg ctggcgcttc atccgggtct tcatcaagac catcaggcgc     360
gatatctttg gcggcctggt cctcctgaag gtgaaggcaa aggtgcgaca gtgcctgcag     420
gagcggcgga cagtgcccat tttgtttgcc tctaccgttc ggcgccaccc cgacaagacg     480
gccctgatct tcgagggcac agatacccac tggaccttcc gccagctgga tgagtactca     540
agcagtgtag ccaacttcct gcaggcccgg ggcctggcct cgggcgatgt ggctgccatc     600
ttcatggaga accgcaatga gttcgtgggc ctatggctgg catggccaa gctcggtgtg     660 gaggcagccc tcatcaacac caacctgcgg cgggatgctc tgctccactg cctcaccacc     720
tcgcgcgcac gggcccttgt ctttggcagc gaaatggcct cagccatctg tgaggtccat     780
gccagcctgg accctcgct cagcctcttc tgctctggct cctgggagcc cggtgcggtg     840
cctccaagca cagaacacct ggaccctctg ctgaaagatg ctcccaagca ccttcccagt     900
tgccctgaca agggcttcac agataaactg ttctacatct acacatccgg caccacaggg     960
```

-continued

```
ctgcccaagg ccgccatcgt ggtgcacagc aggtattacc gcatggctgc cctggtgtac    1020
tatggattcc gcatgcggcc caacgacatc gtctatgact gcctccccct ctaccactca    1080
gcaggaaaca tcgtgggaat cggccagtgc ctgctgcatg gcatgacggt ggtgattcgg    1140
aagaagttct cagcctcccg gttctgggac gattgtatca agtacaactg cacgattgtg    1200
cagtacattg tgaactgtgt ccgctacctc ctgaaccagc caccgcggga ggcagaaaac    1260
cagcaccagg ttcgcatggc actaggcaat ggcctccggc agtccatctg gaccaacttt    1320
tccagccgct tccacatacc ccaggtggct gagttctacg gggccacaga gtgcaactgt    1380
agcctgggca acttcgacag ccaggtgggg gcctgtggtt caatagccg catcctgtcc     1440 ttcgtgtacc ccatccggtt ggtacgtgtc aacgaggaca ccatggagct gatccggggg    1500
cccgacggcg tctgcattcc ctgccagcca ggtgagccgg ccagctggt gggccgcatc     1560 atccagaaag accccctgcg ccgcttcgat ggctacctca accagggcgc caacaacaag    1620
aagattgcca aggatgtctt caagaagggg gaccaggcct accttactgg tgatgtgctg    1680
gtgatggacg agctgggcta cctgtacttc cgagaccgca ctggggacac gttccgctgg    1740
aaaggtgaga acgtgtccac caccgaggtg gaaggcacac tcagccgcct gctggacatg    1800
gctgacgtgg ccgtgtatgg tgtcgaggtg ccaggaaccg agggccgggc cggaatggct    1860
gctgtggcca gccccactgg caactgtgac ctggagcgct ttgctcaggt cttggagaag    1920
gaactgcccc tgtatgcgcg ccccatcttc ctgcgcctcc tgcctgagct gcacaaaaca    1980
ggaacctaca agttccagaa gacagagcta cggaaggagg ctttgacccc ggctattgtg    2040
aaagacccgc tgttctatct agatgcccag aagggccgct acgtcccgct ggaccaagag    2100
gcctacagcc gcatccaggc aggcgaggag aagctgtgat tccccccatc cctctgaggg    2160
ccggcggatg ctggatccgg agccccaggt tccgccccag agcggtcctg acaaggcca     2220 gaccaaagca agcagggcct ggcacctcca tcctgaggtg ctgcccctcc atccaaaact    2280
gccaagtgac tcattgcctt cccaacccCtt ccagaggctt tctgtgaaag tctcatgtcc    2340
aagttccgtc tttctgggctg gcaggccct ctggttccca ggctgagact gacgggtttt    2400
ctcaggatga tgtcttgggt gagggtaggg agaggacaag gggtcaccga gcccttccca    2460
gagagcaggg agcttataaa tggaaccaga gcagaagtcc ccagactcag gaagtcaaca    2520
gagtgggcag ggacagtggt agcatccatc tggtggccaa agagaatcgt agccccagag    2580
ctgcccaagt tcactgggct ccaccccac ctccaggagg ggaggagagg acctgacatc     2640
tgtaggtggc ccctgatgcc ccatctacag caggaggtca ggaccacgcc cctggcctct    2700
ccccactccc ccatcctcct ccctgggtgg ctgcctgatt atccctcagg cagggcctct    2760
cagtccttgt gggtctgtgt cacctccatc tcagtcttgg cctggctatg aggggaggag    2820
gaatgggaga gggggctcag gggccaataa actctgcctt gagtcctcct aaaaaaaaaa    2880
aaaaaaaaaa aaaaaaaaa aaaaaa                                          2907
```

<210> SEQ ID NO 53
<211> LENGTH: 643
<212> TYPE: PRT
<213> ORGANISM: Homo sapiens

<400> SEQUENCE: 53

```
Met Leu Leu Gly Ala Ser Leu Val Gly Val Leu Phe Ser Lys Leu
 1               5                  10                  15

Val Leu Lys Leu Pro Trp Thr Gln Val Gly Phe Ser Leu Leu Phe Leu
            20                  25                  30
```

```
Tyr Leu Gly Ser Gly Gly Trp Arg Phe Ile Arg Val Phe Ile Lys Thr
         35                  40                  45

Ile Arg Arg Asp Ile Phe Gly Gly Leu Val Leu Leu Lys Val Lys Ala
 50                  55                  60

Lys Val Arg Gln Cys Leu Gln Glu Arg Thr Val Pro Ile Leu Phe
 65                  70                  75                  80

Ala Ser Thr Val Arg Arg His Pro Asp Lys Thr Ala Leu Ile Phe Glu
                 85                  90                  95

Gly Thr Asp Thr His Trp Thr Phe Arg Gln Leu Asp Glu Tyr Ser Ser
                100                 105                 110

Ser Val Ala Asn Phe Leu Gln Ala Arg Gly Leu Ala Ser Gly Asp Val
                115                 120                 125

Ala Ala Ile Phe Met Glu Asn Arg Asn Glu Phe Val Gly Leu Trp Leu
        130                 135                 140

Gly Met Ala Lys Leu Gly Val Glu Ala Ala Leu Ile Asn Thr Asn Leu
145                 150                 155                 160

Arg Arg Asp Ala Leu Leu His Cys Leu Thr Thr Ser Arg Ala Arg Ala
                165                 170                 175

Leu Val Phe Gly Ser Glu Met Ala Ser Ala Ile Cys Glu Val His Ala
                180                 185                 190

Ser Leu Asp Pro Ser Leu Ser Leu Phe Cys Ser Gly Ser Trp Glu Pro
                195                 200                 205

Gly Ala Val Pro Pro Ser Thr Glu His Leu Asp Pro Leu Leu Lys Asp
        210                 215                 220

Ala Pro Lys His Leu Pro Ser Cys Pro Asp Lys Gly Phe Thr Asp Lys
225                 230                 235                 240

Leu Phe Tyr Ile Tyr Thr Ser Gly Thr Thr Gly Leu Pro Lys Ala Ala
                245                 250                 255

Ile Val Val His Ser Arg Tyr Tyr Arg Met Ala Ala Leu Val Tyr Tyr
                260                 265                 270

Gly Phe Arg Met Arg Pro Asn Asp Ile Val Tyr Asp Cys Leu Pro Leu
        275                 280                 285

Tyr His Ser Ala Gly Asn Ile Val Gly Ile Gly Gln Cys Leu Leu His
        290                 295                 300

Gly Met Thr Val Val Ile Arg Lys Lys Phe Ser Ala Ser Arg Phe Trp
305                 310                 315                 320

Asp Asp Cys Ile Lys Tyr Asn Cys Thr Ile Val Gln Tyr Ile Gly Glu
                325                 330                 335

Leu Cys Arg Tyr Leu Leu Asn Gln Pro Pro Arg Glu Ala Glu Asn Gln
                340                 345                 350

His Gln Val Arg Met Ala Leu Gly Asn Gly Leu Arg Gln Ser Ile Trp
                355                 360                 365

Thr Asn Phe Ser Ser Arg Phe His Ile Pro Gln Val Ala Glu Phe Tyr
        370                 375                 380

Gly Ala Thr Glu Cys Asn Cys Ser Leu Gly Asn Phe Asp Ser Gln Val
385                 390                 395                 400

Gly Ala Cys Gly Phe Asn Ser Arg Ile Leu Ser Phe Val Tyr Pro Ile
                405                 410                 415

Arg Leu Val Arg Val Asn Glu Asp Thr Met Glu Leu Ile Arg Gly Pro
                420                 425                 430

Asp Gly Val Cys Ile Pro Cys Gln Pro Gly Glu Pro Gly Gln Leu Val
        435                 440                 445
```

```
Gly Arg Ile Ile Gln Lys Asp Pro Leu Arg Arg Phe Asp Gly Tyr Leu
    450                 455                 460
Asn Gln Gly Ala Asn Asn Lys Lys Ile Ala Lys Asp Val Phe Lys Lys
465                 470                 475                 480
Gly Asp Gln Ala Tyr Leu Thr Gly Asp Val Leu Val Met Asp Glu Leu
                485                 490                 495
Gly Tyr Leu Tyr Phe Arg Asp Arg Thr Gly Asp Thr Phe Arg Trp Lys
            500                 505                 510
Gly Glu Asn Val Ser Thr Thr Glu Val Glu Gly Thr Leu Ser Arg Leu
        515                 520                 525
Leu Asp Met Ala Asp Val Ala Val Tyr Gly Val Glu Val Pro Gly Thr
    530                 535                 540
Glu Gly Arg Ala Gly Met Ala Ala Val Ala Ser Pro Thr Gly Asn Cys
545                 550                 555                 560
Asp Leu Glu Arg Phe Ala Gln Val Leu Glu Lys Glu Leu Pro Leu Tyr
                565                 570                 575
Ala Arg Pro Ile Phe Leu Arg Leu Leu Pro Glu Leu His Lys Thr Gly
            580                 585                 590
Thr Tyr Lys Phe Gln Lys Thr Glu Leu Arg Lys Glu Gly Phe Asp Pro
        595                 600                 605
Ala Ile Val Lys Asp Pro Leu Phe Tyr Leu Asp Ala Gln Lys Gly Arg
    610                 615                 620
Tyr Val Pro Leu Asp Gln Glu Ala Tyr Ser Arg Ile Gln Ala Gly Glu
625                 630                 635                 640
Glu Lys Leu

<210> SEQ ID NO 54
<211> LENGTH: 1248
<212> TYPE: DNA
<213> ORGANISM: Homo sapiens
<220> FEATURE:
<221> NAME/KEY: misc_feature
<222> LOCATION: (1)...(1248)
<223> OTHER INFORMATION: n = A,T,C or G

<400> SEQUENCE: 54
gtcgttggga tcctcggctg cttagatctc ggagccacct gtgttctggc ccccaagttc     60
tctacttcct gcttctggga tgactgtcgg cagcatggcg tgacagtgat cctgtatgtg    120
ggcgagctcc tgcgatactt gtgtaacatt ccccagcaac cagaggaccg gacacataca    180
gtccgcctgg caatgggcaa tggactacgg gctgatgtgt ggggagacct tccagcagcg    240
tttcggtcct atttcggatc tngggaagtc ttacgggctt ccacagaagg gcaacatggg    300
gctttagttc aaatattgtt ggggcgctg cggggccctg gggcaaaga tggagcttgc     360 ctcctccgaa tgctgtcccc ctttgagctg gtgcagttcg acatggaggc ggcggagcct    420
gtgagggaca atcagggctt ctgcatccct gtagggctag gggagccggg gctgctgttg    480
accaaggtgg taagccagca acccttcgtg ggctaccgcg gcccccgaga gctgtcggaa    540
cggaagctgg tgcgcaacgt gcggcaatcg ggcgacgttt actacaacac cggggacgta    600
ctggccatgg accgcgaagg cttcctctac ttccgcgacc gactcgggga caccttccga    660
tggaagggcg agaacgtgtc cacgcacgag gtggagggcg tgttgtcgca ggtggacttc    720
ttgcaacagg ttaacgtgta tggcgtgtgc gtgccaggtt gtgagggtaa ggtgggcatg    780
gctgctgtgg cattagcccc cggccagact ttcgacgggg agaagttgta ccagcacgtt    840
cgcgcttggc tccctgccta cgctaccccc catttcatcc gcatccagga cgccatggag    900
```

-continued

```
gtcaccagca cgttcaaact gatgaagacc cggttggtgc gtgagggctt caatgtgggg    960
atcgtggttg accctctgtt tgtactggac aaccgggccc agtccttccg gcccctgacg   1020
gcagaaatgt accaggctgt gtgtgaggga acctggagcc tctgatcacc tggccaaccc   1080
actggggtag ggatcaaagc cagccacccc caccccaaca cactcggtgt ccctttcatc   1140
ctgggcctgt gtgaatccca gcctggccat accctcaacc tcagtgggct ggaaatgaca   1200
gtgggccctg tagcagtggc agaataaact cagmtgygtt cacagaaa               1248
```

<210> SEQ ID NO 55
<211> LENGTH: 354
<212> TYPE: PRT
<213> ORGANISM: Homo sapiens
<220> FEATURE:
<221> NAME/KEY: VARIANT
<222> LOCATION: (1)...(354)
<223> OTHER INFORMATION: Xaa = Any Amino Acid

<400> SEQUENCE: 55

```
Val Val Gly Ile Leu Gly Cys Leu Asp Leu Gly Ala Thr Cys Val Leu
 1               5                  10                  15

Ala Pro Lys Phe Ser Thr Ser Cys Phe Trp Asp Asp Cys Arg Gln His
             20                  25                  30

Gly Val Thr Val Ile Leu Tyr Val Gly Glu Leu Leu Arg Tyr Leu Cys
         35                  40                  45

Asn Ile Pro Gln Gln Pro Glu Asp Arg Thr His Thr Val Arg Leu Ala
     50                  55                  60

Met Gly Asn Gly Leu Arg Ala Asp Val Trp Gly Asp Leu Pro Ala Ala
 65                  70                  75                  80

Phe Arg Ser Tyr Phe Gly Ser Xaa Glu Val Leu Arg Ala Ser Thr Glu
                 85                  90                  95

Gly Gln His Gly Ala Leu Val Gln Ile Leu Leu Gly Ala Leu Arg Gly
            100                 105                 110

Pro Gly Gly Lys Asp Gly Ala Cys Leu Leu Arg Met Leu Ser Pro Phe
        115                 120                 125

Glu Leu Val Gln Phe Asp Met Glu Ala Ala Glu Pro Val Arg Asp Asn
    130                 135                 140

Gln Gly Phe Cys Ile Pro Val Gly Leu Gly Glu Pro Gly Leu Leu Leu
145                 150                 155                 160

Thr Lys Val Val Ser Gln Gln Pro Phe Val Gly Tyr Arg Gly Pro Arg
                165                 170                 175

Glu Leu Ser Glu Arg Lys Leu Val Arg Asn Val Arg Gln Ser Gly Asp
            180                 185                 190

Val Tyr Tyr Asn Thr Gly Asp Val Leu Ala Met Asp Arg Glu Gly Phe
        195                 200                 205

Leu Tyr Phe Arg Asp Arg Leu Gly Asp Thr Phe Arg Trp Lys Gly Glu
    210                 215                 220

Asn Val Ser Thr His Glu Val Glu Gly Val Leu Ser Gln Val Asp Phe
225                 230                 235                 240

Leu Gln Gln Val Asn Val Tyr Gly Val Cys Val Pro Gly Cys Glu Gly
                245                 250                 255

Lys Val Gly Met Ala Ala Val Ala Leu Ala Pro Gly Gln Thr Phe Asp
            260                 265                 270

Gly Glu Lys Leu Tyr Gln His Val Arg Ala Trp Leu Pro Ala Tyr Ala
        275                 280                 285
```

-continued

```
Thr Pro His Phe Ile Arg Ile Gln Asp Ala Met Glu Val Thr Ser Thr
    290                 295                 300

Phe Lys Leu Met Lys Thr Arg Leu Val Arg Glu Gly Phe Asn Val Gly
305                 310                 315                 320

Ile Val Val Asp Pro Leu Phe Val Leu Asp Asn Arg Ala Gln Ser Phe
                325                 330                 335

Arg Pro Leu Thr Ala Glu Met Tyr Gln Ala Val Cys Glu Gly Thr Trp
            340                 345                 350

Arg Leu
```

<210> SEQ ID NO 56
<211> LENGTH: 2885
<212> TYPE: DNA
<213> ORGANISM: Homo sapiens

<400> SEQUENCE: 56

| | | |
|---|---|---|
| aacggcaagt aagcgcaacg caattaatgt gagtagctca ctcattaggc accccaggct | 60 |
| ttacacttta tgcttccggg ctcgtatgtt gtgtggaatt gtgagcggat accaatttca | 120 |
| cacaggaacc agctatgaca tgattacgaa tttaatacga ctcactatag ggaatttggc | 180 |
| cctcgaggcc aagaattcgg cacgaggggt gctgagcccc tgcgcggttt ctggtgcgta | 240 |
| gagactgtaa atcgctgcgc ttctcagtca tcatcatccc agcttttccc ggctcgaatt | 300 |
| cagcctccaa ctcaagctcg cgggaaagac tacctgagag gagaaaagct tctgtccctg | 360 |
| gaccttcttc tgagggtgga gtcggaggct ccctgctttc cagccgccca gtgacccaag | 420 |
| cttaatcttc agcaccactt ggggcgacct tttcggtgca aacctacgat tctgtttctc | 480 |
| aggattcctc cccatcccgc ttcgccccgg aaaagctgac aagaacttca ggtgtaagcc | 540 |
| ctgagtagtg aggatctgcg gtctccgtgg agagctgtgc ctggaagaga aggacgctgg | 600 |
| tgggggctga gatcagagct gtcttctggc ccagttgccc ccatgcttct gtcatggcta | 660 |
| acagttctag ggctggaat ggtcgtcctg cacttcttgc agaaactcct gttcccttac | 720 |
| ttttgggatg acttctggtt cgtgttgaag gtggtgctca ttataattcg gctgaagaag | 780 |
| tatgaaaaga gagggagct ggtgactgtg ctggataaat tcttgagtca tgccaaaaga | 840 |
| caacctcgga aacctttcat catctatgag ggagacatct acacctatca ggatgtagac | 900 |
| aaaaggagca gcagagtggc ccatgtcttc ctgaaccatt cctctctgaa aaggggggac | 960 |
| acggtggctc tgctgatgag caatgagccg gacttcgttc acgtgtggtt cggcctcgcc | 1020 |
| aagctgggct gcgtggtggc ctttctcaac accaacattc gctccaactc cctcctgaat | 1080 |
| tgcatccgcg cctgtgggcc cagagcccta gtggtgggcg cagatttgct tggaacggta | 1140 |
| gaagaaatcc ttccaagcct ctcagaaaat atcagtgttt gggggatgaa agattctgtt | 1200 |
| ccacaaggtg taatttcact caaagaaaaa ctgagcacct cacctgatga gcccgtgcca | 1260 |
| cgcagccacc atgttgtctc actcctcaag tctacttgtc tttacatttt tacctctgga | 1320 |
| acaacaggtc taccaaaagc agctgtgatt agtcagctgc aggttttaag gggttctgct | 1380 |
| gtcctgtggg cttttggttg tactgctcat gacattgttt atataaccct tcctctgtat | 1440 |
| catagttcag cagctatcct gggaatttct ggatgtgttg agttgggtgc cacttgtgtg | 1500 |
| ttaaagaaga aattttcagc aagccagttt tggagtgact gcaagaagta tgatgtgact | 1560 |
| gtgtttcagt atattggaga actttgtcgc taccttttgca aacaatctaa gagagaagga | 1620 |
| gaaaaggatc ataaggtgcg tttggcaatt ggaaatggca tacggagtga tgtatggaga | 1680 |
| gaattttttag acagatttgg aaatataaag gtgtgtgaac tttatgcagc taccgaatca | 1740 |

```
agcatatctt tcatgaacta cactgggaga attggagcaa ttgggagaac aaatttgttt    1800
tacaaacttc tttccacttt tgacttaata aagtatgact ttcagaaaga tgaacccatg    1860
agaaatgagc agggttggtg tattcatgtg aaaaaaggag aacctggact tctcatttct    1920
cgagtgaatg caaaaaatcc cttctttggc tatgctgggc cttataagca cacaaaagac    1980
aaattgcttt gtgatgtttt taagaaggga gatgtttacc ttaatactgg agacttaata    2040
gtccaggatc aggacaattt cctttatttt tgggaccgta ctggagacac tttcagatgg    2100
aaaggagaaa atgtcgcaac cactgaggtt gctgatgtta ttggaatgtt ggatttcata    2160
caggaagcaa acgtctatgg tgtggctata tcaggttatg aaggaagagc aggaatggct    2220
tctattattt taaaaccaaa tacatcttta gatttggaaa aagtttatga acaagttgta    2280
acatttctac cagcttatgc ttgtccacga ttttttaagaa ttcaggaaaa atggaagca    2340 acaggaacat tcaaactatt gaagcatcag ttggtggaag atggatttaa tccactgaaa    2400
atttctgaac cactttactt catggataac ttgaaaaagt cttatgttct actgaccagg    2460
gaactttatg atcaaataat gttaggggaa ataaaacttt aagattttta tatctagaac    2520
tttcatatgc tttcttagga agagtgagag gggggtatat gattctttat gaaatgggga    2580
aagggagcta acattaatta tgcatgtact atatttcctt aatatgagag ataatttttt    2640
aattgcataa gaattttaat ttcttttaat tgatataaac attagttgat tattcttttt    2700
atctatttgg agattcagtg cataactaag tatttccctt aatactaaag attttaaata    2760
ataaatagtg gctagcggtt tggacaatca ctaaaaatgt actttctaat aagtaaaatt    2820
tctaattttg aataaaagat taaattttac tgaaaaaaaa aaaaaaaaaa aaaattggcg    2880
gccgc                                                               2885
```

<210> SEQ ID NO 57
<211> LENGTH: 619
<212> TYPE: PRT
<213> ORGANISM: Homo sapiens

<400> SEQUENCE: 57

```
Met Leu Leu Ser Trp Leu Thr Val Leu Gly Ala Gly Met Val Val Leu
 1               5                  10                  15

His Phe Leu Gln Lys Leu Leu Phe Pro Tyr Phe Trp Asp Asp Phe Trp
                20                  25                  30

Phe Val Leu Lys Val Val Leu Ile Ile Ile Arg Leu Lys Lys Tyr Glu
            35                  40                  45

Lys Arg Gly Glu Leu Val Thr Val Leu Asp Lys Phe Leu Ser His Ala
        50                  55                  60

Lys Arg Gln Pro Arg Lys Pro Phe Ile Ile Tyr Glu Gly Asp Ile Tyr
    65                  70                  75                  80

Thr Tyr Gln Asp Val Asp Lys Arg Ser Ser Arg Val Ala His Val Phe
                85                  90                  95

Leu Asn His Ser Ser Leu Lys Lys Gly Asp Thr Val Ala Leu Leu Met
               100                 105                 110

Ser Asn Glu Pro Asp Phe Val His Val Trp Phe Gly Leu Ala Lys Leu
           115                 120                 125

Gly Cys Val Val Ala Phe Leu Asn Thr Asn Ile Arg Ser Asn Ser Leu
       130                 135                 140

Leu Asn Cys Ile Arg Ala Cys Gly Pro Arg Ala Leu Val Val Gly Ala
   145                 150                 155                 160
```

-continued

```
Asp Leu Leu Gly Thr Val Glu Glu Ile Leu Pro Ser Leu Ser Glu Asn
            165                 170                 175
Ile Ser Val Trp Gly Met Lys Asp Ser Val Pro Gln Gly Val Ile Ser
            180                 185                 190
Leu Lys Glu Lys Leu Ser Thr Ser Pro Asp Glu Pro Val Pro Arg Ser
            195                 200                 205
His His Val Val Ser Leu Leu Lys Ser Thr Cys Leu Tyr Ile Phe Thr
    210                 215                 220
Ser Gly Thr Thr Gly Leu Pro Lys Ala Ala Val Ile Ser Gln Leu Gln
225                 230                 235                 240
Val Leu Arg Gly Ser Ala Val Leu Trp Ala Phe Gly Cys Thr Ala His
            245                 250                 255
Asp Ile Val Tyr Ile Thr Leu Pro Leu Tyr His Ser Ser Ala Ala Ile
            260                 265                 270
Leu Gly Ile Ser Gly Cys Val Glu Leu Gly Ala Thr Cys Val Leu Lys
            275                 280                 285
Lys Lys Phe Ser Ala Ser Gln Phe Trp Ser Asp Cys Lys Lys Tyr Asp
    290                 295                 300
Val Thr Val Phe Gln Tyr Ile Gly Glu Leu Cys Arg Tyr Leu Cys Lys
305                 310                 315                 320
Gln Ser Lys Arg Glu Gly Glu Lys Asp His Lys Val Arg Leu Ala Ile
            325                 330                 335
Gly Asn Gly Ile Arg Ser Asp Val Trp Arg Glu Phe Leu Asp Arg Phe
            340                 345                 350
Gly Asn Ile Lys Val Cys Glu Leu Tyr Ala Ala Thr Glu Ser Ser Ile
            355                 360                 365
Ser Phe Met Asn Tyr Thr Gly Arg Ile Gly Ala Ile Gly Arg Thr Asn
    370                 375                 380
Leu Phe Tyr Lys Leu Leu Ser Thr Phe Asp Leu Ile Lys Tyr Asp Phe
385                 390                 395                 400
Gln Lys Asp Glu Pro Met Arg Asn Glu Gln Gly Trp Cys Ile His Val
            405                 410                 415
Lys Lys Gly Glu Pro Gly Leu Leu Ile Ser Arg Val Asn Ala Lys Asn
            420                 425                 430
Pro Phe Phe Gly Tyr Ala Gly Pro Tyr Lys His Thr Lys Asp Lys Leu
            435                 440                 445
Leu Cys Asp Val Phe Lys Lys Gly Asp Val Tyr Leu Asn Thr Gly Asp
    450                 455                 460
Leu Ile Val Gln Asp Gln Asp Asn Phe Leu Tyr Phe Trp Asp Arg Thr
465                 470                 475                 480
Gly Asp Thr Phe Arg Trp Lys Gly Glu Asn Val Ala Thr Thr Glu Val
            485                 490                 495
Ala Asp Val Ile Gly Met Leu Asp Phe Ile Gln Glu Ala Asn Val Tyr
            500                 505                 510
Gly Val Ala Ile Ser Gly Tyr Glu Gly Arg Ala Gly Met Ala Ser Ile
            515                 520                 525
Ile Leu Lys Pro Asn Thr Ser Leu Asp Leu Glu Lys Val Tyr Glu Gln
    530                 535                 540
Val Val Thr Phe Leu Pro Ala Tyr Ala Cys Pro Arg Phe Leu Arg Ile
545                 550                 555                 560
Gln Glu Lys Met Glu Ala Thr Gly Thr Phe Lys Leu Leu Lys His Gln
            565                 570                 575
Leu Val Glu Asp Gly Phe Asn Pro Leu Lys Ile Ser Glu Pro Leu Tyr
```

```
                    580                 585                 590
Phe Met Asp Asn Leu Lys Lys Ser Tyr Val Leu Leu Thr Arg Glu Leu
        595                 600                 605

Tyr Asp Gln Ile Met Leu Gly Glu Ile Lys Leu
        610                 615

<210> SEQ ID NO 58
<211> LENGTH: 3098
<212> TYPE: DNA
<213> ORGANISM: Rattus norvegicus

<400> SEQUENCE: 58
aagttcccac tccagacttc tgcgagaacc cgtgaggaag cagcgagaac cgggggtttg      60
caagccagag aaggatgcgg actccgggag caggaacagc ctctgtggcc tcattgggc     120 tgctttggct tctgggactt ccgtggacct ggagcgcggc ggcggcgttc ggtgtgtacg    180
tgggtagcgg tggctggcga tttctgcgta tcgtctgcaa gacggcgagg cgagacctct    240
ttggcctctc tgttctgatc cgcgtgcggc tagagctacg acgacaccgg cgagcaggag    300
acacgatccc acgcatcttc caggccgtgg cccagcgaca gccggagcgc ctggcgctgg    360
tagatgcgag tagcggtatc tgctggacct tcgcacagct agacacctac tccaatgctg    420
tggccaatct gttcctccag ctgggctttg cgccaggcga tgtggtggct gtgttcctgg    480
aaggccggcc cgagttcgtg ggactgtggc tgggcctggc caaggccggt gtagtggctg    540
cgcttctcaa tgtcaacctg aggcgggagc cccttgcctt ctgcttgggc acatcagctg    600
ccaaggccct catttatggc ggggagatgg cagcggcggt ggcggaggtg agtgagcagc    660
tggggaagag cctgctcaag ttctgctctg gagatctggg gcctgagagc gtcctgcctg    720
acacgcagct tctggacccc atgcttgctg aggcgcccac cacacccctg gcacaggccc    780
caggcaaggg catggatgat cggctatttt acatctatac ttctgggacc accggacttc    840
ctaaggcggc cattgtggtg cacagcaggt actaccgcat cgcagccttc ggccaccatt    900
cctacagcat gcgggccaac gatgtgctct atgactgcct acctctctac cactcagcag    960
ggaacatcat gggcgtggga cagtgtatca tctacgggtt aacggtggta ctgcgcaaga   1020
agttctccgc cagccgcttc tgggacgact gtgtcaaata taattgcacg gtagtgcagt   1080
acatcggtga aatatgccgc tacctgctaa ggcagccggt tcgcgatgta gagcggcggc   1140
accgcgtgcg cctggccgtg ggtaacggac tgccggcagc catctgggag gagttcacgc   1200
agggtttcgg tgtgcgacag attggcgagt ctacggcgc caccgaatgc aactgcagca   1260
ttgccaacat ggacggcaag gtcggctcct gcggcttcaa cagccgtatc ctcacgcatg   1320
tgtaccccat ccgtctggtc aaggtcaacg aggacacgat ggagccactg agggactccc   1380
aaggcctctg catcccgtgc cagcccgggg aacctgggct tctcgtgggc cagatcaacc   1440
agcaagaccc tctgcggcgc ttcgatggct atgttagtga cagcgccacc aacaagaaga   1500
ttgcccacag cgtgttccga aaggggggaca gcgcctacct ttcaggtgac gtgctagtga   1560
tggacgagct ggggtacatg tacttccgtg accgcagcgg ggataccttc cgatggcgcg   1620
gcgagaacgt atccaccacg gaggtggaag ccgtgctgag ccgcctgttg ggccagacgg   1680
acgtggctgt gtatggagtg gctgtgccag gagtggaggg gaaaagcggc atggcggcca   1740
ttgcagaccc ccacaaccag ctggaccctca actcaatgta ccaggaattg cagaaggttc   1800
ttgcatccta tgcccagccc atcttcctgc gtcttctgcc ccaagtggat acaacaggca   1860
ccttcaagat ccagaagacc cgactacagc gtgaaggctt tgacccccgc cagacctcag   1920
```

```
accggctctt ctttctagac ctgaaacagg gacgctacct accccctggat gagagagtcc   1980 atgcccgcat ctgcgcaggc gacttctcac tctgagcctg gtgagtggga tggccctgga   2040
cttgtgagac cagggagccg gacacccctg ttcaggtgtt tctcctgcct ggccacgtgg   2100
ccagcagcac ctgtgggtgc aggaaactgg aacctgagtg gccgggtgtc cctttcctac   2160
aacccaccat gcacacatct agcctctgcc ttggtctttt tctccatctc tttcctccgt   2220
gcccagcagg agcccacag acacattggc tgctgtgtcc tgcagtggga ccggtgtcta   2280
ggggtccatg ctgcaggctg tgacccgcac tggtgcccac ctcccttccc cattgtgcct   2340
taggttcctc cactgtgcgc cggtgaagca agtgggacc cacatagctg ttgtccctgc   2400
tgagggttgg tagcaaatgc accctcatgt cagctgggag acacatgcag tctcccactg   2460 accccccaatc aactgaagat actgttttgt attattgttt tgagataggg tctcactgtg   2520
gaggccaagc tggcctcagg ctcaccactc tactgcctcc gggcaccagc ctgcagtttg   2580
atgacatgta tgcactattg ttctaagggt cttctgagtc cctgctttcc cctcatgtcc   2640
taaaaccttc cagaactgac tctgatcact tggatgtagc tagtgttggc cctgcccacg   2700
tgtgtcaatt caggggtccc caggcatcat ctctggaggc cctaaccttg gcaaagcttg   2760
gatgtcctca catcacagca ggagacccag gaaggttgct gtggtgtctc ttgggcaccc   2820
ctggcggcag ccgtggacat gcttccctgc tgtgatagcc caaactgttg cctatgacat   2880
ttgaggtcta cccttctggc tgccatggtc cccattgaga tctttggtga ctcacctcag   2940
ccaccaagcc aggcctctgc cttccttcag ctctaagggc atgaagggtg tggacagagc   3000
agccacaggc tgcccacagt cacccacatg caagtgttat ttccttgttt gttttaaaaa   3060
aataaacatg ctgagccttg aaaaaaaaaa aaaaaaa                            3098
```

<210> SEQ ID NO 59
<211> LENGTH: 646
<212> TYPE: PRT
<213> ORGANISM: Rattus norvegicus

<400> SEQUENCE: 59

```
Met Arg Thr Pro Gly Ala Gly Thr Ala Ser Val Ala Ser Leu Gly Leu
 1               5                  10                  15

Leu Trp Leu Leu Gly Leu Pro Trp Thr Trp Ser Ala Ala Ala Ala Phe
            20                  25                  30

Gly Val Tyr Val Gly Ser Gly Trp Arg Phe Leu Arg Ile Val Cys
        35                  40                  45

Lys Thr Ala Arg Arg Asp Leu Phe Gly Leu Ser Val Leu Ile Arg Val
    50                  55                  60

Arg Leu Glu Leu Arg Arg His Arg Arg Ala Gly Asp Thr Ile Pro Arg
65                  70                  75                  80

Ile Phe Gln Ala Val Ala Gln Arg Gln Pro Glu Arg Leu Ala Leu Val
                85                  90                  95

Asp Ala Ser Ser Gly Ile Cys Trp Thr Phe Ala Gln Leu Asp Thr Tyr
            100                 105                 110

Ser Asn Ala Val Ala Asn Leu Phe Leu Gln Leu Gly Phe Ala Pro Gly
        115                 120                 125

Asp Val Val Ala Val Phe Leu Glu Gly Arg Pro Glu Phe Val Gly Leu
    130                 135                 140

Trp Leu Gly Leu Ala Lys Ala Gly Val Val Ala Ala Leu Leu Asn Val
145                 150                 155                 160
```

```
Asn Leu Arg Arg Glu Pro Leu Ala Phe Cys Leu Gly Thr Ser Ala Ala
            165                 170                 175

Lys Ala Leu Ile Tyr Gly Gly Glu Met Ala Ala Val Ala Glu Val
            180                 185                 190

Ser Glu Gln Leu Gly Lys Ser Leu Leu Lys Phe Cys Ser Gly Asp Leu
            195                 200                 205

Gly Pro Glu Ser Val Leu Pro Asp Thr Gln Leu Leu Asp Pro Met Leu
    210                 215                 220

Ala Glu Ala Pro Thr Thr Pro Leu Ala Gln Ala Pro Gly Lys Gly Met
225                 230                 235                 240

Asp Asp Arg Leu Phe Tyr Ile Tyr Thr Ser Gly Thr Thr Gly Leu Pro
            245                 250                 255

Lys Ala Ala Ile Val Val His Ser Arg Tyr Tyr Arg Ile Ala Ala Phe
            260                 265                 270

Gly His His Ser Tyr Ser Met Arg Ala Asn Asp Val Leu Tyr Asp Cys
            275                 280                 285

Leu Pro Leu Tyr His Ser Ala Gly Asn Ile Met Gly Val Gly Gln Cys
    290                 295                 300

Ile Ile Tyr Gly Leu Thr Val Val Leu Arg Lys Lys Phe Ser Ala Ser
305                 310                 315                 320

Arg Phe Trp Asp Asp Cys Val Lys Tyr Asn Cys Thr Val Val Gln Tyr
            325                 330                 335

Ile Gly Glu Ile Cys Arg Tyr Leu Leu Arg Gln Pro Val Arg Asp Val
            340                 345                 350

Glu Arg Arg His Arg Val Arg Leu Ala Val Gly Asn Gly Leu Arg Pro
            355                 360                 365

Ala Ile Trp Glu Glu Phe Thr Gln Gly Phe Gly Val Arg Gln Ile Gly
    370                 375                 380

Glu Phe Tyr Gly Ala Thr Glu Cys Asn Cys Ser Ile Ala Asn Met Asp
385                 390                 395                 400

Gly Lys Val Gly Ser Cys Gly Phe Asn Ser Arg Ile Leu Thr His Val
            405                 410                 415

Tyr Pro Ile Arg Leu Val Lys Val Asn Glu Asp Thr Met Glu Pro Leu
            420                 425                 430

Arg Asp Ser Gln Gly Leu Cys Ile Pro Cys Gln Pro Gly Glu Pro Gly
            435                 440                 445

Leu Leu Val Gly Gln Ile Asn Gln Gln Asp Pro Leu Arg Arg Phe Asp
    450                 455                 460

Gly Tyr Val Ser Asp Ser Ala Thr Asn Lys Lys Ile Ala His Ser Val
465                 470                 475                 480

Phe Arg Lys Gly Asp Ser Ala Tyr Leu Ser Gly Asp Val Leu Val Met
            485                 490                 495

Asp Glu Leu Gly Tyr Met Tyr Phe Arg Asp Arg Ser Gly Asp Thr Phe
            500                 505                 510

Arg Trp Arg Gly Glu Asn Val Ser Thr Thr Glu Val Glu Ala Val Leu
            515                 520                 525

Ser Arg Leu Leu Gly Gln Thr Asp Val Ala Val Tyr Gly Val Ala Val
    530                 535                 540

Pro Gly Val Glu Gly Lys Ser Gly Met Ala Ala Ile Ala Asp Pro His
545                 550                 555                 560

Asn Gln Leu Asp Pro Asn Ser Met Tyr Gln Glu Leu Gln Lys Val Leu
            565                 570                 575

Ala Ser Tyr Ala Gln Pro Ile Phe Leu Arg Leu Leu Pro Gln Val Asp
```

```
                580             585             590
Thr Thr Gly Thr Phe Lys Ile Gln Lys Thr Arg Leu Gln Arg Glu Gly
            595             600             605

Phe Asp Pro Arg Gln Thr Ser Asp Arg Leu Phe Leu Asp Leu Lys
    610             615             620

Gln Gly Arg Tyr Leu Pro Leu Asp Glu Arg Val His Ala Arg Ile Cys
625             630             635             640

Ala Gly Asp Phe Ser Leu
                645

<210> SEQ ID NO 60
<211> LENGTH: 2963
<212> TYPE: DNA
<213> ORGANISM: Rattus norvegicus

<400> SEQUENCE: 60
gacacagtac tgccgatgtt ggacagagga tcgcttaaca gaacgaaatc tcaaaacaaa      60
ttaacaggac ccggttgctt gatttcccaa atcagaaaag gctcgaaatg tctagagggg     120
ctgactgatg cagcggtgac ccggactgga gacagttgga cgcgatcatc tctggtgctt     180
ttgttcaacc ttgaaacctt cgccacagga gacttgcctg agcagagaag caaacgtgga     240
gaaacaaaga gagatctagc gaaaagcctc tgggaccaag aggggaggt gggactctgg      300 gttggcggtg gcacctgctg ccggctatta ataatagggt cgcgatgcgt ttataaggtg     360
tttgattaaa caaagactct atgagagaag aataactagc aacagcccca cgtctgagtc     420
gtcgcctccg accttttca acgtgggttc tttgggccga cgtcgttttg ccgagaacta      480
gatctcacct gaccccagac gctgaaaaca agcgctgtgg catcctgggc cacccaagct     540
gacaagggcg cgcccctga gcacacgagg tgccccacga ggggaggga cccacagccg       600 tcccgcccgc accgcggtgt ccgctgcggg cacctgcagc cgagccgcca cccgcagtcg     660
cagcgcgtcc ggcggccgaa cccggtcgtc agctcgtcag cacctgctct gcttctctcc     720
cgcccgccgc cgcgctgcac gcctcgagcg ctccctcggc cccggcgggg accggggacc     780
ccgcagccac cgccatgctg cctgtgctct acaccggcct ggcggggctg ctgctgctgc     840
ctctgctgct cacctgctgc tgcccctacc tcctccagga cgtgcggttc ttcctgcaac     900
tggccaacat ggcccggcag gtgcgcagct accggcagcg gcgacccgtg cgcaccatcc     960
tgcatgtctt cttggagcaa gcgcgcaaga ccccgcacaa gcccttcctg ctgtttcgcg    1020
acgagacgct tacctacgcc caggtagacc ggcgcagcaa ccaagtagcg cgagcgctgc    1080
atgatcacct gggcctgcgg caggggatt gcgtggccct cttcatgggc aatgagccgg     1140
cctacgtgtg gctctggctg ggactgctca aactgggctg tcccatggcg tgcctcaact    1200
acaacatccg tgccaagtct ctgctacact gctttcagtg ctgcggggcg aaggtgctgc    1260
tggcctcccc agagctacac gaagctgtcg aggaggttct tccaaccctg aaaaggagg     1320 gcgtgtccgt cttctacgta agcagaactt ctaacactaa tggcgtggac acagtactgg    1380
acaaagtaga cggggtgtcg gcggacccca tcccggagtc gtggaggtct gaagtcacgt    1440
tcaccacacc cgcagtctac atatatactt cgggcaccac aggtcttcca aaggctgcaa    1500
ccattaatca ccatcgcctc tggtatggga ccagccttgc cctgaggtcc ggaattaagg    1560
ctcatgacgt catctacacc accatgcccc tgtaccacag cgcggcgctc atgattggcc    1620
tccacggatg cattgtggtt ggggctacat ttgctttgcg gagcaaattt tcagccagcc    1680
agttttggga cgactgcagg aaatacaacg ccactgtcat tcagtacatc ggtgaactgc    1740
```

```
ttcggtacct ctgcaacacg ccccagaaac caaatgaccg ggaccacaaa gtgaaaatag    1800
cactaggaaa tggcttacga ggagatgtgt ggagagagtt catcaagaga tttggggaca    1860
ttcacattta tgagttctac gcttccactg aaggcaacat tggatttatg aactatccaa    1920
gaaaaatcgg agctgttgga agagaaaatt acctacaaaa aaaagttgta aggcacgagc    1980
tgatcaagta tgacgtggag aaggatgagc ctgtccgtga tgcaaatgga tattgcatca    2040
aagtccccaa aggagaggtt ggactcttga tttgcaaaat cacagagctc acaccatttt    2100
ttggctatgc tggaggaaag acccagacag agaagaaaaa gctcagagat gttttttaaga   2160 aaggagacgt ctacttcaac agtggcgatc tcctgatgat cgaccgtgaa aatttcatct    2220
attttcacga cagagttgga gacaccttcc ggtggaaagg agagaatgta gctaccacgg    2280
aagtcgctga cattgtggga ctggtagatt tgttgaaga agtgaatgtt tacggtgtgc     2340
ccgtgccagg tcatgaaggt cgcatcggga tggcctcgat caagatgaaa gaaaactacg    2400
agttcaatgg aaagaaactc tttcagcaca tctcggagta cctgcccagt tactcgaggc    2460
ctcggttcct gagaatacaa gataccattg agatcaccgg gacttttaaa caccgcaaag    2520
tgaccctgat ggaagagggc tttaaccccct cagtcatcaa agataccttg tatttcatgg    2580
atgacacaga aaaacatac gtgcccatga ctgaggacat ttataatgcc ataattgata    2640
agactctgaa gctctgaatg ttgcctggct cctaacactt ccagaaagaa acacaatagg    2700
cctagcatag ccccttcaca tgtgtaatcc aactttaact tgattaaagg ttataggtgt    2760
gatttttcct aggaaattat tcatttaaag gacaattgtt tgtttgtttg tttgttttttt   2820 attaattaca ccagaacgtt tgcaagtaaa aagatttaaa gtcacttatt tttcaatgtg    2880
cacctgccat ttgtccttgc aaacttagct tcttggagag agggccttat ttttttaaag    2940
acataataaa ctatgtaaac act                                           2963
```

<210> SEQ ID NO 61
<211> LENGTH: 620
<212> TYPE: PRT
<213> ORGANISM: Rattus norvegicus

<400> SEQUENCE: 61

```
Met Leu Pro Val Leu Tyr Thr Gly Leu Ala Gly Leu Leu Leu Leu Pro
 1               5                  10                  15

Leu Leu Leu Thr Cys Cys Cys Pro Tyr Leu Leu Gln Asp Val Arg Phe
            20                  25                  30

Phe Leu Gln Leu Ala Asn Met Ala Arg Gln Val Arg Ser Tyr Arg Gln
        35                  40                  45

Arg Arg Pro Val Arg Thr Ile Leu His Val Phe Leu Glu Gln Ala Arg
    50                  55                  60

Lys Thr Pro His Lys Pro Phe Leu Leu Phe Arg Asp Glu Thr Leu Thr
65                  70                  75                  80

Tyr Ala Gln Val Asp Arg Arg Ser Asn Gln Val Ala Arg Ala Leu His
                85                  90                  95

Asp His Leu Gly Leu Arg Gln Gly Asp Cys Val Ala Leu Phe Met Gly
            100                 105                 110

Asn Glu Pro Ala Tyr Val Trp Leu Trp Leu Gly Leu Leu Lys Leu Gly
        115                 120                 125

Cys Pro Met Ala Cys Leu Asn Tyr Asn Ile Arg Ala Lys Ser Leu Leu
    130                 135                 140

His Cys Phe Gln Cys Cys Gly Ala Lys Val Leu Leu Ala Ser Pro Glu
```

```
                145                 150                 155                 160

Leu His Glu Ala Val Glu Val Leu Pro Thr Leu Lys Lys Glu Gly
                165                 170                 175

Val Ser Val Phe Tyr Val Ser Arg Thr Ser Asn Thr Asn Gly Val Asp
                180                 185                 190

Thr Val Leu Asp Lys Val Asp Gly Val Ser Ala Asp Pro Ile Pro Glu
                195                 200                 205

Ser Trp Arg Ser Glu Val Thr Phe Thr Thr Pro Ala Val Tyr Ile Tyr
    210                 215                 220

Thr Ser Gly Thr Thr Gly Leu Pro Lys Ala Ala Thr Ile Asn His His
225                 230                 235                 240

Arg Leu Trp Tyr Gly Thr Ser Leu Ala Leu Arg Ser Gly Ile Lys Ala
                245                 250                 255

His Asp Val Ile Tyr Thr Thr Met Pro Leu Tyr His Ser Ala Ala Leu
                260                 265                 270

Met Ile Gly Leu His Gly Cys Ile Val Gly Ala Thr Phe Ala Leu
    275                 280                 285

Arg Ser Lys Phe Ser Ala Ser Gln Phe Trp Asp Cys Arg Lys Tyr
    290                 295                 300

Asn Ala Thr Val Ile Gln Tyr Ile Gly Glu Leu Leu Arg Tyr Leu Cys
305                 310                 315                 320

Asn Thr Pro Gln Lys Pro Asn Asp Arg Asp His Lys Val Lys Ile Ala
                325                 330                 335

Leu Gly Asn Gly Leu Arg Gly Asp Val Trp Arg Glu Phe Ile Lys Arg
                340                 345                 350

Phe Gly Asp Ile His Ile Tyr Glu Phe Tyr Ala Ser Thr Glu Gly Asn
                355                 360                 365

Ile Gly Phe Met Asn Tyr Pro Arg Lys Ile Gly Ala Val Gly Arg Glu
    370                 375                 380

Asn Tyr Leu Gln Lys Lys Val Val Arg His Glu Leu Ile Lys Tyr Asp
385                 390                 395                 400

Val Glu Lys Asp Glu Pro Val Arg Asp Ala Asn Gly Tyr Cys Ile Lys
                405                 410                 415

Val Pro Lys Gly Glu Val Gly Leu Leu Ile Cys Lys Ile Thr Glu Leu
                420                 425                 430

Thr Pro Phe Phe Gly Tyr Ala Gly Gly Lys Thr Gln Thr Glu Lys Lys
                435                 440                 445

Lys Leu Arg Asp Val Phe Lys Lys Gly Asp Val Tyr Phe Asn Ser Gly
                450                 455                 460

Asp Leu Leu Met Ile Asp Arg Glu Asn Phe Ile Tyr Phe His Asp Arg
465                 470                 475                 480

Val Gly Asp Thr Phe Arg Trp Lys Gly Glu Asn Val Ala Thr Thr Glu
                485                 490                 495

Val Ala Asp Ile Val Gly Leu Val Asp Phe Val Glu Val Asn Val
                500                 505                 510

Tyr Gly Val Pro Val Pro Gly His Glu Gly Arg Ile Gly Met Ala Ser
                515                 520                 525

Ile Lys Met Lys Glu Asn Tyr Glu Phe Asn Gly Lys Lys Leu Phe Gln
    530                 535                 540

His Ile Ser Glu Tyr Leu Pro Ser Tyr Ser Arg Pro Arg Phe Leu Arg
545                 550                 555                 560

Ile Gln Asp Thr Ile Glu Ile Thr Gly Thr Phe Lys His Arg Lys Val
                565                 570                 575
```

Thr Leu Met Glu Glu Gly Phe Asn Pro Ser Val Ile Lys Asp Thr Leu
        580                 585                 590

Tyr Phe Met Asp Asp Thr Glu Lys Thr Tyr Val Pro Met Thr Glu Asp
        595                 600                 605

Ile Tyr Asn Ala Ile Ile Asp Lys Thr Leu Lys Leu
        610                 615                 620

<210> SEQ ID NO 62
<211> LENGTH: 1350
<212> TYPE: DNA
<213> ORGANISM: Rattus norvegicus

<400> SEQUENCE: 62

```
gatcagctct tctatatcta cacgtcgggc accacggggc tacccaaagc tgccattgtg      60
gtgcacagca ggtattaccg aatggctgcc ctggtgtact atggattccg catgcggcct     120
gatgacattg tctatgactg cctcccctc taccactcag caggaaacat tgtgggatt      180
ggccagtgcg tactccacgg catgactgtg gtgatccgga gaagttttc agcctcccgg     240
ttctgggatg actgtatcaa gtacaactgc acaattgtac agtacattgg tgagctttgc     300
cgctacctcc tgaaccagcc accccgtgag gctgagtctc ggcacaaggt gcgcatggca     360
ctgggcaacg gtctccggca gtccatctgg accgacttct ccagccgttt ccacattccc     420
aaggtggccg agttctacgg ggccaccgag tgcaactgta gcttgggcaa ctttgacagc     480
caggtggggg cctgtggctt caatagccgc atcctgtcct ttgtgtaccc catccgcttg     540
gtacgagtca atgaggatac catggaactg atccggggac ccgatggcgt ctgcattccc     600
tgtcaaccag gccagccagg ccagctggtg ggtcgcatca tccagcagga ccccctacgc     660
cgttttgatg gctacctcaa ccagggtgcc aacaacaaga agattgctag tgatgtcttc     720
aagaaagggg accaagccta cctcactggt gacgtgctgg tgatggatga gctgggctac     780
ctgtacttcc gagaccgcac aggggacacg ttccgctgga agggggagaa tgtgtctacc     840
actgaagtgg agggcacact cagccgcctg cttcagatgg cagatgtggc tgtttatggt     900
gttgaggtgc caggagctga gggccgagca ggaatggctg ctgtggcaag ccccactagc     960
aactgtgacc tggagagctt tgcacagacc ttgaaaaagg agctgcccct gtacgcccgc    1020
cccatcttcc tccgcttctt gcctgagctg cacaaaacag gaaccttcaa gttccagaag    1080
acagagttgc ggaaggaggg ctttgacccg tctgttgtga agacccact cttctatttg    1140
gatgcccgga caggctgcta tgttgcactg gaccaagagg cctatacccg catccaggca    1200
ggcgaggaga agctgtgatt tcccccacat ccctctgagg gccagaggat gctggattca    1260
gagccccagc ttccactcca gaagggtgtct gggcaaggcc agaccaaagc tagcagggcc    1320
cgcaccttca ccctaggtgc tgatccccct                                     1350
```

<210> SEQ ID NO 63
<211> LENGTH: 405
<212> TYPE: PRT
<213> ORGANISM: Rattus norvegicus

<400> SEQUENCE: 63

Asp Gln Leu Phe Tyr Ile Tyr Thr Ser Gly Thr Thr Gly Leu Pro Lys
 1               5                  10                  15

Ala Ala Ile Val Val His Ser Arg Tyr Tyr Arg Met Ala Ala Leu Val
            20                  25                  30

Tyr Tyr Gly Phe Arg Met Arg Pro Asp Asp Ile Val Tyr Asp Cys Leu

```
                35                  40                  45
Pro Leu Tyr His Ser Ala Gly Asn Ile Val Gly Ile Gly Gln Cys Val
 50                  55                  60

Leu His Gly Met Thr Val Val Ile Arg Lys Lys Phe Ser Ala Ser Arg
 65                  70                  75                  80

Phe Trp Asp Asp Cys Ile Lys Tyr Asn Cys Thr Ile Val Gln Tyr Ile
                 85                  90                  95

Gly Glu Leu Cys Arg Tyr Leu Leu Asn Gln Pro Pro Arg Glu Ala Glu
                100                 105                 110

Ser Arg His Lys Val Arg Met Ala Leu Gly Asn Gly Leu Arg Gln Ser
                115                 120                 125

Ile Trp Thr Asp Phe Ser Ser Arg Phe His Ile Pro Lys Val Ala Glu
    130                 135                 140

Phe Tyr Gly Ala Thr Glu Cys Asn Cys Ser Leu Gly Asn Phe Asp Ser
145                 150                 155                 160

Gln Val Gly Ala Cys Gly Phe Asn Ser Arg Ile Leu Ser Phe Val Tyr
                165                 170                 175

Pro Ile Arg Leu Val Arg Val Asn Glu Asp Thr Met Glu Leu Ile Arg
                180                 185                 190

Gly Pro Asp Gly Val Cys Ile Pro Cys Gln Pro Gly Gln Pro Gly Gln
                195                 200                 205

Leu Val Gly Arg Ile Ile Gln Gln Asp Pro Leu Arg Arg Phe Asp Gly
    210                 215                 220

Tyr Leu Asn Gln Gly Ala Asn Asn Lys Lys Ile Ala Ser Asp Val Phe
225                 230                 235                 240

Lys Lys Gly Asp Gln Ala Tyr Leu Thr Gly Asp Val Leu Val Met Asp
                245                 250                 255

Glu Leu Gly Tyr Leu Tyr Phe Arg Asp Arg Thr Gly Asp Thr Phe Arg
                260                 265                 270

Trp Lys Gly Glu Asn Val Ser Thr Thr Glu Val Glu Gly Thr Leu Ser
                275                 280                 285

Arg Leu Leu Gln Met Ala Asp Val Ala Val Tyr Gly Val Glu Val Pro
    290                 295                 300

Gly Ala Glu Gly Arg Ala Gly Met Ala Ala Val Ala Ser Pro Thr Ser
305                 310                 315                 320

Asn Cys Asp Leu Glu Ser Phe Ala Gln Thr Leu Lys Lys Glu Leu Pro
                325                 330                 335

Leu Tyr Ala Arg Pro Ile Phe Leu Arg Phe Leu Pro Glu Leu His Lys
                340                 345                 350

Thr Gly Thr Phe Lys Phe Gln Lys Thr Glu Leu Arg Lys Glu Gly Phe
                355                 360                 365

Asp Pro Ser Val Val Lys Asp Pro Leu Phe Tyr Leu Asp Ala Arg Thr
    370                 375                 380

Gly Cys Tyr Val Ala Leu Asp Gln Glu Ala Tyr Thr Arg Ile Gln Ala
385                 390                 395                 400

Gly Glu Glu Lys Leu
                405

<210> SEQ ID NO 64
<211> LENGTH: 3217
<212> TYPE: DNA
<213> ORGANISM: Mus musculus

<400> SEQUENCE: 64
```

-continued

| | |
|---|---|
| atgcgggctc ctggagcagg aacagcctct gtggcctcac tggcgctgct ttggtttctg | 60 |
| ggacttccgt ggacctggag cgcggcggcg gcgttctgtg tgtacgtggg tggcggcggc | 120 |
| tggcgctttc tgcgtatcgt ctgcaagacg gcgaggcgag acctctttgg cctctctgtt | 180 |
| ctgattcgtg ttcggctaga gctgcgacga caccggcgag caggagacac gatcccgtgc | 240 |
| atcttccagg ctgtggcccg cgacaaccca gagcgcctgg cactggtgga cgccagtagt | 300 |
| ggtatatgct ggaccttcgc acagctggac acctactcca atgctgtagc caacctgttc | 360 |
| cgccagctgg gctttgcacc aggcgatgtg gtggctgtgt tcctggaggg ccggccggag | 420 |
| ttcgtgggac tgtggctggg cctggccaag gccggtgtgg tggctgctct tctcaatgtc | 480 |
| aacctgaggc gggagcccct ggccttctgc ctgggcacat cagctgccaa ggccctcatt | 540 |
| tatggcgggg agatggcagc ggcggtggcg gaggtgagcg agcagctggg gaagagcctc | 600 |
| ctcaagttct gctctggaga tctgggggcct gagagcatcc tgcctgacac gcagctcctg | 660 |
| gaccccatgc ttgctgaggc gcccaccaca cccctggcac aagcccccagg caagggcatg | 720 |
| gatgatcggc tgttttacat ctatacttct gggaccaccg ggcttcctaa ggctgccatt | 780 |
| gtggtgcaca gcaggtacta ccgcattgct gcctttggcc accattccta cagcatgcgt | 840 |
| gccgccgatg tgctctatga ctgcctgcca ctctaccact ctgcagggaa catcatgggt | 900 |
| gtggggcagt gcgtcatcta cggggttgacg gtggtactgc gcaagaagtt ctccgccagc | 960 |
| cgcttctggg atgactgtgt caagtacaat gcacggtag tggatgacat aggtgaaatc | 1020 |
| tgccgctacc tgctgaggca gccggttcgc gacgtggagc agcgacaccg cgtgcgcctg | 1080 |
| gccgtgggta atgggctgcg gccagccatc tgggaggagt tcacgcagcg cttcggtgtg | 1140 |
| ccacagatcg gcgagttcta cggcgctacc gagtgcaact gcagcattgc caacatggac | 1200 |
| ggcaaggtcg gctcctgcgg cttcaacagc cgtatcctca cgcatgtgta ccccatccgt | 1260 |
| ctggtcaagt caatgagga cacgatggag ccactgcggg actccagggg cctctgcatc | 1320 |
| ccgtgccagc ccgggggaacc cggccttctc gtgggccaga tcaaccagca ggaccctctg | 1380 |
| cggcgtttcg atggttatgt tagtgacagt gccaccaaca agaagattgc ccacagcgtt | 1440 |
| ttccgaaagg gcgatagcgc ctacctctca ggtgacgtgc tagtgatgga cgagctgggc | 1500 |
| tacatgtatt tccgtgaccg cagcggggac accttccgct ggcgcgggga gaacgtgtcc | 1560 |
| accacggagg tggaagccgt gctgagccgc ctactgggcc agacggacgt ggctgtgtat | 1620 |
| ggggtggctg tgccaggagt ggaggggaaa gctggcatgg cagccatcgc agatccccac | 1680 |
| agccagttgg accctaactc aatgtaccag gaattacaga aggttcttgc atcctatgct | 1740 |
| cggcccatct tcctgcgtct tctgcccag gtggatacca caggcaccttt caagatccag | 1800 |
| aagacccggc tgcagcgtga aggctttgac ccccgtcaga cctcagacag gctcttcttt | 1860 |
| ctagacctga agtccggcac gaggtatcta cccctggatg agagagtcca tgcccgcatt | 1920 |
| tgcgcaggcg acttctcact ctgagcctgg agagtgggct gggcctggac tcctgagacc | 1980 |
| tgggagcctg acacccctct tcgggtgctt ctcctgcctg ccacatggaa cagcagcacc | 2040 |
| tgtgagagta ggaaaatgga acctgagtgg ctgggacccc tctcctactt cccactatgc | 2100 |
| atccattttg cctctgcctt gatcttttc tccatctctt ttctccctac ccagcaggag | 2160 |
| ccccacaaac acatgttggc tgctgtgtcc tgcagttgga ccagtgtcca ggggtacagg | 2220 |
| cttcaggctg tgacccacac tggtacccac ctccctttcc tattttgcct taggttcatc | 2280 |
| cacggttccc ctgtggagca agtgggggcc cacatagctg ctgtccctgc tgagggttgg | 2340 |
| tagcaatcac accctcatgt cagctgggag acacgcgcag tctcccactg accccccaatc | 2400 |

-continued

```
aactgaaaat attgttttga ctacttttg tttttttgtt ttttgtttt ttttttttt    2460 cgagacagag tttctctgta tagccctggc tgtcctggaa ctcactttgt agaccaggct    2520
ggcctcgaac tcaaaaatcc tcctgactct gcctctgctt cccaagtgct gggattaaag    2580
acgtgcgcca ccaccgcctg gctgttttgt attttttgttt tgttttgacg atagggtctc    2640
actgtggagg ccaagctggc ctcagactcc caccccatt gcctctgggc accattctat    2700
attctcagac tgatgacaat gcactagtgt ccctaggagt cttgagtctg cactttcccc    2760
tcatagcctc aagcttccag aactgactct gatcacttgg atgtggctag tgttggctct    2820
acccacatgt gtcaattcag ggtccccag gcatagtctc tggaagccct cacccggaaa    2880
aagcttggag agaccagga aggttgttgt gttctcttgg gcaccccctg gtggcagtcc    2940
tgggcatgct tccgcactgt actggtgcat atagcccaga cctatgacat tgaggtcta    3000 ccttctggc tcctgtggtc cccattgaga tccttggtga ctcacctcag tcaccaagca    3060
gagcctctgc ctgccttcat cttcaaggtc atgaaggatg tggacagagc agctacaggc    3120
tgccagcagt caaccacatg agagtgttac ttccttgttg gttttaaaa aataaatgtg    3180 ctgagcctcg aaaaaaaaaa aaaaaaaaaa aaaaaaa                              3217
```

<210> SEQ ID NO 65
<211> LENGTH: 646
<212> TYPE: PRT
<213> ORGANISM: Mus musculus

<400> SEQUENCE: 65

```
Met Arg Ala Pro Gly Ala Gly Thr Ala Ser Val Ala Ser Leu Ala Leu
 1               5                  10                  15

Leu Trp Phe Leu Gly Leu Pro Trp Thr Trp Ser Ala Ala Ala Ala Phe
            20                  25                  30

Cys Val Tyr Val Gly Gly Gly Trp Arg Phe Leu Arg Ile Val Cys
        35                  40                  45

Lys Thr Ala Arg Arg Asp Leu Phe Gly Leu Ser Val Leu Ile Arg Val
    50                  55                  60

Arg Leu Glu Leu Arg Arg His Arg Arg Ala Gly Asp Thr Ile Pro Cys
65                  70                  75                  80

Ile Phe Gln Ala Val Ala Arg Arg Gln Pro Glu Arg Leu Ala Leu Val
                85                  90                  95

Asp Ala Ser Ser Gly Ile Cys Trp Thr Phe Ala Gln Leu Asp Thr Tyr
            100                 105                 110

Ser Asn Ala Val Ala Asn Leu Phe Arg Gln Leu Gly Phe Ala Pro Gly
        115                 120                 125

Asp Val Val Ala Val Phe Leu Glu Gly Arg Pro Glu Phe Val Gly Leu
    130                 135                 140

Trp Leu Gly Leu Ala Lys Ala Gly Val Val Ala Ala Leu Leu Asn Val
145                 150                 155                 160

Asn Leu Arg Arg Glu Pro Leu Ala Phe Cys Leu Gly Thr Ser Ala Ala
                165                 170                 175

Lys Ala Leu Ile Tyr Gly Gly Glu Met Ala Ala Val Ala Glu Val
            180                 185                 190

Ser Glu Gln Leu Gly Lys Ser Leu Leu Lys Phe Cys Ser Gly Asp Leu
        195                 200                 205

Gly Pro Glu Ser Ile Leu Pro Asp Thr Gln Leu Leu Asp Pro Met Leu
    210                 215                 220
```

```
Ala Glu Ala Pro Thr Thr Pro Leu Ala Gln Ala Pro Gly Lys Gly Met
225                 230                 235                 240

Asp Asp Arg Leu Phe Tyr Ile Tyr Thr Ser Gly Thr Thr Gly Leu Pro
                245                 250                 255

Lys Ala Ala Ile Val Val His Ser Arg Tyr Tyr Arg Ile Ala Ala Phe
                260                 265                 270

Gly His His Ser Tyr Ser Met Arg Ala Ala Asp Val Leu Tyr Asp Cys
                275                 280                 285

Leu Pro Leu Tyr His Ser Ala Gly Asn Ile Met Gly Val Gly Gln Cys
                290                 295                 300

Val Ile Tyr Gly Leu Thr Val Leu Arg Lys Lys Phe Ser Ala Ser
305                 310                 315                 320

Arg Phe Trp Asp Asp Cys Val Lys Tyr Asn Cys Thr Val Val Gln Tyr
                325                 330                 335

Ile Gly Glu Ile Cys Arg Tyr Leu Leu Arg Gln Pro Val Arg Asp Val
                340                 345                 350

Glu Gln Arg His Arg Val Arg Leu Ala Val Gly Asn Gly Leu Arg Pro
                355                 360                 365

Ala Ile Trp Glu Glu Phe Thr Gln Arg Phe Gly Val Pro Gln Ile Gly
370                 375                 380

Glu Phe Tyr Gly Ala Thr Glu Cys Asn Cys Ser Ile Ala Asn Met Asp
385                 390                 395                 400

Gly Lys Val Gly Ser Cys Gly Phe Asn Ser Arg Ile Leu Thr His Val
                405                 410                 415

Tyr Pro Ile Arg Leu Val Lys Val Asn Glu Asp Thr Met Glu Pro Leu
                420                 425                 430

Arg Asp Ser Glu Gly Leu Cys Ile Pro Cys Gln Pro Gly Glu Pro Gly
                435                 440                 445

Leu Leu Val Gly Gln Ile Asn Gln Gln Asp Pro Leu Arg Arg Phe Asp
                450                 455                 460

Gly Tyr Val Ser Asp Ser Ala Thr Asn Lys Lys Ile Ala His Ser Val
465                 470                 475                 480

Phe Arg Lys Gly Asp Ser Ala Tyr Leu Ser Gly Asp Val Leu Val Met
                485                 490                 495

Asp Glu Leu Gly Tyr Met Tyr Phe Arg Asp Arg Ser Gly Asp Thr Phe
                500                 505                 510

Arg Trp Arg Gly Glu Asn Val Ser Thr Thr Glu Val Glu Ala Val Leu
                515                 520                 525

Ser Arg Leu Leu Gly Gln Thr Asp Val Ala Val Tyr Gly Val Ala Val
                530                 535                 540

Pro Gly Val Glu Gly Lys Ala Gly Met Ala Ala Ile Ala Asp Pro His
545                 550                 555                 560

Ser Gln Leu Asp Pro Asn Ser Met Tyr Gln Glu Leu Gln Lys Val Leu
                565                 570                 575

Ala Ser Tyr Ala Arg Pro Ile Phe Leu Arg Leu Leu Pro Gln Val Asp
                580                 585                 590

Thr Thr Gly Thr Phe Lys Ile Gln Lys Thr Arg Leu Gln Arg Glu Gly
                595                 600                 605

Phe Asp Pro Arg Gln Thr Ser Asp Arg Leu Phe Leu Asp Leu Lys
                610                 615                 620

Gln Gly Arg Tyr Val Pro Leu Asp Glu Arg Val His Ala Arg Ile Cys
625                 630                 635                 640

Ala Gly Asp Phe Ser Leu
```

645

<210> SEQ ID NO 66
<211> LENGTH: 2338
<212> TYPE: DNA
<213> ORGANISM: Mus musculus

<400> SEQUENCE: 66

| | | | | | |
|---|---|---|---|---|---|
| gggcggaggc | cgagcccagt | cgccagctcc | tgctctgctc | ctctcccgcc | tgccgccgcg | 60 |
| ctgcacgcct | cgagcactcc | ctcggccccg | gcggggaccg | ggaccccgc | agctaccgcc | 120 |
| atgctgccag | tgctctacac | cggcctggcg | gggctgctgc | tgctgcctct | gctgctcacc | 180 |
| tgctgctgcc | cctacctcct | ccaagatgtg | cggtacttcc | tgcggctggc | caacatggcc | 240 |
| cggcgggtgc | gcagctaccg | gcagcggcga | cccgtgcgta | ccatcctgcg | ggccttcctg | 300 |
| gaacaagcgc | gcaagacccc | acacaagccc | ttcctgctgt | tccgagacga | gacgctcacc | 360 |
| tacgcccagg | tggaccggcg | cagcaaccaa | gtggcgcggg | cgctgcacga | tcaactgggc | 420 |
| ctacgacagg | gggattgcgt | agccctcttc | atgggcaatg | agccggccta | cgtgtggatc | 480 |
| tggctgggac | tgctcaaact | gggctgtccc | atggcgtgcc | tcaactacaa | cattcgtgcc | 540 |
| aagtctctgc | tgcactgctt | tcaatgctgc | ggggcgaagg | tgctgctggc | ctccccagat | 600 |
| ctacaagaag | ctgtggagga | ggttcttcca | accctgaaaa | aggatgccgt | gtccgtcttt | 660 |
| tacgtaagca | gaacttctaa | cacaaatggt | gtggacacaa | tactgacaa | agtagacgga | 720 |
| gtgtcggcgg | aacccacccc | ggagtcgtgg | aggtctgaag | tcactttac | cacgccagca | 780 |
| gtatacattt | atacttcggg | aaccacaggt | cttccaaaaa | gcggaaccat | caatcatcat | 840 |
| cgcctaaggt | atgggacaag | ccttgctatg | tcgagtggga | atcacggcca | aggatgtcat | 900 |
| ctataccaac | aatgcccctg | ttccaacagt | gcaacgctca | agatcggcct | tcacggatgc | 960 |
| atcctgggtt | ggggctactt | taaccttggc | ggggcaaatt | ctcaagcaag | ccaattttgg | 1020 |
| gaacgactgg | caggaaatac | aacgtcaacg | gtcattcagt | acattggtga | actgcttcgg | 1080 |
| tacctgtgca | acacaccgca | gaaaccaaat | gaccgggacc | acaaagtgaa | aaagccctg | 1140 |
| ggaaatggct | tacgaggaga | tgtgtggaga | gagttcatca | agagatttgg | ggacatccac | 1200 |
| gtgtatgagt | ctacgcatc | cactgaaggc | aacattggat | ttgtgaacta | tccaaggaaa | 1260 |
| atcggtgctg | tcgggagagc | aaaactaccta | caaagaaaag | ttgcaaggta | tgagctgatc | 1320 |
| aagtatgacg | tggagaagga | cgagccggtc | cgtgacgcaa | atggatattg | catcaaagtc | 1380 |
| cccaaaggtg | aggttggact | cttggtttgc | aaaatcacac | agctcacacc | atttattggc | 1440 |
| tatgctggag | gaaagaccca | gacagagaag | aaaaaactca | gagatgtctt | taagaaaggc | 1500 |
| gacatctact | tcaacagcgg | agacctcctg | atgatcgacc | gtgagaactt | cgtctacttt | 1560 |
| cacgacaggg | ttggagatac | tttccggtgg | aaaggagaga | acgtagctac | cacagaagtc | 1620 |
| gctgacatcg | tgggactggt | agattttgtt | gaagaagtga | atgtgtatgg | cgtgcctgtg | 1680 |
| ccaggtcatg | agggtcgaat | tgggatggcc | tccctcaaga | tcaaagaaaa | ctacgagttc | 1740 |
| aatggaaaga | aactctttca | acacatcgcg | gagtacctgc | ccagttacgc | gaggcctcgg | 1800 |
| ttcctgagga | tacaagatac | cattgagatc | actgggactt | ttaaacaccg | caaagtgacc | 1860 |
| ctgatggaag | agggcttcaa | tcccacagtc | atcaaagata | ccttgtattt | catggatgat | 1920 |
| gcagagaaaa | catttgtgcc | catgactgag | aacatttata | atgccataat | tgataaaact | 1980 |
| ctgaagctct | gaatattccc | tggtggttta | gctcatgaca | tttccagaaa | gaaactcgat | 2040 |
| agacctcgca | gagccacttc | atacgtagaa | tccaacttta | acttgattga | agactataag | 2100 |

```
gtgcgatttt attttagga aattattcat taaaaggata gttttttt tttttttaa      2160 ttacacctga acctttgcaa gtaaaaagat ttagagacaa ttattttca atgtgcacct      2220 gccatttgtc cttgcaaact aagcttcttg gagagagggc cttattttt taaagacata      2280 ataaactata ttaacactaa aaaaaaaaaa aaaaaaaaaa aaaaaaaaaa aaaaaaa       2338
```

<210> SEQ ID NO 67
<211> LENGTH: 623
<212> TYPE: PRT
<213> ORGANISM: Mus musculus

<400> SEQUENCE: 67

```
Met Leu Pro Val Leu Tyr Thr Gly Leu Ala Gly Leu Leu Leu Pro
 1               5                  10                  15

Leu Leu Leu Thr Cys Cys Cys Pro Tyr Leu Leu Gln Asp Val Arg Tyr
                20                  25                  30

Phe Leu Arg Leu Ala Asn Met Ala Arg Arg Val Arg Ser Tyr Arg Gln
            35                  40                  45

Arg Arg Pro Val Arg Thr Ile Leu Arg Ala Phe Leu Glu Gln Ala Arg
    50                  55                  60

Lys Thr Pro His Lys Pro Phe Leu Leu Phe Arg Asp Glu Thr Leu Thr
65                  70                  75                  80

Tyr Ala Gln Val Asp Arg Arg Ser Asn Gln Val Ala Arg Ala Leu His
                85                  90                  95

Asp Gln Leu Gly Leu Arg Gln Gly Asp Cys Val Ala Leu Phe Met Gly
            100                 105                 110

Asn Glu Pro Ala Tyr Val Trp Ile Trp Leu Gly Leu Leu Lys Leu Gly
        115                 120                 125

Cys Pro Met Ala Cys Leu Asn Tyr Asn Ile Arg Ala Lys Ser Leu Leu
    130                 135                 140

His Cys Phe Gln Cys Cys Gly Ala Lys Val Leu Leu Ala Ser Pro Asp
145                 150                 155                 160

Leu Gln Glu Ala Val Glu Glu Val Leu Pro Thr Leu Lys Lys Asp Ala
                165                 170                 175

Val Ser Val Phe Tyr Val Ser Arg Thr Ser Asn Thr Asn Gly Val Asp
            180                 185                 190

Thr Ile Leu Asp Lys Val Asp Gly Val Ser Ala Glu Pro Thr Pro Glu
        195                 200                 205

Ser Trp Arg Ser Glu Val Thr Phe Thr Thr Pro Ala Val Tyr Ile Tyr
    210                 215                 220

Thr Ser Gly Thr Thr Gly Leu Pro Lys Ser Gly Thr Ile Asn His His
225                 230                 235                 240

Arg Leu Arg Tyr Gly Thr Ser Leu Ala Met Ser Ser Gly Asn His Gly
                245                 250                 255

Gln Gly Cys His Leu Tyr Gln Gln Cys Pro Cys Ser Asn Ser Ala Thr
            260                 265                 270

Leu Lys Ile Gly Leu His Gly Cys Ile Leu Gly Trp Gly Tyr Phe Asn
        275                 280                 285

Leu Gly Gly Ala Asn Ser Gln Ala Ser Gln Phe Trp Glu Arg Leu Ala
    290                 295                 300

Gly Asn Thr Thr Ser Thr Val Ile Gln Tyr Ile Gly Glu Leu Leu Arg
305                 310                 315                 320

Tyr Leu Cys Asn Thr Pro Gln Lys Pro Asn Asp Arg Asp His Lys Val
                325                 330                 335
```

-continued

```
Lys Lys Ala Leu Gly Asn Gly Leu Arg Gly Asp Val Trp Arg Glu Phe
            340                 345                 350
Ile Lys Arg Phe Gly Asp Ile His Val Tyr Glu Phe Tyr Ala Ser Thr
        355                 360                 365
Glu Gly Asn Ile Gly Phe Val Asn Tyr Pro Arg Lys Ile Gly Ala Val
    370                 375                 380
Gly Arg Ala Asn Tyr Leu Gln Arg Lys Val Ala Arg Tyr Glu Leu Ile
385                 390                 395                 400
Lys Tyr Asp Val Glu Lys Asp Glu Pro Val Arg Asp Ala Asn Gly Tyr
                405                 410                 415
Cys Ile Lys Val Pro Lys Gly Val Gly Leu Leu Val Cys Lys Ile
            420                 425                 430
Thr Gln Leu Thr Pro Phe Ile Gly Tyr Ala Gly Gly Lys Thr Gln Thr
        435                 440                 445
Glu Lys Lys Lys Leu Arg Asp Val Phe Lys Lys Gly Asp Ile Tyr Phe
    450                 455                 460
Asn Ser Gly Asp Leu Leu Met Ile Asp Arg Glu Asn Phe Val Tyr Phe
465                 470                 475                 480
His Asp Arg Val Gly Asp Thr Phe Arg Trp Lys Gly Glu Asn Val Ala
                485                 490                 495
Thr Thr Glu Val Ala Asp Ile Val Gly Leu Val Asp Phe Val Glu Glu
            500                 505                 510
Val Asn Val Tyr Gly Val Pro Val Pro Gly His Glu Gly Arg Ile Gly
        515                 520                 525
Met Ala Ser Leu Lys Ile Lys Glu Asn Tyr Glu Phe Asn Gly Lys Lys
    530                 535                 540
Leu Phe Gln His Ile Ala Glu Tyr Leu Pro Ser Tyr Ala Arg Pro Arg
545                 550                 555                 560
Phe Leu Arg Ile Gln Asp Thr Ile Glu Ile Thr Gly Thr Phe Lys His
                565                 570                 575
Arg Lys Val Thr Leu Met Glu Glu Gly Phe Asn Pro Thr Val Ile Lys
            580                 585                 590
Asp Thr Leu Tyr Phe Met Asp Asp Ala Glu Lys Thr Phe Val Pro Met
        595                 600                 605
Thr Glu Asn Ile Tyr Asn Ala Ile Ile Asp Lys Thr Leu Lys Leu
    610                 615                 620
```

<210> SEQ ID NO 68
<211> LENGTH: 1998
<212> TYPE: DNA
<213> ORGANISM: Mus musculus

<400> SEQUENCE: 68

| | | | | | | |
|---|---|---|---|---|---|---|
| gaaagctctg | agagcgggtg | cagtctggcc | tggcgtctcg | cgtacctggc | ccgggagcag | 60 |
| ccgacacaca | ccttcctcat | ccacggcgcg | cagcgcttta | gctacgcgga | ggctgagcgc | 120 |
| gagagcaacc | ggattgctcg | cgcctttctg | cgcgcacggg | gctggaccgg | gggccgccga | 180 |
| ggctcgggca | ggggcagcac | tgaggaaggc | gcacgcgtgg | cgcctccggc | tggagatgcg | 240 |
| gctgctagag | ggacgaccgc | gccccctctg | gcacccgggg | cgaccgtggc | gctgctcctc | 300 |
| ccagcgggcc | cggatttcct | ttggatttgg | ttcggactgg | ccaaagctgg | cctgcgcacg | 360 |
| gcctttgtgc | ccaccgcttt | acgccgagga | cccctgctgc | actgcctccg | cagctgcggt | 420 |
| gcgagtgcgc | tcgtgctggc | cacagagttc | ctggagtccc | tggagccgga | cctgccggcc | 480 |

```
ttgagagcca tggggctcca cctatgggcg acgggccctg aaactaatgt agctggaatc      540
agcaatttgc tatcggaagc agcagaccaa gtggatgagc cagtgccggg gtacctctct      600 gcccccaga acataatgga cacctgcctg tacatcttca cctctggcac tactggcctg       660
cccaaggctg ctcgaatcag tcatctgaag gttctacagt gccaggatt ctaccatctg       720 tgtggagtcc accaggagga cgtgatctac ctcgcactcc cactgtacca catgtctggc      780
tcccttctgg gcattgtggg ctgcttgggc attggggcca ccgtggtgct gaaacccaag      840
ttctcagcta gccagttctg ggacgattgc agaaacaca gggtgacagt gttccagtac       900
attggggagt tgtgccgata cctcgtcaac cagcccccga gcaaggcaga gtttgaccat      960
aaggtgcgct ggcagtgggc agtgggttg cgcccagaca cctgggagcg tttcctgcgg       1020
cgatttggac ctctgcagat actggagacg tatggcatga cagagggcaa cgtagctacg      1080
ttcaattaca caggacggca gggtgcagtg ggcgagctt cctggcttta caagcacatc       1140
ttccccttct ccttgattcg atacgatgtc atgacagggg agcctattcg gaatgcccag      1200
gggcactgca tgaccacatc tccaggtgag ccaggcctac tggtggcccc agtgagccag      1260 cagtcccct tcctgggcta tgctggggct ccggagctgg ccaaggacaa gctgctgaag       1320
gatgtcttct ggtctgggga cgttttcttc aatactgggg acctcttggt ctgtgatgag      1380
caaggctttc ttcacttcca cgatcgtact ggagacacca tcaggtggaa gggagagaat      1440
gtggccacaa ctgaagtggc tgaggtcttg gagaccctgg acttccttca ggaggtgaac      1500
atctatggag tcacggtgcc agggcacgaa ggcagggcag gcatgcggc cttggctctg       1560 cggcccccgc aggctctgaa cctggtgcag ctctacagcc atgtttctga acttgcca        1620 ccgtatgccc gacctcggtt tctcaggctc caggaatctt tggccactac tgagaccttc      1680
aaacagcaga aggttaggat ggccaatgag ggctttgacc ccagtgtact gtctgaccca      1740
ctctatgttc tggaccaaga tagggggcc tacctgcccc tcacacctgc ccggtacagt       1800
gccctcctgt ctggagacct tcgaatctga aaccttccac ttgagggagg ggctcggagg      1860
gtacaggcca ccatggctgc accagggagg gttttcgggt atcttttgta tatggagtca      1920
ttattttgta ataaacagct ggagcttaaa aaaaaaaaa aaaaaaaaa aaaaaaaaa         1980 aaaaaaaaaa aaaaaaaa                                                   1998
```

<210> SEQ ID NO 69
<211> LENGTH: 609
<212> TYPE: PRT
<213> ORGANISM: Mus musculus

<400> SEQUENCE: 69

```
Glu Ser Ser Glu Ser Gly Cys Ser Leu Ala Trp Arg Leu Ala Tyr Leu
 1               5                  10                  15

Ala Arg Glu Gln Pro Thr His Thr Phe Leu Ile His Gly Ala Gln Arg
            20                  25                  30

Phe Ser Tyr Ala Glu Ala Glu Arg Glu Ser Asn Arg Ile Ala Arg Ala
        35                  40                  45

Phe Leu Arg Ala Arg Gly Trp Thr Gly Gly Arg Arg Gly Ser Gly Arg
    50                  55                  60

Gly Ser Thr Glu Glu Gly Ala Arg Val Ala Pro Ala Gly Asp Ala
65                  70                  75                  80

Ala Ala Arg Gly Thr Thr Ala Pro Pro Leu Ala Pro Gly Ala Thr Val
                85                  90                  95

Ala Leu Leu Leu Pro Ala Gly Pro Asp Phe Leu Trp Ile Trp Phe Gly
```

-continued

```
                100                 105                 110
Leu Ala Lys Ala Gly Leu Arg Thr Ala Phe Val Pro Thr Ala Leu Arg
            115                 120                 125

Arg Gly Pro Leu Leu His Cys Leu Arg Ser Cys Gly Ala Ser Ala Leu
130                 135                 140

Val Leu Ala Thr Glu Phe Leu Glu Ser Leu Glu Pro Asp Leu Pro Ala
145                 150                 155                 160

Leu Arg Ala Met Gly Leu His Leu Trp Ala Thr Gly Pro Glu Thr Asn
                165                 170                 175

Val Ala Gly Ile Ser Asn Leu Leu Ser Glu Ala Ala Asp Gln Val Asp
            180                 185                 190

Glu Pro Val Pro Gly Tyr Leu Ser Ala Pro Gln Asn Ile Met Asp Thr
            195                 200                 205

Cys Leu Tyr Ile Phe Thr Ser Gly Thr Thr Gly Leu Pro Lys Ala Ala
            210                 215                 220

Arg Ile Ser His Leu Lys Val Leu Gln Cys Gln Gly Phe Tyr His Leu
225                 230                 235                 240

Cys Gly Val His Gln Glu Asp Val Ile Tyr Leu Ala Leu Pro Leu Tyr
                245                 250                 255

His Met Ser Gly Ser Leu Leu Gly Ile Val Gly Cys Leu Gly Ile Gly
            260                 265                 270

Ala Thr Val Val Leu Lys Pro Lys Phe Ser Ala Ser Gln Phe Trp Asp
            275                 280                 285

Asp Cys Gln Lys His Arg Val Thr Val Phe Gln Tyr Ile Gly Glu Leu
            290                 295                 300

Cys Arg Tyr Leu Val Asn Gln Pro Pro Ser Lys Ala Glu Phe Asp His
305                 310                 315                 320

Lys Val Arg Leu Ala Val Gly Ser Gly Leu Arg Pro Asp Thr Trp Glu
                325                 330                 335

Arg Phe Leu Arg Arg Phe Gly Pro Leu Gln Ile Leu Glu Thr Tyr Gly
            340                 345                 350

Met Thr Glu Gly Asn Val Ala Thr Phe Asn Tyr Thr Gly Arg Gln Gly
            355                 360                 365

Ala Val Gly Arg Ala Ser Trp Leu Tyr Lys His Ile Phe Pro Phe Ser
            370                 375                 380

Leu Ile Arg Tyr Asp Val Met Thr Gly Glu Pro Ile Arg Asn Ala Gln
385                 390                 395                 400

Gly His Cys Met Thr Thr Ser Pro Gly Glu Pro Gly Leu Leu Val Ala
                405                 410                 415

Pro Val Ser Gln Gln Ser Pro Phe Leu Gly Tyr Ala Gly Ala Pro Glu
            420                 425                 430

Leu Ala Lys Asp Lys Leu Leu Lys Asp Val Phe Trp Ser Gly Asp Val
            435                 440                 445

Phe Phe Asn Thr Gly Asp Leu Leu Val Cys Asp Glu Gln Gly Phe Leu
450                 455                 460

His Phe His Asp Arg Thr Gly Asp Thr Ile Arg Trp Lys Gly Glu Asn
465                 470                 475                 480

Val Ala Thr Thr Glu Val Ala Glu Val Leu Glu Thr Leu Asp Phe Leu
                485                 490                 495

Gln Glu Val Asn Ile Tyr Gly Val Thr Val Pro Gly His Glu Gly Arg
            500                 505                 510

Ala Gly Met Ala Ala Leu Ala Leu Arg Pro Pro Gln Ala Leu Asn Leu
            515                 520                 525
```

-continued

```
Val Gln Leu Tyr Ser His Val Ser Glu Asn Leu Pro Pro Tyr Ala Arg
        530                 535                 540

Pro Arg Phe Leu Arg Leu Gln Glu Ser Leu Ala Thr Thr Glu Thr Phe
545                 550                 555                 560

Lys Gln Gln Lys Val Arg Met Ala Asn Glu Gly Phe Asp Pro Ser Val
                565                 570                 575

Leu Ser Asp Pro Leu Tyr Val Leu Asp Gln Asp Ile Gly Ala Tyr Leu
                580                 585                 590

Pro Leu Thr Pro Ala Arg Tyr Ser Ala Leu Leu Ser Gly Asp Leu Arg
        595                 600                 605

Ile
```

<210> SEQ ID NO 70
<211> LENGTH: 2710
<212> TYPE: DNA
<213> ORGANISM: Mus musculus

<400> SEQUENCE: 70

| | | | | | |
|---|---|---|---|---|---|
| atgctgcttg | agcctctct | ggtggggcg | ctactgttct | ccaagctagt | gctgaagctg | 60 |
| ccctggaccc | aggtgggatt | ctccctgttg | ctcctgtact | tggggtctgg | tggctggcgt | 120 |
| ttcatccggg | tcttcatcaa | gacggtcagg | agagatatct | ttggtggcat | ggtgctcctg | 180 |
| aaggtgaaga | ccaaggtgcg | acggtacctt | caggagcgga | agacggtgcc | cctgctgttt | 240 |
| gcttcaatgg | tacagcgcca | cccggacaag | acagccctga | ttttcgaggg | cacagacact | 300 |
| cactggacct | tccgccagct | ggatgagtac | tccagtagtg | tggccaactt | cctgcaggcc | 360 |
| cggggcctgg | cctcaggcaa | tgtagttgcc | ctctttatgg | aaaaccgcaa | tgagtttgtg | 420 |
| ggtctgtggc | taggcatggc | caagctgggc | gtggaggcgg | ctctcatcaa | caccaacctt | 480 |
| aggcgggatg | ccctgcgcca | ctgtcttgac | acctcaaagg | cacgagctct | catctttggc | 540 |
| agtgagatgg | cctcagctat | ctgtgagatc | catgctagcc | tggagcccac | actcagcctc | 600 |
| ttctgctctg | gatcctggga | gcccagcaca | gtgcccgtca | gcacagagca | tctgacccct | 660 |
| cttctggaag | atgccccgaa | gcacctgccc | agtcacccag | acaagggttt | tacagataag | 720 |
| ctcttctaca | tctacacatc | gggcaccacg | gggctaccca | agctgccat | tgtggtgcac | 780 |
| agcaggtatt | atcgtatggc | ttccctggtg | tactatggat | tccgcatgcg | gcctgatgac | 840 |
| attgtctatg | actgcctccc | cctctaccac | tcaagcagga | acatcgtgg | ggattggcag | 900 |
| tgcttactcc | acggcatgac | tgtggtgatc | cggaagaagt | tctcagcctc | ccggttctgg | 960 |
| gatgattgta | tcaagtacaa | ctgcacagtg | gtacagtaca | ttggcgagct | ctgccgctac | 1020 |
| ctcctgaacc | agccaccccg | tgaggctgag | tctcggcaca | aggtgcgcat | ggcactgggc | 1080 |
| aacggtctcc | ggcagtccat | ctggaccgac | ttctccagcc | gtttccacat | ccccaggtg | 1140 |
| gctgagttct | atgggccac | tgaatgcaac | tgtagcctgg | caactttga | cagccgggtg | 1200 |
| ggggcctgtg | gcttcaatag | ccgcatcctg | tcctttgtgt | accctatccg | tttggtacgt | 1260 |
| gtcaatgagg | ataccatgga | actgatccgg | ggacccgatg | gagtctgcat | tccctgtcaa | 1320 |
| ccaggtcagc | caggccagct | ggtgggtcgc | atcatccagc | aggaccctct | cgccgtttc | 1380 |
| gacgggtacc | tcaaccaggg | tgccaacaac | aagaagattg | ctaatgatgt | cttcaagaag | 1440 |
| ggggaccaag | cctacctcac | tggtgacgtc | ctggtgatgg | atgagctggg | ttacctgtac | 1500 |
| ttccgagatc | gcactgggga | cacgttccgc | tggaaagggg | agaatgtatc | taccactgag | 1560 |
| gtggagggca | cactcagccg | cctgcttcat | atggcagatg | tggcagttta | tggtgttgag | 1620 |

```
gtgccaggaa ctgaaggccg agcaggaatg gctgccgttg caagtcccat cagcaactgt      1680
gacctggaga gctttgcaca gaccttgaaa aaggagctgc ctctgtatgc ccgccccatc      1740
ttcctgcgct tcttgcctga gctgcacaag acagggacct tcaagttcca gaagacagag      1800
ttgcggaagg agggctttga cccatctgtt gtgaaagacc cgctgttcta tctggatgct      1860
cggaagggct gctacgttgc actggaccag gaggcctata cccgcatcca ggcaggcgag      1920
gagaagctgt gatttccccc tacatccctc tgagggccag aagatgctgg attcagagcc      1980
ctagcgtcca ccccagaggg tcctgggcaa tgccagacca agctagcag ggcccgcacc       2040 tccgccccta ggtgctgatc tcccctctcc caaactgcca agtgactcac tgccgcttcc      2100
ccgaccctcc agaggctttc tgtgaaagtc tcatccaagc tgtgtcttct ggtccaggcg      2160
tggcccctgg ccccagggtt tctgataggc tcctttagga tggtatcttg ggtccagcgg      2220
gccagggtgt gggagaggag tcactaagat ccctccaatc agaagggagc ttacaaagga      2280
accaaggcaa agcctgtaga ctcaggaagc taagtggcca gagactatag tggccagtca      2340
tcccatgtcc acagaggatc ttggtccaga gctgccaaag tgtcacctct ccctgcctgc      2400
acctctgggg aaaagaggac agcatgtggc cactgggcac ctgtctcaag aagtcaggat      2460
cacacactca gtccttgttt ctccaggttc ccttgttctt gtctcgggga gggagggacg      2520
agtgtcctgt ctgtccttcc tgcctgtctg tgagtctgtg ttgcttctcc atctgtccta      2580
gcctgagtgt gggtggaaca ggcatgagga gagtgtggct caggggccaa taaactctgc      2640
cttgactcct cttaaaaaaa aaaaaaaaaa aaaaaaaaaa aaaaaaaaaa aaaaaaaaaa      2700
aaaaaaaaaa                                                            2710

<210> SEQ ID NO 71
<211> LENGTH: 643
<212> TYPE: PRT
<213> ORGANISM: Mus musculus

<400> SEQUENCE: 71

Met Leu Leu Gly Ala Ser Leu Val Gly Ala Leu Leu Gly Ser Lys Leu
 1               5                  10                  15

Val Leu Lys Leu Pro Trp Thr Gln Val Gly Phe Ser Leu Leu Leu Leu
            20                  25                  30

Tyr Leu Gly Ser Gly Gly Trp Arg Phe Ile Arg Val Phe Ile Lys Thr
        35                  40                  45

Val Arg Arg Asp Ile Phe Gly Gly Met Val Leu Leu Lys Val Lys Thr
    50                  55                  60

Lys Val Arg Arg Tyr Leu Gln Glu Arg Lys Thr Val Pro Leu Leu Phe
65                  70                  75                  80

Ala Ser Met Val Gln Arg His Pro Asp Lys Thr Ala Leu Ile Phe Glu
                85                  90                  95

Gly Thr Asp Thr His Trp Thr Phe Arg Gln Leu Asp Glu Tyr Ser Ser
            100                 105                 110

Ser Val Ala Asn Phe Leu Gln Ala Arg Gly Leu Ala Ser Gly Asn Val
        115                 120                 125

Val Ala Leu Phe Met Glu Asn Arg Asn Glu Phe Val Gly Leu Trp Leu
    130                 135                 140

Gly Met Ala Lys Leu Gly Val Glu Ala Ala Leu Ile Asn Thr Asn Leu
145                 150                 155                 160

Arg Arg Asp Ala Leu Arg His Cys Leu Asp Thr Ser Lys Ala Arg Ala
                165                 170                 175
```

```
Leu Ile Phe Gly Ser Glu Met Ala Ser Ala Ile Cys Glu Ile His Ala
            180                 185                 190

Ser Leu Glu Pro Thr Leu Ser Leu Phe Cys Ser Gly Ser Trp Glu Pro
            195                 200                 205

Ser Thr Val Pro Val Ser Thr Glu His Leu Asp Pro Leu Leu Glu Asp
            210                 215                 220

Ala Pro Lys His Leu Pro Ser His Pro Asp Lys Gly Phe Thr Asp Lys
225                 230                 235                 240

Leu Phe Tyr Ile Tyr Thr Ser Gly Thr Thr Gly Leu Pro Lys Ala Ala
            245                 250                 255

Ile Val Val His Ser Arg Tyr Tyr Arg Met Ala Ser Leu Val Tyr Tyr
            260                 265                 270

Gly Phe Arg Met Arg Pro Asp Asp Ile Val Tyr Asp Cys Leu Pro Leu
            275                 280                 285

Tyr His Ser Ser Arg Lys His Arg Gly Asp Trp Gln Cys Leu Leu His
            290                 295                 300

Gly Met Thr Val Val Ile Arg Lys Lys Phe Ser Ala Ser Arg Phe Trp
305                 310                 315                 320

Asp Asp Cys Ile Lys Tyr Asn Cys Thr Val Val Gln Tyr Ile Gly Glu
            325                 330                 335

Leu Cys Arg Tyr Leu Leu Asn Gln Pro Pro Arg Glu Ala Glu Ser Arg
            340                 345                 350

His Lys Val Arg Met Ala Leu Gly Asn Gly Leu Arg Gln Ser Ile Trp
            355                 360                 365

Thr Asp Phe Ser Ser Arg Phe His Ile Pro Gln Val Ala Glu Phe Tyr
            370                 375                 380

Gly Ala Thr Glu Cys Asn Cys Ser Leu Gly Asn Phe Asp Ser Arg Val
385                 390                 395                 400

Gly Ala Cys Gly Phe Asn Ser Arg Ile Leu Ser Phe Val Tyr Pro Ile
            405                 410                 415

Arg Leu Val Arg Val Asn Glu Asp Thr Met Glu Leu Ile Arg Gly Pro
            420                 425                 430

Asp Gly Val Cys Ile Pro Cys Gln Pro Gly Gln Pro Gly Gln Leu Val
            435                 440                 445

Gly Arg Ile Ile Gln Gln Asp Pro Leu Arg Arg Phe Asp Gly Tyr Leu
            450                 455                 460

Asn Gln Gly Ala Asn Asn Lys Lys Ile Ala Asn Asp Val Phe Lys Lys
465                 470                 475                 480

Gly Asp Gln Ala Tyr Leu Thr Gly Asp Val Leu Val Met Asp Glu Leu
            485                 490                 495

Gly Tyr Leu Tyr Phe Arg Asp Arg Thr Gly Asp Thr Phe Arg Trp Lys
            500                 505                 510

Gly Glu Asn Val Ser Thr Thr Glu Val Glu Gly Thr Leu Ser Arg Leu
            515                 520                 525

Leu His Met Ala Asp Val Ala Val Tyr Gly Val Glu Val Pro Gly Thr
            530                 535                 540

Glu Gly Arg Ala Gly Met Ala Ala Val Ala Ser Pro Ile Ser Asn Cys
545                 550                 555                 560

Asp Leu Glu Ser Phe Ala Gln Thr Leu Lys Lys Glu Leu Pro Leu Tyr
            565                 570                 575

Ala Arg Pro Ile Phe Leu Arg Phe Leu Pro Glu Leu His Lys Thr Gly
            580                 585                 590
```

Thr Phe Lys Phe Gln Lys Thr Glu Leu Arg Lys Glu Gly Phe Asp Pro
            595                 600                 605

Ser Val Val Lys Asp Pro Leu Phe Tyr Leu Asp Ala Arg Lys Gly Cys
        610                 615                 620

Tyr Val Ala Leu Asp Gln Glu Ala Tyr Thr Arg Ile Gln Ala Gly Glu
625                 630                 635                 640

Glu Lys Leu

<210> SEQ ID NO 72
<211> LENGTH: 2277
<212> TYPE: DNA
<213> ORGANISM: Mus musculus

<400> SEQUENCE: 72

| | | | | | |
|---|---|---|---|---|---|
| cactcatcag | agctaagaga | gactacacgc | tctcatctac | ttcagaaaga | gccaatgcca | 60 |
| tgggtatttg | gaagaaacta | accttactgc | tgttgctgct | tctgctggtt | ggcctggggc | 120 |
| agcccccatg | ccagcagct | atggctctgg | ccctgcgttg | gttcctggga | cccccacat | 180 |
| gccttgtgct | gcttggcttg | gcattgctgg | gcagaccctg | gatcagctcc | tggatgcccc | 240 |
| actggctgag | cctggtagga | gcagctctta | ccttattcct | attgcctcta | cagccacccc | 300 |
| cagggctacg | ctggctgcat | aaagatgtgg | ctttcacctt | caagatgctt | ttctatggcc | 360 |
| taaagttcag | gcgacgcctt | aacaaacatc | ctccagagac | ctttgtggat | gctttagagc | 420 |
| ggcaagcact | ggcatggcct | gaccgggtgg | ccttggtgtg | tactgggtct | gagggctcct | 480 |
| caatcacaaa | tagccagctg | gatgccaggt | cctgtcaggc | agcatgggtc | ctgaaagcaa | 540 |
| agctgaagga | tgccgtaatc | cagaacacaa | gagatgctgc | tgctatctta | gttctcccgt | 600 |
| ccaagaccat | ttctgctttg | agtgtgtttc | tggggttggc | caagttgggc | tgccctgtgg | 660 |
| cctggatcaa | tccacacagc | cgagggatgc | ccttgctaca | ctctgtacgg | agctctgggg | 720 |
| ccagtgtgct | gattgtggat | ccagacctcc | aggagaacct | ggaagaagtc | cttcccaagc | 780 |
| tgctagctga | gaacattcac | tgcttctacc | ttggccacag | ctcacccacc | ccggagtag | 840 |
| aggctctggg | agcttccctg | gatgctgcac | cttctgaccc | agtacctgcc | agccttcgag | 900 |
| ctacgattaa | gtggaaatct | cctgccatat | tcatctttac | ttcagggacc | actggactcc | 960 |
| caaagccagc | catcttatca | catgagcggg | tcatacaagt | gagcaacgtg | ctgtccttct | 1020 |
| gtggatgcag | agctgatgat | gtggtctatg | acgtcctacc | tctgtaccat | acgatagggc | 1080 |
| ttgtccttgg | attccttggc | tgcttacaag | ttggagccac | ctgtgtcctg | gcccccaagt | 1140 |
| tctctgcctc | ccgattctgg | gctgagtgcc | ggcagcatgg | cgtaacagtg | atcttgtatg | 1200 |
| tgggtgaaat | cctgcggtac | ttgtgtaacg | tccctgagca | accagaagac | aagatacata | 1260 |
| cagtgcgctt | ggccatggga | actggacttc | gggcaaatgt | gtggaaaaac | ttccagcaac | 1320 |
| gctttggtcc | cattcggatc | tgggaattct | acgatccac | agagggcaat | gtgggcttaa | 1380 |
| tgaactatgt | gggccactgc | ggggctgtgg | aaggaccag | ctgcatcctt | cgaatgctga | 1440 |
| ctcccttga | gcttgtacag | ttcgacatag | agacagcaga | gcctctgagg | acaaacagg | 1500 |
| gttttgcat | tcctgtggag | ccaggaaagc | caggacttct | tttgaccaag | gttcgaaaga | 1560 |
| accaacccttt | cctgggctac | cgtggttccc | aggccgagtc | caatcggaaa | cttgttgcga | 1620 |
| atgtacgacg | cgtaggagac | ctgtacttca | acactgggga | cgtgctgacc | ttggaccagg | 1680 |
| aaggcttctt | ctactttcaa | gaccgccttg | gtgacacctt | ccgtggaag | ggcgaaaacg | 1740 |
| tatctactgg | agaggtggag | tgtgttttgt | ctagcctaga | cttcctagag | gaagtcaatg | 1800 |

-continued

```
tctatggtgt gcctgtgcca gggtgtgagg gtaaggttgg catggctgct gtgaaactgg    1860
ctcctgggaa gactttgat  gggcagaagc tataccagca tgtccgctcc tggctccctg    1920
cctatgccac acctcatttc atccgtatcc aggattccct ggagatcaca aacacctaca    1980
agctggtaaa gtcacggctg gtgcgtgagg gttttgatgt ggggatcatt gctgaccccc    2040
tctacatact ggacaacaag gcccagacct tccggagtct gatgccagat gtgtaccagg    2100
ctgtgtgtga aggaacctgg aatctctgac cacctagcca actggaaggc aatccaaaag    2160
tgtagagatt gacactagtc agcttcacaa agttgtccgg gttccagatg cccatggccc    2220
agtagtactt agagaataaa cttgaatgtg tatacaaaaa aaaaaaaaaa aaaaaaa       2277
```

<210> SEQ ID NO 73
<211> LENGTH: 689
<212> TYPE: PRT
<213> ORGANISM: Mus musculus

<400> SEQUENCE: 73

```
Met Gly Ile Trp Lys Lys Leu Thr Leu Leu Leu Leu Leu Leu Leu Leu
 1               5                  10                  15

Val Gly Leu Gly Gln Pro Pro Trp Pro Ala Ala Met Ala Leu Ala Leu
            20                  25                  30

Arg Trp Phe Leu Gly Asp Pro Thr Cys Leu Val Leu Leu Gly Leu Ala
        35                  40                  45

Leu Leu Gly Arg Pro Trp Ile Ser Ser Trp Met Pro His Trp Leu Ser
    50                  55                  60

Leu Val Gly Ala Ala Leu Thr Leu Phe Leu Leu Pro Leu Gln Pro Pro
65                  70                  75                  80

Pro Gly Leu Arg Trp Leu His Lys Asp Val Ala Phe Thr Phe Lys Met
                85                  90                  95

Leu Phe Tyr Gly Leu Lys Phe Arg Arg Arg Leu Asn Lys His Pro Pro
           100                 105                 110

Glu Thr Phe Val Asp Ala Leu Glu Arg Gln Ala Leu Ala Trp Pro Asp
       115                 120                 125

Arg Val Ala Leu Val Cys Thr Gly Ser Glu Gly Ser Ser Ile Thr Asn
130                 135                 140

Ser Gln Leu Asp Ala Arg Ser Cys Gln Ala Ala Trp Val Leu Lys Ala
145                 150                 155                 160

Lys Leu Lys Asp Ala Val Ile Gln Asn Thr Arg Asp Ala Ala Ala Ile
                165                 170                 175

Leu Val Leu Pro Ser Lys Thr Ile Ser Ala Leu Ser Val Phe Leu Gly
            180                 185                 190

Leu Ala Lys Leu Gly Cys Pro Val Ala Trp Ile Asn Pro His Ser Arg
        195                 200                 205

Gly Met Pro Leu Leu His Ser Val Arg Ser Ser Gly Ala Ser Val Leu
    210                 215                 220

Ile Val Asp Pro Asp Leu Gln Glu Asn Leu Glu Glu Val Leu Pro Lys
225                 230                 235                 240

Leu Leu Ala Glu Asn Ile His Cys Phe Tyr Leu Gly His Ser Ser Pro
                245                 250                 255

Thr Pro Gly Val Glu Ala Leu Gly Ser Leu Asp Ala Pro Ser
            260                 265                 270

Asp Pro Val Pro Ala Ser Leu Arg Ala Thr Ile Lys Trp Lys Ser Pro
        275                 280                 285

Ala Ile Phe Ile Phe Thr Ser Gly Thr Thr Gly Leu Pro Lys Pro Ala
```

-continued

```
                290                 295                 300
Ile Leu Ser His Glu Arg Val Ile Gln Val Ser Asn Val Leu Ser Phe
305                 310                 315                 320

Cys Gly Cys Arg Ala Asp Asp Val Val Tyr Asp Val Leu Pro Leu Tyr
                325                 330                 335

His Thr Ile Gly Leu Val Leu Gly Phe Leu Gly Cys Leu Gln Val Gly
                340                 345                 350

Ala Thr Cys Val Leu Ala Pro Lys Phe Ser Ala Ser Arg Phe Trp Ala
                355                 360                 365

Glu Cys Arg Gln His Gly Val Thr Val Ile Leu Tyr Val Gly Glu Ile
370                 375                 380

Leu Arg Tyr Leu Cys Asn Val Pro Glu Gln Pro Glu Asp Lys Ile His
385                 390                 395                 400

Thr Val Arg Leu Ala Met Gly Thr Gly Leu Arg Ala Asn Val Trp Lys
                405                 410                 415

Asn Phe Gln Gln Arg Phe Gly Pro Ile Arg Ile Trp Glu Phe Tyr Gly
                420                 425                 430

Ser Thr Glu Gly Asn Val Gly Leu Met Asn Tyr Val Gly His Cys Gly
                435                 440                 445

Ala Val Gly Arg Thr Ser Cys Ile Leu Arg Met Leu Thr Pro Phe Glu
450                 455                 460

Leu Val Gln Phe Asp Ile Glu Thr Ala Glu Pro Leu Arg Asp Lys Gln
465                 470                 475                 480

Gly Phe Cys Ile Pro Val Glu Pro Gly Lys Pro Gly Leu Leu Leu Thr
                485                 490                 495

Lys Val Arg Lys Asn Gln Pro Phe Leu Gly Tyr Arg Gly Ser Gln Ala
                500                 505                 510

Glu Ser Asn Arg Lys Leu Val Ala Asn Val Arg Arg Val Gly Asp Leu
                515                 520                 525

Tyr Phe Asn Thr Gly Asp Val Leu Thr Leu Asp Gln Glu Gly Phe Phe
                530                 535                 540

Tyr Phe Gln Asp Arg Leu Gly Asp Thr Phe Arg Trp Lys Gly Glu Asn
545                 550                 555                 560

Val Ser Thr Gly Glu Val Glu Cys Val Leu Ser Ser Leu Asp Phe Leu
                565                 570                 575

Glu Glu Val Asn Val Tyr Gly Val Pro Val Pro Gly Cys Glu Gly Lys
                580                 585                 590

Val Gly Met Ala Ala Val Lys Leu Ala Pro Gly Lys Thr Phe Asp Gly
                595                 600                 605

Gln Lys Leu Tyr Gln His Val Arg Ser Trp Leu Pro Ala Tyr Ala Thr
                610                 615                 620

Pro His Phe Ile Arg Ile Gln Asp Ser Leu Glu Ile Thr Asn Thr Tyr
625                 630                 635                 640

Lys Leu Val Lys Ser Arg Leu Val Arg Glu Gly Phe Asp Val Gly Ile
                645                 650                 655

Ile Ala Asp Pro Leu Tyr Ile Leu Asp Asn Lys Ala Gln Thr Phe Arg
                660                 665                 670

Ser Leu Met Pro Asp Val Tyr Gln Ala Val Cys Glu Gly Thr Trp Asn
                675                 680                 685

Leu
```

<210> SEQ ID NO 74
<211> LENGTH: 2221

<212> TYPE: DNA
<213> ORGANISM: Drosophila melanogaster

<400> SEQUENCE: 74

```
gctctctggg cctatatcaa gctgctgagg tacacgaagc gccatgagcg gctcaactac      60
acggtggcgg acgtcttcga acgaaatgtt caggcccatc cggacaaggt ggctgtggtc     120
agtgagacgc aacgctggac cttccgtcag gtgaacgagc atgcgaacaa ggtggccaat     180
gtgctgcagg ctcagggcta caaaaagggc gatgtggtgg ccctgttgct ggagaaccgc     240
gccgagtacg tggccacctg gctgggtctc tccaagatcg gtgtgatcac accgctgatc     300
aacacgaatc tgcgcggtcc ctccctgctg cacagcatca cggtggccca ttgctcggct     360
ctcatttacg gcgaggactt cctggaagct gtcaccgacg tggccaagga tctgccagcg     420
aacctcacac tcttccagtt caacaacgag aacaacaaca gcgagacgga aagaacata      480
ccgcaggcca agaatctgaa cgcgctgctg accacggcca gctatgagaa gcctaacaag     540
acgcaggtta accaccacga caagctggtc tacatctaca cctccggcac cacaggattg     600
ccaaaggctg cggttatctc tcactcccgt tatctgttta tcgctgctgg catccactac     660
accatgggtt tccaggagga ggacatcttc tacacgccct tgcctttgta ccacaccgct     720
ggtggcatta tgtgcatggg tcagtcggtg ctctttggct ccacggtctc cattcgcaag     780
aagttctcgg catccaacta tttcgccgac tgcgccaagt ataatgcaac tattggtcag     840
tatatcggtg agatggctcg ctacattcta gctacgaaac cctcggaata cgaccagaaa     900
caccgagtgc gtctggtctt tggaaacgga ctgcgaccgc agatttggcc acagtttgtg     960
cagcgcttca acattgccaa ggttggcgag ttctacggcg ccaccgaggg taatgcgaac    1020
atcatgaatc atgacaacac ggtgggcgcc atcggctttg tgtcgcgcat cctgcccaag    1080
atctacccaa tctcgatcat tcgcgccgat ccggacaccg agagcccat tagagatagg    1140
aatggcctat gccaactgtg cgctcccaac gagccaggcg tattcatcgg caagatcgtc    1200
aaaggaaatc cttctcgcga attcctcgga tacgtcgatg aaaaggcctc cgcgaagaag    1260
attgttaagg atgtgttcaa gcatggcgat atggctttca tctccggaga tctgctggtt    1320
gccgacgaga agggttatct gtacttcaag gatcgcaccg tgacaccttc cgctggaag     1380
ggcgagaatg tttccaccag cgaggtggag gcgcaagtca gcaatgtggc cggttacaag    1440
gataccgtcg tttacggcgt aaccattccg cacaccgagg gaagggccgg catggccgcc    1500
atctatgatc cggagcgaga attggacctc gacgtcttcg ccgctagctt ggccaaggtg    1560
ctgcccgcgt acgctcgtcc ccagatcatt cgattgctca ccaaggtgga cctgactgga    1620
acctttaagc tgcgcaaggt agacctgcag aaggagggct acgatccgaa cgcgatcaag    1680
gacgcgctgt actaccagac ttccaagggt cggtacgagc tgctcacgcc ccaggtttac    1740
gaccaggtgc agcgcaacga atccgcttc taagagctgc aatagagttg tgtctgaacc    1800
ttgccttttg cccaatatgc tgttaattag tttgtaaggc taagtgtagt agaggaaaat    1860
cggggaaat cggcagcaaa gatcattcag cctaggagag atgcatccga agcacatttc    1920
catgtcaaca atgcactttt gtatatcgta agcatatata tatcgtatat cgtaaacgta    1980
gttgtatctg catttgtgta gatgatagcc tcctatacgc atttcaattg tttttagcgt    2040
gctaaagaac cttgttaaat gcaatttcag ctattgttta gtcagtttta gtggcattta    2100
cacttccatt ctcgttgcgt ttcgtttttg cctgtacata tgagaagctc tgatgttttt    2160
gtatcaaata aagtttttc cttcaccacg gaccacgtga aaaaaaaaaa aaaaaaaaa     2220
```

-continued a                                                                2221

<210> SEQ ID NO 75
<211> LENGTH: 590
<212> TYPE: PRT
<213> ORGANISM: Drosophila melanogaster

<400> SEQUENCE: 75

```
Ala Leu Trp Ala Tyr Ile Lys Leu Leu Arg Tyr Thr Lys Arg His Glu
 1               5                  10                  15

Arg Leu Asn Tyr Thr Val Ala Asp Val Phe Glu Arg Asn Val Gln Ala
            20                  25                  30

His Pro Asp Lys Val Ala Val Val Ser Glu Thr Gln Arg Trp Thr Phe
        35                  40                  45

Arg Gln Val Asn Glu His Ala Asn Lys Val Ala Asn Val Leu Gln Ala
    50                  55                  60

Gln Gly Tyr Lys Lys Gly Asp Val Val Ala Leu Leu Glu Asn Arg
65                  70                  75                  80

Ala Glu Tyr Val Ala Thr Trp Leu Gly Leu Ser Lys Ile Gly Val Ile
                85                  90                  95

Thr Pro Leu Ile Asn Thr Asn Leu Arg Gly Pro Ser Leu Leu His Ser
            100                 105                 110

Ile Thr Val Ala His Cys Ser Ala Leu Ile Tyr Gly Glu Asp Phe Leu
        115                 120                 125

Glu Ala Val Thr Asp Val Ala Lys Asp Leu Pro Ala Asn Leu Thr Leu
    130                 135                 140

Phe Gln Phe Asn Asn Glu Asn Asn Ser Glu Thr Glu Lys Asn Ile
145                 150                 155                 160

Pro Gln Ala Lys Asn Leu Asn Ala Leu Leu Thr Thr Ala Ser Tyr Glu
                165                 170                 175

Lys Pro Asn Lys Thr Gln Val Asn His His Asp Lys Leu Val Tyr Ile
            180                 185                 190

Tyr Thr Ser Gly Thr Thr Gly Leu Pro Lys Ala Ala Val Ile Ser His
        195                 200                 205

Ser Arg Tyr Leu Phe Ile Ala Ala Gly Ile His Tyr Thr Met Gly Phe
    210                 215                 220

Gln Glu Glu Asp Ile Phe Tyr Thr Pro Leu Pro Leu Tyr His Thr Ala
225                 230                 235                 240

Gly Gly Ile Met Cys Met Gly Gln Ser Val Leu Phe Gly Ser Thr Val
                245                 250                 255

Ser Ile Arg Lys Lys Phe Ser Ser Asn Tyr Phe Ala Asp Cys Ala
            260                 265                 270

Lys Tyr Asn Ala Thr Ile Gly Gln Tyr Ile Gly Glu Met Ala Arg Tyr
        275                 280                 285

Ile Leu Ala Thr Lys Pro Ser Glu Tyr Asp Gln Lys His Arg Val Arg
    290                 295                 300

Leu Val Phe Gly Asn Gly Leu Arg Pro Gln Ile Trp Pro Gln Phe Val
305                 310                 315                 320

Gln Arg Phe Asn Ile Ala Lys Val Gly Glu Phe Tyr Gly Ala Thr Glu
                325                 330                 335

Gly Asn Ala Asn Ile Met Asn His Asp Asn Thr Val Gly Ala Ile Gly
            340                 345                 350

Phe Val Ser Arg Ile Leu Pro Lys Ile Tyr Pro Ile Ser Ile Ile Arg
        355                 360                 365
```

```
Ala Asp Pro Asp Thr Gly Glu Pro Ile Arg Asp Arg Asn Gly Leu Cys
    370                 375                 380
Gln Leu Cys Ala Pro Asn Glu Pro Gly Val Phe Ile Gly Lys Ile Val
385                 390                 395                 400
Lys Gly Asn Pro Ser Arg Glu Phe Leu Gly Tyr Val Asp Glu Lys Ala
                405                 410                 415
Ser Ala Lys Lys Ile Val Lys Asp Val Phe Lys His Gly Asp Met Ala
            420                 425                 430
Phe Ile Ser Gly Asp Leu Leu Val Ala Asp Glu Lys Gly Tyr Leu Tyr
        435                 440                 445
Phe Lys Asp Arg Thr Gly Asp Thr Phe Arg Trp Lys Gly Glu Asn Val
    450                 455                 460
Ser Thr Ser Glu Val Glu Ala Gln Val Ser Asn Val Ala Gly Tyr Lys
465                 470                 475                 480
Asp Thr Val Val Tyr Gly Val Thr Ile Pro His Thr Glu Gly Arg Ala
                485                 490                 495
Gly Met Ala Ala Ile Tyr Asp Pro Glu Arg Glu Leu Asp Leu Asp Val
            500                 505                 510
Phe Ala Ala Ser Leu Ala Lys Val Leu Pro Ala Tyr Ala Arg Pro Gln
        515                 520                 525
Ile Ile Arg Leu Leu Thr Lys Val Asp Leu Thr Gly Thr Phe Lys Leu
    530                 535                 540
Arg Lys Val Asp Leu Gln Lys Glu Gly Tyr Asp Pro Asn Ala Ile Lys
545                 550                 555                 560
Asp Ala Leu Tyr Tyr Gln Thr Ser Lys Gly Arg Tyr Glu Leu Leu Thr
                565                 570                 575
Pro Gln Val Tyr Asp Gln Val Gln Arg Asn Glu Ile Arg Phe
            580                 585                 590

<210> SEQ ID NO 76
<211> LENGTH: 173
<212> TYPE: DNA
<213> ORGANISM: Danio rerio

<400> SEQUENCE: 76
agtgtagata ccacaggaac gtttaaaatc cagaagacca gactgcaaag ggaaggatac      60
gatccacggc tcacaactga ccagatctac ttcctaaact ccagagcagg gcgttacgag     120
cttgtcaacg aggagctgta caatgcattt gaacaagggc aggatttccc ttt            173

<210> SEQ ID NO 77
<211> LENGTH: 57
<212> TYPE: PRT
<213> ORGANISM: Danio rerio

<400> SEQUENCE: 77

Ser Val Asp Thr Thr Gly Thr Phe Lys Ile Gln Lys Thr Arg Leu Gln
1               5                  10                  15
Arg Glu Gly Tyr Asp Pro Arg Leu Thr Thr Asp Gln Ile Tyr Phe Leu
            20                  25                  30
Asn Ser Arg Ala Gly Arg Tyr Glu Leu Val Asn Glu Glu Leu Tyr Asn
        35                  40                  45
Ala Phe Glu Gln Gly Gln Asp Phe Pro
    50                  55

<210> SEQ ID NO 78
<211> LENGTH: 1953
```

<210> SEQ ID NO 78
<211> LENGTH: 1953
<212> TYPE: DNA
<213> ORGANISM: Caenorhabditis elegans

<400> SEQUENCE: 78

| | | | | | | |
|---|---|---|---|---|---|---|
| atgaagctgg | aggagcttgt | gacagttatg | cttctcacag | tggctgtcat | tgctcagaat | 60 |
| cttccgattg | gagtaatatt | ggctggagtt | cttattttat | acatcacagt | ggttcatgga | 120 |
| gatttcattt | atagaagtta | tcttacgttg | aatagggatt | taacaggatt | ggctctaatt | 180 |
| attgaagtca | aaatcgacct | atggtggagg | ttgcatcaga | ataaaggaat | ccatgaactg | 240 |
| tttttggata | ttgtgaaaaa | gaatccaaat | aagccggcga | tgattgacat | cgagacgaat | 300 |
| acaacagaaa | catacgcaga | gttcaatgca | cattgtaata | gatatgccaa | ttatttccag | 360 |
| ggtcttggct | atcgatccgg | agacgttgtc | gccttgtaca | tggagaactc | ggtcgagttt | 420 |
| gtggccgcgt | ggatgggact | cgcaaaaatc | ggagttgtaa | cggcttggat | caactcgaat | 480 |
| ttgaaaagag | agcaacttgt | tcattgtatc | actgcgagca | agacaaaggc | gattatcaca | 540 |
| agtgtaacac | ttcagaatat | tatgcttgat | gctatcgatc | agaagctgtt | tgatgttgag | 600 |
| ggaattgagg | tttactctgt | cggagagccc | aagaagaatt | ctggattcaa | gaatctcaag | 660 |
| aagaagttgg | atgctcaaat | tactacggaa | ccaaagaccc | ttgacatagt | agattttaaa | 720 |
| agtattcttt | gcttcatcta | tacaagtggt | actactggaa | tgccaaaagc | cgctgtcatg | 780 |
| aagcacttca | gatattactc | gattgccgtt | ggagccgcaa | aatcattcgg | aatccgccct | 840 |
| tctgatcgta | tgtacgtctc | gatgccaatt | tatcacactg | cagctggaat | tcttggagtt | 900 |
| gggcaagctc | tgtttgggtgg | atcatcgtgt | gtcattagaa | aaaaattctc | ggctagcaac | 960 |
| ttttggaggg | attgtgtaaa | gtatgattgt | acagtttcac | aatacattgg | agagatttgt | 1020 |
| cggtacttgt | tggctcagcc | agttgtggaa | gaggaatcca | ggcatagaat | gagattgttg | 1080 |
| gttgaaaacg | gactccgtgc | tgaaatctgg | caaccatttg | tagatcgatt | ccgtgtcaga | 1140 |
| attggagaac | tttatggttc | aactgaagga | acttcatctc | tcgtgaacat | tgacggacat | 1200 |
| gtcggagctt | gcggattctt | gccaatatcc | ccattaacaa | agaaaatgca | tccggttcga | 1260 |
| ttaattaagg | ttgatgatgt | cactggagaa | gcaatccgaa | cttccgatgg | actttgcatt | 1320 |
| gcatgtaatc | caggagagtc | tggagcaatg | gtgtcgacga | tcagaaaaaa | taatccatta | 1380 |
| ttgcaattcg | agggatatct | gaataagaag | gaaacgaata | aaaagattat | cagagatgtc | 1440 |
| ttcgcaaagg | gagatagttg | cttttttgact | ggagatcttc | ttcattggga | tcgtcttggt | 1500 |
| tatgtatatt | tcaaggatcg | tactggagat | actttccgtt | ggaagggaga | gaatgtgtcg | 1560 |
| actactgaag | tcgaggcaat | tcttcatcca | attactggat | tgtctgatgc | aactgtttat | 1620 |
| ggtgtagagg | ttcctcaaag | agagggaaga | gttggaatgg | cgtcagttgt | tcgagttgta | 1680 |
| tcgcatgagg | aagatgaaac | tcaatttgtt | catagagttg | gagcaagact | tgcctcttcg | 1740 |
| cttaccagct | acgcgattcc | tcagtttatg | cgaatttgtc | aggatgttga | gaaaacaggt | 1800 |
| acattcaaac | ttgtgaagac | gaatctacaa | cgattaggta | tcatggatgc | tccttcagat | 1860 |
| tcaatttaca | tctacaattc | tgaaaatcgc | aattttgtgc | cgttcgacaa | tgatttgagg | 1920 |
| tgcaaggtct | cactgggaag | ttatccattt | taa | | | 1953 |

<210> SEQ ID NO 79
<211> LENGTH: 650
<212> TYPE: PRT
<213> ORGANISM: Caenorhabditis elegans

<400> SEQUENCE: 79

-continued

```
Met Lys Leu Glu Glu Leu Val Thr Val Met Leu Leu Thr Val Ala Val
  1               5                   10                  15

Ile Ala Gln Asn Leu Pro Ile Gly Val Ile Leu Ala Gly Val Leu Ile
              20                  25                  30

Leu Tyr Ile Thr Val Val His Gly Asp Phe Ile Tyr Arg Ser Tyr Leu
          35                  40                  45

Thr Leu Asn Arg Asp Leu Thr Gly Leu Ala Leu Ile Ile Glu Val Lys
      50                  55                  60

Ile Asp Leu Trp Trp Arg Leu His Gln Asn Lys Gly Ile His Glu Leu
 65                  70                  75                  80

Phe Leu Asp Ile Val Lys Lys Asn Pro Asn Lys Pro Ala Met Ile Asp
                  85                  90                  95

Ile Glu Thr Asn Thr Thr Glu Thr Tyr Ala Glu Phe Asn Ala His Cys
             100                 105                 110

Asn Arg Tyr Ala Asn Tyr Phe Gln Gly Leu Gly Tyr Arg Ser Gly Asp
             115                 120                 125

Val Val Ala Leu Tyr Met Glu Asn Ser Val Glu Phe Val Ala Ala Trp
     130                 135                 140

Met Gly Leu Ala Lys Ile Gly Val Val Thr Ala Trp Ile Asn Ser Asn
145                 150                 155                 160

Leu Lys Arg Glu Gln Leu Val His Cys Ile Thr Ala Ser Lys Thr Lys
                 165                 170                 175

Ala Ile Ile Thr Ser Val Thr Leu Gln Asn Ile Met Leu Asp Ala Ile
             180                 185                 190

Asp Gln Lys Leu Phe Asp Val Glu Gly Ile Glu Val Tyr Ser Val Gly
         195                 200                 205

Glu Pro Lys Lys Asn Ser Gly Phe Lys Asn Leu Lys Lys Leu Asp
     210                 215                 220

Ala Gln Ile Thr Thr Glu Pro Lys Thr Leu Asp Ile Val Asp Phe Lys
225                 230                 235                 240

Ser Ile Leu Cys Phe Ile Tyr Thr Ser Gly Thr Thr Gly Met Pro Lys
                 245                 250                 255

Ala Ala Val Met Lys His Phe Arg Tyr Tyr Ser Ile Ala Val Gly Ala
                 260                 265                 270

Ala Lys Ser Phe Gly Ile Arg Pro Ser Asp Arg Met Tyr Val Ser Met
             275                 280                 285

Pro Ile Tyr His Thr Ala Ala Gly Ile Leu Gly Val Gly Gln Ala Leu
         290                 295                 300

Leu Gly Gly Ser Ser Cys Val Ile Arg Lys Lys Phe Ser Ala Ser Asn
305                 310                 315                 320

Phe Trp Arg Asp Cys Val Lys Tyr Asp Cys Thr Val Ser Gln Tyr Ile
             325                 330                 335

Gly Glu Ile Cys Arg Tyr Leu Leu Ala Gln Pro Val Val Glu Glu Glu
             340                 345                 350

Ser Arg His Arg Met Arg Leu Leu Val Gly Asn Gly Leu Arg Ala Glu
         355                 360                 365

Ile Trp Gln Pro Phe Val Asp Arg Phe Arg Val Arg Ile Gly Glu Leu
     370                 375                 380

Tyr Gly Ser Thr Glu Gly Thr Ser Ser Leu Val Asn Ile Asp Gly His
385                 390                 395                 400

Val Gly Ala Cys Gly Phe Leu Pro Ile Ser Pro Leu Thr Lys Lys Met
                 405                 410                 415

His Pro Val Arg Leu Ile Lys Val Asp Asp Val Thr Gly Glu Ala Ile
```

```
                    420              425              430
Arg Thr Ser Asp Gly Leu Cys Ile Ala Cys Asn Pro Gly Glu Ser Gly
            435              440              445

Ala Met Val Ser Thr Ile Arg Lys Asn Asn Pro Leu Leu Gln Phe Glu
    450              455              460

Gly Tyr Leu Asn Lys Lys Glu Thr Asn Lys Lys Ile Ile Arg Asp Val
465              470              475              480

Phe Ala Lys Gly Asp Ser Cys Phe Leu Thr Gly Asp Leu Leu His Trp
                485              490              495

Asp Arg Leu Gly Tyr Val Tyr Phe Lys Asp Arg Thr Gly Asp Thr Phe
                500              505              510

Arg Trp Lys Gly Glu Asn Val Ser Thr Thr Glu Val Glu Ala Ile Leu
            515              520              525

His Pro Ile Thr Gly Leu Ser Asp Ala Thr Val Tyr Gly Val Glu Val
        530              535              540

Pro Gln Arg Glu Gly Arg Val Gly Met Ala Ser Val Arg Val Val
545              550              555              560

Ser His Glu Glu Asp Glu Thr Gln Phe Val His Arg Val Gly Ala Arg
                565              570              575

Leu Ala Ser Ser Leu Thr Ser Tyr Ala Ile Pro Gln Phe Met Arg Ile
                580              585              590

Cys Gln Asp Val Glu Lys Thr Gly Thr Phe Lys Leu Val Lys Thr Asn
                595              600              605

Leu Gln Arg Leu Gly Ile Met Asp Ala Pro Ser Asp Ser Ile Tyr Ile
            610              615              620

Tyr Asn Ser Glu Asn Arg Asn Phe Val Pro Phe Asp Asn Asp Leu Arg
625              630              635              640

Cys Lys Val Ser Leu Gly Ser Tyr Pro Phe
                645              650

<210> SEQ ID NO 80
<211> LENGTH: 1968
<212> TYPE: DNA
<213> ORGANISM: Caenorhabditis elegans

<400> SEQUENCE: 80
atgagggaaa tgccggacag tcccaagttt gcgttagtca cgtttgttgt gtatgcagtg      60
gttttgtaca atgtcaacag cgttttctgg aaatttgtat tcatcggata tgttgtattt     120
aggctgcttc gcactgattt tggaagaaga gcacttgcca cgttacctag agattttgcg     180
ggactgaagc tcttaatatc ggttaagtcg acaattcgtg gcttgttcaa gaaagatcgc     240
ccaattcatg aaatcttttt gaatcaggtg aaacagcatc caaacaaagt ggcgattatt     300
gaaattgaaa gtggtaggca gttgacgtat caagaattga atgcgttagc taatcagtat     360
gctaaccttt acgtgagtga aggttacaaa atgggcgacg ttgtcgcttt gtttatggaa     420
aatagcatcg acttctttgc aatttggctg gactttcca agattggagt cgtgtcggcg     480
ttcatcaact caaacttgaa gttggagcca ttggcacatt cgattaatgt ttcgaagtgc     540
aaatcatgca ttaccaatat caatctgttg ccgatgttca agccgctcg tgaaaagaat     600
ctgatcagtg acgagatcca cgtgtttctg gctggaactc aggttgatgg acgtcataga     660
agtcttcagc aagatctcca tcttttctct gaggatgaac ctccagttat agacggactc     720
aattttagaa gcgttctgtg ttatatttac acttccggta ctaccggaaa tccaaagcca     780
gccgtcatta acacttccg ttacttctgg attgcgatgg gagcaggaaa agcatttgga     840
```

```
attaataagt cagacgttgt gtacattacg atgccaatgt atcactctgc cgccggtatc    900
atgggtattg gatcattaat tgcattcggg tcgaccgctg ttattaggaa aaagttttcg    960
gcaagcaact tctggaaaga ttgcgtcaag tacaacgtca cagcgacaca gtacattgga   1020
gaaatctgca ggtatcttct ggcagcgaat ccatgtcctg aagagaaaca cacaacgtg    1080
cgattgatgt ggggaaatgg tttgagagga caaatttgga aagagtttgt aggaagattt   1140
ggaattaaga aaattggaga gttgtacggc tcaacagaag gaaactccaa tattgttaac   1200
gtggataacc atgttggagc ttgtggattc atgccaattt atccccatat ggatccctc    1260
tacccagttc gacttattaa ggttgataga gccactggag agcttgaacg tgataagaac   1320
ggactctgtg tgccgtgtgt gcctggtgaa actggggaaa tggttggcgt tatcaaggag   1380
aaagatattc ttctaaagtt cgaaggatat gtcagcgaag gggatactgc aaagaaaatc   1440
tacagagatg tgttcaagca tggagataag gtgtttgcaa gtggagatat tcttcattgg   1500
gatgatcttg gatacttgta ctttgtggac cgttgtggag acactttccg ttggaaaggg   1560
gagaacgtgt caactactga agttgaggga attcttcagc ctgtgatgga tgtggaagat   1620
gcaactgttt atggagtcac tgtcggtaaa atggagggc gtgccggaat ggctggtatt    1680
gtcgtcaagg atgaacgga tgttgagaaa ttcatcgccg atattacttc tcgactgacc    1740
gaaaatctgg cgtcttacgc aatccctgtt ttcattcggc tgtgcaagga agttgatcga   1800
accggaacct tcaaactcaa gaagactgat cttcaaaaac aaggttacga cctggttgct   1860
tgtaaaggag acccaattta ctactggtca gctgcagaaa aatcctacaa accactgact   1920
gacaaaatgc aacaggatat tgacactggt gtttatgatc gcatttaa               1968
```

<210> SEQ ID NO 81
<211> LENGTH: 655
<212> TYPE: PRT
<213> ORGANISM: Caenorhabditis elegans

<400> SEQUENCE: 81

```
Met Arg Glu Met Pro Asp Ser Pro Lys Phe Ala Leu Val Thr Phe Val
  1               5                  10                  15

Val Tyr Ala Val Val Leu Tyr Asn Val Asn Ser Val Phe Trp Lys Phe
             20                  25                  30

Val Phe Ile Gly Tyr Val Val Phe Arg Leu Leu Arg Thr Asp Phe Gly
         35                  40                  45

Arg Arg Ala Leu Ala Thr Leu Pro Arg Asp Phe Ala Gly Leu Lys Leu
     50                  55                  60

Leu Ile Ser Val Lys Ser Thr Ile Arg Gly Leu Phe Lys Lys Asp Arg
 65                  70                  75                  80

Pro Ile His Glu Ile Phe Leu Asn Gln Val Lys Gln His Pro Asn Lys
                 85                  90                  95

Val Ala Ile Ile Glu Ile Glu Ser Gly Arg Gln Leu Thr Tyr Gln Glu
            100                 105                 110

Leu Asn Ala Leu Ala Asn Gln Tyr Ala Asn Leu Tyr Val Ser Glu Gly
        115                 120                 125

Tyr Lys Met Gly Asp Val Val Ala Leu Phe Met Glu Asn Ser Ile Asp
    130                 135                 140

Phe Phe Ala Ile Trp Leu Gly Leu Ser Lys Ile Gly Val Val Ser Ala
145                 150                 155                 160

Phe Ile Asn Ser Asn Leu Lys Leu Glu Pro Leu Ala His Ser Ile Asn
                165                 170                 175
```

```
Val Ser Lys Cys Lys Ser Cys Ile Thr Asn Ile Asn Leu Leu Pro Met
            180                 185                 190

Phe Lys Ala Ala Arg Glu Lys Asn Leu Ile Ser Asp Glu Ile His Val
            195                 200                 205

Phe Leu Ala Gly Thr Gln Val Asp Gly Arg His Arg Ser Leu Gln Gln
            210                 215                 220

Asp Leu His Leu Phe Ser Glu Asp Glu Pro Pro Val Ile Asp Gly Leu
225                 230                 235                 240

Asn Phe Arg Ser Val Leu Cys Tyr Ile Tyr Thr Ser Gly Thr Thr Gly
            245                 250                 255

Asn Pro Lys Pro Ala Val Ile Lys His Phe Arg Tyr Phe Trp Ile Ala
            260                 265                 270

Met Gly Ala Gly Lys Ala Phe Gly Ile Asn Lys Ser Asp Val Val Tyr
            275                 280                 285

Ile Thr Met Pro Met Tyr His Ser Ala Ala Gly Ile Met Gly Ile Gly
            290                 295                 300

Ser Leu Ile Ala Phe Gly Ser Thr Ala Val Ile Arg Lys Lys Phe Ser
305                 310                 315                 320

Ala Ser Asn Phe Trp Lys Asp Cys Val Lys Tyr Asn Val Thr Ala Thr
            325                 330                 335

Gln Tyr Ile Gly Glu Ile Cys Arg Tyr Leu Leu Ala Ala Asn Pro Cys
            340                 345                 350

Pro Glu Glu Lys Gln His Asn Val Arg Leu Met Trp Gly Asn Gly Leu
            355                 360                 365

Arg Gly Gln Ile Trp Lys Glu Phe Val Gly Arg Phe Gly Ile Lys Lys
            370                 375                 380

Ile Gly Glu Leu Tyr Gly Ser Thr Glu Gly Asn Ser Asn Ile Val Asn
385                 390                 395                 400

Val Asp Asn His Val Gly Ala Cys Gly Phe Met Pro Ile Tyr Pro His
            405                 410                 415

Ile Gly Ser Leu Tyr Pro Val Arg Leu Ile Lys Val Asp Arg Ala Thr
            420                 425                 430

Gly Glu Leu Glu Arg Asp Lys Asn Gly Leu Cys Val Pro Cys Val Pro
            435                 440                 445

Gly Glu Thr Gly Glu Met Val Gly Val Ile Lys Glu Lys Asp Ile Leu
            450                 455                 460

Leu Lys Phe Glu Gly Tyr Val Ser Glu Gly Asp Thr Ala Lys Lys Ile
465                 470                 475                 480

Tyr Arg Asp Val Phe Lys His Gly Asp Lys Val Phe Ala Ser Gly Asp
            485                 490                 495

Ile Leu His Trp Asp Asp Leu Gly Tyr Leu Tyr Phe Val Asp Arg Cys
            500                 505                 510

Gly Asp Thr Phe Arg Trp Lys Gly Glu Asn Val Ser Thr Thr Glu Val
            515                 520                 525

Glu Gly Ile Leu Gln Pro Val Met Asp Val Glu Asp Ala Thr Val Tyr
            530                 535                 540

Gly Val Thr Val Gly Lys Met Glu Gly Arg Ala Gly Met Ala Gly Ile
545                 550                 555                 560

Val Val Lys Asp Gly Thr Asp Val Glu Lys Phe Ile Ala Asp Ile Thr
            565                 570                 575

Ser Arg Leu Thr Glu Asn Leu Ala Ser Tyr Ala Ile Pro Val Phe Ile
            580                 585                 590
```

| | | | | | | | | | | | |
|---|---|---|---|---|---|---|---|---|---|---|---|
|Arg|Leu|Cys|Lys|Glu|Val|Asp|Arg|Thr|Gly|Thr|Phe|Lys|Leu|Lys|Lys|
| |  |   |   |595|   |   |   |600|   |   |   |605|   |   |   |

| | | | | | | | | | | | |
|---|---|---|---|---|---|---|---|---|---|---|---|
|Thr|Asp|Leu|Gln|Lys|Gln|Gly|Tyr|Asp|Leu|Val|Ala|Cys|Lys|Gly|Asp|
|   |610|   |   |   |615|   |   |   |620|   |   |   |   |   |   |

| | | | | | | | | | | | |
|---|---|---|---|---|---|---|---|---|---|---|---|
|Pro|Ile|Tyr|Tyr|Trp|Ser|Ala|Ala|Glu|Lys|Ser|Tyr|Lys|Pro|Leu|Thr|
|625|   |   |   |   |630|   |   |   |635|   |   |   |   |640|   |

| | | | | | | | | | | | |
|---|---|---|---|---|---|---|---|---|---|---|---|
|Asp|Lys|Met|Gln|Gln|Asp|Ile|Asp|Thr|Gly|Val|Tyr|Asp|Arg|Ile|
|   |   |   |645|   |   |   |   |650|   |   |   |655|   |   |

<210> SEQ ID NO 82
<211> LENGTH: 1932
<212> TYPE: DNA
<213> ORGANISM: Cochliobolu heterostrophus

<400> SEQUENCE: 82

| | | | | | |
|---|---|---|---|---|---|
|atggcgtgta|tgcatcaggc|tcagctatac|aatgatctag|aggaattgct|aactggtcca|60|
|tcagtaccca|tcgttgctgg|agctgctgga|gctgcagctc|tcactgccta|cattaacgcc|120|
|aaataccaca|tagcccatga|tctcaagacc|ctcggtggtg|gattgacaca|atcgtccgaa|180|
|gcgattgatt|tcataaaccg|ccgcgtcgca|caaaagcgcg|tcctcacgca|ccacatcttc|240|
|caggagcagg|tccaaaaaca|atcaaatcat|ccctttctta|tctttgaggg|caagacatgg|300|
|tcttacaagg|agttctctga|ggcatacacg|agggtcgcga|actggctgat|tgatgagctg|360|
|gacgtacaag|tagggagat|ggtcgcaatt|gatggcggaa|atagtgcaga|gcacctgatg|420|
|ctttggcttg|cacttgatgc|aatcggtgcg|gctacgagtt|ttttgaactg|gaacctgaca|480|
|ggggcagggt|taattcattg|cataaagcta|tgcgaatgtc|gattcgttat|cgcagacatc|540|
|gatattaaag|cgaacattga|accgtgccgt|ggcgaactgg|aggagacggg|catcaacatt|600|
|cactactatg|acccatcctt|catctcatcg|ctaccgaata|acacgccaat|tcccgacagc|660|
|cgcactgaga|acattgaatt|agattcagta|cgaggactga|tatacacatc|tggaaccact|720|
|ggtctaccta|aaggcgtgtt|tataagcact|ggccgcgagc|ttaggactga|ctggtcgatt|780|
|tcaaagtatc|taaatctcaa|gcccacggat|cgaatgtata|catgtatgcc|gctctaccat|840|
|gccgctgcac|acagcctctg|tacagcatca|gttattcatg|gtggaggtac|cgtggtattg|900|
|agcaggaaat|tctcacacaa|gaagttctgg|cctgaagttg|tggcttcgga|agcaaatatc|960|
|attcagtacg|ttggtgaatt|aggtcgatat|ctcctgaatg|gtccaaagag|tccttacgac|1020|
|agggcccata|aagtccagat|ggcgtggggc|aatggcatgc|gtccagacgt|gtgggaagcg|1080|
|tttcgtgaac|gcttcaacat|accaattatt|catgagctct|atgccgcaac|cgatgggctc|1140|
|gggtcaatga|ccaatcgtaa|cgcgggccct|tttacagcaa|actgtattgc|gctgcgaggg|1200|
|ctgatctggc|actggaaatt|tcgaaatcag|gaagtgctgg|tcaagatgga|tctcgatact|1260|
|gatgagatca|tgagagatcg|caatgggttt|gcgatacgat|gcgctgtcaa|tgaacctgga|1320|
|cagatgctt|ttcggctgac|acccgaaact|ctggctggtg|caccaagcta|ctacaacaac|1380|
|gaaacggcca|cacagagcag|gcggattaca|gatgtgtttc|aaaagggtga|cctgtggttc|1440|
|aagtccggtg|acatgctacg|gcaagacgcc|gaaggccgcg|tctactttgt|cgatcgacta|1500|
|ggcgatacgt|tccgctggaa|atccgaaaac|gtttctacca|atgaagtcgc|ggacgtgatg|1560|
|ggcacatttc|ctcagattgc|tgaaacgaat|gtatacggtg|tccttgtgcc|gggtaacgat|1620|
|ggtcgagtgc|gcagcctcaa|ttgtcatggc|agacggcgtg|acagagtcga|cattcgcttc|1680|
|gctgcccttg|caaagcacgc|ccgagatcgg|ttaccgggtt|atgctgtacc|actgtttctg|1740|
|agggtaactc|cagcacttga|atatacgggc|acattaaaga|ttcagaaagg|acgcctcaag|1800|

-continued

```
caggaaggta tagacccaga taagatttcc ggcgaagata agttatactg gctgccgcct   1860
ggtagcgata tatatttacc atttggaaag atggagtggc agggaattgt agataagcgt   1920
atacggctgt ga                                                       1932
```

<210> SEQ ID NO 83
<211> LENGTH: 643
<212> TYPE: PRT
<213> ORGANISM: Cochliobolu heterostrophus

<400> SEQUENCE: 83

```
Met Ala Cys Met His Gln Ala Gln Leu Tyr Asn Asp Leu Glu Glu Leu
 1               5                  10                  15

Leu Thr Gly Pro Ser Val Pro Ile Val Ala Gly Ala Gly Ala Ala
            20                  25                  30

Ala Leu Thr Ala Tyr Ile Asn Ala Lys Tyr His Ile Ala His Asp Leu
        35                  40                  45

Lys Thr Leu Gly Gly Gly Leu Thr Gln Ser Ser Glu Ala Ile Asp Phe
    50                  55                  60

Ile Asn Arg Arg Val Ala Gln Lys Arg Val Leu Thr His His Ile Phe
65                  70                  75                  80

Gln Glu Gln Val Gln Lys Gln Ser Asn His Pro Phe Leu Ile Phe Glu
                85                  90                  95

Gly Lys Thr Trp Ser Tyr Lys Glu Phe Ser Glu Ala Tyr Thr Arg Val
            100                 105                 110

Ala Asn Trp Leu Ile Asp Glu Leu Asp Val Gln Val Gly Glu Met Val
        115                 120                 125

Ala Ile Asp Gly Gly Asn Ser Ala Glu His Leu Met Leu Trp Leu Ala
    130                 135                 140

Leu Asp Ala Ile Gly Ala Ala Thr Ser Phe Leu Asn Trp Asn Leu Thr
145                 150                 155                 160

Gly Ala Gly Leu Ile His Cys Ile Lys Leu Cys Glu Cys Arg Phe Val
                165                 170                 175

Ile Ala Asp Ile Asp Ile Lys Ala Asn Ile Glu Pro Cys Arg Gly Glu
            180                 185                 190

Leu Glu Glu Thr Gly Ile Asn Ile His Tyr Tyr Asp Pro Ser Phe Ile
        195                 200                 205

Ser Ser Leu Pro Asn Asn Thr Pro Ile Pro Asp Ser Arg Thr Glu Asn
    210                 215                 220

Ile Glu Leu Asp Ser Val Arg Gly Leu Ile Tyr Thr Ser Gly Thr Thr
225                 230                 235                 240

Gly Leu Pro Lys Gly Val Phe Ile Ser Thr Gly Arg Glu Leu Arg Thr
                245                 250                 255

Asp Trp Ser Ile Ser Lys Tyr Leu Asn Leu Lys Pro Thr Asp Arg Met
            260                 265                 270

Tyr Thr Cys Met Pro Leu Tyr His Ala Ala His Ser Leu Cys Thr
        275                 280                 285

Ala Ser Val Ile His Gly Gly Thr Val Val Leu Ser Arg Lys Phe
    290                 295                 300

Ser His Lys Lys Phe Trp Pro Glu Val Val Ala Ser Glu Ala Asn Ile
305                 310                 315                 320

Ile Gln Tyr Val Gly Glu Leu Gly Arg Tyr Leu Leu Asn Gly Pro Lys
                325                 330                 335

Ser Pro Tyr Asp Arg Ala His Lys Val Gln Met Ala Trp Gly Asn Gly
```

```
                   340                 345                 350
Met Arg Pro Asp Val Trp Glu Ala Phe Arg Glu Arg Phe Asn Ile Pro
                355                 360                 365

Ile Ile His Glu Leu Tyr Ala Ala Thr Asp Gly Leu Gly Ser Met Thr
            370                 375                 380

Asn Arg Asn Ala Gly Pro Phe Thr Ala Asn Cys Ile Ala Leu Arg Gly
385                 390                 395                 400

Leu Ile Trp His Trp Lys Phe Arg Asn Gln Glu Val Leu Val Lys Met
                405                 410                 415

Asp Leu Asp Thr Asp Glu Ile Met Arg Asp Arg Asn Gly Phe Ala Ile
            420                 425                 430

Arg Cys Ala Val Asn Glu Pro Gly Gln Met Leu Phe Arg Leu Thr Pro
                435                 440                 445

Glu Thr Leu Ala Gly Ala Pro Ser Tyr Tyr Asn Asn Glu Thr Ala Thr
            450                 455                 460

Gln Ser Arg Arg Ile Thr Asp Val Phe Gln Lys Gly Asp Leu Trp Phe
465                 470                 475                 480

Lys Ser Gly Asp Met Leu Arg Gln Asp Ala Glu Gly Arg Val Tyr Phe
                485                 490                 495

Val Asp Arg Leu Gly Asp Thr Phe Arg Trp Lys Ser Glu Asn Val Ser
            500                 505                 510

Thr Asn Glu Val Ala Asp Val Met Gly Thr Phe Pro Gln Ile Ala Glu
            515                 520                 525

Thr Asn Val Tyr Gly Val Leu Val Pro Gly Asn Asp Gly Arg Val Arg
            530                 535                 540

Ser Leu Asn Cys His Gly Arg Arg Asp Arg Val Asp Ile Arg Phe
545                 550                 555                 560

Ala Ala Leu Ala Lys His Ala Arg Asp Arg Leu Pro Gly Tyr Ala Val
                565                 570                 575

Pro Leu Phe Leu Arg Val Thr Pro Ala Leu Glu Tyr Thr Gly Thr Leu
            580                 585                 590

Lys Ile Gln Lys Gly Arg Leu Lys Gln Glu Gly Ile Asp Pro Asp Lys
            595                 600                 605

Ile Ser Gly Glu Asp Lys Leu Tyr Trp Leu Pro Pro Gly Ser Asp Ile
610                 615                 620

Tyr Leu Pro Phe Gly Lys Met Glu Trp Gln Gly Ile Val Asp Lys Arg
625                 630                 635                 640

Ile Arg Leu

<210> SEQ ID NO 84
<211> LENGTH: 597
<212> TYPE: DNA
<213> ORGANISM: Aspergillus nidulans

<400> SEQUENCE: 84
ctttaccatt catcagcttc attctgcatt tttagcttga cggcagccgg gtctacgctg     60
atcatcggcc gcaagttctc cgcgagaaac ttcataaagg aagcgcgcga gaacgacgcc    120
acggtcatcc agtacgtggg tgagaccttg cgatatctgc tcgccacccc cggtgaaacc    180
gatccagtta ctggcgaaga cctggacaaa agcacaata ttcgagcagt atacggcaac    240
gggctacggc cggatatctg gaaccgcttc aaggagcgct tcaacgtgcc gacggttgcc    300
gaattttatg ctgcaaccga gagcccaggc ggaacatgga actattcaac aaatgacttc    360
actgccggag ccattgggca cactggcgtg cttagtggat ggcttcttgg acgcggcctt    420
```

```
actattgtcg aggtggacca ggaatcacag gaaccatggc gcgatcccca aaccgggttc      480
tgcaagccgg tcccgcgagg cgaagcaggc gagctcctgt atgccattga tccggccgac      540
ccgggcgaga ccttccaggg ctactaccgc aactccttta gagcacactg gcggccg         597
```

<210> SEQ ID NO 85
<211> LENGTH: 199
<212> TYPE: PRT
<213> ORGANISM: Aspergillus nidulans

<400> SEQUENCE: 85

```
Leu Tyr His Ser Ser Ala Ser Phe Cys Ile Phe Ser Leu Thr Ala Ala
 1               5                  10                  15

Gly Ser Thr Leu Ile Ile Gly Arg Lys Phe Ser Ala Arg Asn Phe Ile
            20                  25                  30

Lys Glu Ala Arg Glu Asn Asp Ala Thr Val Ile Gln Tyr Val Gly Glu
        35                  40                  45

Thr Leu Arg Tyr Leu Leu Ala Thr Pro Gly Glu Thr Asp Pro Val Thr
    50                  55                  60

Gly Glu Asp Leu Asp Lys Lys His Asn Ile Arg Ala Val Tyr Gly Asn
65                  70                  75                  80

Gly Leu Arg Pro Asp Ile Trp Asn Arg Phe Lys Glu Arg Phe Asn Val
                85                  90                  95

Pro Thr Val Ala Glu Phe Tyr Ala Ala Thr Glu Ser Pro Gly Gly Thr
            100                 105                 110

Trp Asn Tyr Ser Thr Asn Asp Phe Thr Ala Gly Ala Ile Gly His Thr
        115                 120                 125

Gly Val Leu Ser Gly Trp Leu Leu Gly Arg Gly Leu Thr Ile Val Glu
    130                 135                 140

Val Asp Gln Glu Ser Gln Glu Pro Trp Arg Asp Pro Gln Thr Gly Phe
145                 150                 155                 160

Cys Lys Pro Val Pro Arg Gly Glu Ala Gly Glu Leu Leu Tyr Ala Ile
                165                 170                 175

Asp Pro Ala Asp Pro Gly Glu Thr Phe Gln Gly Tyr Tyr Arg Asn Ser
            180                 185                 190

Phe Arg Ala His Trp Arg Pro
        195
```

<210> SEQ ID NO 86
<211> LENGTH: 522
<212> TYPE: DNA
<213> ORGANISM: Magnaporthe grisea
<220> FEATURE:
<221> NAME/KEY: misc_feature
<222> LOCATION: (1)...(522)
<223> OTHER INFORMATION: n = A,T,C or G

<400> SEQUENCE: 86

```
gcaaaggccg acgcgtggct gcggacgggt aacgtgatca gggcggacaa cgaagggcga       60
ctcttcttcc acgaccggat cggagacacg ttccgatgga agggagagac ngtcagcaca      120
caagaggtca gtttggtgct cggacgcacg gactcaatca aggaggccaa cgtgtacggc      180
gtgacggtgc cgaaccacga cgggcgggcc ggctgcgctg cgctcacgct atcagacgct      240
ctggcgactg aaaagaagct gggcgatgag ctgctaaagg gattggctac tcactcgtcg      300
acttcgcttc ccaagtttgc ggtgccgcag ttcctacggg tggtgcgcgg cgagatgcag      360
tcaacgggca ccaacaagca acagaagcac gacctgaggg tgcagggtgt agagccgggc      420
```

```
aaggtgggcg tagacgaggt gtactggttg cggggaggga catatgtacc attcggaaca    480
gaggattggg atgggttgaa gaagggtctt gtgaagttgt ga                       522
```

<210> SEQ ID NO 87
<211> LENGTH: 173
<212> TYPE: PRT
<213> ORGANISM: Magnaporthe grisea

<400> SEQUENCE: 87

```
Ala Lys Ala Asp Ala Trp Leu Arg Thr Gly Asn Val Ile Arg Ala Asp
 1               5                  10                  15

Asn Glu Gly Arg Leu Phe Phe His Asp Arg Ile Gly Asp Thr Phe Arg
            20                  25                  30

Trp Lys Gly Glu Thr Val Ser Thr Gln Glu Val Ser Leu Val Leu Gly
        35                  40                  45

Arg His Asp Ser Ile Lys Glu Ala Asn Val Tyr Gly Val Thr Val Pro
    50                  55                  60

Asn His Asp Gly Arg Ala Gly Cys Ala Ala Leu Thr Leu Ser Asp Ala
65                  70                  75                  80

Leu Ala Thr Glu Lys Lys Leu Gly Asp Glu Leu Leu Lys Gly Leu Ala
                85                  90                  95

Thr His Ser Ser Thr Ser Leu Pro Lys Phe Ala Val Pro Gln Phe Leu
            100                 105                 110

Arg Val Val Arg Gly Glu Met Gln Ser Thr Gly Thr Asn Lys Gln Gln
        115                 120                 125

Lys His Asp Leu Arg Val Gln Gly Val Glu Pro Gly Lys Val Gly Val
    130                 135                 140

Asp Glu Val Tyr Trp Leu Arg Gly Gly Thr Tyr Val Pro Phe Gly Thr
145                 150                 155                 160

Glu Asp Trp Asp Gly Leu Lys Lys Gly Leu Val Lys Leu
                165                 170
```

<210> SEQ ID NO 88
<211> LENGTH: 1872
<212> TYPE: DNA
<213> ORGANISM: Saccharomyces cerevisiae

<400> SEQUENCE: 88

```
atgtctccca tacaggttgt tgtctttgcc ttgtcaagga ttttcctgct attattcaga    60
cttatcaagc taattataac ccctatccag aaatcactgg gttatctatt tggtaattat   120
tttgatgaat tagaccgtaa atatagatac aaggaggatt ggtatattat tccttacttt   180
ttgaaaagcg tgttttgtta tatcattgat gtgagaagac ataggtttca aaactggtac   240
ttatttatta acaggtcca acaaaatggt gaccatttag cgattagtta cacccgtccc   300
atggccgaaa aggagaatt tcaactcgaa acctttacgt atattgaaac ttataacata   360
gtgttgagat tgtctcatat tttgcatttt gattataacg ttcaggccgg tgactacgtg   420
gcaatcgatt gtactaataa acctcttttc gtatttttat ggctttcttt gtggaacatt   480
ggggctattc cagctttttt aaactataat actaaaggca ctccgctggt tcactcccta   540
aagatttcca atattacgca ggtatttatt gaccctgatg ccagtaatcc gatcagagaa   600
tcggaagaag aaatcaaaaa cgcacttcct gatgttaaat aaactatct tgaagaacaa   660 gacttaatgc atgaactttt aaattcgcaa tcaccggaat tcttacaaca agacaacgtt   720
aggacaccac taggcttgac cgattttaaa ccctctatgt aatttatac atctggaacc   780
```

-continued

```
actggtttgc ctaaatccgc tattatgtct tggagaaaat cctccgtagg ttgtcaagtt      840
tttggtcatg ttttacatat gactaatgaa agcactgtgt tcacagccat gccattgttc      900
cattcaactg ctgccttatt aggtgcgtgc gccattctat ctcacggtgg ttgccttgcg      960
ttatcgcata aattttctgc cagtacattt tggaagcaag tttatttaac aggagccacg     1020
cacatccaat atgtcggaga agtctgtaga tacctgttac atacgccaat ttctaagtat     1080
gaaaagatgc ataaggtgaa ggttgcttat ggtaacgggc tgagacctga catctggcag     1140
gacttcagga agaggttcaa catagaagtt attggtgaat ctatgccgc aactgaagct      1200 ccttttgcta caactacctt ccagaaaggt gactttggaa ttggcgcatg taggaactat     1260
ggtactataa ttcaatggtt tttgtcattc aacaaacat tggtaaggat ggacccaaat      1320
gacgattccg ttatatatag aaattccaag ggtttctgcg aagtggcccc tgttggcgaa     1380
ccaggagaaa tgttaatgag aatctttttc cctaaaaaac cagaaacatc ttttcaaggt     1440
tatcttggta atgccaagga acaaagtcc aaagttgtga gggatgtctt cagacgtggc      1500
gatgcttggt atagatgtgg agatttatta aaagcggacg aatatggatt atggtatttc     1560
cttgatagaa tgggtgatac tttcagatgg aaatctgaaa atgtttccac tactgaagta     1620
gaagatcagt tgacggccag taacaaagaa caatatgcac aagttctagt tgttggtatt     1680
aaagtaccta aatatgaagg tagagctggt tttgcagtta ttaaactaac tgacaactct     1740
cttgacatca ctgcaaagac caaattatta atgattcct tgagccggtt aaatctaccg      1800
tcttatgcta tgcccctatt tgttaaattt gttgatgaaa ttaaaatgac agataacctc     1860
ataaaatttt ga                                                          1872
```

<210> SEQ ID NO 89
<211> LENGTH: 623
<212> TYPE: PRT
<213> ORGANISM: Saccharomyces cerevisiae

<400> SEQUENCE: 89

```
Met Ser Pro Ile Gln Val Val Phe Ala Leu Ser Arg Ile Phe Leu
 1               5                  10                  15

Leu Leu Phe Arg Leu Ile Lys Leu Ile Ile Thr Pro Ile Gln Lys Ser
            20                  25                  30

Leu Gly Tyr Leu Phe Gly Asn Tyr Phe Asp Glu Leu Asp Arg Lys Tyr
        35                  40                  45

Arg Tyr Lys Glu Asp Trp Tyr Ile Ile Pro Tyr Phe Leu Lys Ser Val
    50                  55                  60

Phe Cys Tyr Ile Ile Asp Val Arg Arg His Arg Phe Gln Asn Trp Tyr
65                  70                  75                  80

Leu Phe Ile Lys Gln Val Gln Gln Asn Gly Asp His Leu Ala Ile Ser
                85                  90                  95

Tyr Thr Arg Pro Met Ala Glu Lys Gly Glu Phe Gln Leu Glu Thr Phe
            100                 105                 110

Thr Tyr Ile Glu Thr Tyr Asn Ile Val Leu Arg Leu Ser His Ile Leu
        115                 120                 125

His Phe Asp Tyr Asn Val Gln Ala Gly Asp Tyr Val Ala Ile Asp Cys
    130                 135                 140

Thr Asn Lys Pro Leu Phe Val Phe Leu Trp Leu Ser Leu Trp Asn Ile
145                 150                 155                 160

Gly Ala Ile Pro Ala Phe Leu Asn Tyr Asn Thr Lys Gly Thr Pro Leu
                165                 170                 175
```

-continued

```
Val His Ser Leu Lys Ile Ser Asn Ile Thr Gln Val Phe Ile Asp Pro
            180                 185                 190
Asp Ala Ser Asn Pro Ile Arg Glu Ser Glu Glu Ile Lys Asn Ala
            195                 200                 205
Leu Pro Asp Val Lys Leu Asn Tyr Leu Glu Glu Gln Asp Leu Met His
            210                 215                 220
Glu Leu Leu Asn Ser Gln Ser Pro Glu Phe Leu Gln Gln Asp Asn Val
225                 230                 235                 240
Arg Thr Pro Leu Gly Leu Thr Asp Phe Lys Pro Ser Met Leu Ile Tyr
            245                 250                 255
Thr Ser Gly Thr Thr Gly Leu Pro Lys Ser Ala Ile Met Ser Trp Arg
            260                 265                 270
Lys Ser Ser Val Gly Cys Gln Val Phe Gly His Val Leu His Met Thr
            275                 280                 285
Asn Glu Ser Thr Val Phe Thr Ala Met Pro Leu Phe His Ser Thr Ala
            290                 295                 300
Ala Leu Leu Gly Ala Cys Ala Ile Leu Ser His Gly Gly Cys Leu Ala
305                 310                 315                 320
Leu Ser His Lys Phe Ser Ala Ser Thr Phe Trp Lys Gln Val Tyr Leu
            325                 330                 335
Thr Gly Ala Thr His Ile Gln Tyr Val Gly Glu Val Cys Arg Tyr Leu
            340                 345                 350
Leu His Thr Pro Ile Ser Lys Tyr Glu Lys Met His Lys Val Lys Val
            355                 360                 365
Ala Tyr Gly Asn Gly Leu Arg Pro Asp Ile Trp Gln Asp Phe Arg Lys
            370                 375                 380
Arg Phe Asn Ile Glu Val Ile Gly Glu Phe Tyr Ala Ala Thr Glu Ala
385                 390                 395                 400
Pro Phe Ala Thr Thr Thr Phe Gln Lys Gly Asp Phe Gly Ile Gly Ala
            405                 410                 415
Cys Arg Asn Tyr Gly Thr Ile Ile Gln Trp Phe Leu Ser Phe Gln Gln
            420                 425                 430
Thr Leu Val Arg Met Asp Pro Asn Asp Asp Ser Val Ile Tyr Arg Asn
            435                 440                 445
Ser Lys Gly Phe Cys Glu Val Ala Pro Val Gly Glu Pro Gly Glu Met
            450                 455                 460
Leu Met Arg Ile Phe Phe Pro Lys Lys Pro Glu Thr Ser Phe Gln Gly
465                 470                 475                 480
Tyr Leu Gly Asn Ala Lys Glu Thr Lys Ser Lys Val Val Arg Asp Val
            485                 490                 495
Phe Arg Arg Gly Asp Ala Trp Tyr Arg Cys Gly Asp Leu Leu Lys Ala
            500                 505                 510
Asp Glu Tyr Gly Leu Trp Tyr Phe Leu Asp Arg Met Gly Asp Thr Phe
            515                 520                 525
Arg Trp Lys Ser Glu Asn Val Ser Thr Thr Glu Val Glu Asp Gln Leu
            530                 535                 540
Thr Ala Ser Asn Lys Glu Gln Tyr Ala Gln Val Leu Val Gly Ile
545                 550                 555                 560
Lys Val Pro Lys Tyr Glu Gly Arg Ala Gly Phe Ala Val Ile Lys Leu
            565                 570                 575
Thr Asp Asn Ser Leu Asp Ile Thr Ala Lys Thr Lys Leu Leu Asn Asp
            580                 585                 590
```

Ser Leu Ser Arg Leu Asn Leu Pro Ser Tyr Ala Met Pro Leu Phe Val
    595                 600                 605

Lys Phe Val Asp Glu Ile Lys Met Thr Asp Asn Leu Ile Lys Phe
    610                 615                 620

<210> SEQ ID NO 90
<211> LENGTH: 1794
<212> TYPE: DNA
<213> ORGANISM: Mycobacterium tuberculosis

<400> SEQUENCE: 90

| | | | | | |
|---|---|---|---|---|---|
| gtgtccgatt | actacggcgg | cgcacacaca | acggtcaggc | tgatcgacct | ggcaactcgg | 60 |
| atgccgcgag | tgttggcgga | cacgccggtg | attgtgcgtg | gggcaatgac | cgggctgctg | 120 |
| gcccggccga | attccaaggc | gtcgatcggc | acggtgttcc | aggaccgggc | cgctcgctac | 180 |
| ggtgaccgag | tcttcctgaa | attcggcgat | cagcagctga | cctaccgcga | cgctaacgcc | 240 |
| accgccaacc | ggtacgccgc | ggtgttggcc | gcccgcggcg | tcggcccggg | cgacgtcgtt | 300 |
| ggcatcatgt | tgcgtaactc | acccagcaca | gtcttggcga | tgctggccac | ggtcaagtgc | 360 |
| ggcgctatcg | ccggcatgct | caactaccac | cagcgcggcg | aggtgttggc | gcacagcctg | 420 |
| ggtctgctgg | acgcgaaggt | actgatcgca | gagtccgact | tggtcagcgc | cgtcgccgaa | 480 |
| tgcggcgcct | cgcgcggccg | ggtagcgggc | gacgtgctga | ccgtcgagga | cgtggagcga | 540 |
| ttcgccacaa | cggcgcccgc | caccaacccg | gcgtcggcgt | cggcggtgca | agccaaagac | 600 |
| accgcgttct | acatcttcac | ctcgggcacc | accggatttc | ccaaggccag | tgtcatgacg | 660 |
| catcatcggt | ggctgcgggc | gctggccgtc | ttcggaggga | tggggctgcg | gctgaagggt | 720 |
| tccgacacgc | tctacagctg | cctgccgctg | taccacaaca | acgcgttaac | ggtcgcggtg | 780 |
| tcgtcggtga | tcaattctgg | ggcgaccctg | gcgctgggta | agtcgttttc | ggcgtcgcgg | 840 |
| ttctgggatg | aggtgattgc | caaccgggcg | acggcgttcg | tctacatcgg | cgaaatctgc | 900 |
| cgttatctgc | tcaaccagcc | ggccaagccg | accgaccgtg | cccaccaggt | gcgggtgatc | 960 |
| tgcggtaacg | ggctgcggcc | ggagatctgg | gatgagttca | ccacccgctt | cggggtcgcg | 1020 |
| cgggtgtgcg | agttctacgc | cgccagcgaa | ggcaactcgg | cctttatcaa | catcttcaac | 1080 |
| gtgcccagga | ccgccggggt | atcgccgatg | ccgcttgcct | tgtggaata | cgacctggac | 1140 |
| accggcgatc | cgctgcggga | tgcgagcggg | cgagtgcgtc | gggtacccga | cggtgaaccc | 1200 |
| ggcctgttgc | ttagccgggt | caaccggctg | cagccgttcg | acggctacac | cgacccggtt | 1260 |
| gccagcgaaa | agaagttggt | gcgcaacgct | tttcgagatg | gcgactgttg | gttcaacacc | 1320 |
| ggtgacgtga | tgagcccgca | gggcatgggc | catgccgcct | tcgtcgatcg | gctgggcgac | 1380 |
| accttccgct | ggaagggcga | gaatgtcgcc | accactcagg | tcgaagcggc | actggcctcc | 1440 |
| gaccagaccg | tcgaggagtg | cacggtctac | ggcgtccaga | ttccgcgcac | cggcgggcgc | 1500 |
| gccggaatgg | ccgcgatcac | actgcgcgct | ggcgccgaat | tcgacggcca | ggcgctggcc | 1560 |
| cgaacggttt | acggtcactt | gcccggctat | gcacttccgc | tctttgttcg | ggtagtgggg | 1620 |
| tcgctggcgc | acaccacgac | gttcaagagt | cgcaaggtga | agttgcgcaa | ccaggcctat | 1680 |
| ggcgccgaca | tcgaggatcc | gctgtacgta | ctggccggcc | cggacgaagg | atatgtgccg | 1740 |
| tactacgccg | aataccctga | ggaggtttcg | ctcggaaggc | gaccgcaggg | ctag | 1794 |

<210> SEQ ID NO 91
<211> LENGTH: 597
<212> TYPE: PRT
<213> ORGANISM: Mycobacterium tuberculosis -continued

```
<400> SEQUENCE: 91

Met Ser Asp Tyr Tyr Gly Gly Ala His Thr Thr Val Arg Leu Ile Asp
 1               5                  10                  15

Leu Ala Thr Arg Met Pro Arg Val Leu Ala Asp Thr Pro Val Ile Val
                20                  25                  30

Arg Gly Ala Met Thr Gly Leu Leu Ala Arg Pro Asn Ser Lys Ala Ser
            35                  40                  45

Ile Gly Thr Val Phe Gln Asp Arg Ala Ala Arg Tyr Gly Asp Arg Val
        50                  55                  60

Phe Leu Lys Phe Gly Asp Gln Gln Leu Thr Tyr Arg Asp Ala Asn Ala
65                  70                  75                  80

Thr Ala Asn Arg Tyr Ala Ala Val Leu Ala Arg Gly Val Gly Pro
                85                  90                  95

Gly Asp Val Val Gly Ile Met Leu Arg Asn Ser Pro Ser Thr Val Leu
            100                 105                 110

Ala Met Leu Ala Thr Val Lys Cys Gly Ala Ile Ala Gly Met Leu Asn
        115                 120                 125

Tyr His Gln Arg Gly Glu Val Leu Ala His Ser Leu Gly Leu Leu Asp
    130                 135                 140

Ala Lys Val Leu Ile Ala Glu Ser Asp Leu Val Ser Ala Val Ala Glu
145                 150                 155                 160

Cys Gly Ala Ser Arg Gly Arg Val Ala Gly Asp Val Leu Thr Val Glu
                165                 170                 175

Asp Val Glu Arg Phe Ala Thr Thr Ala Pro Ala Thr Asn Pro Ala Ser
            180                 185                 190

Ala Ser Ala Val Gln Ala Lys Asp Thr Ala Phe Tyr Ile Phe Thr Ser
        195                 200                 205

Gly Thr Thr Gly Phe Pro Lys Ala Ser Val Met Thr His His Arg Trp
    210                 215                 220

Leu Arg Ala Leu Ala Val Phe Gly Gly Met Gly Leu Arg Leu Lys Gly
225                 230                 235                 240

Ser Asp Thr Leu Tyr Ser Cys Leu Pro Leu Tyr His Asn Asn Ala Leu
                245                 250                 255

Thr Val Ala Val Ser Ser Val Ile Asn Ser Gly Ala Thr Leu Ala Leu
            260                 265                 270

Gly Lys Ser Phe Ser Ala Ser Arg Phe Trp Asp Glu Val Ile Ala Asn
        275                 280                 285

Arg Ala Thr Ala Phe Val Tyr Ile Gly Glu Ile Cys Arg Tyr Leu Leu
    290                 295                 300

Asn Gln Pro Ala Lys Pro Thr Asp Arg Ala His Gln Val Arg Val Ile
305                 310                 315                 320

Cys Gly Asn Gly Leu Arg Pro Glu Ile Trp Asp Glu Phe Thr Thr Arg
                325                 330                 335

Phe Gly Val Ala Arg Val Cys Glu Phe Tyr Ala Ala Ser Glu Gly Asn
            340                 345                 350

Ser Ala Phe Ile Asn Ile Phe Asn Val Pro Arg Thr Ala Gly Val Ser
        355                 360                 365

Pro Met Pro Leu Ala Phe Val Glu Tyr Asp Leu Asp Thr Gly Asp Pro
    370                 375                 380

Leu Arg Asp Ala Ser Gly Arg Val Arg Val Pro Asp Gly Glu Pro
385                 390                 395                 400

Gly Leu Leu Leu Ser Arg Val Asn Arg Leu Gln Pro Phe Asp Gly Tyr
```

```
                      405                 410                 415
Thr Asp Pro Val Ala Ser Glu Lys Lys Leu Val Arg Asn Ala Phe Arg
            420                 425                 430
Asp Gly Asp Cys Trp Phe Asn Thr Gly Asp Val Met Ser Pro Gln Gly
            435                 440                 445
Met Gly His Ala Ala Phe Val Asp Arg Leu Gly Asp Thr Phe Arg Trp
            450                 455                 460
Lys Gly Glu Asn Val Ala Thr Thr Gln Val Glu Ala Leu Ala Ser
465                 470                 475                 480
Asp Gln Thr Val Glu Glu Cys Thr Val Tyr Gly Val Gln Ile Pro Arg
                485                 490                 495
Thr Gly Gly Arg Ala Gly Met Ala Ala Ile Thr Leu Arg Ala Gly Ala
            500                 505                 510
Glu Phe Asp Gly Gln Ala Leu Ala Arg Thr Val Tyr Gly His Leu Pro
            515                 520                 525
Gly Tyr Ala Leu Pro Leu Phe Val Arg Val Val Gly Ser Leu Ala His
            530                 535                 540
Thr Thr Thr Phe Lys Ser Arg Lys Val Glu Leu Arg Asn Gln Ala Tyr
545                 550                 555                 560
Gly Ala Asp Ile Glu Asp Pro Leu Tyr Val Leu Ala Gly Pro Asp Glu
                565                 570                 575
Gly Tyr Val Pro Tyr Tyr Ala Glu Tyr Pro Glu Glu Val Ser Leu Gly
            580                 585                 590
Arg Arg Pro Gln Gly
            595

<210> SEQ ID NO 92
<211> LENGTH: 646
<212> TYPE: PRT
<213> ORGANISM: Mus musculus

<400> SEQUENCE: 92

Met Arg Ala Pro Gly Ala Gly Thr Ala Ser Val Ala Ser Leu Ala Leu
1               5                   10                  15
Leu Trp Phe Leu Gly Leu Pro Trp Thr Trp Ser Ala Ala Ala Ala Phe
            20                  25                  30
Cys Val Tyr Val Gly Gly Gly Trp Arg Phe Leu Arg Ile Val Cys
            35                  40                  45
Lys Thr Ala Arg Arg Asp Leu Phe Gly Leu Ser Val Leu Ile Arg Val
        50                  55                  60
Arg Leu Glu Leu Arg Arg His Arg Arg Ala Gly Asp Thr Ile Pro Cys
65                  70                  75                  80
Ile Phe Gln Ala Val Ala Arg Arg Gln Pro Glu Arg Leu Ala Leu Val
                85                  90                  95
Asp Ala Ser Ser Gly Ile Cys Trp Thr Phe Ala Gln Leu Asp Thr Tyr
            100                 105                 110
Ser Asn Ala Val Ala Asn Leu Phe Arg Gln Leu Gly Phe Ala Pro Gly
            115                 120                 125
Asp Val Val Ala Val Phe Leu Glu Gly Arg Pro Glu Phe Val Gly Leu
            130                 135                 140
Trp Leu Gly Leu Ala Lys Ala Gly Val Val Ala Ala Leu Leu Asn Val
145                 150                 155                 160
Asn Leu Arg Arg Glu Pro Leu Ala Phe Cys Leu Gly Thr Ser Ala Ala
                165                 170                 175
```

-continued

```
Lys Ala Leu Ile Tyr Gly Gly Glu Met Ala Ala Val Ala Glu Val
            180                 185                 190
Ser Glu Gln Leu Gly Lys Ser Leu Leu Lys Phe Cys Ser Gly Asp Leu
        195                 200                 205
Gly Pro Glu Ser Ile Leu Pro Asp Thr Gln Leu Leu Asp Pro Met Leu
    210                 215                 220
Ala Glu Ala Pro Thr Thr Pro Leu Ala Gln Ala Pro Gly Lys Gly Met
225                 230                 235                 240
Asp Asp Arg Leu Phe Tyr Ile Tyr Thr Ser Gly Thr Thr Gly Leu Pro
                245                 250                 255
Lys Ala Ala Ile Val Val His Ser Arg Tyr Tyr Arg Ile Ala Ala Phe
            260                 265                 270
Gly His His Ser Tyr Ser Met Arg Ala Ala Asp Val Leu Tyr Asp Cys
        275                 280                 285
Leu Pro Leu Tyr His Ser Ala Gly Asn Ile Met Gly Val Gly Gln Cys
    290                 295                 300
Val Ile Tyr Gly Leu Thr Val Leu Arg Lys Lys Phe Ser Ala Ser
305                 310                 315                 320
Arg Phe Trp Asp Asp Cys Val Lys Tyr Asn Cys Thr Val Val Gln Tyr
                325                 330                 335
Ile Gly Glu Ile Cys Arg Tyr Leu Leu Arg Gln Pro Val Arg Asp Val
            340                 345                 350
Glu Gln Arg His Arg Val Arg Leu Ala Val Gly Asn Gly Leu Arg Pro
        355                 360                 365
Ala Ile Trp Glu Glu Phe Thr Gln Arg Phe Gly Val Pro Gln Ile Gly
    370                 375                 380
Glu Phe Tyr Gly Ala Thr Glu Cys Asn Cys Ser Ile Ala Asn Met Asp
385                 390                 395                 400
Gly Lys Val Gly Ser Cys Gly Phe Asn Ser Arg Ile Leu Thr His Val
                405                 410                 415
Tyr Pro Ile Arg Leu Val Lys Val Asn Glu Asp Thr Met Glu Pro Leu
            420                 425                 430
Arg Asp Ser Glu Gly Leu Cys Ile Pro Cys Gln Pro Gly Glu Pro Gly
        435                 440                 445
Leu Leu Val Gly Gln Ile Asn Gln Gln Asp Pro Leu Arg Arg Phe Asp
    450                 455                 460
Gly Tyr Val Ser Asp Ser Ala Thr Asn Lys Lys Ile Ala His Ser Val
465                 470                 475                 480
Phe Arg Lys Gly Asp Ser Ala Tyr Leu Ser Gly Asp Val Leu Val Met
                485                 490                 495
Asp Glu Leu Gly Tyr Met Tyr Phe Arg Asp Arg Ser Gly Asp Thr Phe
            500                 505                 510
Arg Trp Arg Gly Glu Asn Val Ser Thr Thr Glu Val Glu Ala Val Leu
        515                 520                 525
Ser Arg Leu Leu Gly Gln Thr Asp Val Ala Val Tyr Gly Val Ala Val
    530                 535                 540
Pro Gly Val Glu Gly Lys Ala Gly Met Ala Ala Ile Ala Asp Pro His
545                 550                 555                 560
Ser Gln Leu Asp Pro Asn Ser Met Tyr Gln Glu Leu Gln Lys Val Leu
                565                 570                 575
Ala Ser Tyr Ala Arg Pro Ile Phe Leu Arg Leu Leu Pro Gln Val Asp
            580                 585                 590
Thr Thr Gly Thr Phe Lys Ile Gln Lys Thr Arg Leu Gln Arg Glu Gly
```

```
                  595                 600                 605

Phe Asp Pro Arg Gln Thr Ser Asp Arg Leu Phe Phe Leu Asp Leu Lys
            610                 615                 620

Gln Gly Arg Tyr Leu Pro Leu Asp Glu Arg Val His Ala Arg Ile Cys
625                 630                 635                 640

Ala Gly Asp Phe Ser Leu
                645

<210> SEQ ID NO 93
<211> LENGTH: 620
<212> TYPE: PRT
<213> ORGANISM: Mus musculus
<220> FEATURE:
<221> NAME/KEY: VARIANT
<222> LOCATION: (1)...(620)
<223> OTHER INFORMATION: Xaa = Any Amino Acid

<400> SEQUENCE: 93

Met Leu Pro Val Leu Tyr Thr Gly Leu Ala Gly Leu Leu Leu Leu Pro
  1               5                  10                  15

Leu Leu Leu Thr Cys Cys Pro Tyr Leu Leu Gln Asp Val Arg Tyr
             20                  25                  30

Phe Leu Arg Leu Ala Asn Met Ala Arg Arg Val Arg Ser Tyr Arg Gln
         35                  40                  45

Arg Arg Pro Val Arg Thr Ile Leu Arg Ala Phe Leu Glu Gln Ala Arg
     50                  55                  60

Lys Thr Pro His Lys Pro Phe Leu Leu Phe Arg Asp Glu Thr Leu Thr
 65                  70                  75                  80

Tyr Ala Gln Val Asp Arg Arg Ser Asn Gln Val Ala Arg Ala Leu His
                 85                  90                  95

Asp Gln Leu Gly Leu Arg Gln Gly Asp Cys Val Ala Leu Phe Met Gly
            100                 105                 110

Asn Glu Pro Ala Tyr Val Trp Ile Trp Leu Gly Leu Leu Lys Leu Gly
        115                 120                 125

Cys Pro Met Ala Cys Leu Asn Tyr Asn Ile Arg Ala Lys Ser Leu Leu
    130                 135                 140

His Cys Phe Gln Cys Cys Gly Ala Lys Val Leu Leu Ala Ser Pro Asp
145                 150                 155                 160

Leu Gln Glu Ala Val Glu Glu Val Leu Pro Thr Leu Lys Lys Asp Ala
                165                 170                 175

Val Ser Val Phe Tyr Val Ser Arg Thr Ser Asn Thr Asn Gly Val Asp
            180                 185                 190

Thr Ile Leu Asp Lys Val Asp Gly Val Ser Ala Glu Pro Thr Pro Glu
        195                 200                 205

Ser Trp Arg Ser Glu Val Thr Phe Thr Thr Pro Ala Val Tyr Ile Tyr
    210                 215                 220

Thr Ser Gly Thr Thr Gly Leu Pro Lys Ala Ala Thr Ile Asn His His
225                 230                 235                 240

Arg Leu Arg Tyr Gly Thr Gly Leu Ala Met Ser Ser Gly Ile Thr Ala
                245                 250                 255

Gln Asp Val Ile Tyr Thr Thr Met Pro Leu Tyr His Ser Ala Ala Leu
            260                 265                 270

Met Ile Gly Leu His Gly Cys Ile Val Val Gly Ala Xaa Xaa Xaa Leu
        275                 280                 285

Cys Asp Lys Phe Ser Ala Ser Gln Phe Trp Asp Asp Cys Arg Lys Tyr
    290                 295                 300
```

```
Asn Val Thr Val Ile Gln Tyr Ile Gly Glu Leu Leu Arg Tyr Leu Cys
305                 310                 315                 320

Asn Thr Pro Gln Lys Pro Asn Asp Arg Asp His Lys Val Lys Lys Ala
            325                 330                 335

Leu Gly Asn Gly Leu Arg Gly Asp Val Trp Arg Glu Phe Ile Lys Arg
            340                 345                 350

Phe Gly Asp Ile His Val Tyr Glu Phe Tyr Ala Ser Thr Glu Gly Asn
            355                 360                 365

Ile Gly Phe Val Asn Tyr Pro Arg Lys Ile Gly Ala Val Gly Arg Ala
370                 375                 380

Asn Tyr Leu Gln Arg Lys Val Ala Arg Tyr Glu Leu Ile Lys Tyr Asp
385                 390                 395                 400

Val Glu Lys Asp Glu Pro Val Arg Asp Ala Asn Gly Tyr Cys Ile Lys
                405                 410                 415

Val Pro Lys Gly Glu Val Gly Leu Leu Val Cys Lys Ile Thr Gln Leu
            420                 425                 430

Thr Pro Phe Ile Gly Tyr Ala Gly Gly Lys Thr Gln Thr Glu Lys Lys
            435                 440                 445

Lys Leu Arg Asp Val Phe Lys Lys Gly Asp Ile Tyr Phe Asn Ser Gly
450                 455                 460

Asp Leu Leu Met Ile Asp Arg Glu Asn Phe Val Tyr Phe His Asp Arg
465                 470                 475                 480

Val Gly Asp Thr Phe Arg Trp Lys Gly Glu Asn Val Ala Thr Thr Glu
                485                 490                 495

Val Ala Asp Ile Val Gly Leu Val Asp Phe Val Glu Glu Val Asn Val
            500                 505                 510

Tyr Gly Val Pro Val Pro Gly His Glu Gly Arg Ile Gly Met Ala Ser
            515                 520                 525

Leu Lys Ile Lys Glu Asn Tyr Glu Phe Asn Gly Lys Lys Leu Phe Gln
            530                 535                 540

His Ile Ala Glu Tyr Leu Pro Ser Tyr Ala Arg Pro Arg Phe Leu Arg
545                 550                 555                 560

Ile Gln Asp Thr Ile Glu Ile Thr Gly Thr Phe Lys His Arg Lys Val
                565                 570                 575

Thr Leu Met Glu Glu Gly Phe Asn Pro Thr Val Ile Lys Asp Thr Leu
            580                 585                 590

Tyr Phe Met Asp Asp Ala Glu Lys Thr Phe Val Pro Met Thr Glu Asn
            595                 600                 605

Ile Tyr Asn Ala Ile Ile Asp Lys Thr Leu Lys Leu
610                 615                 620

<210> SEQ ID NO 94
<211> LENGTH: 613
<212> TYPE: PRT
<213> ORGANISM: Mus musculus

<400> SEQUENCE: 94

Ala Ala Asp Pro Glu Ser Ser Glu Ser Gly Cys Ser Leu Ala Trp Arg
1               5                   10                  15

Leu Ala Tyr Leu Ala Arg Glu Gln Pro Thr His Thr Phe Leu Ile His
            20                  25                  30

Gly Ala Gln Arg Phe Ser Tyr Ala Glu Ala Glu Arg Glu Ser Asn Arg
            35                  40                  45

Ile Ala Arg Ala Phe Leu Arg Ala Arg Gly Trp Thr Gly Gly Arg Arg
```

-continued

```
            50                  55                  60
Gly Ser Gly Arg Gly Ser Thr Glu Glu Gly Ala Arg Val Ala Pro Pro
65                  70                  75                  80
Ala Gly Asp Ala Ala Arg Gly Thr Thr Ala Pro Pro Leu Ala Pro
                85                  90                  95
Gly Ala Thr Val Ala Leu Leu Leu Pro Ala Gly Pro Asp Phe Leu Trp
                100                 105                 110
Ile Trp Phe Gly Leu Ala Lys Ala Gly Leu Arg Thr Ala Phe Val Pro
            115                 120                 125
Thr Ala Leu Arg Arg Gly Pro Leu Leu His Cys Leu Arg Ser Cys Gly
130                 135                 140
Ala Ser Ala Leu Val Leu Ala Thr Glu Phe Leu Glu Ser Leu Glu Pro
145                 150                 155                 160
Asp Leu Pro Ala Leu Arg Ala Met Gly Leu His Leu Trp Ala Thr Gly
                165                 170                 175
Pro Glu Thr Asn Val Ala Gly Ile Ser Asn Leu Leu Ser Glu Ala Ala
                180                 185                 190
Asp Gln Val Asp Glu Pro Val Pro Gly Tyr Leu Ser Ala Pro Gln Asn
            195                 200                 205
Ile Met Asp Thr Cys Leu Tyr Ile Phe Thr Ser Gly Thr Thr Gly Leu
210                 215                 220
Pro Lys Ala Ala Arg Ile Ser His Leu Lys Val Leu Gln Cys Gln Gly
225                 230                 235                 240
Phe Tyr His Leu Cys Gly Val His Gln Glu Asp Val Ile Tyr Leu Ala
                245                 250                 255
Leu Pro Leu Tyr His Met Ser Gly Ser Leu Leu Gly Ile Val Gly Cys
                260                 265                 270
Leu Gly Ile Gly Ala Thr Val Val Leu Lys Pro Lys Phe Ser Ala Ser
            275                 280                 285
Gln Phe Trp Asp Asp Cys Gln Lys His Arg Val Thr Val Phe Gln Tyr
290                 295                 300
Ile Gly Glu Leu Cys Arg Tyr Leu Val Asn Gln Pro Pro Ser Lys Ala
305                 310                 315                 320
Glu Phe Asp His Lys Val Arg Leu Ala Val Gly Ser Gly Leu Arg Pro
                325                 330                 335
Asp Thr Trp Glu Arg Phe Leu Arg Arg Phe Gly Pro Leu Gln Ile Leu
                340                 345                 350
Glu Thr Tyr Gly Met Thr Glu Gly Asn Val Ala Thr Phe Asn Tyr Thr
            355                 360                 365
Gly Arg Gln Gly Ala Val Gly Arg Ala Ser Trp Leu Tyr Lys His Ile
370                 375                 380
Phe Pro Phe Ser Leu Ile Arg Tyr Asp Val Met Thr Gly Glu Pro Ile
385                 390                 395                 400
Arg Asn Ala Gln Gly His Cys Met Thr Thr Ser Pro Gly Glu Pro Gly
                405                 410                 415
Leu Leu Val Ala Pro Val Ser Gln Ser Pro Phe Leu Gly Tyr Ala
                420                 425                 430
Gly Ala Pro Glu Leu Ala Lys Asp Lys Leu Leu Lys Asp Val Phe Trp
            435                 440                 445
Ser Gly Asp Val Phe Asn Thr Gly Asp Leu Leu Val Cys Asp Glu
            450                 455                 460
Gln Gly Phe Leu His Phe His Asp Arg Thr Gly Asp Thr Ile Arg Trp
465                 470                 475                 480
```

```
Lys Gly Glu Asn Val Ala Thr Thr Glu Val Ala Glu Val Leu Glu Thr
                485                 490                 495

Leu Asp Phe Leu Gln Glu Val Asn Ile Tyr Gly Val Thr Val Pro Gly
            500                 505                 510

His Glu Gly Arg Ala Gly Met Ala Ala Leu Ala Leu Arg Pro Pro Gln
        515                 520                 525

Ala Leu Asn Leu Val Gln Leu Tyr Ser His Val Ser Glu Asn Leu Pro
    530                 535                 540

Pro Tyr Ala Arg Pro Arg Phe Leu Arg Leu Gln Glu Ser Leu Ala Thr
545                 550                 555                 560

Thr Glu Thr Phe Lys Gln Gln Lys Val Arg Met Ala Asn Glu Gly Phe
                565                 570                 575

Asp Pro Ser Val Leu Ser Asp Pro Leu Tyr Val Leu Asp Gln Asp Ile
            580                 585                 590

Gly Ala Tyr Leu Pro Leu Thr Pro Ala Arg Tyr Ser Ala Leu Leu Ser
        595                 600                 605

Gly Asp Leu Arg Ile
    610

<210> SEQ ID NO 95
<211> LENGTH: 506
<212> TYPE: PRT
<213> ORGANISM: Mus musculus

<400> SEQUENCE: 95

His Ala Ser Ala His Ala Ser Gly Met Ala Lys Leu Gly Val Glu Ala
1               5                   10                  15

Ala Leu Ile Asn Thr Asn Leu Arg Arg Asp Ala Leu Arg His Cys Leu
            20                  25                  30

Asp Thr Ser Lys Ala Arg Ala Leu Ile Phe Gly Ser Glu Met Ala Ser
        35                  40                  45

Ala Ile Cys Glu Ile His Ala Ser Leu Glu Pro Thr Leu Ser Leu Phe
    50                  55                  60

Cys Ser Gly Ser Trp Glu Pro Ser Thr Val Pro Val Ser Thr Glu His
65                  70                  75                  80

Leu Asp Pro Leu Leu Glu Asp Ala Pro Lys His Leu Pro Ser His Pro
                85                  90                  95

Asp Lys Gly Phe Thr Asp Lys Leu Phe Tyr Ile Tyr Thr Ser Gly Thr
            100                 105                 110

Thr Gly Leu Pro Lys Ala Ala Ile Val Val His Ser Arg Tyr Tyr Arg
        115                 120                 125

Met Ala Ser Leu Val Tyr Tyr Gly Phe Arg Met Arg Pro Asp Asp Ile
    130                 135                 140

Val Tyr Asp Cys Leu Pro Leu Tyr His Ser Ser Arg Lys His Arg Gly
145                 150                 155                 160

Asp Trp Gln Cys Leu Leu His Gly Met Thr Val Val Ile Arg Lys Lys
                165                 170                 175

Phe Ser Ala Ser Arg Phe Trp Asp Asp Cys Ile Lys Tyr Asn Cys Thr
            180                 185                 190

Val Val Gln Tyr Ile Gly Glu Leu Cys Arg Tyr Leu Leu Asn Gln Pro
        195                 200                 205

Pro Arg Glu Ala Glu Ser Arg His Lys Val Arg Met Ala Leu Gly Asn
    210                 215                 220

Gly Leu Arg Gln Ser Ile Trp Thr Asp Phe Ser Ser Arg Phe His Ile
```

```
                   225                 230                 235                 240
Pro Gln Val Ala Glu Phe Tyr Gly Ala Thr Glu Cys Asn Cys Ser Leu
                        245                 250                 255

Gly Asn Phe Asp Ser Arg Val Gly Ala Cys Gly Phe Asn Ser Arg Ile
            260                 265                 270

Leu Ser Phe Val Tyr Pro Ile Arg Leu Val Arg Val Asn Glu Asp Thr
        275                 280                 285

Met Glu Leu Ile Arg Gly Pro Asp Gly Val Cys Ile Pro Cys Gln Pro
    290                 295                 300

Gly Gln Pro Gly Gln Leu Val Gly Arg Ile Ile Gln Gln Asp Pro Leu
305                 310                 315                 320

Arg Arg Phe Asp Gly Tyr Leu Asn Gln Gly Ala Asn Asn Lys Lys Ile
                325                 330                 335

Ala Asn Asp Val Phe Lys Lys Gly Asp Gln Ala Tyr Leu Thr Gly Asp
            340                 345                 350

Val Leu Val Met Asp Glu Leu Gly Tyr Leu Tyr Phe Arg Asp Arg Thr
        355                 360                 365

Gly Asp Thr Phe Arg Trp Lys Gly Glu Asn Val Ser Thr Thr Glu Val
    370                 375                 380

Glu Gly Thr Leu Ser Arg Leu Leu His Met Ala Asp Val Ala Val Tyr
385                 390                 395                 400

Gly Val Glu Val Pro Gly Thr Glu Gly Arg Ala Gly Met Ala Ala Val
                405                 410                 415

Ala Ser Pro Ile Ser Asn Cys Asp Leu Glu Ser Phe Ala Gln Thr Leu
            420                 425                 430

Lys Lys Glu Leu Pro Leu Tyr Ala Arg Pro Ile Phe Leu Arg Phe Leu
        435                 440                 445

Pro Glu Leu His Lys Thr Gly Thr Phe Lys Phe Gln Lys Thr Glu Leu
    450                 455                 460

Arg Lys Glu Gly Phe Asp Pro Ser Val Val Lys Asp Pro Leu Phe Tyr
465                 470                 475                 480

Leu Asp Ala Arg Lys Gly Cys Tyr Val Ala Leu Asp Gln Glu Ala Tyr
                485                 490                 495

Thr Arg Ile Gln Ala Gly Glu Glu Lys Leu
            500                 505

<210> SEQ ID NO 96
<211> LENGTH: 662
<212> TYPE: PRT
<213> ORGANISM: Mus musculus

<400> SEQUENCE: 96

Met Ala Leu Ala Leu Arg Trp Phe Leu Gly Asp Pro Thr Cys Leu Val
  1               5                  10                  15

Leu Leu Gly Leu Ala Leu Leu Gly Arg Pro Trp Ile Ser Ser Trp Met
                 20                  25                  30

Pro His Trp Leu Ser Leu Val Gly Ala Ala Leu Thr Leu Phe Leu Leu
             35                  40                  45

Pro Leu Gln Pro Pro Gly Leu Arg Trp Leu His Lys Asp Val Ala
         50                  55                  60

Phe Thr Phe Lys Met Leu Phe Tyr Gly Leu Lys Phe Arg Arg Arg Leu
 65                  70                  75                  80

Asn Lys His Pro Pro Glu Thr Phe Val Asp Ala Leu Glu Arg Gln Ala
                 85                  90                  95
```

```
Leu Ala Trp Pro Asp Arg Val Ala Leu Val Cys Thr Gly Ser Glu Gly
            100                 105                 110

Ser Ser Ile Thr Asn Ser Gln Leu Asp Ala Arg Ser Cys Gln Ala Ala
            115                 120                 125

Trp Val Leu Lys Ala Lys Leu Lys Asp Ala Val Ile Gln Asn Thr Arg
            130                 135                 140

Asp Ala Ala Ile Leu Val Leu Pro Ser Lys Thr Ile Ser Ala Leu
145                 150                 155                 160

Ser Val Phe Leu Gly Leu Ala Lys Leu Gly Cys Pro Val Ala Trp Ile
                165                 170                 175

Asn Pro His Ser Arg Gly Met Pro Leu Leu His Ser Val Arg Ser Ser
                180                 185                 190

Gly Ala Ser Val Leu Ile Val Asp Pro Asp Leu Gln Glu Asn Leu Glu
                195                 200                 205

Glu Val Leu Pro Lys Leu Leu Ala Glu Asn Ile His Cys Phe Tyr Leu
            210                 215                 220

Gly His Ser Ser Pro Thr Pro Gly Val Glu Ala Leu Gly Ala Ser Leu
225                 230                 235                 240

Asp Ala Ala Pro Ser Asp Pro Val Pro Ala Ser Leu Arg Ala Thr Ile
                245                 250                 255

Lys Trp Lys Ser Pro Ala Ile Phe Ile Phe Thr Ser Gly Thr Thr Gly
                260                 265                 270

Leu Pro Lys Pro Ala Ile Leu Ser His Glu Arg Val Ile Gln Val Ser
            275                 280                 285

Asn Val Leu Ser Phe Cys Gly Cys Arg Ala Asp Asp Val Val Tyr Asp
            290                 295                 300

Val Leu Pro Leu Tyr His Thr Ile Gly Leu Val Leu Gly Phe Leu Gly
305                 310                 315                 320

Cys Leu Gln Val Gly Ala Thr Cys Val Leu Ala Pro Lys Phe Ser Ala
                325                 330                 335

Ser Arg Phe Trp Ala Glu Cys Arg Gln His Gly Val Thr Val Ile Leu
            340                 345                 350

Tyr Val Gly Glu Ile Leu Arg Tyr Leu Cys Asn Val Pro Glu Gln Pro
            355                 360                 365

Glu Asp Lys Ile His Thr Val Arg Leu Ala Met Gly Thr Gly Leu Arg
            370                 375                 380

Ala Asn Val Trp Lys Asn Phe Gln Gln Arg Phe Gly Pro Ile Arg Ile
385                 390                 395                 400

Trp Glu Phe Tyr Gly Ser Thr Glu Gly Asn Val Gly Leu Met Asn Tyr
                405                 410                 415

Val Gly His Cys Gly Ala Val Gly Arg Thr Ser Cys Ile Leu Arg Met
                420                 425                 430

Leu Thr Pro Phe Glu Leu Val Gln Phe Asp Ile Glu Thr Ala Glu Pro
            435                 440                 445

Leu Arg Asp Lys Gln Gly Phe Cys Ile Pro Val Glu Pro Gly Lys Pro
            450                 455                 460

Gly Leu Leu Leu Thr Lys Val Arg Lys Asn Gln Pro Phe Leu Gly Tyr
465                 470                 475                 480

Arg Gly Ser Gln Ala Glu Ser Asn Arg Lys Leu Val Ala Asn Val Arg
                485                 490                 495

Arg Val Gly Asp Leu Tyr Phe Asn Thr Gly Asp Val Leu Thr Leu Asp
                500                 505                 510

Gln Glu Gly Phe Phe Tyr Phe Gln Asp Arg Leu Gly Asp Thr Phe Arg
```

-continued

```
            515                 520                 525
Trp Lys Gly Glu Asn Val Ser Thr Gly Glu Val Glu Cys Val Leu Ser
        530                 535                 540

Ser Leu Asp Phe Leu Glu Val Asn Val Tyr Gly Val Pro Val Pro
545                 550                 555                 560

Gly Cys Glu Gly Lys Val Gly Met Ala Ala Val Lys Leu Ala Pro Gly
                565                 570                 575

Lys Thr Phe Asp Gly Gln Lys Leu Tyr Gln His Val Arg Ser Trp Leu
                580                 585                 590

Pro Ala Tyr Ala Thr Pro His Phe Ile Arg Ile Gln Asp Ser Leu Glu
                595                 600                 605

Ile Thr Asn Thr Tyr Lys Leu Val Lys Ser Arg Leu Val Arg Glu Gly
                610                 615                 620

Phe Asp Val Gly Ile Ile Ala Asp Pro Leu Tyr Ile Leu Asp Asn Lys
625                 630                 635                 640

Ala Gln Thr Phe Arg Ser Leu Met Pro Asp Val Tyr Gln Ala Val Cys
                645                 650                 655

Glu Gly Thr Trp Asn Leu
                660

<210> SEQ ID NO 97
<211> LENGTH: 650
<212> TYPE: PRT
<213> ORGANISM: Caenorhabditis elegans

<400> SEQUENCE: 97

Met Lys Leu Glu Glu Leu Val Thr Val Met Leu Leu Thr Val Ala Val
1               5                   10                  15

Ile Ala Gln Asn Leu Pro Ile Gly Val Ile Leu Ala Gly Val Leu Ile
                20                  25                  30

Leu Tyr Ile Thr Val Val His Gly Asp Phe Ile Tyr Arg Ser Tyr Leu
            35                  40                  45

Thr Leu Asn Arg Asp Leu Thr Gly Leu Ala Leu Ile Ile Glu Val Lys
        50                  55                  60

Ile Asp Leu Trp Trp Arg Leu His Gln Asn Lys Gly Ile His Glu Leu
65              70                  75                  80

Phe Leu Asp Ile Val Lys Lys Asn Pro Asn Lys Pro Ala Met Ile Asp
                85                  90                  95

Ile Glu Thr Asn Thr Thr Glu Thr Tyr Ala Glu Phe Asn Ala His Cys
                100                 105                 110

Asn Arg Tyr Ala Asn Tyr Phe Gln Gly Leu Gly Tyr Arg Ser Gly Asp
            115                 120                 125

Val Val Ala Leu Tyr Met Glu Asn Ser Val Glu Phe Val Ala Ala Trp
        130                 135                 140

Met Gly Leu Ala Lys Ile Gly Val Val Thr Ala Trp Ile Asn Ser Asn
145                 150                 155                 160

Leu Lys Arg Glu Gln Leu Val His Cys Ile Thr Ala Ser Lys Thr Lys
                165                 170                 175

Ala Ile Ile Thr Ser Val Thr Leu Gln Asn Ile Met Leu Asp Ala Ile
                180                 185                 190

Asp Gln Lys Leu Phe Asp Val Glu Gly Ile Glu Val Tyr Ser Val Gly
            195                 200                 205

Glu Pro Lys Lys Asn Ser Gly Phe Lys Asn Leu Lys Lys Lys Leu Asp
        210                 215                 220
```

```
Ala Gln Ile Thr Thr Glu Pro Lys Thr Leu Asp Ile Val Asp Phe Lys
225                 230                 235                 240

Ser Ile Leu Cys Phe Ile Tyr Thr Ser Gly Thr Thr Gly Met Pro Lys
                245                 250                 255

Ala Ala Val Met Lys His Phe Arg Tyr Tyr Ser Ile Ala Val Gly Ala
                260                 265                 270

Ala Lys Ser Phe Gly Ile Arg Pro Ser Asp Arg Met Tyr Val Ser Met
            275                 280                 285

Pro Ile Tyr His Thr Ala Ala Gly Ile Leu Gly Val Gly Gln Ala Leu
        290                 295                 300

Leu Gly Gly Ser Ser Cys Val Ile Arg Lys Lys Phe Ser Ala Ser Asn
305                 310                 315                 320

Phe Trp Arg Asp Cys Val Lys Tyr Asp Cys Thr Val Ser Gln Tyr Ile
                325                 330                 335

Gly Glu Ile Cys Arg Tyr Leu Leu Ala Gln Pro Val Val Glu Glu Glu
                340                 345                 350

Ser Arg His Arg Met Arg Leu Leu Val Gly Asn Gly Leu Arg Ala Glu
                355                 360                 365

Ile Trp Gln Pro Phe Val Asp Arg Phe Arg Val Arg Ile Gly Glu Leu
        370                 375                 380

Tyr Gly Ser Thr Glu Gly Thr Ser Ser Leu Val Asn Ile Asp Gly His
385                 390                 395                 400

Val Gly Ala Cys Gly Phe Leu Pro Ile Ser Pro Leu Thr Lys Lys Met
                405                 410                 415

His Pro Val Arg Leu Ile Lys Val Asp Asp Val Thr Gly Glu Ala Ile
                420                 425                 430

Arg Thr Ser Asp Gly Leu Cys Ile Ala Cys Asn Pro Gly Glu Ser Gly
        435                 440                 445

Ala Met Val Ser Thr Ile Arg Lys Asn Asn Pro Leu Leu Gln Phe Glu
        450                 455                 460

Gly Tyr Leu Asn Lys Lys Glu Thr Asn Lys Lys Ile Ile Arg Asp Val
465                 470                 475                 480

Phe Ala Lys Gly Asp Ser Cys Phe Leu Thr Gly Asp Leu Leu His Trp
                485                 490                 495

Asp Arg Leu Gly Tyr Val Tyr Phe Lys Asp Arg Thr Gly Asp Thr Phe
                500                 505                 510

Arg Trp Lys Gly Glu Asn Val Ser Thr Thr Glu Val Glu Ala Ile Leu
            515                 520                 525

His Pro Ile Thr Gly Leu Ser Asp Ala Thr Val Tyr Gly Val Glu Val
        530                 535                 540

Pro Gln Arg Glu Gly Arg Val Gly Met Ala Ser Val Val Arg Val Val
545                 550                 555                 560

Ser His Glu Glu Asp Glu Thr Gln Phe Val His Arg Val Gly Ala Arg
                565                 570                 575

Leu Ala Ser Ser Leu Thr Ser Tyr Ala Ile Pro Gln Phe Met Arg Ile
                580                 585                 590

Cys Gln Asp Val Glu Lys Thr Gly Thr Phe Lys Leu Val Lys Thr Asn
                595                 600                 605

Leu Gln Arg Leu Gly Ile Met Asp Ala Pro Ser Asp Ser Ile Tyr Ile
            610                 615                 620

Tyr Asn Ser Glu Asn Arg Asn Phe Val Pro Phe Asp Asn Asp Leu Arg
625                 630                 635                 640

Cys Lys Val Ser Leu Gly Ser Tyr Pro Phe
```

-continued

```
                645                 650

<210> SEQ ID NO 98
<211> LENGTH: 623
<212> TYPE: PRT
<213> ORGANISM: Saccharomyces cerevisiae

<400> SEQUENCE: 98

Met Ser Pro Ile Gln Val Val Phe Ala Leu Ser Arg Ile Phe Leu
 1               5                  10                  15

Leu Leu Phe Arg Leu Ile Lys Leu Ile Ile Thr Pro Ile Gln Lys Ser
                20                  25                  30

Leu Gly Tyr Leu Phe Gly Asn Tyr Phe Asp Glu Leu Asp Arg Lys Tyr
             35                  40                  45

Arg Tyr Lys Glu Asp Trp Tyr Ile Ile Pro Tyr Phe Leu Lys Ser Val
     50                  55                  60

Phe Cys Tyr Ile Ile Asp Val Arg Arg His Arg Phe Gln Asn Trp Tyr
65                   70                  75                  80

Leu Phe Ile Lys Gln Val Gln Gln Asn Gly Asp His Leu Ala Ile Ser
                 85                  90                  95

Tyr Thr Arg Pro Met Ala Glu Lys Gly Glu Phe Gln Leu Glu Thr Phe
            100                 105                 110

Thr Tyr Ile Glu Thr Tyr Asn Ile Val Leu Arg Leu Ser His Ile Leu
        115                 120                 125

His Phe Asp Tyr Asn Val Gln Ala Gly Asp Tyr Val Ala Ile Asp Cys
    130                 135                 140

Thr Asn Lys Pro Leu Phe Val Phe Leu Trp Leu Ser Leu Trp Asn Ile
145                 150                 155                 160

Gly Ala Ile Pro Ala Phe Leu Asn Tyr Asn Thr Lys Gly Thr Pro Leu
                165                 170                 175

Val His Ser Leu Lys Ile Ser Asn Ile Thr Gln Val Phe Ile Asp Pro
            180                 185                 190

Asp Ala Ser Asn Pro Ile Arg Glu Ser Glu Glu Ile Lys Asn Ala
        195                 200                 205

Leu Pro Asp Val Lys Leu Asn Tyr Leu Glu Glu Gln Asp Leu Met His
    210                 215                 220

Glu Leu Leu Asn Ser Gln Ser Pro Glu Phe Leu Gln Gln Asp Asn Val
225                 230                 235                 240

Arg Thr Pro Leu Gly Leu Thr Asp Phe Lys Pro Ser Met Leu Ile Tyr
                245                 250                 255

Thr Ser Gly Thr Thr Gly Leu Pro Lys Ser Ala Ile Met Ser Trp Arg
            260                 265                 270

Lys Ser Ser Val Gly Cys Gln Val Phe Gly His Val Leu His Met Thr
        275                 280                 285

Asn Glu Ser Thr Val Phe Thr Ala Met Pro Leu Phe His Ser Thr Ala
    290                 295                 300

Ala Leu Leu Gly Ala Cys Ala Ile Leu Ser His Gly Gly Cys Leu Ala
305                 310                 315                 320

Leu Ser His Lys Phe Ser Ala Ser Thr Phe Trp Lys Gln Val Tyr Leu
                325                 330                 335

Thr Gly Ala Thr His Ile Gln Tyr Val Gly Glu Val Cys Arg Tyr Leu
            340                 345                 350

Leu His Thr Pro Ile Ser Lys Tyr Glu Lys Met His Lys Val Lys Val
        355                 360                 365
```

-continued

```
Ala Tyr Gly Asn Gly Leu Arg Pro Asp Ile Trp Gln Asp Phe Arg Lys
            370                 375                 380

Arg Phe Asn Ile Glu Val Ile Gly Glu Phe Tyr Ala Ala Thr Glu Ala
385                 390                 395                 400

Pro Phe Ala Thr Thr Thr Phe Gln Lys Gly Asp Phe Gly Ile Gly Ala
                405                 410                 415

Cys Arg Asn Tyr Gly Thr Ile Ile Gln Trp Phe Leu Ser Phe Gln Gln
            420                 425                 430

Thr Leu Val Arg Met Asp Pro Asn Asp Ser Val Ile Tyr Arg Asn
            435                 440                 445

Ser Lys Gly Phe Cys Glu Val Ala Pro Val Gly Glu Pro Gly Glu Met
    450                 455                 460

Leu Met Arg Ile Phe Phe Pro Lys Lys Pro Glu Thr Ser Phe Gln Gly
465                 470                 475                 480

Tyr Leu Gly Asn Ala Lys Glu Thr Lys Ser Lys Val Val Arg Asp Val
                485                 490                 495

Phe Arg Arg Gly Asp Ala Trp Tyr Arg Cys Gly Asp Leu Leu Lys Ala
            500                 505                 510

Asp Glu Tyr Gly Leu Trp Tyr Phe Leu Asp Arg Met Gly Asp Thr Phe
    515                 520                 525

Arg Trp Lys Ser Glu Asn Val Ser Thr Thr Glu Val Glu Asp Gln Leu
    530                 535                 540

Thr Ala Ser Asn Lys Glu Gln Tyr Ala Gln Val Leu Val Gly Ile
545                 550                 555                 560

Lys Val Pro Lys Tyr Glu Gly Arg Ala Gly Phe Ala Val Ile Lys Leu
                565                 570                 575

Thr Asp Asn Ser Leu Asp Ile Thr Ala Lys Thr Lys Leu Leu Asn Asp
            580                 585                 590

Ser Leu Ser Arg Leu Asn Leu Pro Ser Tyr Ala Met Pro Leu Phe Val
    595                 600                 605

Lys Phe Val Asp Glu Ile Lys Met Thr Asp Asn Leu Ile Lys Phe
    610                 615                 620

<210> SEQ ID NO 99
<211> LENGTH: 597
<212> TYPE: PRT
<213> ORGANISM: Mycobacterium tuberculosis

<400> SEQUENCE: 99

Met Ser Asp Tyr Tyr Gly Gly Ala His Thr Thr Val Arg Leu Ile Asp
1               5                   10                  15

Leu Ala Thr Arg Met Pro Arg Val Leu Ala Asp Thr Pro Val Ile Val
            20                  25                  30

Arg Gly Ala Met Thr Gly Leu Leu Ala Arg Pro Asn Ser Lys Ala Ser
        35                  40                  45

Ile Gly Thr Val Phe Gln Asp Arg Ala Ala Tyr Gly Asp Arg Val
    50                  55                  60

Phe Leu Lys Phe Gly Asp Gln Gln Leu Thr Tyr Arg Asp Ala Asn Ala
65              70                  75                  80

Thr Ala Asn Arg Tyr Ala Ala Val Leu Ala Ala Arg Gly Val Gly Pro
                85                  90                  95

Gly Asp Val Val Gly Ile Met Leu Arg Asn Ser Pro Ser Thr Val Leu
            100                 105                 110

Ala Met Leu Ala Thr Val Lys Cys Gly Ala Ile Ala Gly Met Leu Asn
    115                 120                 125
```

```
Tyr His Gln Arg Gly Glu Val Leu Ala His Ser Leu Gly Leu Leu Asp
    130                 135                 140

Ala Lys Val Leu Ile Ala Glu Ser Asp Leu Val Ser Ala Val Ala Glu
145                 150                 155                 160

Cys Gly Ala Ser Arg Gly Arg Val Ala Gly Asp Val Leu Thr Val Glu
                165                 170                 175

Asp Val Glu Arg Phe Ala Thr Thr Ala Pro Ala Thr Asn Pro Ala Ser
            180                 185                 190

Ala Ser Ala Val Gln Ala Lys Asp Thr Ala Phe Tyr Ile Phe Thr Ser
        195                 200                 205

Gly Thr Thr Gly Phe Pro Lys Ala Ser Val Met Thr His His Arg Trp
    210                 215                 220

Leu Arg Ala Leu Ala Val Phe Gly Gly Met Gly Leu Arg Leu Lys Gly
225                 230                 235                 240

Ser Asp Thr Leu Tyr Ser Cys Leu Pro Leu Tyr His Asn Asn Ala Leu
                245                 250                 255

Thr Val Ala Val Ser Ser Val Ile Asn Ser Gly Ala Thr Leu Ala Leu
            260                 265                 270

Gly Lys Ser Phe Ser Ala Ser Arg Phe Trp Asp Glu Val Ile Ala Asn
        275                 280                 285

Arg Ala Thr Ala Phe Val Tyr Ile Gly Glu Ile Cys Arg Tyr Leu Leu
    290                 295                 300

Asn Gln Pro Ala Lys Pro Thr Asp Arg Ala His Gln Val Arg Val Ile
305                 310                 315                 320

Cys Gly Asn Gly Leu Arg Pro Glu Ile Trp Asp Glu Phe Thr Thr Arg
                325                 330                 335

Phe Gly Val Ala Arg Val Cys Glu Phe Tyr Ala Ala Ser Glu Gly Asn
            340                 345                 350

Ser Ala Phe Ile Asn Ile Phe Asn Val Pro Arg Thr Ala Gly Val Ser
        355                 360                 365

Pro Met Pro Leu Ala Phe Val Glu Tyr Asp Leu Asp Thr Gly Asp Pro
    370                 375                 380

Leu Arg Asp Ala Ser Gly Arg Val Arg Val Pro Asp Gly Glu Pro
385                 390                 395                 400

Gly Leu Leu Leu Ser Arg Val Asn Arg Leu Gln Pro Phe Asp Gly Tyr
                405                 410                 415

Thr Asp Pro Val Ala Ser Glu Lys Lys Leu Val Arg Asn Ala Phe Arg
            420                 425                 430

Asp Gly Asp Cys Trp Phe Asn Thr Gly Asp Val Met Ser Pro Gln Gly
        435                 440                 445

Met Gly His Ala Ala Phe Val Asp Arg Leu Gly Asp Thr Phe Arg Trp
    450                 455                 460

Lys Gly Glu Asn Val Ala Thr Thr Gln Val Glu Ala Ala Leu Ala Ser
465                 470                 475                 480

Asp Gln Thr Val Glu Glu Cys Thr Val Tyr Gly Val Gln Ile Pro Arg
                485                 490                 495

Thr Gly Arg Ala Gly Met Ala Ala Ile Thr Leu Arg Ala Gly Ala
            500                 505                 510

Glu Phe Asp Gly Gln Ala Leu Ala Arg Thr Val Tyr Gly His Leu Pro
        515                 520                 525

Gly Tyr Ala Leu Pro Leu Phe Val Arg Val Val Gly Ser Leu Ala His
    530                 535                 540
```

```
Thr Thr Thr Phe Lys Ser Arg Lys Val Glu Leu Arg Asn Gln Ala Tyr
545                 550                 555                 560

Gly Ala Asp Ile Glu Asp Pro Leu Tyr Val Leu Ala Gly Pro Asp Glu
                565                 570                 575

Gly Tyr Val Pro Tyr Tyr Ala Glu Tyr Pro Glu Glu Val Ser Leu Gly
                580                 585                 590

Arg Arg Pro Gln Gly
        595

<210> SEQ ID NO 100
<211> LENGTH: 304
<212> TYPE: PRT
<213> ORGANISM: concensus FATP signature sequence

<400> SEQUENCE: 100

Tyr Ile Tyr Thr Ser Gly Thr Thr Gly Leu Pro Lys Ala Ala Ile Ile
1               5                   10                  15

Val His Ser Arg Tyr Arg Gly Ala Ala Leu His Ser Gly Arg Met
                20                  25                  30

Arg Pro Asp Val Val Tyr Asp Cys Leu Pro Leu Tyr His Ser Ala Ala
        35                  40                  45

Leu Ile Leu Gly Ile Gly Gln Cys Leu Leu His Gly Ala Thr Val Val
    50                  55                  60

Leu Arg Lys Lys Phe Ser Ala Ser Arg Phe Trp Asp Asp Cys Val Lys
65              70                  75                  80

Tyr Asn Val Thr Val Ile Gln Tyr Ile Gly Glu Leu Cys Arg Tyr Leu
                85                  90                  95

Leu Asn Gln Pro Pro Arg Pro Ala Glu Arg His Lys Val Arg Leu
            100                 105                 110

Ala Val Gly Asn Gly Leu Arg Pro Asp Ile Trp Glu Glu Phe Val Ser
            115                 120                 125

Arg Phe Gly Ile Pro Gln Ile Gly Glu Phe Tyr Gly Ala Thr Glu Gly
    130                 135                 140

Asn Cys Ser Leu Met Asn Tyr Asp Gly Lys Val Gly Ala Cys Gly Ser
145                 150                 155                 160

Arg Ile Leu Lys Lys Val Tyr Pro Ile Arg Leu Val Lys Val Asp Glu
                165                 170                 175

Asp Thr Gly Glu Pro Ile Arg Asp Ala Gln Gly Leu Cys Ile Pro Cys
            180                 185                 190

Gln Pro Gly Glu Pro Gly Leu Leu Val Gly Arg Ile Asn Gln Gln Asp
        195                 200                 205

Pro Phe Arg Gly Phe Gly Tyr Gly Ser Glu Gly Ala Thr Asn Lys Lys
    210                 215                 220

Ile Ala Arg Asp Val Phe Lys Lys Gly Asp Val Ala Phe Asn Thr Gly
225                 230                 235                 240

Asp Val Leu Val Met Asp Glu Leu Gly Tyr Leu Tyr Phe Arg Asp Arg
                245                 250                 255

Thr Gly Asp Thr Phe Arg Trp Lys Gly Glu Asn Val Ser Thr Thr Glu
            260                 265                 270

Val Glu Gly Val Leu Ser Arg Leu Asp Phe Val Ala Glu Val Asn Val
        275                 280                 285

Tyr Gly Val Thr Val Pro Gly His Glu Gly Arg Ala Gly Met Ala Ala
    290                 295                 300

<210> SEQ ID NO 101
```

```
<211> LENGTH: 2166
<212> TYPE: DNA
<213> ORGANISM: Homo sapiens
<220> FEATURE:
<221> NAME/KEY: CDS
<222> LOCATION: (19)...(2124)

<400> SEQUENCE: 101
cgacccacgc gtccgggg atg ttt gcg agc ggc tgg aac cag acg gtg ccg         51
                    Met Phe Ala Ser Gly Trp Asn Gln Thr Val Pro
                     1               5                      10 ata gag gaa gcg ggc tcc atg gct gcc ctc ctg ctg ctg ccc ctg ctg         99
Ile Glu Glu Ala Gly Ser Met Ala Ala Leu Leu Leu Leu Pro Leu Leu
         15                  20                  25 ctg ttg cta ccg ctg ctg ctg ctg aag cta cac ctc tgg ccg cag            147
Leu Leu Leu Pro Leu Leu Leu Leu Lys Leu His Leu Trp Pro Gln
             30                  35                  40 ttg cgc tgg ctt ccg gcg gac ttg gcc ttt gcg gtg cga gct ctg tgc         195
Leu Arg Trp Leu Pro Ala Asp Leu Ala Phe Ala Val Arg Ala Leu Cys
         45                  50                  55 tgc aaa agg gct ctt cga gct cgc gcc ctg gcc gcg gct gcc gcc gac         243
Cys Lys Arg Ala Leu Arg Ala Arg Ala Leu Ala Ala Ala Ala Ala Asp
 60                  65                  70                  75 ccg gaa ggt ccc gag ggg ggc tgc agc ctg gcc tgg cgc ctc gcg gaa         291
Pro Glu Gly Pro Glu Gly Gly Cys Ser Leu Ala Trp Arg Leu Ala Glu
                 80                  85                  90 ctg gcc cag cag cgc gcc gcg cac acc ttt ctc att cac ggc tcg cgg         339
Leu Ala Gln Gln Arg Ala Ala His Thr Phe Leu Ile His Gly Ser Arg
             95                 100                 105 cgc ttt agc tac tca gag gcg gag cgc gag agt aac agg gct gca cgc         387
Arg Phe Ser Tyr Ser Glu Ala Glu Arg Glu Ser Asn Arg Ala Ala Arg
         110                 115                 120 gcc ttc cta cgt gcg cta ggc tgg gac tgg gga ccc gac ggc ggc gac         435
Ala Phe Leu Arg Ala Leu Gly Trp Asp Trp Gly Pro Asp Gly Gly Asp
     125                 130                 135 agc ggc gag ggg agc gct gga gaa ggc gag cgg gca gcg ccg gga gcc         483
Ser Gly Glu Gly Ser Ala Gly Glu Gly Glu Arg Ala Ala Pro Gly Ala
140                 145                 150                 155 gga gat gca gcg gcc gga agc ggc gcg gag ttt gcc gga ggg gac ggt         531
Gly Asp Ala Ala Ala Gly Ser Gly Ala Glu Phe Ala Gly Gly Asp Gly
                 160                 165                 170 gcc gcc aga ggt gga gga gag ccc gcc gcc cct ctg tca cct gga gca         579
Ala Ala Arg Gly Gly Gly Glu Pro Ala Ala Pro Leu Ser Pro Gly Ala
             175                 180                 185 act gtg gcg ctg ctc ctc ccc gct ggc cca gag ttt ctg tgg ctc tgg         627
Thr Val Ala Leu Leu Leu Pro Ala Gly Pro Glu Phe Leu Trp Leu Trp
         190                 195                 200 ttc ggg ctg gcc aag gcc ggc ctg cgc act gcc ttt gtg ccc acc gcc         675
Phe Gly Leu Ala Lys Ala Gly Leu Arg Thr Ala Phe Val Pro Thr Ala
     205                 210                 215 ctg cgc cgg ggc ccc ctg ctg cac tgc ctc cgc agc tgc ggc gcg cgc         723
Leu Arg Arg Gly Pro Leu Leu His Cys Leu Arg Ser Cys Gly Ala Arg
220                 225                 230                 235 gcg ctg gtg ctg gcg cca gag ttt ctg gag tcc ctg gag ccg gac ctg         771
Ala Leu Val Leu Ala Pro Glu Phe Leu Glu Ser Leu Glu Pro Asp Leu
                 240                 245                 250 ccc gcc ctg aga gcc atg ggg ctc cac ctg tgg gct gca ggc cca gga         819
Pro Ala Leu Arg Ala Met Gly Leu His Leu Trp Ala Ala Gly Pro Gly
             255                 260                 265 acc cac cct gct gga att agc gat ttg ctg gct gaa gtg tcc gct gaa         867
Thr His Pro Ala Gly Ile Ser Asp Leu Leu Ala Glu Val Ser Ala Glu
```

-continued

```
            270                 275                 280
gtg gat ggg cca gtg cca gga tac ctc tct tcc ccc cag agc ata aca    915
Val Asp Gly Pro Val Pro Gly Tyr Leu Ser Ser Pro Gln Ser Ile Thr
    285                 290                 295 gac acg tgc ctg tac atc ttc acc tct ggc acc acg ggc ctc ccc aag    963
Asp Thr Cys Leu Tyr Ile Phe Thr Ser Gly Thr Thr Gly Leu Pro Lys
300                 305                 310                 315 gct gct cgg atc agt cat ctg aag atc ctg caa tgc cag ggc ttc tat   1011
Ala Ala Arg Ile Ser His Leu Lys Ile Leu Gln Cys Gln Gly Phe Tyr
                320                 325                 330 cag ctg tgt ggt gtc cac cag gaa gat gtg atc tac ctc gcc ctc cca   1059
Gln Leu Cys Gly Val His Gln Glu Asp Val Ile Tyr Leu Ala Leu Pro
            335                 340                 345 ctc tac cac atg tcc ggt tcc ctg ctg ggc atc gtg ggc tgc atg ggc   1107
Leu Tyr His Met Ser Gly Ser Leu Leu Gly Ile Val Gly Cys Met Gly
        350                 355                 360 att ggg gcc aca gtg gtg ctg aaa tcc aag ttc tcg gct ggt cag ttc   1155
Ile Gly Ala Thr Val Val Leu Lys Ser Lys Phe Ser Ala Gly Gln Phe
    365                 370                 375 tgg gaa gat tgc cag cag cac agg gtg acg gtg ttc cag tac att ggg   1203
Trp Glu Asp Cys Gln Gln His Arg Val Thr Val Phe Gln Tyr Ile Gly
380                 385                 390                 395 gag ctg tgc cga tac ctt gtc aac cag ccc ccg agc aag gca gaa cgt   1251
Glu Leu Cys Arg Tyr Leu Val Asn Gln Pro Pro Ser Lys Ala Glu Arg
                400                 405                 410 ggc cat aag gtc cgg ctg gca gtg ggc agc ggg ctg cgc cca gat acc   1299
Gly His Lys Val Arg Leu Ala Val Gly Ser Gly Leu Arg Pro Asp Thr
            415                 420                 425 tgg gag cgt ttt gtg cgg cgc ttc ggg ccc ctg cag gtg ctg gag aca   1347
Trp Glu Arg Phe Val Arg Arg Phe Gly Pro Leu Gln Val Leu Glu Thr
        430                 435                 440 tat gga ctg aca gag ggc aac gtg gcc acc atc aac tac aca gga cag   1395
Tyr Gly Leu Thr Glu Gly Asn Val Ala Thr Ile Asn Tyr Thr Gly Gln
    445                 450                 455 cgg ggc gct gtg ggg cgt gct tcc tgg ctt tac aag cat atc ttc ccc   1443
Arg Gly Ala Val Gly Arg Ala Ser Trp Leu Tyr Lys His Ile Phe Pro
460                 465                 470                 475 ttc tcc ttg att cgc tat gat gtc acc aca gga gag cca att cgg gac   1491
Phe Ser Leu Ile Arg Tyr Asp Val Thr Thr Gly Glu Pro Ile Arg Asp
                480                 485                 490 ccc cag ggg cac tgt atg gcc aca tct cca ggt gag cca ggg ctg ctg   1539
Pro Gln Gly His Cys Met Ala Thr Ser Pro Gly Glu Pro Gly Leu Leu
            495                 500                 505 gtg gcc ccg gta agc cag cag tcc cca ttc ctg ggc tat gct ggc ggg   1587
Val Ala Pro Val Ser Gln Gln Ser Pro Phe Leu Gly Tyr Ala Gly Gly
        510                 515                 520 cca gag ctg gcc cag ggg aag ttg cta aag gat gtc ttc cgg cct ggg   1635
Pro Glu Leu Ala Gln Gly Lys Leu Leu Lys Asp Val Phe Arg Pro Gly
    525                 530                 535 gat gtt ttc ttc aac act ggg gac ctg ctg gtc tgc gat gac caa ggt   1683
Asp Val Phe Phe Asn Thr Gly Asp Leu Leu Val Cys Asp Asp Gln Gly
540                 545                 550                 555 ttt ctc cgc ttc cat gat cgt act gga gac acc ttc agg tgg aag ggg   1731
Phe Leu Arg Phe His Asp Arg Thr Gly Asp Thr Phe Arg Trp Lys Gly
                560                 565                 570 gag aat gtg gcc aca acc gag gtg gca gag gtc ttc gag gcc cta gat   1779
Glu Asn Val Ala Thr Thr Glu Val Ala Glu Val Phe Glu Ala Leu Asp
            575                 580                 585 ttt ctt cag gag gtg aac gtc tat gga gtc act gtg cca ggg cat gaa   1827
```

-continued

```
                Phe Leu Gln Glu Val Asn Val Tyr Gly Val Thr Val Pro Gly His Glu
                            590                 595                 600 ggc agg gct gga atg gca gcc cta gtt ctg cgt ccc ccc cac gct ttg          1875
Gly Arg Ala Gly Met Ala Ala Leu Val Leu Arg Pro Pro His Ala Leu
605                 610                 615 gac ctt atg cag ctc tac acc cac gtg tct gag aac ttg cca cct tat          1923
Asp Leu Met Gln Leu Tyr Thr His Val Ser Glu Asn Leu Pro Pro Tyr
620                 625                 630                 635 gcc cgg ccc cga ttc ctc agg ctc cag gag tct ttg gcc acc aca gag          1971
Ala Arg Pro Arg Phe Leu Arg Leu Gln Glu Ser Leu Ala Thr Thr Glu
                640                 645                 650 acc ttc aaa cag cag aaa gtt cgg atg gca aat gag ggc ttc gac ccc          2019
Thr Phe Lys Gln Gln Lys Val Arg Met Ala Asn Glu Gly Phe Asp Pro
            655                 660                 665 agc acc ctg tct gac cca ctg tac gtt ctg gac cag gct gta ggt gcc          2067
Ser Thr Leu Ser Asp Pro Leu Tyr Val Leu Asp Gln Ala Val Gly Ala
        670                 675                 680 tac ctg ccc ctc aca act gcc cgg tac agc gcc ctc ctg gca gga aac          2115
Tyr Leu Pro Leu Thr Thr Ala Arg Tyr Ser Ala Leu Leu Ala Gly Asn
    685                 690                 695 ctt cga atc tgagaacttc cacacctgag gcacctgaga gaggaactct                  2164
Leu Arg Ile
700 gt                                                                        2166

<210> SEQ ID NO 102
<211> LENGTH: 702
<212> TYPE: PRT
<213> ORGANISM: Homo sapiens

<400> SEQUENCE: 102

Met Phe Ala Ser Gly Trp Asn Gln Thr Val Pro Ile Glu Glu Ala Gly
1               5                   10                  15

Ser Met Ala Ala Leu Leu Leu Pro Leu Leu Leu Leu Pro Leu
            20                  25                  30

Leu Leu Leu Leu Lys Leu His Leu Trp Pro Gln Leu Arg Trp Leu Pro
        35                  40                  45

Ala Asp Leu Ala Phe Ala Val Arg Ala Leu Cys Cys Lys Arg Ala Leu
    50                  55                  60

Arg Ala Arg Ala Leu Ala Ala Ala Ala Asp Pro Glu Gly Pro Glu
65                  70                  75                  80

Gly Gly Cys Ser Leu Ala Trp Arg Leu Ala Glu Leu Ala Gln Gln Arg
                85                  90                  95

Ala Ala His Thr Phe Leu Ile His Gly Ser Arg Arg Phe Ser Tyr Ser
            100                 105                 110

Glu Ala Glu Arg Glu Ser Asn Arg Ala Ala Arg Ala Phe Leu Arg Ala
        115                 120                 125

Leu Gly Trp Asp Trp Gly Pro Asp Gly Gly Asp Ser Gly Glu Gly Ser
    130                 135                 140

Ala Gly Glu Gly Glu Arg Ala Ala Pro Gly Gly Asp Ala Ala Ala
145                 150                 155                 160

Gly Ser Gly Ala Glu Phe Ala Gly Gly Asp Gly Ala Ala Arg Gly Gly
                165                 170                 175

Gly Glu Pro Ala Ala Pro Leu Ser Pro Gly Ala Thr Val Ala Leu Leu
            180                 185                 190

Leu Pro Ala Gly Pro Glu Phe Leu Trp Leu Trp Phe Gly Leu Ala Lys
        195                 200                 205
```

```
Ala Gly Leu Arg Thr Ala Phe Val Pro Thr Ala Leu Arg Arg Gly Pro
    210                 215                 220
Leu Leu His Cys Leu Arg Ser Cys Gly Ala Arg Ala Leu Val Leu Ala
225                 230                 235                 240
Pro Glu Phe Leu Glu Ser Leu Glu Pro Asp Leu Pro Ala Leu Arg Ala
                245                 250                 255
Met Gly Leu His Leu Trp Ala Ala Gly Pro Gly Thr His Pro Ala Gly
                260                 265                 270
Ile Ser Asp Leu Leu Ala Glu Val Ser Ala Glu Val Asp Gly Pro Val
            275                 280                 285
Pro Gly Tyr Leu Ser Ser Pro Gln Ser Ile Thr Asp Thr Cys Leu Tyr
        290                 295                 300
Ile Phe Thr Ser Gly Thr Thr Gly Leu Pro Lys Ala Ala Arg Ile Ser
305                 310                 315                 320
His Leu Lys Ile Leu Gln Cys Gln Gly Phe Tyr Gln Leu Cys Gly Val
                325                 330                 335
His Gln Glu Asp Val Ile Tyr Leu Ala Leu Pro Leu Tyr His Met Ser
            340                 345                 350
Gly Ser Leu Leu Gly Ile Val Gly Cys Met Gly Ile Gly Ala Thr Val
        355                 360                 365
Val Leu Lys Ser Lys Phe Ser Ala Gly Gln Phe Trp Glu Asp Cys Gln
    370                 375                 380
Gln His Arg Val Thr Val Phe Gln Tyr Ile Gly Glu Leu Cys Arg Tyr
385                 390                 395                 400
Leu Val Asn Gln Pro Pro Ser Lys Ala Glu Arg Gly His Lys Val Arg
                405                 410                 415
Leu Ala Val Gly Ser Gly Leu Arg Pro Asp Thr Trp Glu Arg Phe Val
            420                 425                 430
Arg Arg Phe Gly Pro Leu Gln Val Leu Glu Thr Tyr Gly Leu Thr Glu
        435                 440                 445
Gly Asn Val Ala Thr Ile Asn Tyr Thr Gly Gln Arg Gly Ala Val Gly
    450                 455                 460
Arg Ala Ser Trp Leu Tyr Lys His Ile Phe Pro Phe Ser Leu Ile Arg
465                 470                 475                 480
Tyr Asp Val Thr Thr Gly Glu Pro Ile Arg Asp Pro Gln Gly His Cys
                485                 490                 495
Met Ala Thr Ser Pro Gly Glu Pro Gly Leu Leu Val Ala Pro Val Ser
            500                 505                 510
Gln Gln Ser Pro Phe Leu Gly Tyr Ala Gly Gly Pro Glu Leu Ala Gln
        515                 520                 525
Gly Lys Leu Leu Lys Asp Val Phe Arg Pro Gly Asp Val Phe Phe Asn
    530                 535                 540
Thr Gly Asp Leu Leu Val Cys Asp Asp Gln Gly Phe Leu Arg Phe His
545                 550                 555                 560
Asp Arg Thr Gly Asp Thr Phe Arg Trp Lys Gly Glu Asn Val Ala Thr
                565                 570                 575
Thr Glu Val Ala Glu Val Phe Glu Ala Leu Asp Phe Leu Gln Glu Val
            580                 585                 590
Asn Val Tyr Gly Val Thr Val Pro Gly His Glu Gly Arg Ala Gly Met
        595                 600                 605
Ala Ala Leu Val Leu Arg Pro Pro His Ala Leu Asp Leu Met Gln Leu
    610                 615                 620
```

-continued

```
Tyr Thr His Val Ser Glu Asn Leu Pro Pro Tyr Ala Arg Pro Arg Phe
625                 630                 635                 640

Leu Arg Leu Gln Glu Ser Leu Ala Thr Thr Glu Thr Phe Lys Gln Gln
                645                 650                 655

Lys Val Arg Met Ala Asn Glu Gly Phe Asp Pro Ser Thr Leu Ser Asp
                660                 665                 670

Pro Leu Tyr Val Leu Asp Gln Ala Val Gly Ala Tyr Leu Pro Leu Thr
            675                 680                 685

Thr Ala Arg Tyr Ser Ala Leu Leu Ala Gly Asn Leu Arg Ile
        690                 695                 700

<210> SEQ ID NO 103
<211> LENGTH: 19
<212> TYPE: DNA
<213> ORGANISM: Artificial Sequence
<220> FEATURE:
<223> OTHER INFORMATION: Oligonucleotide

<400> SEQUENCE: 103
cccccaccag agaggctcc                                              19

<210> SEQ ID NO 104
<211> LENGTH: 19
<212> TYPE: DNA
<213> ORGANISM: Artificial Sequence
<220> FEATURE:
<223> OTHER INFORMATION: Oligonucleotide

<400> SEQUENCE: 104 ccaccccgg aaagcctgc                                               19

<210> SEQ ID NO 105
<211> LENGTH: 19
<212> TYPE: DNA
<213> ORGANISM: Artificial Sequence
<220> FEATURE:
<223> OTHER INFORMATION: Oligonucleotide

<400> SEQUENCE: 105
ggagcctctc tggtggggg                                              19
```

What is claimed is:

1. An isolated nucleic acid comprising the nucleotide sequence of SEQ ID NO: 24 or SEQ ID NO: 46 or the complement thereof.

2. An isolated nucleic acid which encodes a polypeptide comprising the amino acid sequence of SEQ ID NO: 25 or the complement thereof.

3. An isolated nucleic acid which hybridizes under stringency conditions 6×SSC at 650° C., followed by two or more washes in 0.2×SSC/0.5% SDS at 65° C. to a nucleic acid comprising the nucleotide sequence of SEQ ID NO; 24 or SEQ ID NO: 46 or the complement thereof.

4. An isolated nucleic acid consisting of the nucleotide sequence of SEQ ID NO: 24 or SEQ ID NO: 46 or the complement thereof.

5. An isolated nucleic acid which encodes a polypeptide consisting of the amino acid sequence of SEQ. ID NO: 25 or the complement thereof.

6. An isolated nucleic acid comprising the nucleotide sequence of the coding region of SEQ ID NO: 24 or SEQ ID NO: 46.

7. An isolated nucleic acid comprising a nucleotide sequence having at least 95% identity to the nucleotide sequence of SEQ ID NO; 24 or SEQ ID NO: 46.

8. An isolated nucleic acid encoding a fusion polypeptide, wherein the isolated nucleic acid comprises a nucleotide sequence encoding the amino acid sequence of SEQ ID NO: 25.

9. An isolated nucleic acid comprising at least 1080 contiguous nucleotides of the nucleotide sequence of SEQ ID NO: 24 or SEQ ID NO: 46 or a complement thereof.

10. An isolated nucleic acid comprising a nucleotide sequence which encodes a contiguous portion of at least 360 amino acids of the sequence or SEQ ID NO: 25 or a complement thereof.

11. A vector comprising a nucleic acid of any one of claims 1, 2, 3, 4, 5, 6, 7, 8, 9 or 10.

12. An isolated host cell transfected with the vector of claim 11.

13. A method for producing a polypeptide comprising the step of culturing the host cell of claim 12 under conditions in which the nucleic acid is expressed, thereby producing the polypeptide.

14. An isolated nucleic acid comprising the nucleotide sequence of SEQ ID NO: 101 or the complement thereof.

15. An isolated nucleic acid which encodes a polypeptide comprising the amino acid sequence of SEQ ID NO: 102 or the complement thereof.

16. An isolated nucleic acid which hybridizes under stringency conditions of 6×SSC at 65° C., followed by two or more washes in 0.2×SSC/0.5% SDS at 65° C. to a nucleic acid comprising the nucleotide sequence of SEQ ID NO: 101 or the complement thereof.

17. An isolated nucleic acid consisting of the nucleotide sequence of SEQ ID NO: 101 or the complement thereof.

18. An isolated nucleic acid which encodes a polypeptide consisting of the amino acid sequence of SEQ ID NO: 102 or the complement thereof.

19. An isolated nucleic acid comprising the nucleotide sequence of the coding region of SEQ ID NO: 101.

20. An isolated nucleic acid comprising a nucleotide sequence having at least 95% identity to the nucleotide sequence of SEQ ID NO: 101.

21. An isolated nucleic acid encoding a fusion polypeptide, wherein the isolated nucleic acid comprises a nucleotide sequence encoding the amino acid sequence of SEQ ID NO: 102.

22. An isolated nucleic acid comprising at least 1080 contiguous nucleotides of the nucleotide sequence of SEQ ID NO: 101 or a complement thereof.

23. An isolated nucleic acid comprising a nucleotide sequence which encodes a contiguous portion of at least 360 amino acids of the sequence of SEQ ID NO: 102 or a complement thereof.

24. An isolated nucleic acid comprising at least 30 contiguous nucleotides of the nucleotide sequence of SEQ ID NO: 101.

25. An isolated nucleic acid comprising a nucleotide sequence which encodes a contiguous portion of at least 15 amino acids of the sequence of SEQ ID NO: 102.

26. A vector comprising a nucleic acid of any one of claims 14, 15, 16, 17, 18, 19, 20, 21, 22, 23, 24, or 25.

27. An isolated host cell transfected with the vector of claim 26.

28. A method for producing a polypeptide comprising the step of culturing the host cell of claim 27 under conditions in which the nucleic acid is expressed, thereby producing the polypeptide.

29. An isolated nucleic acid comprising the nucleotide sequence of SEQ ID NO: 26 or SEQ ID NO: 52 or the complement thereof.

30. An isolated nucleic acid which encodes a polypeptide comprising the amino acid sequence of SEQ ID NO: 27 or the complement thereof.

31. An isolated nucleic acid which hybridizes under stringency conditions of 6×SSC at 65° C., followed by two or more washes in 0.2×SSC/0.5% SDS at 65° C. to a nucleic acid comprising the nucleotide sequence of SEQ ID NO: 26 or SEQ ID NO: 52 or the complement thereof.

32. An isolated nucleic acid consisting of the nucleotide sequence of SEQ ID NO: 26 or SEQ ID NO; 52 or the complement thereof.

33. An isolated nucleic acid which encodes a polypeptide consisting of the amino acid sequence of SEQ ID NO: 27 or the complement thereof.

34. An isolated nucleic acid comprising the nucleotide sequence of the coding region of SEQ ID NO: 26 or SEQ ID NO: 52.

35. An isolated nucleic acid comprising a nucleotide sequence having at least 95% identity to the nucleotide sequence of SEQ ID NO: 26 or SEQ ID NO: 52.

36. An isolated nucleic acid encoding a fusion polypeptide, wherein the isolated nucleic acid comprises a nucleotide sequence encoding the amino acid sequence of SEQ ID NO. 27.

37. An isolated nucleic acid comprising at least 1080 contiguous nucleotides of the nucleotide sequence of SEQ ID NO: 26 or SEQ ID NO: 52 or a complement thereof.

38. An isolated nucleic acid comprising a nucleotide sequence which encodes a contiguous portion of at least 360 amino acids of the sequence of SEQ ID NO: 27 or a complement thereof.

39. A vector comprising a nucleic acid of any one of claims 29, 30, 31, 32, 33, 34, 35, 36, 37, or 38.

40. An isolated host cell transfected with the vector of claim 39.

41. A method for producing a polypeptide comprising the step of culturing the host cell of claim 40 under conditions in which the nucleic acid is expressed, thereby producing the polypeptide.

42. An isolated nucleic acid comprising the nucleotide sequence of SEQ ID NO: 54 or the complement thereof.

43. An isolated nucleic acid which encodes a polypeptide comprising the amino acid sequence of SEQ ID NO: 55 or the complement thereof.

44. An isolated nucleic acid consisting of the nucleotide sequence of SEQ ID NO: 54 or the complement thereof.

45. An isolated nucleic acid which encodes a polypeptide consisting of the amino acid sequence of SEQ ID NO: 55 or the complement thereof.

46. An isolated nucleic acid comprising the nucleotide sequence of the coding region of SEQ ID NO: 54.

47. An isolated nucleic acid encoding a fusion polypeptide, wherein the isolated nucleic acid comprises a nucleotide sequence encoding the amino acid sequence of SEQ ID NO: 55.

48. An isolated nucleic acid comprising at least 1080 contiguous nucleotides of the nucleotide sequence of SEQ ID NO: 54 or a complement thereof.

49. An isolated nucleic acid comprising a nucleotide sequence which encodes a contiguous portion of at least 360 amino acids of the sequence of SEQ ID NO: 55 or a complement thereof.

50. An isolated nucleic acid comprising a nucleotide sequence which encodes a contiguous portion of at least 15 amino acids of the sequence of SEQ ID NO: 55.

51. A vector comprising a nucleic acid of any one of claims 42, 43, 44, 45, 46, 47, 48, 49 or 50.

52. An isolated host cell transfected with the vector of claim 51.

53. A method for producing a polypeptide comprising the step of culturing the host cell of claim 52 under conditions in which the nucleic acid is expressed, thereby producing the polypeptide.

54. An isolated nucleic acid comprising the nucleotide sequence of SEQ ID NO: 56 or the complement thereof.

55. An isolated nucleic acid which encodes a polypeptide comprising the amino acid sequence of SEQ ID NO: 57 or the complement thereof.

56. An isolated nucleic acid which hybridizes under stringency conditions of 6×SSC at 65° C., followed by two or more washes in 0.2×SSC/0.5% SDS at 65° C. to a nucleic acid comprising the full coding region of the nucleotide sequence of SEQ ID NO: 56 or the complement thereof.

57. An isolated nucleic acid consisting of the nucleotide sequence of SEQ ID NO: 56 or the complement thereof.

58. An isolated nucleic acid which encodes a polypeptide consisting of the amino acid sequence of SEQ ID NO: 57 or the complement thereof.

59. An isolated nucleic acid comprising the nucleotide sequence of the coding region of SEQ ID NO: 56.

60. An isolated nucleic acid comprising a nucleotide sequence having at least 95% identity to the nucleotide sequence of SEQ ID NO: 56.

61. An isolated nucleic acid encoding a fusion polypeptide, wherein the isolated nucleic acid comprises a nucleotide sequence encoding the amino acid sequence of SEQ ID NO: 57.

62. An isolated nucleic acid comprising at least 1080 contiguous nucleotides of the nucleotide sequence of SEQ ID NO: 56 or a complement thereof.

63. An isolated nucleic acid comprising a nucleotide sequence which encodes a contiguous portion of at least 360 amino acids of the sequence of SEQ ID NO: 57 or a complement thereof.

64. A vector comprising a nucleic acid of any one of claims 54, 55, 56, 57, 58, 59, 60, 61, 62 or 63.

65. An isolated host cell transfected with the vector of claim 64.

66. A method for producing a polypeptide comprising the step of culturing the host cell of claim 65 under conditions in which the nucleic acid is expressed, thereby producing the polypeptide.

* * * * *